United States Patent
Li et al.

(10) Patent No.: US 10,202,388 B2
(45) Date of Patent: Feb. 12, 2019

(54) FUSED-RING COMPOUNDS, PHARMACEUTICAL COMPOSITION AND USES THEREOF

(71) Applicant: SHANGHAI DE NOVO PHARMATECH CO., LTD., Shanghai (CN)

(72) Inventors: Qun Li, Shanghai (CN); Daxin Gao, Shanghai (CN)

(73) Assignee: SHANGHAI DE NOVO PHARMATECH CO., LTD., Shanghai (CN)

( * ) Notice: Subject to any disclaimer, the term of this patent is extended or adjusted under 35 U.S.C. 154(b) by 0 days.

(21) Appl. No.: 15/548,664

(22) PCT Filed: Feb. 3, 2016

(86) PCT No.: PCT/CN2016/073258
§ 371 (c)(1),
(2) Date: Aug. 3, 2017

(87) PCT Pub. No.: WO2016/131380
PCT Pub. Date: Aug. 25, 2016

(65) Prior Publication Data
US 2018/0022752 A1 Jan. 25, 2018

(30) Foreign Application Priority Data

Feb. 16, 2015 (CN) .......................... 2015 1 0086186
Sep. 2, 2015 (CN) .......................... 2015 1 0555406

(51) Int. Cl.
| | |
|---|---|
| C07D 471/14 | (2006.01) |
| C07D 519/00 | (2006.01) |
| C07F 9/6561 | (2006.01) |
| A61K 45/06 | (2006.01) |
| A61K 31/4188 | (2006.01) |
| A61K 31/423 | (2006.01) |
| A61K 31/4245 | (2006.01) |
| A61K 31/428 | (2006.01) |
| A61K 31/437 | (2006.01) |
| A61K 31/439 | (2006.01) |
| A61K 31/4439 | (2006.01) |
| A61K 31/5377 | (2006.01) |
| A61K 31/635 | (2006.01) |
| A61K 31/675 | (2006.01) |
| C07D 487/04 | (2006.01) |

(52) U.S. Cl.
CPC ........ *C07D 487/04* (2013.01); *A61K 31/4188* (2013.01); *A61K 31/423* (2013.01); *A61K 31/428* (2013.01); *A61K 31/4245* (2013.01); *A61K 31/437* (2013.01); *A61K 31/439* (2013.01); *A61K 31/4439* (2013.01); *A61K 31/5377* (2013.01); *A61K 31/635* (2013.01); *A61K 31/675* (2013.01); *A61K 45/06* (2013.01); *C07D 471/14* (2013.01); *C07D 519/00* (2013.01); *C07F 9/6561* (2013.01)

(58) Field of Classification Search
CPC .............. A61K 31/4188; A61K 31/423; A61K 31/4245; A61K 31/428; A61K 31/437; A61K 31/439; A61K 31/4439; A61K 31/5377; A61K 31/635; A61K 31/675; A61K 45/06; C07D 471/14; C07D 487/04; C07D 519/00; C07F 9/6561
See application file for complete search history.

(56) References Cited

U.S. PATENT DOCUMENTS

2014/0066625 A1  3/2014  Mautino et al.

FOREIGN PATENT DOCUMENTS

| JP | 200148786 | 2/2001 |
| JP | 2003517447 A | 5/2003 |
| WO | 2000027822 A2 | 5/2000 |

(Continued)

OTHER PUBLICATIONS

Wolff, Manfred E., Burger's Medicinal Chemistry and Drug Discovery, Fifth Ed., vol. 1: Principles and Practice, John Wiley & Sons, 1995, 975. (Year: 1995).*

(Continued)

*Primary Examiner* — Erich A Leeser
(74) *Attorney, Agent, or Firm* — Harness, Dickey & Pierce, P.L.C.

(57) ABSTRACT

This disclosure is related to a fused-ring compound of formula (I) and/or a pharmaceutically acceptable salt thereof, a pharmaceutical composition comprising the fused ring compound of formula (I) and/or a pharmaceutically acceptable salt thereof, preparation methods thereof, and use thereof in modulating activity of indoleamine 2, 3-dioxygenase (IDO) and/or tryptophan 2, 3-dioxygenase (TDO). This disclosure further provides methods of treating IDO and/or TDO-associated diseases, including cancer, viral infection and autoimmune diseases.

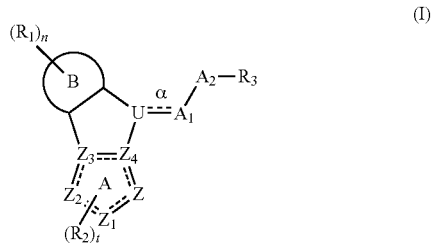

20 Claims, 1 Drawing Sheet

(56) References Cited

FOREIGN PATENT DOCUMENTS

| WO | WO-2010056567 A1 | | 5/2010 |
|---|---|---|---|
| WO | WO-2014159248 A1 | | 10/2014 |
| WO | 2016037026 A1 | | 3/2016 |
| ZA | 98/5551 | * | 1/1999 |
| ZA | 19805551 | | 3/1999 |

OTHER PUBLICATIONS

Banker, Gilbert S. et al., Modem Pharmaceutics, Marcel Dekker, New York, 1996. (Year: 1996).*

May 17, 2016 International Search Report issued in International Patent Application No. PCT/CN2016/073258.

May 17, 2016 Written Opinion of the International Searching Authority issued in International Patent Application No. o. PCT/CN2016/073258.

Milton W. Taylor et al., "Relationship between interferon-r, indoleamine 2,3-dioxygenase, and tryptophan catabolism", the FASEB journal vol. 5, No. 11, pp. 2516-2522, Nov. 2017.

Raghava Potula et al., "Inhibition of indoleamine 2,3-dioxgenase (IDO) enhances elimination of virus-infected macrophages in an animal model of HIV-1 encephalitis", Blood, Oct. 1, 2005 • vol. 106, No. 7.

David H. Munn et al., "Prevention of Allogeneic Fetal Rejection by Tryptophan Catabolism", Science vol. 281 Aug. 21, 1998.

Christopher J.D Austin et al., "Targeting key dioxygenases in tryptophan-kynurenine metabolism for immunomodulation and cancer chemotherapy", Drug Discovery Today * vol. 00, No. 00 * Dec. 2014.

Christiane A. Opitz et al., "An endogenous tumour-promoting ligand of the human aryl hydrocarbon receptor", 198, Natrue, vol. 478, Oct. 13, 2011.

Gilles J. Guillemin et al., "Characterization of the Kynurenine Pathway in Human Neurons", The Journal of Neuroscience, Nov. 21, 2007, 27(47):12884-12892.

Trevor W. Stone et al., "The kynurenine pathway as a therapeutic target in cognitive and neurodegenerative disorders", Br J of Pharmacol, 169(6)1211-27.

Stephen M. Berge et al., Pharmaceutical Salts, Journal of Pharmaceutical Sciences, vol. 66, No. 1, Jan. 1977.

Indoleamine 2,3-dioxygenase. Equilibrium studies of the tryptophan binding to the ferric, ferrous, and Co-bound enzymes, The Journal of Biological Chemistry, vol. 255, No. 4, Issue of Feb. 25, pp. 1339-1345, 1980.

Chinese Patent Application No. 201510086186.1 (not published).

Chinese Patent Application CN105884828A (published).

Chinese Patent Application CN105884780A (published).

Santosh S. Kulkarni, et al., "Three-Dimensional Quantitative Structure-Activity Relationships of Mazindol Analogues at the Dopamine Transporter", J. Med. Chem., No. 45, Jan. 22, 2002 (Jan. 22, 2002), p. 4119-4127.

European Search Report in related application No. 16751911.5 dated Feb. 20, 2018.

Spasov. A. A. et al., Farmakologiya Toksikologiya (Moscow),1990, vol. 53, No. 4, p. 30-33.

The First Office Action of Counterpart Japanese application JP2017-560857 dated Jul. 17, 2018.

* cited by examiner

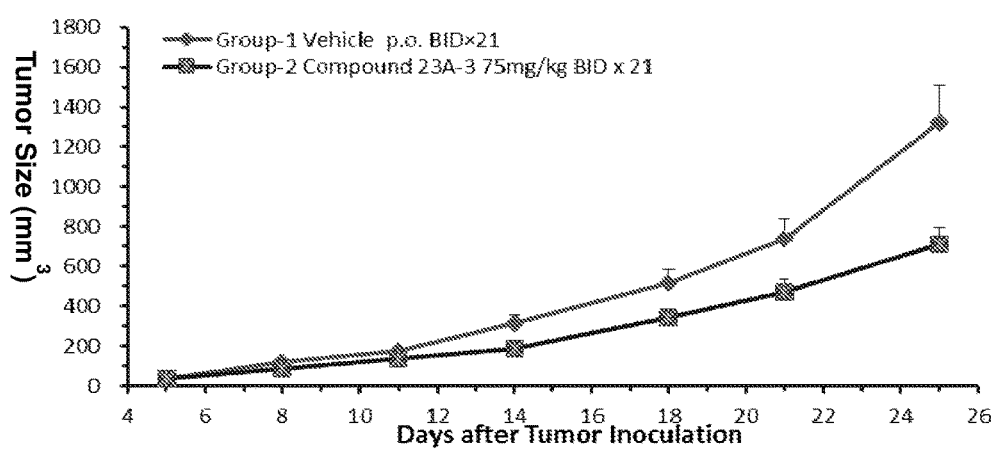

FUSED-RING COMPOUNDS, PHARMACEUTICAL COMPOSITION AND USES THEREOF

CROSS-REFERENCE TO RELATED APPLICATIONS

This application is a 371 U.S. National Stage of International Application No. PCT/CN2016/073258, filed Feb. 3, 2016, which claims the benefit of and priority to Chinese Patent Applications Nos. 201510086186.1, filed Feb. 16, 2015, and 201510555406.0, filed Sep. 2, 2015. The entire disclosures of the above applications are incorporated herein by reference.

FIELD OF THE INVENTION

Disclosed are fused-ring compounds, pharmaceutical compositions, preparation, methods of treatment, and uses thereof.

BACKGROUND OF THE INVENTION

Indoleamine 2, 3-dioxygenase (IDO) is an immune-modulating enzyme produced by activated macrophages and other immune-regulatory cells (can also be exploited by many tumor cells as a strategy to escape immune response). In humans, it is encoded by the gene IDOL (also known as IDO and INDO) and expressed in many tissues, including the central nervous system (CNS), epididymis, intestine, thymus, respiratory tract, spleen, pancreas, placenta, lens, and kidney, as well as in myeloid cells, such as macrophages, dendritic cells, and microglial cells. It can catalyze the first and rate-limiting step in tryptophan catabolism to N-formyl-kynurenine. Deprivation of tryptophan and its derived metabolite can cause potent immune suppression resulting in blockage of T cell growth and activation, induction of T cell apoptosis and increase of regulatory T cells (FASEB J. 1991, 5, 2516-2522). Tryptophan-kynurenine metabolic pathway has been proved to be critical for innate and adaptive immunity. Tryptophan 2, 3-dioxygenase (TDO) is an unrelated hepatic enzyme that also degrades tryptophan along the tryptophan-kynurenine metabolic pathway. In humans, it is encoded by the gene TDO2 and expressed at high levels in the liver, placenta, and brain. It can catalyze the first and rate-limiting step of tryptophan degradation along the tryptophan-kynurenine metabolic pathway and thereby regulates systemic tryptophan levels, the same reaction catalyzed by IDO1.

Numerous preclinical studies have shown this immune tolerance pathway is involved in cancer, autoimmune, infection, transplant rejection and allergy. Increased IDO activity plays an important role in cancer proliferation and metastasis. Studies have shown that IDO can lead to inactivation of tumor specific cytotoxic T lymphocytes which then lose their ability to attack cancer cells. In fact, over-expression of IDO1 is found in many human cancers including prostate, colorectal, pancreatic, cervical, gastric, ovarian, brain and lung cancer. Inhibition of IDO1 can reverse immune function suppressed by tumor, thereby producing an effective anti-tumor immunity. Because IDO1 inhibitors can activate T cells enhancing immune function, IDO1 inhibitors may have therapeutic effect in many areas/diseases including cancer drug resistance and rejection, chronic infection, HIV infection and AIDS, autoimmune diseases such as rheumatoid arthritis, immune tolerance and prevention of fetus rejection. IDO1 inhibitors may also be used to treat neuro or neuropsychiatric disorders such as depression (Protula, et al, 2005, Blood, 106:238290; Munn et al, 1998, Science 281: 11913).

Preclinical and clinical studies have shown that inhibition of IDO1 can enhance immunity and improve efficacy of various chemotherapeutic agents against tumor and other diseases caused by immune-suppression (C. J. D. Austin and L. M. Rendina, Drug Discovery Today 2014, 1-9). IDO1−/− knock-out mice are viable and healthy suggesting inhibition of IDO1 will not cause severe mechanism-based toxicity.

Also TDO expression has been implicated in diseases, including cancer, schizophrenia, depression, and bipolar disorder, and TDO is detected in varieties of human cancers, including hepatocarcinoma, melanoma, and bladder cancer. TDO2 played an important role in tumors immunosuppression. Presence of TDO induces tumor tolerance in the host's immune system by depleting tryptophan levels and producing bioactive metabolites. Depletion of tryptophan reduces T cell proliferation, whereas TDO-derived kynurenines suppress antitumor immune responses and promote tumor cell survival and motility. Systemic blockade by a TDO2 inhibitor restores the ability of mice to reject TDO expressing tumors. These studies suggest a substantial role for TDO2 in immune tolerance and tumor progression, and inhibition of TDO can reactivate the immune system to overcome tumor-induced immune resistance (Nature, 2011, 478, 197-203). Moreover, alterations in TDO function have been associated with the pathogenesis of schizophrenia and affective disorders, this pathway is now considered as a therapeutic target in cognitive diseases like bipolar disorder and neurodegenerative disorder like Alzheimer, motor neuron disease like Multiple sclerosis, Huntington or Parkinson's disease (J. Neurosci. 2007, 27, 12884-12892, Stone T W, 2013, Br J of Pharmacol, 169(6): 1211-27).

There are now efforts in developing IDO1 and/or TDO2 small molecule inhibitors to treat and prevent IDO1/TDO2 related diseases.

Studies have shown that IDO and/or TDO inhibitors are effective in treatment and prevention of immune suppression, tumor suppression, and chronic infection, viral infection including HIV infection, autoimmune diseases and fetus rejection. Inhibition of catabolism of tryptophan represents a good therapeutic approach.

DISCLOSURE OF THE INVENTION

Provided is a compound of formula (I) and/or isomers, prodrugs, stable isotope derivatives thereof, and/or a pharmaceutically acceptable salt thereof;

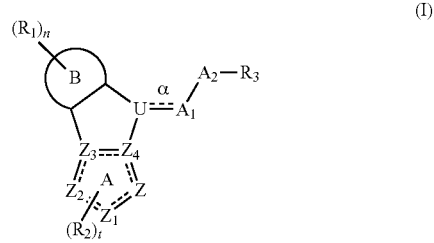

Wherein, n is 1, 2 or 3; t is 1 or 2; U is N, C, or $CR_4$, bond α is a single or double bond; when U is N or $CR_4$, bond α is a single bond; when U is C, bond α is a double bond;

A ring is 5-membered heteroaromatic ring; Z, $Z_1$, $Z_2$, $Z_3$, $Z_4$ are independently N or C, and $Z_3$ and $Z_4$ are not N at the same time;

B ring is benzene or a 5- or 6-membered heteroaromatic ring;

When bond α is a single bond, $A_1$ is —$(CR_9R_{9a})_m$— or —$C_{2-4}$alkenyl-, m is 0, 1, 2, or 3;

When bond α is a double bond, $A_1$ is —$CR_9(CR_9R_{9a})_m$—, m is 0, 1, 2, or 3;

$R_9$ is independently hydrogen, halogen, substituted or unsubstituted alkyl, substituted or unsubstituted cycloalkyl, substituted or unsubstituted heterocyclolalkyl, substituted or unsubstituted alkoxy; $R_{9a}$ is independently hydrogen, deuterium, halogen, substituted or unsubstituted alkyl; or $R_9$ and $R_{9a}$ together with the carbon atom to which they are attached form a 3- to 8-membered mono-cycloalkyl ring;

$A_2$ is —C(=$R_7$)($CR_5R_{5a}$)$_m$—, —($CR_5R_{5a}$)$_m$—, —(C=$R_7$)O—, —($CR_5R_{5a}$)$_m$O—, or —S(O)$_{0-2}$($CR_5R_{5a}$)$_m$—; wherein, m is 0, 1, 2 or 3; $R_5$ and $R_{5a}$ are independently hydrogen, hydroxyl, halogen, alkyl, amino, —$SR_6$, —$OR_6$, —$NR_6R_{6a}$, —$NR_6S(O)_2R_{6a}$, —$S(O)_2NR_6R_{6a}$, —$(CH_2)_rS(O)_{0-2}CH_3$, —$OS(O)_3H$, —OP(O)(O—$R_6$)$_2$, —$OC(O)R_6$, —$OC(O)NR_6R_{6a}$, —$C(O)NR_6R_{6a}$, —$(CH_2)_rC(O)OH$, —$(CH_2)_rOH$, —$(CH_2)_rNR_6R_{6a}$, or —$(CH_2)_rC(O)NR_6R_{6a}$; r is an integer ranging from 1 to 8;

is independently =O, =S, =N($R_6$), or =N(O$R_6$), such as =O, =S, =N—OH, or =NH;

$R_1$ is hydrogen, halogen, hydroxyl, alkyl, alkoxy, alkylthiol, haloalkyl, haloalkoxy, amino, $C_{2-6}$ alkynyl, $C_{2-6}$ alkenyl, aryl, cycloalkyl, heterocycloalkyl, heteroaryl, —SH, —CN, —$NO_2$, —$OC(O)R_6$, —$OC(O)OR_6$, —$OC(O)NR_6R_{6a}$, —$C(O)OR_6$, —$C(O)R_6$, —$C(O)NR_6R_{6a}$, —$NR_6R_{6a}$, —$NR_6C(O)R_{6a}$, —$NR_6C(O)OR_{6a}$, —$NR_6C(O)NR_6R_{6a}$, —$(CH_2)_rNR_6R_{6a}$, —$NR_6S(O)_2R_{6a}$, —$S(O)_{0-2}R_6$, or —$S(O)_2NR_6R_{6a}$; r is an integer ranging from 1 to 8;

$R_2$ is hydrogen, halogen, hydroxyl, alkyl, alkoxy, alkylthiol, haloalkyl, haloalkoxy, amino, $C_{2-6}$ alkynyl, $C_{2-6}$ alkenyl, aryl, cycloalkyl, heterocycloalkyl, heteroaryl, —SH, —CN, —$NO_2$, or —$NR_6R_{6a}$;

$R_6$ and $R_{6a}$ is independently hydrogen, alkyl, haloalkyl, cycloalkyl, heterocycloalkyl, aryl, heteroaryl, heterocycloalkylalkyl, cycloalkylalkyl, arylalkyl, or heteroarylalkyl, or $R_6$ and $R_{6a}$ together with the nitrogen atom to which they are attached, form a 3- to 8-membered mono-heterocycloalkyl ring;

In some embodiments, $R_6$ and $R_{6a}$ are independently hydrogen, $C_{1-4}$ alkyl, halo-$C_{1-4}$ alkyl, $C_{3-8}$ cycloalkyl, 5- to 8-membered heterocycloalkyl, $C_{6-10}$ aryl, 5- to 6-membered heteroaryl, 5- to 8-membered heterocycloalkyl-$C_{1-4}$ alkyl, $C_{3-8}$ cycloalkyl-$C_{1-4}$ alkyl, $C_{6-10}$ aryl-$C_{1-4}$ alkyl, or 5- to 6-membered heteroaryl-$C_{1-4}$ alkyl, or $R_6$ and $R_{6a}$ together with the nitrogen atom to which they are attached, form a 3- to 8-membered mono-heterocycloalkyl ring;

$R_3$ is substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted bridged tricycloalkyl, or substituted or unsubstituted bridged heterocycloalkyl; provided that when U is C or $CR_4$ and B ring is benzene, $R_3$ is substituted or unsubstituted $C_{9-20}$ cycloalkyl, substituted or unsubstituted bridged tricycloalkyl, or substituted or unsubstituted bridged heterocycloalkyl;

$R_4$ is hydrogen, deuterium, halogen, —CN, —C(O)OH, tetrazole, substituted or unsubstituted alkyl, substituted or unsubstituted alkoxy.

DETAILED DESCRIPTION OF THE INVENTION

In some embodiments, as $R_9$ in $A_1$, the substituted alkyl, substituted cycloalkyl, substituted heterocycloalkyl, or substituted alkoxy is alkyl, cycloalkyl, heterocycloalkyl, or alkoxy substituted by one or more substituent(s) at any position independently selected from halogen, hydroxyl, alkyl, heterocycloalkyl, cycloalkyl, alkoxy, amino, aryl, heteroaryl, —$SR_6$, —$NR_6R_{6a}$, —$S(O)_2NR_6R_{6a}$, —$NR_8C(O)NR_6R_{6a}$, —$NR_6C(O)R_{6a}$, —$NR_6S(O)_2R_{6a}$, —$C(O)R_6$, —$S(O)_{0-2}R_6$, —$C(O)OR_6$, —$C(O)NR_6R_{6a}$, —$(CH_2)_rOH$, and —$(CH_2)_rNR_6R_{6a}$, wherein $R_6$ and $R_{6a}$ are the same as described above, including the embodiments thereof, and r is an integer ranging from 1 to 8.

In some embodiments, as $R_{9a}$ in $A_1$, the substituted alkyl is alkyl substituted by one or more substituent(s) at any position independently selected from hydroxyl, halogen, and $C_{3-6}$ cycloalkyl.

In some embodiments, $R_9$ is hydrogen, halogen, substituted or unsubstituted $C_{1-4}$ alkyl (such as methyl, ethyl, propyl, or isopropyl), or substituted or unsubstituted $C_{1-4}$ alkoxy, wherein the substituted $C_{1-4}$ alkyl or substituted $C_{1-4}$ alkoxy is a $C_{1-4}$ alkyl or $C_{1-4}$ alkoxy substituted by one or more substituent(s) at any position independently selected from halogen, hydroxyl, alkyl, heterocycloalkyl, cycloalkyl, alkoxy, amino, aryl, heteroaryl, —$SR_6$, —$NR_6R_{6a}$, —$S(O)_2NR_6R_{6a}$, —$NR_6C(O)NR_6R_{6a}$, —$NR_6C(O)R_{6a}$, —$NR_6S(O)_2R_{6a}$, —$C(O)R_6$, —$S(O)_{0-2}R_6$, —$C(O)OR_6$, —$C(O)NR_6R_{6a}$, —$(CH_2)_rOH$, and —$(CH_2)_rNR_6R_{6a}$, wherein $R_6$ and $R_{6a}$ are the same as described above, including the embodiments thereof, and r is an integer ranging from 1 to 8.

In some embodiments, $R_{9a}$ is hydrogen, deuterium, halogen, or substituted or unsubstituted $C_{1-4}$ alkyl, wherein the substituted $C_{1-4}$ alkyl is alkyl substituted by one or more substituent(s) at any position independently selected from hydroxyl, halogen, and $C_{3-6}$ cycloalkyl.

In some embodiments, $A_1$ is —$CH_2$—, —CHF—, —$CF_2$—, —$CHCH_3$— or —$C(CH_3)_2$—.

In some embodiments, $R_5$ or $R_{5a}$ in $A_2$ is hydrogen, —$SR_6$, —$OR_6$, —$NR_6R_{6a}$, —$NHSO_2R_6$, —$NR_6SO_2R_{6a}$, —$OP(O)(O—R_6)_2$, —$OC(O)R_6$, wherein $R_6$ and $R_{6a}$ are the same as described above, including the embodiments thereof; in some embodiments, $R_6$, $R_{6a}$ are independently hydrogen, $C_{1-4}$ alkyl, halo-$C_{1-4}$ alkyl, $C_{3-8}$ cycloalkyl, 5- to 8-membered heterocycloalkyl, $C_{6-10}$ aryl, 5- to 6-membered heteroaryl, 5- to 8-membered heterocycloalkyl-$C_{1-4}$ alkyl, $C_{3-8}$ cycloalkyl-$C_{1-4}$ alkyl, $C_{6-10}$ aryl-$C_{1-4}$ alkyl, 5- to 6-membered heteroaryl-$C_{1-4}$ alkyl, or $R_6$, $R_{6a}$ together with the nitrogen atom to which they are attached, form a 3- to 8-membered mono-heterocycloalkyl ring.

In some embodiments, $A_2$ is —CHF—, —CH(CN)—, —CH(COOH)—, —CH(OH)—, —CH(OPO$_3$H)—, or —C(CH$_3$)(OH)—.

In some embodiments, $A_2$ is

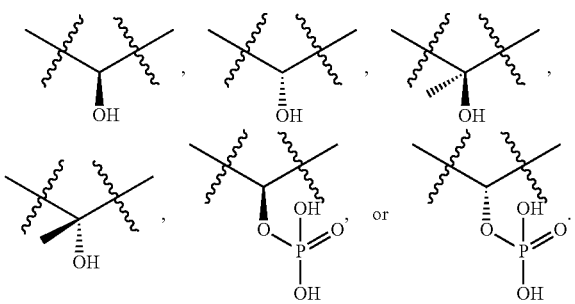

In some embodiments, A-ring is 5-membered aza-aryl, such as 5-membered diaza-aryl.

In some embodiments, Z, $Z_1$, $Z_2$, $Z_3$, and $Z_4$ in A ring are selected from (1) $Z_1$ and $Z_4$ are N; Z, $Z_2$, $Z_3$ are C; (2) $Z_1$ and $Z_3$ are N; Z, $Z_2$ and $Z_4$ are C; (3) Z, $Z_1$ and $Z_4$ are N; $Z_2$ and $Z_3$ are C; (4) $Z_1$, $Z_2$ and $Z_3$ are N; Z and $Z_4$ are C; (5) $Z_1$, $Z_2$ and $Z_4$ are N; Z and $Z_3$ are C; (6) Z, $Z_1$ are $Z_3$ are N; $Z_2$ and $Z_4$ are C; and (7) Z, $Z_1$ and $Z_2$ are N; $Z_3$ and $Z_4$ are C.

When U is $CR_4$, Z, $Z_1$, $Z_2$, $Z_3$, and $Z_4$ in A ring, for example, are selected from 1) $Z_1$ and $Z_4$ are N; Z, $Z_2$ and $Z_3$ are C; and 2) $Z_1$ and $Z_3$ are N; Z, $Z_2$ and $Z_4$ are C.

When U is N, Z, $Z_1$, $Z_2$, $Z_3$, and $Z_4$ in A ring, for example, is a ring wherein $Z_1$ and $Z_3$ are N; Z, $Z_2$ and $Z_4$ are C.

In some embodiments, B-ring is a 5- to 6-membered heteroaryl, such as thiophene, pyridine, or pyrimidine.

In some embodiments, $R_1$ is —OH, —SH, —CN, hydrogen, halogen, amino, $C_{1-3}$ alkoxy, $C_{1-3}$ alkylthiol, $C_{1-3}$ alkyl (such as methyl, ethyl, propyl or isopropyl), halo-$C_{1-3}$ alkyl or halo-$C_{1-3}$ alkoxy.

In some embodiments, $R_1$ is H, F, Cl, Br, —CH$_3$, —CN, —OCH$_3$, —OCF$_3$, or —NH$_2$.

In some embodiments, n is 1 or 2, such as 1.

In some embodiments, $R_2$ is —OH, —SH, —NH$_2$, hydrogen, halogen, $C_{1-3}$ alkoxy, $C_{1-3}$ alkylthiol, $C_{1-3}$ alkyl, or halo-$C_{1-3}$ alkyl.

In some embodiments, $R_2$ is H, or —NH$_2$.

In some embodiments, t is 1.

In some embodiments, bond α is a single bond.

In some embodiments, $R_3$ is substituted or unsubstituted $C_{1-3}$ alkyl, substituted or unsubstituted $C_{3-12}$ cycloalkyl, substituted or unsubstituted 3- to 12-membered heterocycloalkyl, substituted or unsubstituted $C_{6-10}$ aryl, substituted or unsubstituted 5- to 10-membered heteroaryl, substituted or unsubstituted bridged $C_{7-10}$ tricycloalkyl, or substituted or unsubstituted bridged 7- to 10-membered heterocycloalkyl. In some embodiments, when B ring is benzene ring, $R_3$ is substituted or unsubstituted bridged 7- to 10-membered heterocycloalkyl. In some embodiments, when B ring is benzene, $R_3$ is substituted or unsubstituted bridged $C_{7-10}$ tricycloalkyl.

In some embodiments, $R_3$, as substituted or unsubstituted $C_{3-12}$cycloalkyl, is substituted or unsubstituted $C_{3-8}$ mono-cycloalkyl, or substituted or unsubstituted $C_{7-12}$ bicycloalkyl.

In some embodiments, $R_3$, as substituted or unsubstituted 3- to 12-membered heterocycloalkyl, is substituted or unsubstituted 3- to 8-membered mono-heterocycloalkyl.

In some embodiments, $R_3$, as substituted or unsubstituted $C_{6-10}$ aryl, is substituted or unsubstituted phenyl, or substituted or unsubstituted naphthyl.

In some embodiments, $R_3$, as substituted or unsubstituted $C_{3-8}$ mono-cycloalkyl is substituted or unsubstituted cyclohexyl.

In some embodiments, $R_3$, as substituted or unsubstituted $C_{7-12}$ bicycloalkyl, is substituted or unsubstituted bicyclo[2.2.1]heptyl (including:

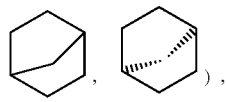), substituted or unsubstituted (1R, 5S)-bicyclo[3.2.1]octyl

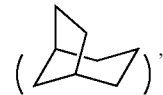, or substituted or unsubstituted decahydronaphthalenyl

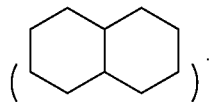.

In some embodiments, $R_3$, as substituted or unsubstituted bridged 7- to 10-membered heterocycloalkyl is substituted or unsubstituted 2-azabicyclo[2.2.1]heptyl (including:

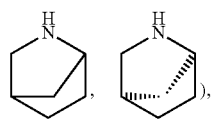), substituted or unsubstituted 2-oxabicyclo[2.2.1]heptyl (including:

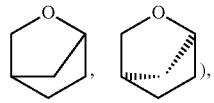), substituted or unsubstituted 2,5-diazabicyclo[2.2.1]heptyl (including:

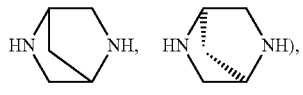), substituted or unsubstituted (1S, 5S)-9-oxabicyclo[3.3.1]nonyl

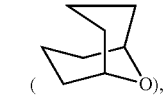, substituted or unsubstituted (1R, 5S)-8-oxabicyclo[3.2.1]octyl

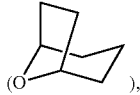

substituted or unsubstituted (1R, 5S)-3-oxabicyclo[3.2.1]octyl

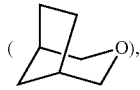

substituted or unsubstituted (1R, 5S)-3-azabicyclo [3.2.1]octyl

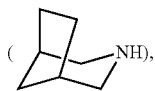

substituted or unsubstituted (1R, 5S)-8-azabicyclo[3.2.1]octyl

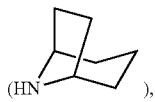

substituted or unsubstituted quinuclidinyl

substituted or unsubstituted 2-aza-bicyclo[2.2.2]octyl

or substituted or unsubstituted 2-azaadamantanyl

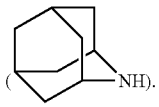

In some embodiments, $R_3$, as substituted or unsubstituted bridged $C_{7-10}$ tricycloalkyl, is substituted or unsubstituted adamantanyl

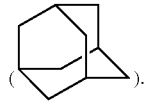

As group $R_3$, in some embodiments, substituted alkyl, substituted cycloalkyl, substituted heterocycloalkyl, substituted bridged tricycloalkyl, and substituted bridged heterocycloalkyl refer to alkyl, cycloalkyl, heterocycloalkyl, bridged tricycloalkyl and bridged heterocycloalkyl substituted by one or more $R_{10}$ and/or $R_{10a}$ at any position; As group $R_3$, in some embodiments, the substituted aryl, substituted heteroaryl refer to aryl and heteroaryl substituted by one or more $R_{10}$ at any position.

When $R_3$ is substituted, it is, for example, substituted by 1 to 3 $R_{10}$ at any position.

Wherein, $R_{10}$ is independently -L-C($R_8$)=$R_{10a}$, —NO$_2$, —CN, —OH, —NH$_2$, —SH, halogen, substituted or unsubstituted alkyl, substituted or unsubstituted alkoxy, substituted or unsubstituted aryl, substituted or unsubstituted heteroaryl, substituted or unsubstituted cycloalkyl, substituted or unsubstituted heterocycloalkyl, substituted or unsubstituted arylalkyl, substituted or unsubstituted heteroarylalkyl, substituted or unsubstituted cycloalkylalkyl, substituted or unsubstituted heterocycloalkylalkyl, substituted or unsubstituted bridged tricycloalkyl, substituted or unsubstituted $C_{2-6}$ alkynyl, substituted or unsubstituted $C_{2-6}$ alkenyl, —$C_{2-6}$ alkynyl-$R_{8b}$, -L-$R_8$, —O-L-$R_8$, —S(O)$_{0-2}$-L-$R_8$, —N($R_8$)-L-$R_{8b}$, -L-O$R_{8b}$, -L-OC(O)$R_{8b}$, -L-OC(O)NR$_8$R$_{8b}$, -L-OC(O)OR$_{8b}$, -L-OP(O)(O—$R_8$)$_2$, -L-B(O—$R_8$)$_2$, -L-OS(O)$_2$(OH), -L-OS(O)$_{1-2}$R$_{8b}$, -L-S(O)$_{1-2}$OR$_{8b}$, -L-S(O)$_2$NR$_8$R$_{8b}$, -L-S(O)$_{0-2}$R$_{8b}$, -L-S(O)$_2$N(R$_8$)C(O)NR$_8$R$_{8b}$, -L-C(O)OR$_{8b}$, -L-C(O)N(OH)R$_{8b}$, -L-C(=R$_7$)NR$_8$R$_{8b}$, -L-C(O)R$_{8b}$, -L-NR$_8$R$_{8b}$, -L-N(R$_8$)C(O)OR$_{8b}$, -L-N(R$_8$)C(O)N(R$_8$)S(O)$_2$R$_{8b}$, -L-N(R$_8$)OR$_{8b}$, -L-N(R$_8$)C(=R$_7$)NR$_8$R$_{8b}$, -L-N(R$_8$)S(O)$_{1-2}$R$_{8b}$, -L-N(R$_8$)S(O)$_{1-2}$NR$_8$R$_{8b}$, -L-N(R$_8$)C(=R$_7$)R$_{8b}$, wherein $R_7$ is the same as described above, including any embodiment thereof, and $R_8$, $R_{8b}$ may together with the nitrogen atom to which they are attached, form a 3- to 8-membered mono-heterocycloalkyl ring.

In some embodiments, $R_{10}$ is independently —NO$_2$, —CN, —OH, —NH$_2$, —SH, halogen, substituted or unsubstituted alkyl, substituted or unsubstituted alkoxy, substituted or unsubstituted aryl, substituted or unsubstituted heteroaryl, —N(R$_8$)-L-R$_{8b}$, -L-R$_8$, —O-L-R$_8$, -L-C(O)R$_{8b}$, -L-C(=R$_7$)NR$_8$R$_{8b}$, -L-S(O)$_2$R$_{8b}$, -L-NR$_8$R$_{8b}$, -L-N(R$_8$)C(=R$_7$)NR$_8$R$_{8b}$, -L-N(R$_8$)C(=R$_7$)R$_{8b}$ and -L-N(R$_8$)S(O)$_2$R$_{8b}$, wherein $R_7$ is the same as described above, including any embodiment thereof, and $R_8$ and $R_{8b}$ may together with the nitrogen atom to which they are attached, form a 3- to 8-membered mono-heterocycloalkyl ring.

As group $R_{10}$, in some embodiments, the substituted or unsubstituted alkyl is, for example, substituted or unsubstituted $C_{1-4}$ alkyl, such as substituted or unsubstituted methyl, substituted or unsubstituted ethyl, substituted or unsubstituted propyl, or substituted or unsubstituted isopropyl.

As group $R_{10}$, in some embodiments, the substituted or unsubstituted alkoxy is, for example, substituted or unsubstituted $C_{1-4}$ alkoxy.

As group $R_{10}$, in some embodiments, the substituted or unsubstituted aryl is, for example, substituted or unsubstituted $C_{6-10}$ aryl, such as substituted or unsubstituted phenyl or substituted or unsubstituted naphthyl.

As group $R_{10}$, in some embodiments, the substituted or unsubstituted heteroaryl for $R_{10}$ is, for example, substituted or unsubstituted 5- to 10-membered heteroaryl, such as substituted or unsubstituted pyridinyl, substituted or unsubstituted pyrimidinyl, substituted or unsubstituted benzoxazolyl, substituted or unsubstituted benzo[d]isoxazolyl, substituted or unsubstituted benzothiazolyl, or substituted or unsubstituted oxazolo[5,4-b]pyridinyl.

As group $R_{10}$, in some embodiments, the substituted or unsubstituted cycloalkyl is, for example, substituted or unsubstituted $C_{3-8}$ cycloalkyl, further for example, substituted or unsubstituted mono-$C_{3-8}$ cycloalkyl.

As group $R_{10}$, in some embodiments, the substituted or unsubstituted heterocycloalkyl is, for example, substituted or unsubstituted 5- to 8-membered heterocycloalkyl, such as substituted or unsubstituted mono-5- to 8-membered heterocycloalkyl.

As group $R_{10}$, in some embodiments, the substituted or unsubstituted cycloalkylalkyl is, for example, substituted or unsubstituted $C_{3-8}$ cycloalkyl-$C_{1-4}$alkyl.

As group $R_{10}$, in some embodiments, the substituted or unsubstituted heterocycloalkyl-alkyl is, for example, 5- to 8-membered heterocycloalkyl-$C_{1-4}$ alkyl.

As group $R_{10}$, in some embodiments, the substituted or unsubstituted arylalkyl is, for example, substituted or unsubstituted $C_{6-10}$ aryl-$C_{1-4}$alkyl, more preferred substituted or unsubstituted phenyl-$C_{1-4}$alkyl.

As group $R_{10}$, in some embodiments, the substituted or unsubstituted heteroarylalkyl is, for example, substituted or unsubstituted 5- to 6-membered heteroaryl-$C_{1-4}$ alkyl.

As group $R_{10}$, in some embodiments, the substituted or unsubstituted bridged tricycloalkyl is, for example, substituted or unsubstituted adamantanyl.

when said $R_{10}$ is substituted alkyl, substituted alkoxy, substituted cycloalkyl, substituted heterocycloalkyl, substituted aryl, substituted heteroaryl, substituted cycloalkylalkyl, substituted heterocycloalkylalkyl, substituted arylalkyl, substituted heteroarylalkyl, substituted bridged tricycloalkyl, substituted $C_{2-6}$ alkenyl, or substituted $C_{2-6}$ alkynyl, it is substituted by 1 to 3 $R_{13}$ at any position; wherein, $R_{13}$ is —OH, —SH, —CN, —NO$_2$, —NH$_2$, halogen, alkylthiol, —C(=R$_7$)NR$_6$R$_{6a}$, —OC(O)R$_6$, —OC(O)OR$_6$, —OC(O)NR$_6$R$_{6a}$, —C(O)OR$_6$, —C(O)R$_6$, —C(O)NR$_6$R$_{6a}$, —NR$_6$R$_{6a}$, —NR$_6$C(O)R$_{6a}$, —NR$_6$C(=R$_7$)R$_{6a}$, —NR$_6$C(O)OR$_{6a}$, —NR$_6$C(O)NR$_6$R$_{6a}$, —NR$_6$C(=R$_7$)NR$_6$R$_{6a}$, —(CH$_2$)$_r$NR$_6$R$_{6a}$, —NR$_6$S(O)$_2$R$_{6a}$, —NR$_6$S(O)$_2$NR$_6$R$_{6a}$, —S(O)$_{0-2}$R$_6$, —S(O)$_2$NR$_6$R$_{6a}$, substituted or unsubstituted alkyl, substituted or unsubstituted alkoxy, substituted or unsubstituted $C_{2-6}$ alkenyl, substituted or unsubstituted $C_{2-6}$ alkynyl, substituted or unsubstituted aryl, substituted or unsubstituted cycloalkyl, substituted or unsubstituted heterocycloalkyl, or substituted or unsubstituted heteroaryl; wherein $R_7$, $R_6$ and $R_{6a}$ are the same as described above, including each embodiment thereof; and wherein the substituted alkyl, substituted alkoxy, substituted $C_{2-6}$ alkenyl, substituted $C_{2-6}$ alkynyl, substituted aryl, substituted heteroaryl, substituted cycloalkyl, or substituted heterocycloalkyl as $R_{13}$ refer to alkyl, alkoxy, $C_{2-6}$ alkenyl, $C_{2-6}$ alkynyl, aryl, heteroaryl, cycloalkyl, or heterocycloalkyl substituted by 1 to 3 substituent(s) at any position independently selected from $C_{1-3}$ alkyl, halogen, $C_{1-3}$alkoxy, halo-$C_{1-3}$alkoxy, hydroxyl, and amino.

$R_{13}$ as a substituent for $R_{10}$ is, in some embodiments, F, Cl, Br, —OH, —SH, —CN, —NO$_2$, —NH$_2$, $C_{1-4}$alkylthiol, $C_{3-8}$cycloalkyl, —C(O)NR$_6$R$_{6a}$, —OC(O)R$_6$, —OC(O)OR$_6$, —OC(O)NR$_6$R$_{6a}$, —C(O)OR$_6$, —C(O)R$_6$, —C(O)NR$_6$R$_{6a}$, —NR$_6$R$_{6a}$, —NR$_6$C(O)R$_{6a}$, —NR$_6$C(O)R$_{6a}$, —NR$_6$C(O)OR$_{6a}$, —NR$_6$C(O)NR$_6$R$_{6a}$, —NR$_6$C(O)NR$_6$R$_{6a}$, —(CH$_2$)$_r$NR$_6$R$_{6a}$, —NR$_6$S(O)$_2$R$_{6a}$, —NR$_6$S(O)$_2$NR$_6$R$_{6a}$, —S(O)$_{0-2}$R$_6$, —S(O)$_2$NR$_6$R$_{6a}$, substituted or unsubstituted $C_{1-4}$ alkyl, substituted or unsubstituted $C_{1-4}$ alkoxy, substituted or unsubstituted $C_{2-6}$ alkenyl, substituted or unsubstituted $C_{2-6}$ alkynyl, substituted or unsubstituted phenyl, substituted or unsubstituted 5- to 6-membered heteroaryl, substituted or unsubstituted $C_{3-8}$ cycloalkyl, or substituted or unsubstituted 5- to 8-membered heterocycloalkyl; wherein $R_6$ and $R_{6a}$ are the same as described above, including each embodiment thereof; and wherein the substituted $C_{1-4}$ alkyl, substituted $C_{1-4}$ alkoxy, substituted $C_{2-6}$ alkenyl, substituted $C_{2-6}$ alkynyl, substituted phenyl, substituted 5- to 6-membered heteroaryl, substituted $C_{3-8}$ cycloalkyl, or substituted 5- to 8-membered heterocycloalkyl as $R_{13}$ refer to $C_{1-4}$ alkyl, $C_{1-4}$ alkoxy, $C_{2-6}$ alkenyl, $C_{2-6}$ alkynyl, phenyl, 5- to 6-membered heteroaryl, $C_{3-8}$ cycloalkyl, or 5- to 8-membered heterocycloalkyl substituted by 1 to 3 substituent(s) at any position independently selected from $C_{1-3}$ alkyl, halogen, $C_{1-3}$ alkoxy, halo-$C_{1-3}$ alkoxy hydroxyl, and amino.

The

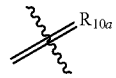

group is selected from =O, =S, =N($R_{8b}$), =N(O$R_{8b}$), =C($R_{8b}$)$_2$, =C($R_{8b}$)(O$R_{8b}$), and =C($R_{8b}$)(NH$R_{8b}$).

The

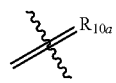

group is, for example, =O, =S, =N($R_{8b}$), or =N(O$R_{8b}$).

L is a bond or $L_1$: $L_1$ is —(C$R_8R_{8a}$)$_r$—; wherein r is an integer ranging from 1 to 8, such as ranging from 1 to 5; or $R_8$ and $R_{8a}$ together with the carbon atom to which they are attached, form a 3- to 8-membered mono-cycloalkyl ring.

In some embodiments, $L_1$ is —CH$_2$—, —CH$_2$CH$_2$—, —CH$_2$CH$_2$CH$_2$— or —C(CH$_3$)$_2$—.

$R_8$ is independently hydrogen, substituted or unsubstituted alkyl, substituted or unsubstituted alkoxy, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, one-end modified or unmodified polyethylene glycol, monosaccharide, disaccharide, amino acid, peptide with 3-20 amino acid residues, or

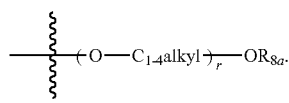

In some embodiments, $R_8$ is hydrogen, substituted or unsubstituted $C_{1-4}$ alkyl, substituted or unsubstituted $C_{1-4}$ alkoxy, substituted or unsubstituted $C_{3-8}$ cycloalkyl, substituted or unsubstituted 5- to 8-membered heterocycloalkyl, substituted or unsubstituted $C_{6-10}$ aryl, substituted or unsubstituted 5- to 10-membered heteroaryl, substituted or unsubstituted $C_{3-8}$ cycloalkyl-$C_{1-4}$ alkyl, substituted or unsubstituted 5- to 8-membered heterocycloalkyl-$C_{1-4}$ alkyl, substituted or unsubstituted $C_{6-10}$ aryl $C_{1-4}$ alkyl, substituted or unsubstituted 5- to 6-membered heteroaryl-$C_{1-4}$ alkyl, or

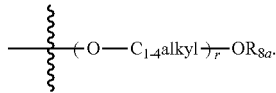

$R_{8a}$ is selected from hydrogen, halogen, hydroxyl, amino, substituted or unsubstituted alkyl, substituted or unsubstituted alkoxy, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, and substituted or unsubstituted heteroarylalkyl.

In some embodiments, $R_{8a}$ is hydrogen, halogen, hydroxyl, amino, substituted or unsubstituted $C_{1-4}$ alkyl, substituted or unsubstituted $C_{1-4}$ alkoxy, substituted or unsubstituted $C_{3-8}$ cycloalkyl, substituted or unsubstituted 5- to 8-membered heterocycloalkyl, substituted or unsubstituted $C_{6-10}$ aryl, substituted or unsubstituted 5- to 10-membered heteroaryl, substituted or unsubstituted $C_{3-8}$ cycloalkyl-$C_{1-4}$ alkyl, substituted or unsubstituted 5- to 8-membered heterocycloalkyl-$C_{1-4}$ alkyl, substituted or unsubstituted $C_{6-10}$ aryl $C_{1-4}$alkyl, substituted or unsubstituted 5- to 6-membered heteroaryl-$C_{1-4}$ alkyl.

$R_{8b}$ is selected from hydrogen, substituted or unsubstituted alkyl, substituted or unsubstituted alkoxy, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, -$L_1$-$R_8$, -$L_1$-$OR_8$, -$L_1$-$N(R_8)_2$, -$L_1$-$C(O)OR_8$, -$L_1$-$OC(O)R_8$, -$L_1$-$C(O)N(R_8)_2$, -$L_1$-$N(R_8)C(O)R_8$, -$L_1$-$N(R_8)C(O)N(R_8)_2$, -$L_1$-$N(R_8)C(S)N(R_8)_2$, -$L_1$-$OS(O)_{1-2}R_8$, -$L_1$-$S(O)_{1-2}OR_8$, -$L_1$-$S(O)_{0-2}R_8$, -$L_1$-$N(R_8)S(O)_2N(R_8)_2$, -$L_1$-$N(R_8)S(O)_2R_8$, -$L_1$-$N(R_8)C(O)N(R_8)S(O)_2R_8$, -$L_1$-$S(O)_2N(R_8)_2$, and -$L_1$-$OP(O)(O—R_8)_2$, wherein $R_8$ and $L_1$ are the same as described above, including the embodiments thereof.

In some embodiments, $R_{8b}$ is hydrogen, substituted or unsubstituted $C_{1-4}$ alkyl, substituted or unsubstituted $C_{1-4}$ alkoxy, substituted or unsubstituted $C_{3-8}$ cycloalkyl, substituted or unsubstituted 5- to 8-membered heterocycloalkyl, substituted or unsubstituted $C_{6-10}$ aryl, substituted or unsubstituted 5- to 10-membered heteroaryl, substituted or unsubstituted $C_{3-8}$ cycloalkyl-$C_{1-4}$ alkyl, substituted or unsubstituted 5- to 8-membered heterocycloalkyl-$C_{1-4}$ alkyl, substituted or unsubstituted $C_{6-10}$ aryl-$C_{1-4}$ alkyl, substituted or unsubstituted 5- to 6-membered heteroaryl-$C_{1-4}$alkyl, -$L_1$-$R_8$, -$L_1$-$OR_8$, -$L_1$-$N(R_8)_2$, -$L_1$-$C(O)OR_8$, -$L_1$-$OC(O)R_8$, -$L_1$-$C(O)N(R_8)_2$, -$L_1$-$N(R_8)C(O)R_8$, -$L_1$-$N(R_8)C(O)N(R_8)_2$, -$L_1$-$N(R_8)C(S)N(R_8)_2$, -$L_1$-$OS(O)_{1-2}R_8$, -$L_1$-$S(O)_{1-2}OR_8$, -$L_1$-$S(O)_{0-2}R_8$, -$L_1$-$N(R_8)S(O)_2N(R_8)_2$, -$L_1$-$S(O)_2N(R_8)_2$, -$L_1$-$N(R_8)S(O)_2R_8$, -$L_1$-$N(R_8)C(O)N(R_8)S(O)_2R_8$, or -$L_1$-$OP(O)(O—R_8)_2$, wherein $R_8$ and $L_1$ are the same as described above, including the embodiments thereof.

In each embodiment, when $R_8$, $R_{8a}$ or $R_{8b}$ is substituted alkyl, substituted alkoxy, substituted cycloalkyl, substituted heterocycloalkyl, substituted aryl, substituted heteroaryl, substituted cycloalkylalkyl, substituted heteroalkylalkyl, substituted arylalkyl, substituted heteroarylalkyl, the substituents therein can be 1 to 3 $R_{14}$ group at any position independently selected from —OH, —SH, —CN, —$NO_2$, —$NH_2$, halogen, alkylthiol, —C(=$R_7$)$NR_6R_{6a}$, —OC(O)$R_6$, —OC(O)$OR_6$, —OC(O)$NR_6R_{6a}$, —C(O)$OR_6$, —C(O)$R_6$, —C(O)$NR_6R_{6a}$, —$NR_6R_{6a}$, —$NR_6C(O)R_{6a}$, —$NR_6C(=R_7)R_{6a}$, —$NR_6C(O)$ $OR_{6a}$, —$NR_6C(O)NR_6R_{6a}$, —$NR_6C(=R_7)NR_6R_{6a}$, —$(CH_2)_rNR_6R_{6a}$, —$NR_6S(O)_2R_{6a}$, —$NR_6S(O)_2NR_6R_{6a}$, —$S(O)_{0-2}R_6$, —$S(O)_2NR_6R_{6a}$, substituted or unsubstituted alkyl, substituted or unsubstituted alkoxy, substituted or unsubstituted $C_{2-6}$ alkenyl, substituted or unsubstituted $C_{2-6}$ alkynyl, substituted or unsubstituted aryl, substituted or unsubstituted cycloalkyl, substituted or unsubstituted heterocycloalkyl, and substituted or unsubstituted heteroaryl; wherein $R_7$, $R_6$ and $R_{6a}$ are the same as described above, including each embodiment thereof; and wherein the substituted alkyl, substituted alkoxy, substituted $C_{2-6}$ alkenyl, substituted $C_{2-6}$ alkynyl, or substituted aryl, substituted heteroaryl, substituted cycloalkyl, or substituted heterocycloalkyl as $R_{14}$ refer to alkyl, alkoxy, $C_{2-6}$ alkenyl, $C_{2-6}$ alkynyl, aryl, heteroaryl, cycloalkyl, or heterocycloalkyl substituted by 1 to 3 substituent(s) at any position independently selected from $C_{1-3}$ alkyl, halogen, $C_{1-3}$ alkoxy, halo-$C_{1-3}$ alkoxy, hydroxyl, and amino.

In each embodiment of $R_8$, $R_{8a}$, or $R_{8b}$, wherein $R_{14}$ is, for example, F, Cl, Br, —OH, —SH, —CN, —$NO_2$, —$NH_2$, $C_{1-4}$alkylthiol, $C_{3-8}$cycloalkyl, —C(O)$NR_6R_{6a}$, —OC(O)$R_6$, —OC(O)$OR_6$, —OC(O)$NR_6R_{6a}$, —C(O)$OR_6$, —C(O)$R_6$, —C(O)$NR_6R_{6a}$, —$NR_6R_{6a}$, —$NR_6C(O)R_{6a}$, —$NR_6C(O)R_{6a}$, —$NR_6C(O)OR_{6a}$, —$NR_6C(O)NR_6R_{6a}$, —$NR_6C(O)NR_6R_{6a}$, —$(CH_2)_rNR_6R_{6a}$, —$NR_6S(O)_2R_{6a}$, —$NR_6S(O)_2NR_6R_{6a}$, —$S(O)_{0-2}R_6$, —$S(O)_2NR_6R_{6a}$, substituted or unsubstituted $C_{1-4}$ alkyl, substituted or unsubstituted $C_{1-4}$ alkoxy, substituted or unsubstituted $C_{2-6}$ alkenyl, substituted or unsubstituted $C_{2-6}$ alkynyl, substituted or unsubstituted phenyl, substituted or unsubstituted 5- to 6-membered heteroaryl, substituted or unsubstituted $C_{3-8}$ cycloalkyl, or substituted or unsubstituted 5- to 8-membered heterocycloalkyl; wherein $R_6$ and $R_{6a}$ are the same as described above, including each embodiment thereof and wherein the substituted $C_{1-4}$ alkyl, substituted $C_{1-4}$ alkoxy, substituted $C_{2-6}$ alkenyl, substituted phenyl, substituted $C_{2-6}$ alkynyl, substituted 5- to 6-membered heteroaryl, substituted $C_{3-8}$ cycloalkyl, or substituted 5- to 8-membered heterocycloalkyl as $R_{13}$ refer to $C_{1-4}$ alkyl, $C_{1-4}$ alkoxy, $C_{2-6}$ alkenyl, $C_{2-6}$ alkynyl, phenyl, 5- to 6-membered heteroaryl, $C_{3-8}$ cycloalkyl, or 5- to 8-membered heterocycloalkyl substituted by 1 to 3 substituent(s) at any position independently selected from $C_{1-3}$ alkyl, halogen, $C_{1-3}$ alkoxy, halo-$C_{1-3}$ alkoxy hydroxyl, and amino.

In some embodiments, $R_{10}$ is hydrogen, F, Cl, Br, methyl, ethyl, methoxy, ethoxy, isopropoxy, cyclohexyloxy, phenoxy, benzyloxy, phenyl, pyridinyl, pyrimidinyl, tetrazole, carboxyl, —OH, —$NO_2$, —$NH_2$, —NHC(O)$CH_3$, —C(O)$NH_2$, —CN, —$OCF_3$, —$CF_3$, —$CH_2OH$, —$CH_2NH_2$, —$OP(O)(OH)_2$,

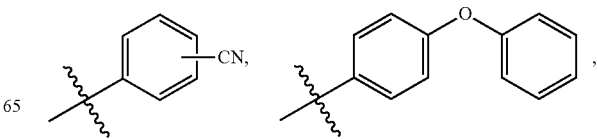

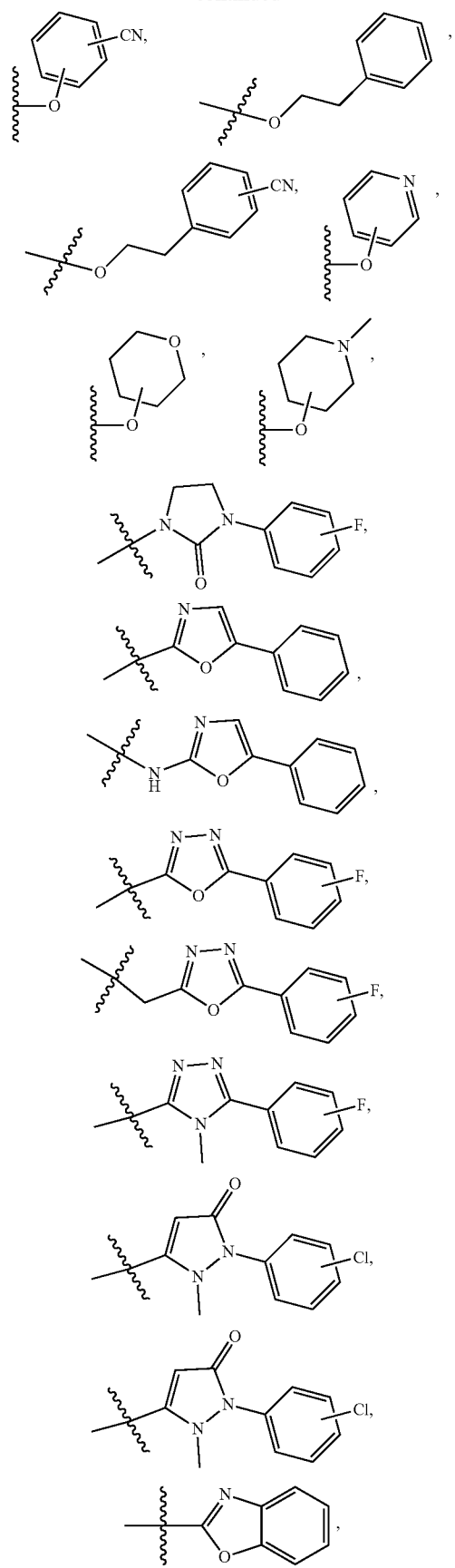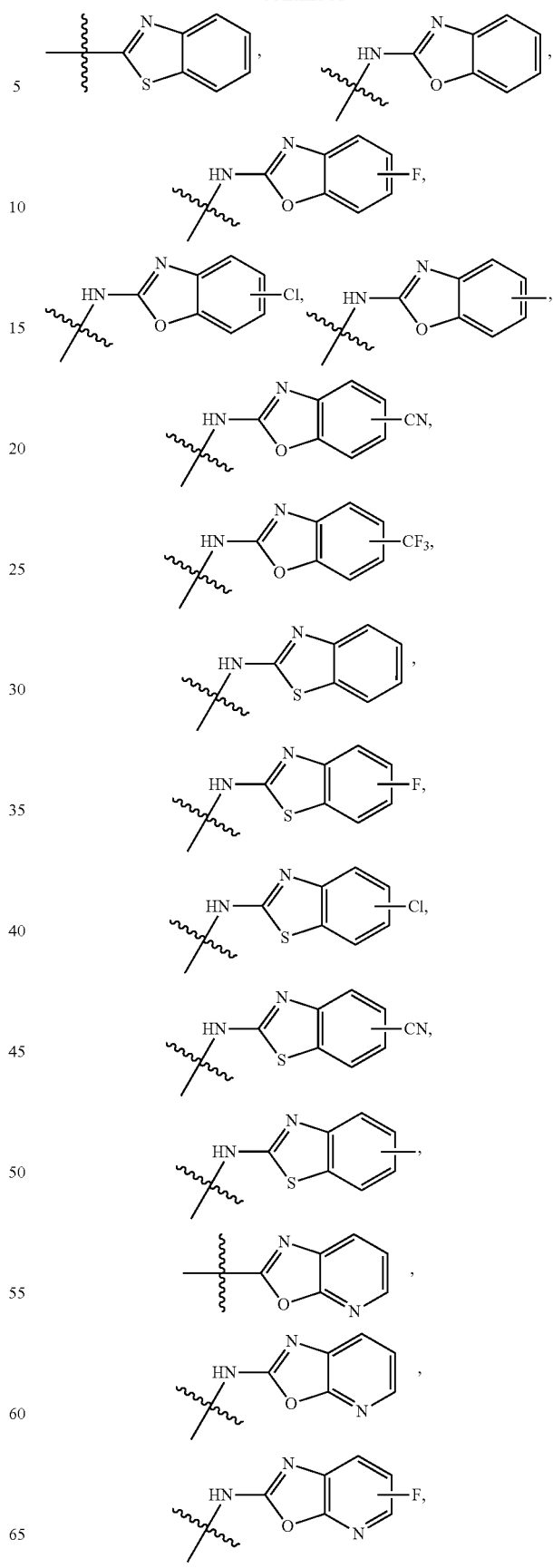

-continued
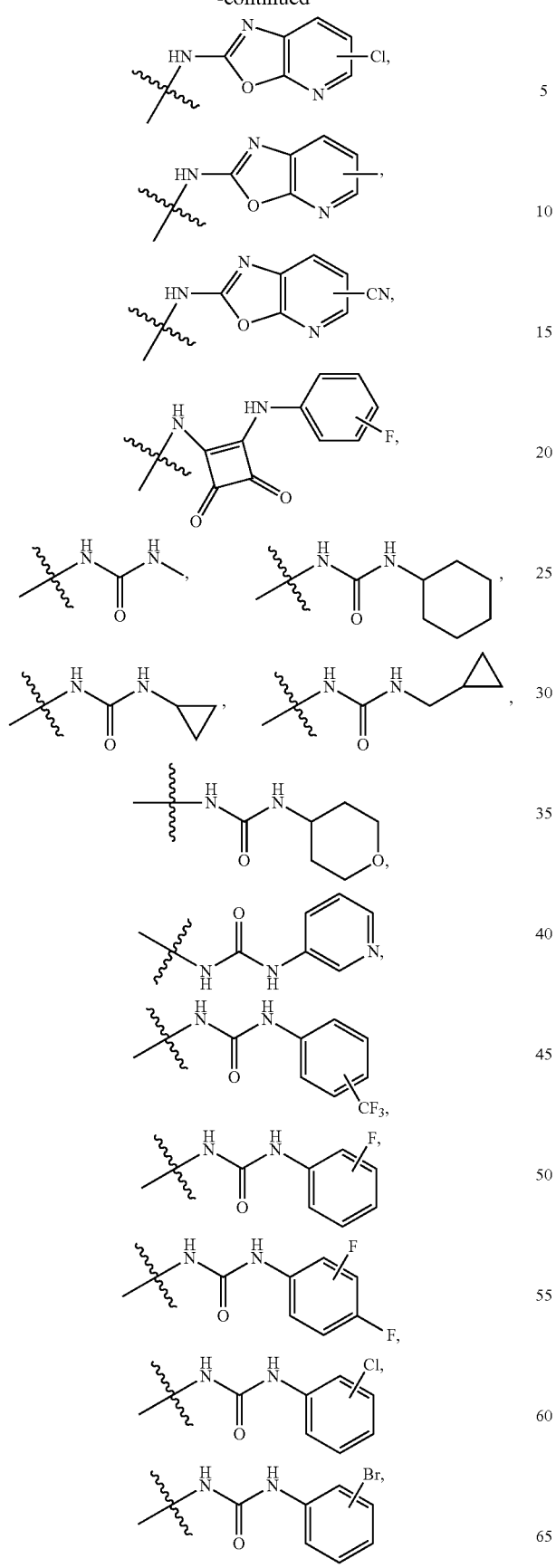
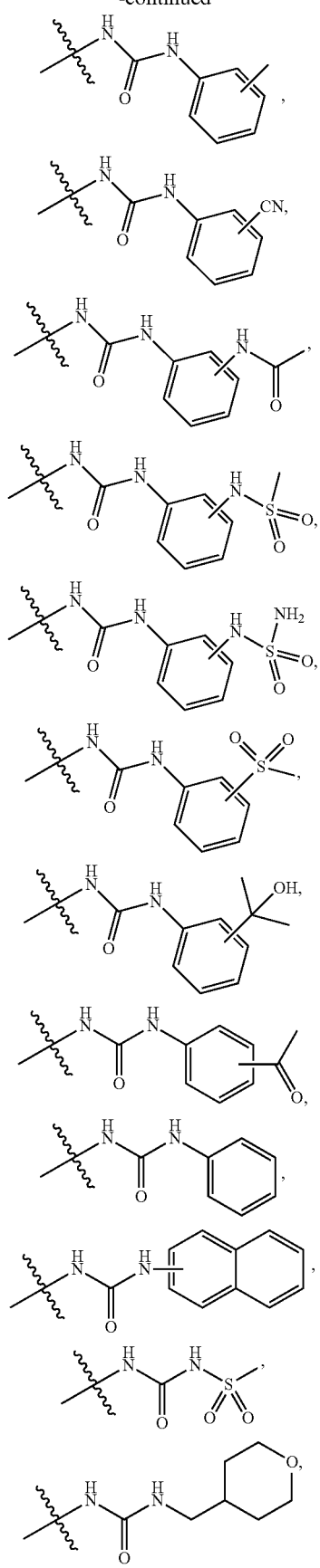

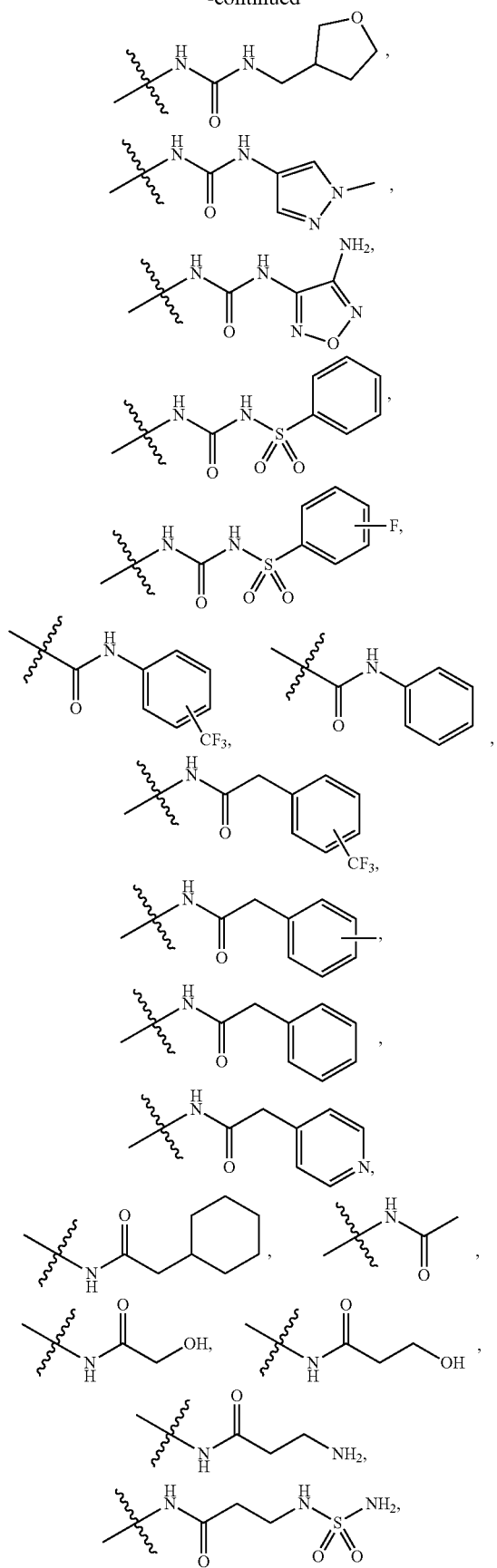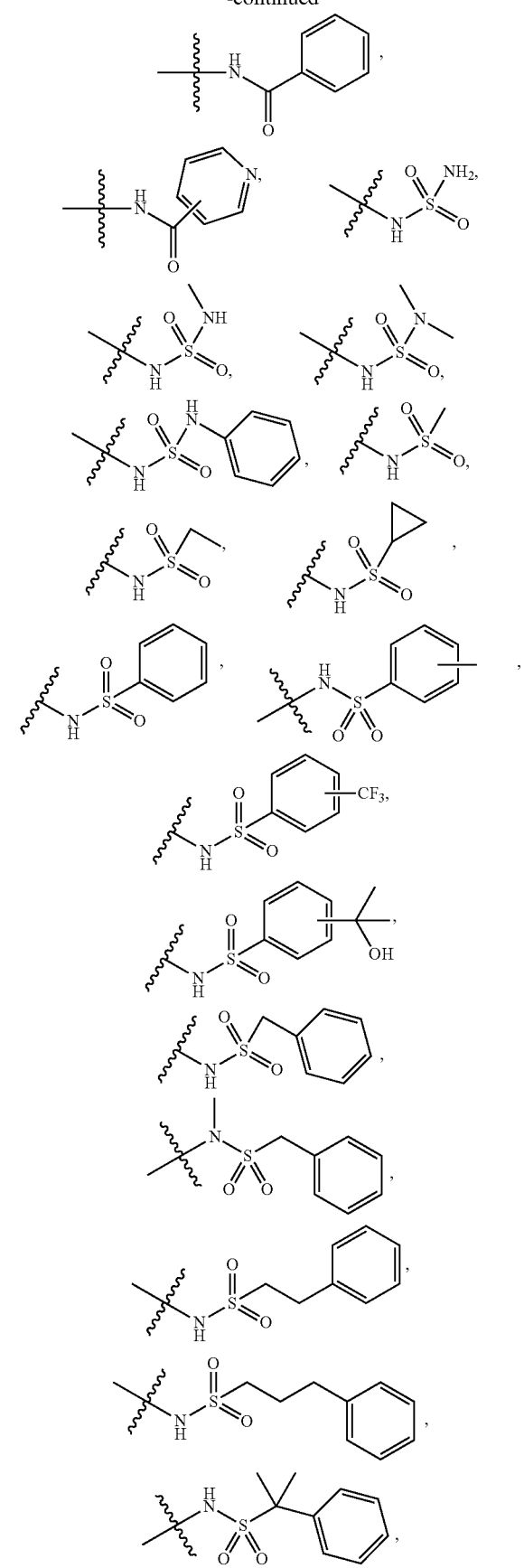

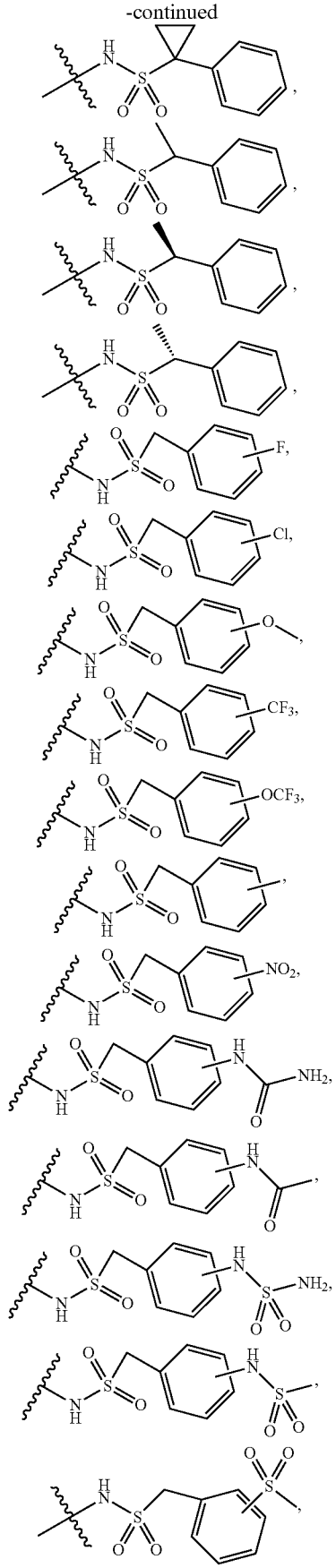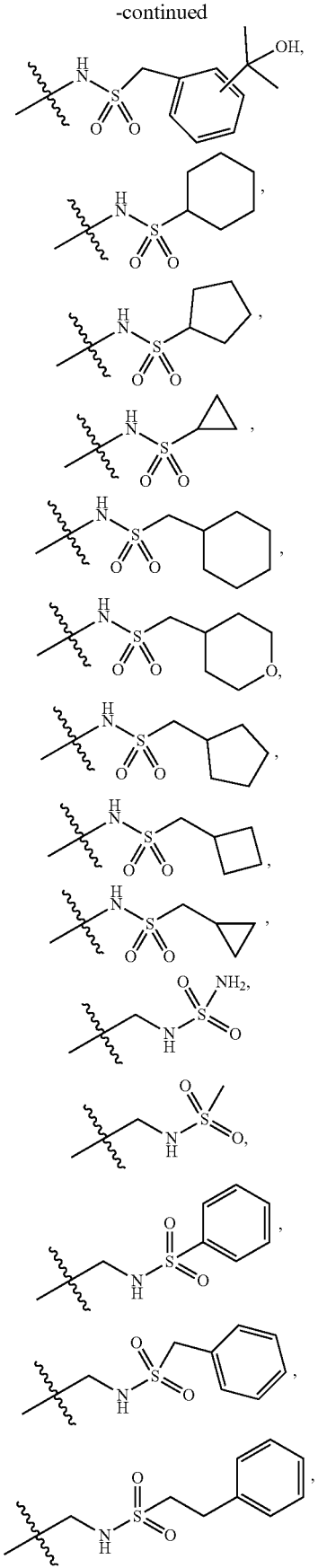

-continued
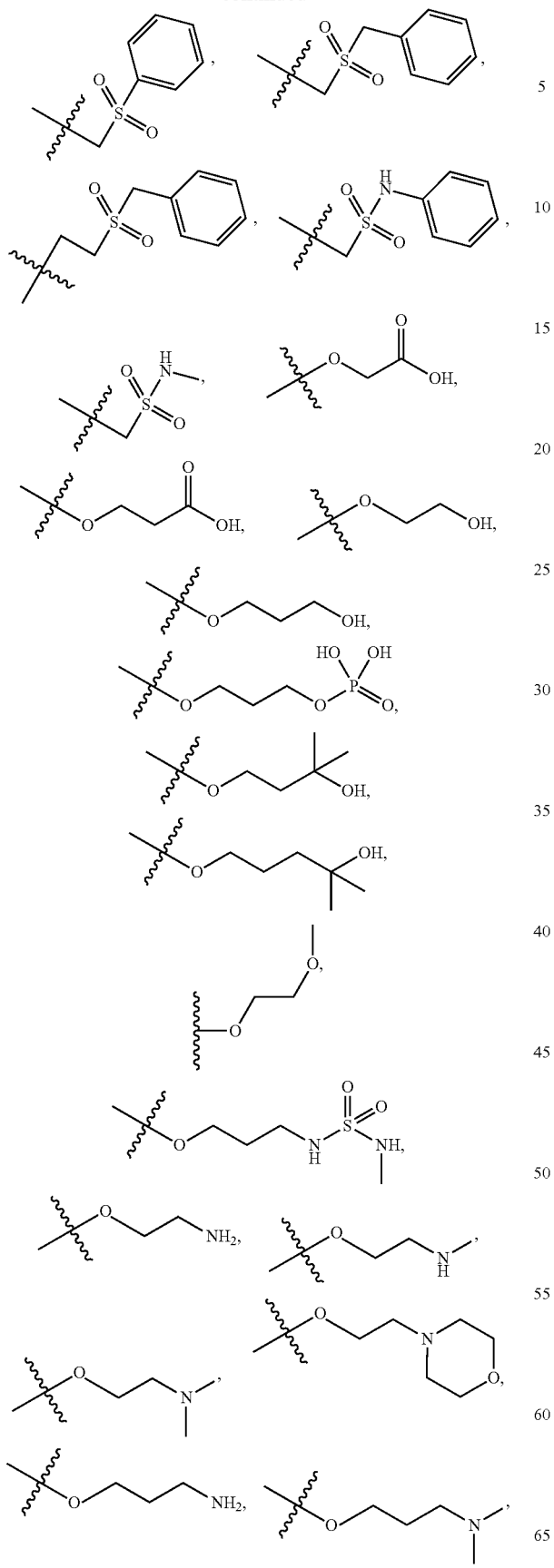
-continued
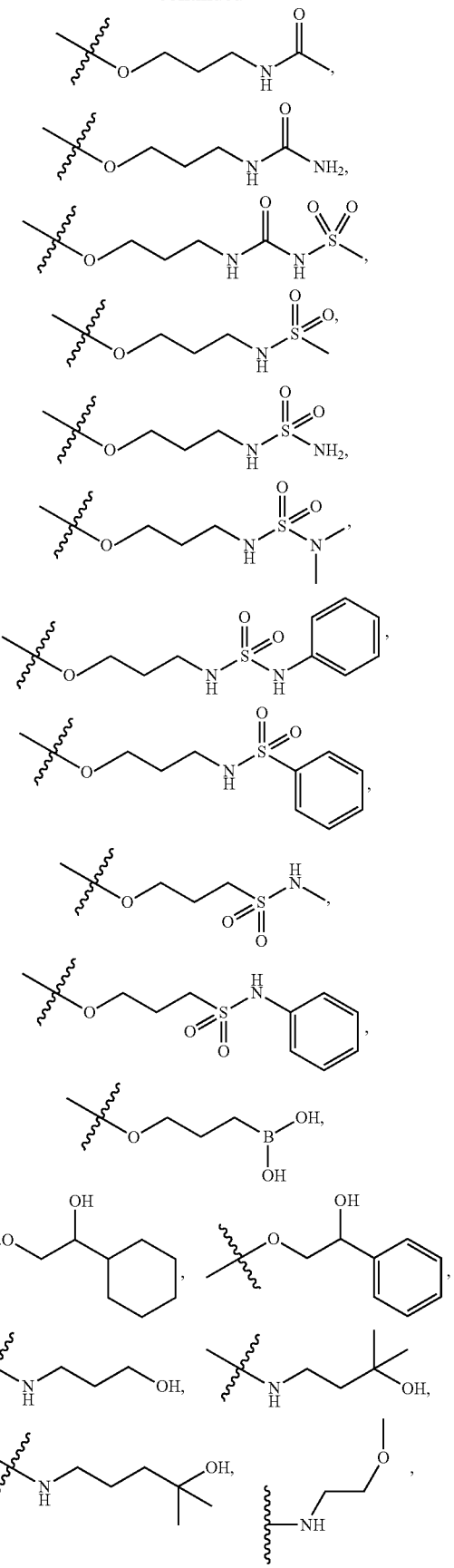

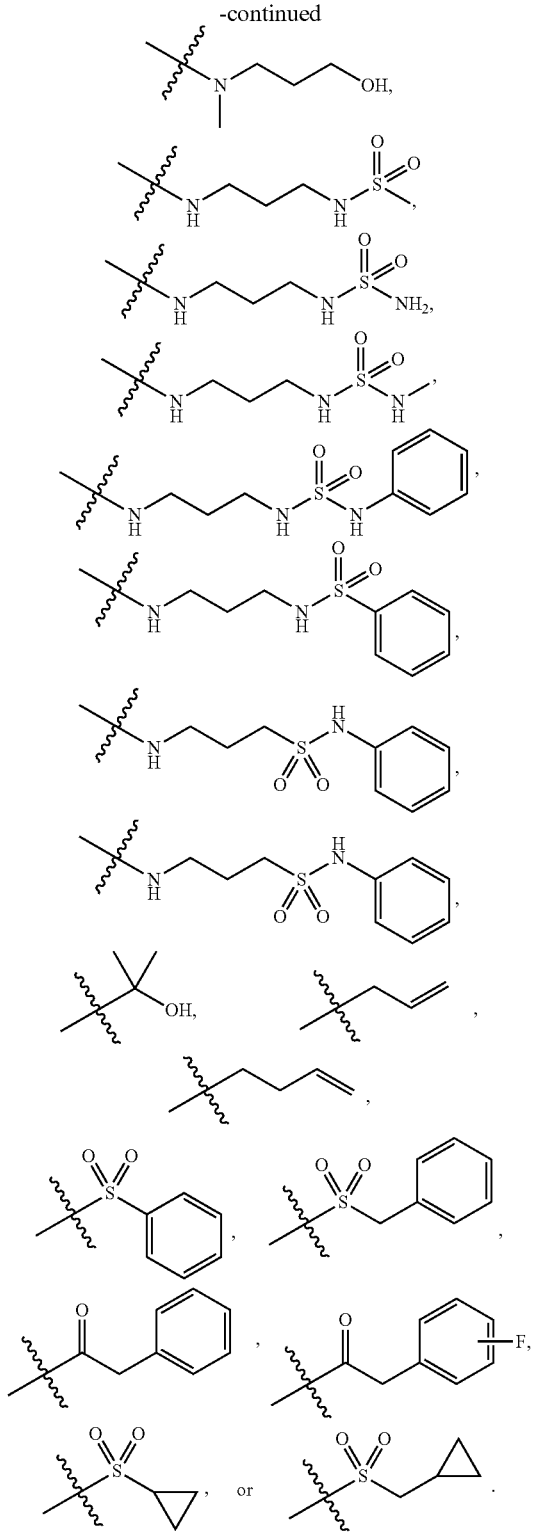
In some embodiments, $R_{10a}$ is
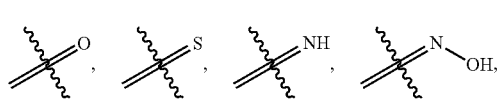
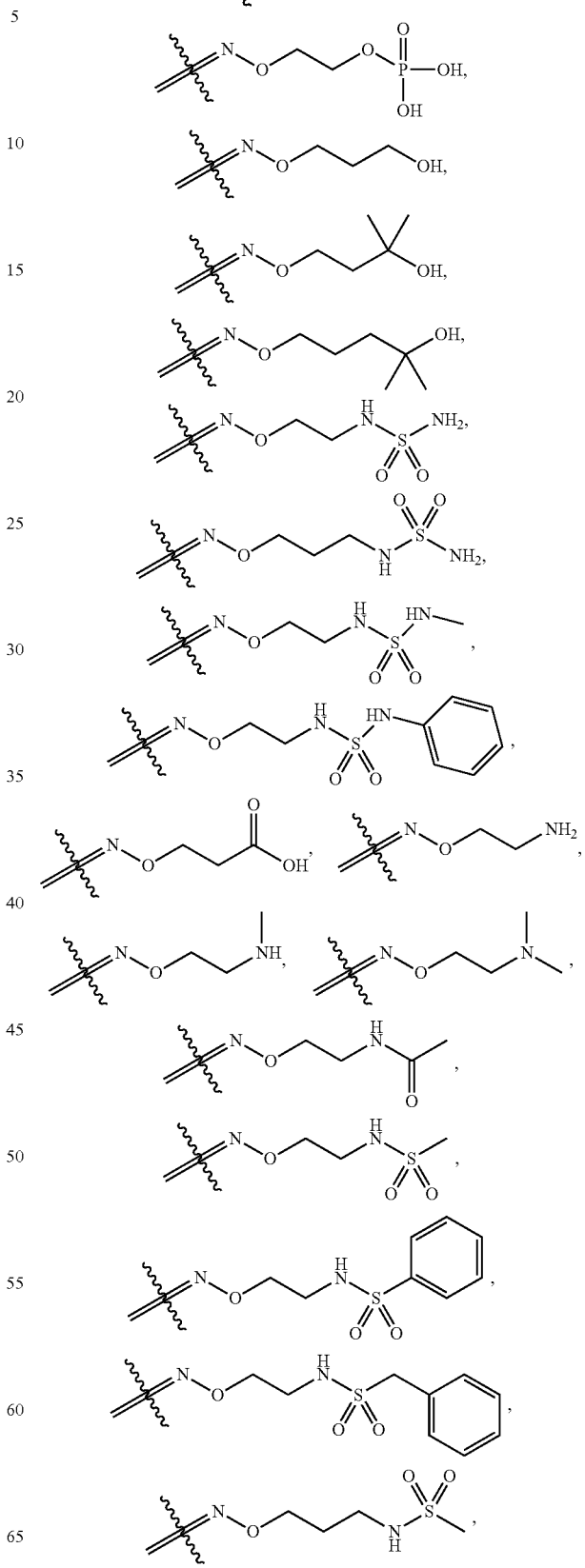

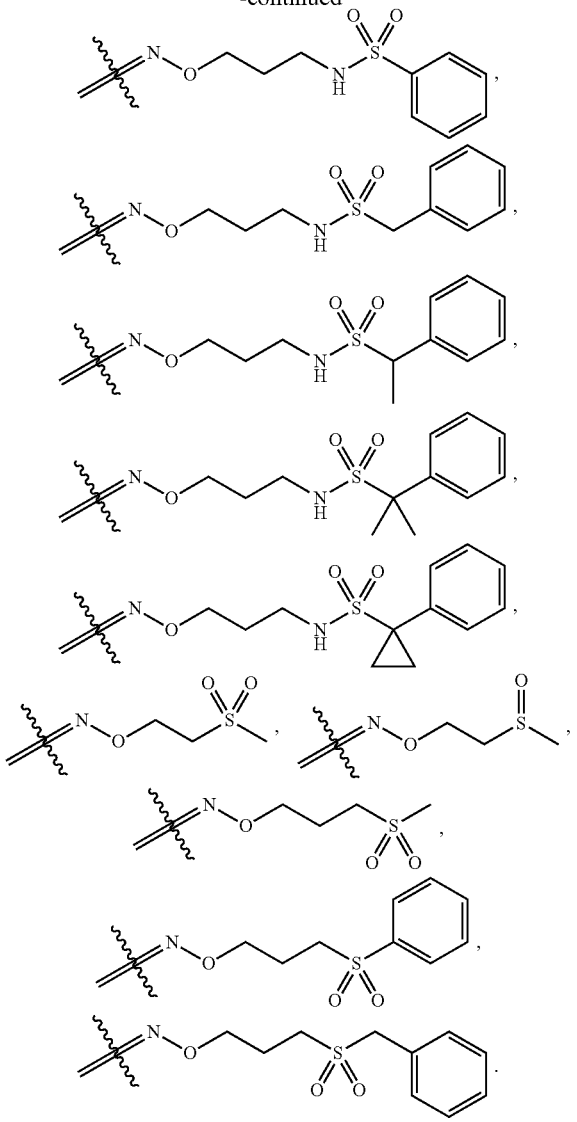
In some embodiments, $R_3$ is
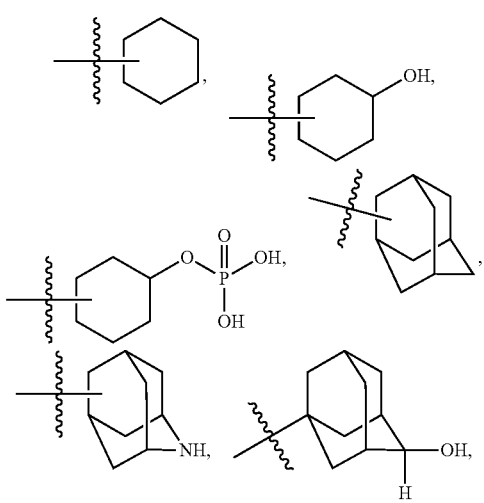
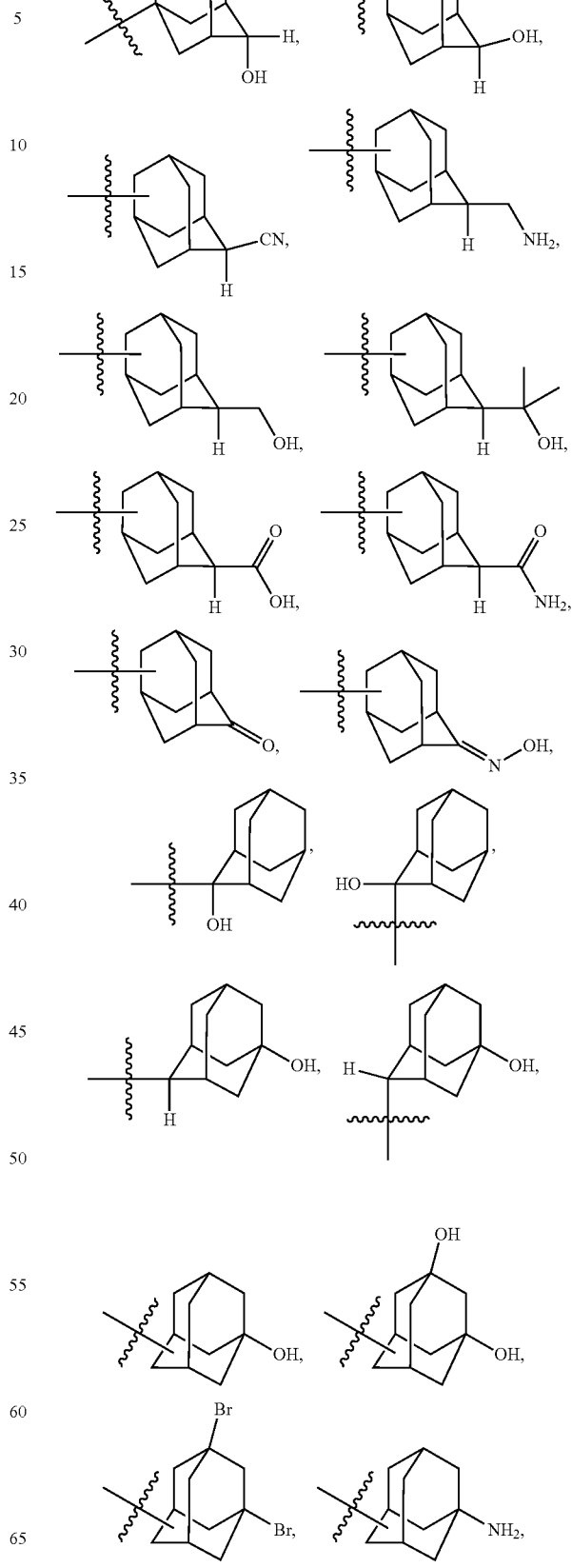

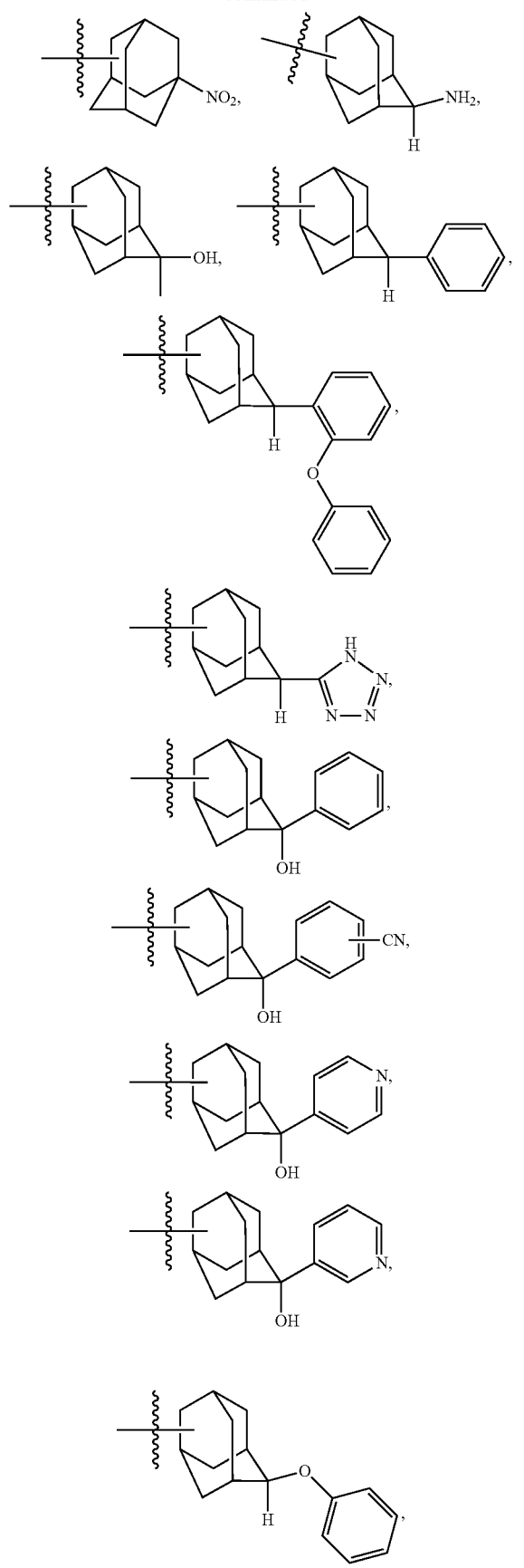
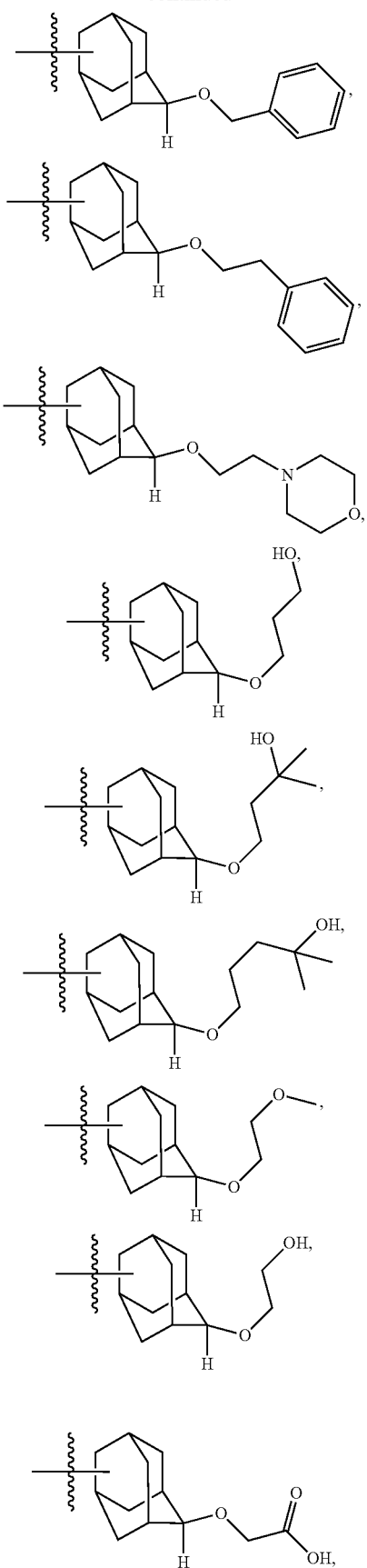

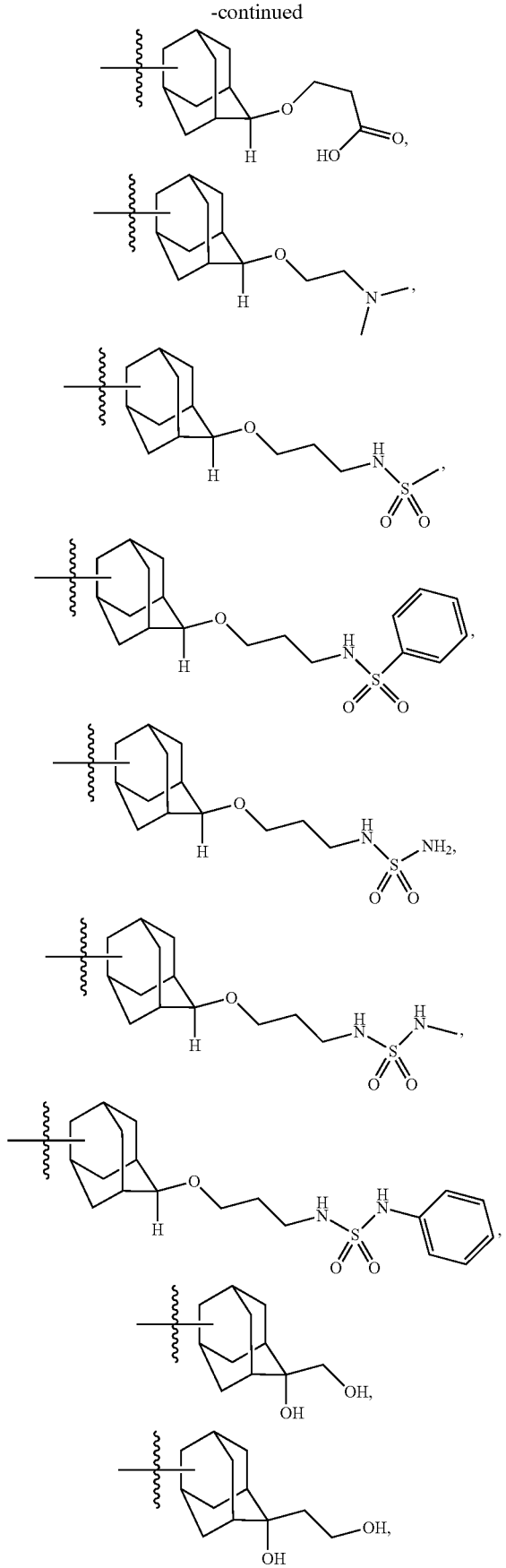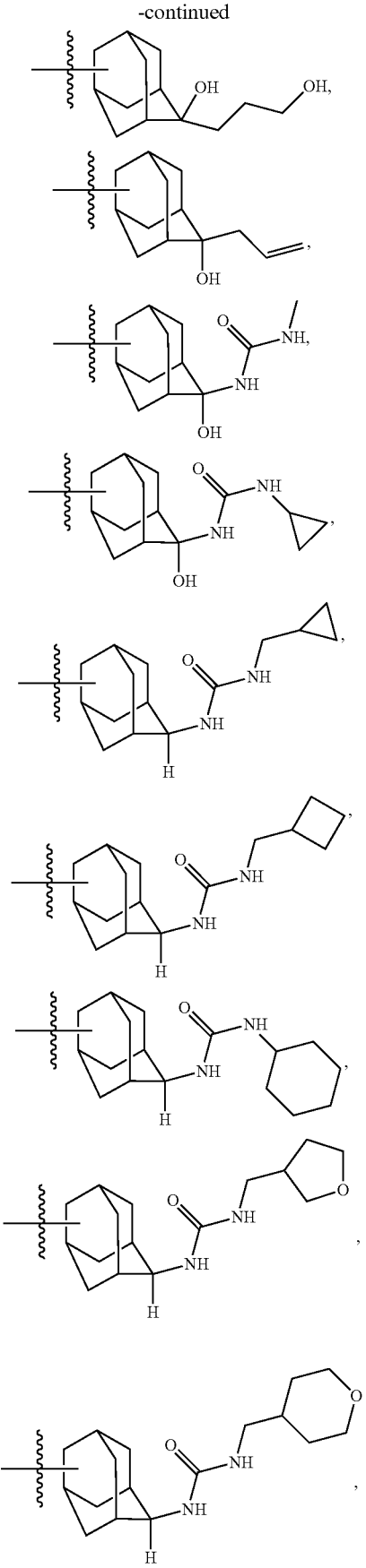

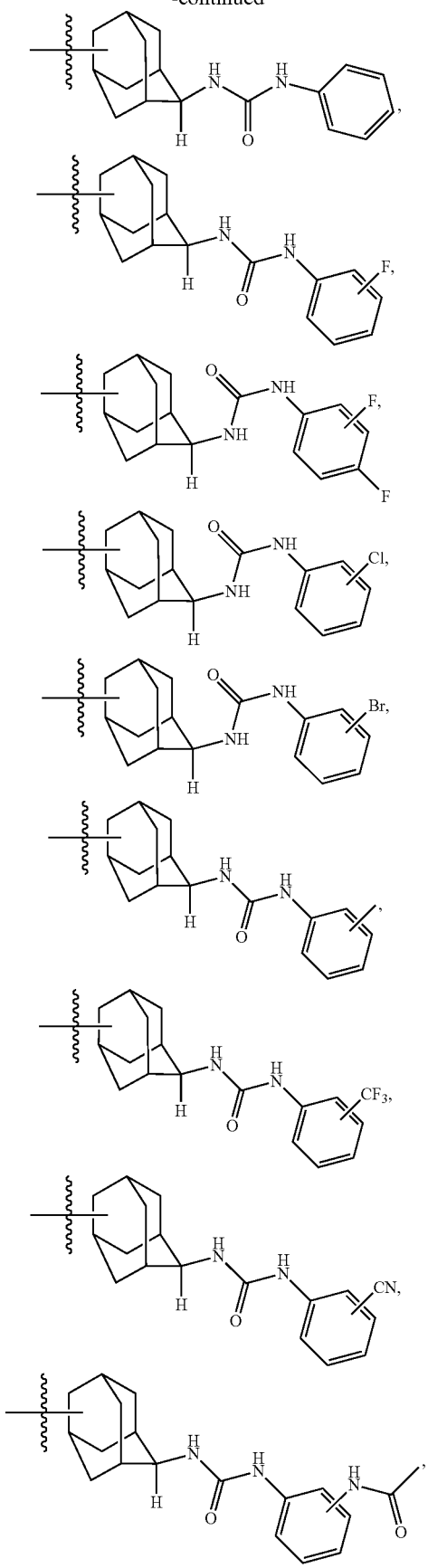
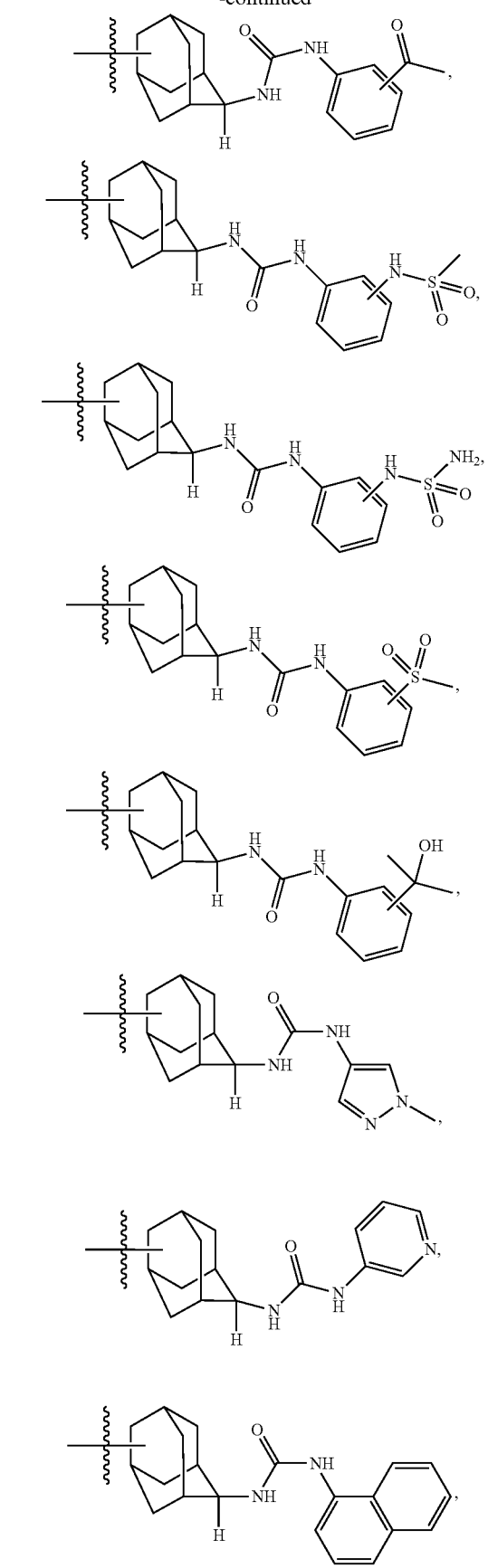

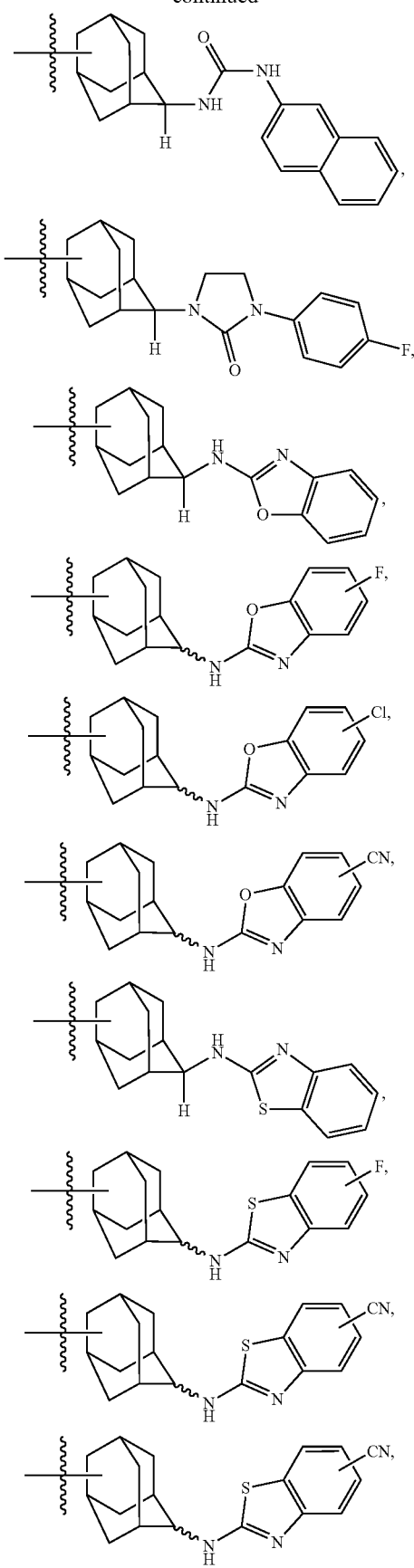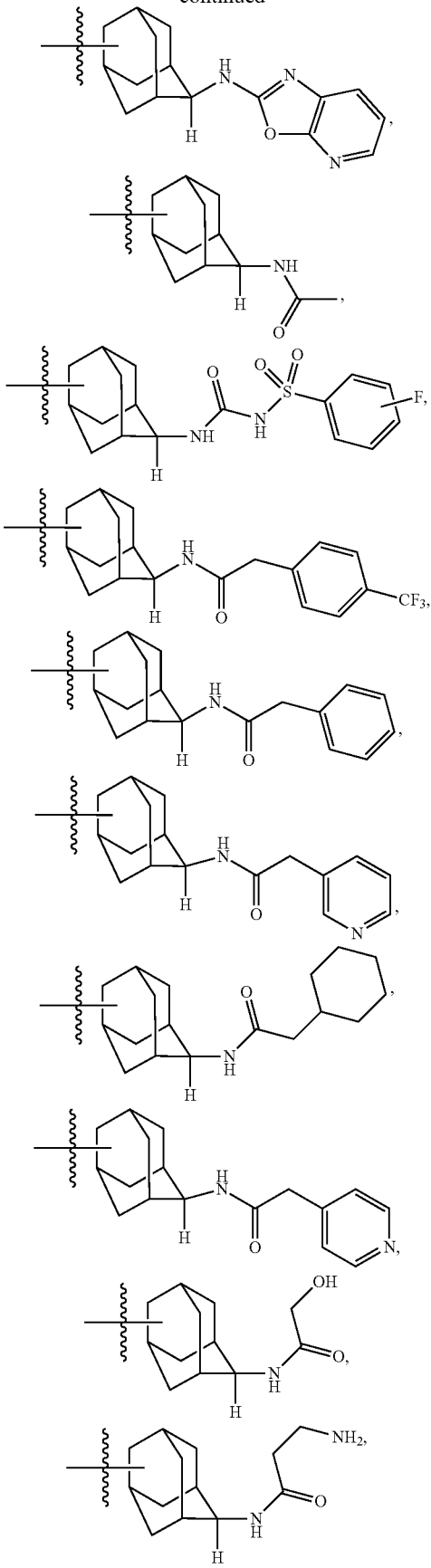

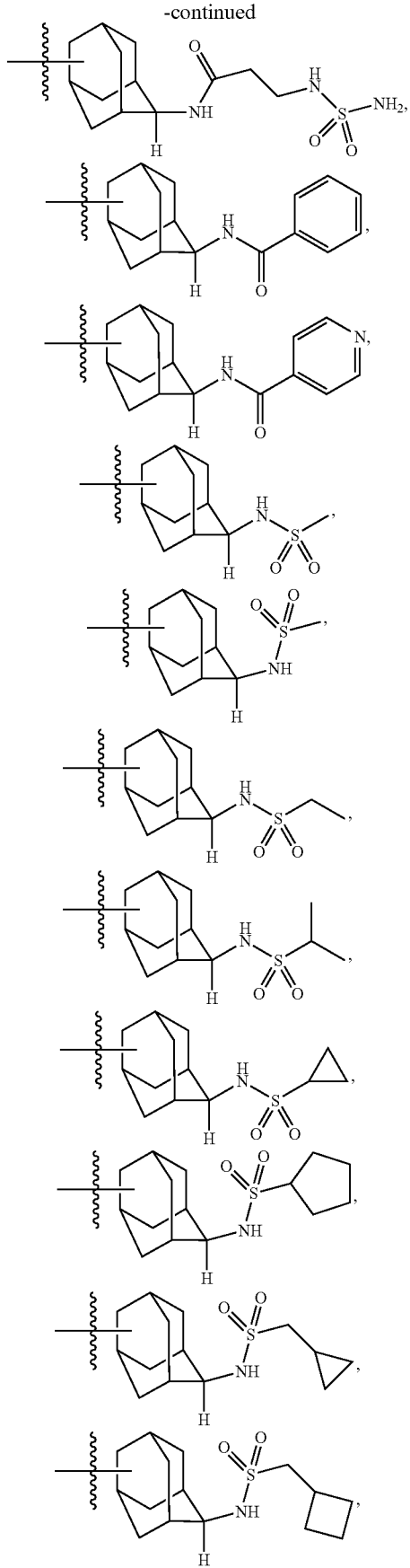
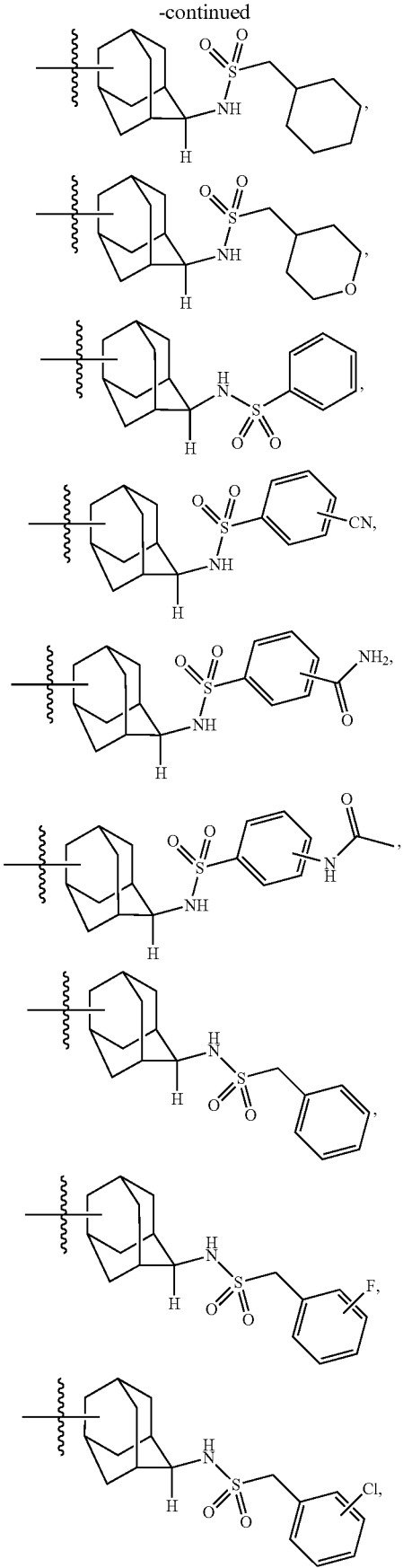

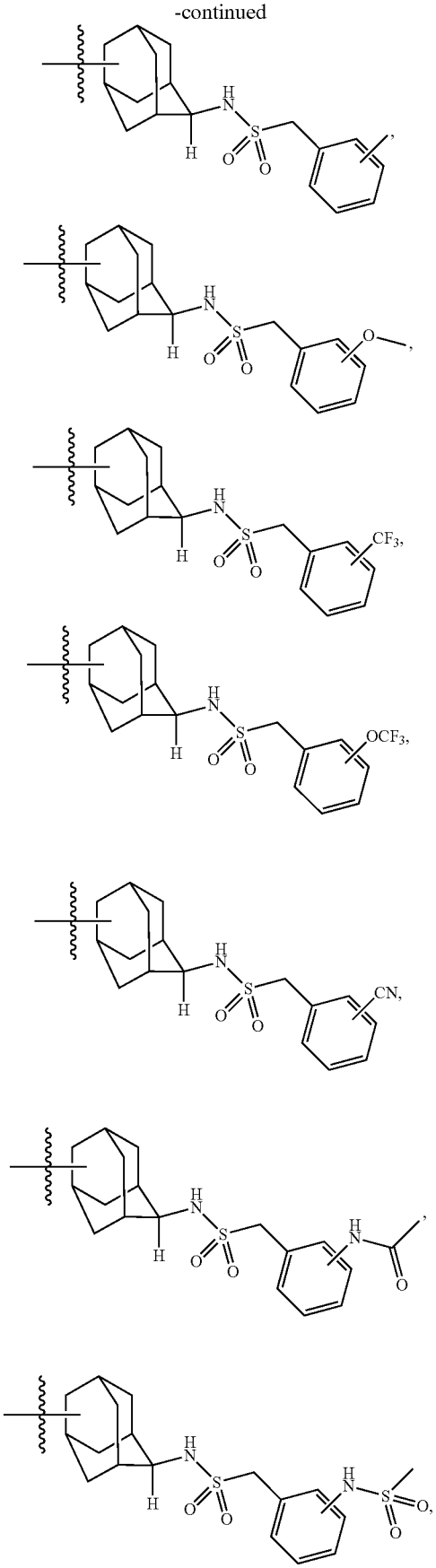
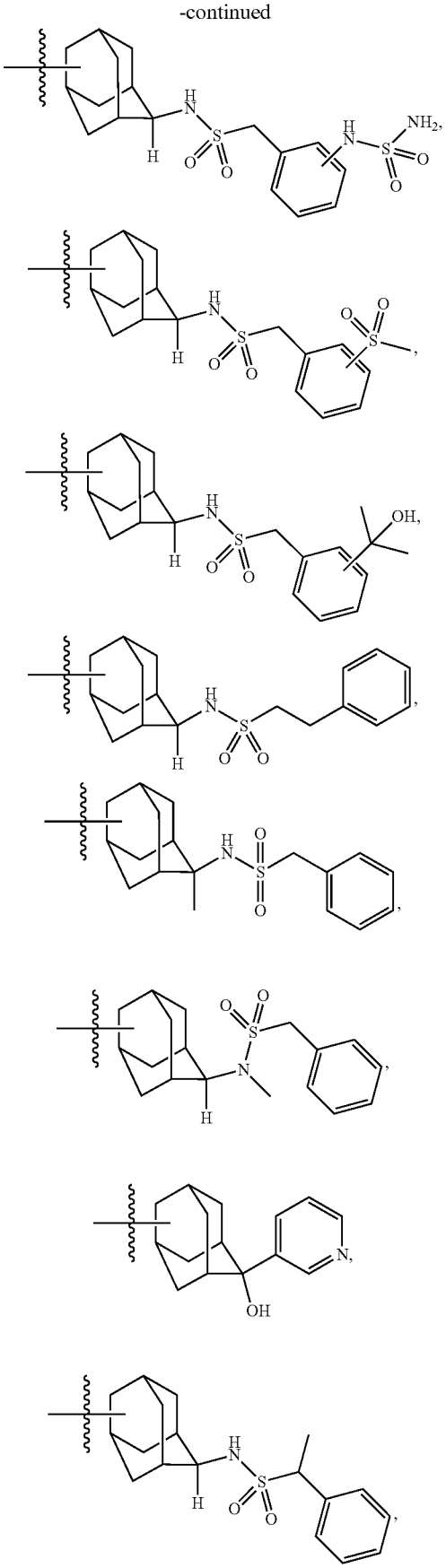

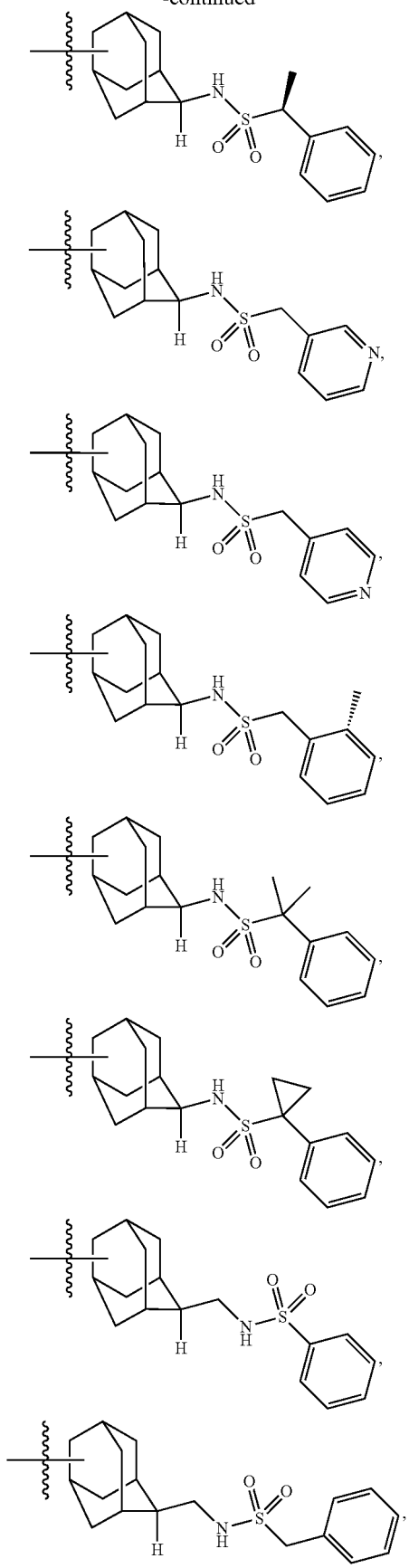
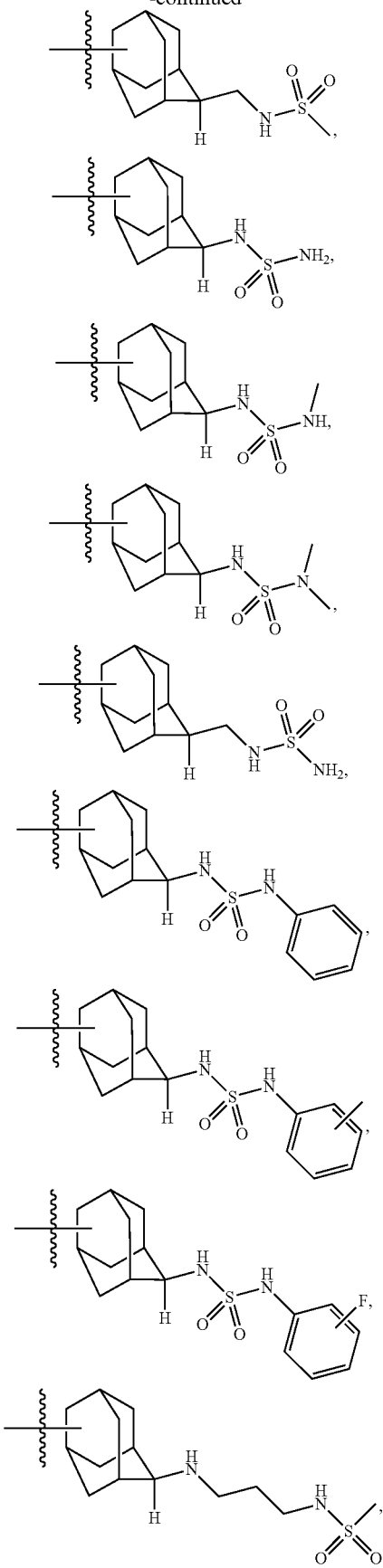

-continued
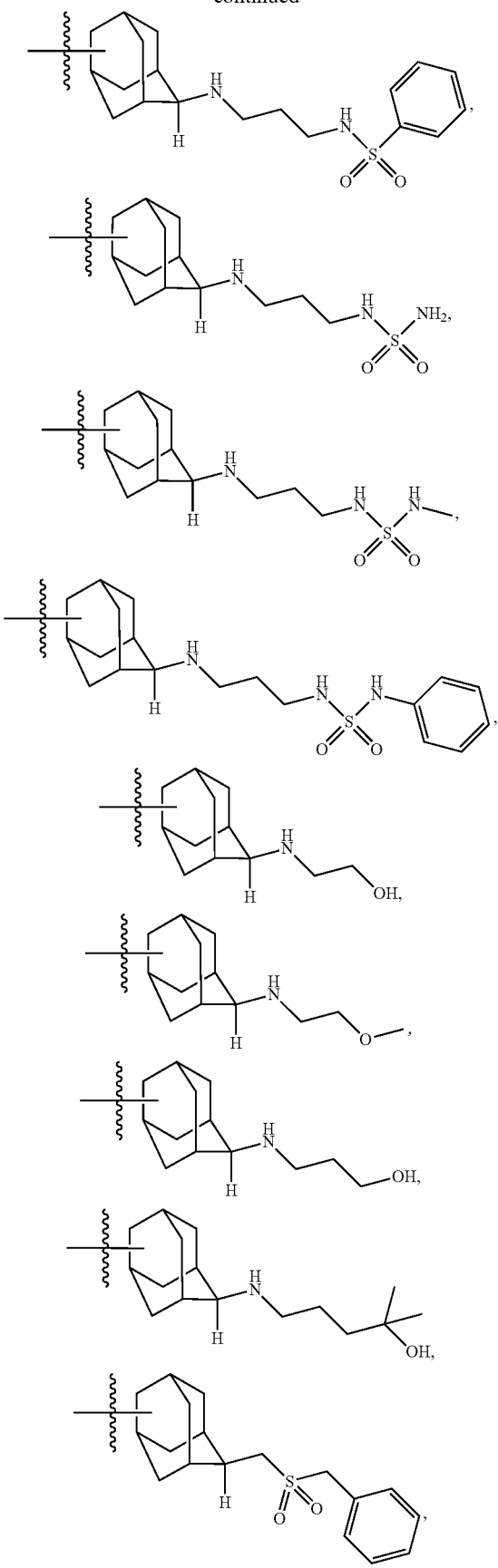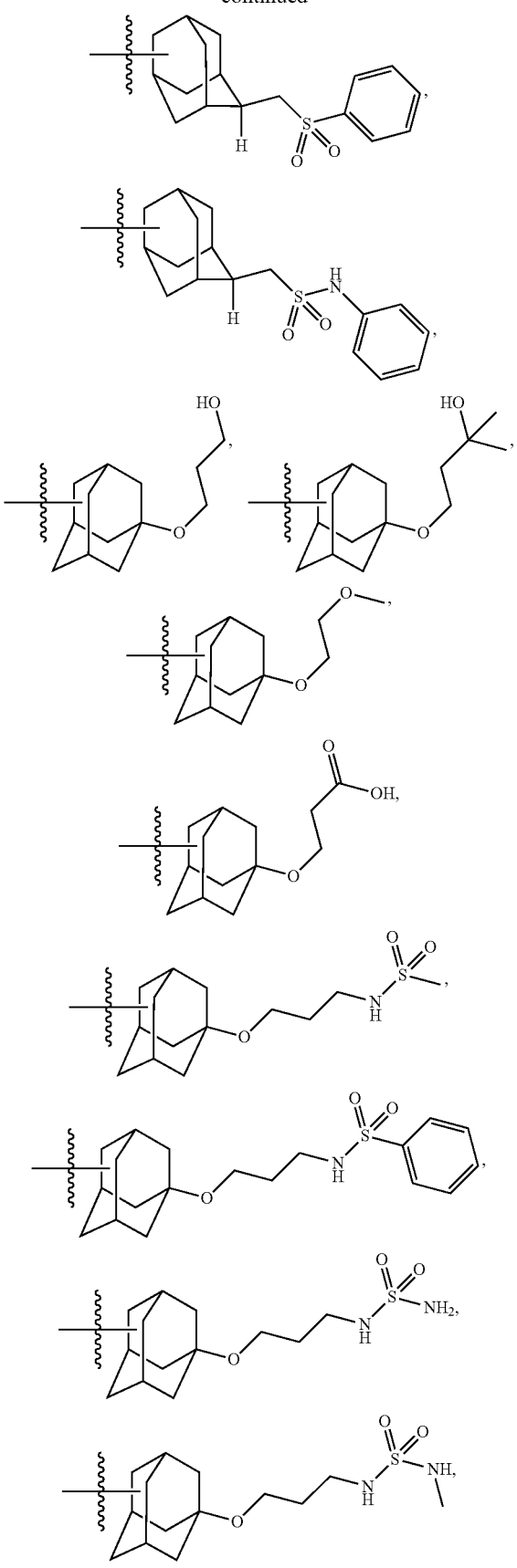

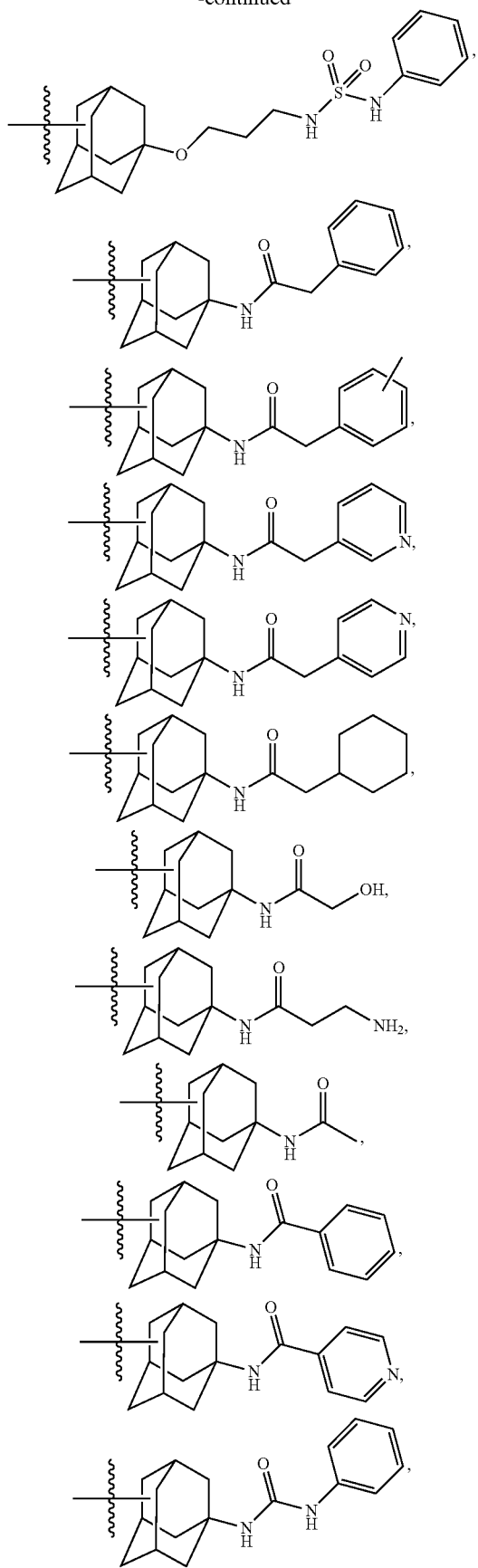
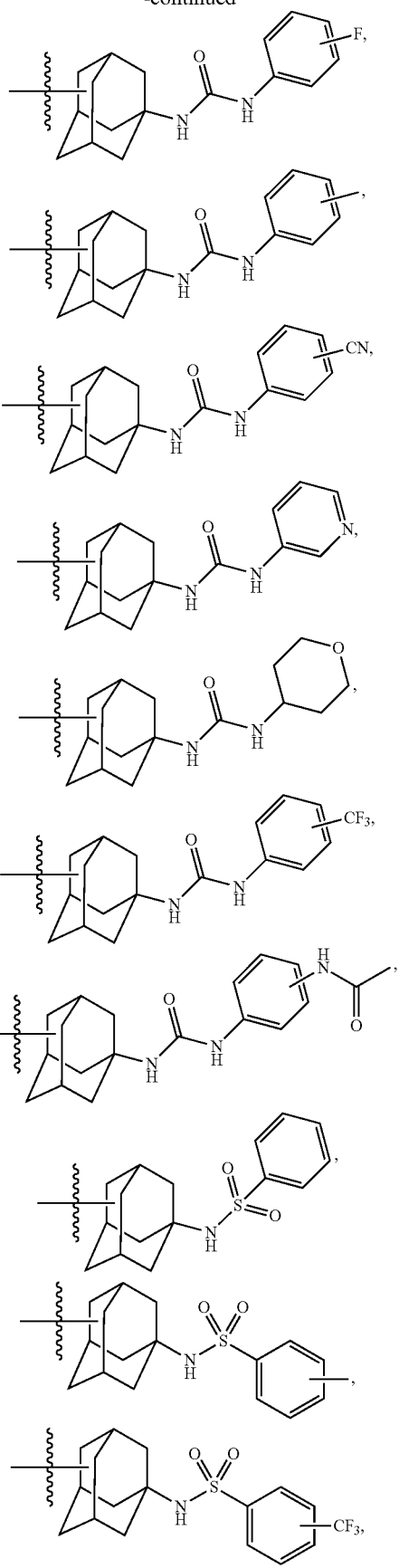

-continued
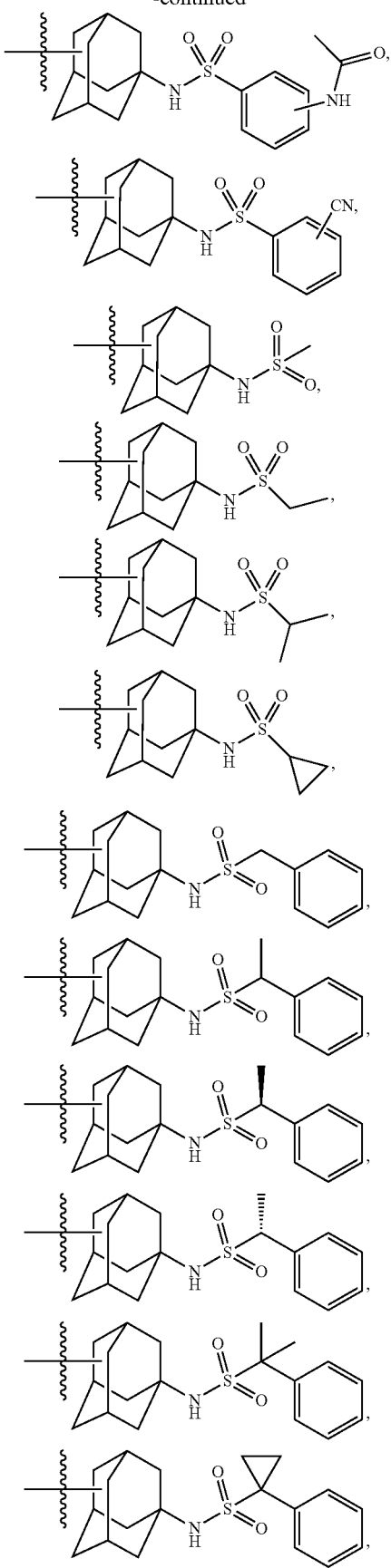
-continued
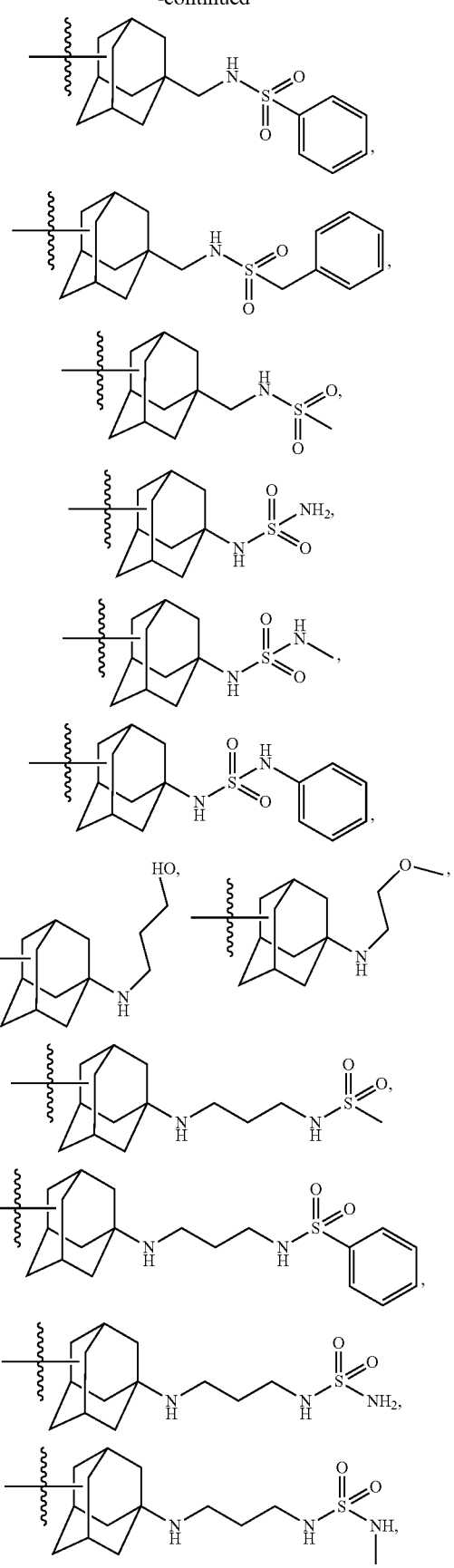

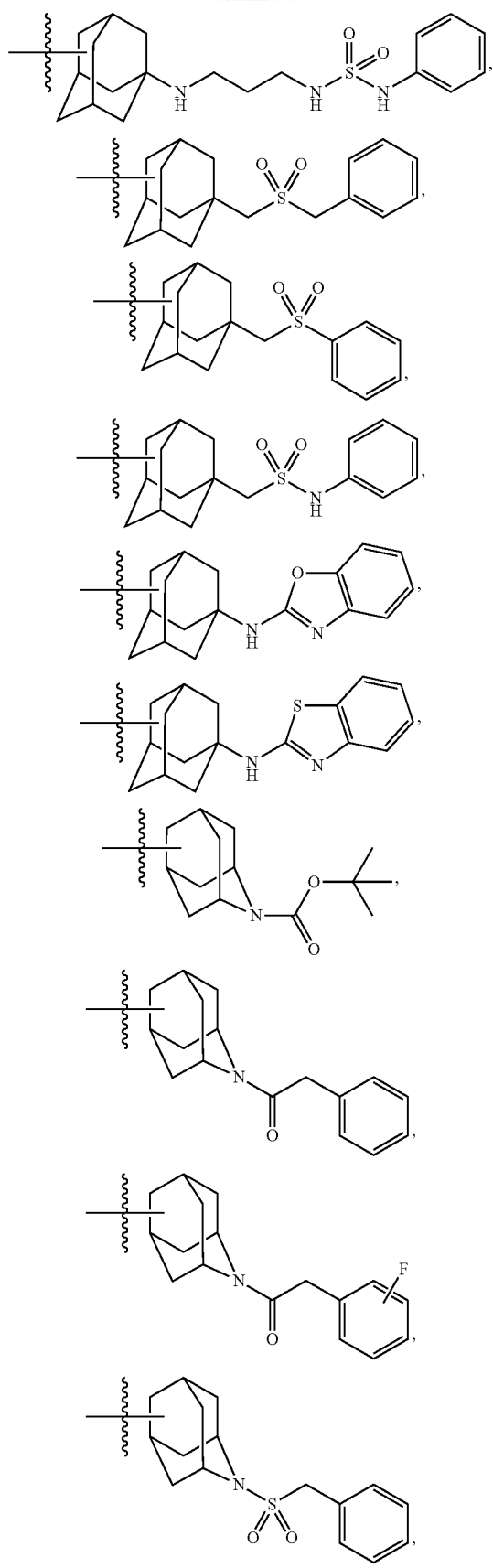
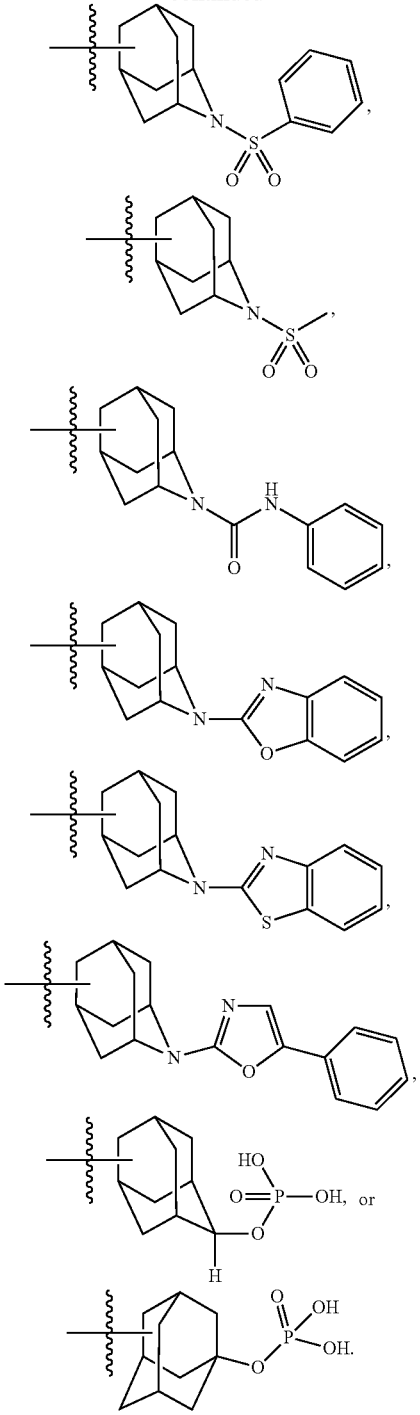

The substituted alkyl or substituted alkoxy for $R_4$ can be alkyl or alkoxy substituted by one or more, such as 1 to 3, $R_{12}$ group at any position independently selected from halogen, hydroxyl, alkyl, substituted or unsubstituted cycloalkyl, substituted or unsubstituted heterocycloalkyl, bridged tricycloalkyl, alkoxy, aryl, heteroaryl, amino, —$SR_6$, —$NR_6R_{6a}$, —$S(O)_2NR_6R_{6a}$, —$NR_6C(O)NR_6R_{6a}$, —$C(O)R_6$, —$S(O)_{0\text{-}2}R_6$, —$C(O)OR_6$, —$(CH_2)_rOH$, and —$(CH_2)_rNR_6R_{6a}$, wherein $R_6$, and $R_{6a}$ are the same as described above, and r is an integer ranging from 1 to 8.

The substituted cycloalkyl or substituted heterocycloalkyl for $R_{12}$ is cycloalkyl or heterocycloalkyl substituted by one or more of substituent(s) independently selected from hydroxyl, amino, and halogen.

In some embodiments, $R_{12}$ is hydroxyl, alkoxy, cyclohexyl, adamantanyl or amino.

In some embodiments, $R_4$ is hydrogen, fluorine, hydroxyl, $C_{1-4}$ alkoxy, or substituted or unsubstituted $C_{1-4}$ alkyl.

In some embodiments, $R_4$ is hydrogen, fluorine, hydroxyl, or methyl.

Combination of any embodiment of the variables $A_1$, $A_2$, U, B, Z, $Z_1$-$Z_4$, $R_1$-$R_{13}$ as described above is within the scope of formula (I) of the disclosure.

In some embodiments, the compound of formula (I) and/or a pharmaceutically acceptable salt thereof is 1) a compound of formula (IA) and/or a pharmaceutically acceptable salt thereof, 2) a compound of formula (IB) and/or a pharmaceutically acceptable salt thereof, 3) a compound of formula (IC) and/or a pharmaceutically acceptable salt thereof, or 4) a compound of formula (ID) and/or a pharmaceutically acceptable salt thereof,

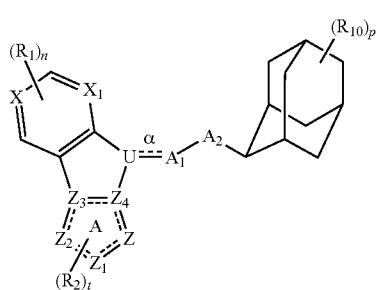
(IA)

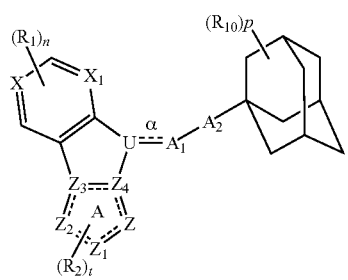
(IB)

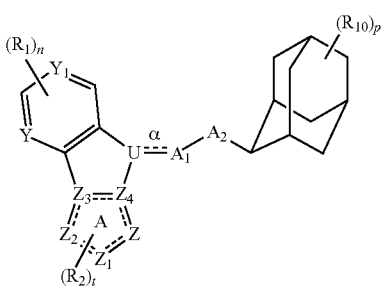
(IC)

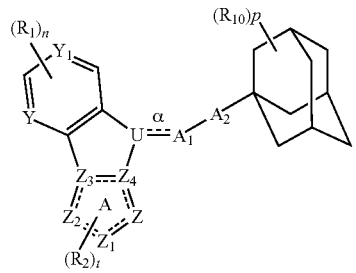
(ID)

Wherein,

Y, $Y_1$, X, and $X_1$ are independently C or N; and p is 1 or 2;

Z, $Z_1$, $Z_2$, $Z_3$, $Z_4$, $R_1$, $R_2$, U, bond α, $A_1$, $A_2$, $R_{10}$, and n are the same as described for formula (I), including each of the embodiments thereof.

Combination of any embodiment of Y, $Y_1$, X, $X_1$, p (as described for formulae (IA)-(ID)), Z, $Z_1$, $Z_2$, $Z_3$, $Z_4$, $R_1$, $R_2$, U, bond α, $A_1$, $A_2$, $R_{10}$, n and t as described for formula (I) is within the scope of formulae (IA)-(ID).

Combination of the embodiments described below for formulae (IA)-(ID) is also within the scope of formulae (IA)-(ID).

In some embodiments of formulae (IA)-(ID), bond α is a single bond, and U is $CR_4$, wherein $R_4$ is the same as described for formula (I), including each of the embodiments thereof.

In some embodiments of formulae (IA)-(ID), Y, $Y_1$, X, and $X_1$ are C.

In Some embodiments of formulae (IA)-(IB), one of X and $X_1$ is N and the other is C.

In some embodiments of formulae (IC)-(ID), one of Y and $Y_1$ is N and the other is C.

In some embodiments of formulae (IA)-(ID), n is 2, and $R_1$ is independently selected from —OH, —SH, —CN, hydrogen, halogen, amino, $C_{1-3}$ alkoxy, $C_{1-3}$ alkylthiol, $C_{1-3}$ alkyl (such as methyl, ethyl, propyl or isopropyl), halo-$C_{1-3}$ alkyl and halo-$C_{1-3}$ alkoxy.

In some embodiments of formulae (IA)-(ID), t is 2, and $R_2$ is independently selected from —OH, —SH, —$NH_2$, hydrogen, halogen, $C_{1-3}$ alkoxy, $C_{1-3}$ alkylthiol, $C_{1-3}$ alkyl, and halo-$C_{1-3}$ alkyl.

In some embodiments of formulae (IA)-(ID), Z and $Z_2$ are C, $Z_1$ is N, and one of $Z_3$ and $Z_4$ is N and the other is C.

In some embodiments of formulae (IA)-(ID), $A_1$ is —$CH_2$—, —CHF—, —$CF_2$—, —$CHCH_3$— or —$C(CH_3)_2$—.

In some embodiments of formulae (IA)-(ID), $A_2$ is is —CHF—, —CH(CN)—, —CH(COOH)—, —CH(OH)—, —CH($OPO_3$H)—, —C($CH_3$)(OH)—,

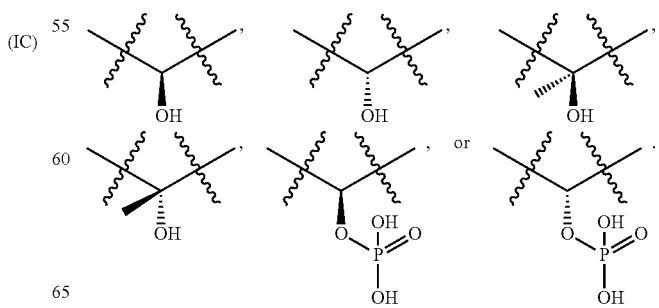

In some embodiments, the compound of formula (I) and/or a pharmaceutically acceptable salt thereof is
1) a compound of formula (IA-1) and/or a pharmaceutically acceptable salt thereof, or
2) a compound of formula (IB-1) and/or a pharmaceutically acceptable salt thereof,

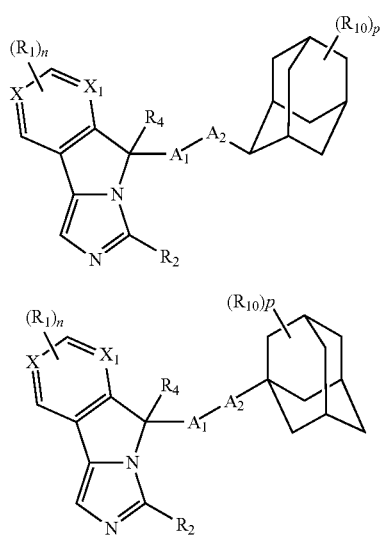

(IA-1)

(IB-1)

Wherein,
X and $X_1$ are independently C or N; p is 1 or 2,
$R_1$, $R_2$, $R_4$, $R_{10}$, $A_1$, $A_2$, and n are the same as described for formula (I), including each of the embodiments thereof.

Combination of any embodiment of X, $X_1$, p (as described for formulae (IA-1) and (IB-1)), $R_1$, $R_2$, $A_1$, $A_2$, $R_4$, $R_{10}$ and n as described for formula (I) is within the scope of formulae (IA-1) and (IB-1).

Combination of the embodiments described below for formulae (IA-1) and (IB-1) is also within the scope of formulae (IA-1) and (IB-1).

In some embodiments of formulae (IA-1) and (IB-1), X and $X_1$ are C.

In Some embodiments of formulae (IA-1) and (IB-1), one of X and $X_1$ is N and the other is C.

In some embodiments of formulae (IA-1) and (IB-1), n is 2, and $R_1$ is independently selected from —OH, —SH, —CN, hydrogen, halogen, amino, $C_{1-3}$ alkoxy, $C_{1-3}$ alkylthiol, $C_{1-3}$ alkyl (such as methyl, ethyl, propyl or isopropyl), halo-$C_{1-3}$ alkyl and halo-$C_{1-3}$ alkoxy.

In some embodiments of formulae (IA-1) and (IB-1), $R_2$ is independently selected from —OH, —SH, —NH$_2$, hydrogen, halogen, $C_{1-3}$ alkoxy, $C_{1-3}$ alkylthiol, $C_{1-3}$ alkyl, and halo-$C_{1-3}$ alkyl.

In some embodiments of formulae (IA-1) and (IB-1), $A_1$ is —CH$_2$—, —CHF—, —CF$_2$—, or —CHCH$_3$— or —C(CH$_3$)$_2$—.

In some embodiments of formulae (IA-1) and (IB-1), $A_2$ is —CHF—, —CH(CN)—, —CH(COOH)—, —CH(OH)—, —CH(OPO$_3$H)—, —C(CH$_3$)(OH)—,

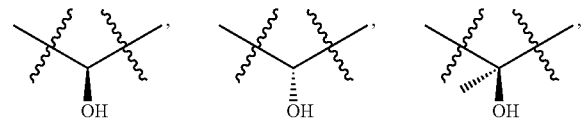

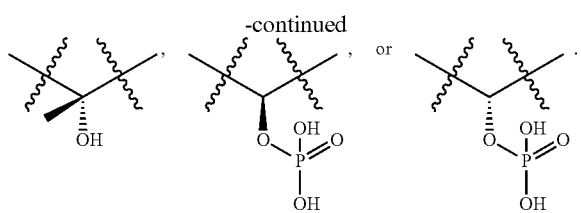

In some embodiments, the compound of formula (I) and/or a pharmaceutically acceptable salt thereof is
1) a compound of formula (IE) and/or a pharmaceutically acceptable salt thereof, or
2) a compound of formula (IF) and/or a pharmaceutically acceptable salt thereof,

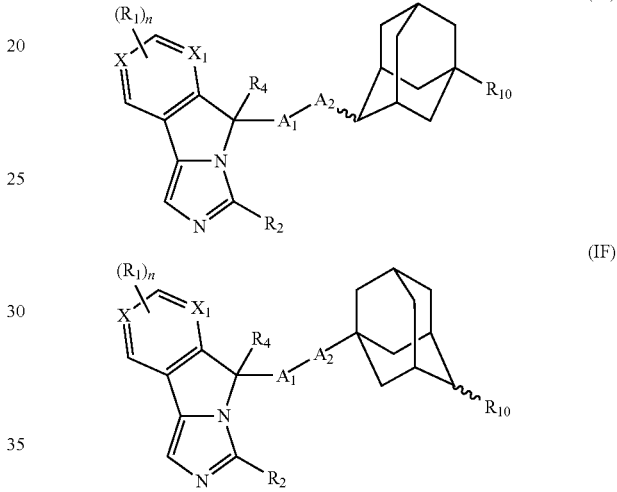

Wherein,
X and $X_1$ are independently C or N;
$R_1$, $R_2$, $R_4$, $R_{10}$, $A_1$, $A_2$, and n are the same as described for formula (I), including each of the embodiments thereof,
the stereoisomeric configurations of the single bond labeled with ⌇ are cis, trans, or a mixture of cis/trans.

Combination of any embodiment of X, $X_1$ (as described for formulae (IE)-(IF)), $R_1$, $R_2$, $A_1$, $A_2$, $R_4$, $R_{10}$ and n as described for formula (I) is within the scope of formulae (IE) and (IF).

Combination of the embodiments described below for formulae (IE) and (IF) is also within the scope of formulae (IE) and (IF).

In some embodiments of formulae (IE) and (IF), X and $X_1$ are C.

In Some embodiments of formulae (IE) and (IF), one of X and $X_1$ is N and the other is C.

In some embodiments of formulae (IE) and (IF), n is 2, and $R_1$ is independently selected from —OH, —SH, —CN, hydrogen, halogen, amino, $C_{1-3}$ alkoxy, $C_{1-3}$ alkylthiol, $C_{1-3}$ alkyl (such as methyl, ethyl, propyl or isopropyl), halo-$C_{1-3}$ alkyl and halo-$C_{1-3}$ alkoxy.

In some embodiments of formulae (IE) and (IF), $R_2$ is independently selected from H and amino.

In some embodiments of formulae (IE) and (IF), $A_1$ is —CH$_2$—, —CHF—, —CF$_2$—, or —CHCH$_3$— or —C(CH$_3$)$_2$—.

In some embodiments of formulae (IE) and (IF), $A_2$ is —CHF—, —CH(CN)—, —CH(COOH)—, —CH(OH)—, —CH(OPO$_3$H)—, —C(CH$_3$)(OH)—,

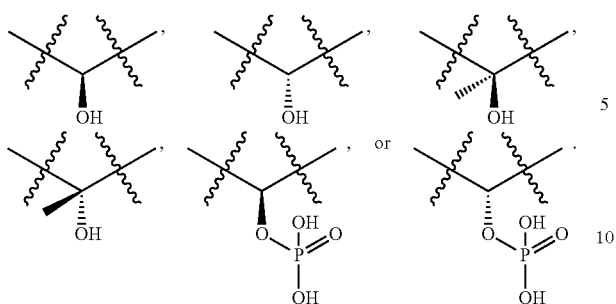

In some embodiments, the compound of formula (I) and/or a pharmaceutically acceptable salt thereof is a compound of formula (IF-1) and/or a pharmaceutically acceptable salt thereof,

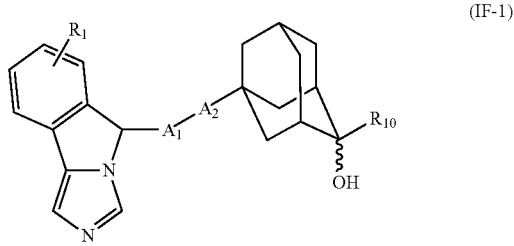

(IF-1)

Wherein, $R_1$, $A_1$, $A_2$ and $R_{10}$ are the same as described for formula (I), including each of the embodiments thereof, the stereoisomeric configurations of the single bond labeled with ⌇ are cis, trans, or a mixture of cis/trans.

Combination of any embodiment of $R_1$, $A_1$, $A_2$, and $R_{10}$ as described for formula (I) is within the scope of formulae (IF-1).

Combination of the embodiments described below for formula (IF-1) is also within the scope of formula (IF-1).

In some embodiments of formulae (IF-1), $R_1$ is hydrogen or halogen;

In some embodiments of formulae (IF-1), $R_{10}$ is independently substituted or unsubstituted hydrogen, alkyl, substituted or unsubstituted aryl, substituted or unsubstituted heteroaryl, -L-$R_8$, wherein substituted alkyl, aryl, and heteroaryl are substituted by 1, 2, or 3 $R_{13}$, further wherein $R_8$, and $R_{13}$ are the same as described for formula (I), including each embodiment thereof.

In some embodiments, the compound of formula (I) and/or a pharmaceutically acceptable salt thereof is 1) a compound of formula (IG) and/or a pharmaceutically acceptable salt thereof, or 2) a compound of formula (IH) and/or a pharmaceutically acceptable salt thereof,

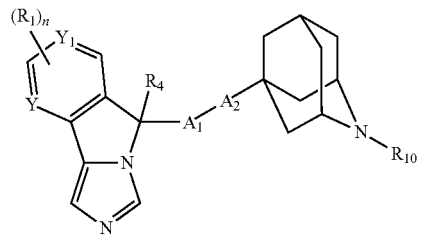

(IG)

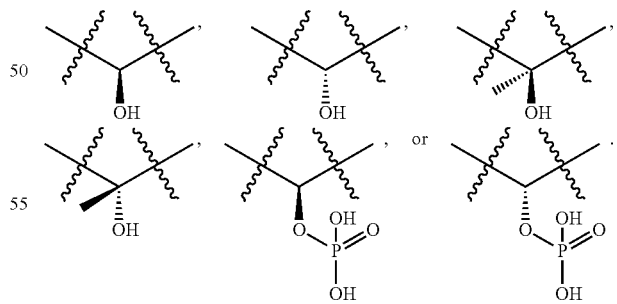

(IH)

Wherein,

Y, $Y_1$, X, and $X_1$ are independently C or N;

$R_1$, $R_4$, $A_1$, $A_2$, $R_{10}$, and n are the same as described for formula (I), including each of the embodiments thereof.

Combination of any embodiment of Y, $Y_1$, X, $X_1$ (as described for formulae (IG)-(IH)), $R_1$, $R_4$, $A_1$, $A_2$, $R_{10}$, and n as described for formula (I) is within the scope of formulae (IG)-(IH).

Combination of the embodiments described below for formulae (IG)-(IH) is also within the scope of formulae (IG)-(IH).

In some embodiments of formulae (IG) and (IH), Y, $Y_1$, X, and $X_1$ are C.

In Some embodiments of formula (IG), one of X and $X_1$ is N and the other is C.

In some embodiments of formula (IH), one of Y and $Y_1$ is N and the other is C.

In some embodiments of formulae (IG) and (IH), n is 2, and $R_1$ is independently selected from —OH, —SH, —CN, hydrogen, halogen, amino, $C_{1-3}$ alkoxy, $C_{1-3}$ alkylthiol, $C_{1-3}$ alkyl (such as methyl, ethyl, propyl or isopropyl), halo-$C_{1-3}$ alkyl and halo-$C_{1-3}$ alkoxy.

In some embodiments of formulae (IG) and (IH), $A_1$ is —$CH_2$—, —CHF—, —$CF_2$—, —$CHCH_3$— or —$C(CH_3)_2$—.

In some embodiments of formulae (IG) and (IH), $A_2$ is is —CHF—, —CH(CN)—, —CH(COOH)—, —CH(OH)—, —CH($OPO_3H$)—, —C($CH_3$)(OH)—,

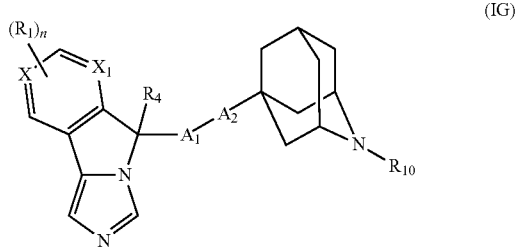

In some embodiments, the compound of formula (I) and/or a pharmaceutically acceptable salt thereof is 1) a compound of formula (IJ) and/or a pharmaceutically acceptable salt thereof, or 2) a compound of formula (IK) and/or a pharmaceutically acceptable salt thereof,

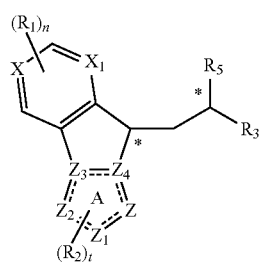

(IJ)

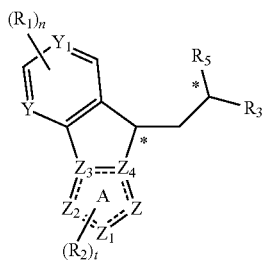

(IK)

Wherein,

Y, $Y_1$, X, and $X_1$ are independently C or N;

Z, $Z_1$, $Z_2$, $Z_3$, $Z_4$, $R_1$, $R_2$, $R_3$, $R_5$, n and t are the same as described for formula (I), including each of the embodiments thereof, the stereoisomeric configurations of carbon atoms labeled with * are respectively (S, S), (S, R), (R, S), (R, R).

Combination of any embodiment of Y, $Y_1$, X, $X_1$ (as described for formulae (IJ) and (IK), Z, $Z_1$, $Z_2$, $Z_3$, $Z_4$, $R_1$, $R_2$, $R_3$, $R_5$, n and t as described for formula (I) is within the scope of formulae (IJ) and (IK).

Combination of any embodiment described below for formulae (IJ) and (IK) is also within the scope of formulae (IJ) and (IK).

In some embodiments of formulae (IJ) and (IK), Y, $Y_1$, X, and $X_1$ are C.

In some embodiments of formula (IJ), one of X and $X_1$ is N and the other is C.

In some embodiments of formula (IK), one of Y and $Y_1$ is N and the other is C.

In some embodiments of formulae (IJ) and (IK), n is 2, and $R_1$ is independently selected from —OH, —SH, —CN, hydrogen, halogen, amino, $C_{1-3}$alkoxy, $C_{1-3}$alkylthiol, $C_{1-3}$alkyl (such as methyl, ethyl, propyl or isopropyl), halo-$C_{1-3}$alkyl and halo-$C_{1-3}$alkoxy.

In some embodiments of formulae (IJ) and (IK), t is 2, and $R_2$ is independently selected from —OH, —SH, —NH$_2$, hydrogen, halogen, $C_{1-3}$ alkoxy, $C_{1-3}$ alkylthiol, $C_{1-3}$ alkyl, and halo-$C_{1-3}$ alkyl.

In some embodiments of formulae (IJ) and (IK), Z and $Z_2$ are C, $Z_1$ is N, and one of $Z_3$ and $Z_4$ is N and the other is C.

In some embodiments of formulae (IJ) and (IK), $R_5$ is independently H, OH, alkyl, —OR$_6$, and —OP(O)(O—R$_6$)$_2$, wherein $R_6$ is H or alkyl.

In some embodiments of formulae (IJ) and (IK), $R_3$ is unsubstituted adamantanyl or adamantanyl substituted with 1 or 2 $R_{10}$, $R_{10}$ is the same as described for formula (I), including each embodiment thereof.

In some embodiments of formulae (IJ) and (IK), $R_3$ is unsubstituted 2-azaadamantanyl or 2-azaadamantanyl substituted with 1 or 2 $R_{10}$, $R_{10}$ is the same as described for formula (I), including each embodiment thereof.

In some embodiments of formulae (IJ) and (IK), $R_{10}$ is independently —NO$_2$, —CN, —OH, —NH$_2$, —SH, halogen, substituted or unsubstituted alkyl, substituted or unsubstituted alkoxy, substituted or unsubstituted aryl, substituted or unsubstituted heteroaryl, —N(R$_8$)-L-R$_{8b}$, -L-R$_8$, —O-L-R$_8$, -L-C(O)R$_{8b}$, -L-C(=R$_7$)NR$_8$R$_{8b}$, -L-S(O)$_2$R$_{8b}$, -L-NR$_8$R$_{8b}$, -L-N(R$_8$)C(=R$_7$)NR$_8$R$_{8b}$, -L-N(R$_8$)C(=R$_7$)R$_{8b}$, and -L-N(R$_8$)S(O)$_2$R$_{8b}$, wherein substituted alkyl, substituted alkoxy, substituted aryl, and substituted heteroaryl are substituted by 1, 2, or 3 $R_{13}$, further wherein $R_7$, $R_8$, $R_{8b}$, and $R_{13}$ are the same as described for formula (I), including each embodiment thereof.

In some embodiments, the compound of formula (I) and/or a pharmaceutically acceptable salt thereof is selected from the following compounds:

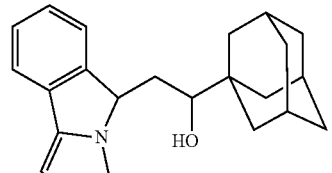


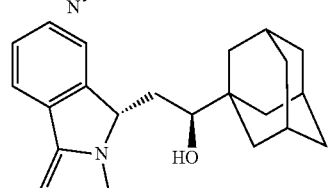

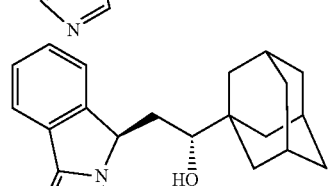

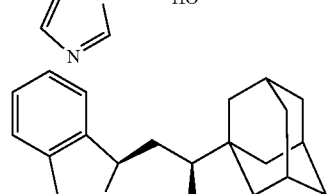

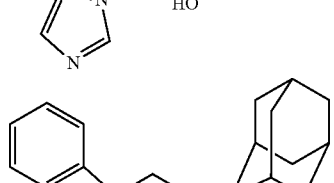

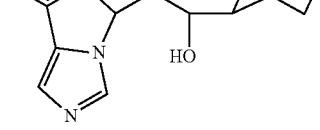

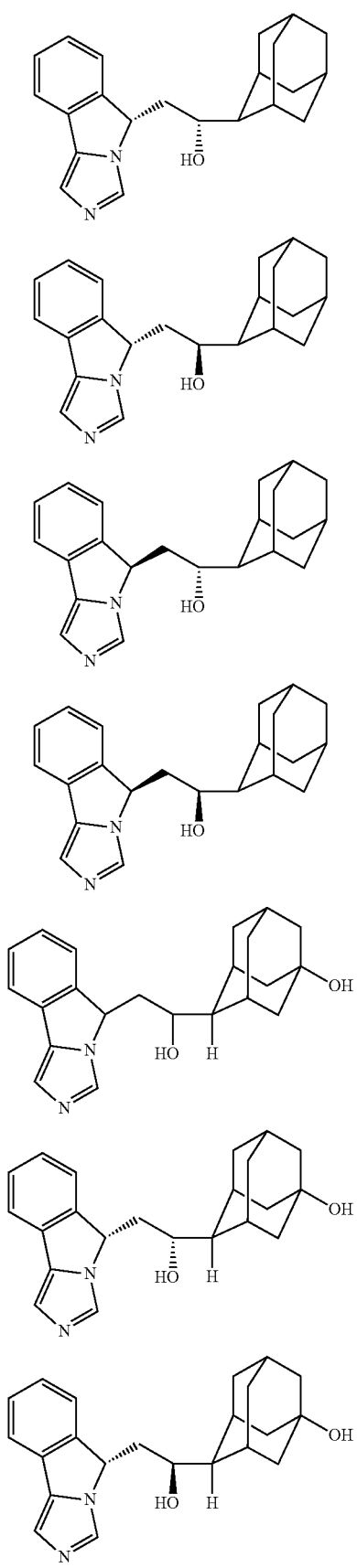
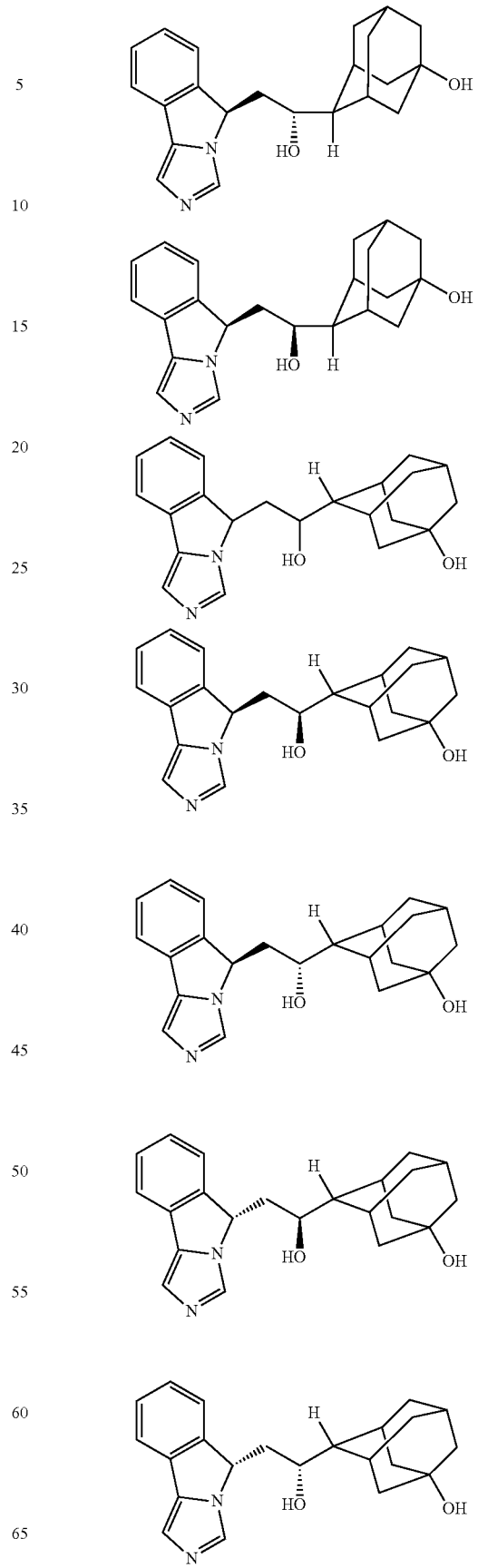

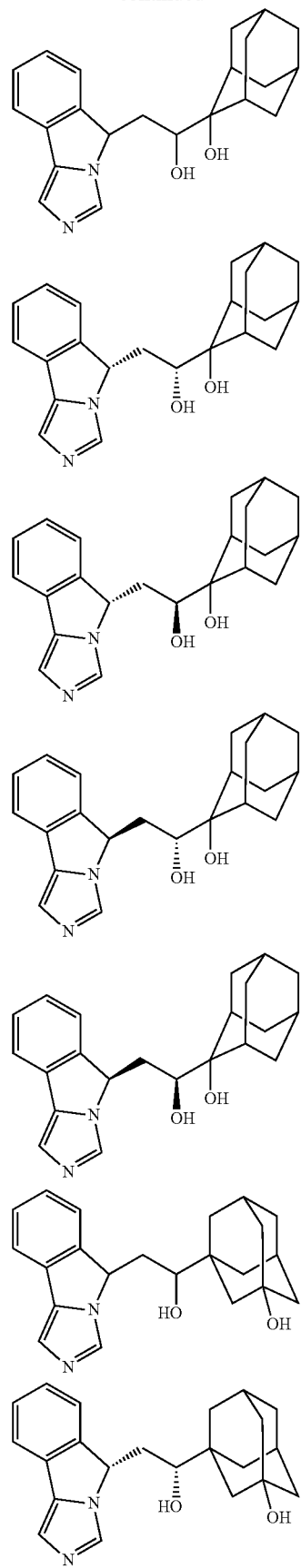
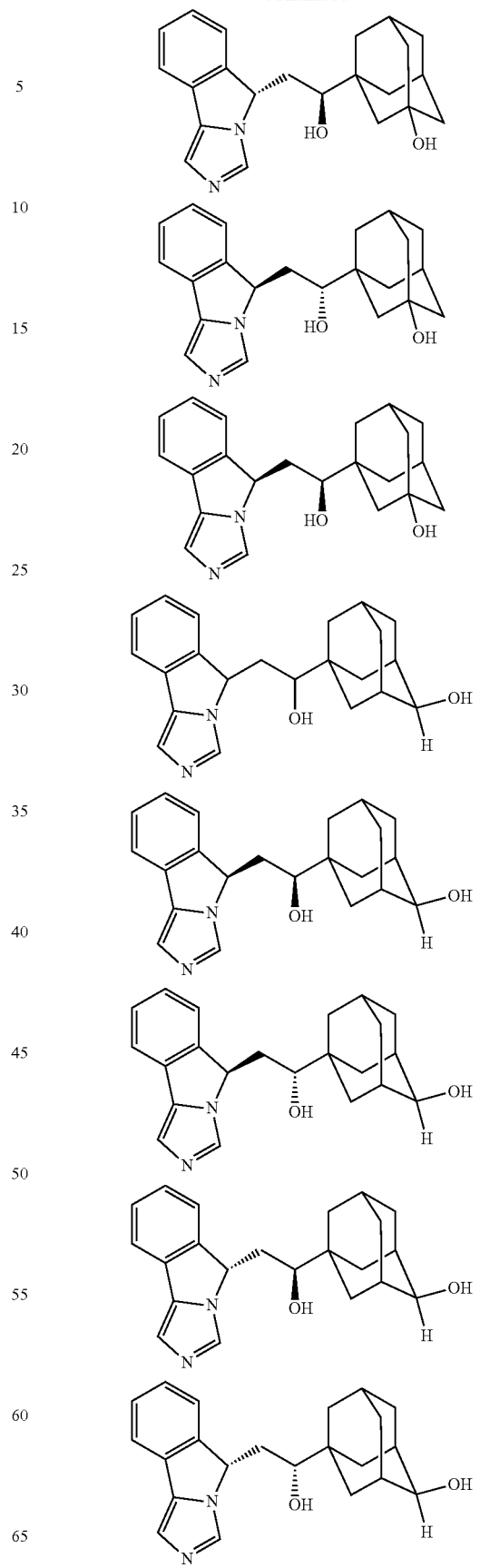

-continued
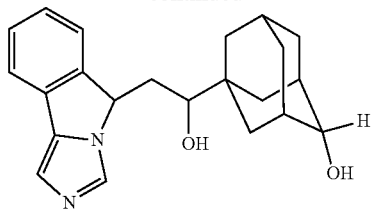
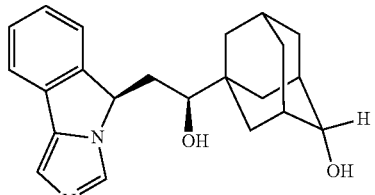
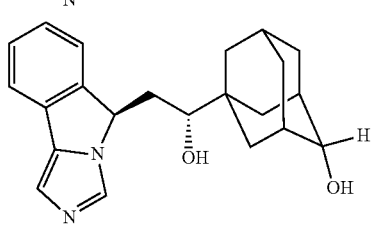
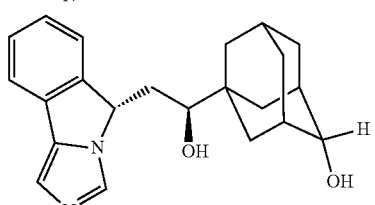
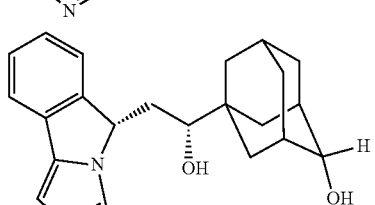

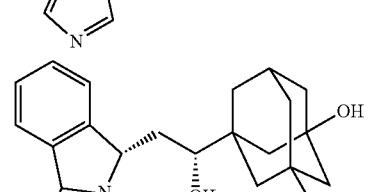
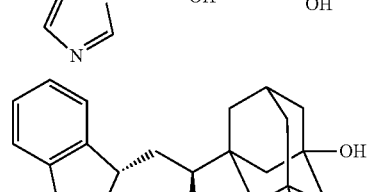
-continued
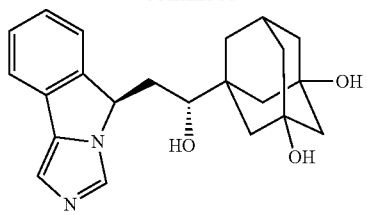
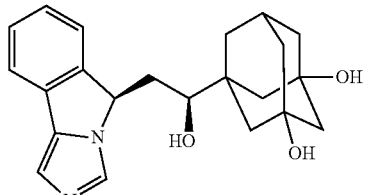
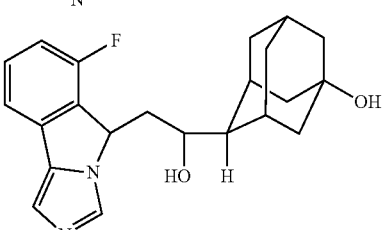
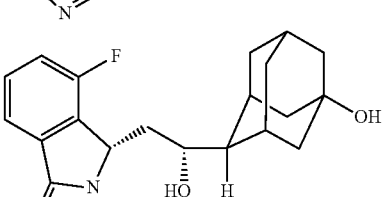
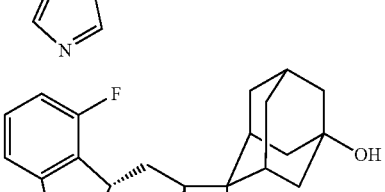
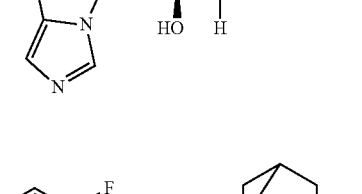
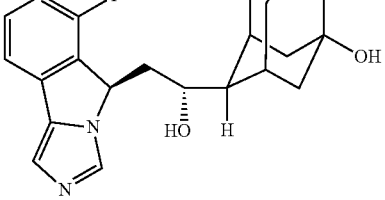
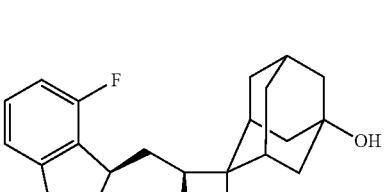

63
-continued
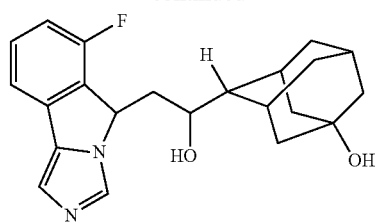
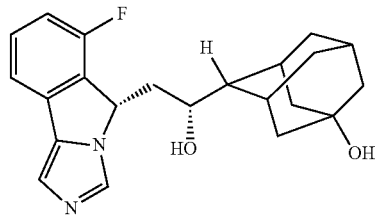
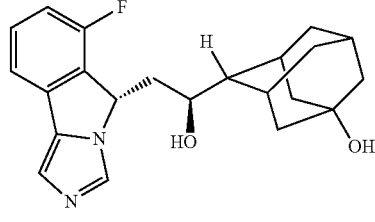
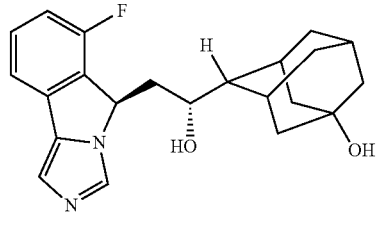
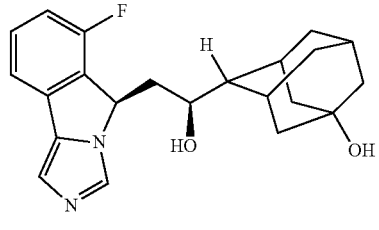
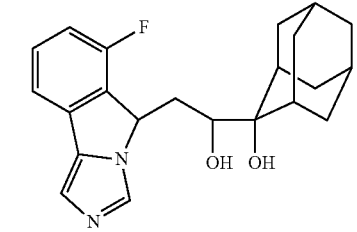
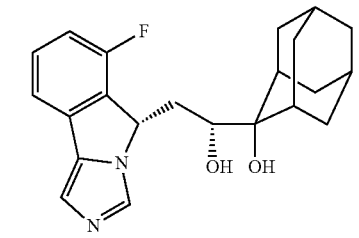
64
-continued
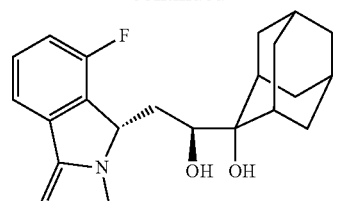
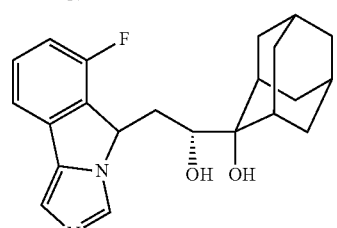
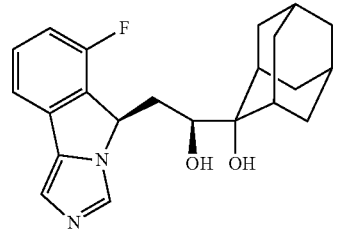
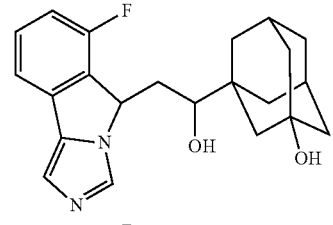
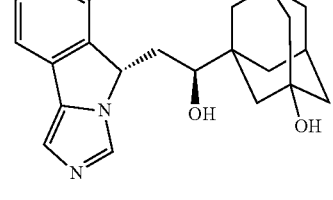
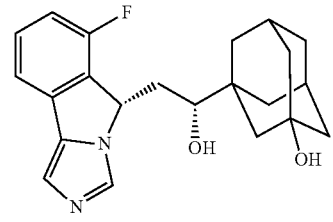
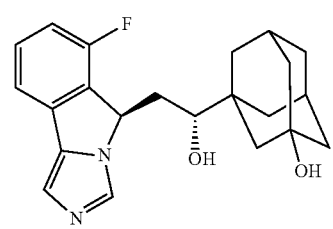

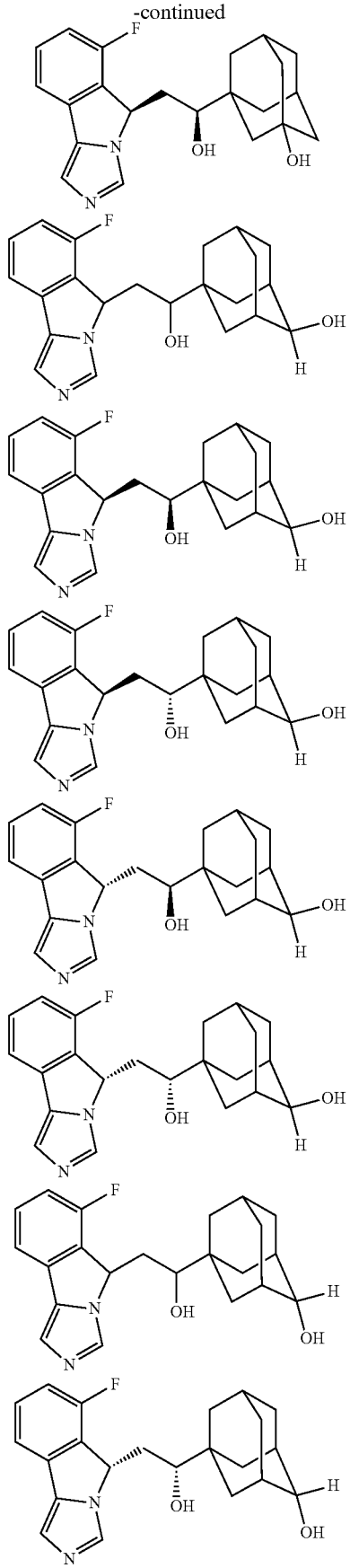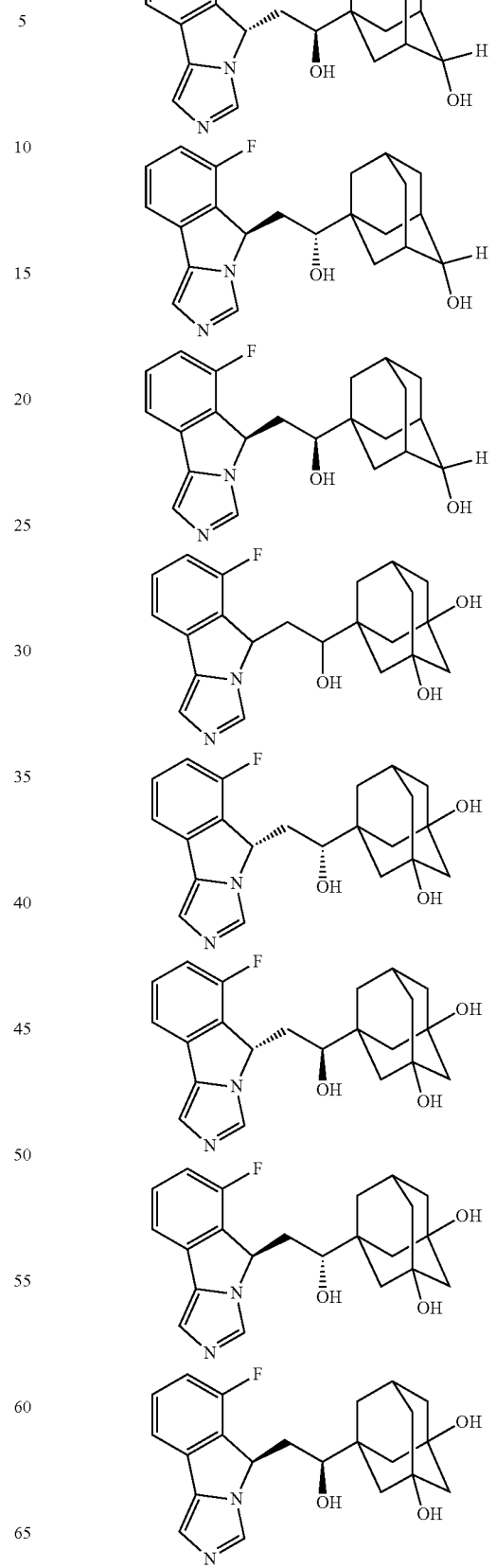

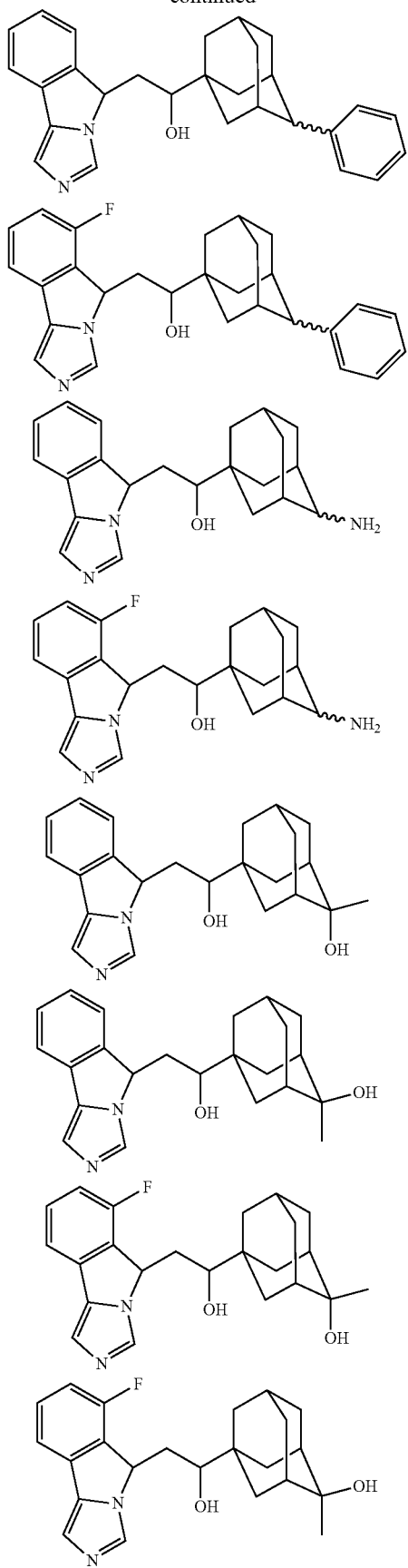
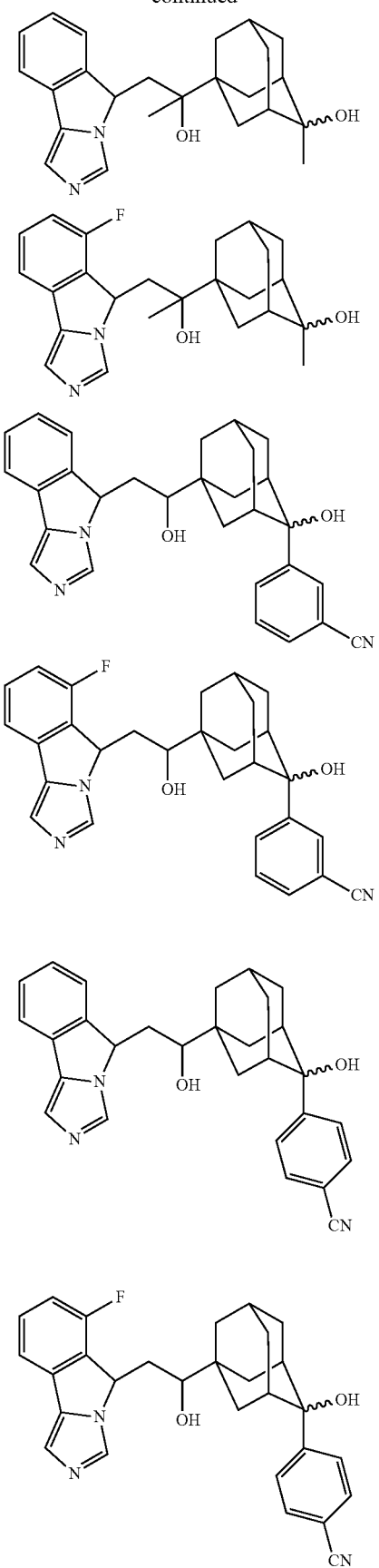

69
-continued
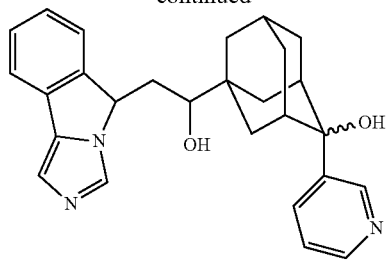
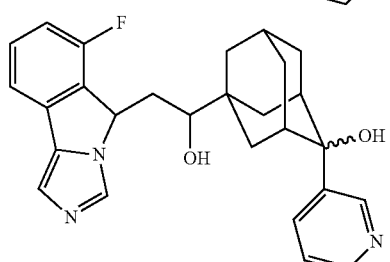
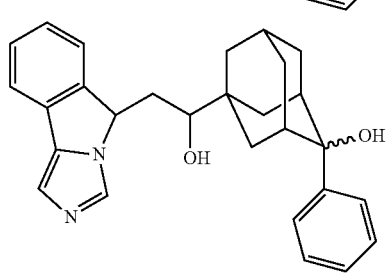
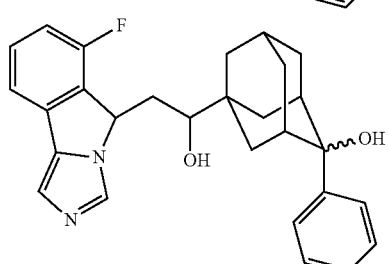
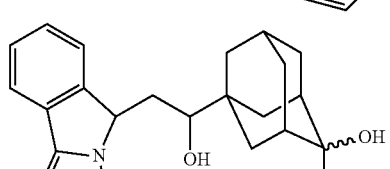
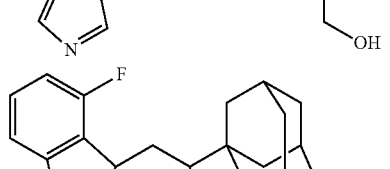
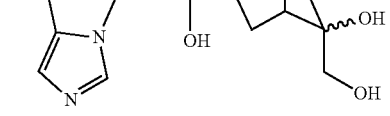
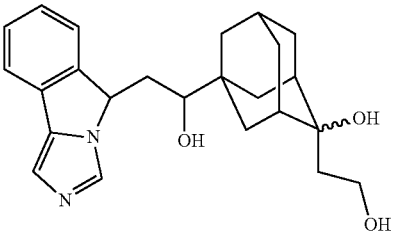
70
-continued
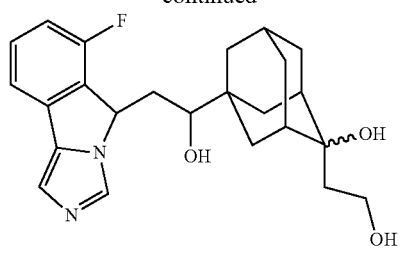
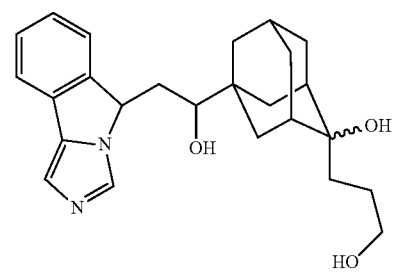
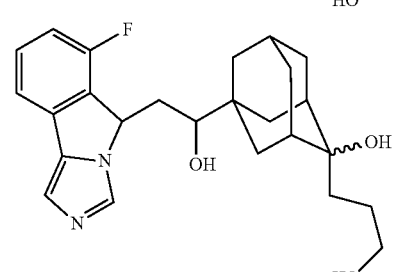
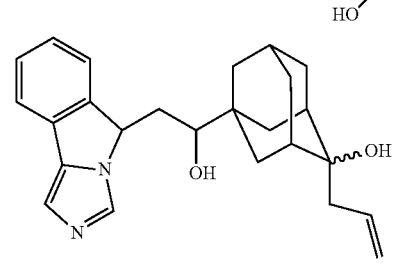
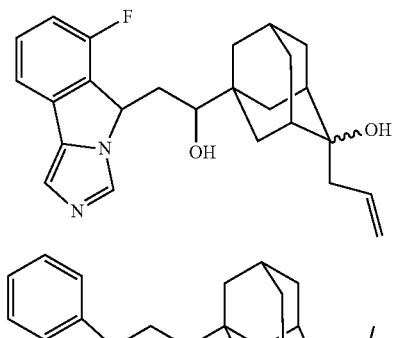
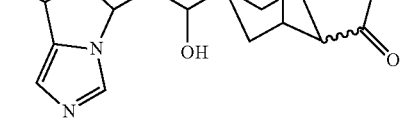
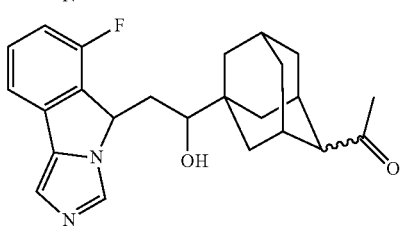

71
-continued
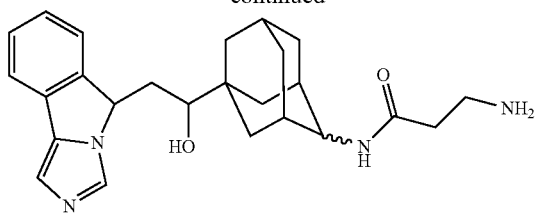
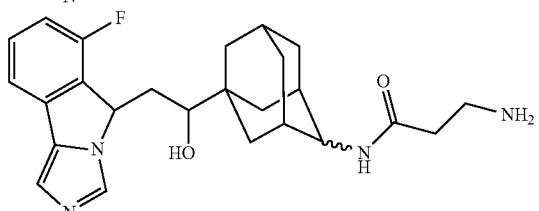
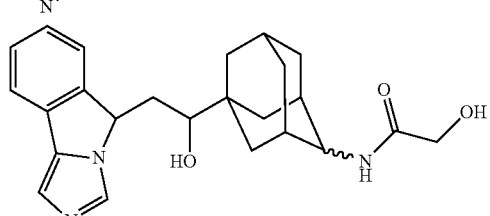
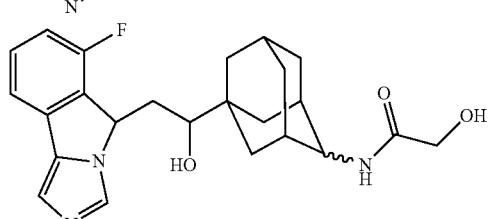
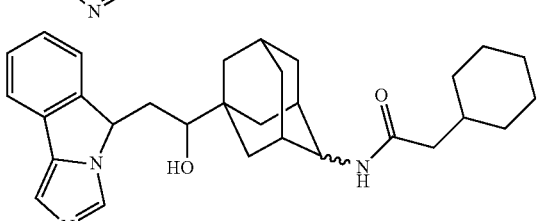
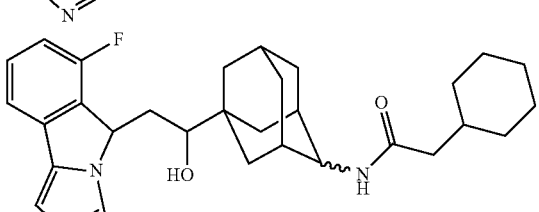
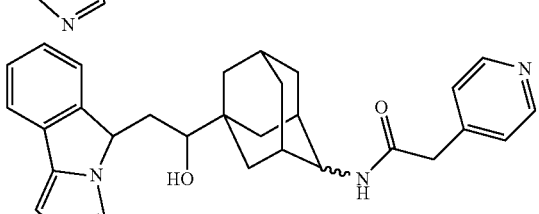
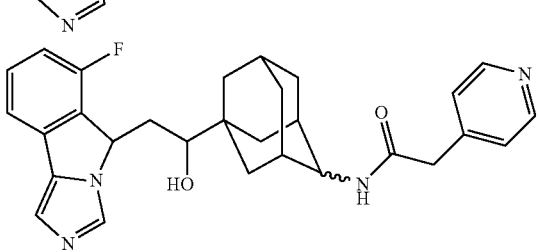
72
-continued
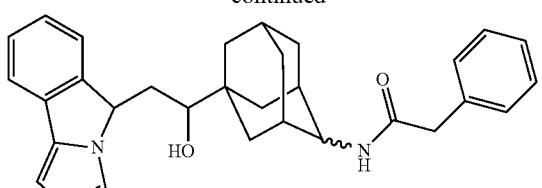
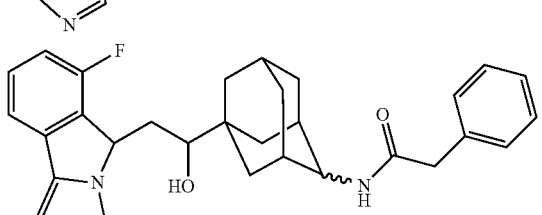
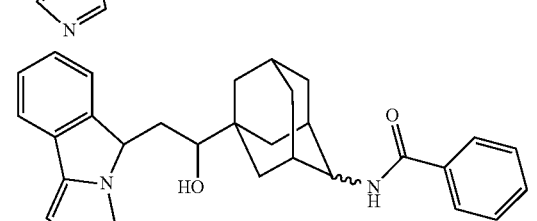
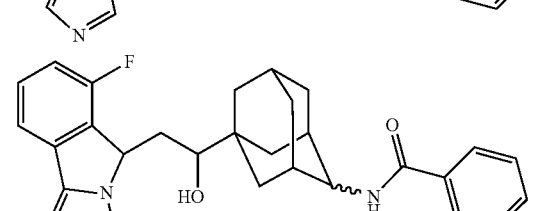
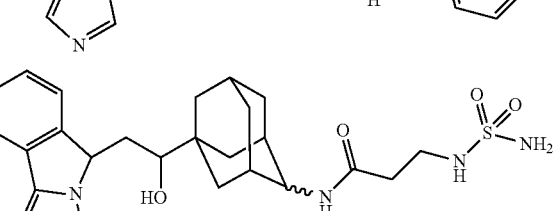
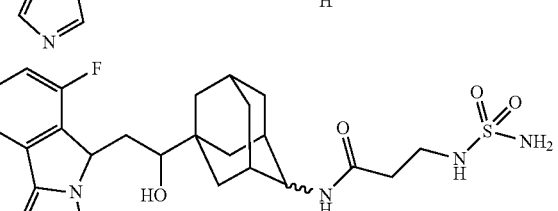
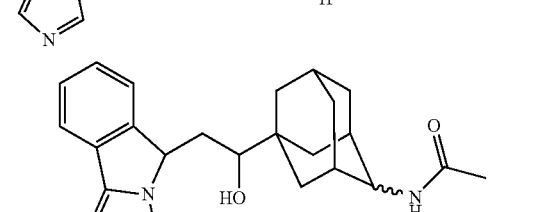
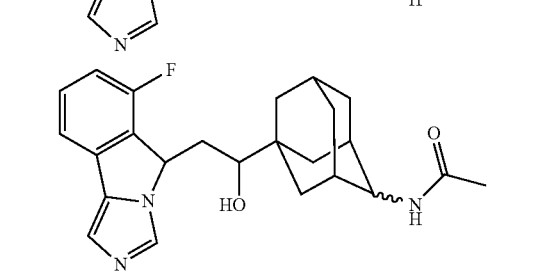

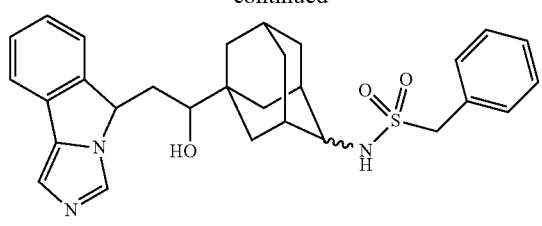
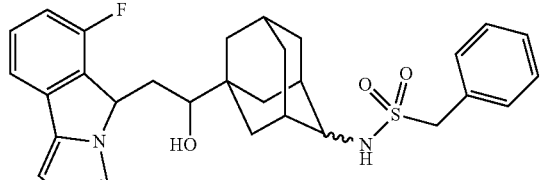
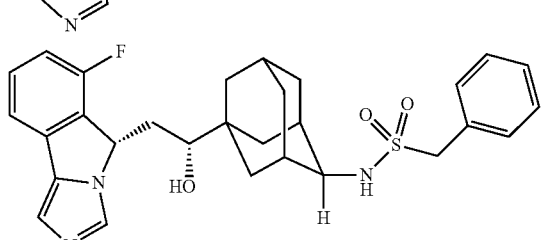
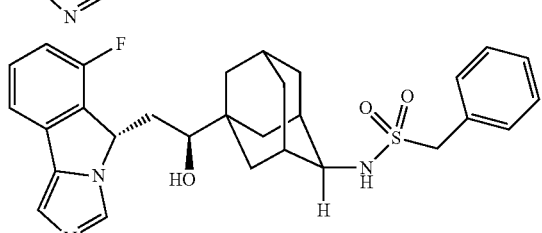
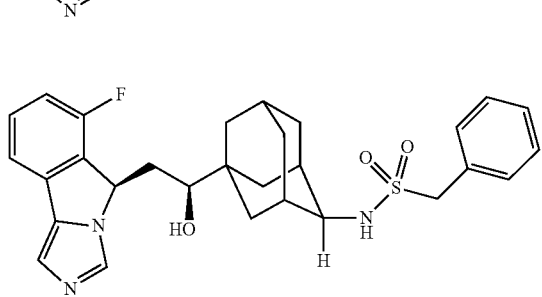
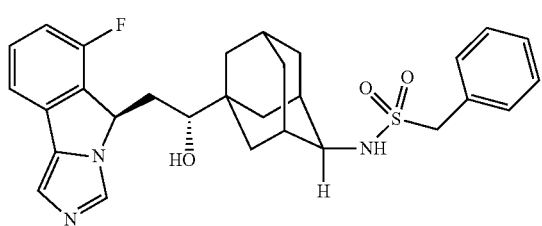
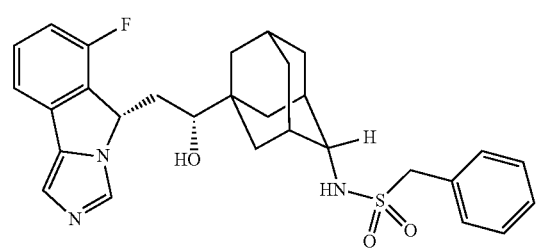
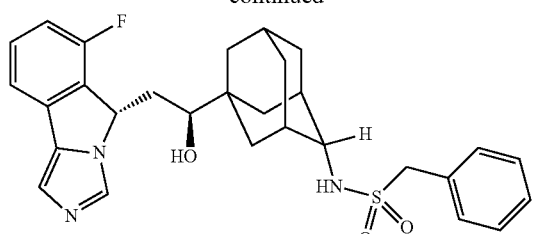
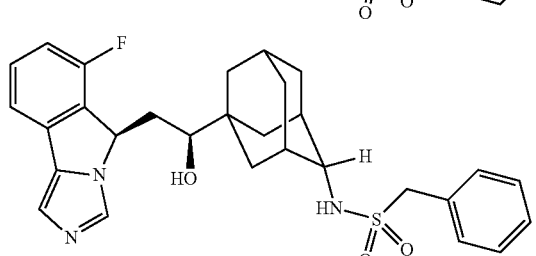
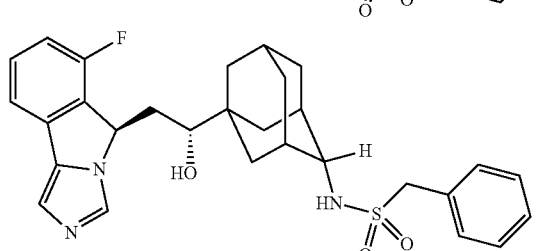
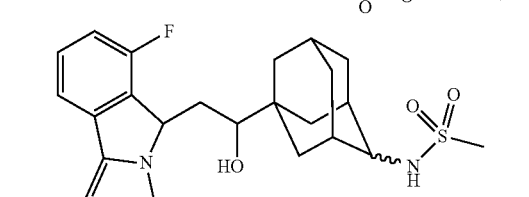
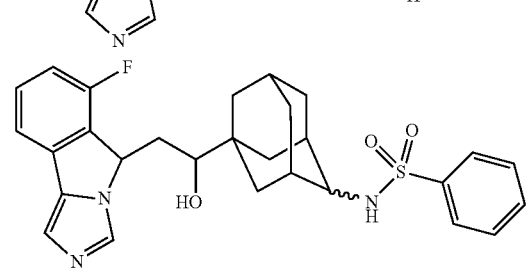
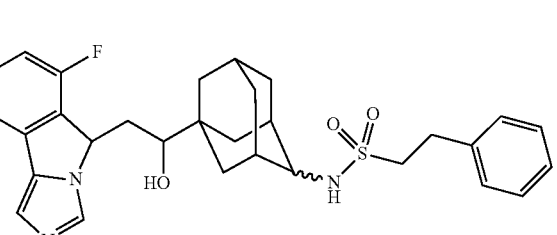
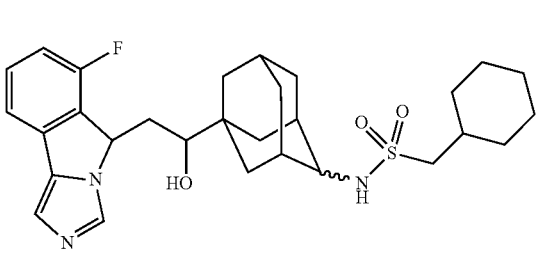

75
-continued
76
-continued
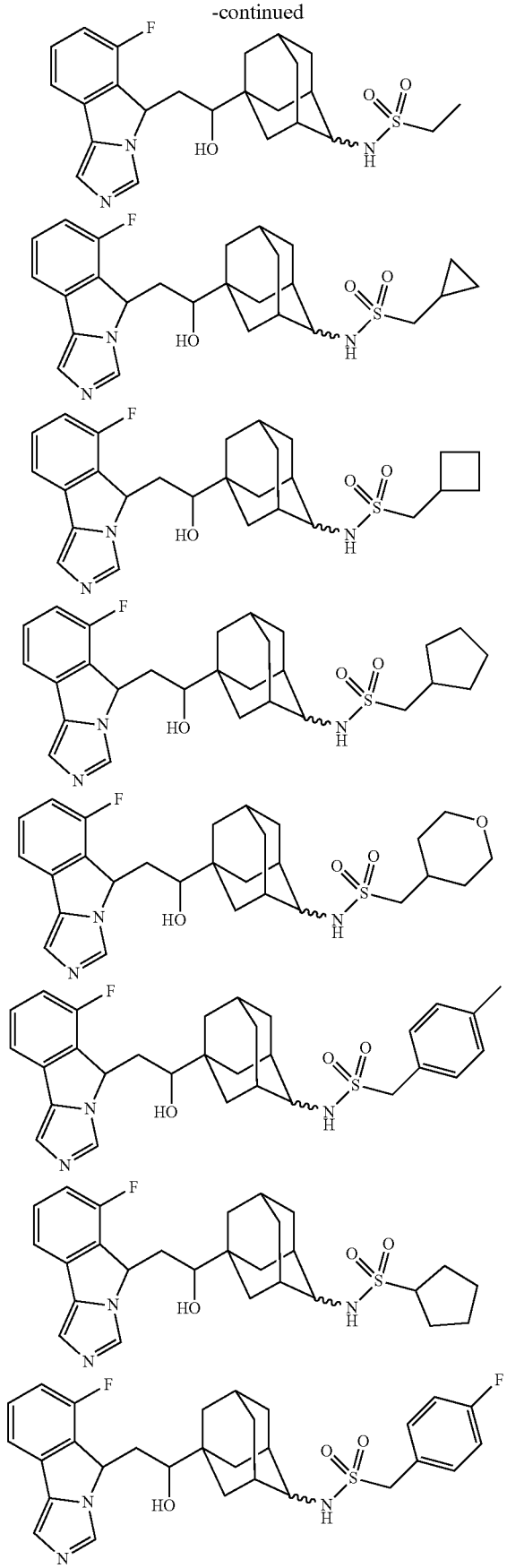
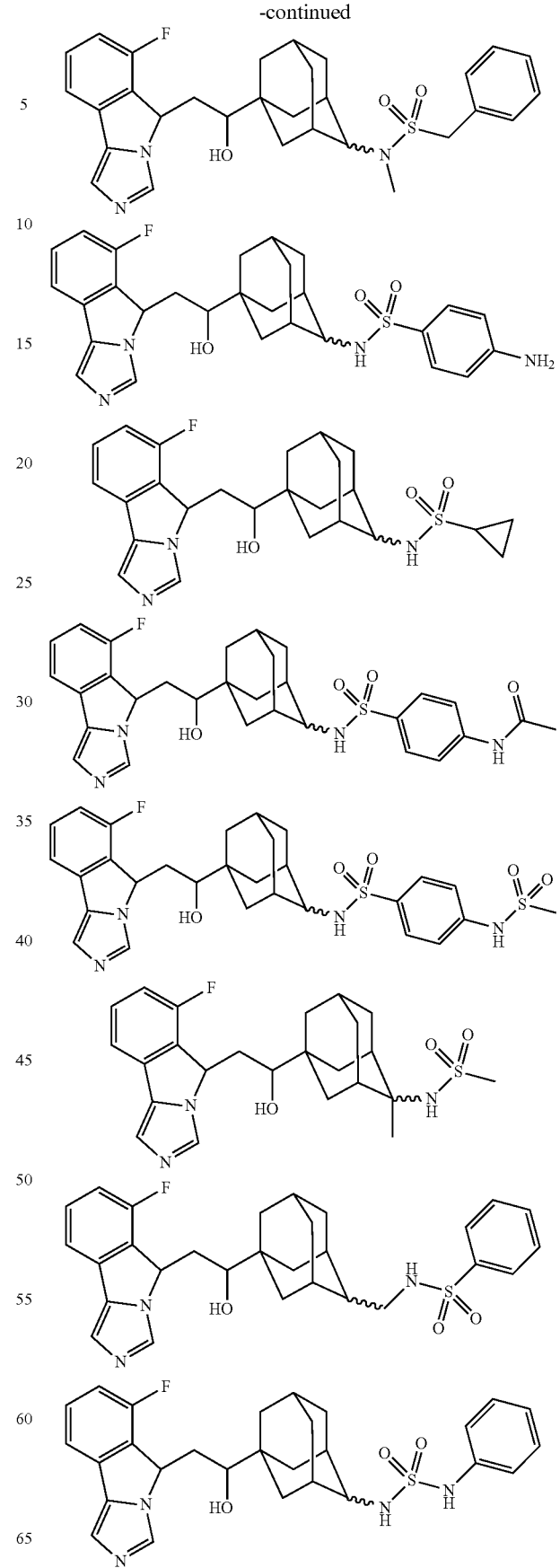

77
-continued
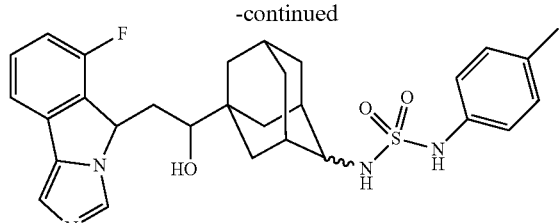
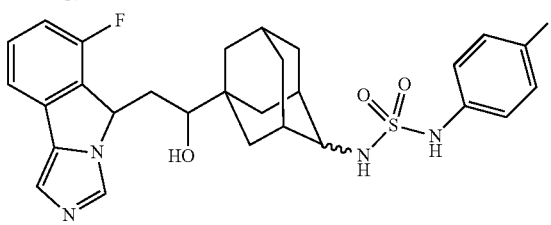
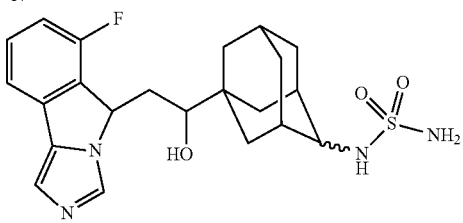
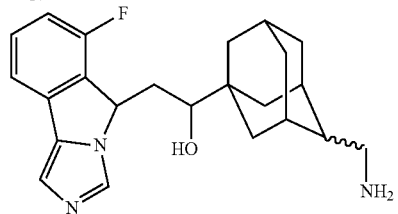
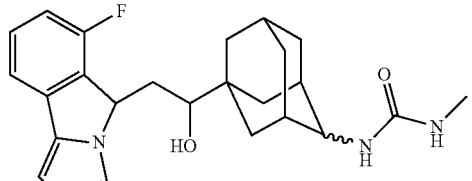
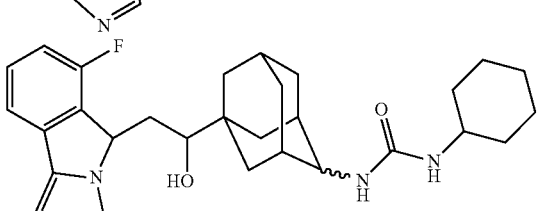
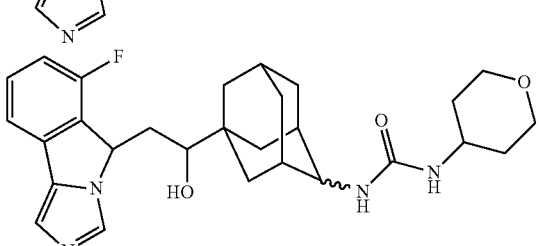
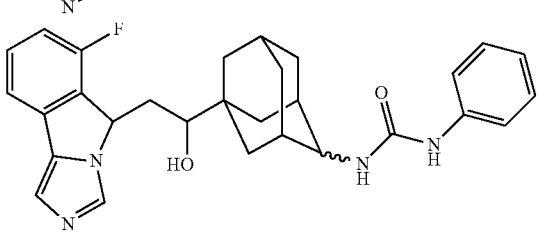
78
-continued
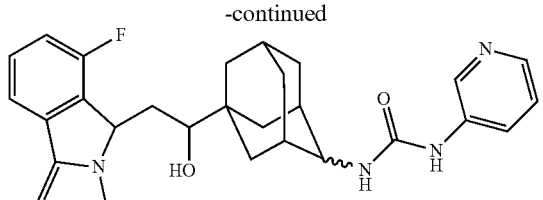
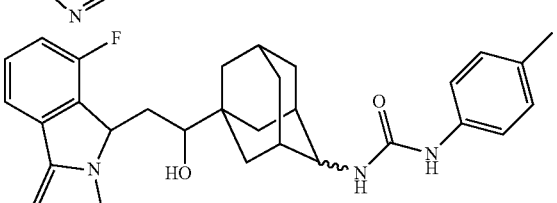
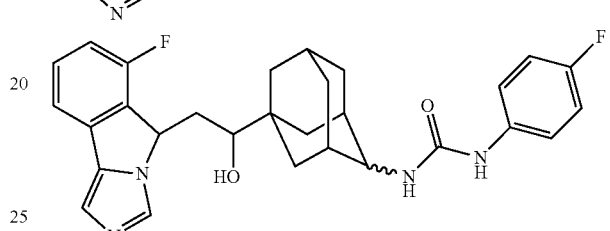
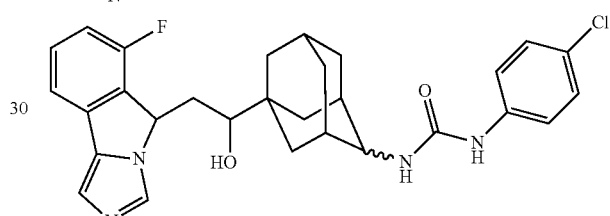
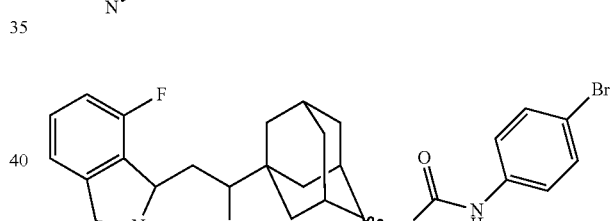
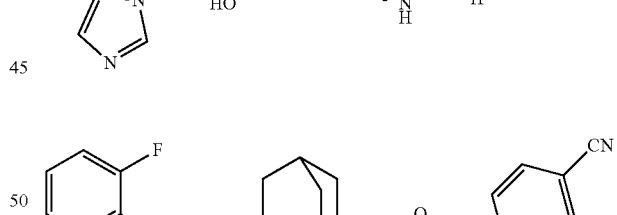
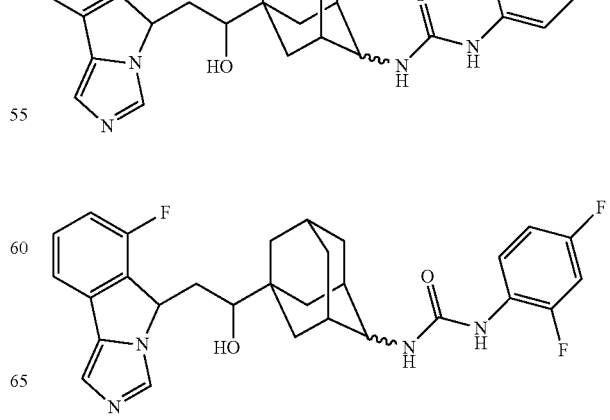

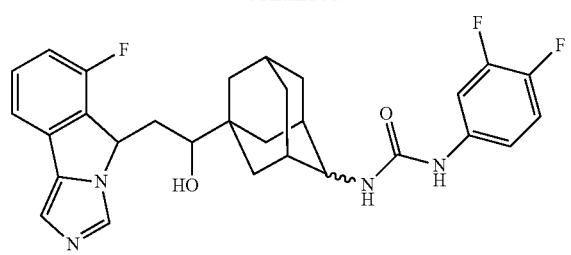
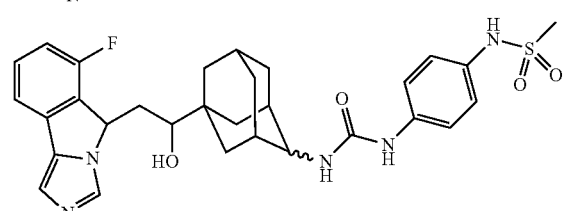
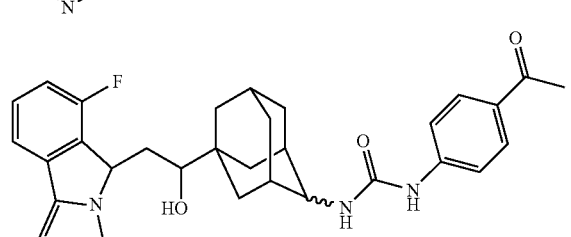
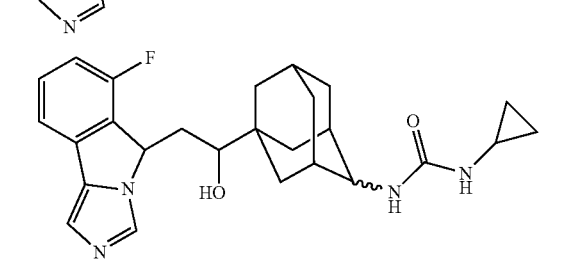
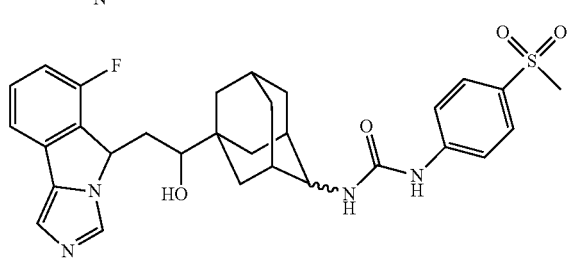
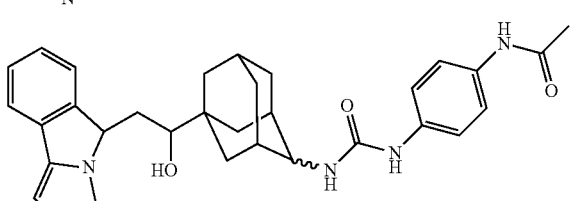
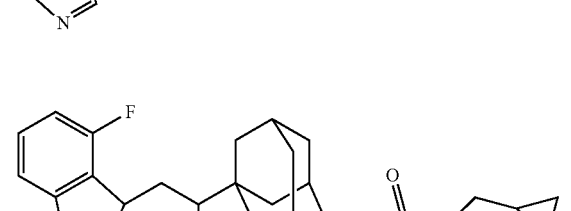
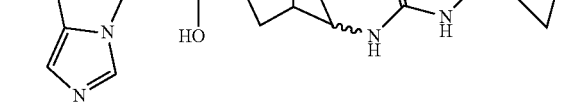
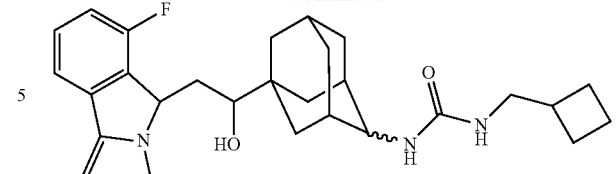
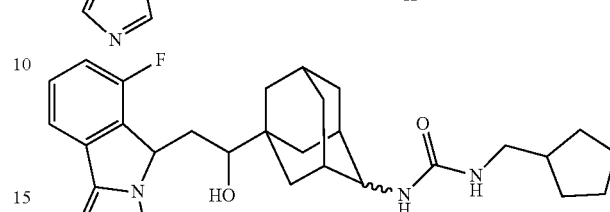
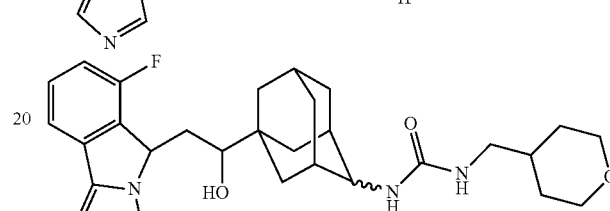
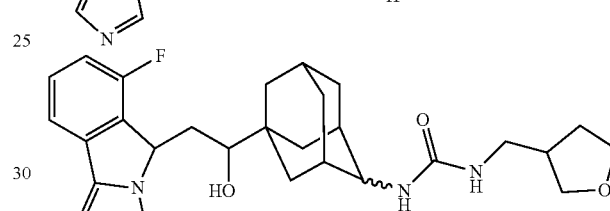
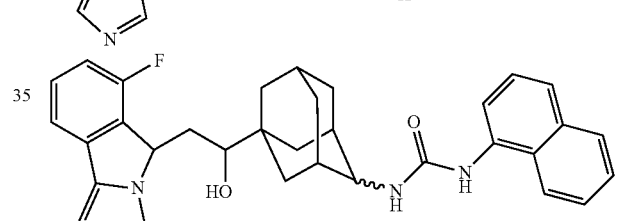
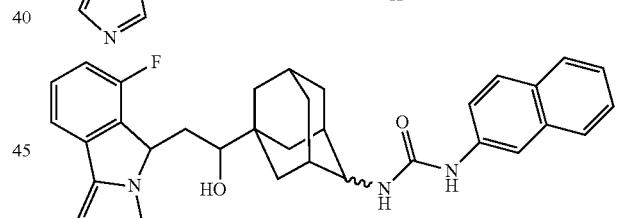
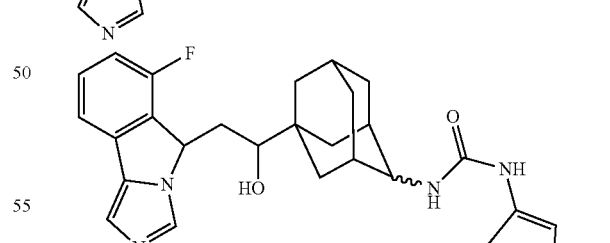
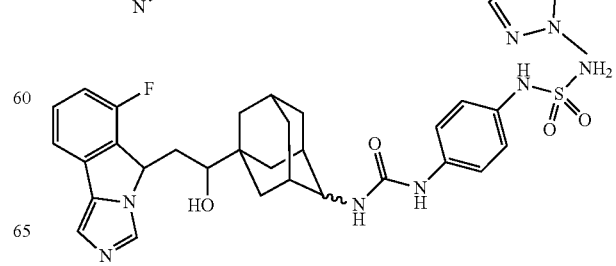

-continued
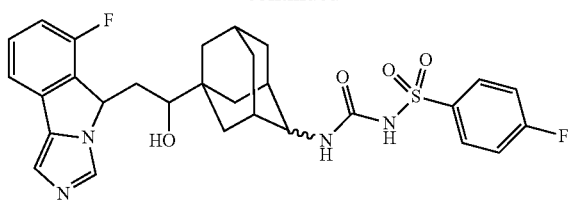
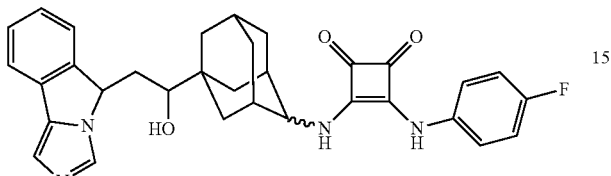
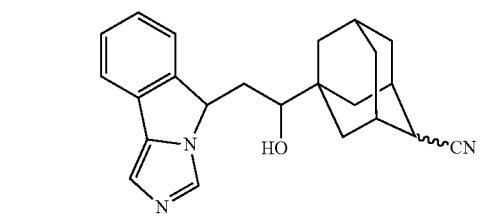
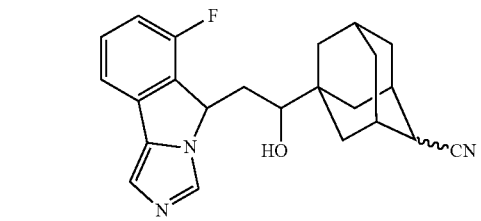
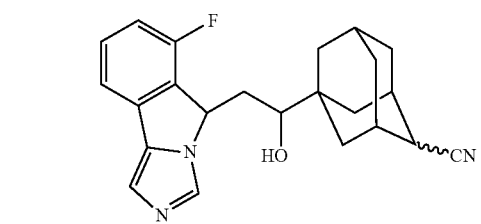
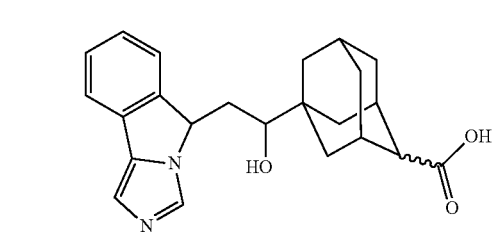
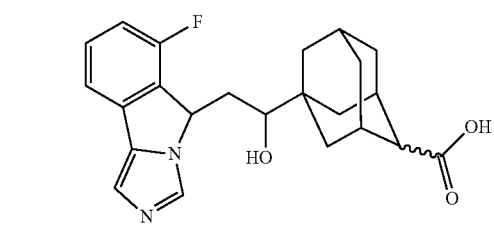
-continued
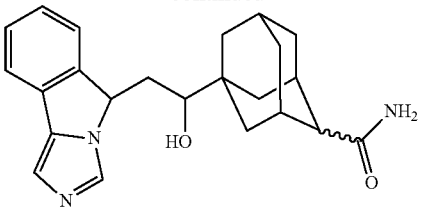
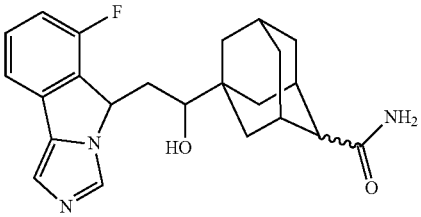
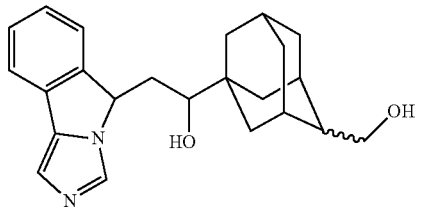
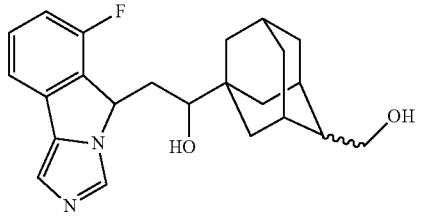
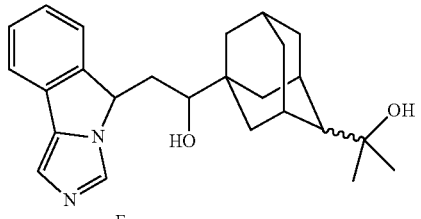
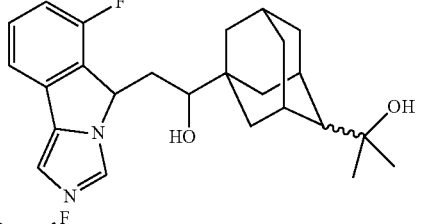
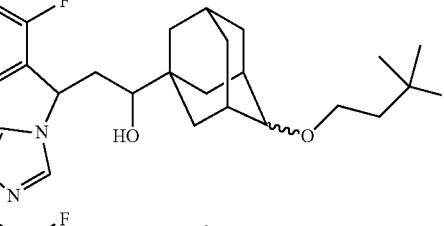
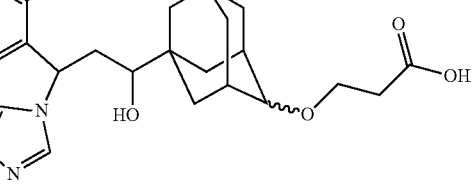

83
-continued
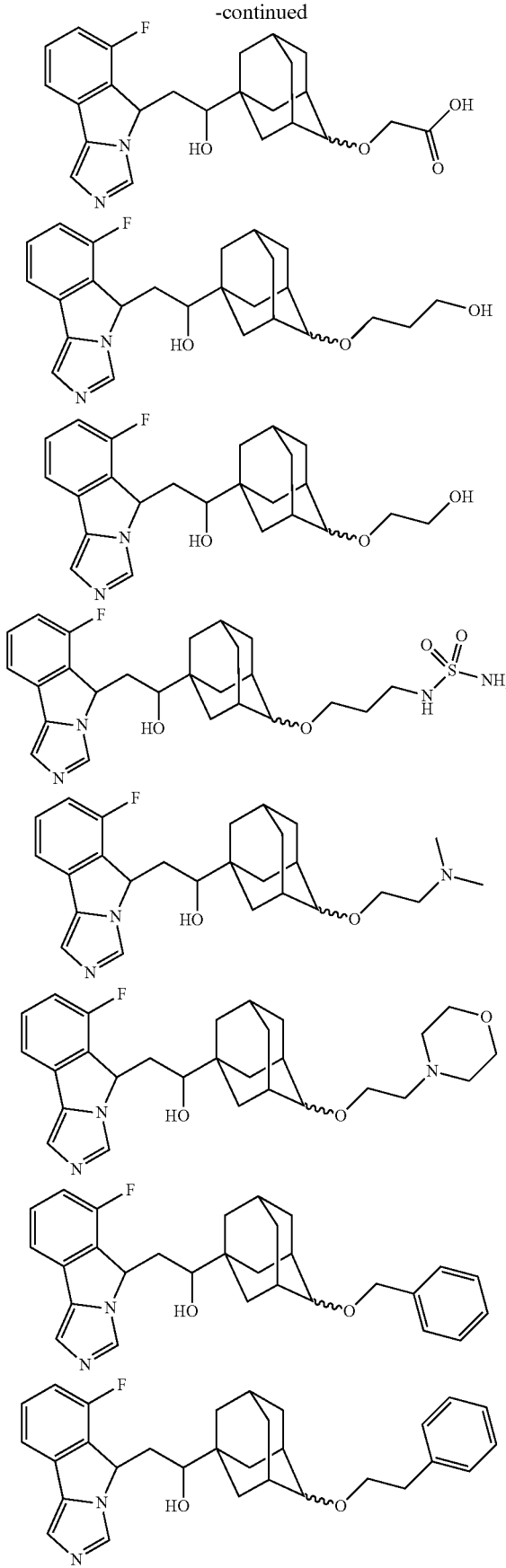
84
-continued
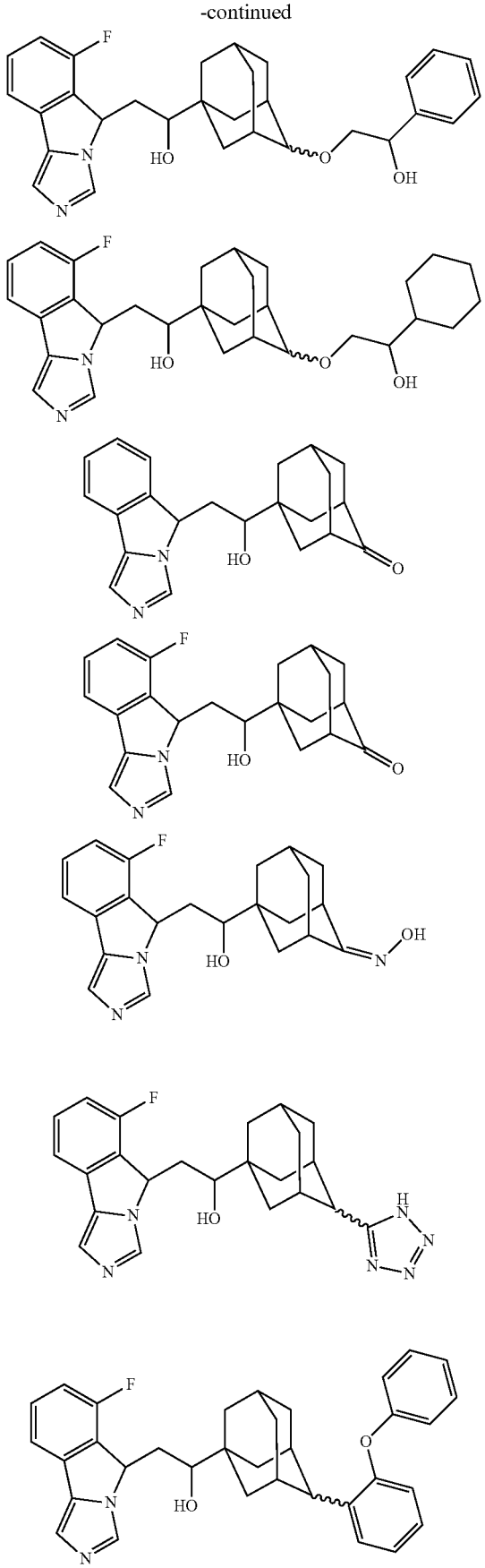

-continued
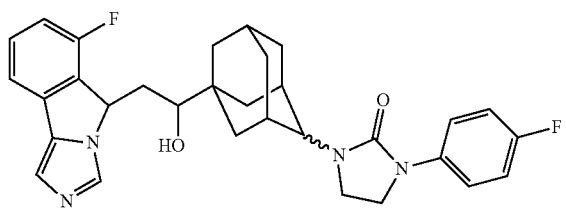
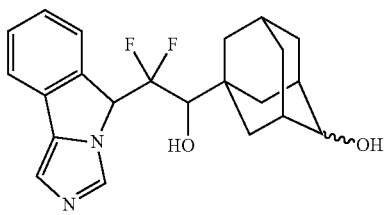
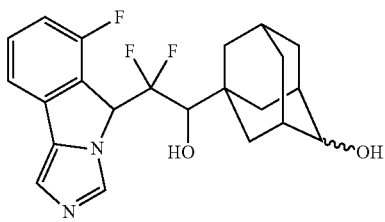
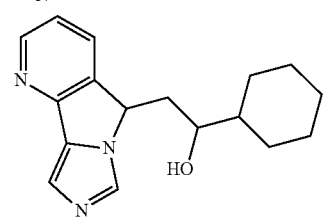
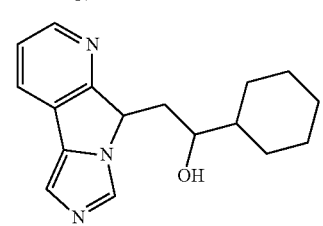
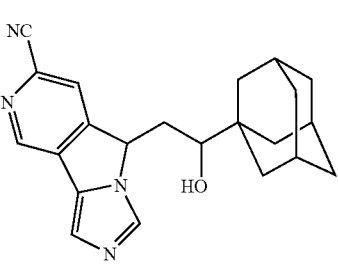
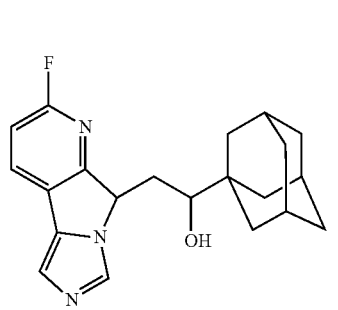
-continued
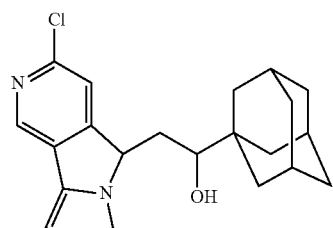
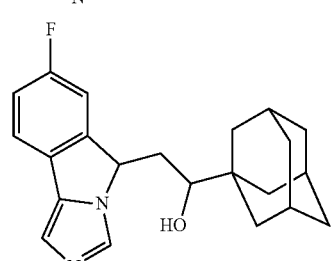
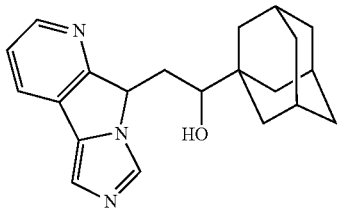
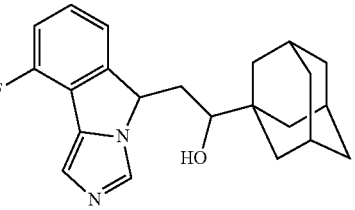
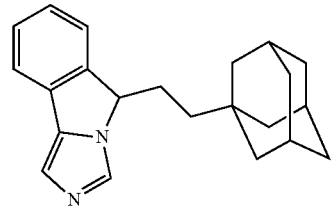
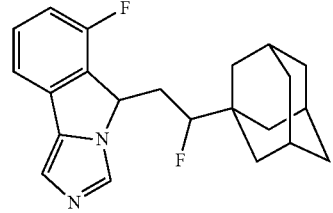
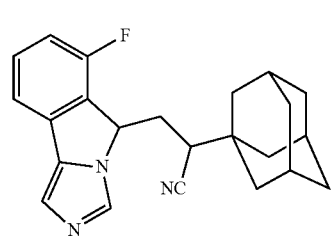

87
-continued
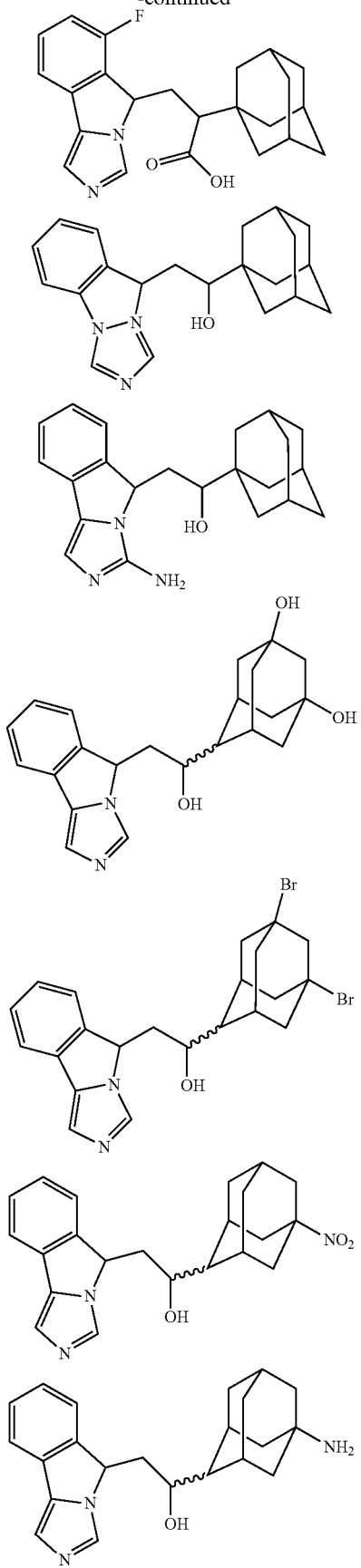
88
-continued
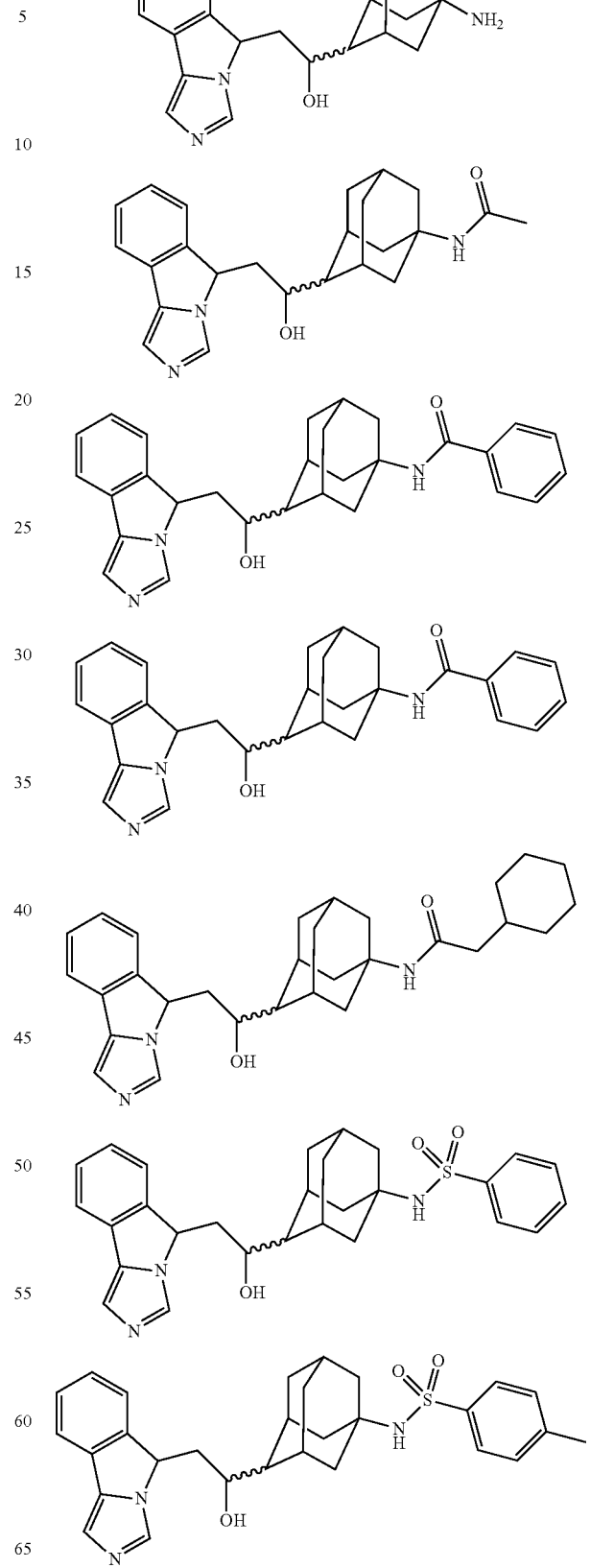

89
-continued
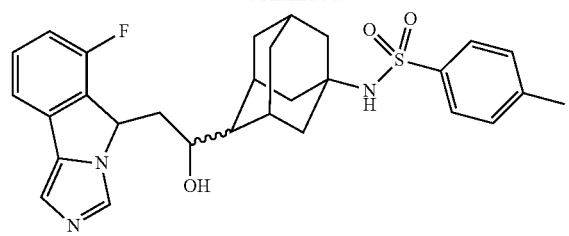
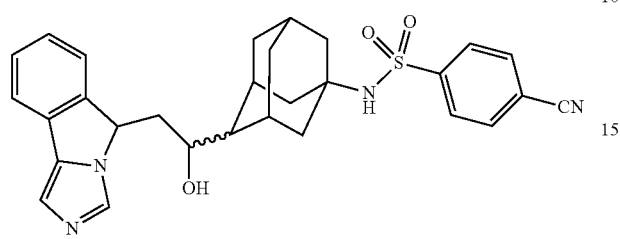
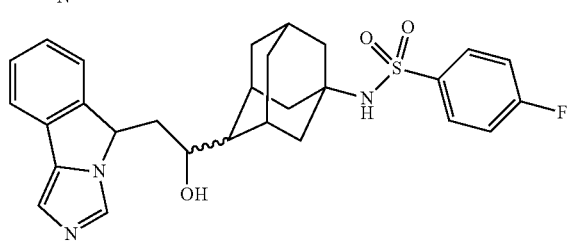
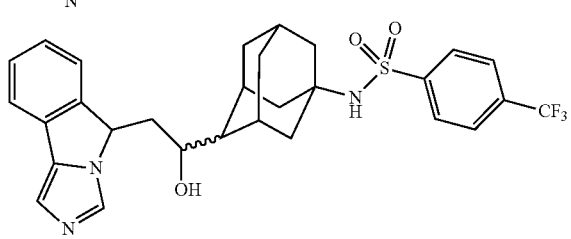
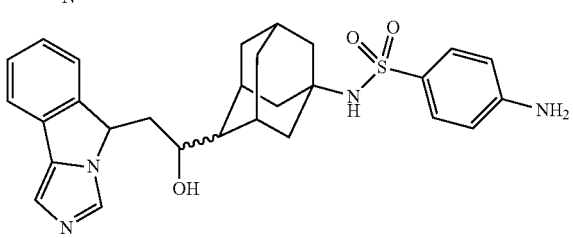
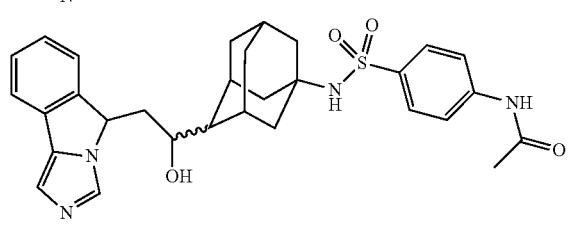
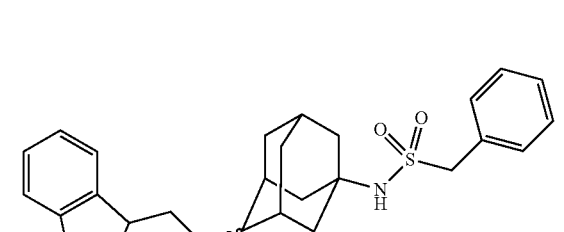
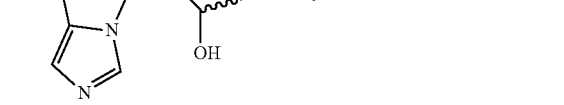
90
-continued
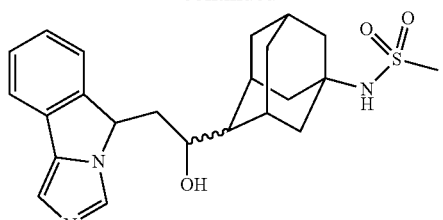
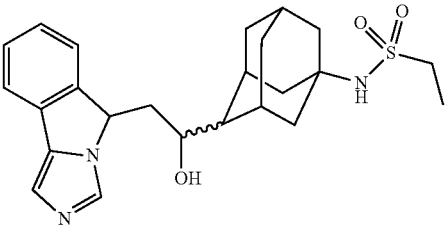
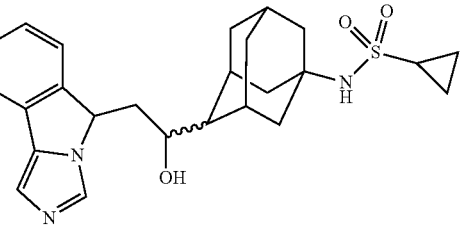
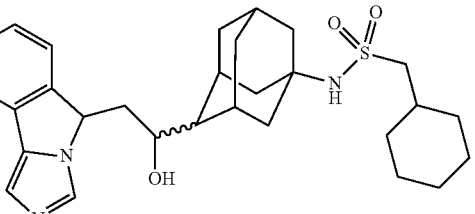
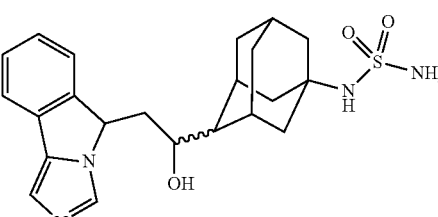
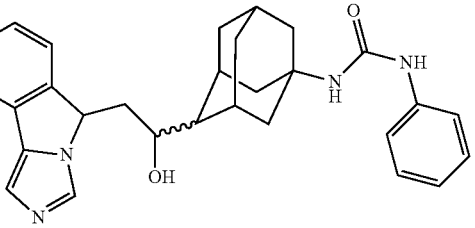
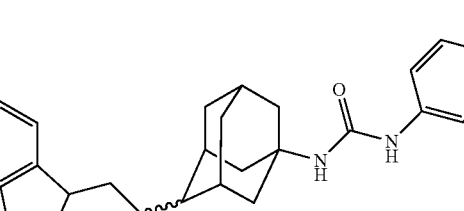

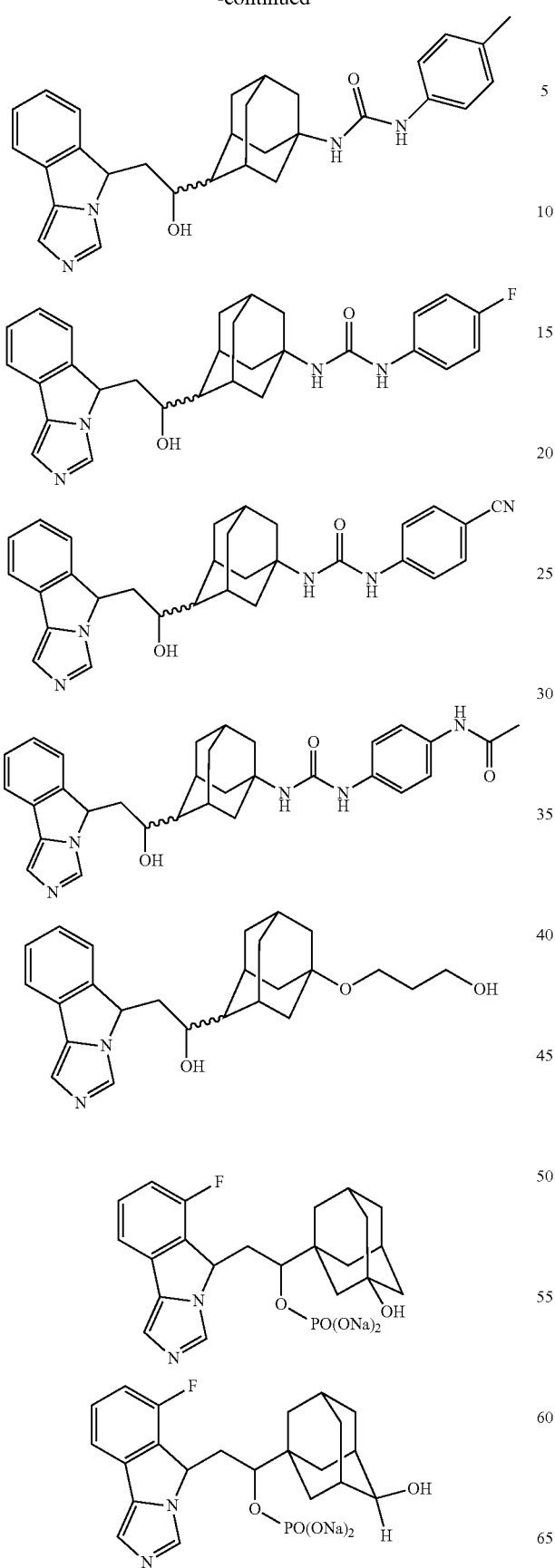
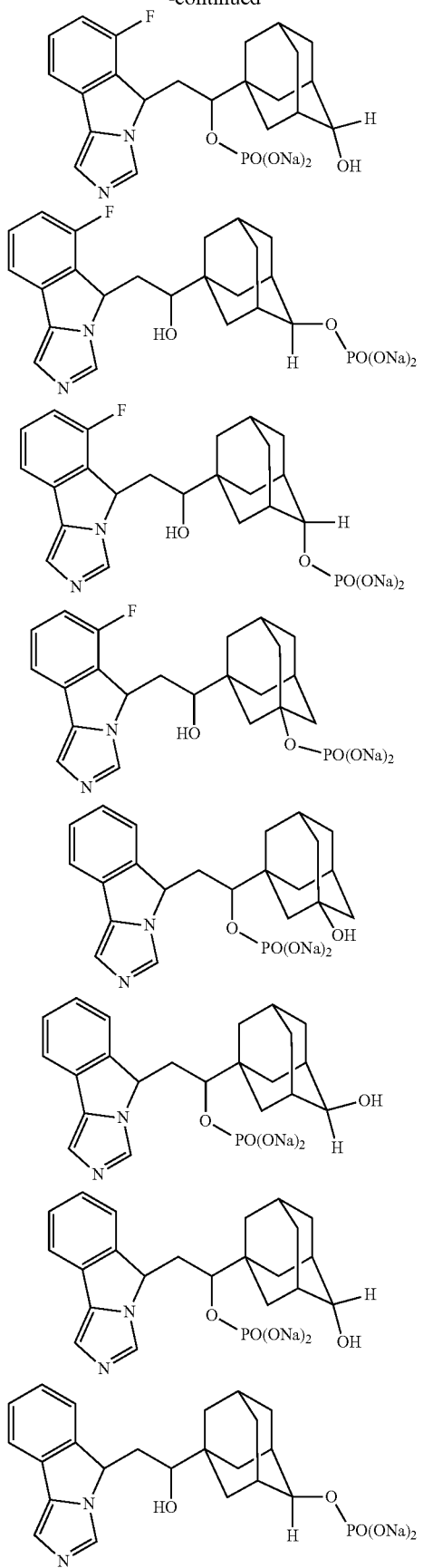

93
-continued
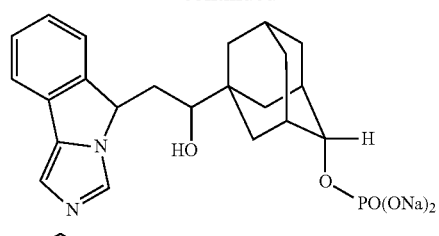
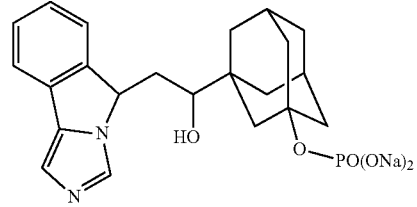
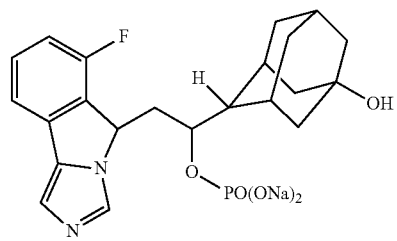
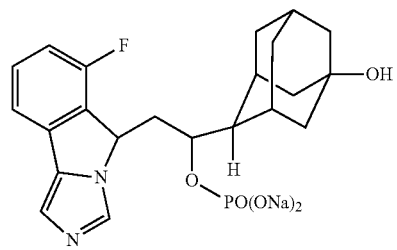
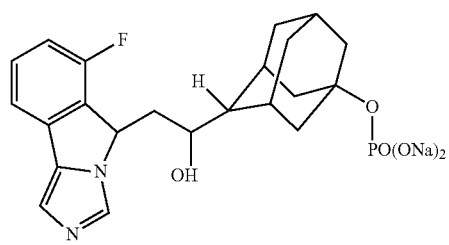
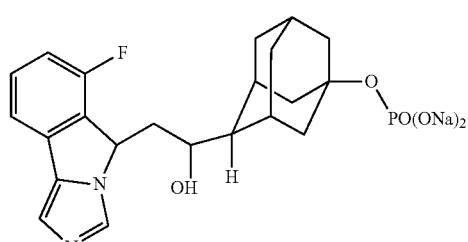
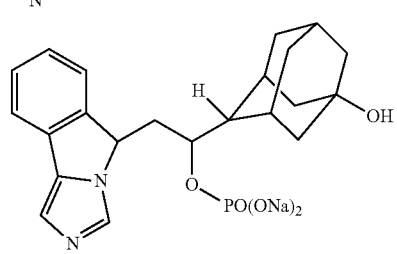
94
-continued
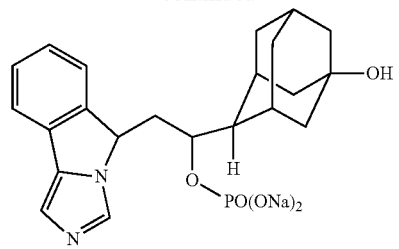
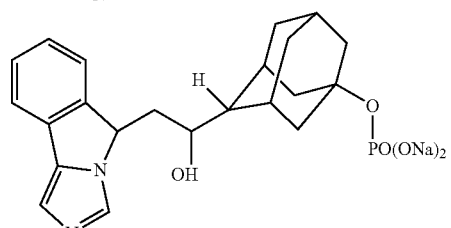
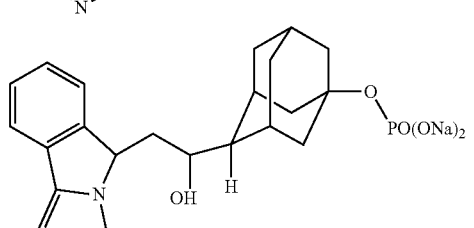
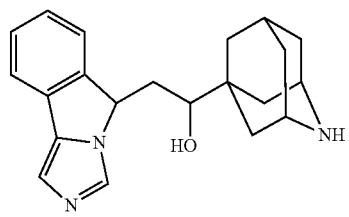
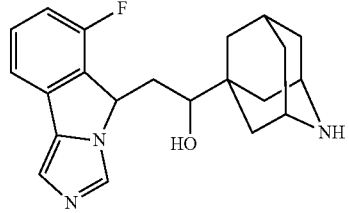
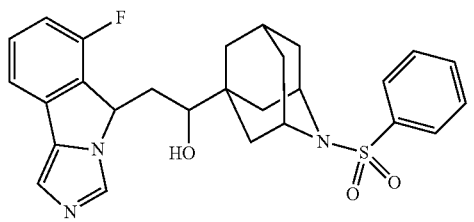
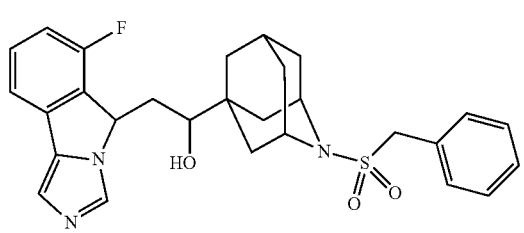

95
-continued
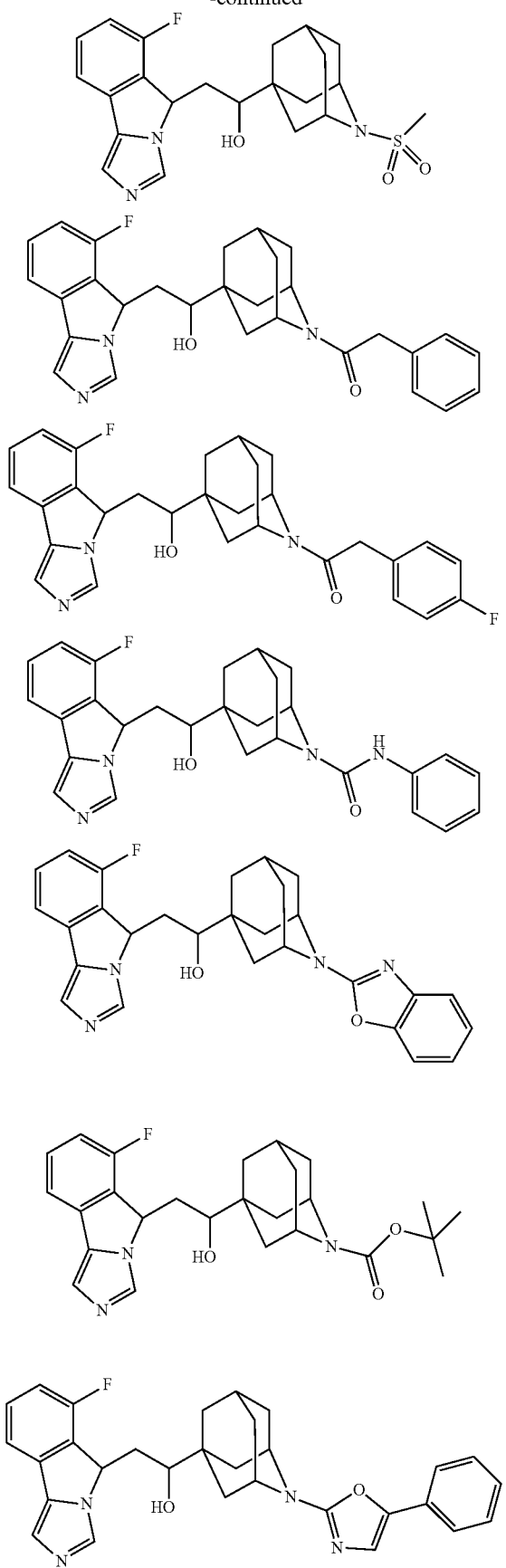
96
-continued
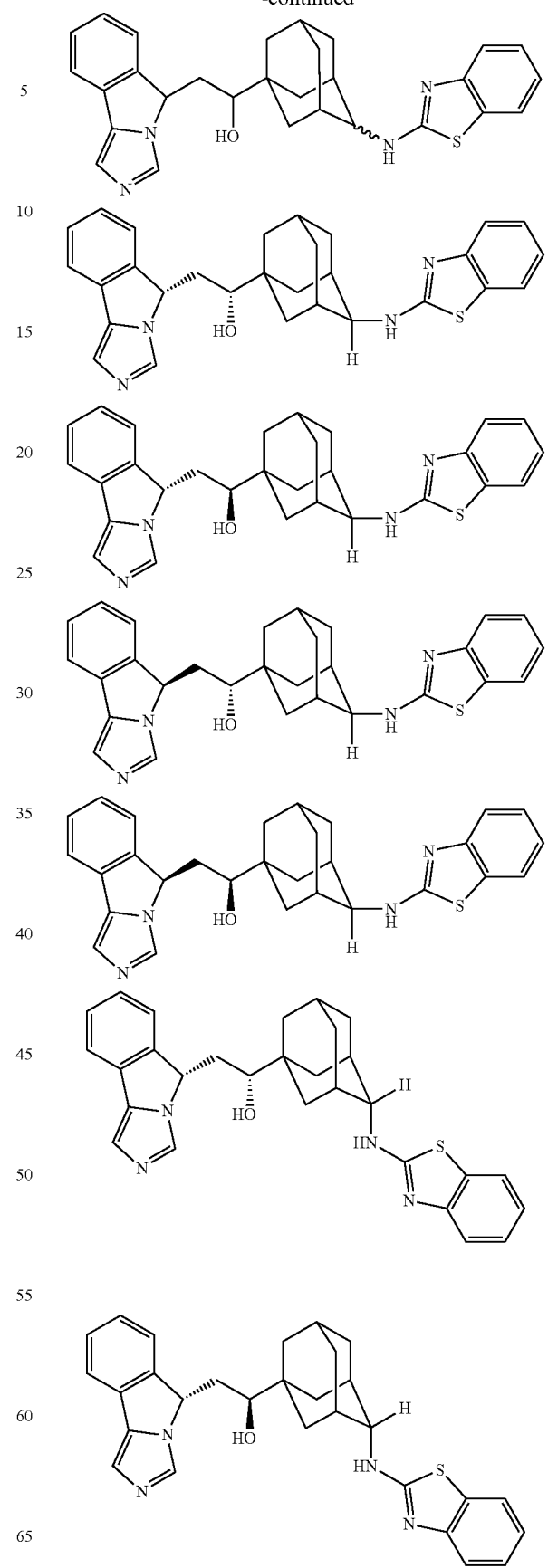

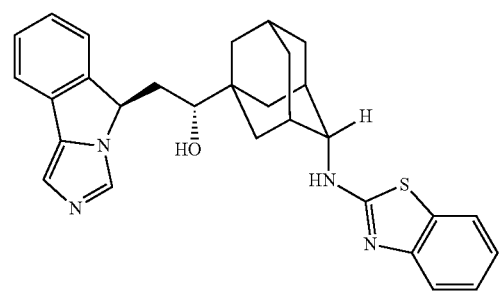
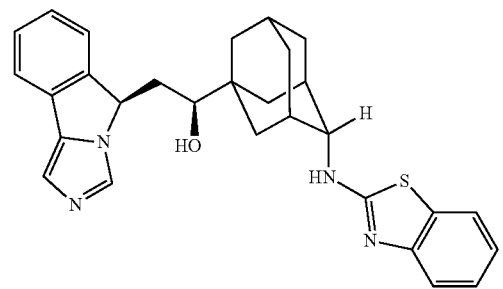
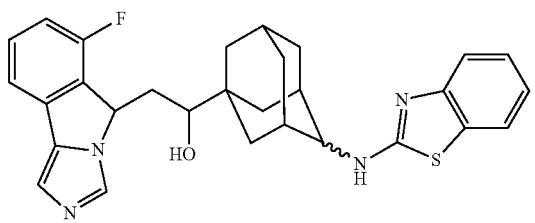
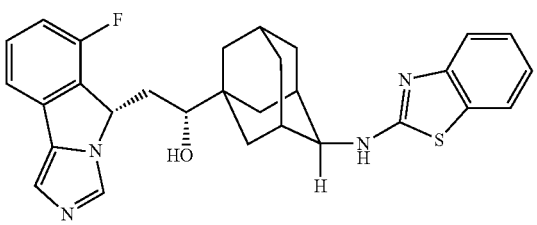
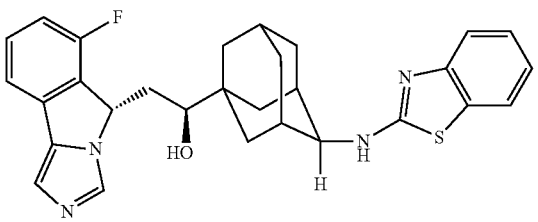
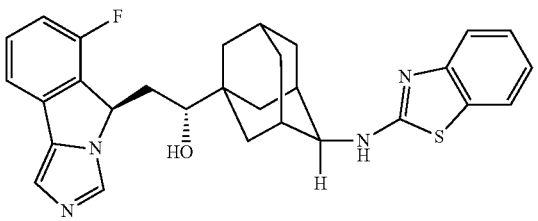
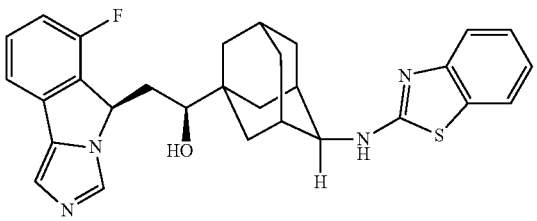
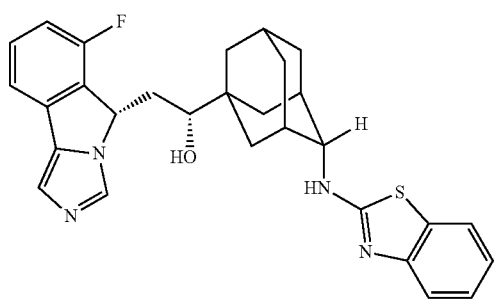
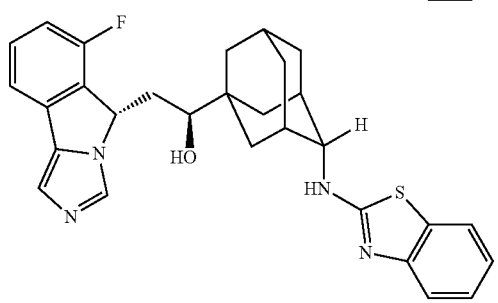
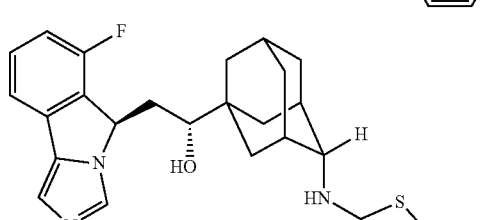
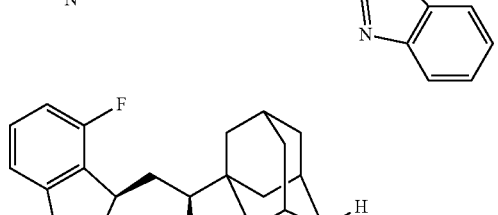
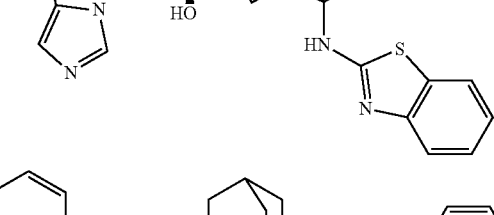
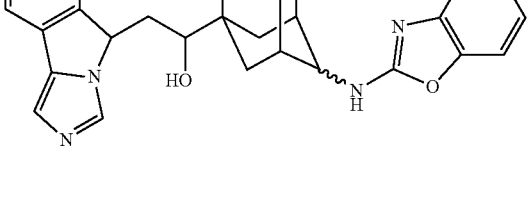
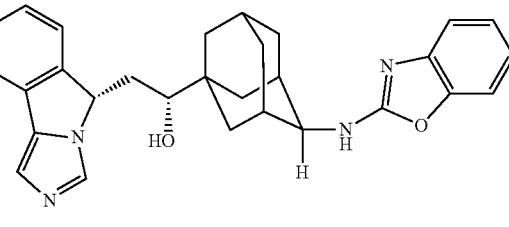

99
-continued
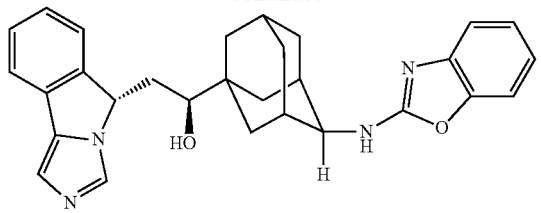

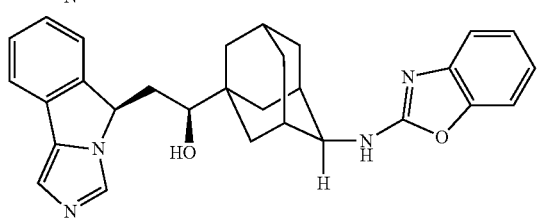
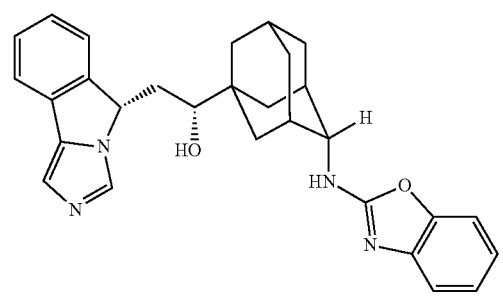
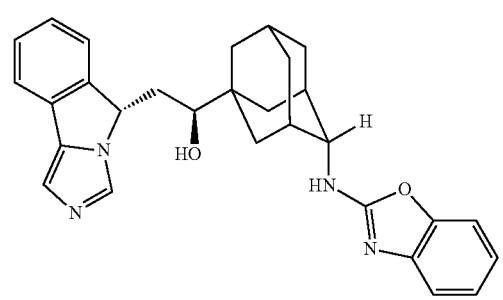
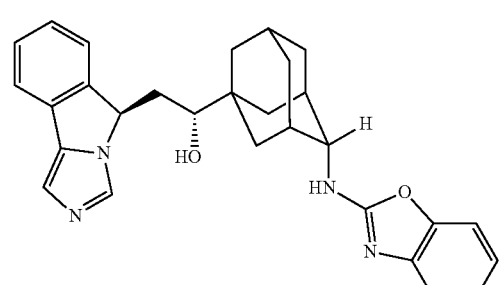
100
-continued
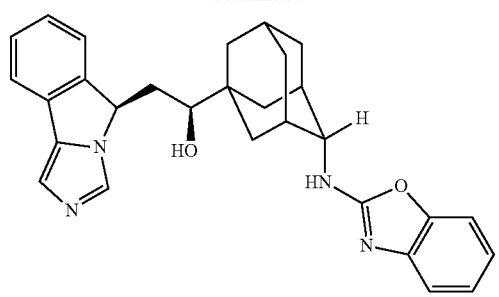
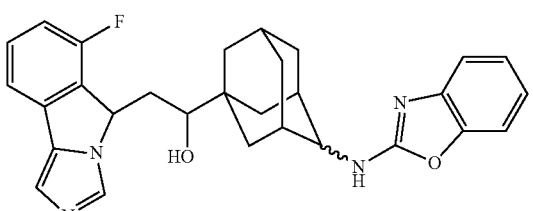
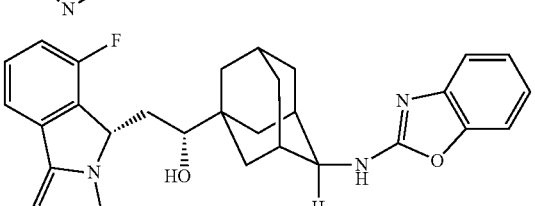
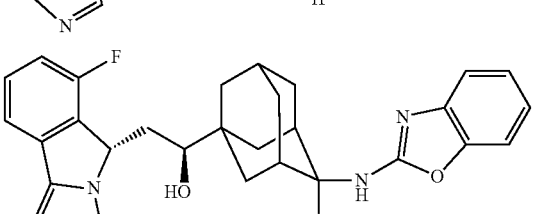
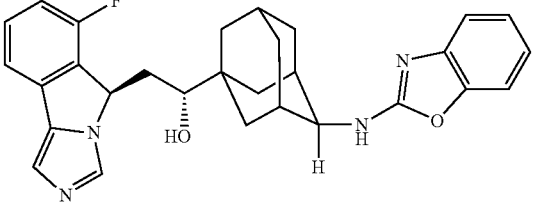
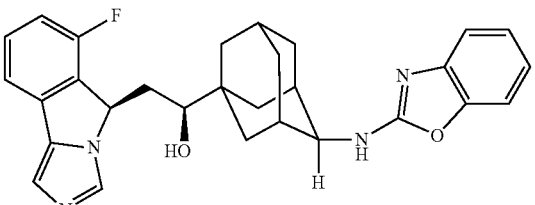
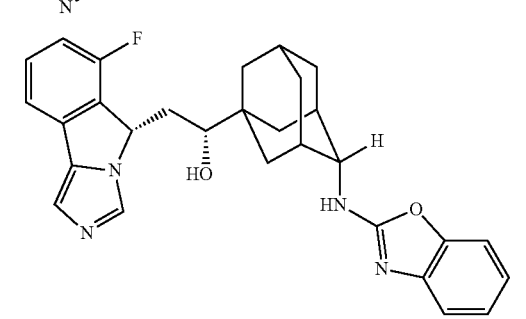

101
-continued
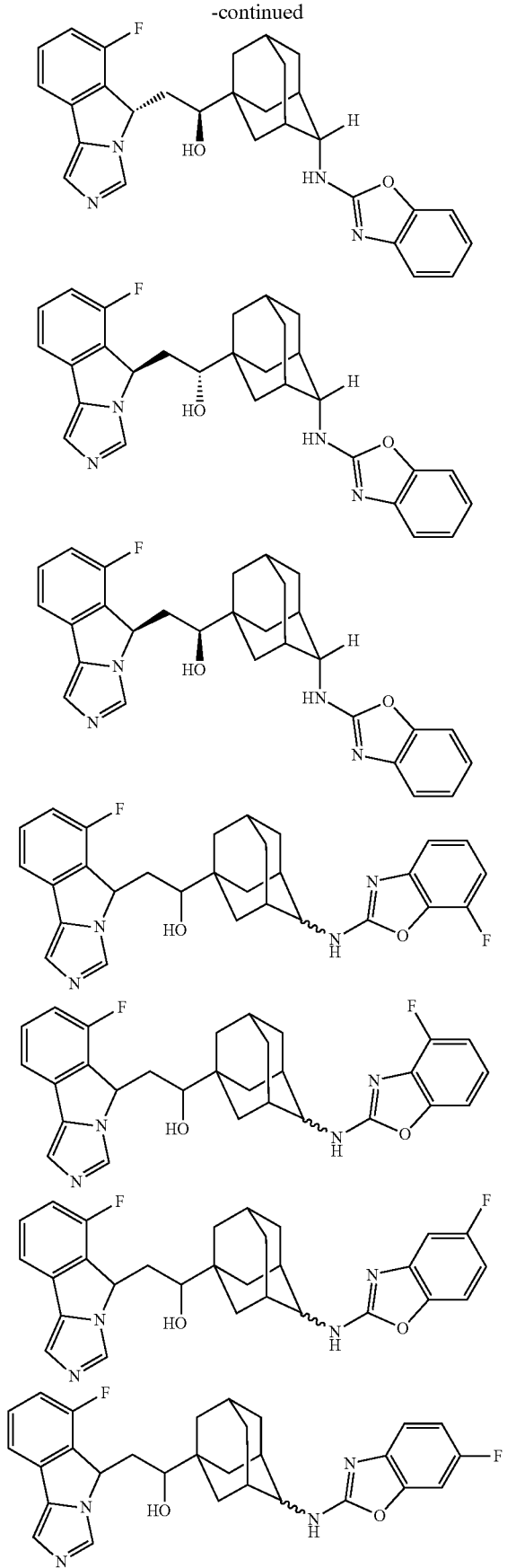
102
-continued
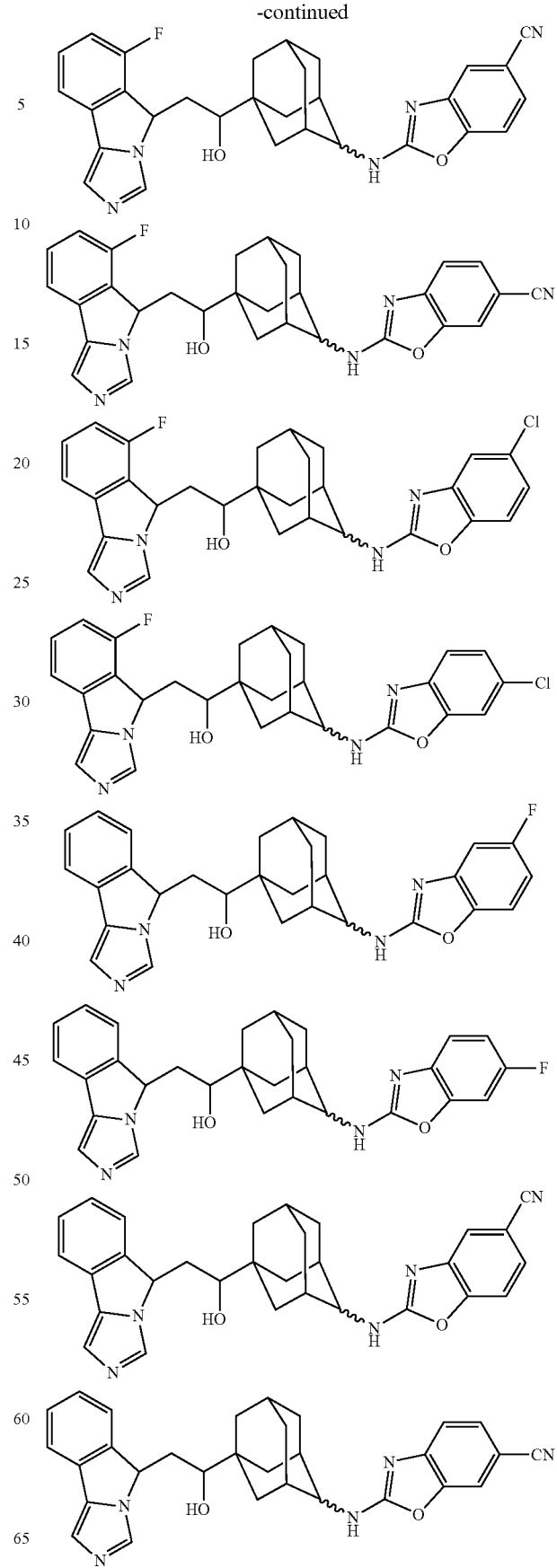

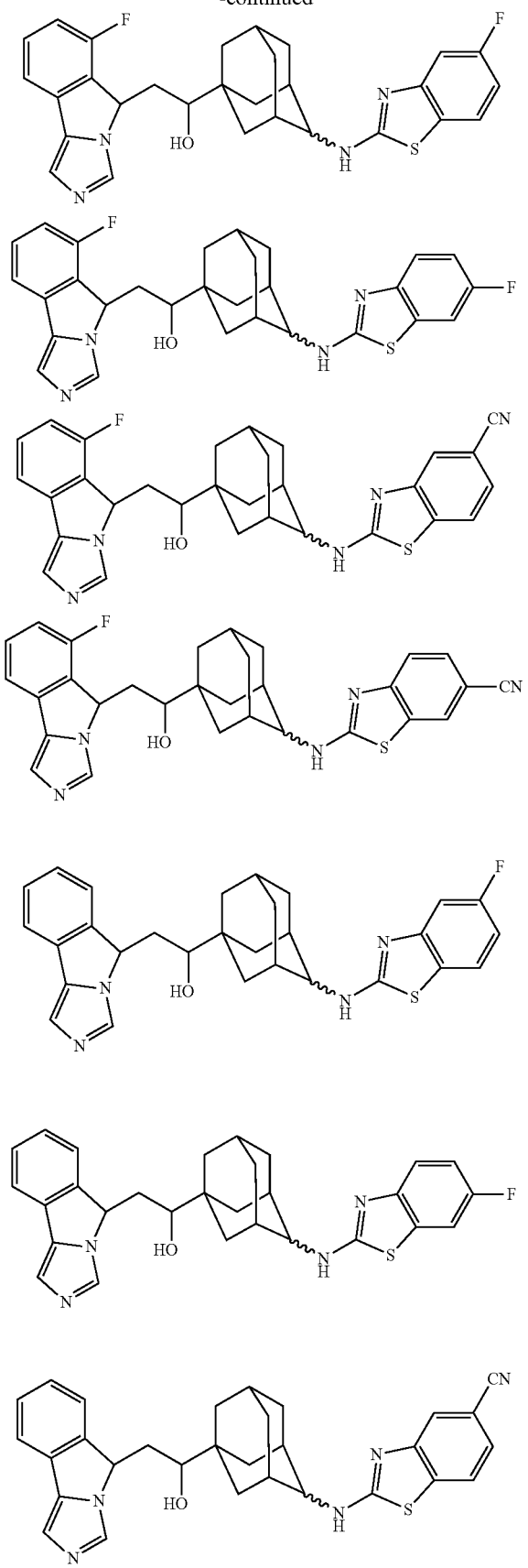

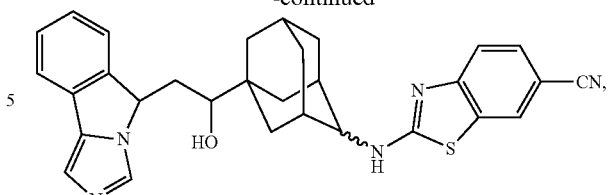

and/or a pharmaceutically acceptable salt thereof.

Also provided a pharmaceutical composition comprising 1) a compound of formula (I) and/or a pharmaceutically acceptable salt thereof, and 2) a pharmaceutically acceptable excipient. The compound of formula (I) and/or a pharmaceutically acceptable salt can be any embodiment thereof disclosed herein.

In some embodiments, the pharmaceutical composition comprises a therapeutically-effective amount of the compound of formula (I) and/or a pharmaceutically acceptable salt thereof.

In some embodiments, the pharmaceutical composition described herein further comprises another active pharmaceutical ingredient for treatment of cancer, viral infection or autoimmune disease.

A pharmaceutically acceptable excipient refers to an excipient that is useful in preparing a pharmaceutical composition that is compatible with active ingredients of the composition and not deleterious to the subject to be treated. These excipients include, for example, binders, surfactants, diluents, buffering agents, antiadherents, glidants, hydrophilic or hydrophobic polymers, retardants, stabilizing agents or stabilizers, disintegrants or superdisintegrants, antioxidants, antifoaming agents, fillers, flavors, colors, lubricants, sorbents, preservatives, plasticizers, and sweeteners. Acceptable excipients are non-toxic, aid administration, and do not adversely affect the therapeutic benefit of the compound disclosed herein. Such excipient may be any solid, liquid, semi-solid or, in the case of an aerosol composition, gaseous excipient that is generally available to one of skill in the art.

These pharmaceutical compositions can be prepared in various pharmaceutical formulations and dosage forms depending upon the therapeutic aims, for example, tablets, pills, powders, liquids, suspensions, emulsions, particles, capsules, suppositories and injections (solutions and suspensions), etc.

The compositions such as tablets can be prepared in a manner well known in the pharmaceutical art by using excipients to make the compositions to form into shapes. Said excipients include, for example, lactose, sugar, sodium chloride, glucose, urea, starch, calcium carbonate, kaolin, crystalline cellulose, and silicic acid, etc.; binders, for example, water, ethanol, propanol, common syrup, glucose solution, starch solution, gelatin solution, carboxymethylcellulose, shellac, methylcellulose, potassium carbonate, and polyvinyl pyrrolidone, etc.; disintegrating agents, for example, dry starch, sodium alginate, agar powder, kelp powder, calcium bicarbonate, calcium carbonate, polyoxyethylene sorbitan monooleate, lauryl sodium sulfate, glycerin monostearate, starch, and lactose, etc.; agents which inhibit disintegrating, for example, sugar, tristearin, coconut oil, and hardened vegetable oil, etc.; absorbent enhancers, for example, quaternary ammonium base, and lauryl sodium sulfate, etc.; wetting agents, for example, glycerin and starch, etc.; absorbent, for example, starch, lactose, bolus alba, bentonite, and silicious colloid, etc.; lubricants, for example, pure talcum, stearate, boric acid powder, and polyethylene glycol, etc. sugar coated tablets, gelatin film coated tablets, enteric coated tablets, film coated tablets, bilayer tablets, and multi-layer tablets can be made according to need by using common coating materials.

The compositions such as pills can be prepared in a manner well known in the pharmaceutical art by using excipients to make the compositions to form into shapes. Said excipients can be carriers, for example, lactose, starch, coconut oil, hardened vegetable oil, kaolin, and talcum powder, etc.; binders, for example, gum arabic powder, gum tragacanth powder, gelatin and ethanol, etc.; disintegrating agents, for example, agar powder, and kelp powder, etc.

The compositions such as suppositories can be prepared in a manner well known in the pharmaceutical art by using excipients to make the compositions to form into shapes, such as, polyethylene glycol, coconut oil, higher alcohols, higher esters, gelatin, and semi synthesis glyceride, etc.

To prepare compositions such as injections, the solution or suspension is disinfected (it would be good to add suitable amount of sodium chloride, glucose, or glycerol), and then formulated as osmotic injections. The injections can be prepared in a manner well known in the pharmaceutical art by using excipients, such as, water, ethanol, propane diol, ethoxy stearic alcohol and polyvinylsorbitol ester and polyoxyethylene sorbitan monooleate, etc. In addition, the injections can contain commonly used solubilizers, buffering agents, and analgesic agents, etc.

The fused-ring compound of the formula (I) and/or a pharmaceutically acceptable salt thereof of any embodiment disclosed herein in the pharmaceutical composition can be effective over a wide range without a specific limitation, usually the amount of the active ingredient can be in a range of 5-95% w/w of the total mass of the composition, such as in a range of 30-80% w/w.

The compositions can be administered in a unit dosage form without specific limitation. The chosen dosage of administration is dependent upon the age, weight and sex of the individual patients, and other circumstances and the severity of the patient's symptoms. The dose forms can be tablets, pills, solutions, suspensions, emulsions, particles, or capsules; injections can be administered alone, or incorporated with injectable solutions (such as glucose or amino acid solutions) for intravenous injections; suppositories are administered into the rectum.

Also the use of a fused-ring compound of the formula (I) and/or a pharmaceutically acceptable salt thereof any embodiment disclosed herein or use of the pharmaceutical composition disclosed herein is not especially limited, provided is an use of a fused-ring compound of the formula (I) and/or a pharmaceutically acceptable salt thereof of any embodiment disclosed herein or an use of the pharmaceutical composition disclosed herein in the preparation of IDO1 and/or TDO2 inhibitors. The IDO1 and/or TDO2 inhibitors described refer to compounds capable of inhibiting IDO1 and/or TDO2 activity or expression (including abnormal activity and/or overexpression), and reversing IDO1 and/or TDO2-mediated immune-suppression.

Also provided use of a fused-ring compound of the formula (I) and/or a pharmaceutically acceptable salt thereof of any embodiment described herein of any embodiment disclosed herein or use of the pharmaceutical composition disclosed herein in the preparation of a drug which can stimulate T cell proliferation.

Also provided use of a fused-ring compound of the formula (I) and/or a pharmaceutically acceptable salt thereof of any embodiment disclosed herein or use of the pharmaceutical composition disclosed herein in the preparation of a drug in treating, alleviating, ameliorating and/or prevention of IDO1 and/or TDO2 mediated relevant diseases by administering to the individual (e.g., patient) in need of such treatment a therapeutically effective amount or dose of a compound of the present invention or a pharmaceutical composition thereof. The described IDO1 and/or TDO2 mediated diseases refer to any disease, condition or disorder that may be prevented, ameliorated or treated using an IDO1 and/or TDO2 inhibitor. Typically said IDO1 and/or TDO2 mediated diseases are caused by immune-suppression. The described diseases include but are not limited to: viral or other infections (such as: skin infection, gastrointestinal infection, urogenital infection, systemic infection, etc), cancer, or autoimmune diseases (such as: rheumatoid arthritis, SLE, psoriasis, etc).

Also provided use of a fused-ring compound of the formula (I) and/or a pharmaceutically acceptable salt thereof of any embodiment disclosed herein or use of the pharmaceutical composition disclosed herein combined with one or more additional pharmaceutical agents or treatment methods for preventing, ameliorating and/or treating IDO1 and/or TDO2 mediated diseases, wherein said IDO1 and/or TDO2 mediated diseases are caused by immune-suppression. The described diseases include but are not limited to: viral or other infections (such as: skin infection, gastrointestinal infection, urogenital infection, systemic infection, etc), cancer, or autoimmune diseases (such as: rheumatoid arthritis, SLE, psoriasis, etc). The additional pharmaceutical agents can be combined with the present compounds in a single dosage form, or can be administered simultaneously or sequentially as separate dosage forms.

In some embodiments the additional pharmaceutical agents or treatment methods for treatment of cancer are selected from but not limited to anti-microtubule agents, alkylating agents, topoisomerase I/II inhibitors, platinum coordination complexes, antimetabolites, hormones and hormone analogues, signal transduction pathway inhibitors, angiogenesis inhibitors, targeted therapeutics (such as specific kinase inhibitors), immunotherapeutic agents, pro-apoptotic agents, cell cycle signaling inhibitors and radiation.

In some embodiments the additional pharmaceutical agents for treatment of cancer are selected form anti-microtubule agents, including but not limited to: vinblastine analogues (such as: vinblastine, vincristine, vinorelbine, and vindesine), taxanes analogues (such as: paclitaxel and docetaxel) and eribulin mesylate.

In some embodiments the additional pharmaceutical agents for treatment of cancer are selected form alkylating agents, including but not limited to: nitrogen mustards, ethylenimine derivatives, alkyl sulfonates, nitrosoureas and triazenes.

In some embodiments the additional pharmaceutical agents for treatment of cancer are selected form topoisomerase I/II inhibitors, such as: irinotecan, doxorubicin, topotecan and dexrazoxane.

In some embodiments the additional pharmaceutical agents for treatment of cancer are selected form platinum coordination complexes, such as: cisplatin and carboplatin.

In some embodiments the additional pharmaceutical agents for treatment of cancer are selected form antimetabolites, including but not limited to: folic acid antagonists, pyrimidine analogs, purine analogs and adenosine deaminase inhibitors; such as: methotrexate, 5-fluorouracil, floxuridine, cytarabine, 6-mercaptopurine, 6-thioguanine, fludarabine phosphate, pentostatine, and gemcitabine.

In some embodiments the additional pharmaceutical agents for treatment of cancer are selected from immunotherapeutic agents, including but not limited to: anti-tumor vaccines (such as: synthetic peptides, DNA vaccines and recombinant viruses), an oncolytic virus, an immune stimulatory antibody, a novel adjuvant, a cytokine therapy (such as: IL2 and GM-CSF), a chimeric antigen receptor T cell therapy (CAR-T), a small molecule immune modulator, tumor microenvironment modulators, and anti-angiogenic agents. wherein said immune stimulatory antibodies are selected from but not limited to 1) an antagonist of a protein that inhibits T cell activation (e.g., immune checkpoint inhibitors) such as: CTLA4 (e.g., ipilimumab, and tremelimumab), PD-1 (e.g., pembrolizumab and nivolumab), PD-L1 (e.g., durvalumab, avelumab, and atezolizumab), LAG3, and TIM3; 2) an agonist of a protein that stimulates T cell activation such as GITR, OX40, OX40L, 4-1BB (CD137), CD27, and CD40.

In some embodiments the additional pharmaceutical agents for treatment of cancer are selected from signal transduction pathway inhibitors (STI), a signal transduction inhibitor is an agent that selectively inhibits one or more vital steps in signaling pathways, in normal function of cancer cells, thereby leading to apoptosis, including but not limited to: BCR/ABL kinase inhibitors, epidermal growth factor receptor inhibitors, her-2/neu receptor inhibitors, AKT family kinase inhibitors or inhibitors of PI3K-pathway, cell cycle checkpoint inhibitors.

In some embodiments the additional pharmaceutical agents for treatment of cancer are selected from angiogenesis inhibitors, including but not limited to: inhibitors VEGF/VEGFR pathway, Src family kinase inhibitors or inhibitors of Src pathway, c-Fes tyrosine kinase inhibitors.

Also provided use of a fused-ring compound of the formula (I) and/or a pharmaceutically acceptable salt thereof of any embodiment disclosed herein or use of the pharmaceutical composition disclosed herein in the preparation of a drug in treating, alleviating and/or preventing cancer, viral infection, or autoimmune diseases related immune-suppression.

The described viral infections include but are not limited to: infections caused by flu, hepatitis C (HCV), human papilloma virus (HPV), cytomegalovirus (CMV), Epstein-Barr virus (EBV), poliovirus, chickenpox-zoster virus, Coxsackie virus, or human immunodeficiency virus (HIV), and the like.

The described cancers may be solid tumors or liquid tumors.

In some embodiments the solid tumors include but are not limited to the tumor of eye, bone, lung, gastric, pancreas, breast, prostate, brain (including glioblastomas and medulloblastomas), ovarian (including those arising from epithelial cells, stromal cells, germ cells and mesenchymal cells), bladder, testis, spinal cord, kidney (including adenocarcinoma and Wilms tumor), mouth, lip, throat, oral cavity (including squamous cell carcinoma), nasal cavity, small intestine, colon, rectum, parathyroid gland, gall bladder, bile duct, cervix, heart, hypopharyngeal gland, bronchus, liver, ureter, vagina, anus, laryngeal gland, thyroid (including thyroid adenocarcinoma and medullary carcinoma), esophagus, nasopharyngeal gland, pituitary gland, salivary gland, adrenal glands, head and neck, intraepithelial neoplasia (including Bowen's disease and Paget's disease), sarcomas (including leiomyosarcoma, rhabdomyosarcoma, liposarcoma, fibrosarcoma and osteosarcoma), skin (including melanoma, Kaposi's sarcoma, basocellular cancer and squamous cell cancer) and the like.

In some embodiments the liquid tumors include but are not limited to the tumor of lymphoid (including acute lymphocytic leukemia, lymphomas, myelomas, chronic lymphoid leukemias, Hodgkin's disease, non-Hodgkin's lymphomas and lymphocytic lymphomas, T cell chronic lymphoid leukemias and B cell chronic lymphoid leukemias), myeloid and AIDs associated leukemias.

The described autoimmune diseases include but are not limited to: rheumatoid arthritis, systemic lupus erythematosus, mixed connective tissue disease (MCTD), systemic scleroderma (including: CREST syndrome), multiple myositis, nodular vasculitis, kidney diseases (including: Goodpastures syndrome, acute glomerulonephritis, primary membrano-proliferative glomerulonephritis, etc), endocrine related diseases (including: type I diabetes, hypogonadism, pernicious anemia, hyperthyroidism, etc), liver diseases (including: primary biliary cirrhosis, autoimmune cholangitis, autoimmune hepatitis, primary sclerotic cholangitis, etc), or autoimmune reaction caused by infections (such as: AIDS, malaria, etc).

Also provided use of a fused-ring compound of the formula (I) and/or a pharmaceutically acceptable salt thereof of any embodiment disclosed herein or use of the pharmaceutical composition disclosed herein in suppressing the tryptophan metabolism in the drug compound inhibitory system. The system refers to organisms, tissues or cells expressing IDO1/TDO2.

The described organism primarily refers to mammals, such as humans. The described method of tryptophan metabolism in the inhibitory system includes the following steps: to inhibit tryptophan metabolism by administrating efficacious dose of compound of formula (I) to mammals.

Further provided a method of treating a disease treatable by inhibition of IDO1 and/or TDO2 in a mammal which method comprises administering to the mammal in recognized need of such treatment, a therapeutically effective amount of a fused-ring compound of the formula (I) and/or a pharmaceutically acceptable salt thereof of any embodiment disclosed herein or a therapeutically effective amount of the pharmaceutical composition disclosed herein. In some embodiments, the mammal is a human.

In some embodiments, the disease treatable by inhibition of IDO1 and/or TDO2 is cancer, viral infection, or autoimmune disease, including any specific type thereof disclosed herein.

Further provided methods for synthesizing the fused-ring compounds of formula (I), which can be any of the following:

Method 1:

Scheme I

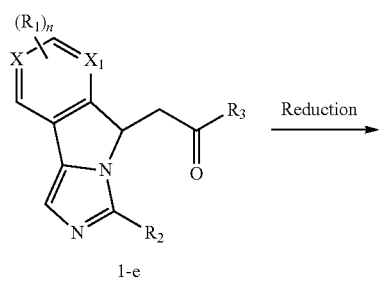

1-e

-continued

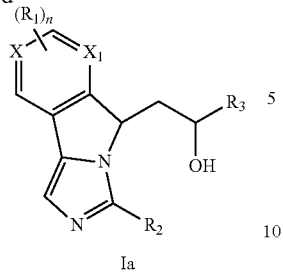

Ia

In Scheme I, intermediates 1-e are reduced to obtain compounds Ia. In the described reduction reactions, reductants such as sodium borohydride (NaBH$_4$) or lithium borohydride (LiBH$_4$) is usually used in methanol or ethanol, or lithium aluminum hydride (LiAlH$_4$) is used in tetrahydrofuran (THF), the reaction temperature is preferred between 0° C. to room temperature.

Scheme 2

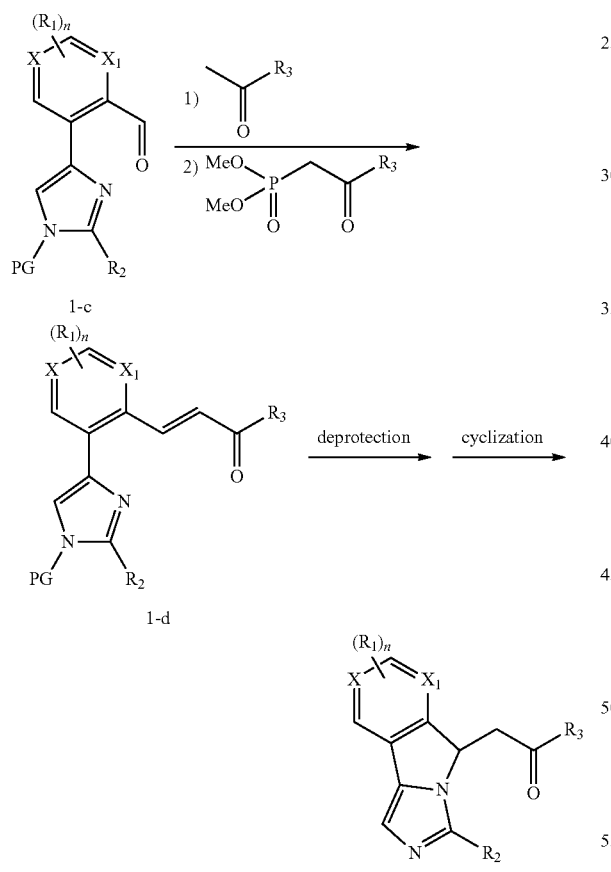

PG = Trt or Boc

Herein, Boc is t-butyloxycarbonyl group, Trt is trityl group; intermediates 1-e are synthesized according to Scheme 2, compounds 1-d are obtained via 1) aldol condensation (R$_2$ is H), or 2) HWE olefenation reaction (R$_2$ is Boc-protected amino group), after deprotection under acidic conditions, compounds 1-d are cyclized to afford intermediates 1-e, when the protection group PG is Boc, it can be deprotected by trifluoroacetic acid/dichloromethane and hydrogen chloride/methanol; solvents used in the described cyclization reactions are preferred protic solvents, methanol is more preferred.

Scheme 3

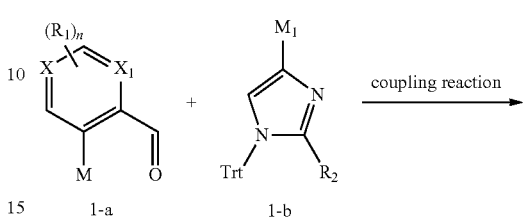

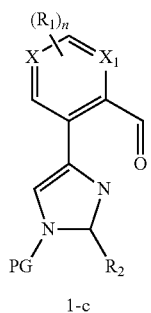

1-c

Scheme 3-1

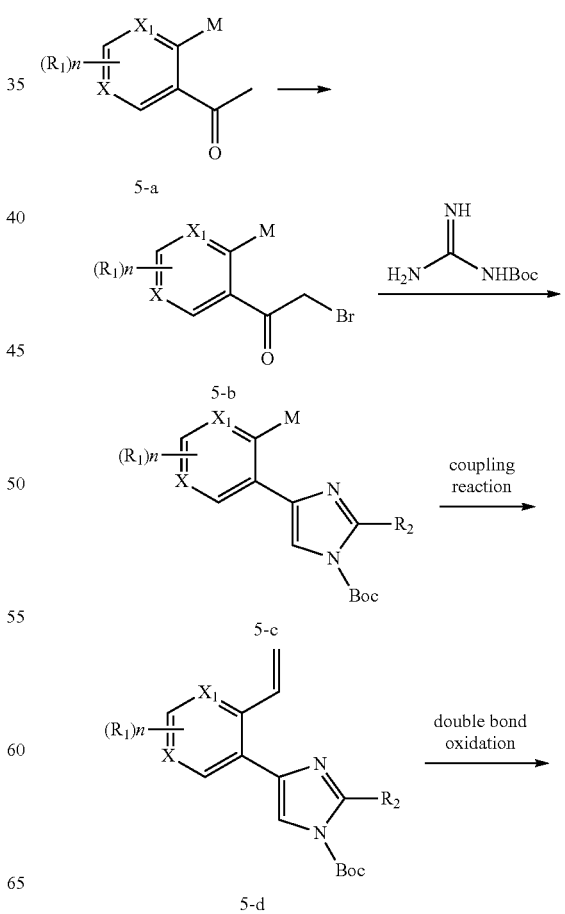

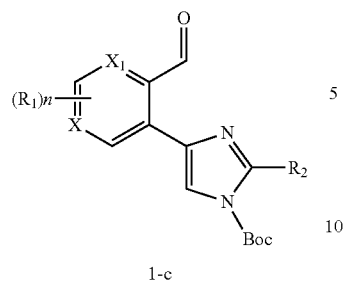

1-c

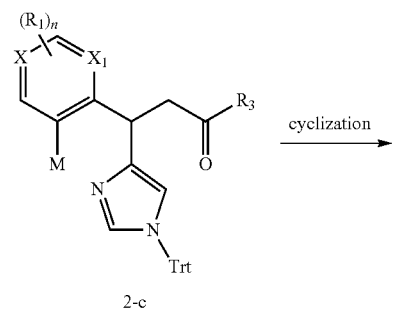

2-c

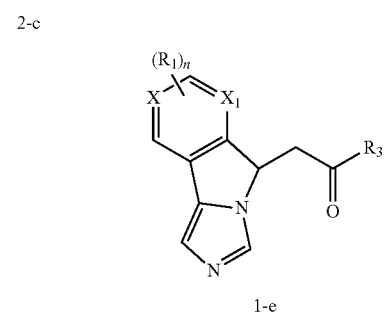

1-e

Intermediates 1-c are synthesized according to Scheme 3, herein M is bromine, iodine or boronic acid; $M_1$ is iodine or n-$Bu_3$Sn-group; $R_2$ is hydrogen; compounds 1-a are coupled with compounds 1-b to obtain 1-c, the described coupling reactions include Suzuki, Stille or Negishi coupling reactions.

Intermediates 1-c are synthesized according to Scheme 3-1, herein M is bromine or iodine, $R_2$ is amino; compounds 5-b are reacted with Boc-protected guanidine to give compounds 5-c, which are further reacted with tributylvinyltin via Stille coupling to give 5-d, the double bond of 5-d is oxidized in $NaIO_4$/$OsO_4$ to afford aldehyde compounds 1-c. In the described coupling, double bond oxidation, and HWE olefenation reactions, if compounds 5-c, 5-d or 1-c contain amino group (for example, $R_2$ is amino), the amino group should be protected to avoid any side reactions. If amino protecting group is present, it needs to be deprotected so that the cyclization reactions can occur to afford compounds 1-e. Any appropriate amino protecting group, such as t-butyloxycarbonyl group (Boc), can be used in the above reactions. If Boc is used as protecting group, the deprotection reaction can be done in the following commonly used conditions, for example, p-toluenesulfonic acid/methanol, TFA/$CH_2Cl_2$, saturated HCl/ether, or trimethylsilyl trifluoromethanesulfonate/2,6-lutidine/$CH_2Cl_2$.

Intermediates 1-e can be synthesized according to scheme 4, herein M is bromine or iodine. Firstly, under basic conditions, such as in presence of potassium hydroxide or sodium hydroxide, compounds 2-a can be transformed to compounds 2-b in protic solvent, which is preferred methanol; 1-trityl-4-iodoimidazole is treated with Grinard reagent, such as isopropylmagnesium bromide (i-PrMgCl), to obtain a Grinard product, which is reacted with compounds 2-b in presence of CuCl, to give compounds 2-c. Compound 2-c is cyclized in the presence of 4,7-dimethoxy-1,10-phenanthroline, $Cs_2CO_3$ and CuCl to afford intermediates 1-e.

Method 2:

Scheme 4

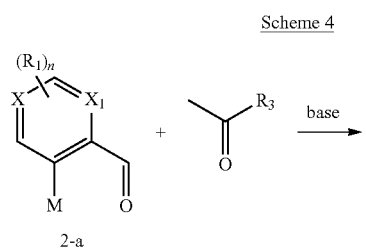

2-a

Scheme 5

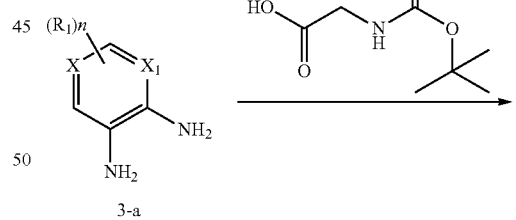

3-a

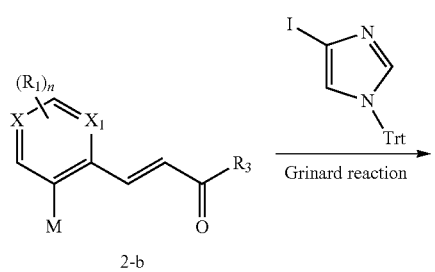

2-b

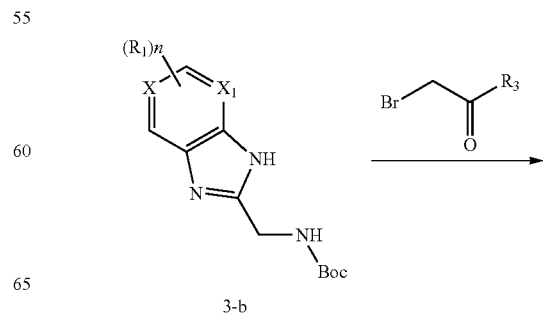

3-b

-continued

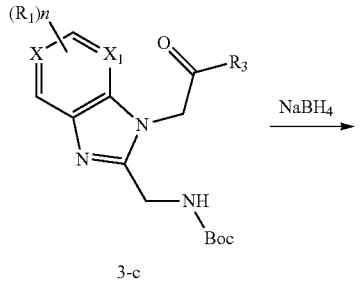

3-c

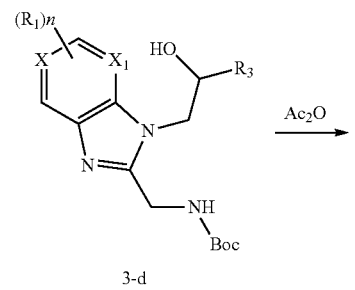

3-d

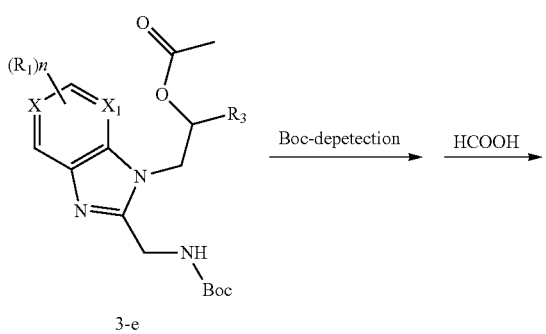

3-e

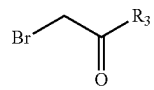

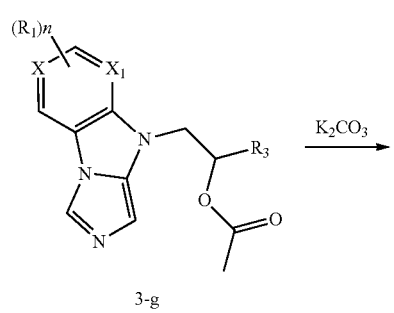

3-f

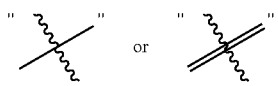

3-g

-continued

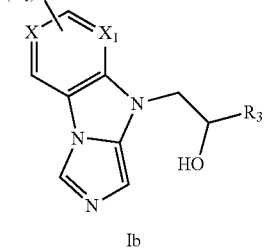

Ib

Scheme 5 describes synthetic methods for compounds of formula Ib. Compounds 3-a is condensed with Boc-protected glycine and then cyclized to give compounds 3-b. The described reaction, for example, uses N,N'-dicyclohexylcarbodiimide as coupling reagent and protic solvent, such as, THF as solvent. Compound 3-b is reacted with $$\underset{\text{Br}}{\overset{\text{O}}{\bigvee}} R_3$$

and $K_2CO_3$ in N, N-dimethyl formamide (DMF), the nucleophilic reaction renders intermediate 3-c. The carbonyl group of 3-c is reduced to give 3-d, in which the hydroxyl group was protected by acetic anhydride ($Ac_2O$), then reacted with formic acid to afford compound 3-f. Compound 3-f is further heated with $POCl_3$ to cyclize and afford compound 3-g, in which the acetyl group is deprotected and compound of formula Ib is obtained.

Under acid conditions, such as when p-TsOH, HCl, or TFA, etc. is used in the last step in the above methods 1 and 2, or during the purification process, if the above acids are present in the eluents of preparative HPLC, the obtained compounds of formula Ia, or Ib are corresponding salts of p-TsOH, HCl or TFA, etc.

In this disclosure, all of the reaction conditions and procedures in the above methods 1 to 3 are commonly used reaction conditions and procedures.

As used herein unless otherwise stated, if "substituted or unsubstituted" is absent in front of an organic group, it is meant that the organic group is unsubstituted, for example, "alkyl" means unsubstituted alkyl, "cycloalkyl" means unsubstituted cycloalkyl.

Unless clearly indicated otherwise, use of the terms "a", "an" and the like refers to one or more.

Unless clearly indicated otherwise, use of the symbol in compounds, substituents and groups to show the bond that is the point of attachment of the moiety or substituent to the parent molecular moiety.

Unless clearly indicated otherwise, use of the term "substituted by one or more substituent(s)" and the like refers to a compound, substituent or group which is substituted by 1, 1 to 2, 1 to 3, or 1 to 4 substituent(s).

As one of ordinary skill in the art will recognize, combinations of substituents envisioned by this disclosure are those combinations that result in the formation of stable or chemically feasible compounds.

As used herein, "combination of any embodiment" of variables (such as $R_1$-$R_{13}$, etc) can be illustrated with the following example: variable 1 and variable 2 are used to define a compound of formula X; variable 1 has broad embodiment and narrow embodiments, variable 2 has broad embodiment and narrow embodiments; combination of any embodiment of variable 1 with any embodiment of variable 2 refers to a combination of any embodiment of variables 1 and variable 2. Each of the combinations is a proper description of formula X and within the scope of disclosure.

As used herein, the phrase "any position" in the sentence of "the substituted group can be substituted by one or more groups at any position" means reasonable position that is well known in the art; the described "one or more groups" means, for example, 1 to 3 groups.

Unless otherwise stated, the following terms in the description and claims have the following definitions:

The term "alkyl" as used herein, refers to a saturated aliphatic hydrocarbon group including 1 to 20 carbon atoms straight chain and branched chain groups. Preferably an alkyl group is a moderate size alkyl having 1 to 10 carbon atoms, more preferably having 1 to 8 carbon atoms. Representative examples of alkyl include, but are not limited to: methyl, ethyl, n-propyl, iso-propyl, n-butyl, sec-butyl, iso-butyl, tert-butyl, n-pentyl, n-hexyl, n-heptyl, n-octyl, n-nonyl, and n-decyl, 4,4-dimethylpentyl, 2,2,4-trimethylpentyl, undecanyl, docecanyl, and their isomers. When an "alkyl" group is a linking group between two moieties, such as —($CH_2$)$_m$—, then it may also be a straight or branched chain; examples include, but are not limited to —$CH_2$—, —$CH_2CH_2$—, —$CH_2CH(CH_3)$—.

The term "cycloalkyl" as used herein, refers to a saturated or partially unsaturated monocyclic or bicyclic cycloalkyl ring group containing 3 to 20 carbon atoms, and the C atoms can be oxidized in the cyclic ring system. "mono-cycloalkyl" are cyclic hydrocarbon groups containing 3 to 20 carbon atoms, more preferably having 3 to 8 carbon atoms, examples of monocyclic cycloalkyl include, but are not limited to: cyclopropyl, cyclobutyl, cyclopentyl, cyclohexyl, cycloheptyl, cyclooctyl, cyclodecanyl, cyclodocecanyl, and cyclohexenyl. "bicycloalkyl" include "bridged bicycloalkyl", "fused bicycloalkyl" and "spiro cycloalkyls". "bridged bicycloalkyl" contains a monocyclic cycloalkyl ring where two non-adjacent carbon atoms of the monocyclic ring are linked by an alkylene bridge of one to three additional carbon atoms (i.e. a bridging group of the form —($CH_2$)$_q$—, where q is 1, 2, 3). Representative examples of bridged bicycloalkyl include, but are not limited to, bicyclo[2.2.1] heptenes, bicyclo[3.1.1]heptanes, bicyclo[2.2.1]heptanes, bicyclo[2.2.2]octane, bicyclo[3.2.2] nonane, bicyclo[3.3.1]nonane, and bicycle[4.2.1]nonane, etc. "fused bicycloalkyl" contains a monocyclic cycloalkyl ring fused to either a phenyl, a monocyclic cycloalkyl, or a monocyclic heteroaryl. Representative fused bicycloalkyl include, but are not limited to, bicyclo[4.2.0]octa-1,3,5-triene, 2,3-dihydro-1H-indene, 6,7-dihydro-5H-cyclopenta[b] pyridine, 5,6-dihydro-4H-cyclopenta[b]thiophene, and decahydronaphthalene, etc. "Spiro cycloalkyl" contains two monocyclic ring systems which share a carbon atom forming a bicyclic ring system. Representative spiro cycloalkyls include, but are not limited to,

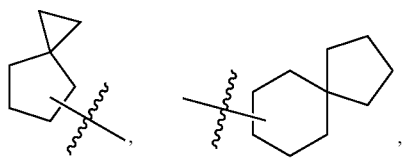

etc. "bicyclic cycloalkyl" are more preferably having 7 to 12 carbon atoms, mono-cycloalkyl or bicycloalkyl is attached to the parent molecular moiety through any carbon atom contained within the cycloalkyl ring.

The term "bridged tricycloalkyl" as used herein, refers to 1) a bridged bicycloalkyl ring where two non-adjacent carbon atoms of the bridged bicycloalkyl ring are linked by an alkylene bridge of one to three additional carbon atoms (i.e. a bridging group of the form —($CH_2$)$_q$—, where q is 1, 2, 3), or 2) a fused bicycloalkyl ring where two unshared ring atoms on each ring are linked by an alkylene bridge of one to three additional carbon atoms (i.e. a bridging group of the form —($CH_2$)$_q$—, where q is 1, 2, 3), wherein, the described "a fused bicycloalkyl ring" refers to a mono-cycloalkyl ring fused to a mono-cycloalkyl ring. Representative bridged tricycloalkyl includes, but is not limited to adamantanyl

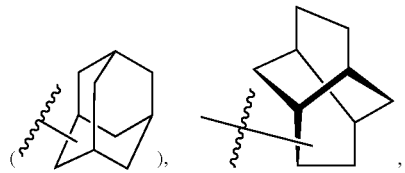

etc. Bridged tricycloalkyl, as used herein, is appended to the parent molecular moiety through any ring atom. The described ring atom specifically refers to the carbon atom on the ring skeleton.

The term "heterocycloalkyl" as used herein, refers to mono-heterocycloalkyl or a bi-heterocycloalkyl, which is a saturated or partially unsaturated (containing 1 or 2 double bonds) non-aromatic ring system consisting of carbon atoms and at least one heteroatom independently selected from O, N, and S. In the present disclosure, the heterocyclyl preferably contains 1, 2, 3, or 4 heteroatoms, and the N, C or S can independently be oxidized in the cyclic ring system. The N atom can further be substituted to form tertiary amine or ammonium salts. "mono-heterocycloalkyl" is preferred to be 3- to 10-membered monocyclic heterocycloalkyl, is more preferred to be 3- to 8-membered monocyclic heterocycloalkyl. Representative examples include: aziridinyl, tetrahydrofuran-2-yl, morpholin-4-yl, thiomorpholin-4-yl, thiomorpholin-4-yl-S-oxide, piperidin-1-yl, N-alkyl-piperidin-4-yl, pyrrolidin-1-yl, N-alkyl-pyrrolidin-2-yl, pyrazin-1-yl, and 4-alkyl-pyrazin-1-yl, etc. "bi-heterocycloalkyl" include "fused bi-heterocycloalkyl" and "spiro heterocycloalkyl"; wherein "fused bi-heterocycloalkyl" contains a mono-heterocycloalkyl ring which is fused to either a phenyl, a mono-cycloalkyl, a mono-heterocycloalkyl, or a mono-heteroaryl. Representative examples of fused bi-heterocycloalkyl include, but are not limited to, 2,3-dihydrobenzofuranyl, 1,3-dihydroisobenzofuranyl, indolinyl, 2,3-dihydrobenzo[b] thiophenyl, 4H-chromenyl, 1,2,3,4-tetrahydroquinolinyl, benzo[d][1,3]dioxolyl,

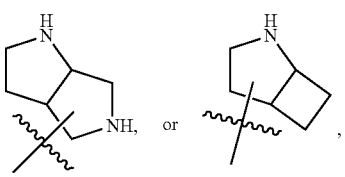

etc. "Spiro heterocycloalkyl" contains two mono-heterocycloalkyl or one mono-cycloalkyl and one mono-heterocycloalkyl which share a carbon atom to form a bicyclic ring system. Representative spiro heterocycloalkyl includes, but is not limited to,

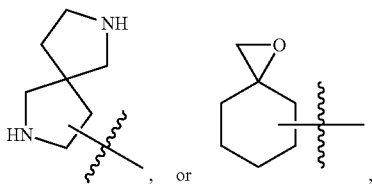

etc. wherein, the bi-heterocycloalkyl prefers 7 to 12 membered bi-heterocycloalkyl. Mono-heterocycloalkyl or bi-heterocycloalkyl is attached to the parent molecular moiety through any ring atom contained within the ring system. Herein, the ring atoms are specifically referred to the carbon and/or nitrogen atoms which form the cyclic ring skeleton.

The term "bridged heterocycloalkyl" as used herein, refers to "bridged bi-heterocycloalkyl" or "bridged tri-heterocycloalkyl". Wherein the "bridged bi-heterocycloalkyl" refers to a monocyclic heterocycloalkyl ring where two non-adjacent ring atoms are linked by a bridge linker, said bridge linker is selected from one to three additional carbon atoms or heteroatoms (the described linkers include, but are not limited to: —CH$_2$—, —O—, —NH—, —S—, —CH$_2$CH$_2$—, —CH$_2$O—, —CH$_2$S—, —CH$_2$NH—, —CH$_2$CH$_2$CH$_2$—, —CH$_2$OCH$_2$—, —CH$_2$CH$_2$O—, —CH$_2$CH$_2$NH—, —CH$_2$NHCH$_2$—). Wherein the "bridged tri-heterocycloalkyl" refers to 1) a bridged bi-heterocycloalkyl ring where two non-adjacent ring atoms are linked by a bridge linker, said bridge linker is selected from one to three additional carbon atoms or heteroatoms, or 2) a fused bi-heterocycloalkyl ring where two unshared ring atoms on each ring are linked by a bridge linker, said bridge linker is selected from one to three additional carbon atoms or heteroatoms, wherein the described "a bridge linker" include, but is not limited to: —CH$_2$—, —O—, —NH—, —S—, —CH$_2$CH$_2$—, —CH$_2$O—, —CH$_2$S—, —CH$_2$NH—, —CH$_2$CH$_2$CH$_2$—, —CH$_2$OCH$_2$—, —CH$_2$CH$_2$O—, —CH$_2$CH$_2$NH—, —CH$_2$NHCH$_2$—, wherein the described "fused bi-heterocycloalkyl ring" refers to a mono-heterocycloalkyl ring fused to a monocyclic cycloalkyl ring or mono-heterocycloalkyl ring. Representative bridged heterocycloalkyl includes "bridged bi-heterocycloalkyl" and "bridged tri-heterocycloalkyl", said bridged bi-heterocycloalkyl includes, but is not limited to:

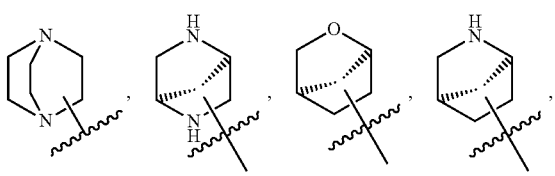

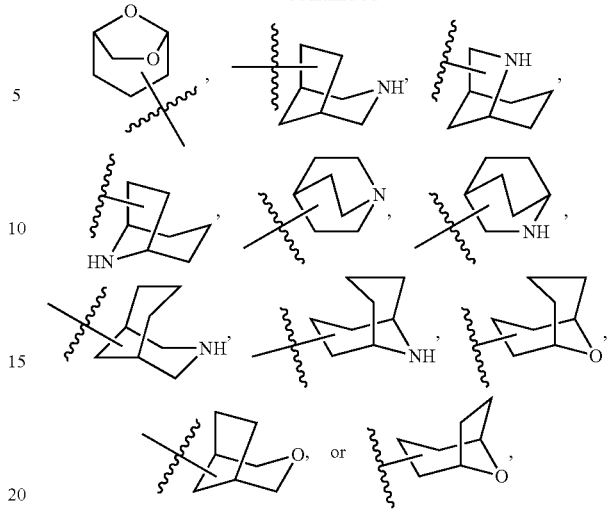

etc. Said bridged triheterocycloalkyl includes, but is not limited to:

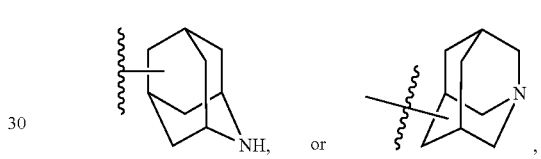

etc. Wherein, the bridged heterocycloalkyl is 7- to 12-membered bridged bi-heterocycloalkyls or 7 to 12-membered bridged tri-heterocyloalkyls; the bridged heterocycloalkyl is preferred 7- to 10-membered bridged heterocycloalkyl. Bridged heterocycloalkyl is attached to the parent molecular moiety through any ring atom contained within the ring system. Herein, the ring atoms are specifically referred to the carbon and/or nitrogen atoms which form the cyclic ring skeleton.

The term "cycloalkylalkyl" as used herein, refers to a cycloalkyl, as defined herein, appended to the parent molecular moiety through an alkyl group, as defined herein. Wherein, "cycloalkylalkyl" include the definitions of the above alkyl and cycloalkyl.

The term "heterocycloalkylalkyl" as used herein, refers to a heterocycloalkyl, as defined herein, appended to the parent molecular moiety through an alkyl group, as defined herein. Wherein, "heterocycloalkylalkyl" include the definitions of the above alkyl and heterocycloalkyl.

The term "alkoxy" as used herein, refers to an alkyl, cycloalkyl or heterocycloalkyl group, as defined herein, appended to the parent molecular moiety through an oxygen atom. Alkoxy groups include alkyloxy, cycloalkyloxy, and heterocycloalkyloxy. Wherein, "alkoxy" includes the definitions of the above alkyl, heterocycloalkyl, and cycloalkyl.

The term "alkylthio" as used herein, means a cyclic or non-cyclic alkyl group, as defined herein, appended to the parent molecular moiety through a thio atom. Alkylthio groups include alkylthio, cycloalkylthio, and heterocycloalkylthio. Wherein, "alkylthio" includes the definitions of the above alkyl, heterocycloalkyl, and cycloalkyl.

The term "cycloalkylalkoxy" as used herein, refers to an alkyl hydrogen atom of the alkoxy group, as defined herein, is substituted by a cycloalkyl. Wherein, "cycloalkylalkoxy" includes the definitions of the above cycloalkyl and alkoxy.

The term "alkenyl" as used herein, refers to a straight, branched chain or cyclic non-aromatic hydrocarbon ring containing from 1 to 3 carbon-carbon double bonds, preferable one carbon-carbon double bond. The term "$C_{2-4}$alkenyl" means alkenyl containing 2 to 4 carbon atoms, the term "$C_{2-6}$ alkenyl" means alkenyl containing 2 to 6 carbon atoms. Representative examples of alkenyl include, but are not limited to, vinyl, 2-propenyl, 2-butenyl, 2-methylbutenyl and cyclohexenyl. Wherein the alkenyl can be further substituted.

The term "alkynyl" as used herein, refers to a straight, branched chain or cyclic non-aromatic hydrocarbon ring containing from 1 to 3 carbon-carbon triple bonds, preferable one carbon-carbon triple bond. The term "$C_{2-6}$ alkynyl" means alkynyl containing 2-6 carbon atoms. Representative examples of alkynyl include, but are not limited to, ethynyl, 2-propynyl, 2-butynyl, and 3-methylbutynyl.

The term "aryl" as used herein, refers to any stable 6 to 10 membered mono or bicyclic aromatic group, for example, phenyl, naphthyl, tetrahydronaphthyl, 2,3-dihydro-1H-indenyl, or biphenyl, etc.

The term "heteroaryl", as used herein, refers to a 5- to 7-membered monocyclic heteroaryl or a 7- to 12-membered bicyclic ring group containing at least one heteroatom independently selected from O, N, and S. The heteroaryl prefers a 5- to 10-membered heteroaryl. The monocyclic heteroaryl prefers a 5- to 6-membered ring. In the present disclosure, the number of heteroatoms prefers to be 1, 2 or 3. Representative monocyclic heteroaryls include, but are not limited to, furyl, thienyl, pyrrolyl, imidazolyl, 1,2,4-triazolyl, 1,2,3-triazolyl, tetrazolyl, pyridyl, pyrimidyl, and pyrazinyl, etc.; bicyclic heteroaryls include, but are not limited to, indazolyl, isoindazolyl, indolyl, isoindolyl, benzofuranyl, benzothienyl, benzothiazolyl

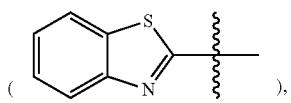 [SMILES: *c1nc2ccccc2s1]

benzoxazolyl

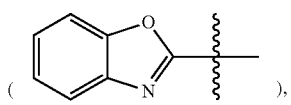 [SMILES: *c1nc2ccccc2o1]

benzo[d]isoxazolyl

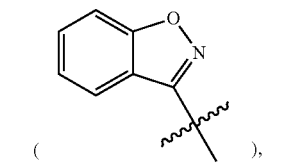 [SMILES: *c1noc2ccccc12]

oxazolo[5,4-b]pyridinyl

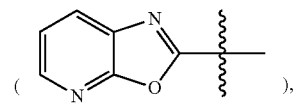

quinolinyl, isoquinolinyl, and quinazolinyl, etc.

The term "arylalkyl", as used herein, refers to an aryl group, as defined herein, appended to the parent molecular moiety through an alkyl. Wherein, "arylalkyl" includes the definitions of the above alkyl and aryl.

The term "heteroarylalkyl", as used herein, refers to a heteroaryl group, as defined herein, appended to the parent molecular moiety through an alkyl. Wherein, "heteroarylalkyl" includes the definitions of the above alkyl and heteroaryl.

The term "arylalkoxy", as used herein, refers to an alkyl hydrogen atom of the alkoxy group, as defined herein, is substituted by an aryl. Wherein, "arylalkoxy" includes the definitions of the above aryl and alkoxy.

The term "heteroarylalkoxy", as used herein, refers to an alkyl hydrogen atom of the alkoxy group, as defined herein, is substituted by a heteroaryl. Wherein, "heteroarylalkoxy" includes the definitions of the above heteroaryl and alkoxy.

The term "halo" or "halogen" as used herein refers to Cl, Br, I or F.

The term "haloalkyl" as used herein, refers to an alkyl group as defined herein, is substituted by at least one halogen, as defined herein. Wherein, "haloalkyl" includes the definitions of the above halogen and alkyl.

The term "haloalkoxy" as used herein, means an alkoxy group as defined herein, is substituted by at least one halogen, as defined herein. Wherein, "haloalkoxy" includes the definitions of the above halogen and alkoxy.

The term "amino" as used herein, refers to —NH$_2$. The term "alkylamino" as used herein, refers to an amino group on which at least one hydrogen is substituted by alkyl, cycloalkyl, or heterocycloalkyl. Representative alkylamino groups include, but are not limited to, —NHCH$_3$, —N(CH$_3$)$_2$,

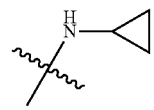

The term "aminoalkyl" as used herein, refers to a hydrogen atom of an alkyl, cycloalkyl or heterocycloalkyl group is substituted by an amino group. Representative aminoalkyl groups include, but are not limited to, —CH$_2$NH$_2$. Wherein, "alkylamino" and "aminoalkyl" include the definitions of the above alkyl, heterocycloalkyl and cycloalkyl.

The term "amino acid" as used herein, refers to a carboxylic acid containing an amino group, including natural or unnatural amino acid. Natural amino acid is preferred. The defined amino acids include, but are not limited to, alanine, valine, leucine, isoleucine, proline, phenylalanine, tryptophane, methionine, glycine, serine, threonine, cysteine, tyrosine, asparagine, glutamine, lysine, arginine, histidine, aspartic acid, or glutamic acid. The defined amino acid is appended to the parent moiety through amino, or carboxylic acid via condensation reaction, or utilizing thiol or hydroxyl to connect to the parent molecular moiety by forming thiol ether or ether bond.

The term "peptide" as used herein, refers to a structure formed by at least three amino acids via condensation reactions. The defined peptide prefers to contain 3 to 20 amino acid residues.

The term "monosaccharide" as used herein, refers to multihydroxyaldehyde, or multihydroxyketone containing 3 to 6 carbon atoms, preferably containing 5 to 6 carbon atoms. The defined monosaccharides include, but are not limited to, D-(−)-ribose, D-(−)-2-deoxyribose, D-(+)-xylose, L-(+)-arabinose, D-(+)-glucose, D-(+)-mannose, D-(+)-galactose, D-(−)-fructose. The defined monosaccharide prefers to connect to the parent molecular moiety through a glycosidic bond.

The term "disaccharide" as used herein, refers to a structure formed by two monosaccharide molecules via a glycosidic bond. The defined disaccharides include, but are not limited to, maltose, sucrose, or lactose.

The term "polyethylene glycol" as used herein, refers to the oligomer or polymer formed by ethylene oxide. The defined PEG is appended to the parent molecular moiety using a hydroxyl group at one end by forming an ether bond.

The term "adamantanyl" as used herein, refers to

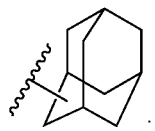

The term "2-azaadmantanyl" as used herein, refers to

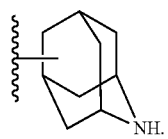

The term "=" as used herein, refers to a double bond.

The term "room temperature" as used herein, refers to 15-30° C.

The compound of formula (I) as well as any embodiment thereof includes isotope-labelled derivatives thereof. The described isotope-labeled derivatives include: the hydrogen atom (1 to 5) of a compound of formula (I) is substituted by 1 to 5 deuterium atoms, respectively; the carbon atom (1 to 3) of a compound of formula (I) is substituted is substituted by 1 to 3 $C_{14}$ atoms; or the oxygen atom of a compound of formula (I) is substituted by 1 to 3 $O_{18}$ atoms.

The term "IDO/TDO" is, for example, "IDO1", "TDO2" or "IDO1 and TDO2".

The term "IDO/TDO inhibitors" is for example "IDO1 inhibitors" or "IDO1 and TDO2 inhibitors".

The term "prodrug" as used herein, refers to compound which can be transformed to the original active compound after in vivo metabolism. In general, prodrug is not an active material, or is less active than the parent compound, but can provide convenient manipulation, administration, or improving metabolic properties. The term "compound" as used herein is intended to include prodrug thereof to the extent they can be made by one of ordinary skill in the art by routine experimentation.

The term "pharmaceutically acceptable salts" as used herein, has been discussed in Berge, et al., "Pharmaceutically acceptable salts", J. Pharm. Sci., 66, 1-19 (1977), and is apparent to all the medicinal chemists. The defined pharmaceutically acceptable salts are generally not toxic, and can provide needed pharmacokinetic properties, orally bioavailable, and ADME properties. In the present disclosure, the compound of formula (I) could contains acidic, basic or zwitteric groups. Pharmaceutically acceptable salts can be prepared from the described compound in this disclosure by reacting with the free acids to form the corresponding salt, for examples, hydrochloride, hydrobromide, sulfate, pyrosulfate, bisulfate, sulfite, bisulfate, phosphate, hydrophosphate, dihydrophosphate, metaphosphate, pyrophosphate, nitrate, acetate, propionate, octoate, decanoate, formate, acrylate, isobutyrate, caproate, enanthate, oxalate, malonate, succinate, suberate, benzoate, methyl benzoate, phthalate, maleate, mesylate, tosylate, (D, L)-malate, citrate, (D, L)-tartrate, fumarate, succinate, lactate, trifluoromethanesulfonate, trifluoroacetate, naphthyl-1-sulfonate, mandelate, pyruvate, stearate, ascorbate, salicylate. When the compounds described in this disclosure contain acidic group, their pharmaceutically acceptable salts also include: alkali metal salts, for example, sodium or potassium salts; alkaline-earth metal salts, for example, calcium or magnesium salts, organic base salts, for example, salts formed with ammonia, alkylamines, hydroxyalkylamines, amino acids (lysine, arginine), and N-methyl-D-glucamine, etc.

The pharmaceutically acceptable salts as used herein, is synthesized by conventional chemical methods.

Generally, the salt described above can be prepared by reacting the free acid or base forms of these compounds with stoichiometric amount of the base or acid in an appropriate solvent or a solvent mixture.

The compounds of the present disclosure may have asymmetric centers, creating "isomers." The term "isomers" as used herein, refers to the stereoisomers, which include, enantiomers and diastereomers, wherein cis/trans isomers belong to diastereomers. Therefore, in the present disclosure, the compounds of formula (I) can be enantiomers, diastereomers, and their mixtures, all of these stereoisomers are included in this disclosure. In the present disclosure, when compounds of formula (I) and their salts are stereoisomers (for example, they contain one or more chiral carbons), individual stereoisomers (enantiomers and diastereoisomers) and their mixtures (enantiomeric and diastereomeric mixtures) are included in the range of this disclosure. The present disclosure includes individual stereoisomers, and mixtures of these stereoisomers of compounds of formula (I) and there salts of any embodiment disclosed herein, in which the configurations of one or more chiral carbons are inverted. The disclosure includes all of the possibilities of the enantiomeric and diastereomeric mixtures, herein, the diastereomers include cis/trans isomers. The present disclosure includes all of the combinations of the stereoisomers of all of the above defined specific groups.

Certain compounds of the present disclosure can exist as tautomers and/or geometric isomers. All possible tautomers and Z and E geometric isomers, as individual forms and mixtures thereof are within the scope of this disclosure.

All of the specific stereoisomers of the compounds in this disclosure can be isolated and purified from the mixtures of the stereoisomers, the separation methods of the enantiomers and diastereoisomers are the conventional methods in the art. For example, mixtures of diastereomers (such as cis/trans isomers) can be separated by traditional separation/purification technology, such as recrystallization or chromatography. Enantiomeric mixtures can be transformed to diastereoisomeric mixtures, then separated by recrystallization or chromatography, or they can be directly separated by chiral chromatography, or they can be separated by any known chiral separation technologies and obtain single isomers.

Under the basis of no violation of common sense in the art, the above described preferred conditions, can be combined together, to achieve the preferred examples in this disclosure.

In the present disclosure, all of the reagents and materials are commercially available.

BRIEF DESCRIPTION OF THE FIGURES

FIG. 1 showed the result of animal model assays, wherein the mean tumor volume of the mice treated with either vehicle or compounds is measured and plotted versus the dosing days. It can be seen that compounds of the present disclosure has significant tumor growth inhibition effect.

EXAMPLES

The following examples serve to illustrate the compounds in this disclosure and the preparation process, but the examples should not be considered as limiting the scope of the disclosure. The ⁓ bond at the saturated carbon, in the compounds below, denotes that the compound is described as a mixture of cis/trans isomers, a cis-isomer, or a trans-isomer.

All the structures of the compounds in the present disclosure were confirmed by $^1$H NMR and MS.

$^1$H NMR chemical shifts ($\delta$) were recorded in ppm ($10^{-6}$). NMR Spectra: Bruker AVANCE-400 spectrometer in proper solvent: DMSO-$d_6$, CDCl$_3$, MeOD-$d_4$, $\delta$ in ppm rel. to Me$_4$Si as internal standard.

The analytical low-resolution mass spectra (MS) were recorded on Ultimate 3000 HPLC-MSQ Plus MS using a Kinetex 2.6u C18 100A (4.6×50 mm) LCMS-02-001 using a gradient elution method. The gradient elution method is: 95% (v/v %) solvent A and 5% (v/v %) solvent B (less than 1.5 mins or more than 3 mins), then 5% (v/v %) solvent A and 95% (v/v %) solvent B (form 1.5 mins to 3 mins). "v/v %" as used herein, means volume percentage. Solvent A: 10 mM ammonium bicarbonate aqueous solution; Solvent B: acetonitrile.

All the chiral compounds or chiral intermediates in the present disclosure could be separated and analyzed by supercritical fluid chromatography (SFC) or chiral high performance liquid chromatography (Chiral HPLC).

Chiral resolution was performed on Prep SFC-80 (Thar, Waters), flow rate: 80 g/min, column temperature: 35° C., detection wavelength: 214 and/or 254 nM.

Wherein Chiral resolution

Method A: chiral column: Cellulose-4 30×250 mm, 5 um (Lux), mobile phase: CO$_2$/ethanol (0.1% ethanol ammonia)=60/40, sample concentration: 40-60 mg/mL (ethanol), injection volume: 0.5 mL.

Method B: chiral column: AS 50×250 mm, 5 um (Daicel), mobile phase: CO$_2$/methanol (0.2% methanol ammonia)=60/40, sample concentration: 2.2 mg/mL (methanol), injection volume: 9.5 mL.

Method C: chiral column: AD 30×250 mm, 5 um (Daicel), mobile phase: CO$_2$/methanol (0.2% methanol ammonia)=45/55, sample concentration: 40 mg/mL (methanol), injection volume: 0.7~1.5 mL.

Method D: chiral column: CHIRALPAK AD-H 20×250 mm, 5 um (Daicel), mobile phase: CO$_2$/methanol (0.2% methanol ammonia)=55/45, sample concentration: 5.6 mg/mL (methanol), injection volume: 1.0 mL.

Method E: chiral column: CHIRALPAK OZ-H 20×250 mm, 5 um (Daicel), mobile phase: CO$_2$/methanol (0.2% methanol ammonia)=50/50, sample concentration: 2.1 mg/mL (methanol), injection volume: 1.0 mL.

Method F: chiral column: CHIRALPAK OJ-H 20×250 mm, 5 um (Daicel), mobile phase: CO$_2$/methanol (0.2% methanol ammonia)=60/40, sample concentration: 1.7 mg/mL (methanol), injection volume: 3.0 mL.

Method G: chiral column: CHIRALPAK AS-H 20×250 mm, 5 um (Daicel), mobile phase: CO$_2$/methanol (0.2% methanol ammonia)=70/30, sample concentration: 20 mg/mL (methanol), injection volume: 2.0 mL.

Method H: chiral column: CHIRALPAK IC 20×250 mm, 5 um (Daicel), mobile phase: CO$_2$/methanol (0.2% methanol ammonia)=65/35, sample concentration: 13 mg/mL (methanol), injection volume: 1.6 mL.

Method I: chiral column: CC4 4.6×250 mm, mobile phase: CO$_2$/methanol (0.2% methanol ammonia)=55/45, sample concentration: 12 mg/mL (methanol), injection volume: 2.5 mL.

Method J: chiral column: OZ-H 4.6×250 mm, 5 um (Daicel), mobile phase: CO$_2$/methanol (0.2% methanol ammonia)=60/40, sample concentration: 8.0 mg/mL (methanol), injection volume: 4.5 mL.

Chiral resolution was performed on HPLC-Gilson GX-281 Method Station, flow rate: 50 mL/min, column temperature: 35° C., detection wavelength: 214 and/or 254 nM.

Wherein chiral resolution

Method K: chiral column: CHIRALPAK AS-H 20×250 mm, 10 um (Daicel), mobile phase: n-hexane (0.1% diethylamine)/ethanol (0.1% diethylamine)=90/10, sample concentration: 6.5 mg/mL (ethanol), injection volume: 0.5 mL.

Method L: chiral column: AY-H 20×250 mm, 10 um (Daicel), mobile phase: n-hexane (0.1% diethylamine)/ethanol (0.1% diethylamine)=90/10, sample concentration: 12.8 mg/mL (ethanol), injection volume: 0.5 mL.

Chiral analysis was performed on SFC Method Station (Thar, Waters), flow rate: 3 mL/min, column temperature: 40° C., detection wavelength: 214 and/or 254 nM. Chiral analysis method A: chiral column: Cellulose-4 4.6×250 mm, 5 um (Lux), mobile phase: CO$_2$/(ethanol:hexane=1:1) (0.1% diethylamine)=60/40; Method B: chiral column: CHIRALPAK AS-H 4.6×150 mm, 5 um (Daicel), mobile phase: CO$_2$/methanol: (0.2% methanol ammonia)=75/25; Method C: chiral column: CHIRALPAK AD-H 4.6×150 mm, 5 um (Daicel), mobile phase: CO$_2$/methanol: (0.2% methanol ammonia)=55/45; Method D: chiral column: CHIRALPAK AD-H 4.6×150 mm, 5 um (Daicel), mobile phase: CO$_2$/methanol: (0.2% methanol ammonia)=60/40; Method E: chiral column: CHIRALPAK OZ-H 4.6×250 mm, 5 um (Daicel), mobile phase: CO$_2$/methanol: (0.2% methanol ammonia)=55/45; Method F: CHIRALPAK IC 4.6×150 mm, 5um (Daicel), mobile phase: CO$_2$/methanol: (0.2% methanol ammonia)=65/35.

Chiral analysis was performed on SHIMADZU HPLC, flow rate: 1.0 mL/min, column temperature: 40° C., detection wavelength: 214 and/or 254 nM. Chiral analysis method G: chiral column: AS-H 20×250 mm, 5 um (Daicel), mobile phase: n-hexane (0.1% diethylamine)/ethanol (0.1% diethylamine)=85/15; method H: chiral column: AS-H 20×250 mm, 5 um (Daicel), mobile phase: n-hexane (0.1% diethylamine)/ethanol (0.1% diethylamine)=95/5.

All the compounds or intermediates in the present disclosure were purified by preparative high performance liquid chromatography (pre-HPLC), flash column chromatography, preparative thin layer chromatography (pre-TLC), or column chromatography.

pre-HPLC purification was performed on Shimadzu LC-20 HPLC, mobile phase A: 0.05% trifluoroacetic acid (TFA) in water, mobile phase B: acetonitrile, detection wavelength: 214, 254 and/or 262 nM. the flow rate of purification method A, F, J, K, L is 10 mL/min; the flow rate of purification method C, G and N is 75 mL/min; the flow rate of purification method B, D, E, H, I, and M is 15 mL/min; the column of purification method A, D, E, F, H, I, J, K, and L is waters xbridge Pre C18, 10 um, 19×250 mm; the column of purification method B, M is Shimadzu, shim-pack PRC-005, 20×250 mm; the column of purification method C, G and N is Welch Ultimate XB-C18, 10 um, 50×250 mm.

The gradient elution of method A to M is:

Method A: 28~72% (v/v %) mobile phase A and 72~28% (v/v %) mobile phase B;

Method B: 25~75% (v/v %) mobile phase A and 75~25% (v/v %) mobile phase B;

Method C: 30~60% (v/v %) mobile phase A and 70~40% (v/v %) mobile phase B;

Method D: 30~70% (v/v %) mobile phase A and 70~30% (v/v %) mobile phase B;

Method E: 30~60% (v/v %) mobile phase A and 70~40% (v/v %) mobile phase B;

Method F: 20~50% (v/v %) mobile phase A and 80~50% (v/v %) mobile phase B;

Method G: 95~60% (v/v %) mobile phase A and 5~40% (v/v %) mobile phase B;

Method H: 60~95% (v/v %) mobile phase A and 40~5% (v/v %) mobile phase B;

Method I: 35~60% (v/v %) mobile phase A and 65~40% (v/v %) mobile phase B;

Method J: 75~70% (v/v %) mobile phase A and 25~30% (v/v %) mobile phase B;

Method K: 18~82% (v/v %) mobile phase A and 82~18% (v/v %) mobile phase B;

Method L: 20~80% (v/v %) mobile phase A and 80~20% (v/v %) mobile phase B;

Method M: 65~80% (v/v %) mobile phase A and 35~20% (v/v %) mobile phase B;

Method N: 5~33% (v/v %) mobile phase A and 95~67% (v/v %) mobile phase B.

TLC was Yantai Huanghai HSGF254 or Qingdao GF254 silica gel plate.

Column chromatography generally used Yantai Huanghai 200-300 mesh silica gel as carrier.

Synthesis of the Intermediates

Intermediate 1: Synthesis of 2-(1-trityl-1H-imidazol-4-yl)benzaldehyde (1.1)

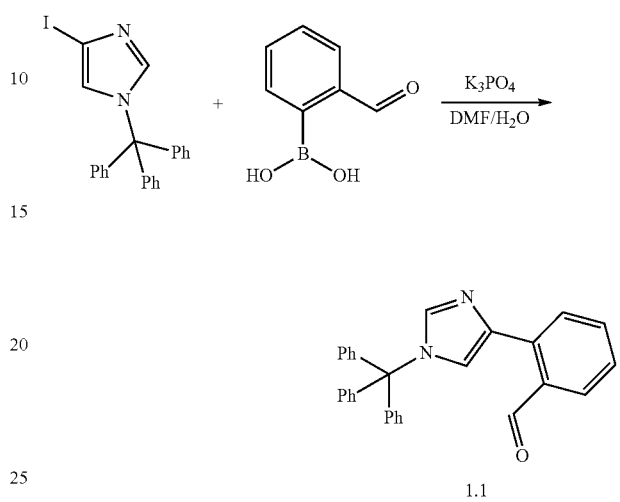

To a solution of (2-formylphenyl)boronic acid (2.0 g, 13.3 mmol) in a mixed solvent of N,N-dimethylformamide (DMF) (60 mL) and water (12 mL) was successively added 4-iodo-1-trityl-1H-imidazole (6.1 g, 14.0 mmol), and potassium phosphate (5.6 g, 26.6 mmol). After degassing with nitrogen, the resulted mixture was added tetrakis (triphenylphosphine)palladium(0) (Pd(PPh$_3$)$_4$) (300 mg, 0.26 mmol). The resulted mixture was degassed with nitrogen and stirred at 90° C. for overnight under nitrogen. And then the mixture was cooled down to room temperature and filtered, the filtrate was added water (60 mL), extracted with ethyl acetate (100 mL×2). The combined organic phase was washed with brine (25 mL), dried over sodium sulfate, filtered and concentrated. The residue was purified by column chromatography on silica gel (petroleum ether:ethyl acetate=6:1) to afford compound 1.1 (3.3 g, yield: 60%) as a white solid.

m/z: [M+H]$^+$ 415

The following compounds were prepared according to Intermediate 1 compound 1.1, by replacing (2-formylphenyl)boronic acid to corresponding substituted formylphenyl boronic acid.

| NO. | Structure | Name | MS |
|---|---|---|---|
| 2.1 | | 2-fluoro-6-(1-trityl-1H-imidazol-4-yl)benzaldehyde | m/z: [M + H] $^+$433 |

-continued

| NO. | Structure | Name | MS |
|---|---|---|---|
| 3.1 | | 5-fluoro-2-(1-trityl-1H-imidazol-4-yl)benzaldehyde | m/z: [M + H] +433 |
| 4.1 | | 3-fluoro-2-(1-trityl-1H-imidazol-4-yl)benzaldehyde | m/z: [M + H] +433 |

Intermediate 2: Synthesis of
2-(1-trityl-1H-imidazol-4-yl)nicotinaldehyde (5.1)

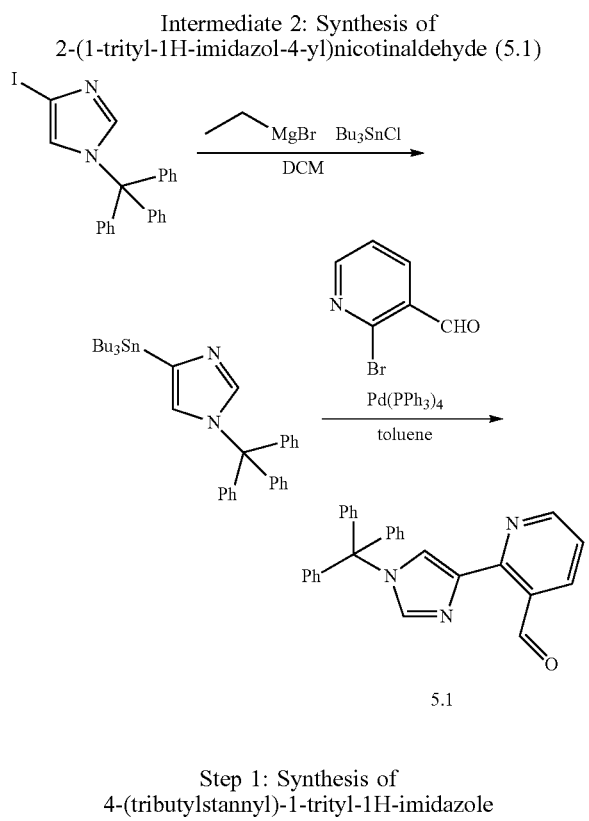

Step 1: Synthesis of
4-(tributylstannyl)-1-trityl-1H-imidazole

To an ice-salt bath cooling solution of 4-iodo-1-trityl-1H-imidazole (2.5 g, 5.7 mmol) in dichloromethane (DCM) (30 mL) was added ethylmagnesium bromide (2.5 mL, 7.5 mmol, 3.0 M solution in diethyl ether) slowly. The resulted mixture was stirred at room temperature for 1 h, then added chlorotributyltin (2.6 g, 8.0 mmol). The resulted mixture was stirred at room temperature for 2 h, then added saturated ammonium chloride solution (50 mL), the mixture was extracted with dichloromethane (100 mL×2). The combined organic phase was washed with brine (25 mL), dried over sodium sulfate, filtered and concentrated. The residue was recrystallization with a mixed solvent (petroleum ether:ethyl acetate=6:1) to afford 4-(tributylstannyl)-1-trityl-1H-imidazole (2.6 g, yield: 76%) as a white solid.

m/z: [M+H]+ 601

Step 2: Synthesis of
2-(1-trityl-1H-imidazol-4-yl)nicotinaldehyde

To a mixture of 2-bromonicotinaldehyde (500 mg, 2.7 mmol) and 4-(tributyl stannyl)-1-trityl-1H-imidazole (1.6 g, 2.7 mmol) in toluene (20 mL) was added Pd(PPh3)4 (150 mg, 0.13 mmol) after degassing with nitrogen, the resulted mixture was stirred at reflux for 3 h under nitrogen. The resulted mixture was cooled down to room temperature, filtered, and the filtrate was concentrated. The residue was purified by column chromatography on silica gel (petroleum ether:ethyl acetate=4:1) to afford compound 5.1 (400 mg, yield: 36%) as a white solid.

m/z: [M+H]+ 416

The following compounds were prepared according to Intermediate 2 compound 5.1, by replacing 2-bromonicotinaldehyde to corresponding 3-bromopicolinaldehyde, 3-bromo-6-fluoropicolinaldehyde and 5-bromo-2-chloroisonicotinaldehyde in step 2.

| No. | Structure | Name | MS |
|---|---|---|---|
| 6.1 | 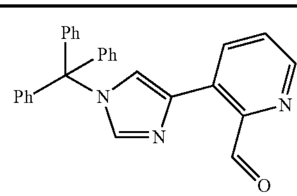 | 3-(1-tirityl-1H-imidazol-4-yl)picolinaldehyde | m/z: [M + H] +416 |

| No. | Structure | Name | MS |
|---|---|---|---|
| 7.1 | 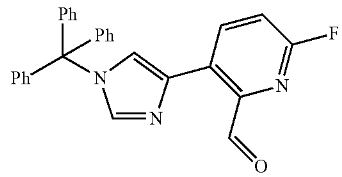 [SMILES: O=Cc1nc(F)ccc1-c1cn(C(c2ccccc2)(c2ccccc2)c2ccccc2)cn1] | 6-fluoro-3-(1-trityl-1H-imidazol-4-yl)picolinaldehyde | m/z: [M + H] +434 |
| 8.1 | 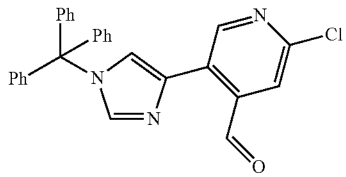 [SMILES: O=Cc1cc(Cl)ncc1-c1cn(C(c2ccccc2)(c2ccccc2)c2ccccc2)cn1] | 2-chloro-5-(1-trityl-1H-imidazol-4-yl)isonicotinaldehyde | m/z: [M + H] +450 |

Intermediate 3: Synthesis of tert-butyl 2-((tert-butoxycarbonyl)amino)-4-(2-formyl phenyl)-1H-imidazole-1-carboxylate (9.1)

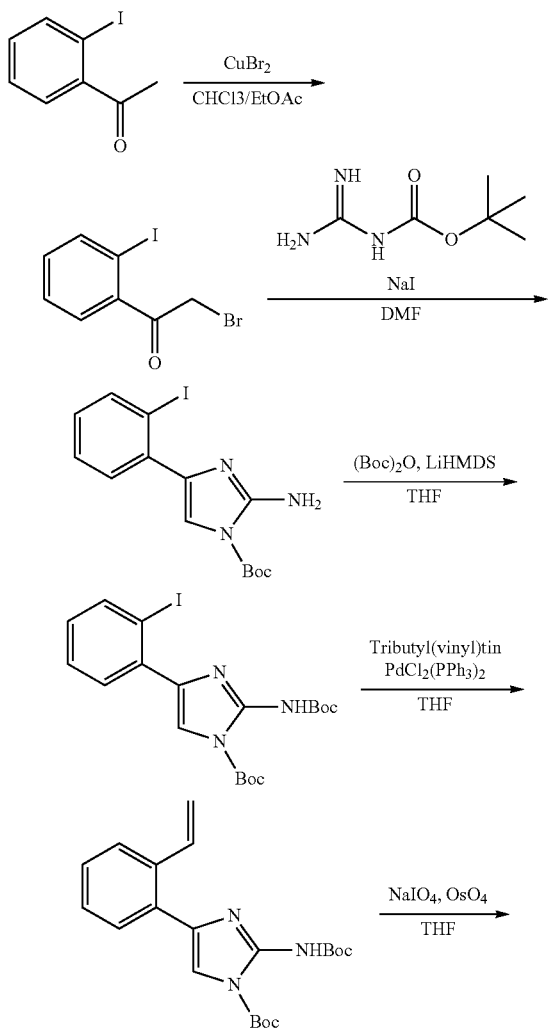

-continued

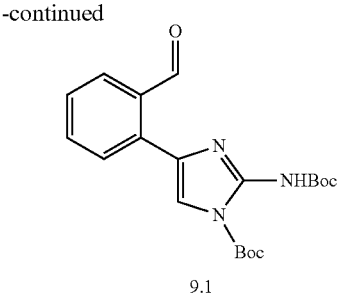

9.1

Step 1: Synthesis of 2-bromo-1-(2-iodophenyl)ethanone

To a solution of 1-(2-iodophenyl)ethanone (4.0 g, 16.3 mmol) in a mixed solvent of chloroform (50 mL) and ethyl acetate (50 mL) was added cupric bromide (7.26 g, 32.5 mmol). The resulted mixture was stirred at reflux for 3 h, then cooled down to room temperature, filtered, the filter cake was washed with ethyl acetate (50 mL), the filtrate was concentrated, the residue was purified by flash chromatography (petroleum ether:ethyl acetate=50:1) to afford 2-bromo-1-(2-iodophenyl) ethanone (4.65 g, yield: 88%) as a light yellow oil.

$^1$H NMR (400 MHz, CDCl$_3$-d): δ 7.98 (d, J=8.0 Hz, 1H), 7.47 (d, J=8.0 Hz, 2H), 7.19-7.21 (m, 1H), 4.47 (s, 2H).

Step 2: Synthesis of tert-butyl 2-amino-4-(2-iodophenyl)-1H-imidazole-1-carboxylate To a solution of 2-bromo-1-(2-iodophenyl)ethanone (2.25 g, 6.92 mmol) in DMF (30 mL) was successively added Boc-guanidine (3.3 g, 20.8 mmol) and sodium iodide (2.08 g, 13.8 mmol). The resulted mixture was stirred at room temperature for overnight, then added cold water (50 mL), the mixture was extracted with ethyl acetate (50 mL×2). The combined organic phase was washed with brine (25 mL), dried over sodium sulfate, filtered and concentrated. The residue was purified by flash column chromatography on silica gel (petroleum ether:ethyl acetate=10:1) to afford tert-butyl 2-amino-4-(2-iodophenyl)-1H-imidazole-1-carboxylate (900 mg, yield: 34%) as a white solid.

¹H NMR (400 MHz, CDCl₃-d): δ 7.94 (dd, J=1.6, 7.6 Hz, 1H), 7.67 (dd, J=1.6, 7.6 Hz, 1H), 7.41 (s, 1H), 7.37 (t, J=6.4 Hz, 1H), 6.98 (dd, J=2.0, 8.0 Hz, 1H), 6.16 (s, 2H), 1.65 (s, 9H).

Step 3: Synthesis of tert-butyl 2-((tert-butoxycarbonyl)amino)-4-(2-iodophenyl)-1H-imidazole-1-carboxylate To an ice-cooling solution of tert-butyl 2-amino-4-(2-iodophenyl)-1H-imidazole-1-carboxylate (700 mg, 1.82 mmol) in tetrahydrofuran (50 mL) was added lithium bis(trimethylsilyl) amide (LiHMDS) (2.8 mL, 3.63 mmol, 1.3 M solution in tetrahydrofuran) slowly, then added di-tert-butyl dicarbonate ((Boc)₂O) (476 mg, 2.18 mmol). The resulted mixture was stirred in ice-bath for 2 h, and then the reaction was quenched by addition of saturated ammonium chloride solution (25 mL), the mixture was extracted with ethyl acetate (50 mL×2). The combined organic phase was washed with brine (50 mL), dried over sodium sulfate, filtered and concentrated. The residue was purified by flash column chromatography on silica gel (petroleum ether:ethyl acetate=20:1) to afford tert-butyl 2-((tert-butoxycarbonyl)amino)-4-(2-iodophenyl)-1H-imidazole-1-carboxylate (650 mg, yield: 74%) as a brown solid.

Step 4: Synthesis of tert-butyl 2-((tert-butoxycarbonyl)amino)-4-(2-vinylphenyl)-1H-imidazole-1-carboxylate To a solution of tert-butyl 2-((tert-butoxycarbonyl)amino)-4-(2-iodophenyl)-1H-imidazole-1-carboxylate (790 mg, 1.63 mmol) in tetrahydrofuran (THF) (50 mL) was successively added tributyl(vinyl)tin (775 mg, 2.44 mmol) and bis(triphenylphosphine) palladium(II) chloride (PdCl₂(PPh₃)₂) (114 mg, 0.16 mmol). The resulted mixture was stirred at 80° C. for 3 h, then cooled down to room temperature, evaporated, the residue was purified by flash column chromatography on silica gel (petroleum ether:ethyl acetate=7:1) to afford tert-butyl 2-((tert-butoxycarbonyl)amino)-4-(2-vinylphenyl)-1H-imidazole-1-carboxylate (550 mg, yield: 88%) as a yellow solid.

¹H NMR (400 MHz, DMSO-d₆): δ 9.59 (s, 1H), 7.60-7.64 (m, 2H), 7.43 (s, 1H), 7.33-7.35 (m, 2H), 7.16-7.21 (m, 1H), 5.75 (dd, J=1.2, 17.6 Hz, 1H), 3.31 (dd, J=1.2, 11.2 Hz, 1H), 1.56 (s, 9H), 1.45 (s, 9H).

Step 5: Synthesis of tert-butyl 2-((tert-butoxycarbonyl)amino)-4-(2-formylphenyl)-1H-imidazole-1-carboxylate To a solution of tert-butyl 2-((tert-butoxycarbonyl)amino)-4-(2-vinylphenyl)-1H-imidazole-1-carboxylate (550 mg, 1.43 mmol) in a mixed solvent of THF (50 mL) and water (25 mL) was successively added sodium periodate (917 mg, 4.28 mmol) and osmium tetroxide (36 mg, 0.014 mmol). The resulted mixture was stirred at room temperature for 3 h, the reaction was quenched by addition of sodium thiosulfate solution (25 mL, 1.0 M), and the mixture was extracted with ethyl acetate (25 mL×2). Then the combined organic phase was washed with brine (25 mL), dried over sodium sulfate, filtered and concentrated. The residue was purified by flash column chromatography on silica gel (petroleum ether:ethyl acetate=5:1) to afford compound 9.1 (650 mg, yield: 74%) as a yellow solid.

m/z: [M+H]⁺ 388

Intermediate 4: Synthesis of 1-(adamantan-2-yl)ethanone (10.1)

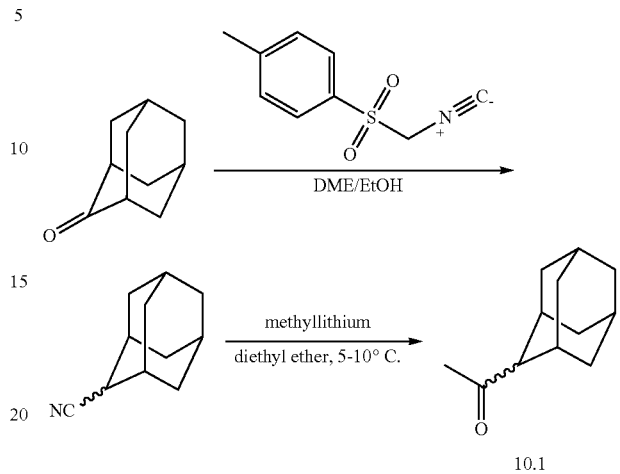

Step 1: Synthesis of adamantane-2-carbonitrile

To a solution of adamantan-2-one (2.5 g, 16.6 mmol) in a mixture solution of 1,2-dimethoxyethane (DME) (58 mL) and ethanol (1.7 mL) was added 1-((isocyanomethyl) sulfonyl)-4-methylbenzene (4.2 g, 21.6 mmol) under N₂, the resulted mixture was cooled down to 0° C. with ice-bath, then added potassium tert-butanolate (t-BuOK) (5.7 g, 51 mmol) in small portions and kept the inner temperature between 2~10° C. The resulted mixture was stirred at room temperature for 2 h, then filtered, the filtrate was concentrated to afford the residue, which was purified by column chromatography on silica gel (petroleum ether:ethyl acetate=30:1) to afford adamantane-2-carbonitrile (2.2 g, yield: 85%) as a white solid.

Step 2: Synthesis of 1-(adamantan-2-yl)ethanone

To an ice-cooling solution of adamantane-2-carbonitrile (2.1 g, 13.7 mmol) in diethyl ether (60 mL) was slowly added methyllithium (27 mL, 1.6 M solution in diethyl ether) and kept the inner temperature between 5~10° C. The resulted mixture was stirred at room temperature for 30 min, then quenched by addition of water (46 mL), the organic phase was washed with brine, dried over sodium sulfate, filtered and concentrated. The residue was dissolved in acetone (28 mL), added hydrochloric acid solution (28 mL, 6.0 M). The resulted mixture was stirred at reflux for 2 h, then cooled down to room temperature, the solvent was evaporated under vacuum, then water (50 mL) was added, and the mixture was extracted with ethyl acetate (150 mL), the organic phase was washed with brine, dried over sodium sulfate, filtered and concentrated, the residue was purified by column chromatography on silica gel (petroleum ether:ethyl acetate=10:1) to afford compound 10.1 (1.2 g, yield: 49%) as a yellow solid.

¹H NMR (400 MHz, DMSO-d₆): δ 2.54 (br s, 1H), 2.29 (br s, 1H), 2.08 (s, 3H), 1.61-1.66 (m, 11H), 1.52-1.55 (m, 2H).

1-(5-hydroxyadamantan-2-yl)ethanone (11.1) was prepared according to Intermediate 4 compound 10.1, by using 5-hydroxyadamantan-2-one as a starting material to afford compound 11.1 (a mixture of cis/trans isomers) as a white solid.

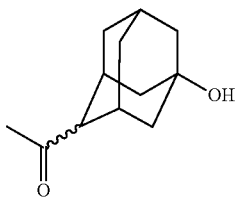

11.1 m/z: [M+H]$^+$ 195.

Intermediate 5: Synthesis of 1-(5, 7-dibromoadamantan-2-yl)ethanone (12.1) and 1-(5,7-dihydroxy adamantan-2-yl)ethanone (13.1)

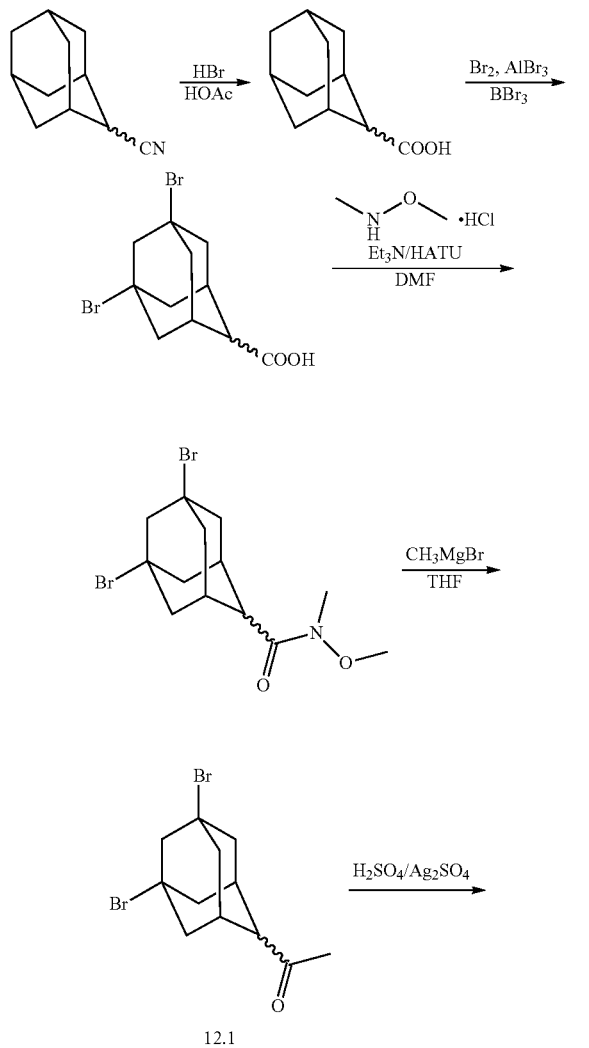

12.1

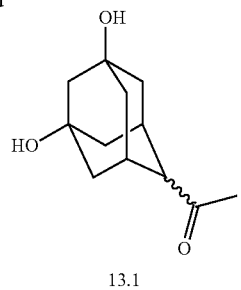

13.1

Step 1: Synthesis of adamantane-2-carboxylic Acid

A solution of adamantane-2-carbonitrile (19.3 g, 0.10 mol) in a mixed solvent of acetic acid (56 mL) and hydrobromic acid (224 mL, 48% solution in water) was stirred at 120° C. for overnight. The resulted mixture was cooled down to the room temperature, then poured into ice water, filtered, the filter cake was washed with water, dried under vacuum to afford adamantane-2-carboxylic acid (21.0 g, yield: 97%) as a white solid.

$^1$H NMR (400 MHz, DMSO-d$_6$): δ 12.08 (s, 1H), 2.50-2.53 (m, 1H), 2.21 (s, 1H), 1.69-1.75 (m, 11H), 1.55-1.58 (m, 2H).

Step 2: Synthesis of 5, 7-dibromoadamantane-2-carboxylic Acid

A mixture of adamantane-2-carboxylic acid (5.7 g, 31.6 mmol), aluminium bromide (AlBr$_3$) (18.9 g, 69.6 mmol), boron tribromide (BBr$_3$) (2.40 g, 9.49 mmol), and bromine (Br$_2$) (40 mL) was stirred at 0° C. for 30 min, and then stirred at 70° C. for 48 h. The resulted mixture was cooled down to the room temperature, and then the reaction was quenched by addition of saturated sodium hydrogen sulfite solution until the color of mixture changed from reddish brown to yellow. The precipitation was filtered, and washed with water, dried under vacuum to afford 5,7-dibromoadamantane-2-carboxylic acid (7.0 g, yield: 66%) as a yellow solid.

$^1$H NMR (400 MHz, DMSO-d$_6$): δ 12.56 (s, 1H), 2.83 (s, 2H), 2.73 (s, 1H), 2.48 (s, 2H), 2.21-2.35 (m, 8H).

Step 3: Synthesis of 5, 7-dibromo-N-methoxy-N-methyladamantane-2-carboxamide

To the solution of 5, 7-dibromoadamantane-2-carboxylic acid (1.01 g, 3.0 mmol) in DMF (20 mL) was successively added N,O-dimethylhydroxylamine hydrochloride (440 mg, 4.5 mmol) and 1-[bis(dimethylamino)methylene]-1H-1,2,3-triazolo[4,5-b] pyridinium 3-oxid hexafluorophosphate (HATU) (1.71 g, 4.5 mmol). The resulted mixture was stirred at room temperature for 4 h, then diluted with water, and extracted with ethyl acetate (50 mL×2). The combined organic phase was washed with brine, dried over sodium sulfate, filtered and concentrated to afford 5,7-dibromo-N-methoxy-N-methyladamantane-2-carboxamide (970 mg, yield: 85%) as a white solid.

$^1$H NMR (400 MHz, DMSO-d$_6$): δ 3.67 (s, 3H), 3.10 (s, 3H), 2.97 (s, 1H), 2.84 (s, 2H), 2.72-2.75 (m, 2H), 2.32-2.39 (m, 6H), 2.13-2.16 (m, 2H).

Step 4: Synthesis of 1-(5, 7-dibromoadamantan-2-yl)ethanone (12.1)

To an ice-cooling solution of 5, 7-dibromo-N-methoxy-N-methyladamantane-2-carboxamide (970 mg, 2.55 mmol) in THF (50 mL) was added methylmagnesium bromide (CH$_3$MgBr) (4.24 mL, 12.7 mmol, 3.0 M solution in diethyl ether). The resulted mixture was stirred at room temperature for 3 h, and then the reaction was quenched by addition of saturated ammonium chloride solution (20 mL), and extracted with ethyl acetate (25 mL×2), The combined organic phase was washed with brine (25 mL), dried over sodium sulfate, filtered and concentrated to afford compound 12.1 (850 mg, yield: 99%) as a brown solid.

$^1$H NMR (400 MHz, DMSO-d$_6$): δ 2.82 (s, 2H), 2.72 (s, 1H), 2.57-2.58 (m, 2H), 2.34-2.35 (m, 4H), 2.19-2.21 (m, 4H), 2.13 (s, 3H).

Step 5: Synthesis of 1-(5, 7-dihydroxyadamantan-2-yl)ethanone (13.1)

To a mixture of concentrated sulfuric acid (10.0 mL) in water (3.0 mL) was successively added silver sulfate (1.69 g, 5.43 mmol) and compound 12.1 (730 mg, 2.17 mmol). The resulted mixture was stirred at 100° C. for 3 h, then cooled down to room temperature, diluted with cooled water (20 mL), added sodium hydroxide powder in small portions to adjusted the pH to 8~9, then the mixture was evaporated under vacuum, the residue was soaked with n-butyl alcohol (50 mL), and filtered, the filtrate was concentrated to afford compound 13.1 (450 mg, yield: 99%) as a light yellow solid.

$^1$H NMR (400 MHz, DMSO-d$_6$): δ 4.30-4.70 (br s, 2H), 2.32 (s, 1H), 2.09 (s, 3H), 1.61 (s, 2H), 1.44-1.53 (m, 8H), 1.29-1.32 (m, 2H).

Intermediate 6: Synthesis of 1-(3-hydroxyadamantan-1-yl)ethanone (14.1)

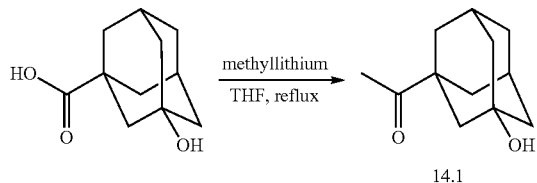

14.1

To an ice-cooling solution of 3-hydroxyadamantane-1-carboxylic acid (1.2 g, 6.0 mmol) in THF (60 mL) was slowly added methyllithium (40 mL, 1.2 M solution in diethyl ether). The resulted mixture was stirred at reflux for 2 h, then cooled down to 0° C., added trimethylsilyl chloride ((CH$_3$)$_3$SiCl) (21 mL). The resulted mixture was stirred at room temperature for 15 min, then added hydrochloric acid solution (45 mL, 1.0 M). The resulted mixture was stirred for 30 min, then extracted with ethyl acetate (75 mL×2), The combined organic phase was washed with brine, dried over sodium sulfate, filtered and concentrated. The residue was purified by column chromatography on silica gel (dichloromethane:methanol=95:5) to afford compound 14.1 (400 mg, yield: 34%) as a yellow solid.

$^1$H NMR (400 MHz, CDCl$_3$-d): δ 2.3 (br s, 2H), 2.1 (s, 3H), 1.65-1.80 (m, 10H), 1.6 (s, 2H), 1.55 (br s, 1H).
m/z: [M+H]$^+$ 195

Intermediate 7: Synthesis of 1-(4-hydroxyadamantan-1-yl)ethanone (15.1) and 1-(4-((tetrahydro-2H-pyran-2-yl)oxy)adamantan-1-yl)ethanone (55.1)

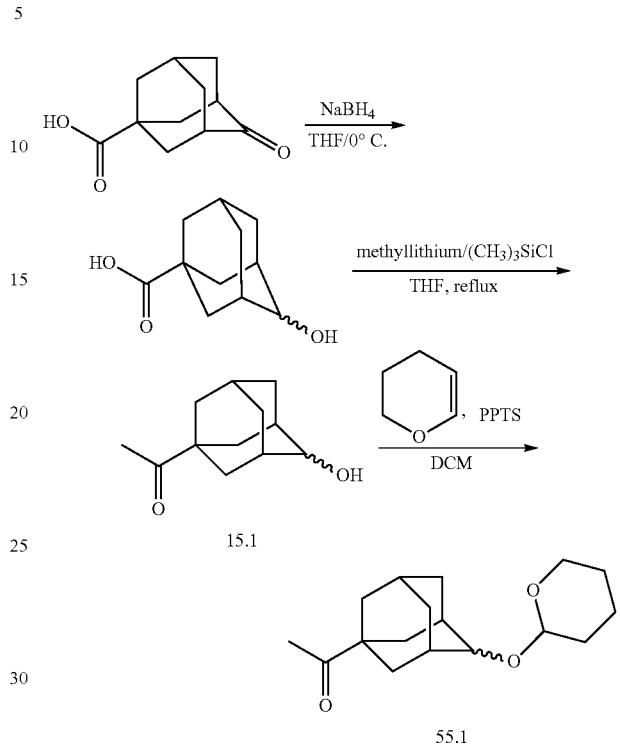

15.1

55.1

Step 1: Synthesis of 4-hydroxyadamantane-1-carboxylic Acid

To an ice-cooling solution of 4-oxoadamantane-1-carboxylic acid (3.0 g, 15.5 mmol) in a mixture solution of tetrahydrofuran (20 mL) and ethanol (20 mL) was added sodium borohydride (NaBH$_4$) (2.7 g, 73.4 mmol). The resulted mixture was stirred at room temperature for 2 h, then cooled down to 0° C., added hydrochloric acid solution (10 mL, 1.0 M) slowly under stirring, then extracted with ethyl acetate (60 mL×2), The combined organic phase was washed with brine, dried over sodium sulfate, filtered and concentrated. The residue was purified by column chromatography on silica gel (dichloromethane:methanol=95:5) to afford 4-hydroxyadamantane-1-carboxylic acid (2.5 g, yield: 82%) as a white solid.

Step 2: Synthesis of 1-(4-hydroxyadamantan-1-yl)ethanone

To an ice-cooling solution of 4-hydroxyadamantane-1-carboxylic acid (2.5 g, 12.8 mmol) in THF (100 mL) was added methyllithium (48 mL, 1.6 M solution in diethyl ether). The resulted mixture was stirred at reflux for 2 h, then cooled down to 0° C., and then the mixture was added trimethylsilyl chloride (34.7 g, 320 mmol) under stirring. The resulted mixture was warmed up to room temperature, added hydrochloric acid solution (50 mL, 1.0 M) and stirred for 0.5 h, then extracted with ethyl acetate (100 mL×2). The combined organic phase was washed with brine, dried over sodium sulfate, filtered and concentrated. The residue was purified by column chromatography on silica gel (dichloromethane:methanol=95:5) to afford compound 15.1 (2.0 g, yield: 80%) as a white solid.

m/z: [M+H]⁺ 195

Step 3: Synthesis of 1-(4-((tetrahydro-2H-pyran-2-yl)oxy)adamantan-1-yl)ethanone (55.1)

To a solution of compound 15.1 (0.93 g, 4.79 mmol) and 3,4-dihydro-2H-pyran (0.66 mL, 7.18 mmol) in dichloromethane (10 mL) was added pyridinium toluene-4-sulphonate (PPTS) (120 mg, 0.48 mmol). The resulted mixture was stirred at room temperature for overnight, and then the mixture was diluted with dichloromethane and washed with water and brine, dried over sodium sulfate, filtered and concentrated to afford compound 55.1. Then compound 55.1 (a mixture of cis/trans isomers) was purified by column chromatography on silica gel (petroleum ether:ethyl acetate=4:1) to afford two isomers (cis-isomer and trans-isomer), the less polar isomer 55.1A (328 mg) was first collected, then the more polar isomer 55.1B (386 mg) was collected.

m/z: [M+H]⁺ 279

Intermediate 8: Synthesis of 1-(4-hydroxy-4-phenyladamantan-1-yl)ethanone (16.1)

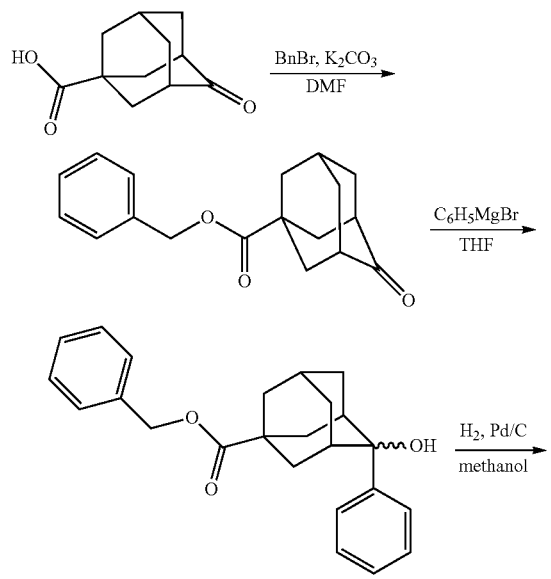

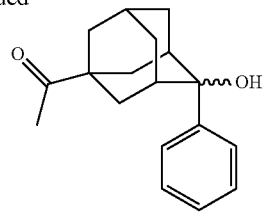

16.1

Step 1: Synthesis of Benzyl 4-oxoadamantane-1-carboxylate

To a solution of 4-oxoadamantane-1-carboxylic acid (3.00 g, 15.5 mmol) in DMF (30 mL) was successively added potassium carbonate (3.20 g, 15.5 mmol) and benzyl bromide (3.17 g, 18.5 mmol). The resulted mixture was stirred at room temperature for 1 h, then added water (100 mL), and extracted with ethyl acetate (100 mL×3). The combined organic phase was washed with brine, dried over sodium sulfate, filtered and concentrated. The residue was purified by flash column chromatography on silica gel (dichloromethane:methanol=95:5) to afford benzyl 4-oxoadamantane-1-carboxylate (3.9 g, yield: 89%) as a colorless oil.

¹H NMR (400 MHz, CDCl₃-d): δ 7.42-7.28 (m, 5H), 5.12 (s, 2H), 2.60 (s, 2H), 2.28-2.17 (m, 5H), 2.16-2.12 (m, 2H), 2.08-1.95 (m, 4H).

Step 2: Synthesis of Benzyl 4-hydroxy-4-phenyladamantane-1-carboxylate

To an ice-cooling solution of benzyl 4-oxoadamantane-1-carboxylate (2.00 g, 7.03 mmol) in THF (20 mL) was added phenylmagnesium bromide (8.5 mL, 8.50 mmol, 1.0 M solution in THF). The resulted mixture was stirred at room temperature for 2 h, then water (60 mL) was added, and extracted with ethyl acetate (60 mL×2). The combined organic phase was washed with brine, dried over sodium sulfate, filtered and concentrated. The residue was purified by flash column chromatography on silica gel (0~100% solution of ethyl acetate in petroleum ether) to afford benzyl 4-hydroxy-4-phenyladamantane-1-carboxylate (2.3 g, yield: 90%) as a white solid.

¹H NMR (400 MHz, CDCl₃-d): δ 7.58-7.51 (m, 2H), 7.44-7.23 (m, 8H), 5.15 (s, 1H), 5.01 (s, 1H), 2.73-2.59 (m, 3H), 2.50-2.39 (m, 1H), 2.14-1.59 (m, 10H).

Step 3: Synthesis of 4-hydroxy-4-phenyladamantane-1-carboxylic Acid

To a solution of benzyl 4-hydroxy-4-phenyladamantane-1-carboxylate (2.0 g, 5.52 mmol) in methanol (50 mL) was added wet palladium-carbon catalyst (Pd/C) (0.2 g, 10%). The resulted mixture was stirred at room temperature under hydrogen (1 atm) for 1 h, then filtered through celite, and the filter bed was washed with methanol (30 mL×2), the filtrate was evaporated under vacuum to afford 4-hydroxy-4-phenyladamantane-1-carboxylic acid (1.50 g, yield: 99%) as an off-white solid.

m/z: [M−1]⁻ 271

Step 4: Synthesis of 1-(4-hydroxy-4-phenyladamantan-1-yl)ethanone

To an ice-cooling solution of 4-hydroxy-4-phenyladamantane-1-carboxylic acid (1.50 g, 5.51 mmol) in THF (15 mL) was added methyllithium (20.6 mL, 33.1 mmol, 1.6 M solution in diethyl ether). The resulted mixture was stirred at 60° C. for 2 h, then cooled down to room temperature, the mixture was added trimethylsilyl chloride (3.59 g, 33.1 mmol). The resulted mixture was stirred at room temperature for 15 min, then added with water (50 mL), and extracted with ethyl acetate (50 mL×2). The combined organic phase was washed with brine, dried over sodium sulfate, filtered and concentrated to afford compound 16.1 (0.9 g, yield: 60%) as a yellow oil.

m/z: [M+1]$^+$ 271

1-(4-hydroxy-4-methyladamantan-1-yl)ethanone (17.1) was prepared according to Intermediate 8 compound 16.1, by replacing phenylmagnesium bromide (1.0 M solution in THF) to methylmagnesium bromide (3.0 M solution in diethyl ether) in step 2, as a yellow oil.

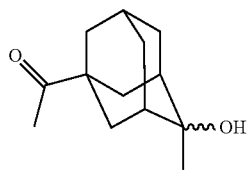

17.1 m/z: [M+1]$^+$ 209

Intermediate 9: Synthesis of
1-(4-phenyladamantan-1-yl)ethanone (18.1)

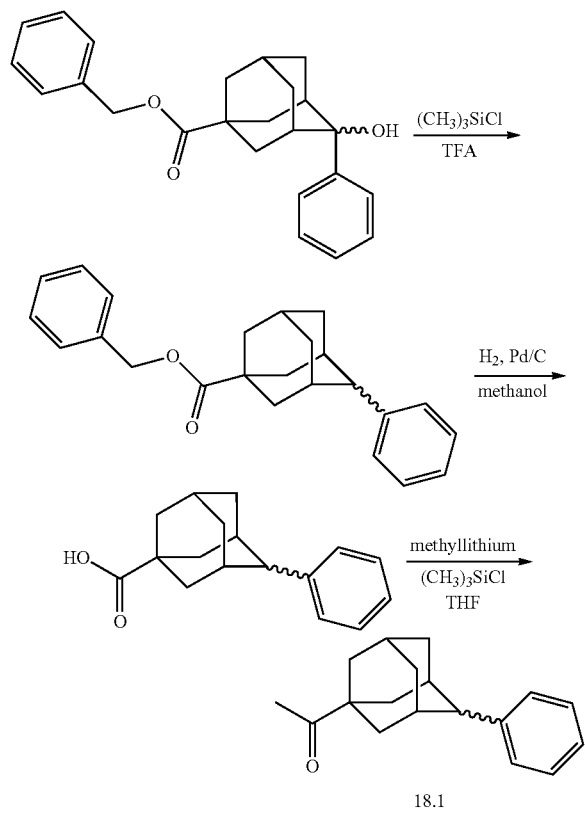

18.1

Step 1: Synthesis of Benzyl 4-phenyladamantane-1-carboxylate

To an ice-cooling mixture of benzyl 4-hydroxy-4-phenyladamantane-1-carboxylate (724 mg, 2.0 mmol) in trimethylsilyl chloride (5 mL) was added trifluoroacetic acid (5 mL). The resulted mixture was stirred at room temperature for 2 h, then added water (30 mL), extracted with ethyl acetate (10 mL×2). The combined organic phase was washed with brine, dried over sodium sulfate, filtered and concentrated. The residue was purified by flash column chromatography on silica gel (petroleum ether:ethyl acetate=5:1) to afford benzyl 4-phenyladamantane-1-carboxylate (510 mg, yield: 74%) as a colorless oil.

m/z: [M+H]$^+$ 347

Step 2: Synthesis of 4-phenyladamantane-1-carboxylic Acid

To a solution of benzyl 4-phenyladamantane-1-carboxylate (347 mg, 1.0 mmol) in methanol (15 mL) was added Pd/C (80 mg). The resulted mixture was stirred at room temperature under hydrogen (1 atm) for 1 h, then filtered through celite, and the filter bed was washed with methanol (60 mL), the filtrate was evaporated under vacuum to afford 4-phenyladamantane-1-carboxylic acid (220 mg, yield: 86%) as an off-white solid.

m/z: [M+H]$^+$ 257

Step 3: Synthesis of 1-(4-phenyladamantan-1-yl)ethanone (18.1)

To an ice-cooling solution of 4-phenyladamantane-1-carboxylic acid (220 mg, 0.86 mmol) in THF (5 mL) was added methyllithium (3.1 mL, 5 mmol, 1.6 M solution in diethyl ether). The resulted mixture was stirred at 60° C. for 2 h, then cooled down to room temperature, added trimethylsilyl chloride (0.86 g, 8.0 mmol). The resulted mixture was stirred at room temperature for 15 min, then diluted with water (20 mL), extracted with ethyl acetate (10 mL×2). The combined organic phase was washed with brine, dried over sodium sulfate, filtered and concentrated to afford compound 18.1 (145 mg, yield: 66%) as a yellow oil.

m/z: [M+H]$^+$ 255

Intermediate 10: Synthesis of
1-(adamantan-1-yl)-2-bromoethanone (19.1)

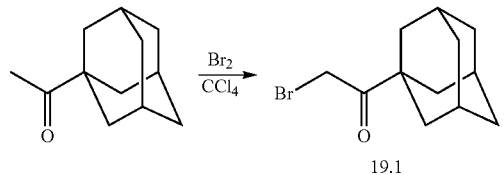

19.1

To an ice-cooling solution of 1-(adamantan-1-yl)ethanone (1.78 g, 10.0 mmol) in THF (30 mL) was added Br$_2$ (1.70 g, 10.7 mmol, dissolved in 5 mL THF). The resulted mixture was stirred at room temperature for 4 h, and then the reaction was quenched by addition of saturated sodium thiosulfate solution (20 mL), extracted with dichloromethane (100 mL). The organic phase was washed with brine, dried over sodium sulfate, filtered and concentrated to afford compound 19.1 (2.0 g, yield: 78%) as a yellow solid.

Intermediate 11: Synthesis of Dimethyl (2-(adamantan-1-yl)-2-oxoethyl) phosphonate (20.1)

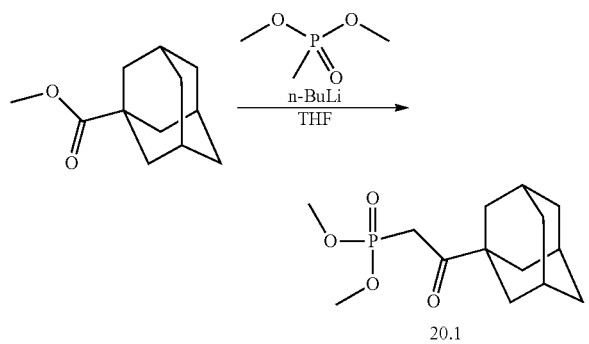

20.1

To a dry ice-acetone bath cooling solution of methyl adamantane-1-carboxylate (1.0 g, 5.15 mmol) in THF (30 mL) was added n-butyllithium (4.5 mL, 11.3 mmol, 2.5 M solution in toluene) dropwise. The resulted mixture was stirred at −78° C. for 1 h, then slowly added dimethyl methylphosphonate (1.4 g, 11.3 mmol). The resulted mixture was slowly warmed up to 0° C. under stirring, and then the reaction was quenched by addition of saturated ammonium chloride solution (20 mL), extracted with ethyl acetate (50 mL×2). The combined organic phase was washed with brine (25 mL), dried over sodium sulfate, filtered and concentrated. The residue was purified by flash column chromatography on silica gel (petroleum ether:ethyl acetate=1:1) to afford compound 20.1 (1.03 g, yield: 70%) as a light yellow oil.

$^1$H NMR (400 MHz, CDCl$_3$-d): δ 3.82 (s, 3H), 3.79 (s, 3H), 3.19 (s, 1H), 3.14 (s, 1H), 2.06-2.08 (m, 3H), 1.82-1.84 (m, 6H), 1.70-1.75 (m, 6H).

m/z: [M+H]$^+$ 287

Intermediate 12: Synthesis of 1-(5-aminoadamantan-2-yl)ethanone (21.1)

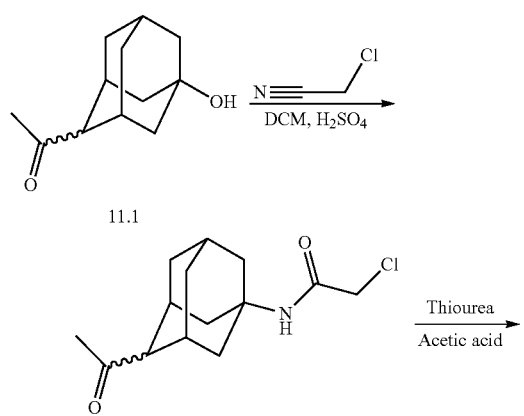

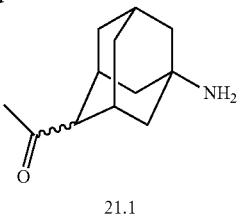

21.1

Step 1: Synthesis of N-(4-acetyladamantan-1-yl)-2-chloroacetamide

A mixture of 1-(5-hydroxyadamantan-2-yl)ethanone (25 g, 0.12 mol), chloroacetonitrile (50 mL) in dichloromethane (50 mL) was stirred at 0-5° C. Concentrated sulfuric acid (5 mL) was added dropwise to the mixture. The resulted mixture was stirred at reflux for 4 h. Then the reaction mixture was cooled down to 0-5° C., saturated sodium bicarbonate solution was added dropwise to the mixture to adjust the pH to 8-9, Then the mixture was extracted with ethyl acetate (50 mL×3). The combined organic phase was washed with brine (25 mL), dried over sodium sulfate, filtered and concentrated to afford the crude product, which was purified by flash column chromatography on silica gel (0~30% solution of ethyl acetate in petroleum ether) to afford N-(4-acetyladamantan-1-yl)-2-chloroacetamide (27.8 g, yield: 80%) as a light yellow oil.

m/z: [M+H]$^+$ 270

Step 3: Synthesis of 1-(5-aminoadamantan-2-yl)ethanone

A mixture of N-(4-acetyladamantan-1-yl)-2-chloroacetamide (10 g, 37.0 mmol), thiourea (3.0 g, 39.0 mmol) in acetic acid (20 mL) was heated up to 90° C., and stirred for 3 h. Then the mixture was concentrated to dryness, saturated sodium bicarbonate solution was added to the residue to adjust the Ph to 8-9, then extracted with dichloromethane (20 mL×3). The combined organic phase was washed with brine (25 mL), dried over sodium sulfate, filtered and concentrated to afford compound 21.1 (3.8 g, yield: 53%) as a yellow oil.

m/z: [M+H]$^+$ 194

Intermediate 13: Synthesis of 1-(4-acetyladamantan-1-yl)-3-(4-cyanophenyl)urea (22.1)

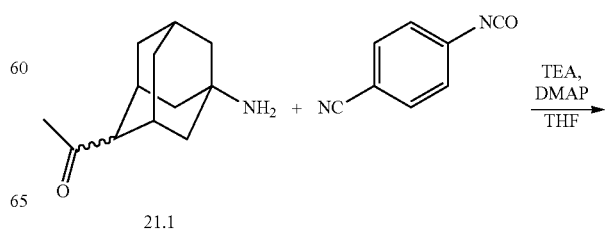

21.1

143
-continued

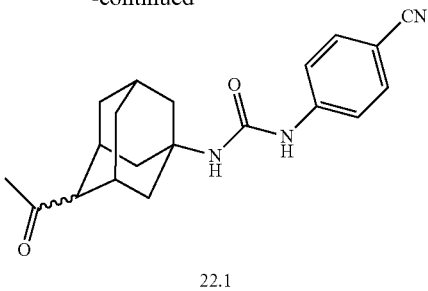

22.1

A mixture of 1-(5-aminoadamantan-2-yl)ethanone (150 mg, 0.78 mmol), 4-isocyanato benzonitrile (168 mg, 1.17 mmol), triethylamine (TEA) (237 mg, 2.34 mmol) and 4-dimethyl aminopyridine (DMAP) (10 mg, 0.078 mmol) in THF (10 mL) was stirred at room temperature for 3 h and then concentrated to afford the crude product, which was purified by flash column chromatography (0~60% solution of ethyl acetate in petroleum ether) to afford compound 22.1 (200 mg, yield: 76%) as a pale yellow solid.

m/z: [M+H]$^+$ 338

Compounds 23.1~26.1 were prepared according to Intermediate 13 compound 22.1, by replacing 4-isocyanatobenzonitrile to corresponding substituted or unsubstituted phenyl isocyanate.

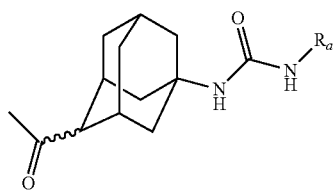

23.1~26.1

144
Intermediate 14: Synthesis of
N-(4-acetyladamantan-1-yl)-4-cyanobenzene sulfonamide (31.1)

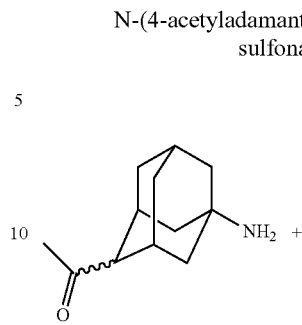

To a solution of 1-(5-aminoadamantan-2-yl)ethanone (500 mg, 2.6 mmol) and 4-cyanobenzene-1-sulfonyl chloride (625 mg, 3.1 mmol) in THF (20 mL) was added TEA (450 mg, 3.9 mmol) and DMAP (75 mg, 0.61 mmol). The resulted mixture was stirred at room temperature for 5 h, then filtered, the filter cake was washed with dichloromethane, the filtrated was concentrated, the residue was purified by column chromatography on silica gel (petroleum ether: ethyl acetate=2:1) to afford compound 31.1 (550 mg, yield: 59%) as a light yellow solid.

m/z: [M+H]$^+$ 359

| No. | $R_a$ | Name | MS |
|---|---|---|---|
| 23.1 | phenyl | 1-(4-acetyladamantan-1-yl)-3-phenylurea | m/z: [M + H] $^+$313 |
| 24.1 | 4-fluorophenyl | 1-(4-acetyladamantan-1-yl)-3-(4-fluorophenyl)urea | m/z: [M + H] $^+$331 |
| 25.1 | 4-methylphenyl | 1-(4-acetyladamantan-1-yl)-3-(p-tolyl)urea | m/z: [M + H] $^+$327 |
| 26.1 | 4-nitrophenyl | 1-(4-acetyladamantan-1-yl)-3-(4-nitrophenyl)urea | m/z: [M + H] $^+$358 |

Compounds 32.1-40.1 were prepared according to Intermediate 14 compound 31.1, by replacing 4-cyanobenzene-1-sulfonyl chloride to corresponding sulfonyl chloride.

Intermediate 15: Synthesis of N-(4-acetyladamantan-1-yl)acetamide (51.1)

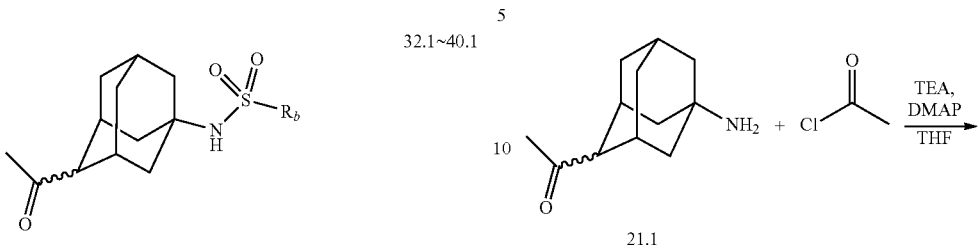

| No. | $R_b$ | Name | MS |
|---|---|---|---|
| 32.1 | benzyl | N-(4-acetyladamantan-1-yl)-1-phenylmethanesulfonamide | m/z: [M + H] $^+$348 |
| 33.1 | 4-CF$_3$-phenyl | N-(4-acetyladamantan-1-yl)-4-(trifluoromethyl)benzenesulfonamide | m/z: [M + H] $^+$402 |
| 34.1 | 4-methylphenyl | N-(4-acetyladamantan-1-yl)-4-methylbenzenesulfonamide | m/z: [M + H] $^+$348 |
| 35.1 | 4-NO$_2$-phenyl | 1-(4-acetyladamantan-1-yl)-3-(4-nitrophenyl)urea | m/z: [M + H] $^+$358 |
| 36.1 | —CH$_3$ | N-(4-acetyladamantan-1-yl)-methanesulfonamide | m/z: [M + H] $^+$272 |
| 37.1 | —CH$_2$CH$_3$ | N-(4-acetyladamantan-1-yl)-ethanesulfonamide | m/z: [M + H] $^+$286 |
| 38.1 | cyclopropyl | N-(4-acetyladamantan-1-yl)-cyclopropanesulfonamide | m/z: [M + H] $^+$298 |
| 39.1 | NHC(O)O-tBu | tert-butyl N-(4-acetyladamantan-1-yl)-sulfamoylcarbamate | m/z: [M-Boc] $^-$271 |
| 40.1 | cyclohexylmethyl | N-(4-acetyladamantan-1-yl)-1-cyclohexylmethanesulfonamide | m/z: [M + H] $^+$354 |

147 -continued

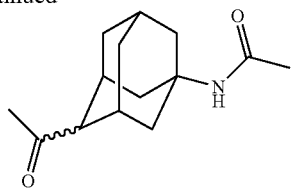

51.1

A mixture of 1-(5-aminoadamantan-2-yl)ethanone (330 mg, 1.55 mmol), acetyl chloride (174 mg, 2.22 mmol), TEA (500 mg, 4.95 mmol) and DMAP (15 mg, 0.155 mmol) in THF (30 mL) was stirred at room temperature for 3 h and then concentrated to afford the crude product, which was purified by flash column chromatography on silica gel (0~60% solution of ethyl acetate in petroleum ether) to afford compound 51.1 (318 mg, yield: 79%) as a pale yellow solid.

m/z: [M+H]$^+$ 236

Compounds 52.1~54.1 was prepared according to Intermediate 15 compound 51.1, by replacing acetyl chloride to corresponding benzoyl chloride.

52.1~54.1

148

Intermediate 16: Synthesis of Compound 57.1

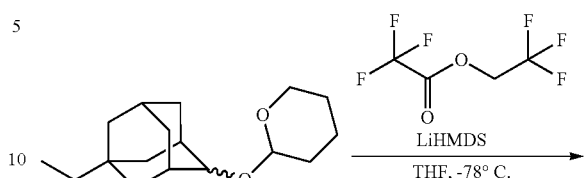

55.1B 56.1

57.1

Step 1: Synthesis of Compound 56.1

To a solution of compound 55.1B (736 mg, 2.64 mmol) in THF (10 mL) was added LiHMDS (3.2 mL, 1.0 M in THF) drop-wise at −78° C. during 45 min, then the mixture was added 2,2,2-trifluoroethyl trifluoroacetate (777 mg, 3.97 mmol) drop-wise, and the resulted mixture was stirred for 15 min at the same temperature. Then the reaction mixture was quenched with saturated ammonium chloride solution (20 mL) and stirred for 0.5 h. After that, the mixture was extracted with dichloromethane (15 mL×3). The combined organic phase was washed with brine (15 mL), dried over sodium sulfate, filtered and concentrated to afford compound 56.1 (520 mg, yield: 53%) as a yellow oil.

m/z: [M−H]$^-$ 373

| No. | R$_c$ | Name | MS |
|---|---|---|---|
| 52.1 | phenyl | N-(4-acetyladamantan-1-yl)benzamide | m/z: [M + H] $^+$298 |
| 53.1 | 4-methylbenzyl | N-(4-acetyladamantan-1-yl)-2-(p-tolyl)acetamide | m/z: [M + H] $^+$326 |
| 54.1 | cyclohexylmethyl | N-(4-acetyladamantan-1-yl)-2-cyclohexylacetamide | m/z: [M + H] $^+$318 |

Step 2: Synthesis of 57.1

To a solution of compound 56.1 (0.52 g, 1.39 mmol) in acetonitrile (15 mL) was added Selectfluor® (CAS: 140681-55-6) (1.23 g, 3.47 mmol). The resulted mixture was stirred at room temperature for overnight, and then the reaction was diluted with ethyl acetate (30 mL) and filtered through a pad of Celite and the filter cake was washed with ethyl acetate (5 mL×3). The combined organic phase was concentrated, the residue was dissolved in dichloromethane (20 mL), and washed with water (20 ml). The aqueous layer was extracted with dichloromethane (20 mL). The combined organic phase was dried over sodium sulfate, filtered and concentrated. The residue was purified by column chromatography on silica gel (0~10% solution of methanol in dichloromethane) to afford compound 57.1 (400 mg, yield: 67%) as a yellow oil.

m/z: [M−H]⁻ 427

Intermediate 17: Synthesis of tert-butyl 5-acetyl-2-azaadamantane-2-carboxylate (60.1)

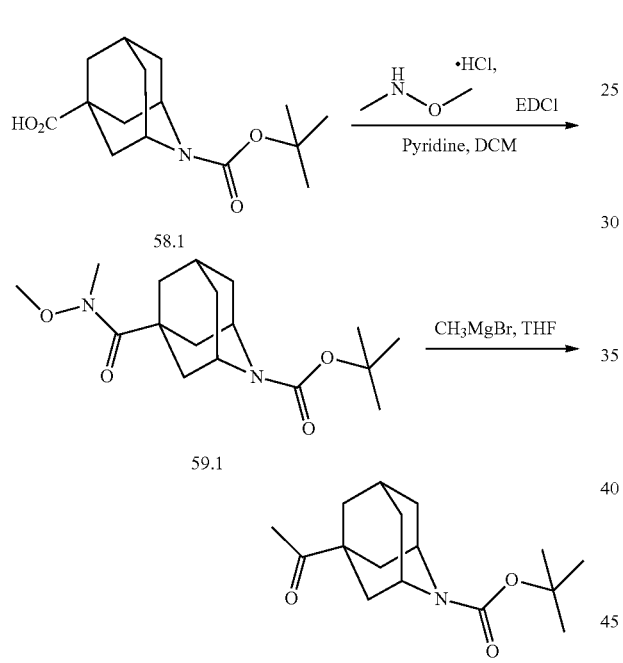

Step 1: Synthesis of Compound 59.1

Compound 58.1 was prepared according to WO2013/111150A1 (intermediate-9, page 72).

To a solution of compound 58.1 (790 mg, 2.81 mmol), N,O-dimethylhydroxyl amine hydrochloride (548 mg, 5.62 mmol) and EDCI (1.076 g, 5.61 mmol) in DCM (20 mL) was added pyridine (1.11 g, 14.04 mmol). The mixture was stirred at room temperature for 3 h, and then quenched with 1M hydrogen chloride (20 mL, 1.0 M in H₂O). The organic phase was separated and washed with brine, dried over sodium sulfate and concentrated to afford compound 59.1 (850 mg, yield 93%) as a brown oil.

Step 2: Synthesis of Compound 60.1

To an ice-cooling solution of compound 59.1 (850 mg, 2.62 mmol) in THF (10 mL) was added CH₃MgBr (2.6 mL, 8.4 mmol, 3.0 M solution in diethyl ether). The mixture was allowed to slowly warm to room temperature and stirred for 2 h, and then quenched with saturated saturated ammonium chloride solution solution. The resulting mixture was extracted with ethyl acetate (30 mL×3). The combined phase was washed with brine, dried over sodium sulfate and concentrated to afford compound 60.1 (710 mg, yield 97%) as a brown oil.

Intermediate 18: Synthesis of 1-(4-methoxyadamantan-1-yl)ethanone (61.1)

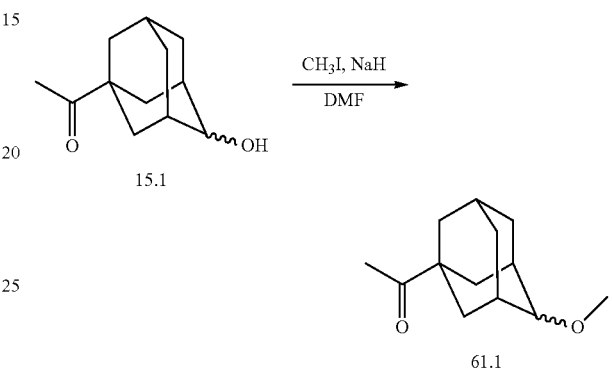

To an ice-cooling solution of compound 15.1 (150 mg, 0.77 mmol) in DMF (5 mL) was added NaH (61.8 mg, 1.54 mmol), the mixture was stirred at room temperature for 0.5 h, and then the mixture was added iodomethane (329 mg, 2.32 mmol), the resulted mixture was stirred at room temperature for overnight, then the reaction was quenched by addition of H₂O (20 mL), extracted with ethyl acetate (30 mL×3). The combined phase was washed with brine, dried over sodium sulfate and filtered thought a celit pad, the filtrate was concentrated to afford compound 61.1 (160 mg, yield 100%) as a yellow oil.

Intermediate 19: Synthesis of Compound 62.1

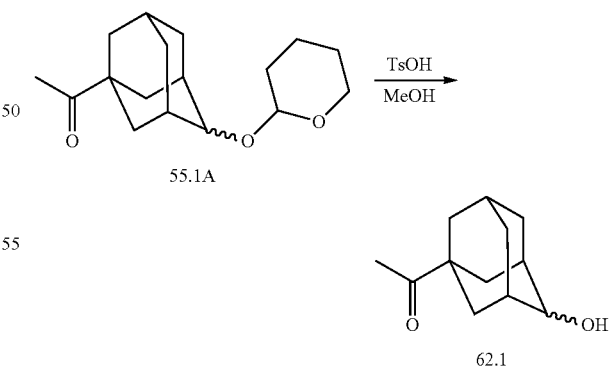

To a solution of compound 55.1A (300 mg, 1.08 mmol) in MeOH (5 mL) was added n-butyllithium (19 mg, 0.11 mmol). The resulted mixture was stirred at room temperature for 2 h, and then the reaction was quenched by addition of sodium bicarbonate solution (20 mL), extracted with DCM (50 mL×2). The combined organic phase was washed with brine (25 mL), dried over sodium sulfate, filtered and concentrated to afford compound 62.1 (207 mg, yield: 99%) as a light yellow solid.

m/z: [M+H]$^+$ 195

Synthesis of the Compounds

Example 1: Synthesis of Compound 1

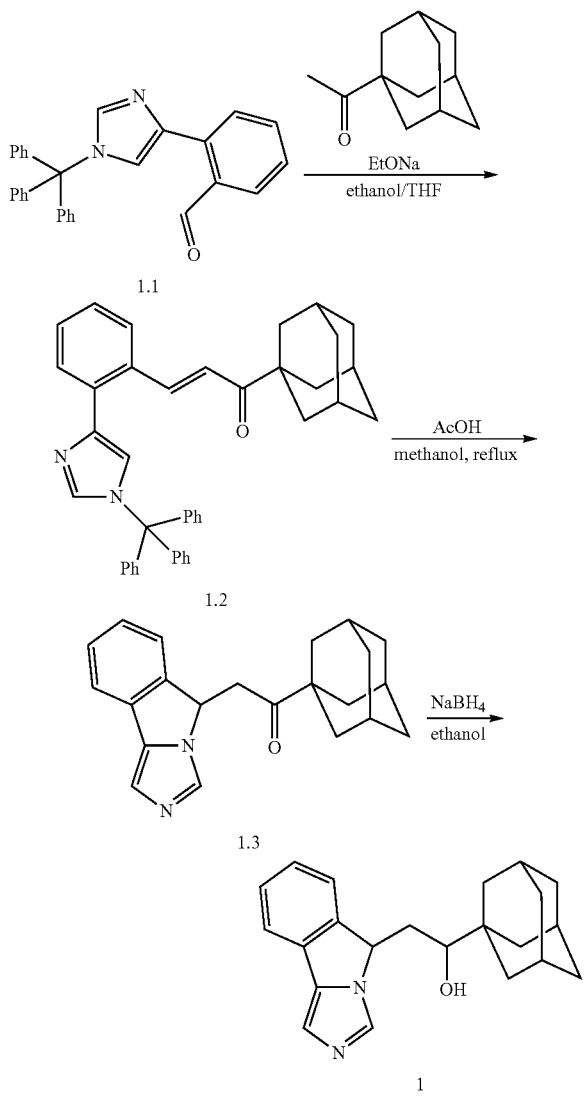

Step 1: Synthesis of Compound 1.2

To a solution of compound 1.1 (500 mg, 1.2 mmol) and 1-(adamantan-1-yl)ethanone (235 mg, 1.3 mmol) in a mixed solvent of ethanol (5 mL) and THF (5 mL) was added sodium ethoxide (122 mg, 1.8 mmol). The resulted mixture was stirred at room temperature for overnight, then the mixture was added water (30 mL), and extracted with ethyl acetate (60 mL×2). Then the combined organic phase was washed with brine, dried over sodium sulfate, filtered and concentrated. The residue was purified by column chromatography on silica gel (petroleum ether:ethyl acetate=2:1) to afford compound 1.2 (400 mg, yield: 62%) as a white solid.

m/z: [M+H]$^+$ 575

Step 2: Synthesis of Compound 1.3

To a solution of compound 1.2 (400 mg, 0.70 mmol) in methanol (5 mL) was added acetic acid (1.2 mL). The resulted mixture was stirred at reflux for 3 h, then diluted with water (30 mL), the mixture was extracted with ethyl acetate (60 mL). The organic phase was washed with saturated sodium bicarbonate solution (30 mL) and brine, dried over sodium sulfate, filtered and concentrated. The residue was purified by column chromatography on silica gel (petroleum ether:ethyl acetate=1:1) to afford compound 1.3 (174 mg, yield: 75%) as a white solid.

m/z: [M+H]$^+$ 333

Step 3: Synthesis of Compound 1

To a solution of compound 1.3 (170 mg, 0.51 mmol) in ethanol (5 mL) was added NaBH$_4$ (39 mg, 1.02 mmol). The resulted mixture was stirred at room temperature for 2 h, then diluted with water (30 mL). The mixture was extracted with ethyl acetate (60 mL), then the organic phase was washed with brine, dried over sodium sulfate, filtered and concentrated. The residue was purified by column chromatography on silica gel (petroleum ether:ethyl acetate=1:1) to afford compound 1 (a mixture of stereoisomers) (126 mg, yield: 74%) as a white solid.

$^1$H NMR (400 MHz, DMSO-d$_6$): δ 7.95 (s, 1H), 7.57-7.61 (m, 2H), 7.39 (t, J=7.2 Hz, 1H), 7.28 (t, J=7.2 Hz, 1H), 7.12 (s, 1H), 5.35-5.38 (m, 1H), 4.87 (s, J=6.4 Hz, 1H), 3.36-3.38 (m, 1H), 2.08-2.12 (m, 1H), 1.93 (s, 3H), 1.77-1.79 (m, 1H), 1.44-1.67 (m, 12H).

m/z: [M+H]$^+$ 335

Synthesis of Compound 1-A

To a solution of compound 1 (30 mg) in methanol (2.0 mL) was added a solution of hydrogen chloride in methanol (0.5 mL, 4.0 M). The resulted mixture was stirred at room temperature for 30 min, then evaporated to afford the crude compound, the crude compound was washed with diethyl ether, filtered to afford compound 1-A (22 mg, yield: 65%) as a HCl salt of compound 1, which was a white solid.

The following compounds 2~31 and corresponding HCl salts were prepared according to compounds 1 and 1-A, by using compound 1.1, 2.1, 3.1, 4.1, 5.1, 6.1, 7.1 or 8.1 and corresponding adamantanone (Any compound of 2~31 and corresponding HCl salt is a mixture of stereoisomers).

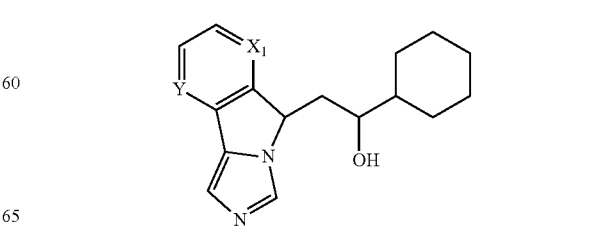

| No. | Y | X₁ | ¹H NMR and/or MS |
|---|---|---|---|
| 2 | N | C | ¹H NMR (400 MHz, CDCl₃-d): δ 8.54-8.55 (m, 1 H), 7.87 (d, J = 5.2 Hz, 1 H), 7.76 (d, J = 8.0 Hz, 1 H), 7.50 (d, J = 2.8 Hz, 1 H), 7.14-7.17 (m, 1 H), 5.44-5.48 (m, 1 H), 3.69-3.71 (m, 1 H), 2.22-2.30 (m, 1 H), 2.00-2.07 (m, 1 H), 1.86-1.67 (m, 6 H), 0.91-1.38 (m, 5 H); m/z: [M + H]⁺284 |
| 3 | C | N | ¹H NMR (400 MHz, CDCl₃-d): δ 8.38 (dd, J = 1.6, 4.8 Hz, 1 H), 7.89-7.82 (m, 2 H), 7.30-7.33 (m, 2 H), 5.32-5.38 (m, 1 H), 3.86-3.97 (m, 1 H), 2.18-2.40 (m, 1 H), 2.13-2.06 (m, 1 H), 1.96-2.03 (m, 1 H), 1.69-1.81 (m, 4 H), 1.43-1.52 (m, 1 H), 1.01-1.31 (m, 5 H); m/z: [M + H]⁺284 |

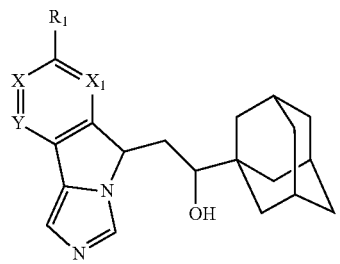

| No. | Y | X | X₁ | R₁ | ¹H NMR and/or MS |
|---|---|---|---|---|---|
| 4 | C | C | N | H | m/z: [M + H]⁺336 |
| 5 | C | C | N | F | ¹H NMR (400 MHz, MeOD-d₄): δ 9.24 (s, 1 H), 8.39 (dd, J = 7.2, 8.0 Hz, 1 H), 7.84 (s, 1 H), 7.24-7.36 (m, 1 H), 5.67 (t, J = 5.8 Hz, 1 H), 3.62 (dd, J = 2.4, 11.2 Hz, 1 H), 2.44-2.67 (m, 1 H), 2.05-2.16 (m, 1 H), 1.97-2.04 (m, 3 H), 1.58-1.81 (m, 12 H); m/z: [M + H]⁺354 |
| 6 | C | N | C | Cl | ¹H NMR (400 MHz, MeOD-d₄): δ 9.21, 9.28 (two s, 1 H), 8.89, 8.90 (two d, J = 0.8 Hz, 1 H), 7.86-7.91 (m, 2 H), 5.97-5.99 (two m, 1 H), 3.34-3.38 (m, 0.5 H), 3.04-3.08 (m, 0.5 H), 2.21-2.52 (m, 2 H), 1.98-2.03 (s, 3 H), 1.49-1.82 (m, 12 H); m/z: [M + H]⁺370 |
| 7 | C | C | C | F | m/z: [M + H]⁺353 |

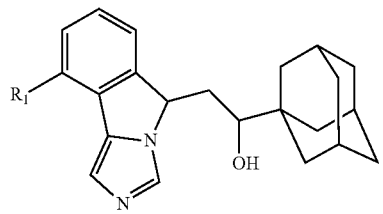

| No. | R₁ | ¹H NMR and/or MS |
|---|---|---|
| 8 | F | (HCl salt) ¹H NMR (400 MHz, DMSO-d₆): δ 14.93 (br s, 1 H), 9.46 (s, 1 H), 8.01 (d, J = 0.8 Hz, 1 H), 7.54-7.63 (m, 3 H), 7.42-7.47 (m, 1 H), 5.85 (t, J = 6.8 Hz, 1 H), 3.39 (d, J = 9.6 Hz, 1 H), 2.18-2.26 (m, 1 H), 2.02-2.08 (m, 1 H), 1.94 (s, 3 H), 1.45-1.68 (m, 12 H); m/z: [M + H]⁺353 |

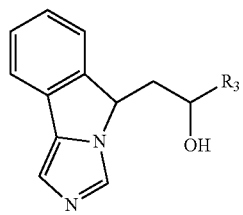

| No. | R₃ | ¹H NMR and/or MS |
|---|---|---|
| 9 | adamantyl-OH | m/z: [M + H]⁺ 351 |
| 10 | adamantyl-OH | m/z: [M + H]⁺ 351 |
| 11 | adamantyl(Me)-OH | m/z: [M + H]⁺ 365 |
| 12 | adamantyl(Ph)-OH | m/z: [M + H]⁺ 427 |
| 13 | adamantyl | ¹H NMR (400 MHz, DMSO-d₆): δ 7.93 (s, 1 H), 7.61 (d, J = 8.2 Hz, 2 H), 7.39 (t, J = 7.2 Hz, 1 H), 7.30 (t, J = 8.0 Hz, 1 H), 7.12 (s, 1 H), 5.44-5.47 (m, 1 H), 4.96 (d, J = 7.2 Hz, 1 H), 4.10-4.13 (m, 1 H), 2.23 (br s, 1 H), 1.94-2.00 (m, 2 H), 1.36-1.87 (m, 14 H); m/z:[M + H]⁺ 335 |
| 14 | adamantyl-OH | (HCl salt) ¹H NMR (400 MHz, DMSO-d₆): δ 14.55 (br s, 1 H), 9.39 (s, 1 H), 7.93-7.94 (m, 1 H), 7.87-7.89 (m, 1 H), 7.77-7.79 (m, 1 H), 7.53-7.57 (m, 2 H), 5.82-5.86 (m, 1 H), 4.05 - 4.06 (m, 1 H), 3.65- 3.67 (m, 1 H), 2.39-2.40 (m, 1 H), 2.02-2.09 (m, 2 H),1.81-1.89 (m, 2 H), 1.32-1.71 (m, 12 H); m/z: [M + H]⁺ 351 |
| 15 | adamantyl-NHSO₂-C₆H₄-CH₃ | m/z: [M + H]⁺ 504 |
| 16 | adamantyl-NHSO₂-CH₂-C₆H₅ | ¹HNMR (400 MHz, CDCl₃-d): δ 7.90, 7.91 (two s, 1 H), 7.56-7.58 (m, 1 H), 7.50 (dd, J = 7.6, 20.4 Hz, 1 H), 7.34-7.42 (m, 6 H), 7.27-7.29 (m, 1 H), 7.17 (d, J = 5.6 Hz, 1 H), 5.35-5.47 (two m, 1 H), 4.20-4.27 (m, 2 H), 4.09 - 4.17 (m, 1 H), 1.51-2.47 (m, 16 H); m/z: [M + H]⁺ 504 |

-continued

| No. | R₃ | ¹H NMR and/or MS |
|---|---|---|
| 17 | (adamantyl-NH-SO₂-C₆H₄-NO₂) | m/z: [M + H] ⁺535 |
| 18 | (adamantyl-NH-C(O)-Ph) | (HCl salt) ¹H NMR (400 MHz, DMSO-d₆): δ 14.55 (br, s, 1 H), 9.37, 9.41, 9.45 (three s, 1 H), 7.93 (s, 1 H), 7.75-7.89 (m, 4 H), 7.40-7.69 (m, 7 H), 5.86 (t, J = 13.2 Hz, 1 H), 5.25-5.34 (m, 1 H), 4.14-4.24 (m, 1 H), 1.34-2.44 (m, 14 H); m/z: [M + H] ⁺454 |
| 19 | (adamantyl-NH-C(O)-CH₃) | (HCl salt) ¹H NMR (400 MHz, DMSO-d₆): δ 14.55 (s, 1 H), 9.36, 9.46 (two s, 1 H), 7.93 (s, 1 H), 7.86-7.88 (m, 1 H), 7.77-7.81 (m, 1 H), 7.51-7.58 (m, 2 H), 7.33 (d, J = 5.2 Hz, 1 H), 5.84 (t, J = 12.8 Hz, 1 H), 4.10-4.15 (m, 2 H), 1.24-1.64 (m, 5 H), 1.74 (d, J = 2.0 Hz, 3 H), 1.83-2.35 (m, 9 H); m/z: [M + H] ⁺392 |

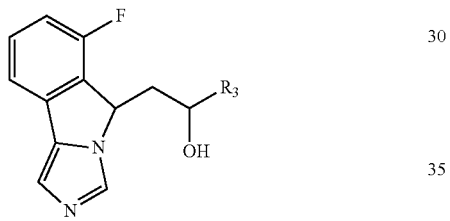

| No. | R₃ | ¹H NMR and/or MS |
|---|---|---|
| 21 | (adamantyl) | ¹H NMR (400 MHz, CDCl₃-d): δ 7.83-7.89 (m, 1 H), 7.32-7.37 (m, 2 H), 7.20-7.21 (m, 1 H), 6.92-6.97 (m, 1 H), 5.47-5.68 (m, 1 H), 3.27-3.34 (m, 1 H), 2.39-2.50 (m, 1 H), 2.02-2.11 (m, 4 H), 1.50-1.74 (m, 12 H); m/z: [M + H] ⁺353 |
| 22 | (adamantyl-OH) | ¹H NMR (400 MHz, CDCl₃-d): δ 7.86 (s, 1 H), 7.33-7.40 (m, 2 H), 7.22 (s, 1 H), 6.78-6.93 (m, 1 H), 5.50 (t, J = 4.8 Hz, 1 H), 3.35 (d, J = 10.4 Hz, 1 H), 2.37-2.43 (m, 1 H), 2.24-2.28 (m, 2 H), 2.09-2.17 (m, 1 H), 1.42-1.73 (m, 12 H); m/z: [M + H] ⁺369 |
| 23 | (adamantyl-OH) | (HCl salt) ¹H NMR (400 MHz, DMSO-d₆): δ 14.43 (br s, 1 H), 9.36 (s, 1 H), 7.99 (s, 1 H), 7.72 (d, J = 8.0 Hz, 1 H), 7.60-7.61 (m, 1 H), 7.35-7.38 (m, 1 H), 5.99-6.03 (m, 1 H), 3.57 (s, 1 H), 3.14-3.16 (m, 1 H), 2.38-2.50 (m, 1 H), 1.99-2.02 (m, 3 H), 1.76-1.80 (m, 3 H), 1.39-1.48 (m, 8 H), 1.23-1.25 (m, 2 H); m/z: [M + H] ⁺369 |

-continued

| No. | R₃ | ¹H NMR and/or MS |
|---|---|---|
| 24 | 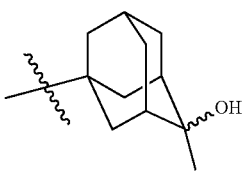 [SMILES: *C12CC3CC(C1)C(C)(O)C(C3)C2] | m/z: [M + H]⁺383 |
| 25 | 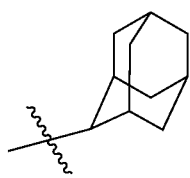 [SMILES: *C1C2CC3CC(C2)CC1C3] | (HCl salt) ¹H NMR (400 MHz, DMSO-d₆): δ 9.29 (s, 1 H), 7.95 (s, 1 H), 7.69-7.73 (m, 1 H), 7.57-7.62 (m, 1 H), 7.30-7.39 (m, 1 H), 6.02-6.05 (m, 1 H), 4.87-4.90 (m, 1 H), 3.87-3.93 (m, 1 H), 2.13-2.18 (m, 1 H), 1.35-1.96 (m, 15 H): m/z: [M + H]⁺353 |
| 26 | 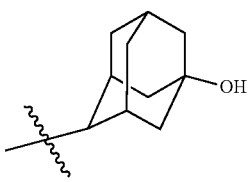 [SMILES: *C1C2CC3CC1CC(O)(C3)C2] | (HCl salt) ¹H NMR (400 MHz, DMSO-d₆): δ 14.63 (br s, 1 H), 9.36 (s, 1 H), 8.00 (d, J = 0.8 Hz, 1 H), 7.71 (d, J = 8.0 Hz, 1 H), 7.61-7.64 (m, 1 H), 7.35-7.39 (m, 1 H), 6.04-6.07 (m, 1 H), 3.76- 3.81 (m, 1 H), 3.61-3.63 (m, 1 H), 2.26-2.31 (m, 2 H), 1.92-2.01 (m, 3 H), 1.70- 1.72 (m, 1 H), 1.30-1.64 (m, 11 H); m/z: [M + H]⁺369 |
| 27 | 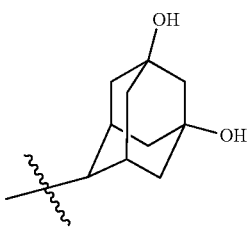 [SMILES: *C1C2CC3(O)CC1CC(O)(C2)C3] | (HCl salt) ¹H NMR (400 MHz, DMSO-d₆): δ 14.52 (s, 1 H), 9.35 (s, 1 H), 7.93 (s, 1 H), 7.87 (d, J = 6.8 Hz, 1 H), 7.77 (d, J = 6.4 Hz, 1 H), 7.53-7.59 (m, 2 H), 5.83 (t, J = 6.4 Hz, 1 H), 3.99-4.03 (m, 1 H), 2.44 (s, 1 H), 2.00-2.12 (m, 2 H), 1.94 (s, 1 H), 1.73 (d, J = 11.6 Hz, 1 H), 1.34-1.58 (m, 7 H), 1.15-1.30 (m, 4 H); m/z: [M + H]⁺385 |
| 28 | 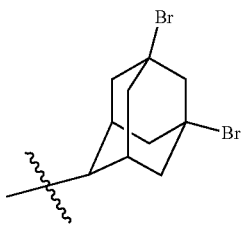 [SMILES: *C1C2CC3(Br)CC1CC(Br)(C2)C3] | (HCl salt) m/z: [M + H]⁺509 |
| 29 | 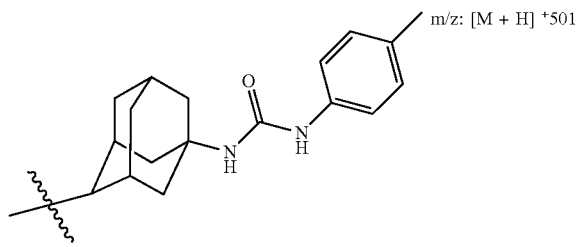 | m/z: [M + H]⁺501 |
| 30 | 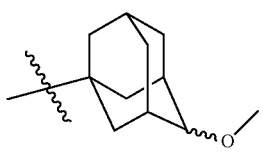 [SMILES: *C12CC3CC(C1)C(OC)C(C3)C2] | ¹H NMR (400 MHz, MeOD-d₄): δ 9.14, 9.16, 9.21 (three s, 1 H), 7.83 (s, 1 H), 7.42-7.73 (m, 2 H), 7.25-7.35 (m, 1 H), 5.93-6.12 (two m, 1 H), 3.33-3.45 (overlapping with solvent, 4 H), 2.59-2.66 (m, 1 H), 1.22 -2.10 (m, 15 H); m/z: [M + H] 383 |

| No. | R₃ | ¹H NMR and/or MS |
|---|---|---|
| 31 | 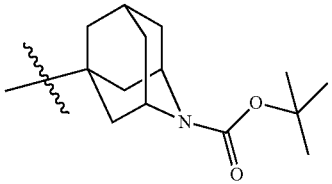 [SMILES: *C12CC3CC(C1)N(C(=O)OC(C)(C)C)C(C3)C2] | m/z: [M + H] ⁺501 |

Example 2: Separation of Compound 1

A mixture of stereoisomers of compound 1 (5.1 g) was separated by SFC (Chiral resolution method: A) to afford single diasteromers 1-1 (520 mg), 1-2 (1.07 g), 1-3 (1.04 g) and 1-4 (1.45 g).

| No. | Chiral resolution method | Compound No. of a single diasteromer | Retention Time (Chiral analysis method A) |
|---|---|---|---|
| 1 | A | 1-1 | 4.85 min |
|   |   | 1-2 | 5.38 min |
|   |   | 1-3 | 6.64 min |
|   |   | 1-4 | 8.76 min |

Example 3: Separation of Compound 10

Compound 10 (a mixture of stereoisomers) was separated by pre-HPLC (Separation method: B) to afford 10A (128 mg, the peak time: 9.75~11.8 min) and 10B (140 mg, the peak time: 12.3~15.2 min). The HCl salts of 10A and 10B were prepared according to the preparation method of compound 1-A.

10A (HCl salt): ¹H NMR (400 MHz, DMSO-d₆): δ 9.21 (s, 1H), 7.86-7.88 (m, 1H), 7.78 (s, 1H), 7.71-7.73 (m, 1H), 7.56-7.82 (m, 2H), 5.77-5.90 (m, 1H), 3.77-3.81 (m, 1H), 3.60-3.63 (m, 1H), 2.25-2.31 (m, 1H), 2.10-2.21 (m, 3H), 1.93-2.01 (m, 3H), 1.31-1.74 (m, 11H).

10B (HCl salt): ¹H NMR (400 MHz, DMSO-d₆): δ 9.23 (s, 1H), 7.55-7.87 (m, 5H), 5.78-5.90 (m, 1H), 3.78 (s, 1H), 3.56-3.66 (m, 1H), 3.33-3.37 (m, 1H), 2.01-2.29 (m, 2H), 1.64-1.81 (m, 6H), 1.18-1.56 (m, 9H).

Example 4: Separation of Compound 11

Compound 11 (a mixture of stereoisomers) was separated according to the method of compound 10, by pre-HPLC (Separation method: E) to afford 11A (the peak time: 9.8~11.8 min) and 11B (the peak time: 12.3~15.2 min). Both 11A and 11B were TFA salts.

A mixture of stereoisomers of compound 11A (1.5 g) was separated by SFC (Chiral resolution method: G) to afford single diasteromers 11A-1 (20 mg), 11A-2 (400 mg), 11A-3 (390 mg) and 11A-4 (30 mg).

| No. | Chiral resolution method | Compound No. of a single diasteromer | Retention Time (Chiral analysis method B) |
|---|---|---|---|
| 11A | G | 11A-1 | 2.61 min |
|   |   | 11A-2 | 2.95 min |
|   |   | 11A-3 | 3.49 min |
|   |   | 11A-4 | 4.72 min |

11A: ¹H NMR (400 MHz, MeOD-d₄): δ 9.12, 9.19, 9.20 (three s, 1H), 7.87-8.02 (m, 1H), 7.77 (s, 1H), 7.70-7.72 (m, 1H), 7.55-7.64 (m, 2H), 5.74-5.90 (m, 1H), 3.57-3.61 (m, 1H), 2.22-2.30 (m, 3H), 2.12-2.15 (m, 1H), 1.71-1.86 (m, 2H), 1.60-1.71 (m, 4H), 1.40-1.60 (m, 5H), 1.29 (s, 3H).

11B: ¹H NMR (400 MHz, MeOD-d₄): δ 9.00, 9.03, 9.10, 9.19 (four s, 1H), 7.71-7.76 (m, 1H), 7.68-7.70 (m, 1H), 7.63-7.68 (m, 1H), 7.50-7.59 (m, 2H), 5.77-5.87 (m, 1H), 3.34-3.57 (m, 1H), 2.15-2.25 (m, 1H), 2.09-2.15 (m, 3H), 1.76-1.90 (m, 4H), 1.31-1.76 (m, 4H), 1.20-1.42 (m, 3H), 1.27 (s, 3H).

11A-2: ¹H NMR (400 MHz, MeOD-d₄): δ 9.22 (s, 1H), 7.86-7.89 (m, 1H), 7.78 (s, 1H), 7.69-7.73 (m, 1H), 7.54-7.59 (m, 2H), 5.78 (t, J=5.6 Hz, 1H), 3.60 (dd, J=2.0, 10.8 Hz, 1H), 2.25-2.31 (m, 3H), 2.09-2.17 (m, 1H), 1.74-1.89 (m, 5H), 1.42-1.63 (m, 6H), 1.32 (s, 3H).

Example 5: Separation of Compounds 12, 15, and 29

Compound 12 (a mixture of stereoisomers) was separated according to the method of compound 10, by pre-HPLC (Separation method: F) to afford 12A (the peak time: 11.5~14.8 min) and 12B (the peak time: 16.8-19.0 min). Both 12A and 12B were TFA salts.

12A: ¹H NMR (400 MHz, MeOD-d₄): δ 9.08 (s, 1H), 7.77-7.84 (m, 1H), 7.70 (d, J=1.1 Hz, 1H), 7.47-7.60 (m, 4H), 7.28-7.46 (m, 3H), 7.19-7.28 (m, 1H), 5.63 (t, J=6.0 Hz, 1H), 3.42 (dd, J=2.7, 11.3 Hz, 1H), 2.62-2.71 (m, 2H), 2.37-2.51 (m, 2H), 2.06-2.21 (m, 1H), 1.89-2.05 (m, 2H), 1.43-1.72 (m, 8H).

12B: ¹H NMR (400 MHz, MeOD-d₄): δ 9.20 (s, 1H), 7.83-7.88 (m, 1H), 7.61-7.82 (m, 2H), 7.47-7.60 (m, 4H), 7.31-7.39 (m, 2H), 7.25 (t, J=6.9 Hz, 1H), 5.77 (t, J=6.0 Hz, 1H), 3.65 (dd, J=2.6, 11.1 Hz, 1H), 2.61-2.71 (m, 2H), 2.39-2.51 (m, 1H), 2.09-2.37 (m, 3H), 1.79-1.89 (m, 1H), 1.38-1.75 (m, 8H).

Compound 15 (a mixture of stereoisomers) was separated according to the method of compound 10, by pre-HPLC (Separation method: I) to afford 15A (the peak time: 7.5~8.5 min) and 15B (the peak time: 9.2~10.8 min). The HCl salts of 15A and 15B were prepared according to the preparation method of compound 1-A.

15A (HCl salt): ¹H NMR (400 MHz, DMSO-d₆): δ 7.90, 7.91, 7.92 (three s, 1H), 7.56-7.72 (m, 4H), 7.43-7.47 (m, 1H), 7.22-7.39 (m, 4H), 7.12 (d, J=10.8 Hz, 1H), 5.39-5.42 (m, 1H), 4.93-5.07 (m, 1H), 3.90-4.02 (m, 1H), 3.17 (d, J=5.6 Hz, 1H), 2.32-2.40 (m, 3H), 1.02-2.21 (m, 15H).

15B (HCl salt): $^1$H NMR (400 MHz, DMSO-d$_6$): δ 9.27, 9.30 (two s, 1H), 7.83-7.95 (m, 2H), 7.20-7.76 (m, 5H), 7.45 (d, J=10.0 Hz, 1H), 7.36 (d, J=8.0 Hz, 1H), 7.30 (d, J=8.0 Hz, 1H), 5.75-5.85 (m, 1H), 5.07-5.29 (m, 1H), 3.95-4.30 (m, 1H), 2.34-2.40 (m, 3H), 2.15-2.33 (m, 1H), 1.15-2.07 (m, 15H).

Compound 29 (a mixture of stereoisomers) was separated according to the method of compound 10, by pre-HPLC (Separation method: I) to afford 29A (the peak time: 7.8-10.2 min) and 29B. Hydrochloride salt of 29A was prepared according to the preparation method of compound 1-A.

29A (HCl salt): $^1$H NMR (400 MHz, DMSO-d$_6$): δ 9.27 (s, 1H), 7.96, 7.99 (two s, 1H), 7.69-7.74 (m, 3H), 7.57-7.65 (m, 1H), 7.32-7.47 (m, 4H), 5.98-6.07 (two m, 1H), 3.60-3.89 (m, 2H), 2.37, 2.38 (two s, 3H), 2.08-2.27 (m, 2H), 1.17-1.94 (m, 14H).

Example 6: Separation of Compound 23

Compound 23 (a mixture of stereoisomers) was separated according to the method of compound 10, by pre-HPLC (Separation method: A) to afford 23A (the peak time: 6.8~9.7 min) and 23B (the peak time: 10.5-14.5 min).

A mixture of stereoisomers of compound 23A (2.0 g) was separated by SFC (Chiral resolution method: B) to afford single diasteromers 23A-1 (147 mg), 23A-2 (401 mg), 23A-3 (330 mg) and 23A-4 (69 mg).

| No. | Chiral resolution method | Compound No. of a single diasteromer | Retention Time (Chiral analysis method B) |
|---|---|---|---|
| 23A | B | 23A-1 | 3.21 min |
|  |  | 23A-2 | 3.70 min |
|  |  | 23A-3 | 4.30 min |
|  |  | 23A-4 | 5.27 min |

The HCl salts of 23A, 23B and 23A-3 were prepared according to the preparation method of compound 1-A.

23A (HCl salt): $^1$H NMR (400 MHz, DMSO-d$_6$): δ 14.74 (br s, 1H), 9.36-9.47 (m, 1H), 7.99 (s, 1H), 7.58-7.74 (m, 2H), 7.33-7.41 (m, 1H), 5.96-6.08 (m, 1H), 3.57 (s, 1H), 2.98-3.16 (m, 1H), 2.33-2.48 (m, 1H), 1.92-2.13 (m, 3H), 1.72-1.86 (m, 3H), 1.14-1.55 (m, 9H).

23B (HCl salt): $^1$H NMR (400 MHz, DMSO-d$_6$): δ 14.77 (br s, 1H), 9.37-9.42 (m, 1H), 7.80 (s, 1H), 7.49-7.75 (m, 2H), 7.33-7.44 (m, 1H), 5.98-6.09 (m, 1H), 3.57 (s, 1H), 3.07-3.20 (m, 1H), 2.33-2.44 (m, 1H), 1.91-2.05 (m, 2H), 1.52-1.75 (m, 6H), 1.02-1.41 (m, 7H).

23A-3 (HCl salt): $^1$H NMR (400 MHz, DMSO-d$_6$): δ 14.67 (br s, 1H), 9.35 (d, J=4.0 Hz, 1H), 7.99 (s, 1H), 7.71 (d, J=7.6 Hz, 1H), 7.58-7.63 (m, 1H), 7.34-7.38 (m, 1H), 5.99 (t, J=4.8 Hz, 1H), 4.89 (br s, 1H), 3.58 (s, 1H), 3.14-3.17 (m, 1H), 2.44-2.51 (m, 1H), 1.94-2.03 (m, 3H), 1.77-1.80 (m, 3H), 1.23-1.52 (m, 8H).

Example 7: Separation of Compound 26

Compound 26 (a mixture of stereoisomers) was separated by column chromatography on silica gel (dichloromethane:methanol=15:1) to afford 26A (128 mg, less polar) and 26B (124 mg, more polar).

A mixture of stereoisomers of compound 26A (900 mg) was separated by SFC (Chiral resolution method: C) to afford single diasteromers 26A-2 (256 mg), and 26A-3 (215 mg), and a mixture of diasteromers 26A-1+26A-4 (70 mg).

| No. | Chiral resolution method | Compound No. of a single diasteromer | Retention Time (Chiral analysis method C) |
|---|---|---|---|
| 26A | B | 26A-2 | 2.16 min |
|  |  | 26A-3 | 3.15 min |

The HCl salts of 26A, and 26B were prepared according to the preparation method of compound 1-A.

26A (HCl salt): $^1$H NMR (400 MHz, DMSO-d$_6$): δ 14.63 (br, s, 1H), 9.36 (s, 1H), 8.00 (d, J=0.8 Hz, 1H), 7.71 (d, J=8.0 Hz, 1H), 7.61-7.64 (m, 1H), 7.35-7.39 (m, 1H), 6.04-6.07 (m, 1H), 3.76-3.81 (m, 1H), 3.61-3.63 (m, 1H), 2.26-2.31 (m, 2H), 1.92-2.01 (m, 3H), 1.70-1.72 (m, 1H), 1.30-1.64 (m, 11H).

26B (HCl salt): $^1$H NMR (400 MHz, DMSO-d$_6$): δ 14.61 (br, s, 1H), 9.37 (s, 1H), 8.00 (s, 1H), 7.71-7.75 (m, 1H), 7.64-7.59 (m, 1H), 7.35-7.39 (m, 1H), 6.04-6.07 (m, 1H), 3.84-3.89 (m, 1H), 3.67-3.69 (m, 1H), 2.22-2.26 (m, 2H), 1.92-1.99 (m, 3H), 1.72-1.75 (m, 1H), 1.31-1.66 (m, 11H).

26A-3: $^1$H NMR (400 MHz, CDCl3-d): δ 8.21 (s, 1H), 7.36-7.43 (m, 2H), 7.24 (s, 1H), 6.98-7.03 (m, 1H), 5.63 (t, J=5.2 Hz, 1H), 4.11-4.16 (m, 1H), 2.44-2.53 (m, 4H), 1.89-2.17 (m, 4H), 1.50-1.79 (m, 10H).

Example 8: Separation of Compound 14

Compound 14 (a mixture of stereoisomers) was separated according to the method of compound 26, by column chromatography on silica gel (dichloromethane:methanol=15:1) to afford 14A and 14B.

A mixture of stereoisomers of compound 14A (560 mg) was separated by SFC (Chiral resolution method: C) to afford single diasteromers 14A-1 (135 mg), 14A-4 (132 mg), and a mixture of diasteromers 14A-2+14A-3 (43 mg).

| No. | Chiral resolution method | Compound No. of a single diasteromer | Retention Time (Chiral analysis method D) |
|---|---|---|---|
| 14A | C | 14A-1 | 2.22 min |
|  |  | 14A-4 | 7.08 min |

The HCl salts of 14A, 14B and 14A-4 were prepared according to the preparation method of compound 1-A.

14A (HCl salt): $^1$H NMR (400 MHz, DMSO-d$_6$): δ 14.55 (br s, 1H), 9.39 (s, 1H), 7.93-7.94 (m, 1H), 7.87-7.89 (m, 1H), 7.77-7.79 (m, 1H), 7.53-7.57 (m, 2H), 5.82-5.86 (m, 1H), 4.05-4.06 (m, 1H), 3.65-3.67 (m, 1H), 2.39-2.40 (m, 1H), 2.02-2.09 (m, 2H), 1.81-1.89 (m, 2H), 1.32-1.71 (m, 12H).

14B (HCl salt): $^1$H NMR (400 MHz, DMSO-d$_6$): δ 14.55 (br s, 1H), 9.35 (s, 1H), 7.93-7.94 (m, 1H), 7.86-7.89 (m, 1H), 7.77-7.79 (m, 1H), 7.52-7.58 (m, 2H), 5.82-5.85 (m, 1H), 4.11-4.13 (m, 1H), 3.72-3.74 (m, 1H), 2.25-2.35 (m, 1H), 1.99-2.10 (m, 2H), 1.82-1.85 (m, 2H), 1.31-1.68 (m, 12H).

14A-4 (HCl salt): $^1$H NMR (400 MHz, DMSO-d$_6$): δ 14.68 (br s, 1H), 9.38 (s, 1H), 7.96 (d, J=1.2 Hz, 1H), 7.87-7.89 (m, 1H), 7.77-7.79 (m, 1H), 7.52-7.59 (m, 2H), 5.85 (t, J=6.6 Hz, 1H), 4.03-4.09 (m, 1H), 2.40 (s, 1H), 1.81-2.13 (m, 5H), 1.25-1.68 (m, 10H).

Example 9: Synthesis of Compound 10A-2 and 10A-3

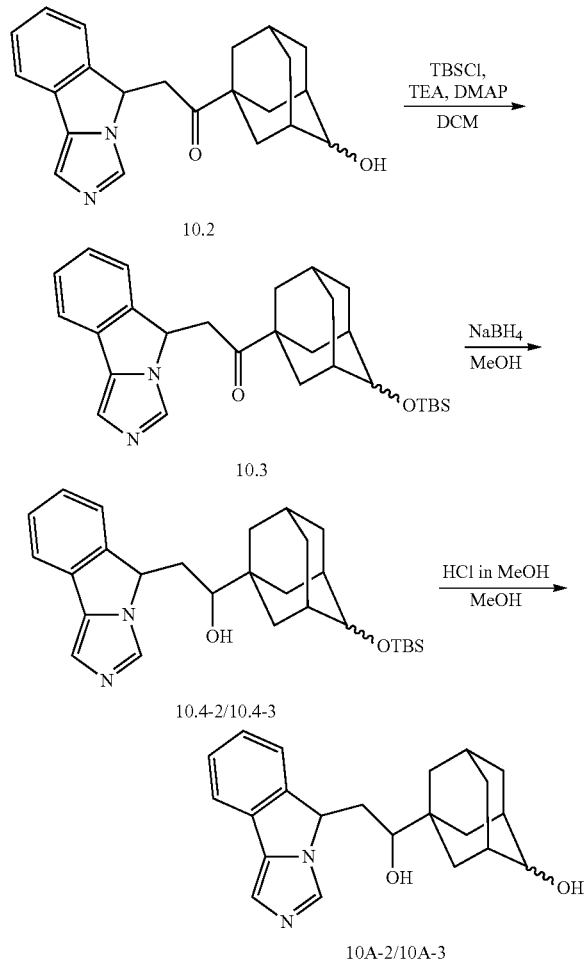

10.2

10.3

10.4-2/10.4-3

10A-2/10A-3

Step 1: Synthesis of Compound 10.3

Compound 10.2 was prepared according to example 1 compound 1.3 in step 2, by using compound 1.1 and 62.1 as starting materials.

A solution of compound 10.2 (1.2 g, 3.44 mmol), tert-butyldimethylsilyl chloride (TBSCl) (780 mg, 5.17 mmol), Et$_3$N (700 mg, 6.88 mmol), and catalytic amount of DMAP in DCM (15 mL) was stirred at room temperature for 36 h, then diluted with DCM (20 mL) and the organic phase was washed with water (20 mL) and brine, dried over sodium sulfate, filtered and concentrated. The residue was purified by column chromatography on silica gel (dichloromethane:methanol=100:1~50:1) to afford compound 10.3 (1.1 g, yield: 69%) as a white solid.

Step 2: Synthesis and Chiral Resolution of Compound 10.4

To an ice-cooling solution of compound 10.3 (1.10 g, 2.38 mmol) in MeOH (5 mL) was added NaBH$_4$ (135 mg, 3.57 mmol), the resulted mixture was stirred at 0° C. for 0.5 h. And then the reaction was quenched by addition of saturated sodium dihydrogen phosphate solution. The mixture was extracted with DCM (20 mL×3), The combined organic phase was dried over sodium sulfate, filtered and concentrated to afford compound 10.4 (960 mg, yield: 87%).

Compound 10.4 (960 mg) was separated by SFC (Chiral resolution method: H) to afford single diasteromers 10.4-2 (330 mg), 10.4-3 (343 mg) and mixture of diasteromers 45A-1+45A-4 (60 mg).

| No. | Chiral resolution method | Compound No. of a single diasteromer | Retention Time (Chiral analysis method F) |
|---|---|---|---|
| 10.4 | H | 10.4-2 | 2.70 min |
|  |  | 10.4-3 | 3.45 min | m/z: [M+H]$^+$ 465

Step 3: Synthesis of Compound 10A-2 and 10A-3

To a solution of compound 10.4-2 (330 mg, 0.71 mmol) in methanol (2.0 mL) was added a solution of hydrogen chloride in methanol (0.5 mL, 1.0 M). The resulted mixture was stirred at room temperature for 2 h, then evaporated to afford the crude compound, the crude compound was dissolved in water (10 mL) and adjusted pH to 8 with saturated sodium bicarbonate solution, and the aqueous phase was extracted with ethyl acetate (10 mL×3), The combined organic phase was dried over sodium sulfate, filtered and concentrated. The residue was purified by column chromatography on silica gel (dichloromethane:methanol=95:5) to afford compound 10A-2 (150 mg, yield: 60%) as a white solid. Compound 10A-3 was prepared according to the synthesis of compound 10A-2, by using compound 10.4-3 (340 mg, 0.73 mmol) as starting material to afford compound 10A-3 (190 mg, yield: 74%) as a white solid.

The HCl salts of compounds 10A-2 and 10A-3 were prepared according to the preparation method of compound 1-A.

m/z: [M+H]$^+$ 351

10A-2 (HCl salt): $^1$H NMR (400 MHz, DMSO-d$_6$): δ 14.68 (br s, 1H), 9.38 (s, 1H), 7.92 (s, 1H), 7.87 (d, J=6.8 Hz, 1H), 7.76 (d, J=6.8 Hz, 1H), 7.50-7.58 (m, 2H), 5.76 (t, J=6.4 Hz, 1H), 3.49-3.60 (overlapping with solvent, 2H), 2.13-2.20 (m, 1H), 1.97-2.04 (m, 3H), 1.24-1.81 (m, 12H).

10A-3 (HCl salt): $^1$H NMR (400 MHz, DMSO-d$_6$): δ 14.72 (br s, 1H), 9.39 (s, 1H), 7.93 (s, 1H), 7.87 (d, J=6.4 Hz, 1H), 7.76 (d, J=6.8 Hz, 1H), 7.50-7.58 (m, 2H), 5.77 (t, J=6.4 Hz, 1H), 3.44-3.47 (overlapping with solvent, 2H), 2.12-2.20 (m, 1H), 1.97-2.04 (m, 3H), 1.24-1.81 (m, 13H).

Example 10: Synthesis of Compound 35

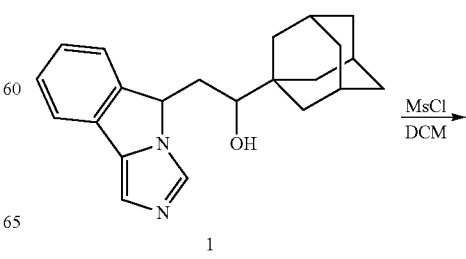

1

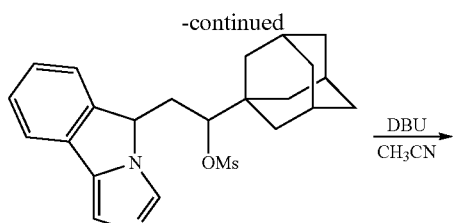

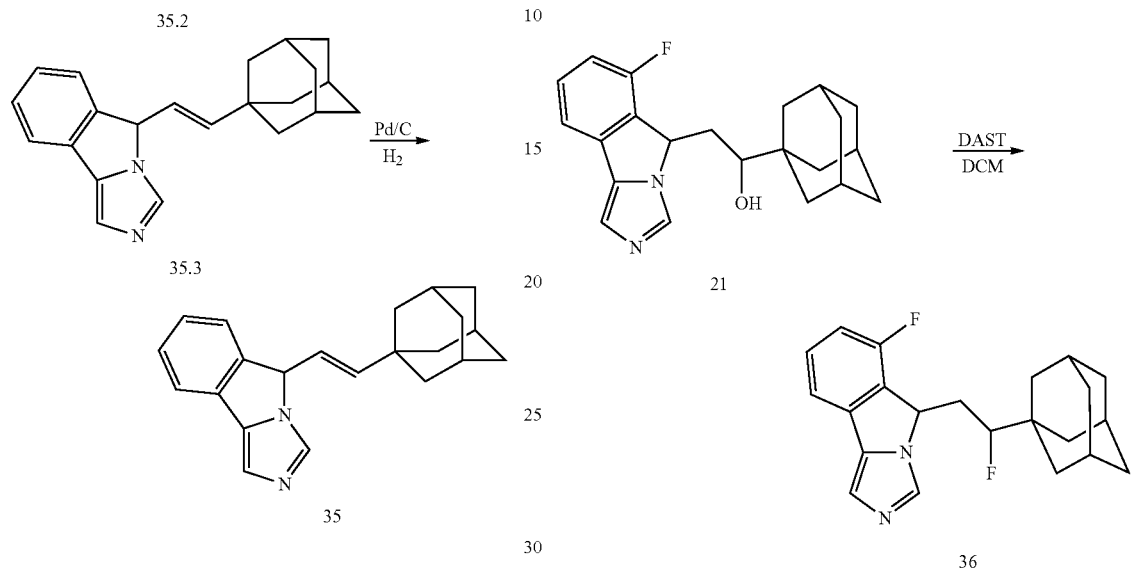

Step 1: Synthesis of Compound 35.2

To an ice-cooling solution of compound 1 (275 mg, 0.82 mmol), and TEA (166 mg, 1.64 mmol) in dichloromethane (10 mL) was added methanesulfonyl chloride (MSCl) (113 mg, 0.99 mmol) dropwise. The resulted mixture was stirred at room temperature for overnight, and then the mixture was diluted with dichloromethane (10 mL) and washed with water and brine, dried over sodium sulfate, the organic phase was filtered and concentrated. The residue was purified by column chromatography on silica gel (dichloromethane:methanol=50:1) to afford compound 35.2 (80 mg, yield: 24%) as an oil.

m/z: [M+H]$^+$ 413

Step 2: Synthesis of Compound 35.3

A solution of compound 35.2 (100 mg, 0.24 mmol) and 1,8-Diazabicyclo [5.4.0]undec-7-ene (DBU) (73 mg, 0.48 mmol) in acetonitrile (5 mL) was stirred at reflux for overnight, and then the mixture was concentrated to afford the crude compound 35.3, which was used directly for next step without further purification.

m/z: [M+H]$^+$ 317

Step 3: Synthesis of Compound 35

To a solution of compound 35.3 (80 mg, 0.25 mmol) in methanol (10 mL) was added Pd/C (30 mg, 10%). The resulted mixture was stirred under hydrogen (1 atm) at room temperature for overnight. Then the mixture was filtered through a celite pad, and the filtrate was concentrated, the residue was purified by pre-HPLC to afford compound 35 (TFA salt, 25 mg, yield: 32%) as a white solid.

$^1$H NMR (400 MHz, MeOD-d$_4$): δ 7.75 (s, 1H), 7.56 (d, J=7.6 Hz, 1H), 7.35-7.41 (m, 2H), 7.26-7.30 (m, 1H), 7.21 (s, 1H), 5.18 (t, J=5.18 Hz, 1H), 2.10-2.19 (m, 1H), 1.88-1.94 (m, 4H), 1.55-1.74 (m, 6H), 1.42 (s, 6H), 0.94-1.07 (m, 2H).

m/z: [M+H]$^+$ 319

Example 11: Synthesis of Compound 36

To a solution of compound 21 (100 mg, 0.28 mmol) in dichloromethane (5 mL) was added diethylaminosulfurtrifluoride (DAST) (274 mg, 1.7 mmol) at −40° C. under nitrogen. The resulted mixture was stirred at −40° C. for 10 min, then the mixture was slowly warmed up to room temperature and stirred for overnight. The reaction mixture was diluted with dichloromethane and washed with saturated sodium bicarbonate solution (30 mL). The organic phase was washed with brine, dried over sodium sulfate, filtered and concentrated. The residue was purified by pre-HPLC to afford compound 36 (TFA salt, 23 mg, yield: 23%) as a white solid.

$^1$H NMR (400 MHz, MeOD-d$_4$): δ 9.18, 9.36 (two s, 1H), 7.86, 7.87 (two s, 1H), 7.60-7.76 (m, 2H), 7.27-7.35 (m, 1H), 6.00-6.09 (two m, 1H), 1.32-2.47 (m, 18H).

m/z: [M+H]$^+$ 355

Example 12: Synthesis of Compounds 37 and 38

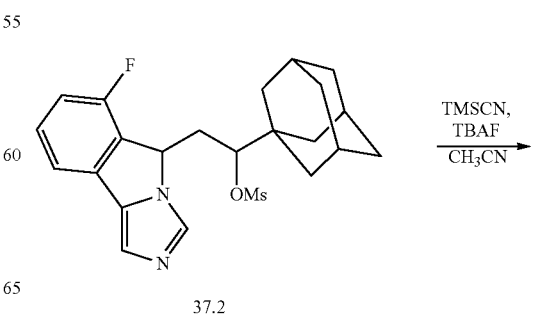

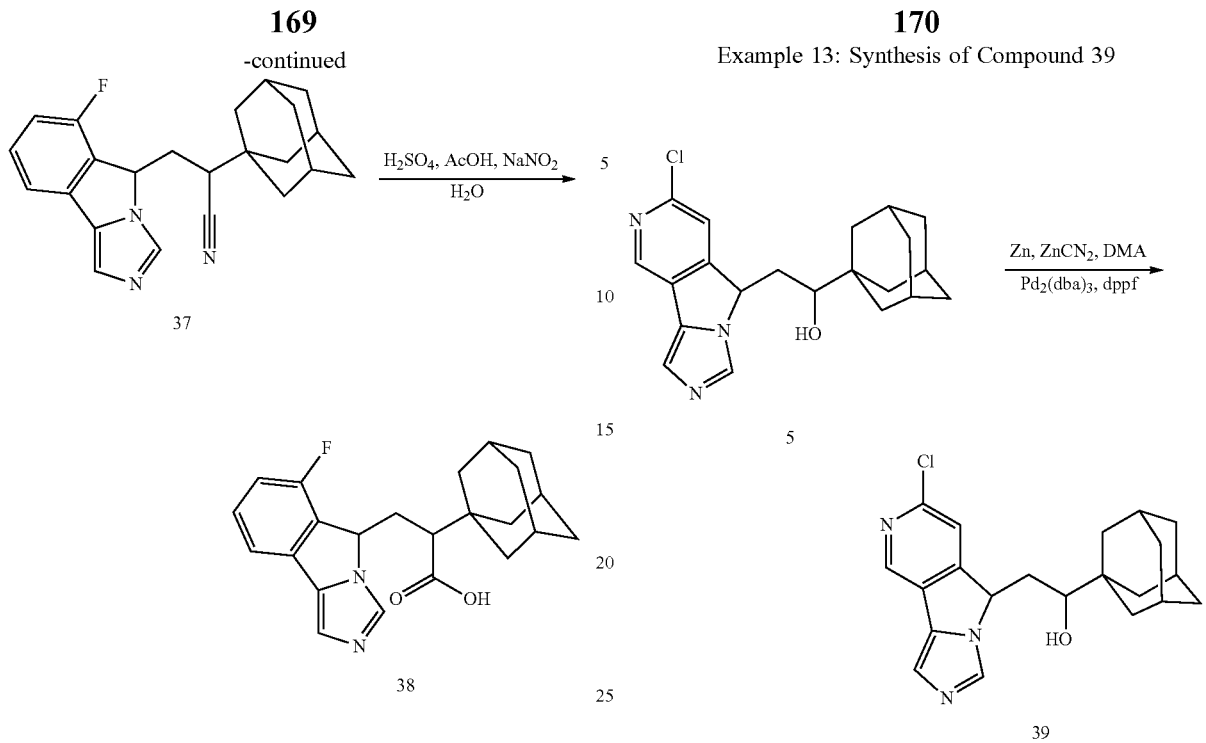

Compound 37.2 was prepared according to Example 10 compound 35.2, by using compound 21 as stating material.

Step 1: Synthesis of Compound 37

A solution of compound 37.2 (100 mg, 0.24 mmol), trimethylsilylcarbonitrile (TMSCN) (138 mg, 1.4 mmol) and tetrabutyl ammonium fluoride (TBAF) (1.4 mL, 1.4 mmol) in acetonitrile (5 mL) was stirred at 90° C. for overnight, and then the mixture was concentrated to dryness. The residue was purified by column chromatography on silica gel (dichloromethane:methanol=50:1) to afford compound 37 (100 mg, yield: 40%) as a white solid.

$^1$H NMR (400 MHz, MeOD-$d_4$): δ 8.99 (s, 1H), 7.60-7.68 (m, 2H), 7.42-7.49 (m, 2H), 7.05 (s, 1H), 2.23 (s, 2H), 2.01 (s, 3H), 1.78-1.86 (m, 6H), 1.61 (d, J=2.4 Hz, 5H), 1.32-1.40 (m, 2H).

m/z: [M+H]$^+$ 362

Step 2: Synthesis of Compound 38

To an ice-cooling mixture of compound 37 (20 mg, 0.055 mmol) in H$_2$O (1.0 mL) was successively added H$_2$SO$_4$ (0.5 mL, 70% w/w) and acetic acid (1.5 mL). The resulted mixture was stirred at 110° C. for 1 h, and then sodium nitrite (30 mg, dissolved in 0.3 mL water) was added dropwise. The resulted mixture was stirred at 110° C. for overnight. Then filtered, the filtrated was concentrated to dryness. The residue was purified by pre-HPLC to afford compound 38 (TFA salt, 6.5 mg, yield: 31%) as a white solid.

$^1$H NMR (400 MHz, MeOD-$d_4$): δ 9.04 (s, 1H), 7.64 (s, 1H), 7.45-7.51 (m, 1H), 7.26-7.35 (m, 2H), 6.52 (s, 1H), 2.29 (s, 2H), 1.95-2.05 (m, 3H), 1.64-1.78 (m, 6H), 1.51 (d, J=2.0 Hz, 5H), 1.24-1.32 (m, 2H).

m/z: [M+H]$^+$ 381

Example 13: Synthesis of Compound 39

A mixture of compound 5 (200 mg, 0.28 mmol), Zn powder (21 mg, 0.32 mmol) (freshly activated), Zn(CN)$_2$ (190 mg, 1.62 mmol), tris(dibenzylideneacetone)dipalladium(0) (Pd$_2$(dba)$_3$) (60 mg, 0.09 mmol) and 1,1'-Bis(diphenylphosphino) ferrocene (dppf) (101 mg, 0.18 mmol) in degassed N,N-dimethylacetamide (DMA) (10 mL) was degassed for three times under N$_2$ protection, and then stirred at 120° C. for 1 h, the reaction was quenched by addition of water (50 mL). The mixture was extracted with ethyl acetate (30 mL×3). The combined organic phase was washed with brine (15 mL), dried over sodium sulfate, filtered and concentrated. The residue was purified by pre-TLC (dichloromethane:methanol=20:1) to afford compound 39 (39 mg, yield: 20%) as a white solid.

$^1$H NMR (400 MHz, MeOD-$d_4$): δ 9.29, 9.35 (two s, 1H), 9.22 (dd, J=7.6, 0.9 Hz, 1H), 8.29 (d, J=3.7 Hz, 1H), 8.04 (s, 1H), 5.92-6.08 (m, 1H), 3.05-3.36 (m, 1H), 2.41-2.58 (m, 1H), 2.24-2.36 (m, 1H), 1.96-2.04 (br s, 3H), 1.51-1.81 (m, 12H).

m/z: [M+H]$^+$ 361

Example 14: Synthesis of Compound 40

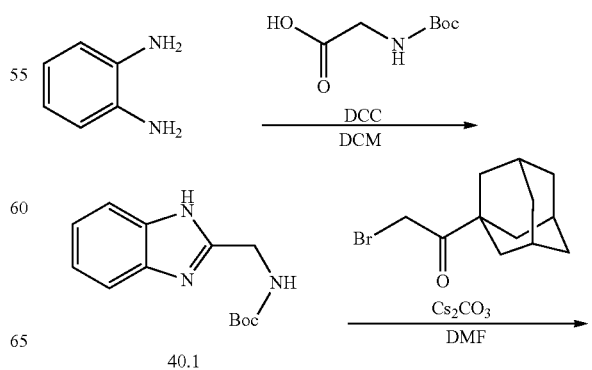

-continued

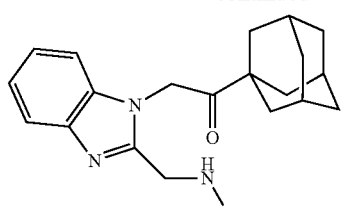

40.2

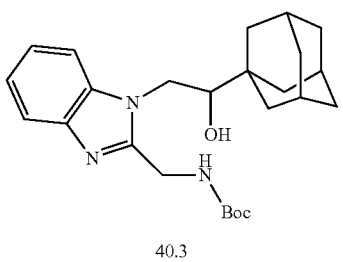

40.3

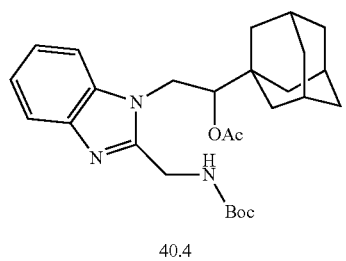

40.4

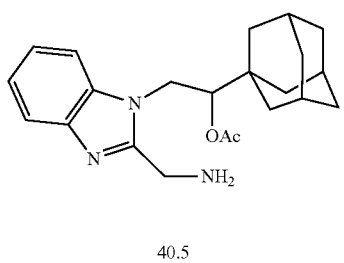

40.5

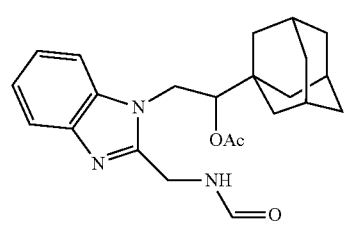

40.6

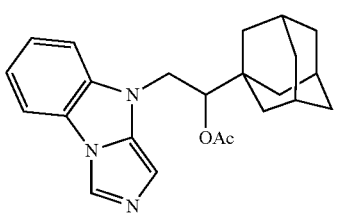

40.7

-continued

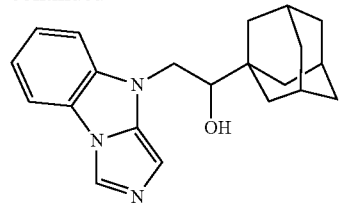

40

Step 1: Synthesis of Compound 40.1

To a solution of benzene-1, 2-diamine (2.8 g, 25.8 mmol) and 2-((tert-butoxycarbonyl)amino) acetic acid (5.4 g, 31.0 mmol) in THF (100 mL) was added dicyclohexyl carbodiimide (DCC) (8.0 g, 38.8 mmol). The resulted mixture was stirred at room temperature for overnight, then filtered, the filter cake was washed with dichloromethane (100 mL×2). The filtrate was concentrated, and the residue was purified by column chromatography on silica gel (dichloromethane:methanol=10:1) to afford an intermediate. A solution of the intermediate in a mixed solvent of methanol (30 mL) and acetic acid (7 mL) was stirred at reflux for overnight, then the mixture was cooled down to room temperature, concentrated, the residue was added saturated sodium bicarbonate solution (30 mL), extracted with dichloromethane (15 mL×3). The combined organic phase was washed with brine, dried over sodium sulfate, filtered and concentrated. The residue was purified by column chromatography on silica gel (petroleum ether:ethyl acetate=4:1) to afford compound 40.1 (2.6 g, yield: 42%) as a colorless oil.

Step 2: Synthesis of Compound 40.2

To a solution of compound 40.1 (1.0 g, 4.05 mmol) in DMF (20 mL) was successively added cesium carbonate (2.9 g, 8.9 mmol) and 1-(adamantan-1-yl)-2-bromoethanone (1.1 g, 4.45 mmol). The resulted mixture was stirred at 60° C. for 4 h, then added water (40 mL), extracted with dichloromethane (15 mL×3). The combined organic phase was washed with brine, dried over sodium sulfate, filtered and concentrated. The residue was purified by column chromatography on silica gel (dichloromethane:methanol=20:1) to afford compound 40.2 (1.3 g, yield: 76%) as a white solid.

Step 3: Synthesis of Compound 40.3

To an ice-cooling solution of compound 40.2 (930 mg, 2.2 mmol) in methanol (15 mL) was added NaBH$_4$ (39 mg, 1.02 mmol). The resulted mixture was stirred at room temperature for 2 h, then added water (5 mL), the mixture was stirred at room temperature for 2 h, then concentrated. The residue was extracted with dichloromethane (20 mL). The organic phase was washed with brine, dried over sodium sulfate, filtered and concentrated. The residue was purified by column chromatography on silica gel (dichloromethane:methanol=10:1) to afford compound 40.3 (694 mg, yield: 74%) as a white solid.

Step 4: Synthesis of Compound 40.4

To a solution of compound 40.3 (514 mg, 1.2 mmol) in pyridine (10 mL) was added acetic anhydride (185 mg, 1.8 mmol) dropwise, then added catalytic amount of DMAP. The resulted mixture was stirred at reflux for overnight, and then the mixture was concentrated. The residue was dissolved in dichloromethane (20 mL). The organic phase was washed with brine, dried over sodium sulfate, filtered and concentrated to afford compound 40.4 (540 mg, yield: 96%) as a white solid.

Step 5: Synthesis of Compound 40.5

To a solution of compound 40.4 (540 mg, 1.1 mmol) in dichloromethane (5 mL) was added TFA (5 mL), the resulted mixture was stirred at room temperature for 3 h, and then concentrated, the residue was dissolved in dichloromethane (15 mL) and washed with brine, dried over sodium sulfate, filtered and concentrated to afford compound 40.5 (320 mg, yield: 75%) as a light yellow solid.

m/z: [M+H]$^+$ 368

Step 6: Synthesis of Compound 40.6

A solution of compound 40.5 (320 mg, 0.87 mmol) in acetic acid (5 mL) was stirred at 90~100° C. for 3 h, then cooled down to room temperature, the solvent was evaporated, the residue was diluted with dichloromethane (10 mL), and the organic phase was washed with water and brine, dried over sodium sulfate, filtered and concentrated, the residue was purified by column chromatography on silica gel (dichloromethane:methanol=10:1) to afford 40.6 (276 mg, yield: 80%) as a white solid.

m/z: [M+H]$^+$ 396

Step 7: Synthesis of Compound 40.7

To a solution of compound 40.6 (253 mg, 0.6 mmol) in toluene (10 mL) was added phosphorus oxychloride (POCl$_3$) (286 mg, 1.8 mmol) at room temperature. The resulted mixture was stirred at reflux for 3 h, then the solvent was evaporated, the residue was diluted with dichloromethane (10 mL), the organic phase was washed with saturated sodium bicarbonate solution till pH=7, then washed with water and brine, dried over sodium sulfate, filtered and concentrated, the residue was purified by column chromatography on silica gel (dichloromethane:methanol=10:1) to afford compound 40.7 (150 mg, yield: 67%) as a white solid.

m/z: [M+H]$^+$ 378

Step 8: Synthesis of Compound 40

To a solution of compound 40.7 (150 mg, 0.4 mmol) in a mixed solvent of methanol (10 mL) and water (1 mL) was added potassium carbonate (165 mg, 1.2 mmol), the resulted mixture was stirred at room temperature for 3 h, and then the solvent was concentrated, the residue was diluted with dichloromethane (10 mL), the organic phase was washed with water and brine, dried over sodium sulfate, filtered and concentrated, the residue was purified by column chromatography on silica gel (dichloromethane:methanol=10:1) to afford compound 40 (80 mg, yield: 60%) as a light yellow solid.

$^1$H NMR (400 MHz, CDCl$_3$-d): δ 7.74 (s, 1H), 7.60-7.62 (d, 1H), 7.33-7.37 (t, J=16.0 Hz, 1H), 7.25-7.28 (m, 1H), 7.12-7.16 (t, J=16.0 Hz, 1H), 6.50 (s, 1H), 4.12-4.17 (m, 1H), 3.94-4.03 (m, 1H), 3.60-3.63 (m, 2H), 2.10 (m, 3H), 1.73-1.83 (m, 12H).

m/z: [M+H]$^+$ 336

Example 15: Synthesis of Compound 41

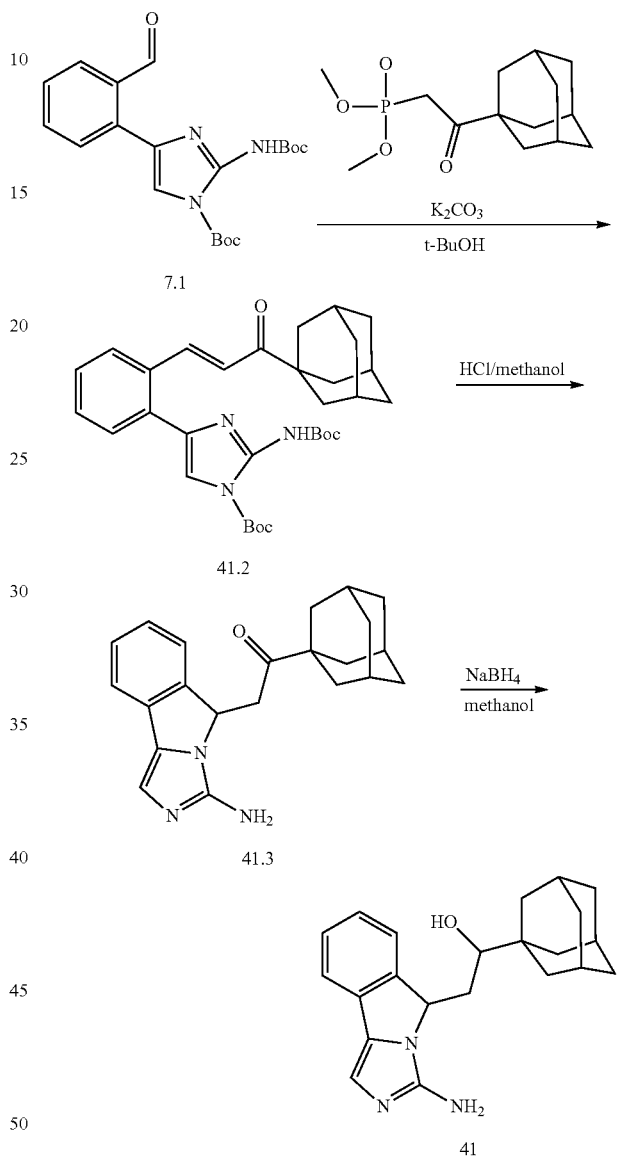

Step 1: Synthesis of Compound 41.2

To a solution of compound 40.7 (150 mg, 0.4 mmol) and dimethyl (2-(-adamantan-1-yl)-2-oxoethyl)phosphonate (142 mg, 0.50 mmol) in tert-butyl alcohol (t-BuOH) (15 mL) was added potassium carbonate (170 mg, 1.23 mmol). The resulted mixture was stirred at 80° C. for 2 h, and then concentrated, the residue was added cold-water (10 mL), the mixture was extracted with ethyl acetate (25 mL×2). The combined organic phase was washed with brine (25 mL), dried over sodium sulfate, filtered and concentrated. The residue was purified by flash column chromatography on silica gel (petroleum ether:ethyl acetate=7:1) to afford compound 41.2 (85 mg, yield: 38%) as a light yellow solid.

Step 2: Synthesis of Compound 41.3

To a solution of compound 41.2 (45 mg, 0.082 mmol) in methanol (1.0 mL) was added a solution of hydrogen chloride in methanol (0.5 mL, 4.0 M). The resulted mixture was stirred at 60° C. for overnight, then the solvent was evaporated to afford the crude compound, the crude compound was diluted with cold-water (10 mL), adjusted pH to 8-9 with saturated sodium bicarbonate solution, the mixture was extracted with dichloromethane (25 mL×2). The combined organic phase was washed with brine (25 mL), dried over sodium sulfate, filtered and concentrated. The residue was purified by flash column chromatography on silica gel (petroleum ether:ethyl acetate=4:1) to afford compound 41.3 (15 mg, yield: 52%) as a light yellow solid.

m/z: [M+H]$^+$ 348

Step 3: Synthesis of Compound 41

To an ice-cooling solution of compound 41.3 (15 mg, 0.043 mmol) in methanol (2.5 mL) was added NaBH$_4$ (3.3 mg, 0.086 mmol). The resulted mixture was stirred at room temperature for 30 min, then poured into ice-water, filtered, the filter cake was washed with ice water, dried under vacuum to afford compound 41 (15 mg, yield: 100%) as a light yellow solid.

$^1$H NMR (400 MHz, MeOD-d$_4$): δ 7.67-7.69 (m, 1H), 7.57-7.59 (m, 1H), 7.45-7.49 (m, 2H), 7.07 (s, 1H), 5.46-5.48 (m, 1H), 3.43 (dd, J=2.0, 11.6 Hz, 1H), 2.31-2.34 (m, 1H), 1.98-2.01 (m, 1H), 1.75-1.78 (m, 3H), 1.28-1.36 (m, 12H).

m/z: [M+H]$^+$ 350

Example 16: Synthesis of Compounds 63 and 80

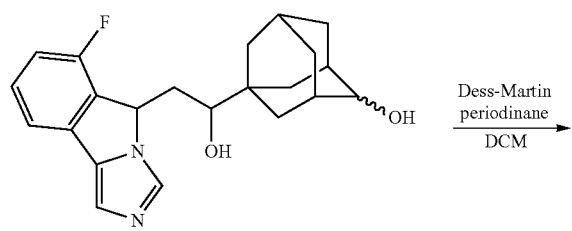

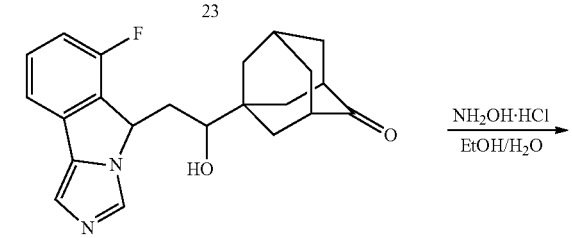

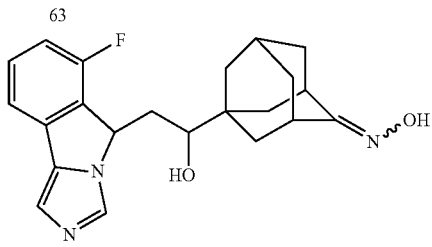

Step 1: Synthesis of Compound 63

To a solution of compound 23 (2.0 g, 13.7 mmol) in dichloromethane (20 mL) was added Dess-Martin periodinane (2.76 g, 6.51 mmol). The resulted mixture was stirred at reflux for 0.5 h, then filtered. The filtrate was added water (20 mL), and extracted with dichloromethane (20 mL×2). The combined organic phase was washed with brine, dried over sodium sulfate, filtered and concentrated, the residue was purified by flash column chromatography on silica gel (0~10% solution of methanol in dichloromethane) to afford compound 63 (0.6 g, yield: 30%) as a light yellow solid.

$^1$H NMR (400 MHz, MeOD-d$_4$): δ 9.12, 9.15, 9.19 (three s, 1H), 7.81-7.83 (m, 1H), 7.57-7.71 (m, 2H), 7.27-7.33 (m, 1H), 5.90-6.10 (two m, 1H), 3.40, 3.53 (two d, J=2.0, 10.8 Hz, 1H), 2.43-2.66 (m, 2H), 1.66-2.19 (m, 9H), 1.28-1.56 (m, 4H).

m/z: [M+H]$^+$ 367

Step 2: Synthesis of Compound 80

To a solution of compound 63 (40 mg, 0.11 mmol) in a mixed solvent of ethanol (0.5 mL) and H$_2$O (0.5 mL) was added hydroxylamine hydrochloride (38 mg, 0.50 mmol) and sodium hydroxide (20 mg 0.5 mmol) at room temperature. The resulted mixture was stirred at room temperature for 12 h. The reaction was quenched by addition of saturated ammonium chloride solution (5 mL), and then extracted with ethyl acetate (5 mL), the organic phase was washed with brine (5 mL), dried over sodium sulfate and concentrated to dryness. The residue was purified by pre-HPLC to afford compound 80 (TFA salt, 14 mg, yield: 27%) as a white solid.

$^1$H NMR (400 MHz, MeOD-d$_4$): δ 9.16, 9.21 (two s, 1H), 7.80 (d, J=1.2 Hz, 1H), 7.58-7.73 (m, 2H), 7.28-7.35 (m, 1H), 5.93-6.12 (two m, 1H), 3.43-3.64 (m, 2H), 2.47-2.65 (m, 2H), 1.49-2.14 (m, 12H).

m/z: [M+H]$^+$ 382

Example 17: Synthesis of Compounds 76 and 77

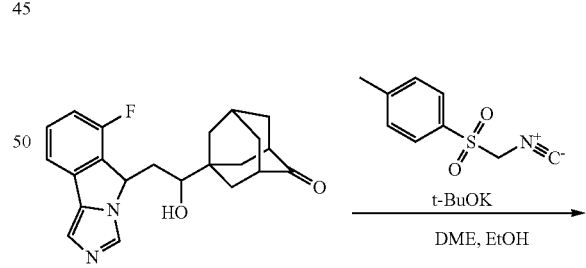

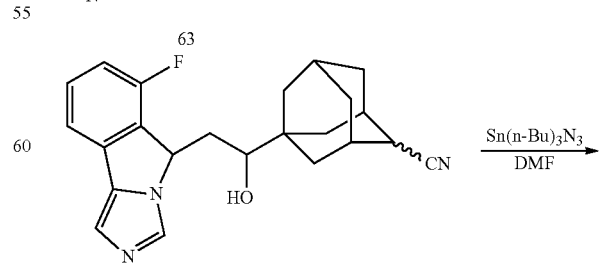

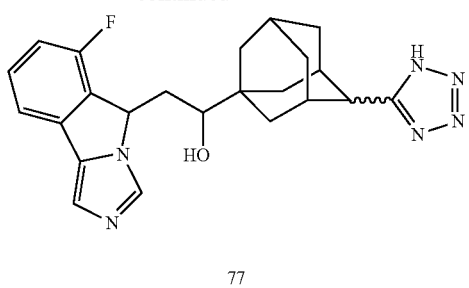

77

Step 1: Synthesis of Compound 76

To an ice-cooling mixture of compound 63 (390 mg, 1.06 mmol) in a mixed solvent of DME (4 mL) and ethanol (0.4 mL) was added tosylmethyl isocyanide (311 mg, 1.60 mmol), then t-BuOK (287 mg, 2.55 mmol) was added by small portions. The resulted mixture was stirred at room temperature for 16 h. Then the mixture was quenched by addition of water (10 mL), extracted with ethyl acetate (10 mL×3). The combined organic phase was washed with brine, dried over sodium sulfate, filtered and concentrated. The residue was purified by column chromatography on silica gel (ethyl acetate: petroleum ether=9:1) to afford compound 76 (160 mg, yield: 40%) as an off-white solid.

m/z: [M+H]$^+$ 378

Step 2: Synthesis of Compound 77

To a solution of compound 76 (40 mg, 0.41 mmol) in DMF (1.0 mL) was added tributyltin azide (Sn(n-Bu)$_3$N$_3$) (666 mg, 2.0 mmol) at room temperature. Then the resulted mixture was stirred at 130° C. for 24 h. The reaction was quenched by addition of saturated ammonium chloride solution (10 mL), extracted with ethyl acetate (10 mL), washed with brine (10 mL), dried over sodium sulfate and concentrated to dryness. The residue was purified by pre-HPLC to afford compound 77 (TFA salt, 1.1 mg, yield: 2%) as a yellow solid.

m/z: [M+H]$^+$ 421

Example 18: Synthesis of Compound 43

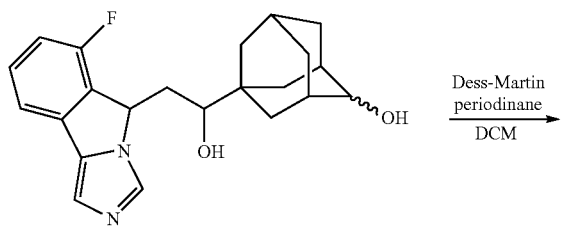

23

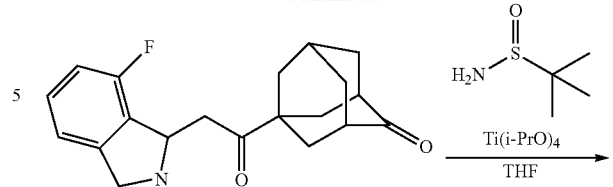

43.2

43.3

42

43

Step 1: Synthesis of 43.2

To a solution of compound 23 (5.0 g, 13.7 mmol) in dichloromethane (50 mL) was added Dess-Martin periodinane (17.6 g, 41.0 mmol). The resulted mixture was stirred at room temperature for 5 h, then filtered, the filter cake was washed with dichloromethane, the filtrate was concentrated, the residue was purified by column chromatography on silica gel (petroleum ether:ethyl acetate=9:1) to afford compound 43.2 (4.4 g, yield: 89%) as a light yellow powder.

m/z: [M+H]$^+$ 365

Step 2: Synthesis of Compound 43.3

To a solution of compound 43.2 (4.0 g, 11.0 mmol) and (S)-tert-butanesulfinamide (2.0 g, 16.5 mmol) in THF (40 mL) was added titanium tetraisopropanolate (6.2 g, 22.0 mmol) under nitrogen. The resulted mixture was stirred at reflux for overnight, and then cooled down to room temperature, the reaction was quenched by addition of water (20 mL), then extracted with ethyl acetate (50 mL×3). The combined organic phase was washed with brine, dried over sodium sulfate, filtered and concentrated, the residue was purified by column chromatography on silica gel (petroleum ether:ethyl acetate=9:1) to afford compound 43.3 (4.5 g, yield: 88%) as a light yellow solid.

m/z: [M+H]$^+$ 468

Step 3: Synthesis of 42

To an ice-cooling solution of compound 43.2 (4.5 g, 9.62 mmol) in methanol (45 mL) was added NaBH$_4$ (1.8 g, 48.1 mmol). The resulted mixture was stirred at room temperature for 2 h, and then the reaction was quenched by addition of water (50 mL), and extracted with ethyl acetate (50 mL×3). The combined organic phase was washed with brine, dried over sodium sulfate, filtered and concentrated to afford compound 42 (3.5 g, yield: 77%) as a yellow solid.

m/z: [M+H]$^+$ 472

Step 4: Synthesis of 43

To a solution of compound 42 (3.5 g, 7.42 mmol) in 1,4-dioxane (20 mL) was added a solution of hydrogen chloride in methanol (10 mL, 4.0 M). The resulted mixture was stirred at room temperature for 1 h, and then the mixture was concentrated to afford compound 43 (HCl salt, 3.5 g, yield: 100%) as a yellow solid.

Compound 43 (a mixture of stereoisomers) (1.5 g) was separated by pre-HPLC (Separation method: G) to afford 43A (750 mg, the peak time: 13.0~16.5 min) and 43B (520 mg, the peak time: 17.2~19.2 min) as white solids.

43: $^1$H NMR (400 MHz, MeOD-d$_4$): δ 9.24-9.26 (m, 1H), 7.85 (s, 1H), 7.61-7.72 (m, 2H), 7.28-7.33 (m, 1H), 5.96-5.98 (m, 1H), 3.48-3.51 (m, 1H), 3.41 (s, 1H), 1.50-2.65 (m, 15H).

m/z: [M+H]$^+$ 368

Example 19: Synthesis of Compound 44

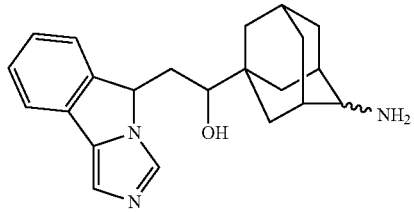

44

Compound 44 was prepared according to example 18, by using compound 10 as a starting material to afford compound 44, as a HCl salt.

$^1$H NMR (400 MHz, DMSO-d$_6$): δ 9.27 (s, 1H), 7.87-7.95 (m, 4H), 7.74 (d, J=7.6 Hz, 1H), 7.50-7.58 (m, 2H), 5.74 (t, J=6.8 Hz, 1H), 5.21 (br s, 1H), 3.25 (s, 1H), 0.84-2.18 (m, 16H).

m/z: [M+H]$^+$ 350

Example 20: Synthesis and Separation of Compound 78

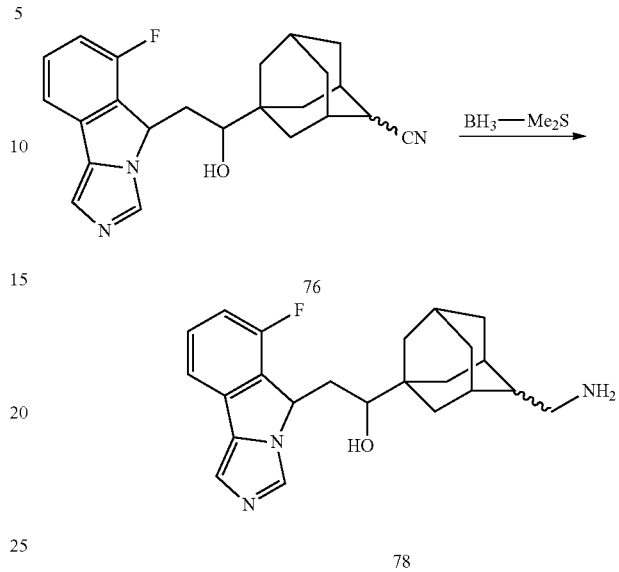

A solution of compound 76 (25 mg, 0.66 mmol) in borane-methyl sulfide complex (3 mL) was stirred at 40° C. under a nitrogen atmosphere for overnight. The reaction mixture was poured into ice water (10 mL), and extracted with ethyl acetate (5 mL×3). The combined organic phase was washed with brine (5 mL), dried over sodium sulfate, filtered and concentrated to afford compound 78 (11.0 mg, yield: 44%) as a yellow solid.

m/z: [M+H]$^+$ 382

Example 21: Synthesis and Chiral Resolution of Compound 45

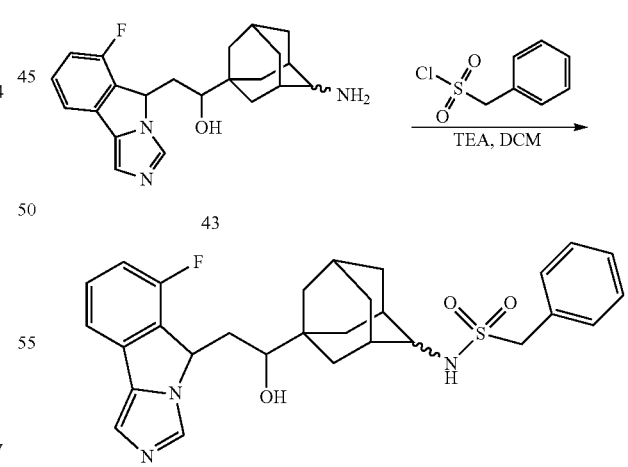

To a solution of compound 43 (1.2 g, 2.72 mmol) and TEA (1.4 g, 13.6 mmol) in dichloromethane (200 mL) was added phenylmethanesulfonyl chloride (623 mg, 3.27 mmol). The resulted mixture was stirred at room temperature for 3 h, then concentrated, the residue was purified by column chromatography on silica gel (5~10% solution of methanol in dichloromethane) to afford compound 45 (1.2 g, yield: 77%) as a white solid.

Compound 45 (a mixture of stereoisomers) was separated by pre-HPLC (Separation method: C) to afford 45A (400 mg, the peak time: 13.0~15.0 min) and 45B (330 mg, the peak time: 15.5~17.5 min).

Compound 45A (900 mg) was separated by SFC (Chiral resolution method: D) to afford mixture of diasteromers 45A-1+45A-2 (70 mg) and 45A-3+45A-4 (75 mg).

The mixture of diasteromers 45A-1+45A-2 (50 mg) was separated by SFC (Chiral resolution method: E) to afford single diasteromer 45A-1 (10 mg).

The mixture of diasteromers 45A-3+45A-4 (50 mg) was separated by SFC (Chiral resolution method: E) to afford single diasteromer 45A-4 (16 mg).

| No. | Compound No. of a single diasteromer | Retention Time (Chiral analysis method E) |
|---|---|---|
| 45A | 45A-1 | 6.98 min |
|  | 45A-4 | 8.95 min | m/z: [M+H]$^+$ 522

45A-1: $^1$H NMR (400 MHz, MeOD-d$_4$): δ 8.07 (s, 1H), 7.36-7.47 (m, 7H), 7.21 (s, 1H), 7.03-7.08 (m, 1H), 5.58 (t, J=4.8 Hz, 1H), 4.34 (s, 2H), 3.21 (s, 1H), 3.11-3.13 (m, 1H), 2.45-2.49 (m, 1H), 1.30-1.97 (m, 14H).

45A-4: $^1$H NMR (400 MHz, MeOD-d$_4$): δ 8.58 (s, 1H), 7.35-7.57 (m, 8H), 7.15-720 (m, 1H), 5.58 (t, J=4.8 Hz, 1H), 4.34 (s, 2H), 3.22-3.26 (m, 2H), 2.50-2.55 (m, 1H), 1.30-1.97 (m, 14H).

Example 22: Synthesis of Compounds 46-48, 64-71

Compounds 46-48, 64-71 were prepared according to example 21 compound 45, by using compound 43 and corresponding sulfonyl chloride as starting materials.

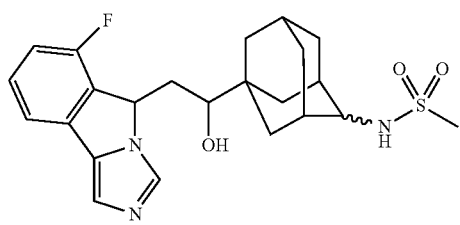
46

Compound 46 (a mixture of stereoisomers) was separated by pre-HPLC (Separation method: H) to afford 46A (the peak time: 13.0-16.5 min) and 46B (the peak time: 17.2-19.0 min).

46: $^1$H NMR (400 MHz, MeOD-d$_4$): δ 7.97, 8.03 (two s, 1H), 7.42-7.47 (m, 2H), 7.18 (s, 1H), 7.02-7.68 (m, 1H), 5.59 (t, J=4.8 Hz, 1H), 3.46 (br s, 1H), 3.15-3.21 (m, 1H), 2.95 (s, 3H), 2.52 (dd, J=3.2, 13.2 Hz, 1H), 1.25-2.05 (m, 14H).

m/z: [M+H]$^+$ 446

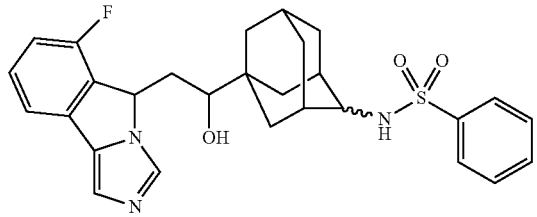
47

Compound 47 (a mixture of stereoisomers) was separated by pre-HPLC (Separation method: D) to afford 47A (the peak time: 9.8-12.0 min) and 47B (the peak time: 12.8-15.8 min).

m/z: [M+H]$^+$ 508

47A: $^1$H NMR (400 MHz, MeOD-d$_4$): δ 9.08, 9.17 (two s, 1H), 7.84-7.92 (m, 2H), 7.74-7.83 (m, 1H), 7.49-7.70 (m, 5H), 7.23-7.32 (m, 1H), 5.85-6.07 (m, 1H), 3.34-3.37 (m, 0.5H), 3.15-3.24 (m, 1H), 2.85-2.91 (m, 0.5H), 2.43-2.58 (m, 1H), 2.15-2.33 (m, 1H), 1.83-2.03 (m, 4H), 1.73-1.82 (m, 2H), 1.34-1.61 (m, 7H).

47B: $^1$H NMR (400 MHz, MeOD-d$_4$): δ 9.12, 9.18 (two s, 1H), 7.84-7.90 (m, 2H), 7.78-7.83 (m, 1H), 7.64-7.72 (m, 1H), 7.51-7.64 (m, 4H), 7.27-7.34 (m, 1H), 5.89-6.11 (m, 1H), 3.37-3.42 (m, 0.5H), 3.12-3.19 (m, 1H), 2.88-2.94 (m, 0.5H), 2.48-2.64 (m, 1H), 2.16-2.36 (m, 1H), 1.42-2.03 (m, 13H).

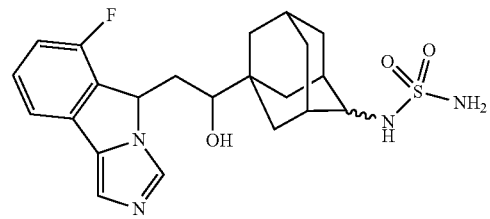
48

Compound 48 (a mixture of stereoisomers) was separated by pre-HPLC (Separation method: E) to afford 48A (the peak time: 10.0-11.0 min) and 48B (the peak time: 13.0-14.0 min).

m/z: [M+H]$^+$ 447

48A: $^1$H NMR (400 MHz, MeOD-d$_4$): δ 9.15, 9.19 (two s, 1H), 7.82 (s, 1H), 7.58-7.72 (m, 2H), 7.28-7.33 (m, 1H), 7.92-7.95 (m, 1H), 3.42-3.47 (m, 2H), 2.61-2.67 (m, 1H), 1.31-2.21 (m, 14H).

48B: $^1$H NMR (400 MHz, MeOD-d$_4$): δ 9.15, 9.19 (two s, 1H), 7.72 (s, 1H), 7.55-7.72 (m, 2H), 7.18-7.36 (m, 1H), 7.93-7.94 (m, 1H), 3.39-3.48 (m, 2H), 2.62-2.66 (m, 1H), 1.32-2.14 (m, 14H).

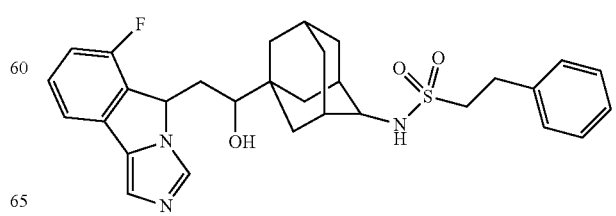
64 m/z: [M+H]⁺ 536

¹H NMR (400 MHz, MeOD-d₄): δ 9.14, 9.20 (two s, 1H), 7.83 (two s, 1H), 7.58-7.73 (m, 2H), 7.21-7.33 (m, 6H), 5.91-6.12 (two m, 1H), 3.41-3.49 (m, 2H), 1.31-3.31 (m, 19H).

65

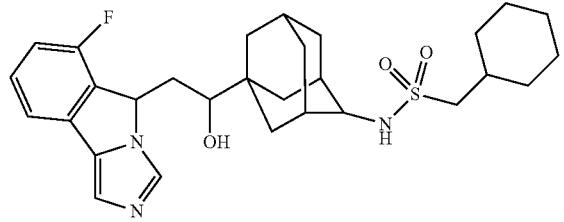

m/z: [M+H]⁺ 528

¹H NMR (400 MHz, MeOD-d₄): δ 9.15, 9.21 (two s, 1H), 7.83 (s, 1H), 7.60-7.70 (m, 2H), 7.28-7.33 (m, 1H), 5.93-6.13 (two m, 1H), 3.42-3.46 (m, 2H), 2.92-2.95 (m, 2H), 2.60-2.66 (m, 1H), 1.07-2.07 (m, 25H).

66

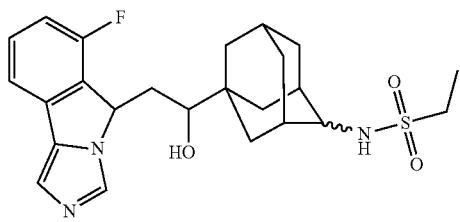

m/z: [M+H]⁺ 460

67

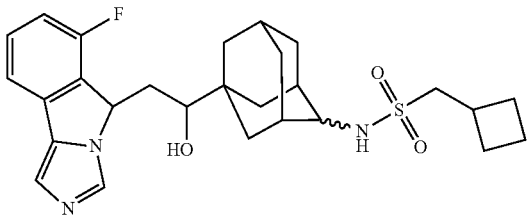

Compound 67 (a mixture of stereoisomers) was separated by pre-HPLC (Separation method: F) to afford 67A (the peak time: 11.0-12.9 min) and 67B (the peak time: 13.0-15.6 min).

m/z: [M+H]⁺ 500

67A: ¹H NMR (400 MHz, MeOD-d₄): δ 9.12, 9.18 (two s, 1H), 7.80 (s, 1H), 7.55-7.72 (m, 2H), 7.24-7.33 (m, 1H), 5.87-6.13 (two m, 1H), 3.37-3.46 (m, 2H), 3.07-3.17 (m, 2H), 2.73-2.87 (m, 1H), 2.48-2.66 (m, 1H), 2.14-2.23 (m, 2H), 1.80-2.09 (m, 10H), 1.43-1.72 (m, 8H).

67B: ¹H NMR (400 MHz, MeOD-d₄): δ 9.11, 9.17 (two s, 1H), 7.80 (s, 1H), 7.56-7.71 (m, 2H), 7.26-7.33 (m, 1H), 5.89-5.95 (two m, 1H), 3.38-3.45 (m, 2H), 3.09-3.16 (m, 2H), 2.73-2.84 (m, 1H), 2.58-2.67 (m, 1H), 2.14-2.22 (m, 2H), 1.73-2.08 (m, 13H), 1.34-1.65 (m, 5H).

68

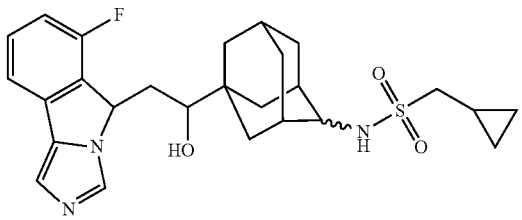

m/z: [M+H]⁺ 486

69

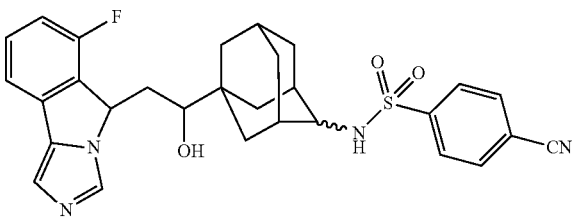

Compound 69 (a mixture of stereoisomers) was separated by pre-HPLC (Separation method: E) to afford 69A (the peak time: 5.5-7.0 min) and 69B (the peak time: 7.5-8.5 min).

m/z: [M+H]⁺ 533

69A: ¹H NMR (400 MHz, MeOD-d₄): δ 9.11, 9.17 (two s, 1H), 7.93-8.06 (m, 4H), 7.69 (s, 1H), 7.58-7.65 (m, 2H), 7.27-7.33 (m, 1H), 5.91-6.07 (two m, 1H), 3.19-3.39 (overlapping with solvent, 2H), 2.50-2.61 (m, 1H), 1.25-2.14 (m, 14H).

69B: ¹H NMR (400 MHz, MeOD-d₄): δ 9.13, 9.19 (two s, 1H), 7.93-8.05 (m, 4H), 7.71 (s, 1H), 7.59-7.67 (m, 2H), 7.30-7.34 (m, 1H), 5.92-6.11 (two m, 1H), 3.24-3.43 (overlapping with solvent, 2H), 2.50-2.63 (m, 1H), 1.30-2.06 (m, 14H).

70

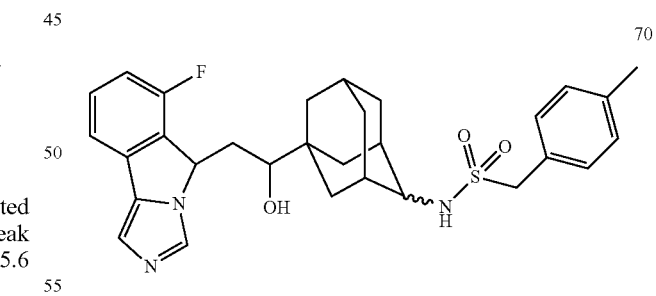

Compound 70 (a mixture of stereoisomers) was separated by pre-HPLC (Separation method: E) to afford 70A (the peak time: 6.0-7.5 min) and 70B (the peak time: 8.0-9.5 min).

m/z: [M+H]⁺ 536

70A: ¹H NMR (400 MHz, MeOD-d₄): δ 9.13, 9.19 (two s, 1H), 7.83 (d, J=1.2 Hz, 1H), 7.61-7.70 (m, 2H), 7.31-7.34 (m, 3H), 7.18-7.20 (m, 2H), 5.91-5.94 (m, 1H), 4.30 (s, 2H), 3.37-3.42 (m, 1H), 3.15-3.19 (m, 1H), 2.57-2.61 (m, 1H), 2.34 (s, 3H), 1.32-2.19 (m, 14H).

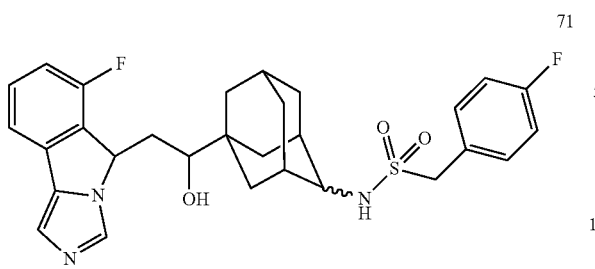

71 m/z: [M+H]+ 540

Example 23: Synthesis of Compound 75

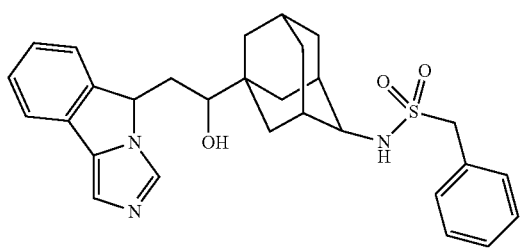

75

Compounds 75 were prepared according to example 21 compound 45, by using compound 44 and corresponding sulfonyl chloride as starting materials.

Compound 75 (a mixture of stereoisomers) was separated by pre-HPLC (Separation method: E) to afford 75A (the peak time: 8.2-10.0 min) and 75B (the peak time: 10.4-12.5 min).

m/z: [M+H]+ 504

Example 24: Synthesis of Compound 81A-85A

Compounds 81A~85A were prepared according to example 21 compound 45, by using compound 43A and corresponding sulfonyl chloride as starting materials.

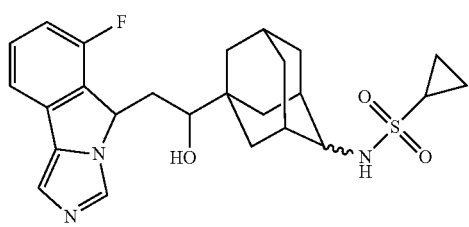

81A m/z: [M+H]+ 472

$^1$H NMR (400 MHz, MeOD-d$_4$): δ 9.14, 9.20 (two s, 1H), 7.82 (d, J=0.8 Hz, 1H), 7.59-7.72 (m, 2H), 7.29-7.38 (m, 1H), 5.93-6.12 (two m, 1H), 3.34-3.54 (m, 2H), 2.47-2.72 (m, 2H), 1.90-2.10 (m, 6H), 1.43-1.73 (m, 8H), 0.93-1.09 (m, 4H).

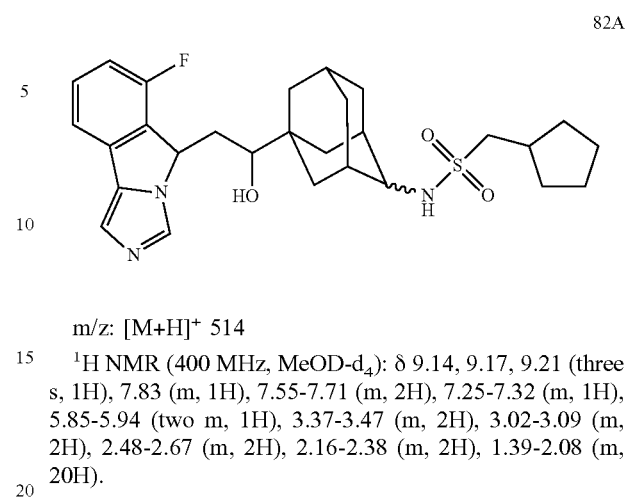

82A m/z: [M+H]+ 514

$^1$H NMR (400 MHz, MeOD-d$_4$): δ 9.14, 9.17, 9.21 (three s, 1H), 7.83 (m, 1H), 7.55-7.71 (m, 2H), 7.25-7.32 (m, 1H), 5.85-5.94 (two m, 1H), 3.37-3.47 (m, 2H), 3.02-3.09 (m, 2H), 2.48-2.67 (m, 2H), 2.16-2.38 (m, 2H), 1.39-2.08 (m, 20H).

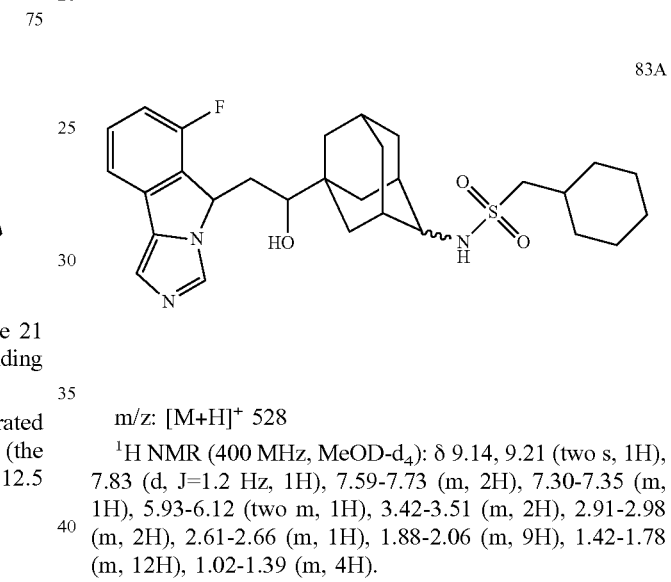

83A m/z: [M+H]+ 528

$^1$H NMR (400 MHz, MeOD-d$_4$): δ 9.14, 9.21 (two s, 1H), 7.83 (d, J=1.2 Hz, 1H), 7.59-7.73 (m, 2H), 7.30-7.35 (m, 1H), 5.93-6.12 (two m, 1H), 3.42-3.51 (m, 2H), 2.91-2.98 (m, 2H), 2.61-2.66 (m, 1H), 1.88-2.06 (m, 9H), 1.42-1.78 (m, 12H), 1.02-1.39 (m, 4H).

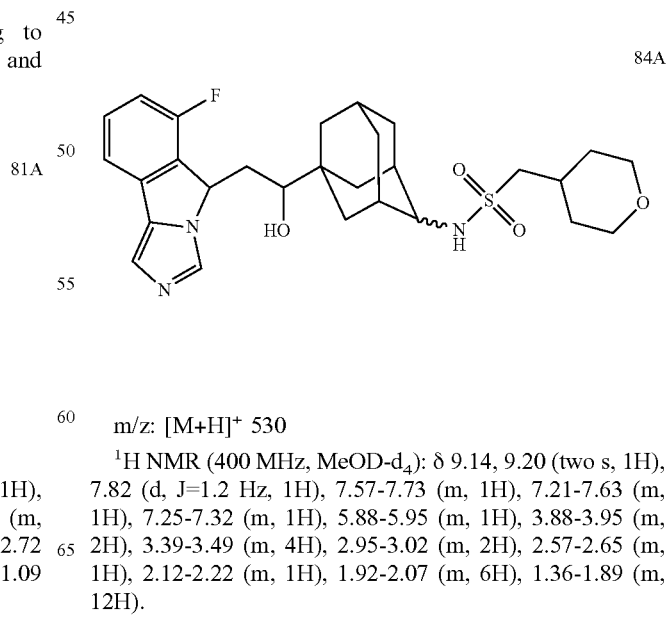

84A m/z: [M+H]+ 530

$^1$H NMR (400 MHz, MeOD-d$_4$): δ 9.14, 9.20 (two s, 1H), 7.82 (d, J=1.2 Hz, 1H), 7.57-7.73 (m, 1H), 7.21-7.63 (m, 1H), 7.25-7.32 (m, 1H), 5.88-5.95 (m, 1H), 3.88-3.95 (m, 2H), 3.39-3.49 (m, 4H), 2.95-3.02 (m, 2H), 2.57-2.65 (m, 1H), 2.12-2.22 (m, 1H), 1.92-2.07 (m, 6H), 1.36-1.89 (m, 12H).

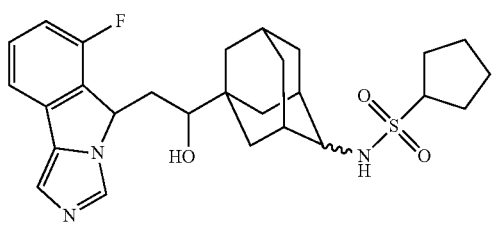

85A m/z: [M+H]+ 500

¹H NMR (400 MHz, MeOD-d₄): δ 9.20 (s, 1H), 7.83 (s, 1H), 7.59-7.70 (m, 2H), 7.29-7.33 (m, 1H), 5.93-5.95 (m, 1H), 3.42-3.57 (m, 2H), 2.61-2.66 (m, 1H), 1.98-2.23 (m, 7H), 0.90-1.83 (m, 16H).

Example 25: Synthesis of Compound 79

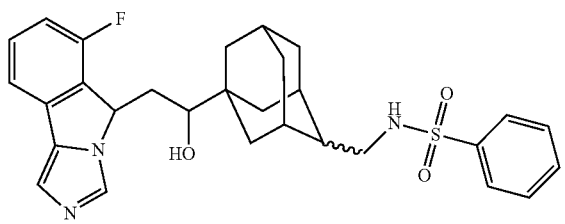

79

Compounds 79 were prepared according to example 21 compound 45, by using compound 78 and corresponding sulfonyl chloride as starting materials.

m/z: [M+H]+ 522

¹H NMR (400 MHz, MeOD-d₄): δ 9.08 (s, 1H), 7.87-7.52 (m, 8H), 7.34-7.28 (m, 1H), 6.09-6.03 (m, 1H), 2.91-2.82 (m, 2H), 2.54-2.44 (m, 1H), 2.29-2.15 (m, 2H), 2.07-1.41 (m, 14H).

Example 26: Synthesis of Compound 86

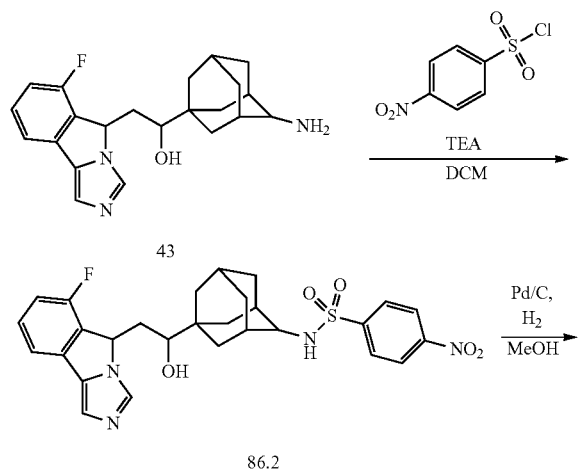

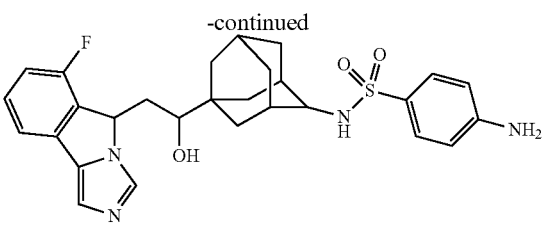

86

Step 1: Synthesis of Compound 86.2

To a solution of compound 43 (400 mg, 1.09 mmol) in dichloromethane (4 mL) was successively added TEA (330 mg, 3.27 mmol) and 4-nitrobenzene-1-sulfonyl chloride (361 mg, 1.63 mmol). The resulted mixture was stirred at room temperature for 1 h, then added water (10 mL) and extracted with ethyl acetate (20 mL×3). The combined organic phase was washed with brine, dried over sodium sulfate, filtered and concentrated, the residue was purified by column chromatography on silica gel (ethyl acetate:petroleum ether=9:1) to afford compound 86.2 (320 mg, yield: 53%) as a yellow solid.

m/z: [M+H]+ 553

Step 2: Synthesis of Compound 86

To a solution of compound 86.2 (320 mg, 0.58 mmol) in methanol (5 mL) was added Pd/C (30 mg, 10%). The resulted mixture was stirred under hydrogen (1 atm) at room temperature for 16 h. The mixture was filtered through a celite pad, and the filtrate was concentrated, the residue was triturated with 10% solution of ethyl acetate in petroleum ether, then filtered to afford compound 86 (240 mg, yield: 85%) as a yellow solid.

m/z: [M+H]+ 523

Example 27: Synthesis of Compound 87

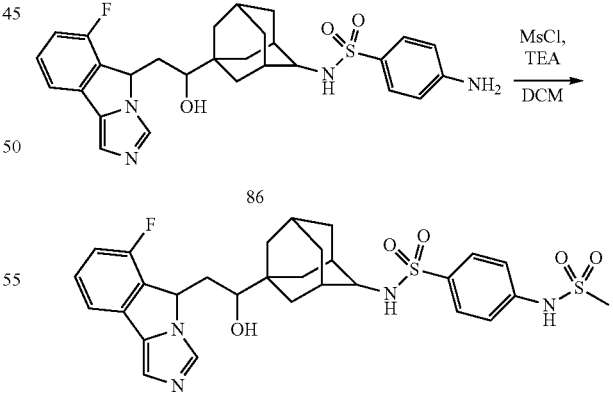

To a solution of compound 86 (50 mg, 0.10 mmol) in dichloromethane (4 mL) was successively added TEA (19 mg, 0.19 mmol) and MSCl (12 mg, 0.10 mmol). The resulted mixture was stirred at room temperature for 1 h, then added water (10 mL) and extracted with ethyl acetate (20 mL×3).

The combined organic phase was washed with brine, dried over sodium sulfate, filtered and concentrated, the residue was purified by pre-TLC (dichloromethane:methanol=10:1) to afford compound 87 (7 mg, yield: 12%) as a yellow solid.

m/z: [M+H]⁺ 601

$^1$H NMR (400 MHz, MeOD-d$_4$): δ 8.22-8.34 (m, 1H), 7.82-7.88 (m, 2H), 7.45-7.55 (m, 2H), 7.33-7.39 (m, 3H), 7.07-7.14 (m, 2H), 5.65-5.87 (m, 1H), 3.08 (s, 3H), 2.48-2.55 (m, 1H), 1.16-2.05 (m, 15H).

Example 28: Synthesis of Compound 88

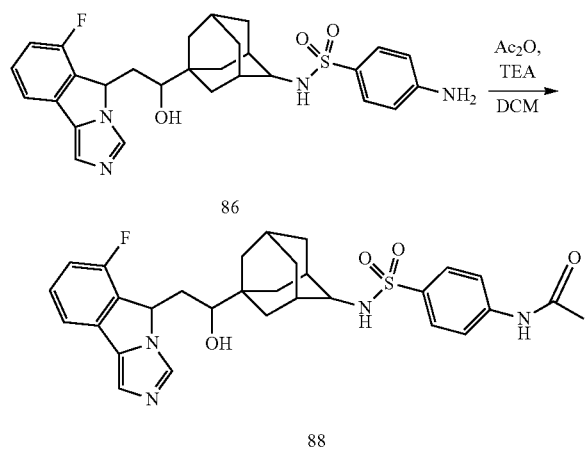

To a solution of compound 86 (50 mg, 0.10 mmol) in dichloromethane (4 mL) was successively added TEA (19 mg, 0.19 mmol) and acetic anhydride (10 mg, 0.10 mmol). The resulted mixture was stirred at room temperature for 16 h, then the mixture was added water (10 mL) and extracted with ethyl acetate (20 mL×3). The combined organic phase was washed with brine, dried over sodium sulfate, filtered and concentrated, the residue was purified by pre-TLC (dichloromethane:methanol=10:1) to afford compound 88 (6 mg, yield: 12%) as a yellow solid.

$^1$H NMR (400 MHz, MeOD-d$_4$): δ 7.95-8.02 (m, 1H), 7.74-7.86 (m, 4H), 7.41-7.47 (m, 2H), 7.17-7.22 (m, 1H), 7.00-7.07 (m, 1H), 5.55-5.69 (two m, 1H), 3.05-3.20 (m, 2H), 2.43-2.47 (m, 1H), 2.17 (s, 3H), 1.25-2.07 (m, 14H).

m/z: [M+H]⁺ 565

Example 29: Synthesis of Compound 89

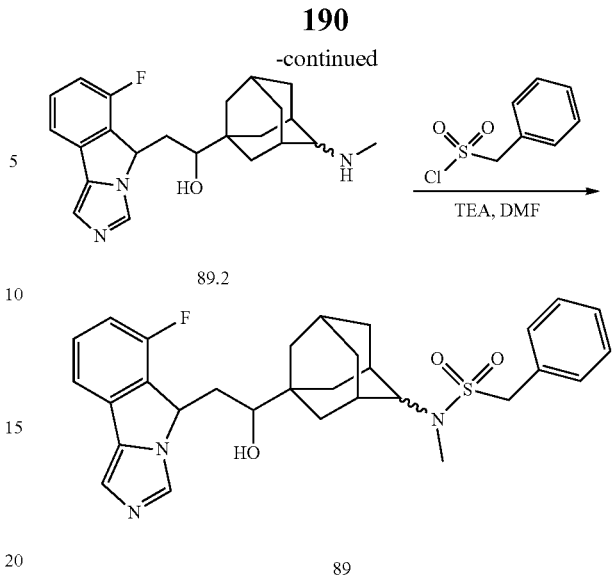

Step 1: Synthesis of Compound 89.2

To a solution of compound 63 (100 mg, 0.27 mmol) in methanol (2.0 mL) was successively added methylamine hydrochloride (36 mg, 0.54 mmol), catalytic amount of ZnCl$_2$ and sodium cyanoborohydride (NaBH$_3$CN) (34 mg, 0.54 mmol). The resulted mixture was stirred at room temperature for 12 h, and then the reaction was quenched by addition of saturated ammonium chloride solution (10 mL), extracted with ethyl acetate (10 mL). The organic phase was washed with brine (10 mL), dried over sodium sulfate and concentrated to dryness to afford compound 89.2 (80 mg, yield: 77%) as a light yellow oil.

Step 2: Synthesis of Compound 89

To a solution of compound 89.2 (80 mg, 0.21 mmol) in DMF (1.0 mL) was added TEA (42 mg, 0.4 mmol) and phenylmethanesulfonyl chloride (76 mg 0.4 mmol) at room temperature. The resulted mixture was stirred at room temperature for 12 h, and then the reaction was quenched by addition of saturated ammonium chloride solution (10 mL), extracted with ethyl acetate (10 mL), washed with brine (10 mL), dried over sodium sulfate and concentrated to dryness. The residue was purified by pre-HPLC to afford compound 89 (TFA salt, 4.5 mg, yield: 4%) as a white solid.

$^1$H NMR (400 MHz, MeOD-d$_4$): δ 9.10, 9.16 (two s, 1H), 7.77-7.82 (m, 1H), 7.55-7.71 (m, 2H), 7.26-7.45 (m, 6H), 5.86-6.10 (two m, 1H), 4.28-4.39 (m, 2H), 3.37 (dd, J=2.0, 10.9 Hz, 1H), 2.83-2.98 (m, 3H), 1.20-2.59 (m, 16H).

m/z: [M+H]⁺ 536

Example 30: Synthesis of Compound 90

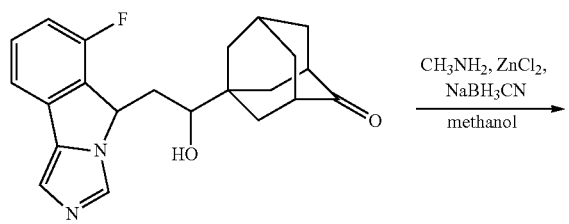

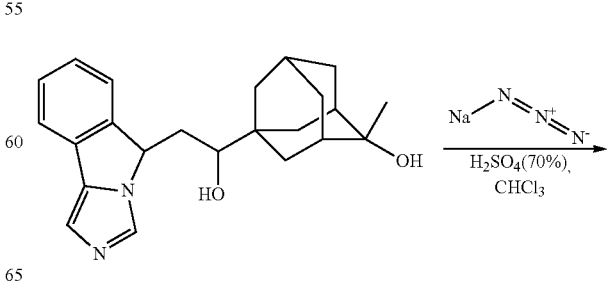

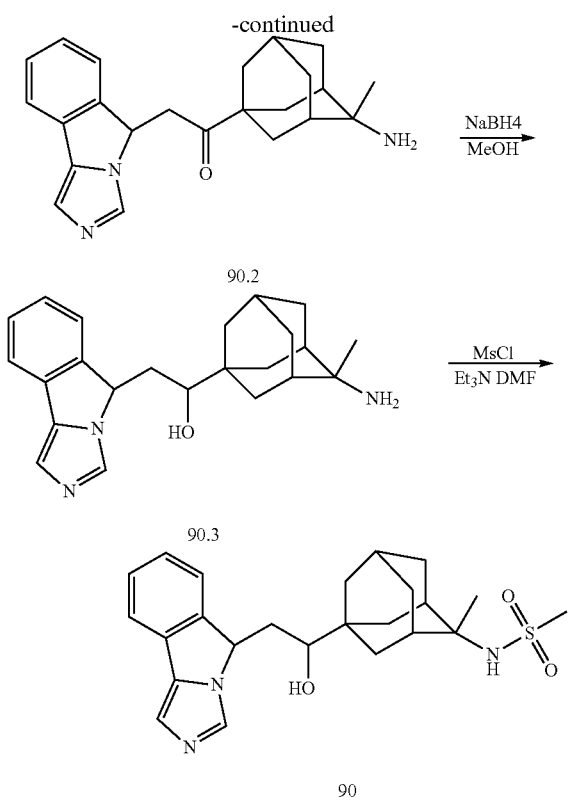

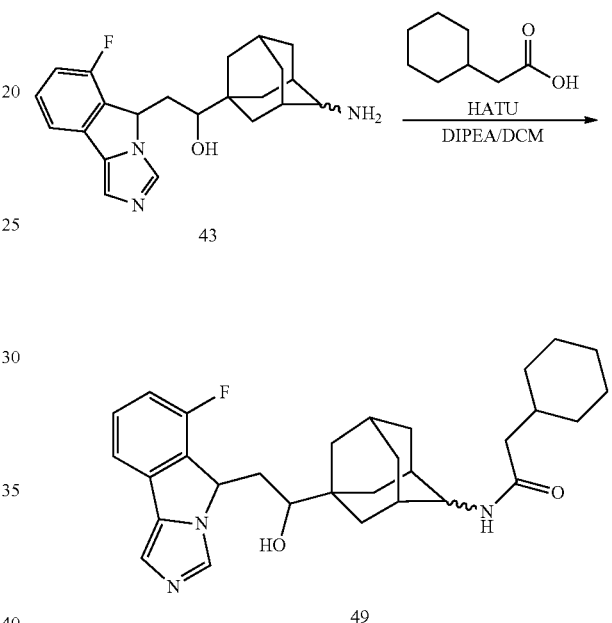

Step 1: Synthesis of Compound 90.2

Compound 11 (124 mg, 0.34 mmol) was added to a vigorously stirred mixture of $H_2SO_4$ (1.6 mL, 70% w/w) and chloroform (4 mL) at 0° C. Then sodium azide (132.17 mg, 2.03 mmol) was added in small portions. The resulted mixture was stirred at room temperature for 1 h. The pH was adjusted to around 8 by progressively adding sodium bicarbonate powder at 0° C. The mixture was extracted with dichloromethane (20 mL×3). The combined organic phase was washed with water, brine, dried over sodium sulfate, filtered and concentrated to afford compound 90.2 (110 mg, yield: 89%) as a yellow solid.

m/z: $[M+H]^+$ 362

Step 2: Synthesis of Compound 90.3

To an ice-cooling solution of compound 90.2 (110 mg, 0.30 mmol) in methanol (5 mL) was added $NaBH_4$ (46.05 mg, 1.22 mmol) in small portions. The resulted mixture was stirred at room temperature for 15 min, and then the reaction was quenched by addition of water (20 mL), and then extracted with ethyl acetate (20 mL×3). The combined organic phase was washed with brine, dried over sodium sulfate, filtered and concentrated to afford compound 90.3 (110 mg, yield: 99%) as a yellow solid.

m/z: $[M+H]^+$ 364

Step 3: Synthesis of Compound 90

To an ice-cooling solution of compound 90.3 (100 mg, 0.28 mmol) in dichloromethane (2 mL) was added methanesulfonyl chloride (37.8 mg, 0.33 mmol) dropwise. The resulted mixture was stirred at room temperature for 2.5 h, and then washed with water (5 mL) and brine (5 mL), dried over sodium sulfate and concentrated to dryness. The residue was purified by pre-HPLC to afford compound 90 (TFA salt, 3.6 mg, yield: 3%) as a white solid.

$^1$H NMR (400 MHz, MeOD-$d_4$): δ 9.08, 9.15 (two s, 1H), 7.80-7.87 (m, 1H), 7.72-7.76 (m, 1H), 7.66-7.71 (m, 1H), 7.51-7.58 (m, 2H), 5.69-5.77 (two m, 1H), 4.03-4.13 (m, 1H), 3.59-3.66 (m, 1H), 2.93 (s, 3H), 1.87-2.29 (m, 7H), 1.51-1.82 (m, 7H), 1.34-1.38 (m, 3H).

m/z: $[M+H]^+$ 442

Example 31: Synthesis of Compound 49

To a solution of compound 43 (100 mg, 0.23 mmol), 2-cyclohexylacetic acid (39 mg, 0.27 mmol), and N,N-diisopropylethylamine (DIPEA) (117 mg, 0.91 mmol) in dichloromethane (5 mL) was added HATU (130 mg, 0.34 mmol). The resulted mixture was stirred at room temperature for 4 h, then added water (5 mL). The mixture was extracted with dichloromethane (5 mL×3). The combined organic phase was washed with saturated sodium bicarbonate solution and brine, dried over sodium sulfate, filtered and concentrated, the residue was purified by pre-HPLC (Separation method: E) to afford compound 49 (TFA salt, 43 mg, yield: 38%) as a white solid.

$^1$H NMR (400 MHz, MeOD-$d_4$): δ 9.15, 9.19 (two s, 1H), 7.82 (s, 1H), 7.66-7.72 (m, 1H), 7.55-7.64 (m, 1H), 7.26-7.34 (m, 1H), 5.89-5.96 (m, 1H), 3.82-3.91 (m, 1H), 3.42-3.50 (m, 1H), 2.60-2.66 (m, 1H), 1.94-2.12 (m, 5H), 1.09-1.86 (m, 20H), 0.88-1.03 (m, 2H).

m/z: $[M+H]^+$ 492

Example 32: Synthesis of Compounds 50-53

Compounds 50~53 were prepared according to example 31 compound 49, by using compound 44 and corresponding acid as starting materials.

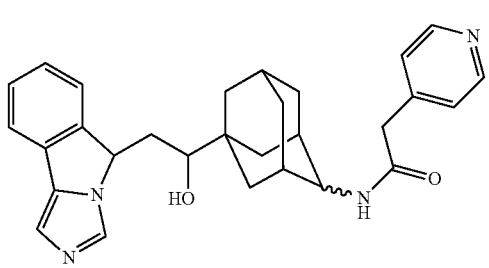

50

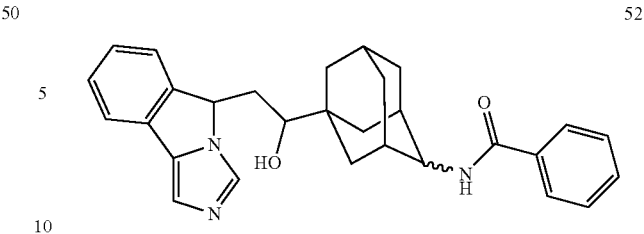

52

Compound 50 (a mixture of stereoisomers) was separated by pre-HPLC (Separation method: F) to afford 50A (the peak time: 10.0~11.0 min) and 50B (the peak time: 10.8~12.3 min).

m/z: [M+H]+ 469

50A: $^1$H NMR (400 MHz, MeOD-d$_4$): δ 9.09, 9.16 (two s, 1H), 8.75 (d, J=5.9 Hz, 2H), 7.95 (d, J=6.2 Hz, 2H), 7.81-7.87 (m, 1H), 7.73-7.76 (m, 1H), 7.67-7.71 (m, 1H), 7.51-7.58 (m, 2H), 5.74 (t, J=6.0 Hz, 1H), 3.83-4.02 (m, 2H), 3.60 (dd, J=2.7, 11.0 Hz, 1H), 2.07-2.32 (m, 2H), 1.94-2.04 (m, 5H), 1.48-1.80 (m, 7H), 1.23-1.43 (m, 2H).

50B: $^1$H NMR (400 MHz, MeOD-d$_4$): δ 9.10, 9.17 (two s, 1H), 8.73 (d, J=5.4 Hz, 2H), 7.94 (d, J=6.2 Hz, 2H), 7.81-7.88 (m, 1H), 7.74-7.78 (m, 1H), 7.67-7.73 (m, 1H), 7.52-7.60 (m, 2H), 5.76 (t, J=6.0 Hz, 1H), 3.87-3.98 (m, 2H), 3.61 (dd, J=2.6, 11.1 Hz, 1H), 2.10-2.35 (m, 2H), 1.93-2.07 (m, 3H), 1.24-1.87 (m, 11H).

Compound 52 (a mixture of stereoisomers) was separated by pre-HPLC (Separation method: E) to afford 52A (the peak time: 12.0~13.8 min) and 52B (the peak time: 14.8~16.3 min).

m/z: [M+H]+ 454

52A: $^1$H NMR (400 MHz, MeOD-d$_4$): δ 9.19 (s, 1H), 7.85-7.65 (m, 5H), 7.60-7.49 (m, 5H), 5.75-5.73 (m, 1H), 4.10 (a, 1H), 3.57-3.55 (m, 1H), 2.20-2.45 (m, 5H), 1.80-2.10 (m, 4H), 1.49-1.61 (m, 3H), 1.50-1.45 (m, 1H).

52B: $^1$H NMR (400 MHz, MeOD-d$_4$): δ 9.18 (s, 1H), 7.88-7.62 (m, 3H), 7.62-7.60 (m, 2H), 7.10-7.29 (m, 5H), 5.74-5.72 (m, 1H), 3.94 (m, 1H), 3.57-3.50 (m, 1H), 2.23-2.01 (m, 7H), 1.95-1.43 (m, 8H).

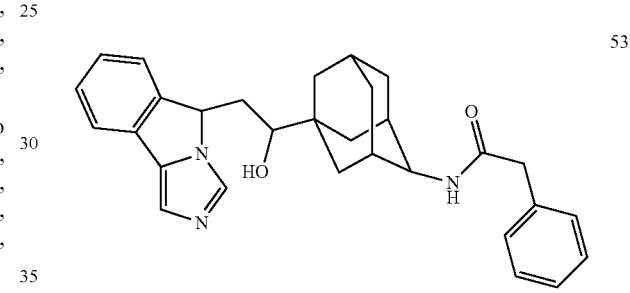

53

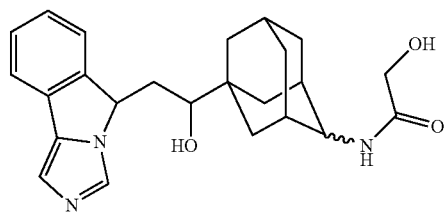

51

Compound 51 (a mixture of stereoisomers) was separated by pre-HPLC (Separation method: E) to afford 51A (the peak time: 8.5~10.0 min) and 51B (the peak time: 10.0~11.0 min).

m/z: [M+H]+ 408

51A: $^1$H NMR (400 MHz, MeOD-d$_4$): δ 9.10, 9.17 (two s, 1H), 7.80-7.90 (m, 1H), 7.75 (d, J=1.1 Hz, 1H), 7.68-7.72 (m, 1H), 7.52-7.59 (m, 2H), 5.75 (t, J=6.0 Hz, 1H), 3.97-4.01 (m, 2H), 3.94 (br s, 1H), 3.61 (dd, J=2.7, 11.0 Hz, 1H), 2.07-2.35 (m, 2H), 1.93-2.06 (m, 3H), 1.46-1.92 (m, 7H), 1.24-1.40 (m, 3H).

51B: $^1$H NMR (400 MHz, MeOD-d$_4$): δ 9.10, 9.17 (two s, 1H), 7.81-7.88 (m, 1H), 7.73-7.78 (m, 1H), 7.67-7.72 (m, 1H), 7.52-7.60 (m, 2H), 5.75 (t, J=5.8 Hz, 1H), 3.89-4.05 (m, 3H), 3.59 (dd, J=2.6, 11.1 Hz, 1H), 2.08-2.32 (m, 2H), 1.96-2.07 (m, 3H), 1.22-1.88 (m 10H).

Compound 53 (a mixture of stereoisomers) was separated by pre-HPLC (Separation method: E) to afford 53A (the peak time: 9.3~10.8 min) and 53B (the peak time: 10.8~12.3 min).

m/z: [M+H]+ 468

53A: $^1$H NMR (400 MHz, MeOD-d$_4$): δ 9.18 (s, 1H), 7.84-7.88 (m, 1H), 7.80 (s, 1H), 7.65-7.71 (m, 1H), 7.60-7.62 (m, 2H), 7.27-7.29 (m, 1H), 7.19-7.23 (m, 2H), 7.12-7.14 (m, 1H), 5.76 (t, J=4.0 Hz, 1H), 5.51 (s, 1H), 3.89-3.94 (m, 1H), 3.50-3.57 (m, 2H), 2.18-2.23 (m, 3H), 1.96-2.14 (m, 4H), 1.80-1.93 (m, 3H), 1.32-1.66 (m, 6H).

53B: $^1$H NMR (400 MHz, MeOD-d$_4$): δ 9.19 (s, 1H), 7.71-7.78 (m, 4H), 7.55-7.59 (m, 2H), 7.45-7.53 (m, 2H), 5.78 (t, J=4.0 Hz, 1H), 5.51 (s, 1H), 4.11 (s, 1H), 3.63 (d, J=12 Hz, 1H), 2.14-2.23 (m, 5H), 1.96-2.04 (m, 2H), 1.86-1.93 (m, 5H), 1.22-1.66 (m, 6H).

Example 33: Synthesis of Compounds 121A

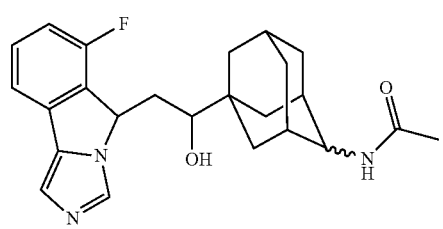

121A

Compound 121A was prepared according to example 31 compound 49, by using compound 43A and corresponding acid as starting materials.

m/z: [M+H]$^+$ 410

$^1$H NMR (400 MHz, MeOD-d$_4$): δ 9.13, 9.20 (two s, 1H), 7.82 (s, 1H), 7.52-7.73 (m, 2H), 7.25-7.33 (m, 1H), 5.90-6.14 (two m, 1H), 3.84-3.88 (m, 1H), 3.33-3.34 (m, 1H), 2.62-2.66 (m, 1H), 1.49-2.21 (m, 17H).

Example 34: Synthesis of Compound 91

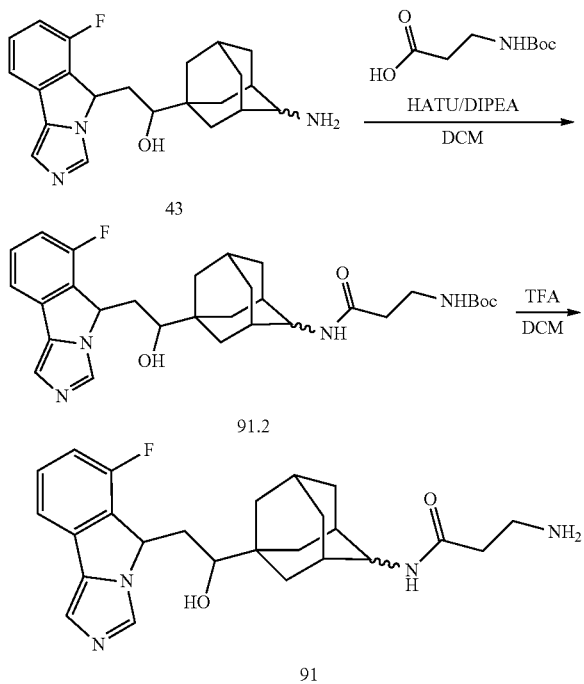

Step 1: Synthesis of Compound 91.2

To an ice-cooling solution of compound 43 (300 mg, 0.82 mmol) in dichloromethane (10 mL) was successively added 3-((tert-butoxycarbonyl)amino)propanoic acid (0.154 g, 0.82 mmol), DIPEA (0.422 g, 3.27 mmol) and HATU (0.464 g, 1.22 mmol). The resulted mixture was stirred at room temperature for 2 h, and then diluted with dichloromethane, washed with water (10 mL), brine (10 mL), dried over sodium sulfate, filtered and concentrated to dryness. The residue was purified by flash column chromatography on silica gel (0-100% solution of ethyl acetate in petroleum ether) to afford compound 91.2 (240 mg, yield: 55%) as a yellow solid.

m/z: [M+H]$^+$ 539

Step 2: Synthesis of Compound 91

To an ice-cooling solution of compound 91.2 (240 mg, 0.45 mmol) in dichloromethane (5 mL) was added TFA (1 mL) drop wise. The resulted mixture was stirred at room temperature for 2 h, and then concentrated to dryness to afford compound 91. Then compound 91 (a mixture of stereoisomers) was separated by pre-HPLC (Separation method: F) to afford 91A (7.1 mg, the peak time: 5.8-7.2 min) and 91B (3.8 mg, the peak time: 7.4-8.8 min). Both 91A and 91B were TFA salts.

m/z: [M+H]$^+$ 439

91A: $^1$H NMR (400 MHz, MeOD-d$_4$): δ 9.13, 9.19 (two s, 1H), 7.81 (s, 1H), 7.53-7.73 (m, 2H), 7.23-7.34 (m, 1H), 5.88-6.14 (two m, 1H), 3.84-3.95 (m, 1H), 3.40-3.47 (m, 1H), 3.13-3.22 (m, 2H), 2.58-2.72 (m, 3H), 1.89-2.07 (m, 6H), 1.44-1.75 (m, 8H).

91B: $^1$H NMR (400 MHz, MeOD-d$_4$): δ 9.13, 9.18 (two s, 1H), 7.81 (s, 1H), 7.56-7.73 (m, 2H), 7.23-7.32 (m, 1H), 5.87-6.13 (two m, 1H), 3.89-3.99 (m, 1H), 3.40-3.48 (m, 1H), 3.16 (t, J=6.4 Hz, 2H), 2.57-2.68 (m, 3H), 1.91-2.07 (m, 4H), 1.36-1.86 (m, 10H).

Example 35: Synthesis of Compound 92

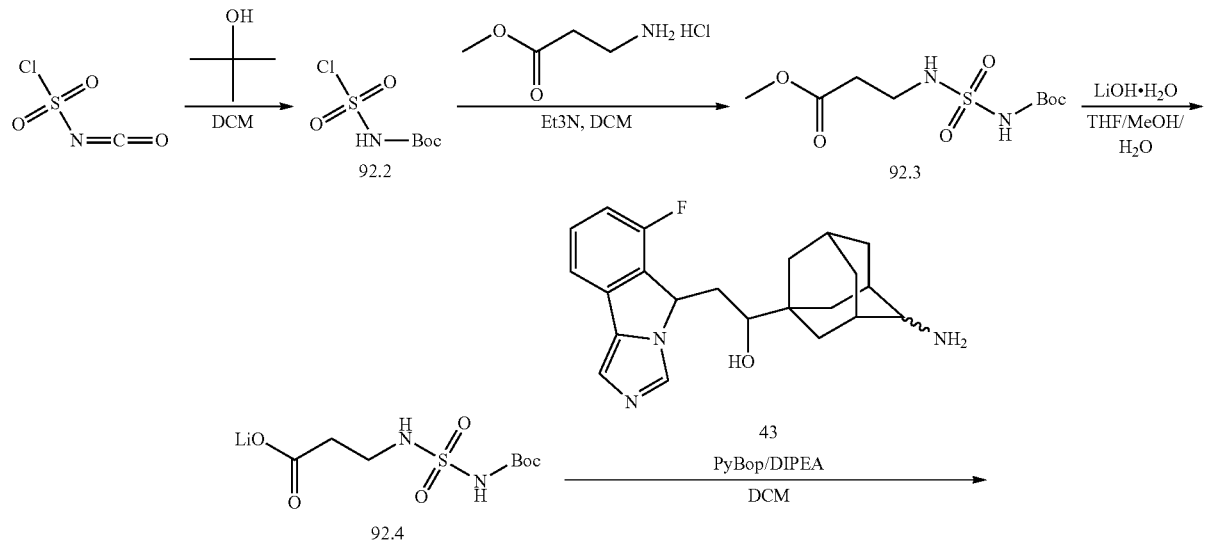

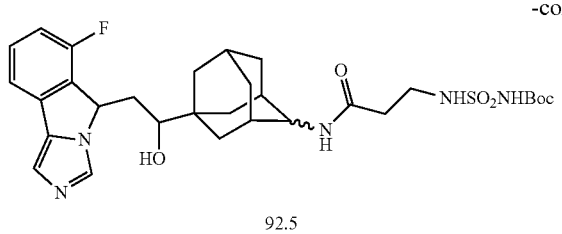

92.5

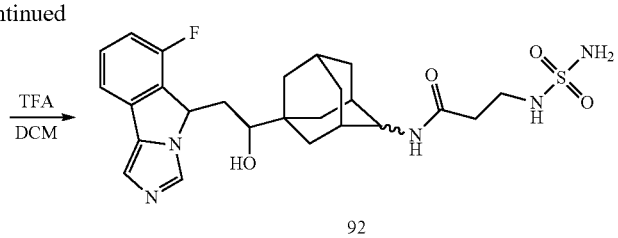

92

Step 1 & 2: Synthesis of Compound 92.3

To an ice-cooling solution of tert-butanol (2.4 mL, 26.2 mmol) in dichloromethane (20 mL) was added sulfurisocyanatidic chloride (2.03 g, 14.3 mmol) over 0.5 h while maintaining the inner temperature below 10° C. The resulting compound 92.2 solution was held at 0° C. for 1 h and then was added to an ice-cooling solution of methyl 3-aminopropanoate hydrochloride (1.90 g, 13.6 mmol) and triethylamine (4 mL, 28.9 mmol) in dichloromethane (30 mL). The reaction mixture was warmed up to room temperature and stirred for 18 h. The mixture was diluted with dichloromethane (25 mL) and washed with an aqueous solution of acetic acid (30 mL, 1.0%) and brine (30 mL), dried over sodium sulfate, filtered, and concentrated to afford compound 92.3 (1.62 g, yield: 42%) as a white solid.

$^1$H NMR (400 MHz, CDCl$_3$-d) δ 8.75 (br. S, 1H), 5.52 (br. S, 1H), 3.64 (s, 3H), 3.20 (t, J=6.7 Hz, 2H), 2.58 (t, J=6.7 Hz, 2H), 1.42 (s, 9H).

Step 3: Synthesis of Compound 92.4

A solution of compound 92.3 (0.70 g, 2.48 mmol) and lithium hydroxide monohydrate (0.22 g, 5.21 mmol) in a mixed solvent of THF (1 mL), methanol (1 mL) and water (1 mL) was stirred at room temperature for 3 h. Then the solvent was evaporated under vacuum. The residual aqueous solution was lyophilized to afford compound 92.4 (0.5 g, crude) as a white solid which was used directly to next step without further purification.

Step 4: Synthesis of Compound 92.5

To an ice-cooling solution of compound 43 (80.0 mg, 0.22 mmol), compound 92.4 (89.6 mg, 0.327 mmol), and DIPEA (113 mg, 0.871 mmol) in dichloromethane (5 mL) was added (benzotriazol-1-yl-oxy)tripyrrolidinophosphonium hexafluorophosphate (PyBop) (170 mg, 0.33 mmol). The resulted mixture was stirred at room temperature for 2 h, and then washed with water (5 mL) and brine (5 mL), dried over sodium sulfate, filtered and concentrated to dryness. The residue was purified by flash column chromatography on silica gel (0-100% solution of ethyl acetate in petroleum ether) to afford compound 92.5 (60 mg, yield: 45%) as a yellow solid.

m/z: [M+H]$^+$ 618

Step 5: Synthesis of Compound 92

To an ice-cooling solution of compound 92.5 (60.0 mg, 0.10 mmol) in dichloromethane (5 mL) was added TFA (1 mL) drop wise, the resulted mixture was stirred at room temperature for 2 h, and then concentrated to dryness to afford compound 92 (a mixture of stereoisomers), which was separated by pre-HPLC (Separation method: F) to afford 92A (2.6 mg, the peak time: 9.1-9.9 min) and 92B (3.3 mg, the peak time: 10.2-11.4 min). Both 92A and 92B were TFA salts.

m/z: [M+H]$^+$ 518

92A: $^1$H NMR (400 MHz, MeOD-d$_4$): δ 9.12, 9.19 (two s, 1H), 7.83 (d, J=0.8 Hz, 1H), 7.64-7.84 (m, 2H), 7.26-7.34 (m, 1H), 5.90-6.11 (two m, 1H), 3.81-3.92 (m, 1H), 3.39-3.46 (m, 1H), 3.27-3.30 (overlapping with solvent, 2H), 2.48-2.66 (m, 3H), 1.91-2.22 (m, 6H), 1.38-1.77 (m, 8H).

92B: $^1$H NMR (400 MHz, MeOD-d$_4$): δ 9.09-9.20 (m, 1H), 7.83 (d, J=0.8 Hz, 1H), 7.56-7.72 (m, 2H), 7.24-7.34 (m, 1H), 5.89-6.11 (two m, 1H), 3.85-3.92 (m, 1H), 3.28-3.37 (overlapping with solvent, 3H), 2.43-2.71 (m, 3H), 2.06-2.22 (m, 1H), 1.85-2.06 (m, 4H), 1.41-1.84 (m, 9H).

Example 36: Synthesis of Compound 54

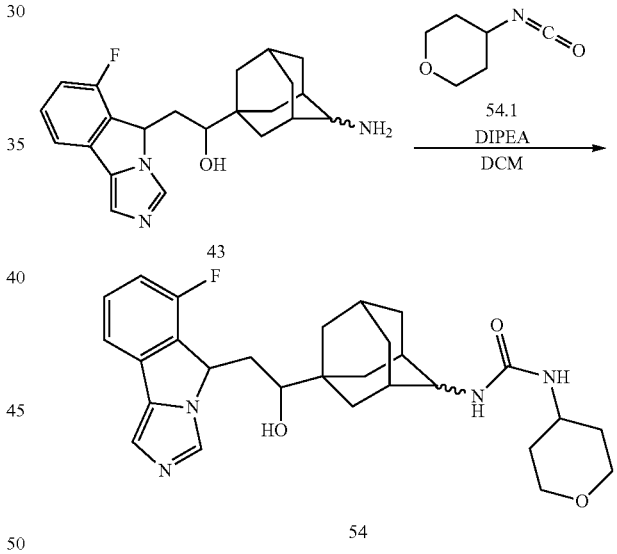

Step 1: Synthesis of 4-isocyanatotetrahydro-2H-pyran (54.1)

Preparation a solution of tetrahydro-2H-pyran-4-amine (200 mg, 1.98 mmol) and DIPEA (562 mg, 4.35 mmol) in dichloromethane (8 mL). To a solution of triphosgene (217 mg, 0.73 mmol) in dichloromethane (2 mL) was added the solution prepared above with a syringe dropwise. The resulted mixture was stirred at room temperature for 2 h to afford a solution of 4-isocyanatotetrahydro-2H-pyran (54.1) in dichloromethane, which can be directly used for next step.

Step 2: Synthesis of Compound 54

A solution of compound 43 (100 mg, 0.23 mmol), compound 54.1 (dissolved in dichloromethane prepared in step 1, 5 mL) and DIPEA (88 mg, 0.68 mmol) in dichloromethane (3 mL) was stirred at room temperature for overnight. The mixture was diluted with water (5 mL), extracted with dichloromethane (5 mL×2). The combined organic phase was washed with brine, dried over sodium sulfate, filtered and concentrated, the residue was purified by pre-HPLC to afford compound 54 (TFA salt, 17.4 mg, yield: 13%) as a white foam.

$^1$H NMR (400 MHz, MeOD-d$_4$): δ 9.13, 9.19 (two s, 1H), 7.81-7.82 (m, 1H), 7.68-7.69 (m, 1H), 7.61-7.67 (m, 1H), 7.30-7.31 (m, 1H), 5.91-5.92 (m, 1H), 3.88-3.92 (m, 2H), 3.70-3.75 (m, 2H), 3.47-3.51 (m, 3H), 2.60-2.62 (m, 1H), 1.19-1.97 (m, 18H).

m/z: [M+H]$^+$ 495

Example 37: Synthesis of Compound 55-56, 97

Compounds 55~56, 97 were prepared according to example 36 compound 54, by using compound 43 and corresponding isocyanate as starting materials.

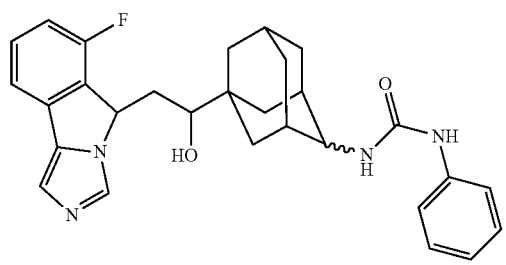

55

$^1$H NMR (400 MHz, MeOD-d$_4$): δ 9.14, 9.20 (two s, 1H), 7.81 (s, 1H), 7.60-7.67 (m, 2H), 7.23-7.34 (m, 5H), 6.95-7.00 (m, 1H), 5.93, 6.17 (br s, 1H), 3.72-3.82 (m, 1H), 3.42-3.44 (m, 1H), 2.61-2.65 (m, 1H), 1.29-2.15 (m, 14H).

m/z: [M+H]$^+$ 487

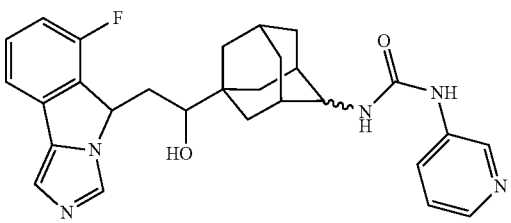

56

Compound 56 (a mixture of stereoisomers) was separated by pre-HPLC (Separation method: F) to afford 56A (the peak time: 7.3~9.0 min) and 56B (the peak time: 9.3~11.5 min).

m/z: [M+H]$^+$ 488

56A: $^1$H NMR (400 MHz, MeOD-d$_4$): δ 9.12, 9.20 (two s, 1H), 9.09-9.15 (m, 1H), 8.34 (d, J=5.2 Hz, 1H), 8.21 (dd, J=1.2, 7.2 Hz, 1H), 7.81-7.84 (m, 2H), 7.67-7.68 (m, 1H), 7.54-7.64 (m, 1H), 7.25-7.35 (m, 1H), 5.93-6.18 (m, 1H), 3.76-3.86 (m, 1H), 3.45 (dd, J=2.0, 10.9 Hz, 1H), 2.63 (dd, J=2.7, 15.2 Hz, 1H), 1.87-2.05 (m, 5H), 1.52-1.77 (m, 7H), 1.28-1.38 (m, 2H).

56B: $^1$H NMR (400 MHz, MeOD-d$_4$): δ 9.09, 9.14, 9.19 (three s, 1H), 9.09 (s, 1H), 8.32 (d, J=5.1 Hz, 1H), 8.14-8.22 (m, 1H), 7.76-7.85 (m, 2H), 7.66-7.72 (m, 1H), 7.54-7.64 (m, 1H), 7.24-7.33 (m, 1H), 5.90-5.95 (m, 1H), 3.81-3.89 (m, 1H), 3.43 (dd, J=2.3, 11.1 Hz, 1H), 2.59-2.66 (m, 1H), 1.96-2.07 (m, 3H), 1.68-1.88 (m, 5H), 1.42-1.64 (m, 4H), 1.25-1.35 (m, 2H).

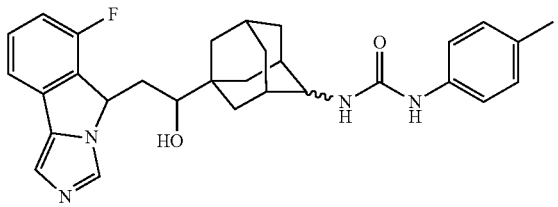

97

$^1$H NMR (400 MHz, MeOD-d$_4$): δ 9.16-9.22 (m, 1H), 7.83-7.84 (m, 1H), 7.59-7.73 (m, 2H), 7.29-7.35 (m, 1H), 7.17-7.26 (m, 2H), 7.02-7.10 (m, 2H), 5.88-6.18 (two m, 1H), 3.76-3.88 (m, 1H), 3.40-3.49 (m, 1H), 2.63-2.67 (m, 1H), 2.28 (d, J=3.2 Hz, 3H), 1.39-2.11 (m, 14H).

m/z: [M+H]$^+$ 501

Example 38: Synthesis of Compounds 55A, 93A-96A

Compounds 55A, 93A~96A were prepared according to example 36 compound 54, by using compound 43A and corresponding isocyanate as starting materials.

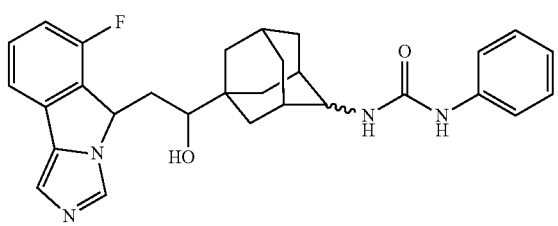

55A $^1$H NMR (400 MHz, MeOD-d$_4$): δ 9.14, 9.20 (two s, 1H), 7.79-7.83 (m, 1H), 7.65-7.72 (m, 1H), 7.55-7.64 (m, 1H), 7.26-7.37 (m, 3H), 7.18-7.26 (m, 2H), 6.91-6.98 (m, 1H), 5.89-6.14 (two m, 1H), 3.75-3.85 (m, 1H), 3.39-3.46 (m, 1H), 2.59-2.68 (m, 1H), 1.87-2.09 (m, 6H), 1.77-1.84 (m, 1H), 1.51-1.73 (m, 7H).

m/z: [M+H]$^+$ 487

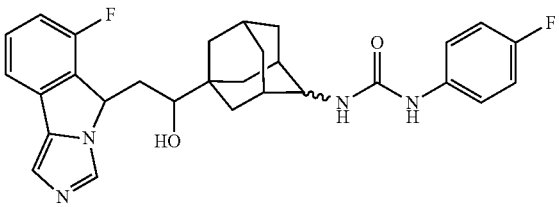

93A $^1$H NMR (400 MHz, MeOD-d$_4$): δ 9.13, 9.20 (two s, 1H), 7.79-7.83 (m, 1H), 7.65-7.72 (m, 1H), 7.56-7.63 (m, 1H), 7.26-7.35 (m, 3H), 6.94-7.01 (m, 2H), 5.90-6.13 (two m, 1H), 3.74-3.83 (m, 1H), 3.40-3.46 (m, 1H), 2.59-2.67 (m, 1H), 1.86-2.08 (m, 6H), 1.50-1.75 (m, 8H).

m/z: [M+H]$^+$ 505

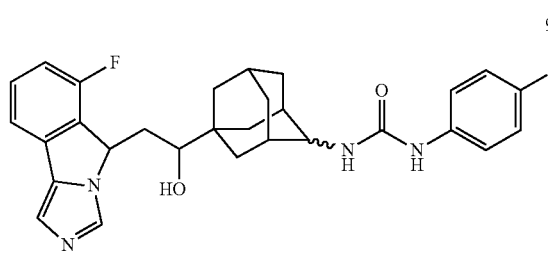

94A

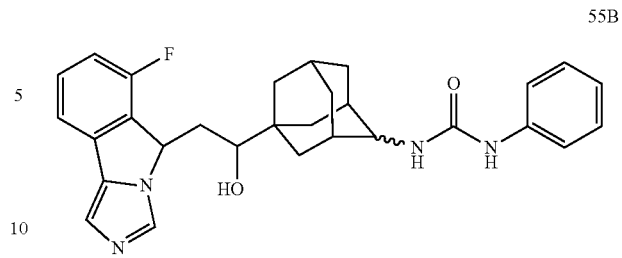

55B

¹H NMR (400 MHz, MeOD-d₄): δ 9.14, 9.21 (two s, 1H), 7.83 (d, J=1.2 Hz, 1H), 7.59-7.71 (m, 2H), 7.46-7.16 (m, 5H), 5.95-6.12 (two m, 1H), 3.78-3.82 (m, 1H), 3.42-3.51 (m, 1H), 2.61-2.69 (m, 1H), 1.89-2.12 (m, 6H), 1.52-1.80 (m, 8H).

m/z: [M+H]⁺ 521

¹H NMR (400 MHz, MeOD-d₄): δ 9.14, 9.19 (two s, 1H), 7.80-7.84 (m, 1H), 7.65-7.72 (m, 1H), 7.57-7.64 (m, 1H), 7.26-7.35 (m, 3H), 7.18-7.26 (m, 2H), 6.91-6.97 (m, 1H), 5.90-6.14 (two m, 1H), 3.78-3.84 (m, 1H), 3.39-3.45 (m, 1H), 2.59-2.64 (m, 1H), 1.96-2.09 (m, 4H), 1.40-1.84 (m, 10H).

m/z: [M+H]⁺ 487

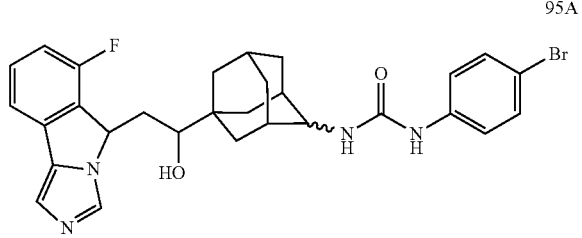 [SMILES: O=C(Nc1ccc(Br)cc1)NC1C2CC3CC1CC(C(O)CC1c4c(F)cccc4-c4cncn41)(C3)C2]

95A

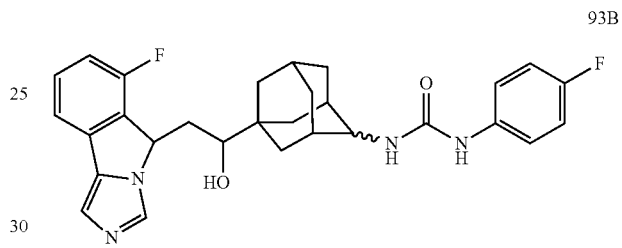

93B

¹H NMR (400 MHz, MeOD-d₄): δ 9.06, 9.14, 7.21 (three s, 1H), 7.83 (d, J=1.2 Hz, 1H), 7.58-7.73 (m, 2H), 7.26-7.44 (m, 5H), 5.92-6.13 (two m, 1H), 3.78-3.82 (m, 1H), 3.44-3.50 (m, 1H), 2.61-2.74 (m, 1H), 1.89-2.10 (m, 6H), 1.53-1.76 (m, 8H).

m/z: [M+H]⁺ 565

¹H NMR (400 MHz, MeOD-d₄): δ 9.13, 9.19 (two s, 1H), 7.79-7.84 (m, 1H), 7.66-7.72 (m, 1H), 7.57-7.64 (m, 1H), 7.27-7.36 (m, 3H), 6.93-7.01 (m, 2H), 5.89-6.14 (two m, 1H), 3.77-3.84 (m, 1H), 3.39-3.42 (m, 1H), 2.58-2.69 (m, 1H), 1.93-2.10 (m, 4H), 1.40-1.87 (m, 10H).

m/z: [M+H]⁺ 505

Example 40: Synthesis of Compound 98A

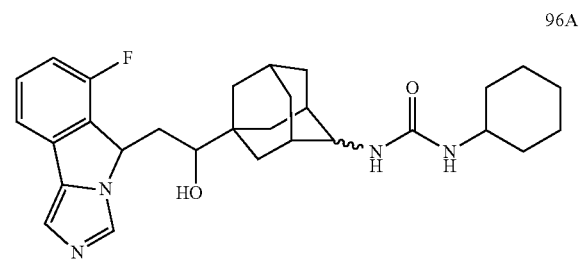 [SMILES: O=C(NC1CCCCC1)NC1C2CC3CC1CC(C(O)CC1c4c(F)cccc4-c4cncn41)(C3)C2]

96A

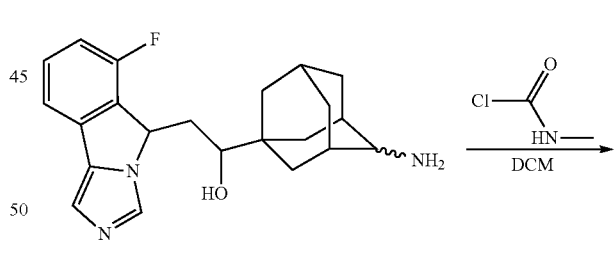

¹H NMR (400 MHz, MeOD-d₄): δ 9.14, 9.21 (two s, 1H), 7.82 (s, 1H), 7.59-7.73 (m, 2H), 7.29-7.33 (m, 1H), 5.58-5.71 (two m, 1H), 3.41-3.73 (m, 3H), 2.55-2.63 (m, 1H), 1.87-2.02 (m, 7H), 1.51-1.77 (m, 10H), 1.16-1.40 (m, 7H).

m/z: [M+H]⁺ 493

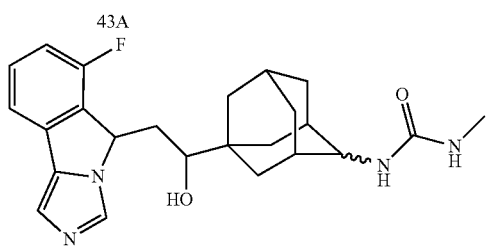

98A

Example 39: Synthesis of Compounds 55B and 93B

Compounds 55B, 93B were prepared according to example 36 compound 54, by using compound 43B and corresponding isocyanate as starting materials.

To a mixture of 43A (50 mg, 0.108 mmol) and TEA (33 mg, 0.324 mmol) in dichloromethane (5 mL) was added methylcarbamic chloride (10 mg, 0.108 mmol). The resulted mixture was stirred at room temperature for 4 h, and then concentrated under reduced pressure. The residue was purified by pre-HPLC to afford compound 98A (TFA salt, 11.4 mg, yield: 20%) as a white solid.

$^1$H NMR (400 MHz, MeOD-d$_4$): δ 9.14, 9.21 (two s, 1H), 7.83 (d, J=1.2 Hz, 1H), 7.59-7.73 (m, 2H), 7.26-7.37 (m, 1H), 5.90-6.02 (two m, 1H), 3.66-3.73 (m, 1H), 3.41-3.48 (m, 1H), 2.71 (d, J=2.8 Hz, 3H), 2.61-2.67 (m, 1H), 1.85-2.12 (m, 6H), 1.42-1.78 (m, 8H).

m/z: [M+H]$^+$ 425

Example 41: Synthesis of Compound 99A

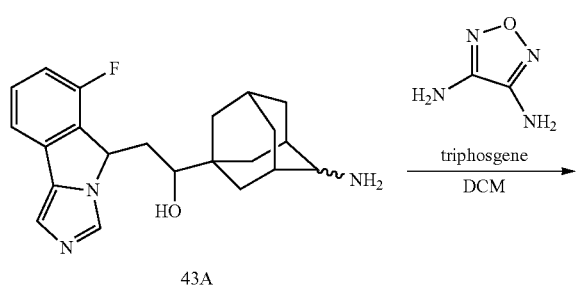

43A

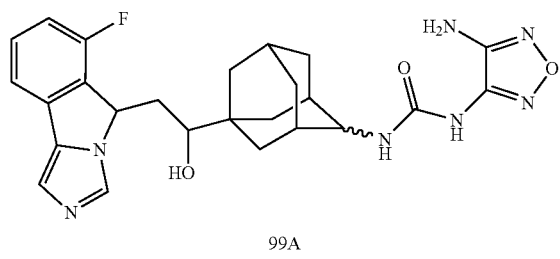

99A

To an ice-cooling mixture of triphosgene (13 mg, 0.043 mmol) in dichloromethane (5 mL) was added 1,2,5-oxadiazole-3,4-diamine (10.8 mg, 0.108 mmol) and TEA (33 mg, 0.324 mmol). The mixture was stirred at room temperature for 1 h, then a solution of compound 43A (50 mg, 0.108 mmol) in dichloromethane (5 mL) was added dropwise. The mixture was stirred at room temperature for 3 h. Then the reaction was poured into water, extracted with a mixed solvent of dichloromethane and methanol (10/1, 30 mL×5). The combined organic phase was dried over sodium sulfate, filtered and concentrated under reduced pressure. The residue was purified by pre-HPLC to afford compound 99A (TFA salt, 2.3 mg, yield: 3%) as a white foam.

$^1$H NMR (400 MHz, MeOD-d$_4$): δ 9.11 (s, 1H), 7.78 (s, 1H), 7.57-7.69 (m, 2H), 7.25-7.33 (m, 1H), 5.93-6.09 (two m, 1H), 3.84-3.90 (m, 1H), 3.41-3.45 (m, 1H), 2.60-2.66 (m, 1H), 1.91-2.10 (m, 6H), 1.51-1.81 (m, 8H).

m/z: [M+H]$^+$ 494

Example 42: Synthesis of Compounds 100~104

Compounds 100-104 were prepared according to example 41 compound 99A, by using compound 43, 44 and corresponding amino as starting materials.

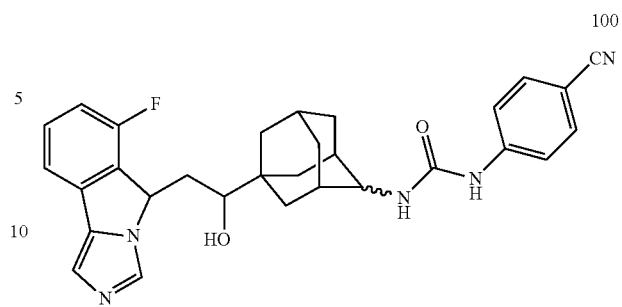

100

$^1$H NMR (400 MHz, MeOD-d$_4$): δ 9.14-9.20 (m, 1H), 7.83 (s, 1H), 7.67-7.74 (m, 1H), 7.53-7.65 (m, 5H), 7.25-7.36 (m, 1H), 5.94-6.12 (m, 1H), 3.81-3.88 (m, 1H), 3.40-3.49 (m, 1H), 2.62-2.68 (m, 1H), 1.89-2.12 (m, 5H), 1.38-1.87 (m, 9H).

m/z: [M+H]$^+$ 512

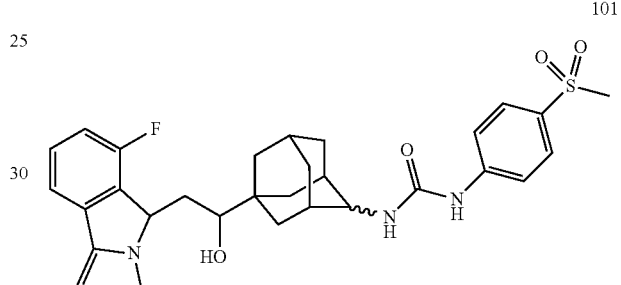

101

$^1$H NMR (400 MHz, MeOD-d$_4$): δ 9.14, 9.20 (two s, 1H), 7.81-7.84 (m, 3H), 7.60-7.71 (m, 4H), 7.30-7.34 (m, 1H), 5.95-6.14 (two m, 1H), 3.81-3.88 (m, 1H), 3.40-3.49 (m, 1H), 3.10 (s, 3H), 2.63-2.68 (m, 1H), 1.89-2.12 (m, 5H), 1.38-1.87 (m, 9H).

m/z: [M+H]$^+$ 565

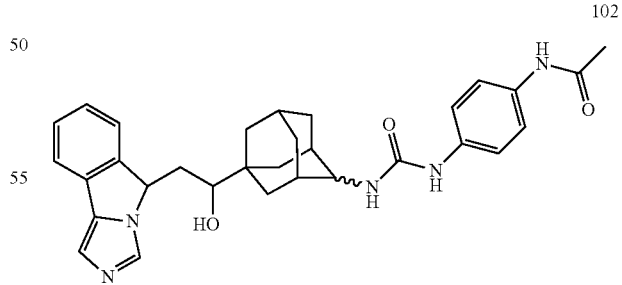

102

$^1$H NMR (400 MHz, MeOD-d$_4$): δ 9.19 (s, 1H), 7.83-7.91 (m, 1H), 7.69-7.80 (m, 2H), 7.54-7.62 (m, 2H), 7.39-7.47 (m, 2H), 7.25-7.33 (m, 2H), 5.78 (t, J=6.0 Hz, 1H), 3.84 (s, 1H), 3.57-3.68 (m, 1H), 2.25-2.35 (m, 1H), 2.15-2.24 (m, 1H), 2.11 (s, 3H), 1.97-2.06 (m, 3H), 1.42-1.87 (m, 10H).

m/z: [M+H]$^+$ 526

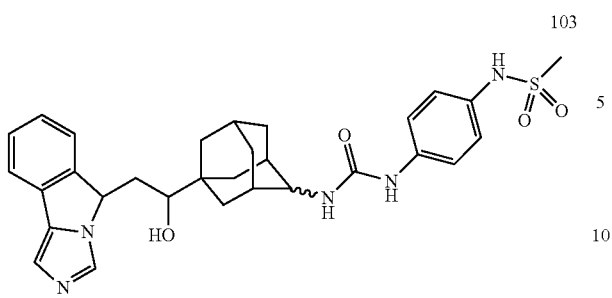

103

¹H NMR (400 MHz, MeOD-d₄): δ 9.12, 9.20 (two s, 1H), 7.83-7.91 (m, 1H), 7.64-7.80 (m, 2H), 7.54-7.61 (m, 2H), 7.30-7.39 (m, 2H), 7.14-7.22 (m, 2H), 5.76-5.93 (two m, 1H), 3.80-3.89 (m, 1H), 3.57-3.68 (m, 1H), 2.89-2.94 (m, 3H), 2.26-2.34 (m, 1H), 2.11-2.24 (m, 1H), 1.43-2.08 (m, 13H).

m/z: [M+H]⁺ 562

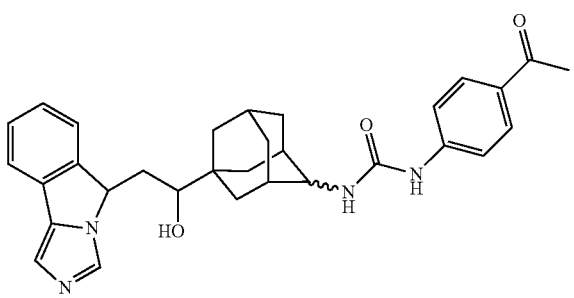

104

¹H NMR (400 MHz, MeOD-d₄): δ 9.12, 9.19 (two s, 1H), 7.86-7.96 (m, 3H), 7.71-7.77 (m, 2H), 7.58-7.61 (m, 2H), 7.49-7.51 (m, 2H), 5.77-5.93 (m, 1H), 3.84-3.90 (m, 1H), 3.61 (dd, J=2.4, 10.8 Hz, 1H), 2.56 (s, 3H), 2.13-2.36 (m, 2H), 1.97-2.09 (m, 3H), 1.44-1.88 (m, 10H).

m/z: [M+H]⁺ 512

Example 43: Synthesis of Compounds 105A-114A

Compounds 105A~114A were prepared according to example 41 compound 99A, by using compound 43A and corresponding amino as starting materials.

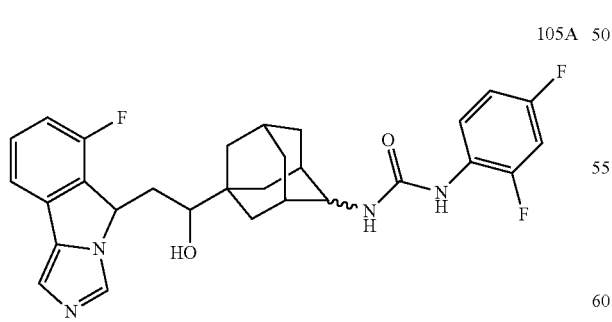

105A

¹H NMR (400 MHz, MeOD-d₄): δ 9.15, 9.22 (two s, 1H), 7.93-8.06 (m, 1H), 7.79-7.88 (m, 1H), 7.57-7.75 (m, 2H), 7.27-7.37 (m, 1H), 6.86-7.02 (m, 2H), 5.94-6.13 (two m, 1H), 3.78-3.87 (m, 1H), 3.42-3.49 (m, 1H), 2.61-2.71 (m, 1H), 1.31-2.06 (m, 14H).

m/z: [M+H]⁺ 523

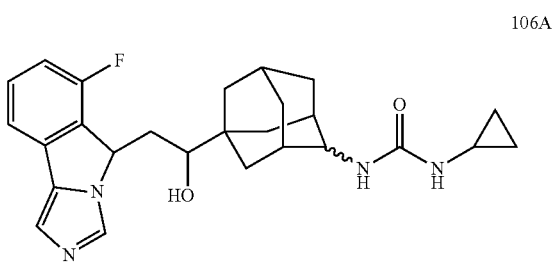 [SMILES: O=C(NC1CC1)NC1C2CC3CC1CC(C(O)CC1c4c(F)cccc4-c4cncn41)(C3)C2]

106A

The HCl salt of 106A was prepared according to the preparation method of compound 1-A.

106A (HCl salt): ¹H NMR (400 MHz, DMSO-d₆): δ 14.92 (br s, 1H), 9.40, 9.54 (two s, 1H), 8.01 (s, 1H), 7.58-7.75 (m, 2H), 7.33-7.41 (m, 1H), 5.60-6.09 (m, 1H), 3.57 (br s, 1H), 3.16 (d, J=9.6 Hz, 1H), 2.32-2.48 (m, 2H), 1.95-2.03 (m, 1H), 1.77-1.84 (m, 4H), 1.12-1.56 (m, 9H), 0.48-0.60 (m, 2H), 0.24-0.34 (m, 2H).

m/z: [M+H]⁺ 451

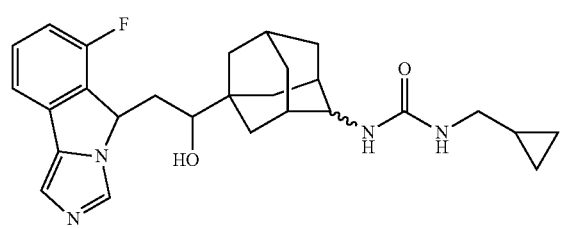

107A

The HCl salt of 107A was prepared according to the preparation method of compound 1-A.

107A (HCl salt): ¹H NMR (400 MHz, DMSO-d₆): δ 9.35-9.60 (m, 1H), 7.99 (s, 1H), 7.69-7.78 (m, 1H), 7.58-7.64 (m, 1H), 7.32-7.41 (m, 1H), 6.07-6.09 (m, 1H), 6.00 (br s, 1H), 3.50-3.56 (overlapping with solvent, 2H), 3.15 (d, J=10.0 Hz, 1H), 2.86 (d, J=8.0 Hz, 2H), 1.97-2.04 (m, 1H), 1.72-1.89 (m, 4H), 0.80-1.52 (m, 10H), 0.34-0.42 (m, 2H), 0.08-0.15 (m, 2H).

m/z: [M+H]⁺ 465

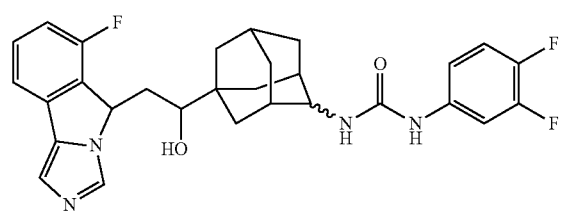

108A

The HCl salt of 108A was prepared according to the preparation method of compound 1-A.

108A (HCl salt): ¹H NMR (400 MHz, DMSO-d₆): δ 8.60 (s, 1H), 7.97 (s, 1H), 7.60-7.66 (m, 1H), 7.40-7.47 (m, 1H), 7.06-7.31 (m, 3H), 6.96 (d, J=8.8 Hz, 1H), 6.47 (d, J=8.0 Hz, 1H), 5.53-5.68 (m, 1H), 4.62 (d, J=6.4 Hz, 1H), 3.65 (d, J=7.2 Hz, 1H), 3.04-3.08 (m, 1H), 2.29-2.40 (m, 1H), 1.27-1.99 (m, 14H).

m/z: [M+H]⁺ 523

109A
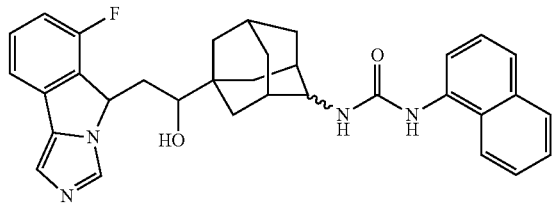
¹H NMR (400 MHz, MeOD-d₄): δ 9.15, 9.22 (two s, 1H), 7.99-8.06 (m, 1H), 7.86-7.93 (m, 1H), 7.78-7.85 (m, 2H), 7.59-7.73 (m, 3H), 7.42-7.56 (m, 3H), 7.28-7.36 (m, 1H), 5.93-5.96 (m, 1H), 3.87-3.90 (m, 1H), 3.44-3.51 (m, 1H), 2.57-2.65 (m, 1H), 1.28-2.31 (m, 14H).
m/z: [M+H]⁺ 537
110A
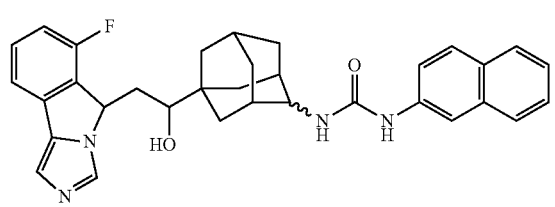
m/z: [M+H]⁺ 537
111A
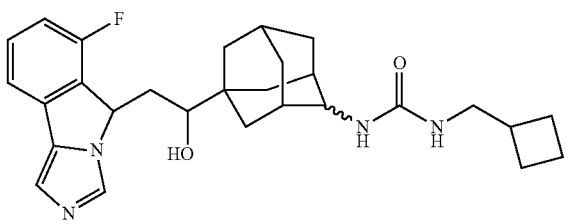
¹H NMR (400 MHz, MeOD-d₄): δ 9.13, 9.19 (two s, 1H), 7.82 (s, 1H), 7.59-7.72 (m, 2H), 7.29-7.34 (m, 1H), 5.93-6.11 (two m, 1H), 3.69-3.73 (m, 1H), 3.35-3.51 (m, 2H), 3.13-3.16 (m, 2H), 2.59-2.66 (m, 1H), 2.40-2.50 (m, 2H), 2.00-2.10 (m, 4H), 1.49-1.96 (m, 15H).
m/z: [M+H]⁺ 479
112A
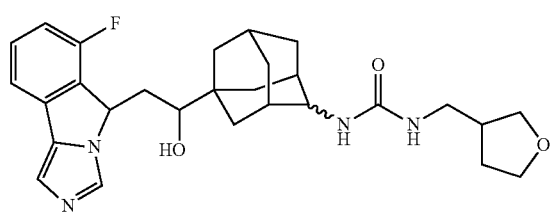
¹H NMR (400 MHz, MeOD-d₄): δ 9.13, 9.20 (two s, 1H), 7.82 (s, 1H), 7.66-7.73 (m, 1H), 7.55-7.64 (m, 1H), 7.26-7.35 (m, 1H), 5.93-6.11 (two m, 1H), 3.70-3.91 (m, 4H), 3.42-3.53 (m, 2H), 3.11-3.26 (m, 2H), 2.55-2.66 (m, 1H), 2.32-2.46 (m, 1H), 1.83-2.12 (m, 7H), 1.31-1.79 (m, 9H).
m/z: [M+H]⁺ 495
113A
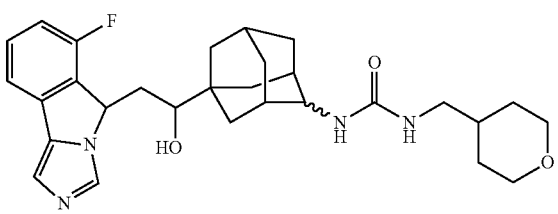
¹H NMR (400 MHz, MeOD-d₄): δ 9.16, 9.22 (two s, 1H), 7.83 (d, J=0.8 Hz, 1H), 7.59-7.73 (m, 2H), 7.29-7.35 (m, 1H), 5.93-6.13 (two m, 1H), 3.95 (dd, J=11.2, 4.0 Hz, 2H), 3.69-3.73 (m, 1H), 3.38-3.45 (m, 3H), 2.96-3.06 (m, 2H), 2.58-2.67 (m, 1H), 1.88-2.08 (m, 6H), 1.43-1.79 (m, 11H), 1.20-1.41 (m, 2H).
m/z: [M+H]⁺ 509
114A
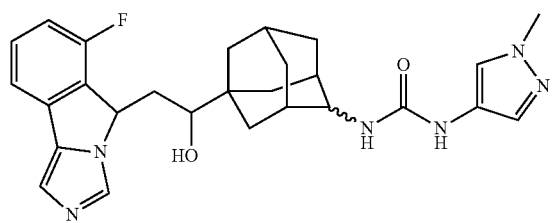
¹H NMR (400 MHz, MeOD-d₄): δ 9.10, 9.17 (two s, 1H), 7.81 (s, 1H), 7.58-7.72 (m, 3H), 7.28-7.36 (m, 2H), 5.93-6.11 (two m, 1H), 5.34-5.39 (m, 1H), 3.84 (s, 3H), 2.64 (dd, J=2.0, 11.2 Hz, 1H), 2.59-2.66 (m, 1H), 2.19-2.24 (m, 1H), 1.50-2.23 (m, 13H).
m/z: [M+H]⁺ 491

Example 44: Synthesis of Compound 130
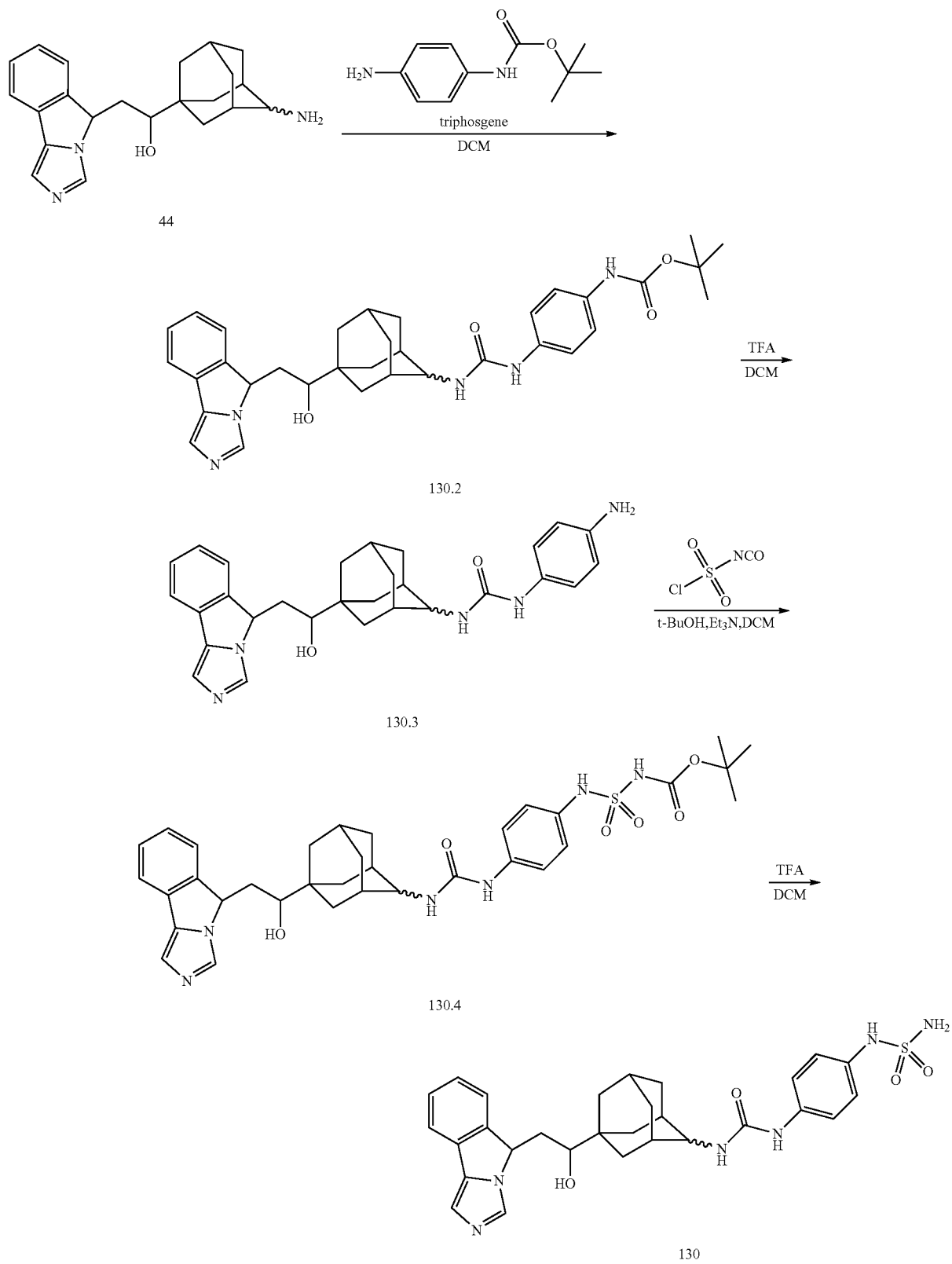

Step 1: Synthesis of Compound 130.2

To an ice-cooling solution of triphosgene (47 mg, 0.15 mmol) in dichloromethane (3 mL) was added a solution of tert-butyl (4-aminophenyl)carbamate (98.3 mg, 0.47 mmol) and TEA (90 mg, 0.86 mmol) in dichloromethane (3 mL). The resulted mixture was stirred for at room temperature for 1 h. Then a solution of compound 44 (100 mg, 0.27 mmol) and TEA (90 mg, 0.86 mmol) in dichloromethane (3 mL) was added to above resulted mixture. The mixture was stirred at room temperature for overnight, and then the reaction was quenched by addition of water and extracted with dichloromethane (10 mL×3). The combined organic phase was dried over sodium sulfate, filtered and concentrated. The residue was purified by pre-TLC (dichloromethane:methanol=10:1) to afford compound 130.2 (100 mg, yield: 60%) as a light brown solid.

m/z: [M+H]+ 584

Step 2: Synthesis of Compound 130.3

To an ice-cooling solution of compound 130.2 (100 mg, 0.17 mmol) in dichloromethane (5 mL) was added TFA (3 mL) drop wise. The mixture was stirred at room temperature for 1 h, and then the reaction was quenched by addition of water and neutralized with saturated sodium bicarbonate solution to pH=7, then the mixture was extracted with a mixed solvent of dichloromethane and methanol (10/1). The combined organic phase was dried over sodium sulfate, filtered and concentrated to afford compound 130.3 (50 mg, yield: 61%) as a light brown oil.

m/z: [M+H]+ 484

Step 3: Synthesis of Compound 130.4

To an ice-cooling stirred solution of sulfurisocyanatidic chloride (14.6 mg, 0.10 mmol) in dichloromethane (3 mL) was added t-BuOH (9.2 mg, 0.12 mmol), the mixture was stirred at room temperature for 15 min. Then above mixture was added to an ice-cooling solution of compound 130.3 (50 mg, 0.10 mmol) and TEA (31 mg, 0.31 mmol) in dichloromethane (15 mL). The resulted mixture was stirred at room temperature for 16 h, and then the reaction was quenched by addition of water and extracted with a mixed solvent of dichloromethane and methanol (10/1). The combined organic phase was dried over sodium sulfate, filtered and concentrated to afford compound 130.4 (69 mg, yield: 100%) as a brown oil.

m/z: [M+H]+ 663

Step 4: Synthesis of Compound 130

To an ice-cooling solution of compound 130.4 (69 mg, 0.10 mmol) in dichloromethane (5 mL) was added TFA (3 mL) drop wise. The mixture was stirred at room temperature for 1 h, and then the reaction was quenched by addition of water and neutralized with saturated sodium bicarbonate solution to pH=7, then the mixture was extracted with mixed solvents of dichloromethane and methanol (10/1). The combined organic phase was dried over sodium sulfate, filtered and concentrated. The residue was purified by pre-HPLC to afford compound 130 (TFA salt, 13 mg, yield: 19%) as an off-white solid.

$^1$H NMR (400 MHz, MeOD-d$_4$): δ 9.11, 9.19 (two s, 1H), 7.82-7.91 (m, 1H), 7.68-7.80 (m, 2H), 7.53-7.61 (m, 2H), 7.26-7.36 (m, 2H), 7.11-7.20 (m, 2H), 5.75-5.90 (two m, 1H), 3.79-3.84 (m, 1H), 3.57-3.67 (m, 1H), 2.24-2.37 (m, 1H), 2.10-2.24 (m, 1H), 1.41-2.07 (m, 13H).

m/z: [M+H]+ 563

Example 45: Synthesis of Compound 122

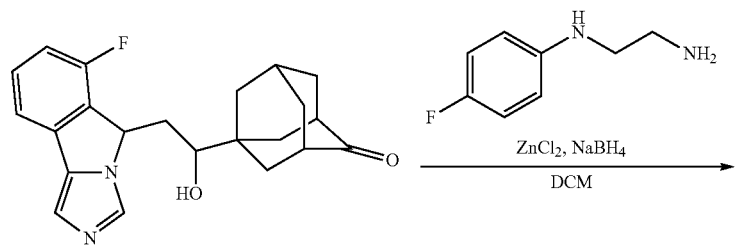

63

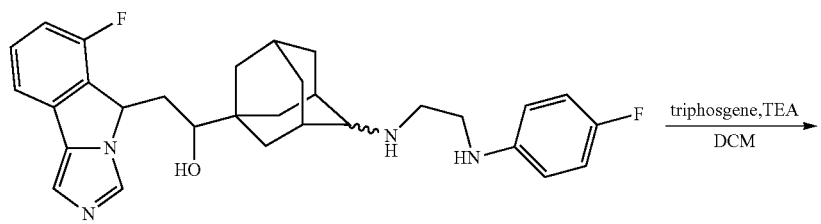

122.2

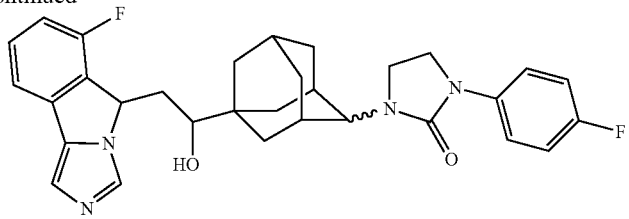

122

Step 1: Synthesis of N¹-(4-fluorophenyl)ethane-1,2-diamine

A mixture of 1-fluoro-4-iodobenzene (1.0 g, 4.5 mmol), ethylenediamine (541 mg, 9.0 mmol) and CuO (358 mg, 4.5 mmol) in MeCN (20 mL) was stirred at 83° C. for 20 h. The mixture was concentrated under vacuum. The residue was dissolved in ethyl acetate and washed with brine. The organic phase was separated, dried over sodium sulfate and concentrated to afford N¹-(4-fluorophenyl)ethane-1,2-diamine (430 mg, yield: 62%) as a yellow oil.

Step 2: Synthesis of Compound 122.2

A mixture of compound 63 (100 mg, 0.273 mmol), N¹-(4-fluorophenyl)ethane-1,2-diamine (46.3 mg, 0.30 mmol), $ZnCl_2$ (37.2 mg, 0.273 mmol) and $NaBH_4$ (20.7 mg, 0.546 mmol) in dichloromethane (3 mL) was stirred at room temperature for 20 h. The mixture was diluted with dichloromethane and washed with brine. The organic layer was separated, dried over sodium sulfate and concentrated to afford compound 122.2 (75 mg, yield: 55%) as a light yellow solid.

m/z: [M+H]⁺ 505

Step 3: Synthesis of Compound 122

To an ice-cooling mixture of compound 122.2 (75 mg, 0.149 mmol) and triphosgene (15.4 mg, 0.052 mmol) in dichloromethane (2 mL) was added TEA (45.1 mg, 0.446 mmol). The mixture was stirred at room temperature for 20 h, and then the mixture was diluted with dichloromethane and washed with brine. The organic phase was separated, dried over sodium sulfate and concentrated. The residue was purified by pre-HPLC to afford compound 122 (TFA salt, 7.6 mg, yield: 10%) as a white foam.

¹H NMR (400 MHz, MeOD-d₄): δ 8.01-8.08 (m, 1H), 7.41-7.53 (m, 4H), 7.16-7.31 (m, 1H), 6.99-7.11 (m, 3H), 5.51-5.74 (two m, 1H), 4.63 (s, 1H), 3.78-3.83 (m, 2H), 3.60-3.71 (m, 3H), 3.14-3.21 (m, 1H), 2.46-2.55 (m, 3H), 1.46-2.08 (m, 11H).

m/z: [M+H]⁺ 531

Example 46: Synthesis of Compound 123

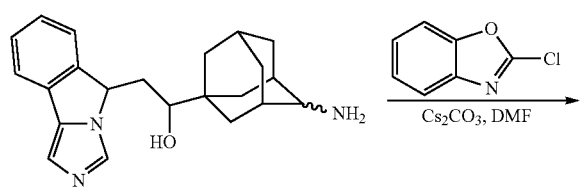

44

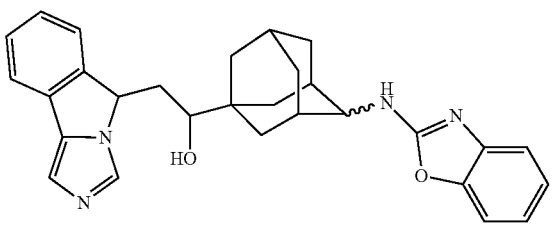

123

A mixture of compound 44 (1.8 g, 5.15 mmol), 2-chlorobenzo[d]oxazole (1.19 g, 7.73 mmol) and cesium carbonate (2.52 g, 7.73 mmol) in DMF (50 mL) was stirred at 0° C. for 3 h. Then the mixture was diluted with ethyl acetate and washed with water (100 mL×3) and brine. The organic phase was separated, dried over sodium sulfate and concentrated to afford compound 123 (a mixture of stereoisomers), which was separated by pre-HPLC (Separation method: N) to afford 123A (830 mg, the peak time: 20.0-23.0 min) and 123B (530 mg, the peak time: 23.5-30.0 min).

Compound 123A (830 mg) was separated by SFC (Chiral resolution method: I) to afford single diasteromers 123A-2 (139 mg) and 123A-4 (183 mg), and a mixture of diasteromers (130 mg).

The mixture of diasteromers (130 mg) was further separated by chiral HPLC (Chiral resolution method: K) to afford single diasteromers 123A-1 (23 mg) and 123A-3 (20 mg).

| No. | Compound No. of a single diasteromer | Retention Time (Chiral analysis method G) |
|---|---|---|
| 123A | 123A-1 | 5.82 min |
|  | 123A-2 | 7.17 min |
|  | 123A-3 | 9.62 min |
|  | 123A-4 | 12.11 min | m/z: [M+H]⁺ 467

123: ¹H NMR (400 MHz, MeOD-d₄): δ 9.13-9.21 (m, 1H), 7.85-7.89 (m, 1H), 7.69-7.80 (m, 2H), 7.53-7.62 (m, 2H), 7.33-7.44 (m, 2H), 7.16-7.32 (m, 2H), 5.77-5.92 (two m, 1H), 3.91-3.97 (m, 1H), 3.62-3.69 (m, 1H), 1.42-2.40 (m, 15H).

Example 47: Synthesis of Compound 124

Compound 124A was prepared according to example 46 compound 123, by using compound 43A and 2-chlorobenzo[d]oxazole as starting materials.

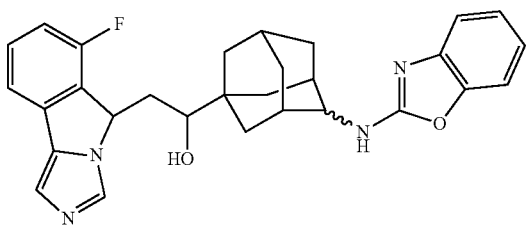

124A

Compound 124A (250 mg) was separated by SFC (Chiral resolution method: J) to afford single diasteromers 124A-2 (23 mg) and 124A-4 (22 mg), and a mixture of diasteromers (140 mg).

The mixture of diasteromers (140 mg) was further separated by chiral HPLC (Chiral resolution method: L) to afford single diasteromers 124A-1 (12 mg) and 124A-3 (14 mg).

| No. | Compound No. of a single diasteromer | Retention Time (Chiral analysis method H) |
|---|---|---|
| 124A | 124A-1 | 25.4 min |
|  | 124A-2 | 42.3 min |
|  | 124A-3 | 48.8 min |
|  | 124A-4 | 60.2 min |

The HCl salts of 124A-1~124A-4 were prepared according to the preparation method of compound 1-A.
m/z: [M+H]$^+$ 485
124A-2: (HCl salt) $^1$H NMR (400 MHz, MeOD-d$_4$): δ 9.24 (s, 1H), 7.86 (d, J=0.8 Hz, 1H), 7.61-7.72 (m, 2H), 7.48-7.50 (m, 1H), 7.26-7.41 (m, 4H), 5.97-5.99 (m, 1H), 3.95 (s, 1H), 3.53-3.55 (m, 1H), 2.66-2.71 (m, 1H), 2.04-2.24 (m, 5H), 1.32-1.87 (m, 9H).
124A-4: (HCl salt) $^1$H NMR (400 MHz, MeOD-d$_4$): δ 9.24 (s, 1H), 7.86 (d, J=0.8 Hz, 1H), 7.61-7.72 (m, 2H), 7.50-7.52 (m, 1H), 7.30-7.42 (m, 4H), 5.97-5.98 (m, 1H), 3.96 (s, 1H), 3.53-3.56 (m, 1H), 2.66-2.70 (m, 1H), 2.04-2.25 (m, 5H), 1.32-1.87 (m, 9H).

Example 48: Synthesis of Compounds 125 and 126

Compounds 125 and 126 was prepared according to example 46 compound 123, by using compound 44 or 43 and 2-chlorobenzo[d]thiazole as starting materials.

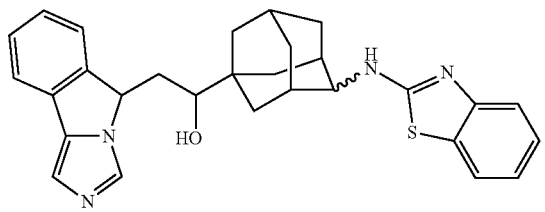

125

Compound 125 (a mixture of stereoisomers) was separated by pre-HPLC (Separation method: M) to afford 125A (the peak time: 17.5-21.0 min) and 125B (the peak time: 21.0-23.0 min).
m/z: [M+H]$^+$ 483
125A: $^1$H NMR (400 MHz, MeOD-d$_4$): δ 9.15, 9.22 (two s, 1H), 7.87-7.91 (m, 1H), 7.66-7.79 (m, 3H), 7.51-7.60 (m, 3H), 7.43 (t, J=7.8 Hz, 1H), 7.27 (t, J=7.4 Hz, 1H), 5.78-5.93 (two m, 1H), 3.98-4.03 (two s, 1H), 3.65-3.70 (m, 1H), 1.25-2.35 (m, 15H).
125B: $^1$H NMR (400 MHz, MeOD-d$_4$): δ 9.14, 9.20 (two s, 1H), 7.86-7.88 (m, 1H), 7.65-7.77 (m, 3H), 7.53-7.60 (m, 3H), 7.46 (t, J=8.2 Hz, 1H), 7.33 (t, J=7.4 Hz, 1H), 5.77-5.92 (two m, 1H), 3.98 (s, 1H), 3.64-3.67 (m, 1H), 1.55-2.05 (m, 15H).

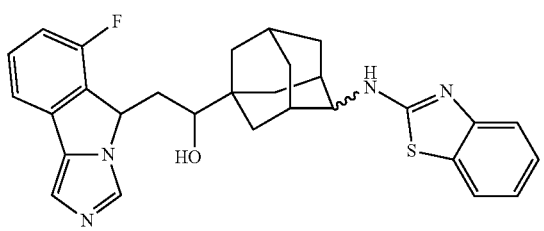

126 m/z: [M+H]$^+$ 501

Example 49: Synthesis of Compound 127

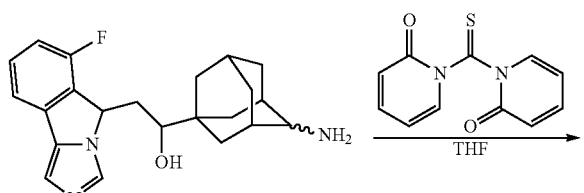

43

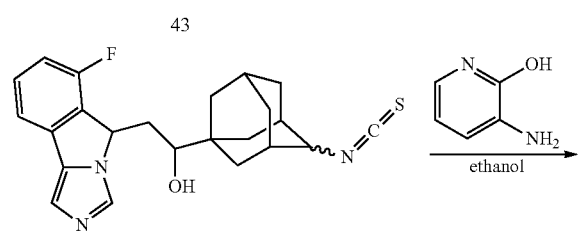

127.2

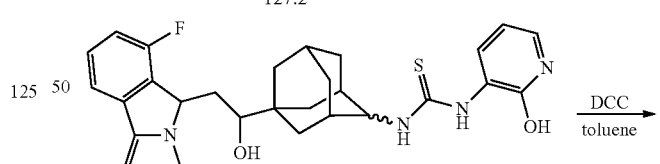

127.3

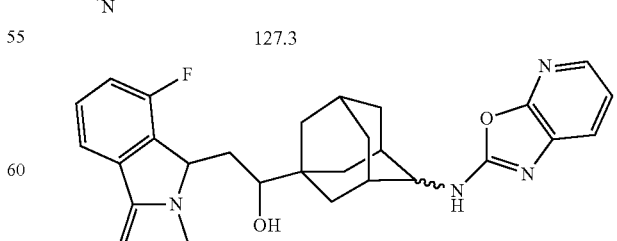

127

Step 1: Synthesis of Compound 127.2

A mixture of compound 43 (240 mg, 0.65 mmol), 1,1'-thiocarbonylbis (pyridin-2(1H)-one) (167 mg, 0.72 mmol) in dry THF (10 mL) was stirred at reflux for 3 h. Then the mixture was cooled down to room temperature and concentrated under vacuum. The residue was purified by column chromatography on silica gel (petroleum ether/ethyl acetate=2/1) to afford compound 127.2 (250 mg, yield: 94%) as a yellow gel.

Step 2: Synthesis of Compound 127.3

A mixture of compound 127.2 (100 mg, 0.24 mmol), 3-aminopyridin-2-ol (27 mg, 0.24 mmol) in ethanol (5 mL) was stirred at reflux for overnight. Then the mixture was cooled down to room temperature and concentrated under vacuum to afford compound 127.3 (127 mg, yield: 100%) as a yellow solid.

m/z: [M+H]$^+$ 520

Step 3: Synthesis of Compound 127

A solution of compound 127.3 (127 mg, 0.24 mmol) and dicyclohexyl carbodiimid (DCC) (75 mg, 0.37 mmol) in toluene (5 mL) was stirred at reflux for overnight under nitrogen. Then the mixture was cooled down to room temperature and concentrated under vacuum. The residue was purified by pre-HPLC to afford compound 127 (TFA salt, 11.1 mg, yield: 10%) as a white solid.

$^1$H NMR (400 MHz, MeOD-d$_4$): δ 9.21-9.23 (m, 1H), 7.84-7.90 (m, 2H), 7.58-7.71 (m, 3H), 7.21-7.36 (m, 2H), 5.96-6.14 (two m, 1H), 3.89-3.93 (m, 1H), 3.48-3.51 (m, 1H), 2.65-2.69 (m, 1H), 1.57-2.23 (m, 14H).

m/z: [M+H]$^+$ 486

Example 50: Synthesis of Compound 151

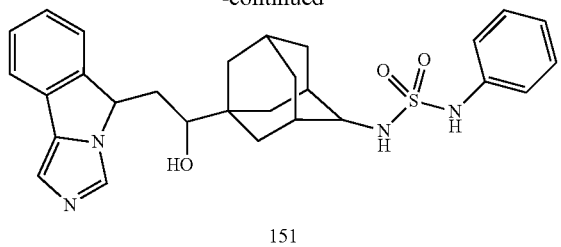

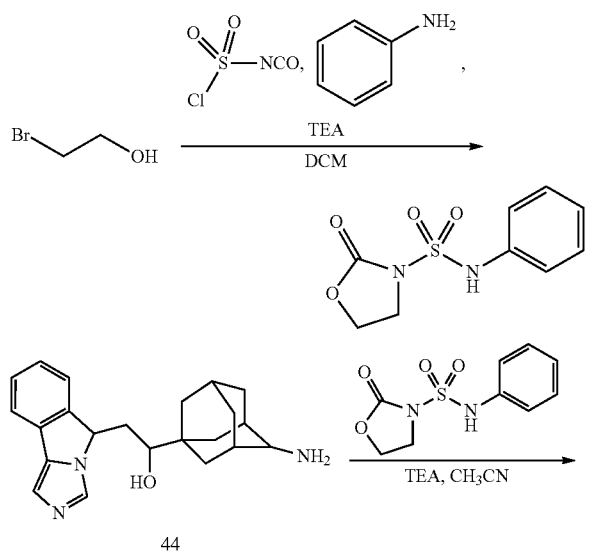

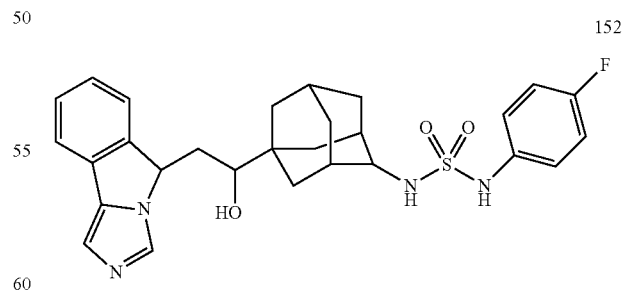

151

Step 1: Synthesis of 2-oxo-N-phenyloxazolidine-3-sulfonamide

To an ice-cooling solution of sulfurisocyanatidic chloride (566 mg, 4.0 mmol) in anhydrous dichloromethane (10 mL) was added 2-bromoethanol (500 mg, 4.0 mmol). The resulted mixture was stirred at 0° C. for 1.5 h, and then added aniline (410 mg, 4.4 mmol). The mixture was slowly warm up to room temperature and stirred for 1.5 h, and then the reaction was quenched by addition of an aqueous solution of hydrochloric acid (2.0 M, 10 mL). The organic phase was separated, dried over sodium sulfate and concentrated to afford 2-oxo-N-phenyloxazolidine-3-sulfonamide (770 mg, yield 79%) as white solid.

Step 2: Synthesis of Compound 151

A mixture of 2-oxo-N-phenyloxazolidine-3-sulfonamide (125 mg, 0.518 mmol), compound 44 (100 mg, 0.259 mmol) and TEA (120 mg, 1.186 mmol) in anhydrous acetonitrile (5 mL) was heated to reflux and stirred for 2 h, and then cooled down to room temperature and concentrated. The residue was purified by pre-HPLC to afford compound 151 (TFA salt, 8.0 mg, yield: 6%) as a white solid.

$^1$H NMR (400 MHz, MeOD-d$_4$): δ 9.08, 9.16 (two s, 1H), 7.56-7.86 (m, 6H), 7.00-7.36 (m, 4H), 5.74-5.85 (m, 1H), 3.33-3.58 (m, 2H), 1.32-2.43 (m, 15H).

m/z: [M+H]$^+$ 505

Example 51: Synthesis of Compounds 152 and 153

Compound 152-153 were prepared according to example 50 compound 151, by using compound 44 and corresponding N-(4-fluorophenyl)-2-oxooxazolidine-3-sulfonamide and 2-oxo-N-(p-tolyl)oxazolidine-3-sulfonamide as starting materials.

152

$^1$H NMR (400 MHz, MeOD-d$_4$): δ 9.08, 9.14, 9.17 (there s, 1H), 7.84-7.88 (m, 1H), 7.76-7.77 (m, 1H), 7.67-7.71 (m, 1H), 7.56-7.59 (m, 2H), 7.17-7.23 (m, 2H), 6.94-7.05 (m, 2H), 5.70-5.90 (m, 1H), 3.52-3.60 (m, 1H), 3.36-3.43 (m, 1H), 1.99-2.27 (m, 2H), 1.29-1.94 (m, 13H).

m/z: [M+H]$^+$ 523

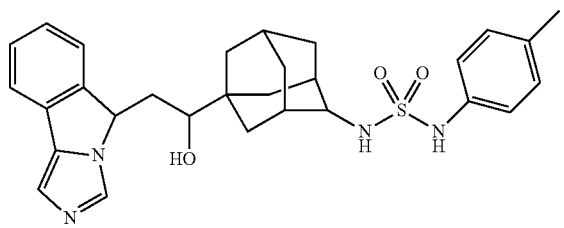

153

¹H NMR (400 MHz, MeOD-d₄): δ 9.07-9.18 (m, 1H), 7.84-7.87 (m, 1H), 7.75-7.77 (m, 1H), 7.68-7.70 (m, 1H), 7.54-7.61 (m, 2H), 7.00-7.18 (m, 4H), 5.71-5.88 (m, 1H), 4.25-4.31 (m, 1H), 3.82-3.86 (m, 1H), 2.01-2.44 (m, 5H), 1.28-1.94 (m, 13H).

m/z: [M+H]⁺ 519

Example 52: Synthesis of Compound 154

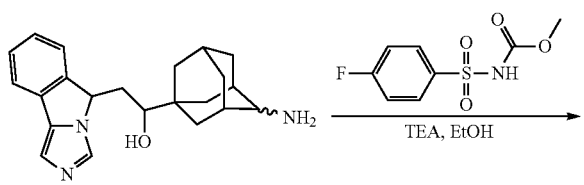

-continued

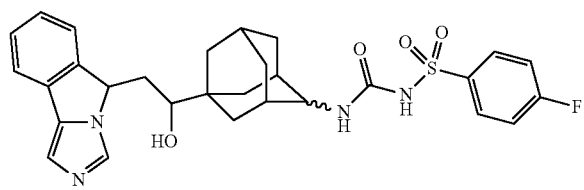

154

Step 1: Synthesis of Methyl (4-fluorophenyl)sulfonylcarbamate

To a mixture of 4-fluorobenzenesulfonamide (200 mg, 1.14 mmol) and TEA (288 mg, 2.85 mmol) in acetonitrile (10 mL) was added methyl carbonochloridate (162 mg, 1.71 mmol). The resulted mixture was stirred at room temperature for 16 h. Then the mixture was concentrated and the residue was poured into saturated sodium bicarbonate solution, and extracted with ethyl acetate (50 mL×3). The combined organic phase was dried over sodium sulfate, and then concentrated to afford methyl (4-fluorophenyl)sulfonylcarbamate (200 mg, yield: 75%) as a white solid.

Step 2: Synthesis of Compound 154

To a mixture of compound 154 (50 mg, 0.118 mmol) and methyl (4-fluorophenyl) sulfonyl carbamate (55 mg, 0.237 mmol) in toluene was added TEA (24 mg, 0.237 mmol). The mixture was stirred at reflux for 4 h. Then the mixture was concentrated. The residue was purified by pre-HPLC to afford compound 154 (TFA salt, 8.5 mg, yield: 11%) as a white solid.

¹H NMR (400 MHz, MeOD-d₄): δ 9.16, 9.18 (two s, 1H), 8.00-8.08 (m, 2H), 7.69-7.88 (m, 3H), 7.54-7.61 (m, 2H), 7.30-7.39 (m, 2H), 5.74-5.76 (m, 1H), 5.36 (t, J=4.4 Hz, 1H), 3.61-3.70 (m, 2H), 1.54-2.12 (m, 14H).

m/z: [M+H]⁺ 551

Example 53: Synthesis of Compound 155

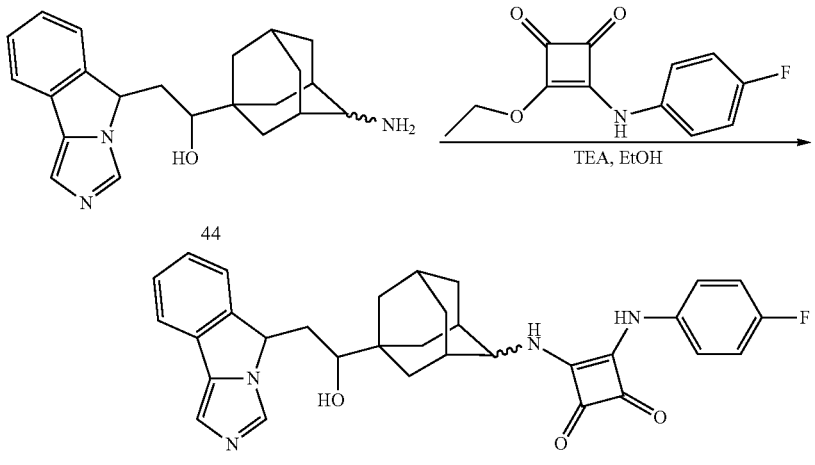

155

Step 1: Synthesis of 3-ethoxy-4-((4-fluorophenyl) amino)cyclobut-3-ene-1,2-dione A solution of 3,4-diethoxycyclobut-3-ene-1,2-dione (340 mg, 2.0 mmol) and 4-fluoroaniline (222 mg, 2.0 mmol) in ethanol (20 mL) was stirred at room temperature for overnight, and then the mixture was concentrated. The residue was purified by pre-TLC (petroleum ether:ethyl acetate=3:1) to afford 3-ethoxy-4-((4-fluorophenyl)amino)cyclobut-3-ene-1,2-dione (320 mg, yield: 68%) as a yellow solid.

Step 2: Synthesis of Compound 155

To a solution of compound 44 (106 mg, 0.25 mmol) in ethanol (20 mL) was added TEA (50 mg, 0.5 mmol) and 3-ethoxy-4-((4-fluorophenyl)amino)cyclobut-3-ene-1,2-dione (59 mg, 0.25 mmol). The resulted mixture was stirred at room temperature for overnight, and then the mixture was concentrated. The residue was purified by pre-HPLC to afford compound 155 (TFA salt, 46.5 mg, yield: 24%) as a white solid.

$^1$H NMR (400 MHz, MeOD-d$_4$): δ 9.14, 9.15, 9.21 (three s, 1H), 7.80-7.95 (m, 1H), 7.71-7.78 (m, 2H), 7.56-7.60 (m, 2H), 7.46-7.55 (m, 2H), 7.05-7.13 (m, 2H), 5.77-5.91 (two m, 1H), 4.28 (s, 1H), 3.61-3.67 (m, 1H), 1.31-2.33 (m, 15H).

m/z: [M+H]$^+$ 539

Example 54: Synthesis of Compounds 57 and 58

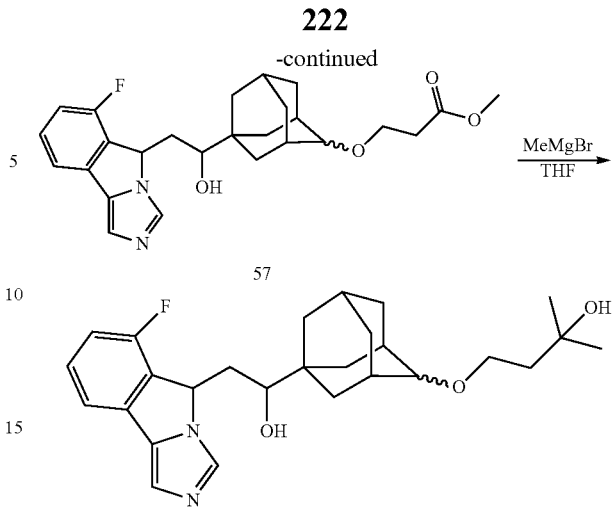

Step 1: Synthesis of Compound 57.2

To a solution of compound 2.1 (300 mg, 0.69 mmol) and 1-(4-hydroxyadamantan-1-yl) ethanone (142 mg, 0.73 mmol) in a mixed solvent of ethanol (5 mL) and THF (5 mL) was added sodium ethoxide (71 mg, 1.04 mmol). The resulted mixture was stirred at room temperature for overnight, and then the mixture was added water (30 mL), extracted with ethyl acetate (60 mL×2). The organic phase was washed with brine, dried over sodium sulfate, filtered and concentrated, the residue was purified by column chromatography on silica gel (petroleum ether:ethyl acetate=2:1) to afford compound 57.2 (280 mg, yield: 66%) as a white solid.

m/z: [M+H]$^+$ 609

Step 2: Synthesis of Compound 57.3

To a solution of compound 57.2 (1.0 g, 1.64 mmol) in THF (10 mL) was successively added sodium hydride (650 mg, 60%, 16.4 mmol) and methyl 3-bromopropanoate (1.4 g, 8.24 mmol). The resulted mixture was stirred at room temperature for 16 h, and then the reaction was quenched by addition of saturated ammonium chloride solution (20 mL), extracted with ethyl acetate (50 mL×2). The combined organic phase was washed with brine (25 mL), dried over sodium sulfate, filtered and concentrated, the residue was purified by column chromatography on silica gel (petroleum ether:ethyl acetate=10:1-5:1) to afford compound 57.3 (300 mg, yield: 26%) as a light yellow solid.

m/z: [M+H]$^+$ 695

Step 3: Synthesis of Compound 57.4

A solution of compound 57.3 (300 mg, 0.43 mmol) and acetic acid (1 mL) in methanol (4 mL) was stirred at 90° C. for 3 h, then the resulted mixture was concentrated, the residue was purified by column chromatography on silica gel (petroleum ether:ethyl acetate=8:1-3:1) to afford compound 57.4 (150 mg, yield: 77%) as a light yellow solid.

m/z: [M+H]$^+$ 453

Step 4: Synthesis of Compound 57

To an ice-cooling solution of compound 57.3 (150 mg, 0.33 mmol) in methanol (2 mL) was added NaBH$_4$ (25 mg, 0.66 mmol) in small portions. The resulted mixture was stirred at room temperature for 1 h, and then the reaction was quenched by addition of water (10 mL), extracted with ethyl acetate (20 mL×3). The combined organic phase was washed with brine (25 mL), dried over sodium sulfate, filtered and concentrated to afford compound 57 (140 mg, yield: 93%) as a yellow solid.

m/z: [M+H]$^+$ 455

Step 5: Synthesis of Compound 58

To a solution of compound 57 (100 mg, 0.22 mmol) in THF (1 mL) was added methylmagnesium bromide (0.36 mL, 1.1 mmol, 3.0 M solution in diethyl ether). The resulted mixture was stirred at room temperature for 1 h, and then the reaction was quenched by addition of saturated ammonium chloride solution, extracted with ethyl acetate (30 mL×2). The combined organic phase was washed with brine, dried over sodium sulfate, filtered and concentrated, the residue was purified by pre-TLC (dichloromethane:methanol=12:1) to afford compound 58 (40 mg, yield: 40%) as an off-white solid.

$^1$H NMR (400 MHz, MeOD-d$_4$): δ 7.97, 8.03 (two s, 1H), 7.42-7.47 (m, 2H), 7.19-7.22 (m, 1H), 7.02-7.09 (m, 1H), 5.56-5.73 (m, 1H), 1.19-3.77 (m, 27H).

m/z: [M+H]$^+$ 455

Example 55: Synthesis of Compound 133

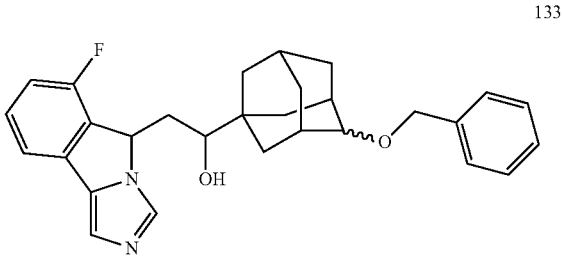 [SMILES: OC(CC1c2c(F)cccc2-c2cncn21)C12CC3CC(C1)C(OCc1ccccc1)C(C3)C2]

133

Compound 133 was prepared according to example 54 compound 57, by replacing methyl 3-bromopropanoate to benzyl bromide in step 2.

$^1$H NMR (400 MHz, MeOD-d$_4$) δ 7.97, 8.01 (two s, 1H), 7.42-7.47 (m, 2H), 7.30-7.38 (m, 4H), 7.24-7.31 (m, 1H), 7.18, 7.21 (two s, 1H), 7.02-7.06 (m, 1H), 5.57-5.72 (m, 1H), 4.53, 4.54 (two s, 2H), 3.53 (s, 1H), 3.12-3.17 (m, 1H), 2.46-2.53 (m, 1H), 1.24-2.21 (m, 14H).

m/z: [M+H]$^+$ 459

Example 56: Synthesis of Compound 59

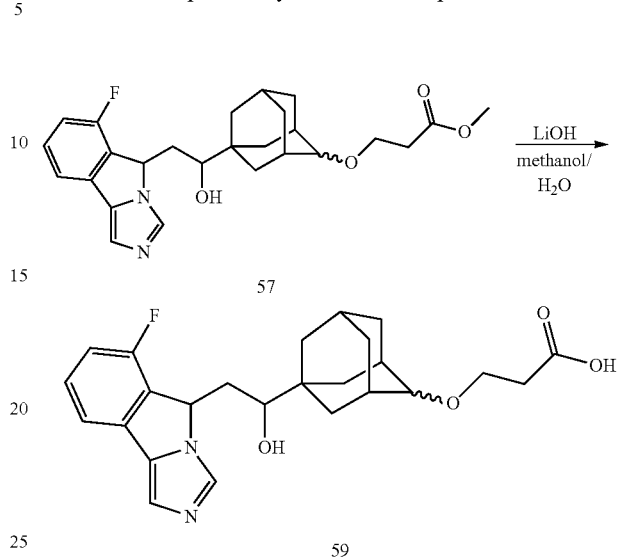

57

59

To a solution of compound 57 (40 mg, 0.088 mmol) in a mixed solvent of methanol (0.5 mL) and water (0.1 mL) was added lithium hydroxide monohydrate (37 mg, 0.88 mmol). The resulted mixture was stirred at room temperature of overnight, then the mixture was adjusted pH=6 with saturated citric acid solution, extracted with ethyl acetate (20 mL×3). The combined organic phase was washed with brine, dried over sodium sulfate, filtered and concentrated, the residue was purified by pre-TLC (dichloromethane:methanol=10:1) to afford compound 59 (40 mg, yield: 40%) as an off-white solid.

$^1$H NMR (400 MHz, MeOD-d$_4$): δ 8.06-8.14 (m, 1H), 7.46-7.49 (m, 2H), 7.24-7.29 (m, 1H), 7.07-7.11 (m, 1H), 5.73-5.75 (m, 1H), 3.71 (t, J=6.4 Hz, 2H), 0.90-2.56 (m, 19H).

m/z: [M+H]$^+$ 441

Example 57: Synthesis of Compound 60

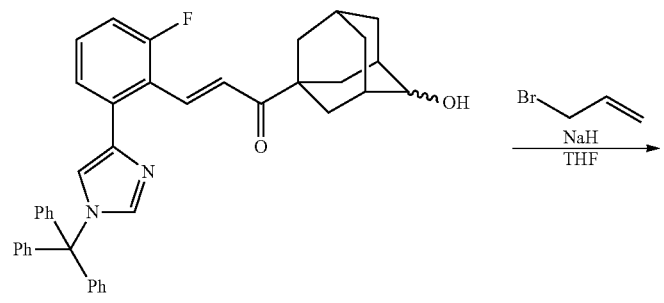

57.2

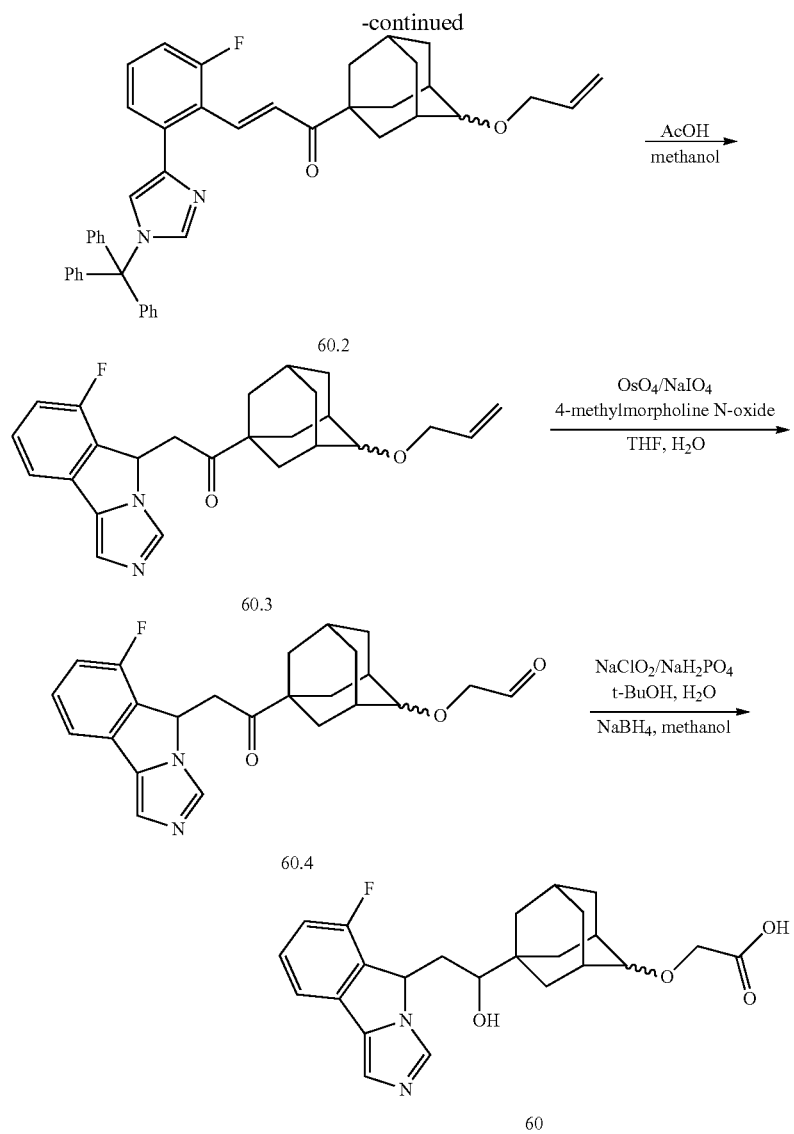

Step 1: Synthesis of Compound 60.2

To a solution of compound 57.2 (1.0 g, 1.64 mmol) in THF (10 mL) was successively added sodium hydride (330 mg, 60%, 8.21 mmol) and allyl bromide (600 mg, 4.93 mmol). The resulted mixture was stirred at room temperature for 16 h, and then the reaction was quenched by addition of saturated ammonium chloride solution (20 mL), and extracted with ethyl acetate (10 mL×3). The combined organic phase was washed with brine (25 mL), dried over sodium sulfate, filtered and concentrated, the residue was purified by column chromatography on silica gel (petroleum ether:ethyl acetate=10:1-5:1) to afford compound 60.2 (600 mg, yield: 56%) as a light yellow solid.

m/z: [M+H]$^+$ 649

Step 2: Synthesis of Compound 60.3

A solution of compound 60.2 (600 mg, 0.92 mmol) and acetic acid (1 mL) in methanol (4 mL) was stirred at 90° C. for 3 h, then the resulted mixture was concentrated, the residue was purified by column chromatography on silica gel (petroleum ether:ethyl acetate=10:1-5:1) to afford compound 60.3 (270 mg, yield: 72%) as a light yellow solid.

m/z: [M+H]$^+$ 407

Step 3: Synthesis of Compound 60.4

To a solution of compound 60.3 (450 mg, 1.1 mmol) in a mixed solvent of THF (4 mL) and H$_2$O (1 mL) was successively added 4-methylmorpholine N-oxide (NMO) (260 mg, 2.2 mmol) and a catalytic amount of osmium tetraoxide (OsO$_4$). The resulted mixture was stirred at room temperature for overnight, and then added methanol (3 mL) and sodium periodate (710 mg, 3.3 mmol). The mixture was stirred at room temperature for 2 h, and then the reaction was quenched by addition of water (10 mL), extracted with ethyl acetate (50 mL×3). The combined organic phase was washed with brine, dried over sodium sulfate, filtered and concentrated to afford compound 60.4 (400 mg, yield: 88%) as a light yellow solid.

m/z: [M+H]$^+$ 409

Step 4: Synthesis of Compound 60

To a solution of compound 60.4 (300 mg, 0.73 mmol) in a mixed solvent of t-BuOH (2 mL) and H$_2$O (1 mL) was successively added sodium dihydrogen phosphate (NaH$_2$PO$_4$) (130 mg, 1.1 mmol) and 2-methylbut-1-ene (100 mg, 1.47 mmol), then sodium chlorite (NaClO$_2$) solution (213 mg, dissolved in 0.5 mL water, 1.1 mmol) was added to the above resulted mixture dropwise. The mixture was stirred at room temperature for 1 h and concentrated, the residue was dissolved in methanol (5 mL), added NaBH$_4$ (40 mg, 1.1 mmol). The resulted mixture was stirred at room temperature for 1 h, then added water (10 mL), and extracted with ethyl acetate (50 mL×3). The combined organic phase was washed with brine, dried over sodium sulfate, filtered and concentrated to afford compound 60 (a mixture of stereoisomers), which was separated by pre-HPLC (Separation method: F) to afford 60A (23 mg, the peak time: 12.0-13.5 min) and 60B (20 mg, the peak time: 13.7-15.8 min). Both 60A and 60B were TFA salts.

m/z: [M+H]$^+$ 427

60A: $^1$H NMR (400 MHz, MeOD-d$_4$): δ 9.14, 9.20 (two s, 1H), 7.82 (s, 1H), 7.60-7.70 (m, 2H), 7.28-7.32 (m, 1H), 5.93-5.94 (m, 1H), 4.12 (s, 2H), 3.41-3.53 (m, 2H), 2.61-2.65 (m, 14H), 1.32-2.14 (m, 14H).

60B: $^1$H NMR (400 MHz, MeOD-d$_4$): δ 9.14, 9.21 (two s, 1H), 7.82 (s, 1H), 7.58-7.69 (m, 2H), 7.28-7.32 (m, 1H), 5.92-5.95 (m, 1H), 4.11 (s, 2H), 3.35-3.53 (m, 2H), 2.61-2.66 (m, 1H), 1.28-2.18 (m, 14H).

Example 58: Synthesis of Compound 61

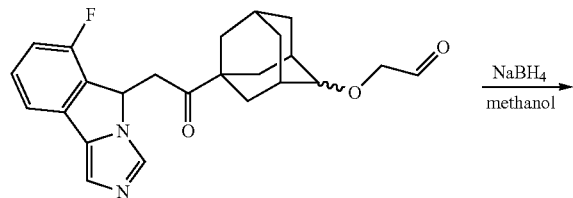

To an ice-cooling solution of compound 60.4 (100 mg, 0.24 mmol) in methanol (2 mL) was added NaBH$_4$ (14 mg, 0.37 mmol) in small portions. The resulted mixture was stirred at room temperature for 2 h, and then the reaction was quenched by addition of water (20 mL), extracted with ethyl acetate (20 mL×3). The combined organic phase was washed with brine, dried over sodium sulfate, filtered and concentrated to afford compound 61 (a mixture of stereoisomers), which was separated by pre-HPLC (Separation method: F) to afford 61A (8 mg, the peak time: 10.5-12.5 min) and 61B (6 mg, the peak time: 13.5-15.5 min). Both 61A and 61B were TFA salts.

m/z: [M+H]$^+$ 413

61A: $^1$H NMR (400 MHz, MeOD-d$_4$): δ 9.15, 9.19 (two s, 1H), 7.82 (s, 1H), 7.60-7.70 (m, 2H), 7.28-7.33 (m, 1H), 5.92-5.94 (m, 1H), 3.69 (t, J=5.6 Hz, 2H), 3.54 (t, J=4.8 Hz, 2H), 3.41-3.46 (m, 2H), 2.61-2.65 (m, 1H), 1.32-2.18 (m, 14H).

61B: $^1$H NMR (400 MHz, MeOD-d$_4$) δ 9.14, 9.20 (two s, 1H), 7.82 (s, 1H), 7.59-7.70 (m, 2H), 7.28-7.32 (m, 1H), 5.92-5.94 (m, 1H), 3.67 (t, J=5.6 Hz, 2H), 3.53 (t, J=4.8 Hz, 2H), 3.35-3.47 (m, 2H), 2.61-2.66 (m, 1H), 1.27-2.15 (m, 14H).

Example 59: Synthesis of Compound 134

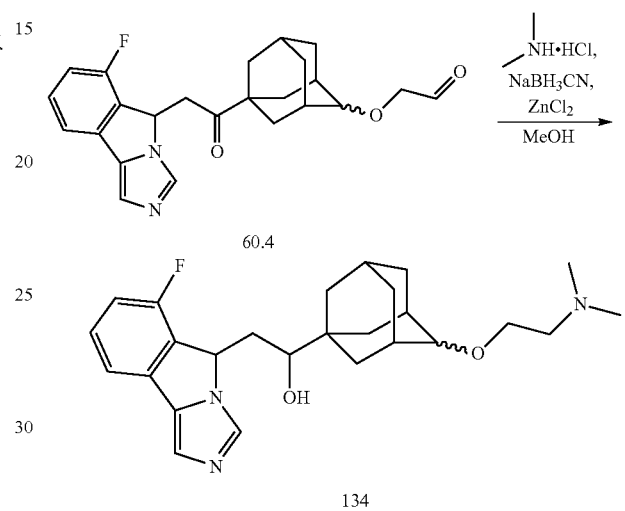

To a solution of compound 60.4 (20.00 mg, 0.049 mmol) in methanol (1 mL) was successively added dimethylamine hydrochloride (4.39 mg, 0.054 mmol), NaBH$_3$CN (3.39 mg, 0.054 mmol) and a catalytic amount of ZnCl$_2$. The resulted mixture was stirred at room temperature for 2 h, and then added NaBH$_4$ (5.51 mg, 0.147 mmol) to the mixture. The mixture was stirred at room temperature for 12 h. The reaction was quenched by addition of saturated ammonium chloride solution (5 mL), extracted with ethyl acetate (5 mL). The organic phase was washed with brine (5 mL), dried over sodium sulfate and concentrated to dryness. The residue was purified by pre-HPLC to afford compound 134 (TFA salt, 7.0 mg, yield: 35%) as a colorless oil.

$^1$H NMR (400 MHz, MeOD-d$_4$): δ 8.94-9.17 (m, 1H), 7.51-7.80 (m, 3H), 7.15-7.31 (m, 1H), 5.82-5.93 (m, 1H), 3.66-3.88 (m, 1H), 3.36-3.54 (m, 3H), 3.33 (s, 6H), 2.60-2.72 (m, 1H), 2.51-2.71 (m, 2H), 1.31-2.18 (m, 14H).

m/z: [M+H]$^+$ 440

Example 60: Synthesis of Compound 135

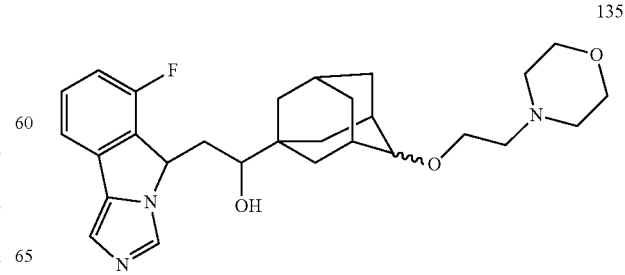

Compound 135 was prepared according to example 59 compound 134, by replacing dimethylamine hydrochloride to morpholine.

Compound 135 (a mixture of stereoisomers) was separated by pre-HPLC (Separation method: F) to afford 135A (the peak time: 9.0~10.3 min) and 135B (the peak time: 10.8-13.0 min).

m/z: [M+H]$^+$ 482.

135A: $^1$H NMR (400 MHz, MeOD-d$_4$): δ 9.14, 9.20 (two s, 1H), 7.82 (s, 1H), 7.59-7.73 (m, 2H), 7.28-7.34 (m, 1H), 5.92-6.12 (two m, 1H), 4.06 (s, 2H), 3.82-3.86 (m, 4H), 3.42-3.55 (m, 6H), 3.27-3.30 (overlapping with solvent, 2H), 2.55-2.65 (m, 1H), 1.32-2.23 (m, 14H).

135B: $^1$H NMR (400 MHz, MeOD-d$_4$): δ 9.14, 9.20 (two s, 1H), 7.83 (s, 1H), 7.59-7.73 (m, 2H), 7.28-7.34 (m, 1H), 5.92-6.11 (two m, 1H), 4.00 (s, 2H), 3.81-3.85 (m, 4H), 3.38-3.56 (m, 6H), 3.27-3.30 (overlapping with solvent, 2H), 2.59-2.62 (m, 1H), 1.26-2.23 (m, 14H).

Example 61: Synthesis of Compound 131

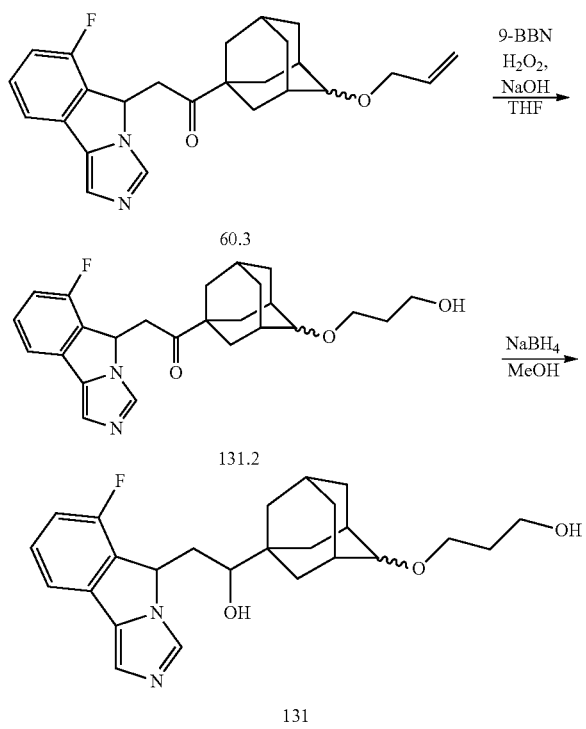

Step 1: Synthesis of Compound 131.2

A solution of compound 60.3 (300 mg, 0.74 mmol) in 9-borabicyclo[3.3.1]nonane (9-BBN) solution (6 mL, 0.5 M solution in THF) was stirred at 40° C. for 16 h. The resulted mixture was cooled down to 0° C., then added 33% H$_2$O$_2$ (2 mL) and an aqueous solution of sodium hydroxide (2 mL, 20%), the mixture was stirred at room temperature for 1 h. The reaction mixture was diluted with water (10 mL), extracted with ethyl acetate (20 mL×3). The combined organic phase was washed with brine, dried over sodium sulfate, filtered and concentrated to afford compound 131.2 (280 mg, yield: 89%) as a light yellow solid.

m/z: [M+H]$^+$ 425

Step 2: Synthesis of Compound 131

To an ice-cooling mixture of 131.2 (100 mg, 0.24 mmol) in methanol (2 mL), was added NaBH$_4$ (14 mg, 0.37 mmol). The resulted mixture was stirred at room temperature for 2 h, and then the reaction was quenched by addition of water (20 mL), extracted with ethyl acetate (20 mL×3). The combined organic phase was washed with brine, dried over sodium sulfate, filtered and concentrated to afford compound 131 (a mixture of stereoisomers), which was separated by pre-HPLC (Separation method: E) to afford 131A (13 mg, the peak time: 6.3-7.3 min) and 131B (5 mg, the peak time: 8.3-9.5 min). Both 131A and 131B were TFA salts.

m/z: [M+H]$^+$ 427

131A: $^1$H NMR (400 MHz, MeOD-d$_4$) δ 9.14, 9.20 (two s, 1H), 7.82 (s, 1H), 7.60-7.73 (m, 2H), 7.28-7.34 (m, 1H), 5.92-6.11 (two m, 1H), 3.65-3.70 (m, 2H), 3.53-3.58 (m, 2H), 3.38-3.45 (m, 1H), 2.88-2.98 (m, 1H), 2.51-2.65 (m, 1H), 2.32-2.37 (m, 1H), 1.23-2.08 (m, 15H).

131B: $^1$H NMR (400 MHz, MeOD-d$_4$) δ 9.13, 9.20 (two s, 1H), 7.82 (s, 1H), 7.60-7.72 (m, 2H), 7.28-7.34 (m, 1H), 5.92-6.11 (two m, 1H), 3.65-3.68 (m, 2H), 3.53-3.58 (m, 2H), 3.50-3.42 (m, 1H), 2.88-2.90 (m, 1H), 2.54-2.64 (m, 1H), 2.32-2.37 (m, 1H), 1.23-2.08 (m, 15H).

Example 62: Synthesis of Compound 132A/132B

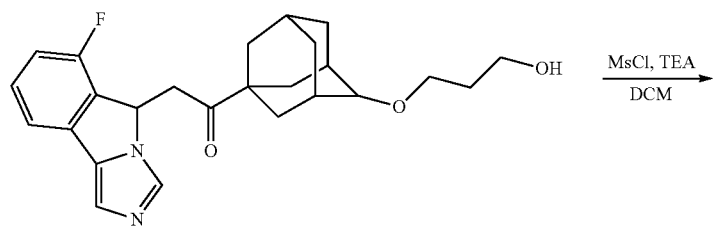

131.2

-continued
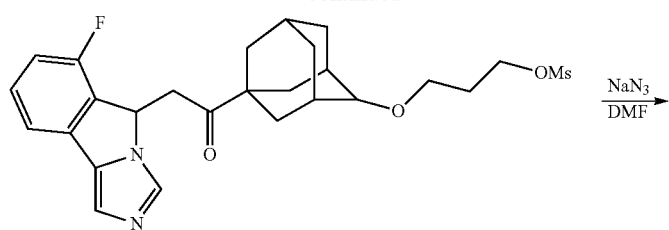# NaN₃ / DMF
132.2
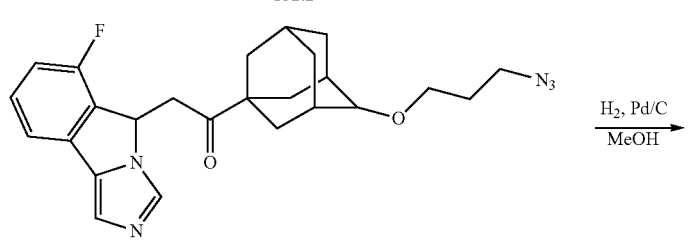# H₂, Pd/C / MeOH
132.3
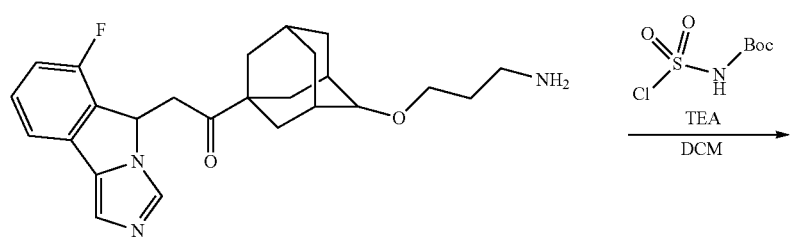# TEA / DCM
132.4
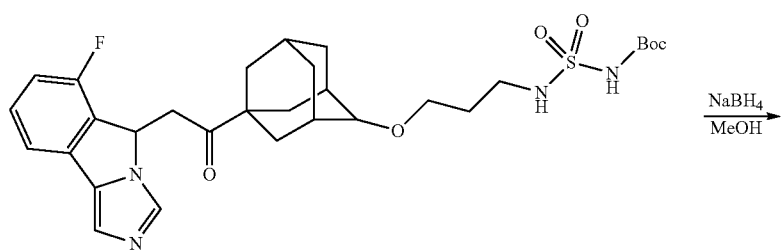# NaBH₄ / MeOH
132.5A/132.5B
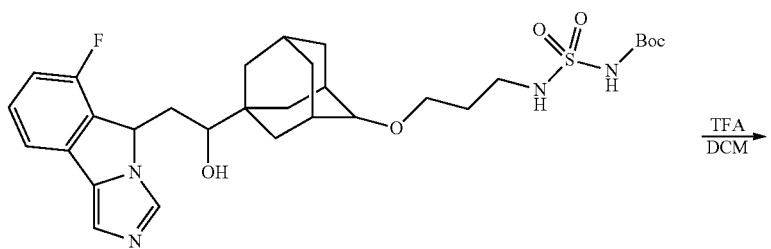# TFA / DCM
132.6A/132.6B
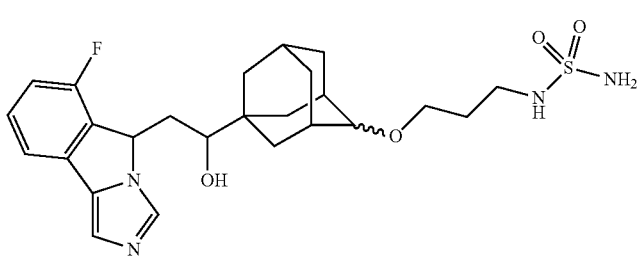
132A/132B

Step 1: Synthesis of Compound 132.2

To a solution of 131.2 (140 mg, 0.33 mmol) in dichloromethane (2 mL) was successively added TEA (100 mg, 0.99 mmol) and MsCl (45 mg, 0.40 mmol). The resulted mixture was stirred at room temperature for 1 h, then added water (10 mL), extracted with ethyl acetate (20 mL×3). The combined organic phase was washed with brine, dried over sodium sulfate, filtered and concentrated to afford compound 132.2 (140 mg, yield: 85%) as a light yellow solid.
m/z: [M+H]⁺ 503

Step 2: Synthesis of Compound 132.3

To a solution of 132.2 (140 mg, 0.28 mmol) in DMF (1.5 mL) was added sodium azide (90 mg, 1.39 mmol). The resulted mixture was stirred at room temperature for 2 h, then added water (20 mL), and extracted with ethyl acetate (20 mL×3). The combined organic phase was washed with brine, dried over sodium sulfate, filtered and concentrated. The residue was purified by pre-TLC (petroleum ether:ethyl acetate=3:1) to afford compound 132.3 (100 mg, yield: 80%) as a light yellow solid.
m/z: [M+H]⁺ 450

Step 3: Synthesis of Compound 132.4

To a solution of compound 132.3 (100 mg, 0.22 mmol) in methanol (2 mL), was added Pd/C (10 mg, 10%) and the mixture was stirred under hydrogen (1 atm) at room temperature for 16 h. The mixture was filtered through a celite pad, and the filtrate was concentrated to afford compound 132.4 (80 mg, 85%) as a light yellow solid.
m/z: [M+H]⁺ 424

Step 4: Synthesis of Compounds 132.5A and 132.5B

To a solution of 132.4 (80 mg, 0.33 mmol) in dichloromethane (2 mL) was successively added TEA (57 mg, 0.57 mmol) and tert-butyl chlorosulfonylcarbamate (49 mg, 0.22 mmol). The resulted mixture was stirred at room temperature for 1 h, then the mixture was directly purified by pre-TLC (petroleum ether:ethyl acetate=1:1) to afford compounds 132.5A (30 mg, more polar) and 132.5B (25 mg, less polar) as light yellow solids.
m/z: [M+H]⁺ 603

Step 5: Synthesis of Compound 132.6A/132.6B

To an ice-cooling solution of 132.5A (30 mg, 0.049 mmol) in methanol (1 mL) was added NaBH₄ (3 mg, 0.075 mmol). The resulted mixture was stirred at room temperature for 2 h, and then the reaction was quenched by addition of water (2 mL), extracted with ethyl acetate (10 mL×3). The combined organic phase was washed with brine, dried over sodium sulfate, filtered and concentrated, the residue was purified by pre-TLC (methanol:dichloromethane=20:1) to afford compound 132.6A (8 mg, yield: 26%) as an off-white solid. Compound 132.6B was prepared according to compound 132.6A, by using compound 132.5B.
m/z: [M+H]⁺ 605

Step 6: Synthesis of Compound 132A/132B

To an ice-cooling solution of compound 132.6A (8 mg, 0.013 mmol) in dichloromethane (1 mL) was added TFA (0.5 mL). The resulted mixture was stirred at room temperature for 2 h. The mixture was concentrated and the residue was lyophilized to afford compound 132A (7 mg, yield: 100%) as a light yellow solid. Compound 132B was prepared according to compound 132A, by using compound 132.6B.
m/z: [M+H]⁺ 505

132A: ¹H NMR (400 MHz, MeOD-d₄) δ 9.13, 9.19 (two s, 1H), 7.82 (s, 1H), 7.58-7.76 (m, 3H), 7.28-7.34 (m, 1H), 5.93-5.94 (m, 1H), 3.54-3.67 (m, 2H), 3.41-3.44 (m, 1H), 3.07-3.19 (m, 2H), 2.61-2.66 (m, 1H), 0.92-2.37 (m, 16H).

132B: 1HNMR (400 MHz, MeOD) δ 9.11, 9.19 (two s, 1H), 7.81 (s, 1H), 7.57-7.76 (m, 3H), 7.27-7.34 (m, 1H), 5.93-5.94 (m, 1H), 3.55-3.59 (m, 2H), 3.41-3.44 (m, 1H), 3.16-3.19 (m, 2H), 2.60-2.66 (m, 1H), 0.87-2.38 (m, 16H).

Example 63: Synthesis of Compounds 136 and 149

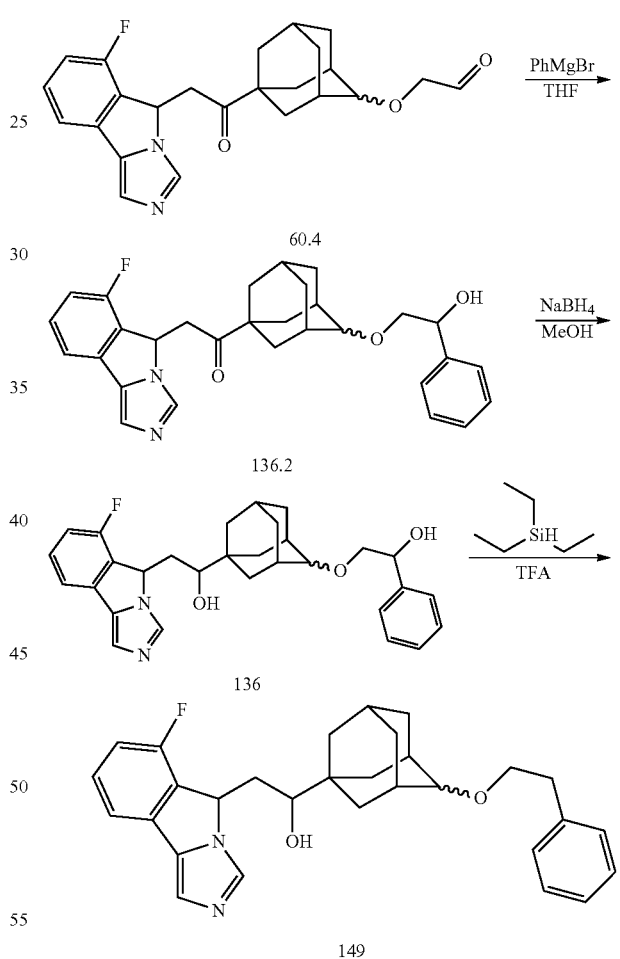

Step 1: Synthesis of Compound 136.2

To an ice-cooling solution of compound 60.4 (40.0 mg, 0.10 mmol) in THF (0.5 mL) was added phenylmagnesium bromide (0.5 mL, 0.5 mmol, 1.0 M solution in THF). The resulted mixture was stirred at 0° C. for 2 h. Then the reaction was quenched by addition of saturated ammonium chloride solution (5 mL), and extracted with ethyl acetate (5 mL), washed with brine (5 mL), dried over sodium sulfate and concentrated to afford compound 136.2 (45 mg, yield: 94%) as a light yellow solid.

Step 2: Synthesis of Compound 136

To an ice-cooling solution of compound 136.2 (45 mg, 0.092 mmol) in methanol (1.0 mL) was added NaBH$_4$ (19 mg, 0.5 mmol). The resulted mixture was stirred at room temperature for 12 h. Then the reaction was quenched by addition of saturated ammonium chloride solution (5 mL), and extracted with ethyl acetate (5 mL), washed with brine (5 mL), dried over sodium sulfate and concentrated to dryness. The residue was purified by pre-HPLC to afford compound 136 (TFA salt, 2.1 mg, yield: 5%) as a white solid.

$^1$H NMR (400 MHz, MeOD-d$_4$): δ 9.12, 9.16, 9.18 (three s, 1H), 7.81-7.85 (m, 1H), 7.58-7.74 (m, 2H), 7.24-7.40 (m, 5H), 6.99-7.19 (m, 1H), 5.85-6.09 (three m, 1H), 4.75-4.83 (m, 1H), 3.51-3.59 (m, 2H), 3.35-3.45 (m, 1H), 2.40-2.64 (m, 1H), 1.40-2.11 (m, 15H).

m/z: [M+H]$^+$ 489

Step 3: Synthesis of Compound 149

A solution of compound 136 (50 mg, 0.102 mmol) in triethylsilane (1.5 mL) was stirred at 0° C. for 10 min. Then trifluoroacetic acid (1.5 mL) was added drop-wise to the mixture at 0° C. The resulted mixture was stirred at room temperature for 1.5 h, and then concentrated to dryness. The residue was purified by pre-HPLC to afford compound 149 (TFA salt, 4.4 mg, yield: 9%) as a white foam.

$^1$H NMR (400 MHz, MeOD-d$_4$): δ 9.11, 9.14, 9.17 (three s, 1H), 7.88-7.77 (m, 1H), 7.75-7.55 (m, 2H), 7.39-7.11 (m, 5H), 7.08-6.83 (m, 1H), 6.12-5.78 (two m, 1H), 3.70-3.57 (m, 2H), 3.43-3.36 (m, 1H), 2.89-2.77 (m, 2H), 2.64-2.34 (m, 1H), 1.24-2.08 (m, 15H).

m/z: [M+H]$^+$ 473

Example 64: Synthesis of Compound 137

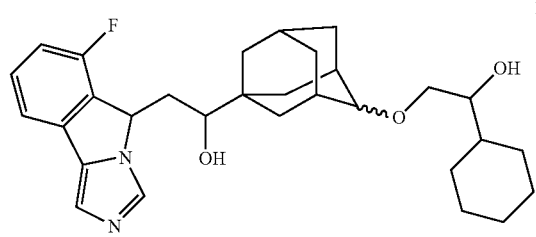

137

Compound 137 was prepared according to example 63 compound 136, by replacing phenylmagnesium bromide to cyclohexylmagnesium bromide (1.0 M solution in THF).

$^1$H NMR (400 MHz, MeOD-d$_4$): δ 9.14, 9.20 (two s, 1H), 7.83 (s, 1H), 7.59-7.73 (m, 2H), 7.29-7.33 (m, 1H), 5.93-6.12 (two m, 1H), 3.51-3.67 (m, 4H), 2.61-2.66 (m, 1H), 2.14-0.98 (m, 26H).

m/z: [M+H]$^+$ 495

Example 65: Synthesis of Compound 140

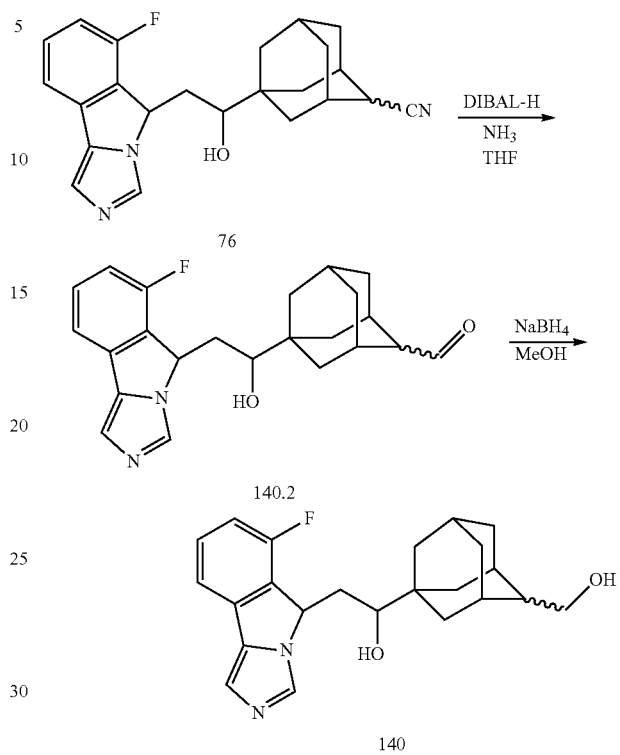

Step 1: Synthesis of Compound 140.2

To an ice-cooling solution of compound 76 (40.0 mg, 0.106 mmol) in anhydrous THF (3 mL) was added diisobutylaluminium hydride (0.7 mL, 1.0 M solution in toluene) under N$_2$. The mixture was stirred at 50° C. for 2.5 h. Then the reaction mixture was poured into saturated ammonium chloride solution (10 mL), and extracted with ethyl acetate (5 mL×3). The combined organic phase was washed with saturated sodium bicarbonate solution (5 mL) and brine (5 mL), dried over sodium sulfate, filtered through a celite pad, the filtrate was concentrated to afford compound 140.2 (30 mg, yield: 74%) as a yellow solid.

m/z: [M+H]$^+$ 381

Step 2: Synthesis of Compound 140

To an ice-cooling solution of compound 140.2 (30.0 mg, 0.079 mmol) in methanol (5 mL) was added NaBH$_4$ (11.9 mg, 0.315 mmol) portion-wise. The mixture was stirred at room temperature for 30 min. And then the reaction was quenched by the addition of water (10 mL), extracted with ethyl acetate (10 mL×3). The combined organic phase was washed with brine, dried over sodium sulfate, filtered and concentrated to dryness. The residue was purified by pre-HPLC to afford compound 140 (TFA salt, 7.4 mg, yield: 19%) as a white foam.

$^1$H NMR (400 MHz, MeOD-d$_4$): δ 9.03-9.20 (m, 1H), 7.79 (s, 1H), 7.65-7.71 (m, 1H), 7.56-7.64 (m, 1H), 7.24-7.33 (m, 1H), 6.04-6.11 (m, 1H), 3.62-3.68 (m, 1H), 3.51-3.60 (m, 1H), 2.86-2.98 (m, 1H), 2.47-2.66 (m, 1H), 2.15-2.36 (m, 1H), 1.30-2.06 (m, 14H).

m/z: [M+H]$^+$ 383

Example 66: Synthesis of Compound 62

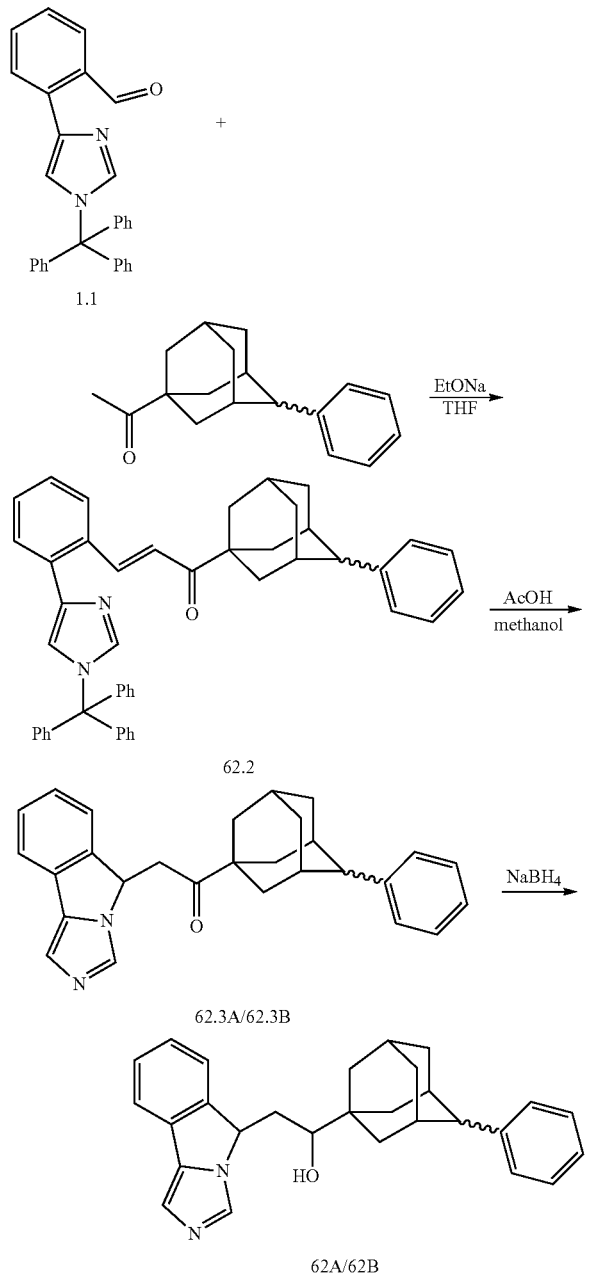

Step 1: Synthesis of Compound 62.2

To a solution of 1-(4-phenyladamantan-1-yl)ethanone (127 mg, 0.5 mmol) in a mixed solvent of ethanol (1 mL) and THF (4 mL) was successively added sodium ethoxide (70 mg, 1.0 mmol) and compound 1.1 (414 mg, 1.0 mmol). The resulted mixture was stirred at 60° C. for 2 h, then cooled down to room temperature. The mixture was added water (20 mL), extracted with ethyl acetate (10 mL×2). The combined organic phase was washed with brine, dried over sodium sulfate, filtered and concentrated, the residue was purified by column chromatography on silica gel (petroleum ether:ethyl acetate=3:1) to afford compound 62.2 (260 mg, yield: 80%) as a yellow solid.

m/z: [M+H]$^+$ 651

Step 2: Synthesis of Compounds 62.3A and 62.3B

A solution of compound 62.2 (210 mg, 0.33 mmol) in a mixed solvent of acetic acid (1 mL) and methanol (4 mL) was stirred at 60° C. for 2 h, and then cooled down to room temperature. The mixture was added water (20 mL), extracted with ethyl acetate (20 mL×2). The combined organic phase was washed with brine, dried over sodium sulfate, filtered and concentrated to afford compound 62.3 (a mixture of stereoisomers), which was separated by column chromatography on silica gel (dichloromethane:methanol=15:1) to afford 62.3A (80 mg, less polar) and 62.3B (25 mg, more polar).

m/z: [M+H]$^+$ 409

Step 3: Synthesis of Compound 62A/62B

To a solution of compound 62.2A (80 mg, 0.19 mmol) in ethanol (3 mL) was added NaBH$_4$ (14.4 mg, 0.38 mmol) in small portions. The resulted mixture was stirred at room temperature for 1 h, and then the reaction was quenched by addition of water (5 mL), extracted with ethyl acetate (3 mL×2). The combined organic phase was washed with brine, dried over sodium sulfate, filtered and concentrated to afford crude compound 62A, then washed with cold methanol to afford compound 62A (68.5 mg, yield: 85%) as a white solid.

Compound 62B was prepared according to compound 62A, by using compound 62.2B as a starting material to afford compound 62B (23.8 mg) as a white solid.

m/z: [M+H]$^+$ 411

62A: $^1$H NMR (400 MHz, MeOD-d$_4$): δ 9.09, 9.21 (two s, 1H), 7.74-7.85 (m, 1H), 7.68-7.75 (m, 2H), 7.48-7.56 (m, 2H), 7.25-7.35 (m, 4H), 7.08-7.11 (m, 1H), 5.68-5.74 (m, 1H), 3.66-3.72 (m, 1H), 2.84 (s, 1H), 2.56 (s, 2H), 2.29-2.34 (m, 1H), 2.16-2.25 (m, 1H), 1.61-1.97 (m, 9H), 1.48-1.50 (m, 2H).

62B: $^1$H NMR (400 MHz, MeOD-d$_4$): δ 7.99, 8.05 (two s, 1H), 7.55-7.65 (m, 2H), 7.27-7.49 (m, 6H), 7.12-7.20 (m, 2H), 5.46-5.55 (m, 1H), 3.49-3.57 (m, 1H), 3.04 (s, 1H), 2.58 (s, 2H), 2.05-2.26 (m, 2H), 1.61-1.95 (m, 9H), 1.46-1.52 (m, 2H).

Example 67: Synthesis of Compound 141

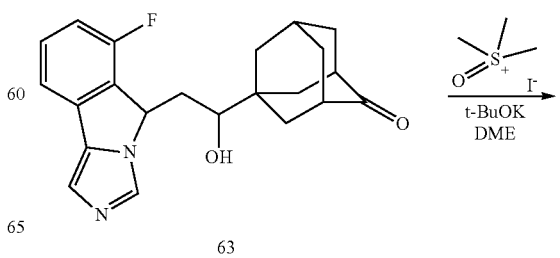

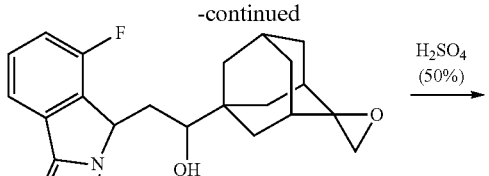

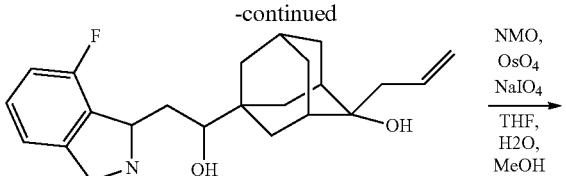

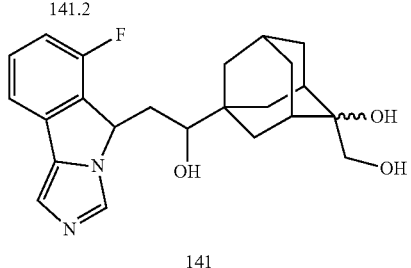

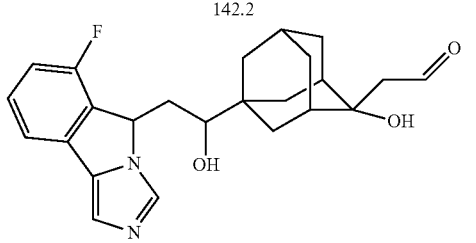

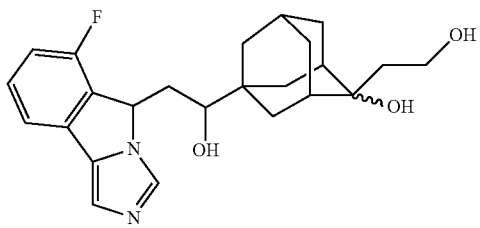

Step 1: Synthesis of 141.2

A mixture of compound 63 (100 mg, 0.273 mmol), trimethylsulfoxonium iodide (180 mg, 0.819 mmol) and potassium tert-butanolate (122 mg, 1.09 mmol) in 1, 2-dimethoxyethane (2 mL) was stirred at refluxed for 18 h, then the mixture was cooled down to room temperature and diluted with water. The organic phase was separated and the aqueous phase was extracted with dichloromethane (10 mL×2). The combined organic phase was washed with brine (15 mL), dried over sodium sulfate, filtered and concentrated to afford compound 141.2 (90 mg, yield: 87%) as a yellow solid.

m/z: [M+H]$^+$ 381

Step 2: Synthesis of 141

A solution of compound 141.2 (40 mg, 0.113 mmol) in 50% H$_2$SO$_4$ mL) was stirred at room temperature for 3 h. Then the mixture was diluted with ice water (10 mL), adjusted pH=8 with solid sodium bicarbonate, and extracted with ethyl acetate (10 mL×3). The combined organic phase was washed with brine (15 mL), dried over sodium sulfate, filtered and concentrated to dryness. The residue was purified by pre-HPLC to afford compound 141 (TFA salt, 1.53 mg, yield: 4%) as a white foam.

$^1$H NMR (400 MHz, MeOD-d$_4$): δ 9.02-9.16 (m, 1H), 7.78 (s, 1H), 7.56-7.71 (m, 2H), 7.25-7.32 (m, 1H), 5.88-6.12 (two m, 1H), 3.57-3.69 (m, 2H), 2.87-3.01 (m, 1H), 2.47-2.65 (m, 1H), 2.16-2.36 (m, 1H), 1.39-2.09 (m, 13H).

m/z: [M+H]$^+$ 399

Example 68: Synthesis of Compound 142

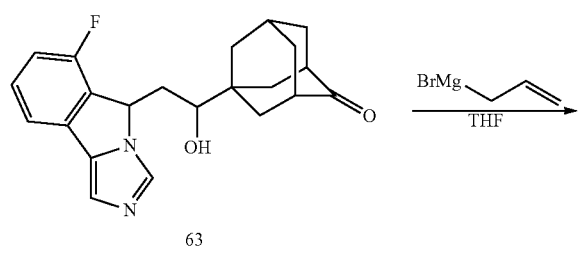

Step 1: Synthesis of Compound 142.2

To a solution of compound 63 (100 mg, 0.27 mmol) in THF (2 mL) was added allylmagnesium bromide (1.3 mL, 1.37 mmol, 1.0 M solution in THF). The resulted mixture was stirred at room temperature for 2 h, and then the reaction was quenched by addition of water (20 mL), extracted with ethyl acetate (20 mL×3). The combined organic phase was washed with brine, dried over sodium sulfate, filtered and concentrated to afford compound 142.2 (105 mg, yield: 94%) as a light yellow solid.

m/z: [M+H]$^+$ 409

Step 2&3: Synthesis of Compound 142

To a mixture of compound 142.2 (105 mg, 0.25 mmol) in a mixed solvent of THF (4 mL) and water (1 mL) was added NMO (58 mg, 0.50 mmol) and a catalytic amount of OsO$_4$. The resulted mixture was stirred at room temperature for 16 h, then the reaction mixture was added methanol (3 mL) and sodium periodate (159 mg, 0.75 mmol) and stirred at room temperature for 2 h, then added NaBH$_4$ (14 mg, 0.37 mmol). The resulted mixture was stirred at room temperature for 1 h, and then the reaction was quenched by addition of water (10 mL), extracted with ethyl acetate (20 mL×3). The combined organic phase was dried over sodium sulfate, filtered and concentrated, the residue was purified by pre-HPLC to afford compound 142 (TFA salt, 2.8 mg, yield: 3% for two steps) as a white foam.

$^1$H NMR (400 MHz, MeOD-d$_4$): δ 9.09, 9.16 (two s, 1H), 7.80 (s, 1H), 7.58-7.75 (m, 3H), 7.27-7.36 (m, 1H), 5.91 (m, 1H), 5.32-5.38 (m, 1H), 4.27-4.32 (m, 1H), 3.75-3.80 (m, 2H), 3.38-3.44 (m, 1H), 2.60-2.66 (m, 1H), 0.90-2.65 (m, 14H).

m/z: [M+H]$^+$ 413

Example 69: Synthesis of Compound 143

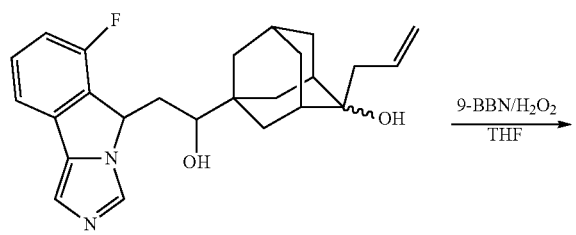

141

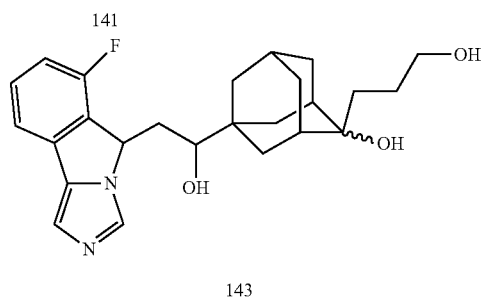

143

To an ice-cooling solution of compound 141 (480 mg, 1.1 mmol) in THF (10 mL) was added 9-BBN (2.2 mL, 2.2 mmol, 1.0 M solution in THF) drop wise. The resulted mixture was stirred at room temperature for 12 h, then successively added $H_2O_2$ (3 mL) and an aqueous solution of sodium hydroxide (3 mL, 20%). The resulted mixture was stirred at room temperature for 1 h and extracted with ethyl acetate (5 mL×3). The combined organic phase was washed with water (15 mL) and brine (5 mL), dried over sodium sulfate, filtered and concentrated to afford compound 143 (a mixture of stereoisomers), which was separated by pre-HPLC (Separation method: E) to afford 143A (10.1 mg, the peak time: 9.0-10.0 min) and 143B (15.5 mg, the peak time: 10.0-11.0 min) as white solids. Both 143A and 143B were TFA salts.

m/z: [M+H]$^+$ 427

143A: $^1$H NMR (400 MHz, MeOD-d$_4$): δ 9.15, 9.21 (two s, 1H), 7.83 (s, 1H), 7.64-7.59 (m, 2H), 7.29-7.34 (m, 1H), 7.19-7.40 (m, 1H), 5.93-6.11 (two m, 1H), 3.54-3.60 (m, 2H), 3.41-3.48 (m, 1H), 2.15-2.30 (m, 2H), 1.68-1.90 (m, 10H), 1.32-1.62 (m, 7H).

143B: $^1$H NMR (400 MHz, MeOD-d$_4$): δ 9.14, 9.21 (two s, 1H), 7.83 (s, 1H), 7.59-7.64 (m, 2H), 7.29-7.34 (m, 1H), 7.28-7.33 (m, 1H), 5.93-6.11 (two m, 1H), 3.46-3.58 (m, 2H), 3.38-3.45 (m, 1H), 1.77-2.06 (m, 11H), 1.26-1.62 (m, 8H).

Example 70: Synthesis of Compound 144

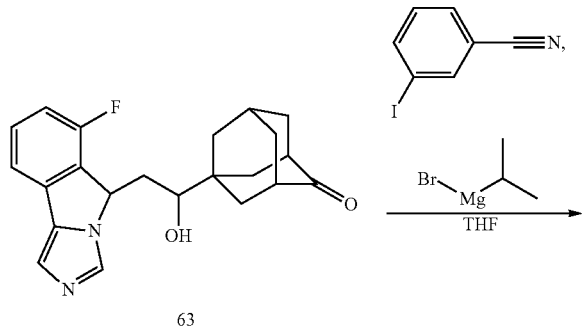

63

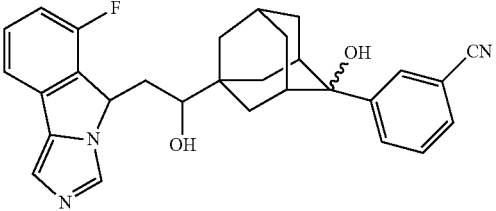

144

To an ice-cooling solution of 3-iodobenzonitrile (313 mg, 1.36 mmol) in THF (3 mL) was added isopropylmagnesium bromide (1.36 mL, 1.0 M solution in THF) drop wise. The mixture was stirred at 0° C. for 1.5 h, then a solution of compound 63 (0.1 g, 0.27 mmol) in THF (2 mL) was quickly added drop-wise to the mixture above. The resulted mixture was stirred at 0° C. for 30 min then warmed up to room temperature and stirred for 1 h. Then the mixture was cooled down to 0° C., and quenched by addition of saturated ammonium chloride solution (5 mL), extracted with dichloromethane (10 mL×3). The combined organic phase was dried over sodium sulfate, filtered and concentrated to afford compound 144 (a mixture of stereoisomers), which was separated by pre-HPLC (Separation method: F) to afford 144A (3.3 mg, the peak time: 13.8-14.2 min) and 144B (14.7 mg, the peak time: 14.3-16.5 min). Both 144A and 144B were TFA salts.

m/z: [M+H]$^+$ 470

144A: $^1$H NMR (400 MHz, MeOD-d$_4$): δ 8.99 (s, 1H), 7.80-7.89 (m, 2H), 7.74 (s, 1H), 7.60-7.68 (m, 2H), 7.47-7.60 (m, 2H), 7.22-7.31 (m, 1H), 5.95-6.03 (m, 1H), 2.75-2.81 (m, 1H), 2.57-2.66 (m, 2H), 2.38-2.47 (m, 2H), 2.15-2.23 (m, 1H), 1.95-2.07 (m, 2H), 1.35-1.67 (m, 8H).

144B: $^1$H NMR (400 MHz, MeOD-d$_4$): δ 9.08 (s, 1H), 7.83-7.89 (m, 2H), 7.74-7.77 (m, 1H), 7.60-7.66 (m, 2H), 7.52-7.60 (m, 2H), 7.21-7.29 (m, 1H), 5.78-5.86 (m, 1H), 2.60-2.69 (m, 2H), 2.38-2.51 (m, 3H), 1.98-2.07 (m, 2H), 1.82-1.92 (m, 1H), 1.40-1.69 (m, 8H).

Example 71: Synthesis of Compounds 145 and 146

Compounds 145~146 were prepared according to example 70 compound 144, by replacing 3-iodobenzonitrile to corresponding aryl or heteroaryl iodide as starting materials.

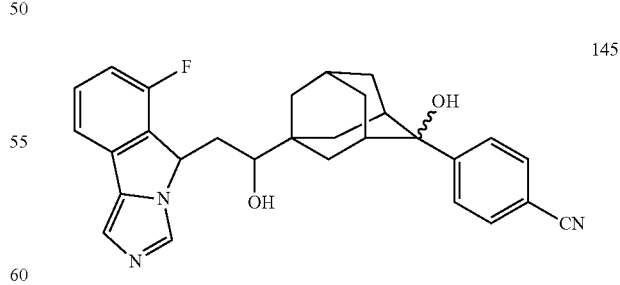

145

$^1$H NMR (400 MHz, MeOD-d$_4$): δ9.00 (s, 1H), 7.52-7.75 (m, 7H), 7.21-7.27 (m, 1H), 5.77-5.81 (m, 1H), 3.24-3.29 (m, 1H), 2.61-2.67 (m, 2H), 2.45-2.48 (m, 1H), 2.42-2.45 (m, 1H), 2.17-2.22 (m, 1H), 1.99-2.04 (m, 2H), 1.83-1.90 (m, 1H), 1.50-1.66 (m, 7H).

m/z: [M+H]$^+$ 470

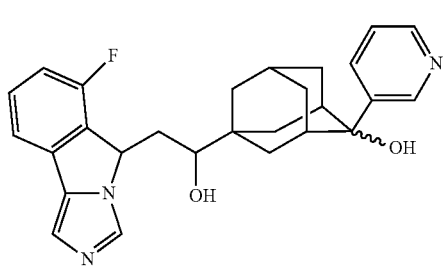

146

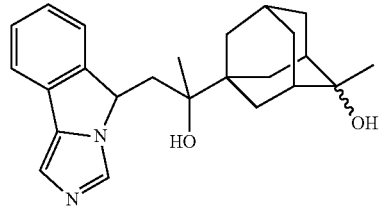

¹H NMR (400 MHz, MeOD-d₄): δ 9.01-9.24 (m, 1H), 8.57-9.00 (m, 3H), 7.91-8.15 (m, 1H), 7.19-7.86 (m, 4H), 5.80-6.05 (three m, 1H), 3.45-3.65 (m, 1H), 2.11-2.85 (m, 4H), 1.25-2.11 (m, 11H).

m/z: [M+H]⁺ 446

Example 72: Synthesis of Compound 147

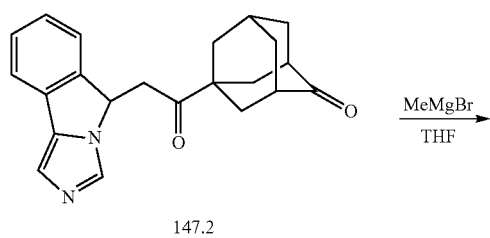

147.2

147

Compound 147.2 was prepared according to compound 43.2 in example 18 step 1, by using compound 10 as a starting material to afford compound 147.2 as a white solid.

To an ice-cooling solution of compound 147.2 (100 mg, 0.29 mmol) in THF (8 mL) was added methylmagnesium bromide (0.29 mL, 0.86 mmol, 3.0 M solution in diethyl ether). The resulted mixture was stirred at room temperature for 1 h, and then the reaction was quenched by addition of saturated ammonium chloride solution (10 mL), extracted with ethyl acetate (5 mL×2). The combined organic phase was washed with brine, dried over sodium sulfate, filtered and concentrated to afford compound 147 (a mixture of stereoisomers), which was separated by pre-HPLC (Separation method: E) to afford 147A (31.5 mg, the peak time: 9.5-11.5 min) and 147B (11.5 mg, the peak time: 12.7~15.1 min). Both 147A and 147B were TFA salts.

m/z: [M+H]⁺ 379

147A: ¹H NMR (400 MHz, MeOD-d₄): δ 9.12 (s, 1H), 7.74-7.86 (m, 1H), 7.62 (s, 1H), 7.51-7.59 (m, 3H), 5.79-5.81 (m, 1H), 2.15-2.22 (m, 4H), 1.69-1.97 (m, 3H), 1.39-1.50 (m, 6H), 1.29-1.39 (m, 8H).

147B: ¹H NMR (400 MHz, MeOD-d₄): δ 9.13 (s, 1H), 7.75-7.87 (m, 1H), 7.59 (s, 1H), 7.52-7.56 (m, 3H), 5.79-5.81 (m, 1H), 2.21-1.95 (m, 4H), 1.95-1.67 (m, 3H), 1.47-1.37 (m, 6H), 1.37-1.27 (m, 8H).

Example 73: Synthesis of Compound 148

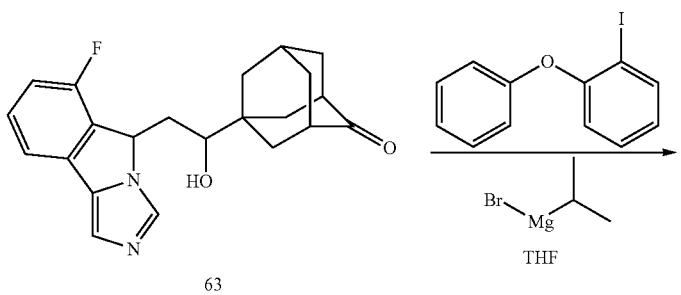

63

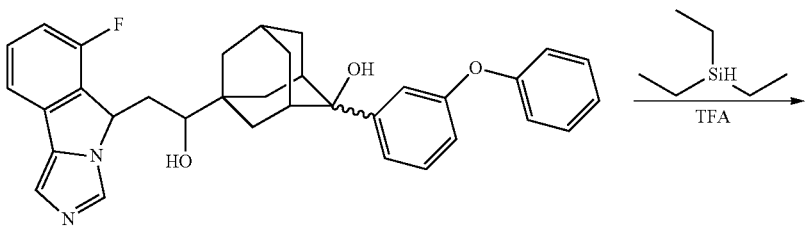

148.2

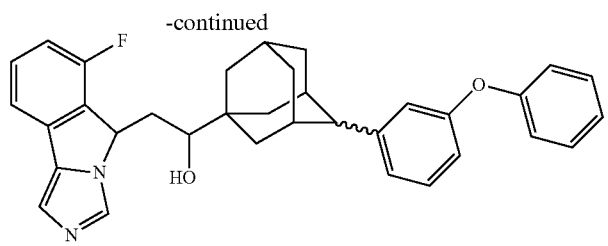

148

Step 1: Synthesis of Compound 148.2

To an ice-cooling mixture of 1-iodo-2-phenoxybenzene (0.404 g, 1.36 mmol) in THF (3 mL) was added isopropylmagnesium bromide (1.36 mL, 1.0 M solution in THF) drop-wise. After stirring at 0° C. for 1.5 h, a solution of compound 63 (100 mg, 0.27 mmol) in THF (2 mL) was quickly added drop-wise to the mixture above. The resulted mixture was stirred at 0° C. for 30 min, then slowly warmed up to room temperature and stirred for 1 h, the reaction mixture was once more cooled down to about 0° C., and saturated ammonium chloride solution (5 mL) was added. Then the solvent was evaporated. The aqueous residue that remained was diluted with water (10 mL), and the mixture was extracted with dichloromethane (10 mL×3). The combined organic phase was washed with brine and dried over sodium sulfate, filtered and concentrated to afford compound 148.2 (80 mg, yield: 55%) as a yellow solid.

m/z: [M+H]$^+$ 537

Step 2: Synthesis of Compound 148

To an ice-cooling solution of compound 148.2 (80 mg, 0.149 mmol) in triethylsilane (1.5 mL) was stirred at 0° C. for 10 min. Then trifluoroacetic acid (1.5 mL) was added drop-wise to the mixture at 0° C. The resulted mixture was stirred at room temperature for 1.5 h, and then concentrated to dryness. The residue was purified by pre-HPLC to afford compound 148 (TFA salt, 5.4 mg, yield: 7%) as a white foam.

$^1$H NMR (400 MHz, MeOD-d$_4$): δ 9.06-9.20 (m, 1H), 7.79 (s, 1H), 7.52-7.70 (m, 3H), 7.25-7.33 (m, 3H), 7.08-7.21 (m, 2H), 7.00-7.07 (m, 1H), 6.78-6.69 (m, 3H), 5.86-6.10 (two m, 1H), 3.33-3.41 (m, 1H), 3.03-3.15 (m, 1H), 2.58-2.66 (m, 1H), 2.42-2.53 (m, 2H), 1.48-2.07 (m, 12H).

m/z: [M+H]$^+$ 521

Example 74: Synthesis of Compound 150

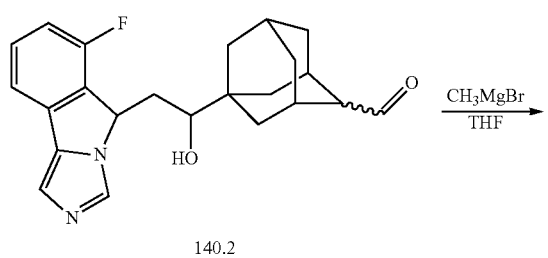

140.2

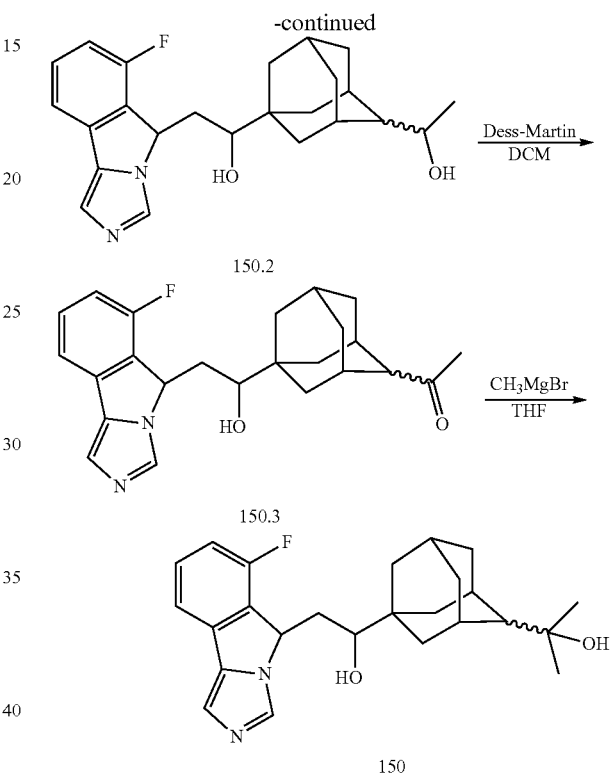

Step 1: Synthesis of 150.2

To an ice-cooling solution of compound 140.2 (58 mg, 0.153 mmol) in THF (2 mL) was added methylmagnesium bromide (0.16 mL, 0.488 mmol, 3.0 M solution in diethyl ether). The resulted mixture was stirred at room temperature for 1 h, and then the reaction was quenched by the addition of saturated ammonium chloride solution (5 mL), extracted with ethyl acetate (10 mL×3). The combined organic phase was washed with brine (15 mL), dried over sodium sulfate, filtered and concentrated to afford compound 150.2 (45 mg, yield: 74%) as a yellow solid.

m/z: [M+H]$^+$ 397

Step 2: Synthesis of 150.3

To an ice-cooling solution of compound 150.2 (45 mg, 0.113 mmol) in dichloromethane (5 mL) was added Dess-Martin periodinane (48 mg, 0.113 mmol). The resulted mixture was stirred at room temperature for 2 h, then filtered, the filtrate was added water (20 mL), extracted with dichloromethane (20 mL×2), the combined organic phase was washed with brine, dried over sodium sulfate, filtered and concentrated. The residue was purified by flash column chromatography on silica gel (0-10% solution of methanol in dichloromethane) to afford compound 150.3 (30 mg, yield: 67%) as a yellow solid.

m/z: [M+H]$^+$ 395

Step 3: Synthesis of 150

To an ice-cooling solution of compound 150.3 (30 mg, 0.076 mmol) in THF (2 mL) was added methylmagnesium bromide (0.08 mL, 0.243 mmol, 3.0 M solution in diethyl ether). The resulted mixture was stirred at room temperature for 1 h, and then the reaction was quenched by the addition of saturated ammonium chloride solution (5 mL), extracted with ethyl acetate (10 mL×3). The combined organic phase was washed with brine (15 mL), dried over sodium sulfate, filtered and concentrated to afford crude compound 150 (a mixture of cis/trans isomers), which was separated by pre-HPLC (Separation method: E) to afford 150A (1.8 mg, the peak time: 7.1-8.7 min) and 150 B (1.1 mg, the peak time: 10.7-12.2 min). Both 150A and 150B were TFA salts.

m/z: [M+H]$^+$ 411

Example 75: Synthesis of Compound 156

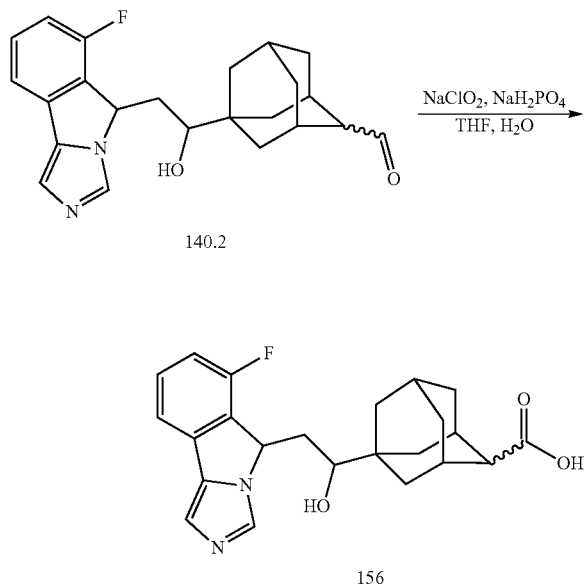

To a mixture of compound 140.2 (40 mg, 0.10 mmol), NaH$_2$PO$_4$ (19 mg, 1.5 mmol) and one drop of 2-Methyl-2-butene in a mixed solvent of THF (2 mL) and water (0.5 mL) was added NaClO$_2$ (14 mg, 1.1 mmol, dissolved in 0.5 mL H$_2$O) dropwise. The resulted mixture was stirred at room temperature for 2 h, and then the mixture was filtered, the filtrate was concentrated to afford compound 156 (a mixture of stereoisomers), which was purified by pre-HPLC (Separation method: F) to afford 156A (1.2 mg, the peak time: 8.5~10.5 min) and 156B (1.6 mg, the peak time: 11.5-14.0 min) as white foams. Both compounds 156A and 156B are TFA salts.

m/z: [M+H]$^+$ 397

Example 76: Synthesis of Compound 157

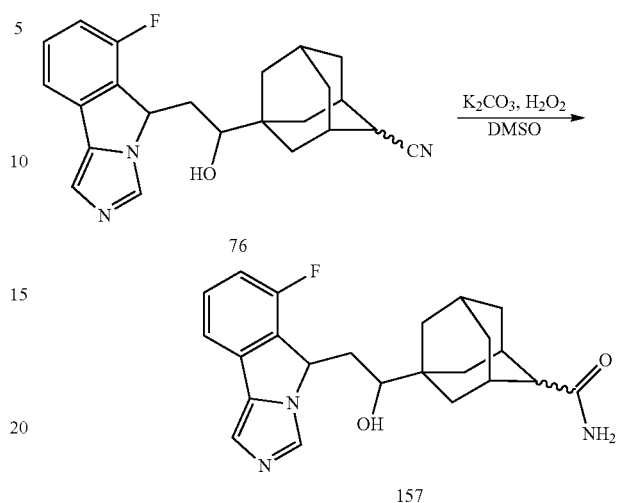

To an ice-cooling mixture of compound 76 (50 mg, 0.132 mmol) and K$_2$CO$_3$ (36 mg, 0.26 mmol) in DMSO (1.0 mL) was added H$_2$O$_2$ (0.8 mL) drop-wise. The reaction mixture was stirred at 0° C. for 2 h, and then the reaction was quenched by addition of saturated aqueous ammonium chloride solution, and the mixture was extracted with dichloromethane (5 mL×3). The combined organic phase was dried over sodium sulfate, filtered and concentrated to afford compound 157 (a mixture of stereoisomers), which was purified by pre-HPLC (Separation method: J) to afford compound 157A (3.3 mg, the peak time: 5.6-7.4 min) and 157B (7.8 mg, the peak time: 8.8-9.8 min) as white solids. Both compounds 157A and 157B are TFA salts.

m/z: [M+H]$^+$ 396

157A: $^1$H NMR (400 MHz, MeOD-d$_4$): δ 9.15, 9.22 (two s, 1H), 7.83 (s, 1H), 7.60-7.69 (m, 2H), 7.27-7.35 (m, 1H), 5.94-6.12 (two m, 1H), 3.36-3.46 (overlapping with solvent, 1H), 2.90-2.98 (m, 1H), 1.50-2.58 (m, 15H).

157B: $^1$H NMR (400 MHz, MeOD-d$_4$): δ 9.10, 9.18 (two s, 1H), 7.80 (s, 1H), 7.60-7.67 (m, 2H), 7.27-7.33 (m, 1H), 5.91-6.10 (two m, 1H), 3.34-3.38 (overlapping with solvent, 1H), 2.90-2.93 (m, 1H), 1.32-2.52 (m, 15H).

Example 77: Synthesis of Compound 158

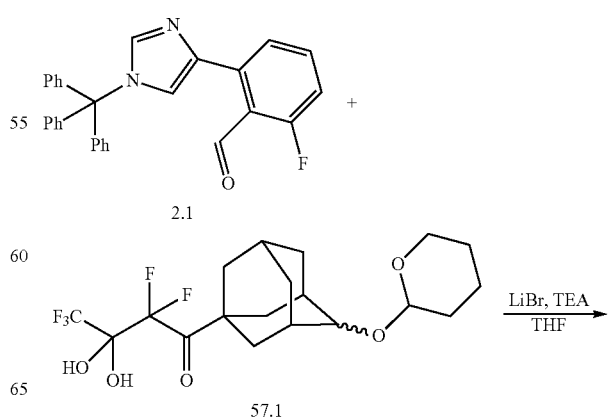

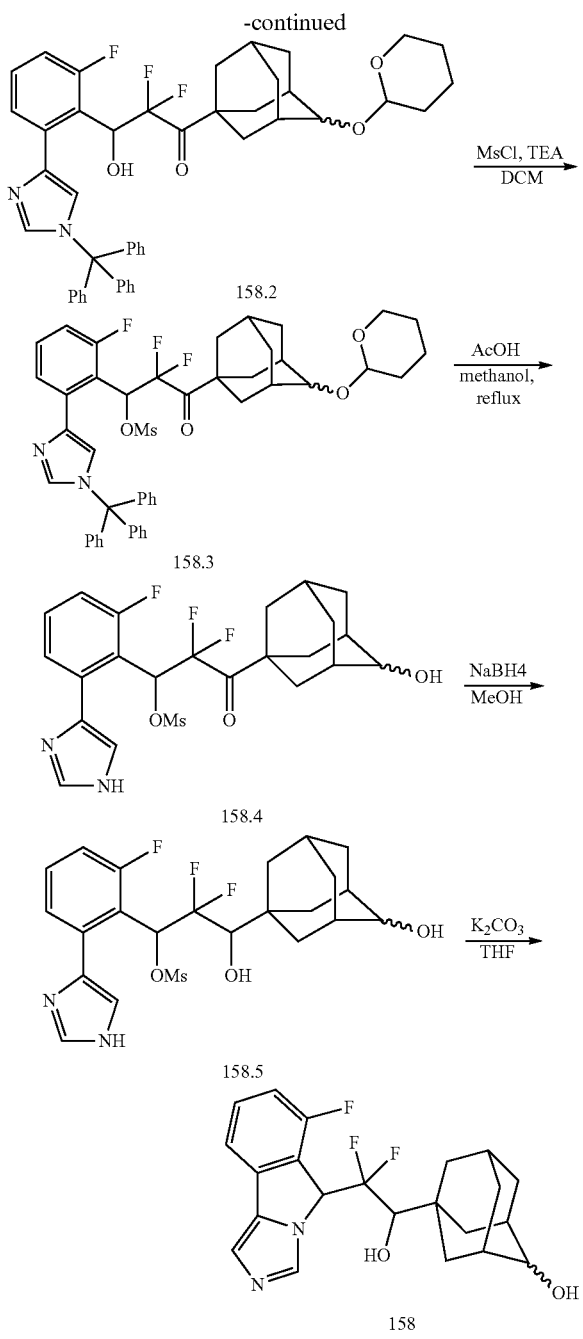

Step 1: Synthesis of Compound 158.2

To a mixture of compound 57.1 (400 mg, 0.93 mmol), compound 2.1 (808 mg, 1.87 mmol) and LiBr (243 mg, 2.80 mmol) in THF (5 mL) was added TEA (177 mg, 1.74 mmol) drop-wise. The resulted mixture was stirred at room temperature for 0.5 h, and then the reaction was quenched by addition of saturated ammonium chloride solution (10 mL) and extracted with ethyl acetate (10 mL×3). The combined organic phase was dried over sodium sulfate, filtered and concentrated, the residue was purified by column chromatography on silica gel (0-10% solution of ethyl acetate in petroleum ether) to afford compound 158.2 (170 mg, yield: 24%) as a yellow white solid.

m/z: [M+H]$^+$ 747

Step 2: Synthesis of Compound 158.3

To an ice-cooling solution of compound 158.2 (1660 mg, 0.22 mmol) and TEA (67 mg, 0.67 mmol) in DCM (5 mL) was added MSCl (31 mg, 0.27 mmol) drop-wise. The resulted mixture was stirred at room temperature for 1 h, and then washed with water (5 mL), brine (5 mL), dried over sodium sulfate, filtered and concentrated to afford compound 158.3 (160 mg, yield: 87%) as a white solid.

m/z: [M+H]$^+$ 825

Step 3: Synthesis of Compound 158.4

A solution of compound 158.3 (160 mg, 0.194 mmol) and acetic acid (0.5 mL) in methanol (2 mL) was stirred at 90° C. overnight, then the resulted mixture was concentrated. The residue was added saturated sodium bicarbonate solution (10 mL) and extracted with ethyl acetate (10 mL×3). The combined organic phase was washed with brine (15 mL), dried over sodium sulfate, filtered and concentrated. The residue was purified by pre-TLC (dichloromethane:methanol=10:1) to afford compound 158.4 (80 mg, yield: 83%) as a yellow solid.

m/z: [M+H]$^+$ 499

Step 4: Synthesis of Compound 158.5

To an ice-cooling solution of compound 158.4 (45 mg, 0.093 mmol) in methanol (5 mL) was added NaBH$_4$ (13.7 mg, 0.361 mmol) in small portions. The resulted mixture was stirred at room temperature for 30 min. And then the reaction was quenched by the addition of water (10 mL), extracted with ethyl acetate (10 mL×3). The combined organic phase was washed with brine, dried over sodium sulfate, filtered and concentrated to afford compound 158.5 (40 mg, yield: 88%) as a yellow solid.

m/z: [M+H]$^+$ 501

Step 5: Synthesis of Compound 158

A mixture of compound 158.5 (40 mg, 0.08 mmol) and K$_2$CO$_3$ in THF (2 mL) was stirred at 60° C. for 5 h under N$_2$. Then the reaction was quenched by the addition of ice water (10 mL), extracted with ethyl acetate (10 mL×3). The combined organic phase was washed with brine, dried over sodium sulfate, filtered and concentrated. The residue was purified by pre-HPLC to afford compound 158 (TFA salt, 1.6 mg, yield: 5%) as a white foam.

$^1$H NMR (400 MHz, MeOD-d$_4$): δ 8.88, 8.97 (two s, 1H), 7.28-7.74 (m, 4H), 6.00-6.29 (two m, 1H), 4.04-4.47 (two m, 1H), 3.63-3.80 (two m, 1H), 1.39-2.23 (m, 13H).

m/z: [M+H]$^+$ 405

Example 78: Synthesis of Compound 161

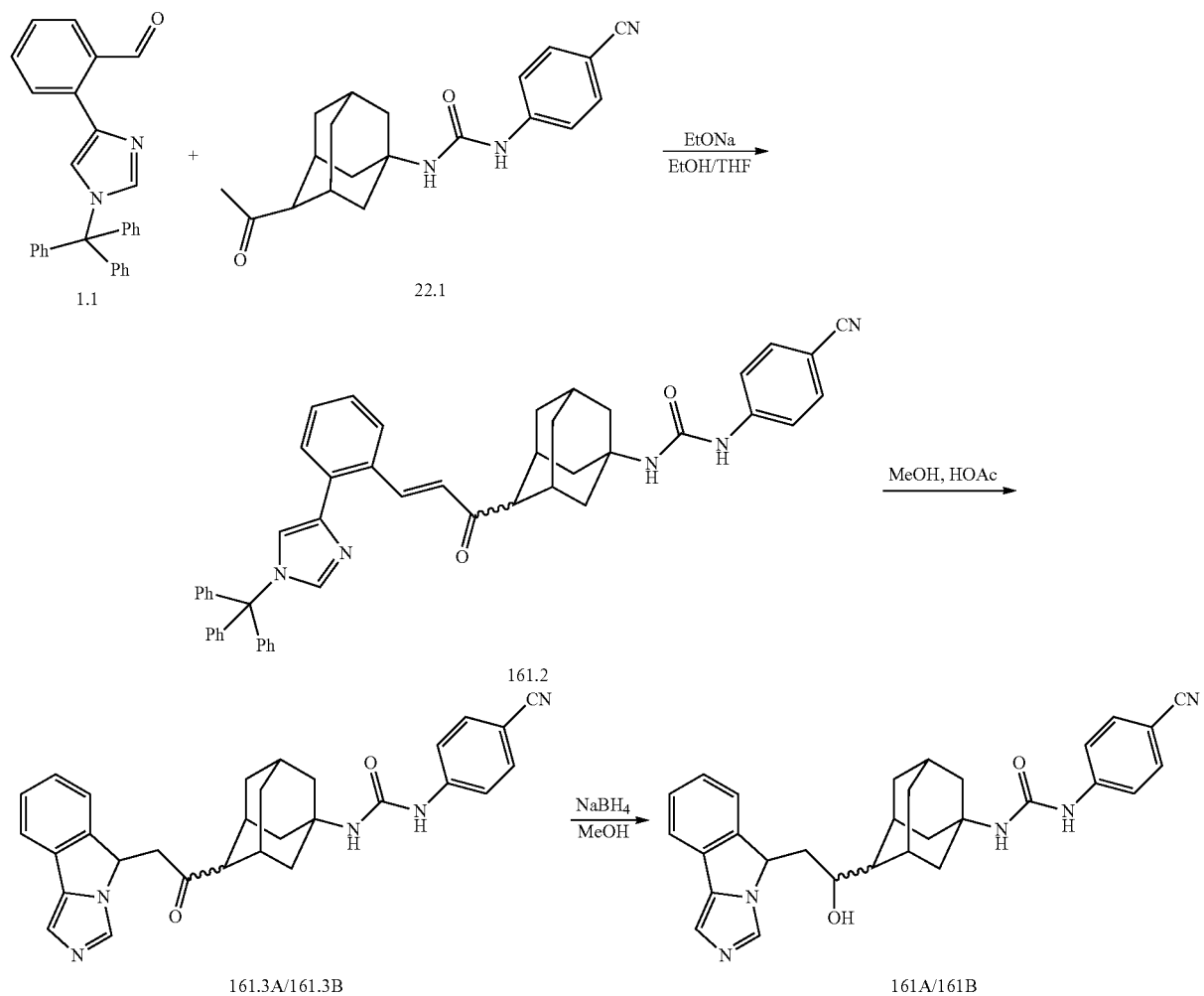

Step 1: Synthesis of Compound 161.2

To a solution of 1-(4-acetyladamantan-1-yl)-3-(4-cyanophenyl)urea (406 mg, 1.2 mmol) and compound 1.1 (500 mg, 1.2 mmol) in THF (30 mL) was added a solution of sodium ethylate (163 mg, 2.4 mmol) in ethanol (5.0 mL) at room temperature. The resulted mixture was stirred at room temperature for overnight, and then the reaction was quenched by addition of cold water (25 mL), extracted with ethyl acetate (2×30 mL). The combined organic phase was washed with brine (25 mL), dried over sodium sulfate and concentrated. The residue was purified by flash column chromatography on silica gel (0~50% solution of ethyl acetate in petroleum ether) to afford compound 161.2 (550 mg, yield: 62%) as a pale yellow solid.

m/z: [M+H]$^+$ 734

Step 2: Synthesis of Compounds 161.3A and 161.3B

A mixture of compound 161.2 (550 mg, 0.75 mmol) in a mixed solvent of methanol (24 mL) and acetic acid (4.0 mL) was stirred at 90° C. for 3 h, then the mixture was concentrated to afford the crude compound 161.3 (a mixture of stereoisomers), which was purified by flash column chromatography on silica gel (0~3% solution of methanol in dichloromethane) to afford 161.3A (150 mg, less polar, yield 41%) and 161.3B (125 mg, more polar, yield 34%) as pale yellow solids.

m/z: [M+H]$^+$ 492

Step 3: Synthesis of Compound 161A/161B

To an ice-cooling solution of compound 161.3A (150 mg, 0.30 mmol) in methanol (5.0 mL) was added NaBH$_4$ (23 mg, 0.61 mmol). After stirring for 30 min, the reaction was quenched by addition of cold water (20 mL). The precipitation was filtered, washed with cold water, dried under vacuum to afford compound 161A (109 mg, yield 72%) as a white solid. Compound 161B was prepared according to the synthesis of compound 161A, by using compound 161.3B (125 mg, 0.25 mmol) to afford compound 161B (94 mg, yield: 75%) as a white solid.

m/z: [M+H]$^+$ 494

161A: $^1$HNMR (400 MHz, DMSO-d$_6$): δ 9.62 (br s, 1H), 8.77 (s, 1H), 7.94, 7.99 (two s, 1H), 7.75 (d, J=8.8 Hz, 1H), 7.60-7.69 (m, 4H), 7.52-7.54 (m, 1H), 7.36-7.40 (m, 1H), 7.28-7.30 (m, 1H), 7.12 (s, 1H), 6.08 (s, 1H), 5.44-5.46 (m, 1H), 5.08-5.06 (m, 1H), 4.12-4.14 (m, 1H), 2.52 (br, s, 1H), 2.32 (br, s, 1H), 1.23-2.02 (m, 12H).

161B: ¹HNMR (400 MHz, DMSO-d₆): δ 8.79 (s, 1H), 7.94, 7.98 (two s, 1H), 7.60-7.65 (m, 4H), 7.49-7.51 (m, 2H), 7.39-7.41 (m, 1H), 7.28-7.30 (m, 1H), 7.12, 7.16 (two s, 1H), 6.12 (s, 1H), 5.44-5.46 (m, 1H), 5.01-5.03 (m, 1H), 4.06-4.08 (m, 1H), 2.48 (br, s, 1H), 1.28-1.98 (m, 13H).

Example 79: Synthesis of Compounds 162A~170A, 162B-170B

Compounds 162A-170A, 162B-170B were prepared according to example 78 compounds 161A and 161B, by replacing 1-(4-acetyladamantan-1-yl)-3-(4-cyanophenyl)urea to corresponding acetyladamantan derivative (compounds 23.1-25.1, 31.1, 33.1, 36.1-38.1).

162A/162B

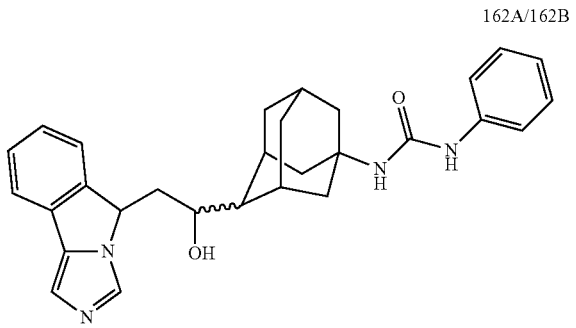 [SMILES: O=C(Nc1ccccc1)NC12CC3CC(C1)C(C(O)CC1c4ccccc4-c4cncn41)C(C3)C2]

The HCl salts of 162A and 162B were prepared according to the preparation method of compound 1-A.

m/z: [M+H]⁺ 467

162A (HCl salt): ¹H NMR (400 MHz, DMSO-d₆): δ 14.56 (br, s, 1H), 9.37, 9.42 (two s, 1H), 8.53, 8.56 (two s, 1H), 7.93, 7.95 (two s, 1H), 7.84-7.93 (m, 2H), 7.53-7.57 (m, 2H), 7.36-7.38 (m, 2H), 7.18-7.22 (m, 2H), 6.86 (t, J=7.6 Hz, 1H), 6.11 (s, 1H), 5.86 (t, J=6.4 Hz, 1H), 4.20 (t, J=4.8 Hz, 1H), 2.39-1.33 (m, 15H).

162B (HCl salt): ¹H NMR (400 MHz, DMSO-d₆): δ 14.45 (br, s, 1H), 9.42, 9.36 (two s, 1H), 8.42, 8.43 (two s, 1H), 7.93, 7.95 (two s, 1H), 7.89-7.78 (m, 2H), 7.57-7.55 (m, 2H), 7.34-7.32 (m, 2H), 7.16-7.20 (m, 2H), 6.85 (t, J=7.2 Hz, 1H), 6.03 (s, 1H), 5.85 (t, J=6.8 Hz, 1H), 4.16 (t, J=4.8 Hz, 1H), 1.48-2.15 (m, 15H).

163A/163B

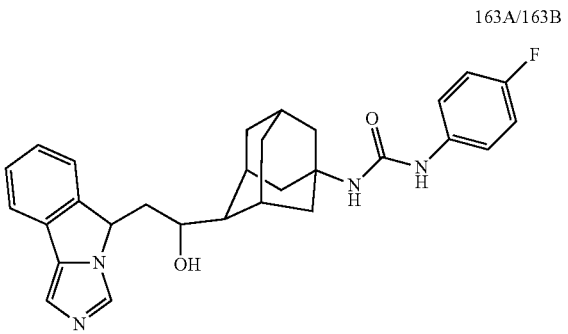 [SMILES: O=C(Nc1ccc(F)cc1)NC12CC3CC(C1)C(C(O)CC1c4ccccc4-c4cncn41)C(C3)C2]

The HCl salts of 163A and 163B were prepared according to the preparation method of compound 1-A.

m/z: [M+H]⁺ 487

163A (HCl salt): ¹H NMR (400 MHz, DMSO-d₆): δ 14.51 (br, s, 1H), 9.36, 9.40 (two s, 1H), 8.57, 8.59 (two s, 1H), 7.93 (s, 1H), 7.83-7.88 (m, 2H), 7.53-7.57 (m, 2H), 7.35-7.38 (m, 2H), 7.02-7.07 (m, 2H), 6.05 (s, 1H), 5.85 (t, J=6.4 Hz, 1H), 4.19 (t, J=4.8 Hz, 1H), 1.45-2.39 (m, 15H).

163B (HCl salt): ¹H NMR (400 MHz, DMSO-d₆): δ 14.60 (br, s, 1H), 9.38, 9.48 (two s, 1H), 8.63, 8.64 (two s, 1H), 7.94, 7.93 (two s, 1H), 7.87-7.89 (m, 2H), 7.54-7.56 (m, 2H), 7.32-7.36 (m, 2H), 7.00-7.04 (m, 2H), 6.10 (s, 1H), 5.86 (t, J=6.0 Hz, 1H), 4.16 (t, J=4.8 Hz, 1H), 2.35 (s, 1H), 1.24-2.12 (m, 14H).

164A/164B

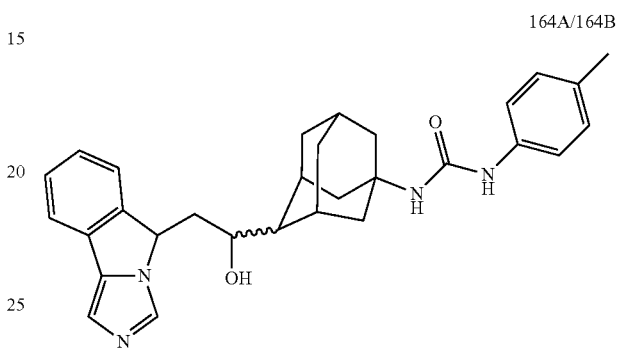

The HCl salts of 164A and 164B were prepared according to the preparation method of compound 1-A.

m/z: [M+H]⁺ 483

164A (HCl salt): ¹H NMR (400 MHz, DMSO-d₆): δ 14.55 (br s, 1H), 9.36, 9.38 (two s, 1H), 8.35 (s, 1H), 7.93 (s, 1H), 7.83-7.88 (m, 2H), 7.51-7.58 (m, 2H), 7.25 (d, J=8.0 Hz, 2H), 7.02-7.0 (d, J=8.4 Hz, 2H), 5.98 (s, 1H), 5.85 (t, J=13.2 Hz, 1H), 5.31-5.34 (m, 1H), 4.16-4.21 (m, 1H), 2.29-2.38 (m, 2H), 2.21 (s, 3H), 1.23-2.16 (m, 12H).

164B (HCl salt): ¹H NMR (400 MHz, DMSO-d₆): δ 14.55 (br s, 1H), 9.36, 9.45 (two s, 1H), 8.39 (s, 1H), 7.92 (s, 1H), 7.86-7.89 (m, 1H), 7.78-7.80 (m, 1H), 7.52-7.58 (m, 2H), 7.22 (d, J=8.8 Hz, 2H), 6.99 (d, J=8.4 Hz, 2H), 6.03 (s, 1H), 5.85 (t, J=13.2 Hz, 1H), 5.31-5.34 (m, 1H), 4.12-4.18 (m, 1H), 2.26-2.35 (m, 2H), 2.19 (s, 3H), 1.23-2.14 (m, 13H).

165A/165B

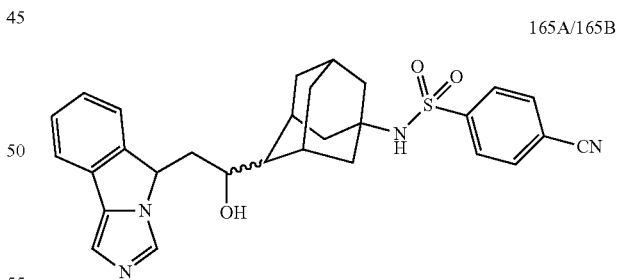

m/z: [M+H]⁺ 515

165A: ¹H NMR (400 MHz, DMSO-d₆): δ 7.87-8.07 (m, 5H), 7.56-7.64 (m, 2H), 7.22-7.47 (m, 2H), 7.11, 7.13 (two s, 1H), 5.40-5.43 (m, 1H), 5.04 (d, J=6.8 Hz, 1H), 3.89-3.96 (m, 1H), 2.31 (s, 1H), 1.92-2.04 (m, 3H), 1.24-1.75 (m, 12H).

165B: ¹H NMR (400 MHz, DMSO-d₆): δ 7.86-8.08 (m, 5H), 7.58 (t, J=8.0 Hz, 2H), 7.25-7.39 (m, 2H), 7.11, 7.13 (two s, 1H), 5.39-5.42 (m, 1H), 4.96 (d, J=6.8 Hz, 1H), 3.96-4.02 (m, 1H), 2.26 (s, 1H), 1.66-2.00 (m, 9H), 1.13-1.39 (m, 6H).

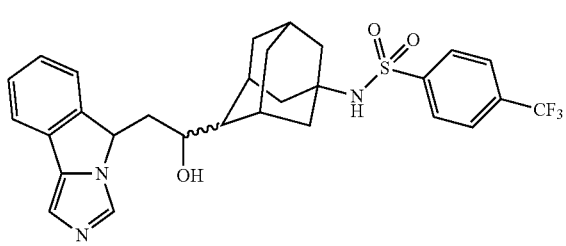

166A/166B

The HCl salts of 166A and 166B were prepared according to the preparation method of compound 1-A.

m/z: [M+H]$^+$ 558

166A (HCl salt): $^1$H NMR (400 MHz, DMSO-d$_6$): δ 7.86-8.06 (m, 6H), 7.58 (t, J=8.0 Hz, 2H), 7.37 (t, J=7.6 Hz, 1H), 7.25-7.29 (m, 1H), 7.10, 7.13 (two s, 1H), 5.39-5.46 (m, 1H), 4.94, 5.02 (two d, J=7.6 Hz, 1H), 3.96-4.02 (m, 1H), 2.26 (s, 1H), 1.92-2.02 (m, 1H), 1.68-1.86 (m, 9H), 1.11-1.39 (m, 5H).

166B (HCl salt): $^1$H NMR (400 MHz, DMSO-d$_6$): δ 9.33, 9.37 (two s, 1H), 7.85-8.03 (m, 6H), 7.75-7.79 (m, 1H), 7.53-7.62 (m, 2H), 5.80-5.84 (m, 1H), 3.99-4.01 (m, 1H), 2.31-2.34 (m, 1H), 1.78-2.08 (m, 6H), 1.24-1.63 (m, 10H).

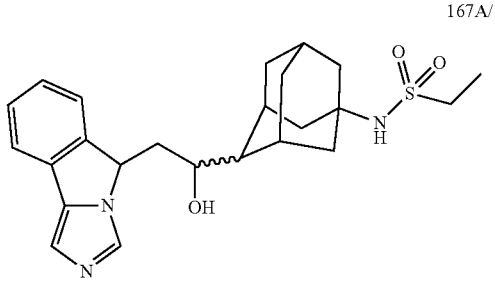

167A/167B

The HCl salts of 167A and 167B were prepared according to the preparation method of compound 1-A.

m/z: [M+H]$^+$ 442

167A (HCl salt): $^1$H NMR (400 MHz, CDCl$_3$-d): δ 7.82, 7.99 (two s, 1H), 7.57 (d, J=7.6 Hz, 1H), 7.52 (d, J=7.6 Hz, 1H), 7.40 (t, J=7.6 Hz, 1H), 7.30-7.32 (m, 1H), 7.17-7.21 (m, 1H), 5.45-5.62 (two m, 1H), 4.11-4.14 (m, 2H), 3.05 (q, J=7.6 Hz, 2H), 2.44 (br s, 1H), 2.19-2.25 (m, 2H), 2.08-2.15 (m, 2H), 1.92-1.96 (m, 2H), 1.72-1.89 (m, 7H), 1.53-1.55 (m, 1H), 1.38 (t, J=7.2 Hz, 3H).

167B (HCl salt): $^1$H NMR (400 MHz, CDCl$_3$-d): δ 7.80, 7.87 (two s, 1H), 7.59 (d, J=7.6 Hz, 1H), 7.48 (d, J=7.6 Hz, 1H), 7.41 (t, J=7.6 Hz, 1H), 7.29-7.31 (m, 1H), 7.21 (s, 1H), 5.45-5.57 (two m, 1H), 4.04-4.09 (m, 2H), 3.07 (q, J=7.6 Hz, 2H), 2.37 (br s, 1H), 2.20-2.24 (m, 2H), 2.08-2.16 (m, 3H), 1.95-2.01 (m, 5H), 1.79-1.83 (m, 1H), 1.42-1.61 (m, 4H), 1.39 (t, J=7.6 Hz, 3H).

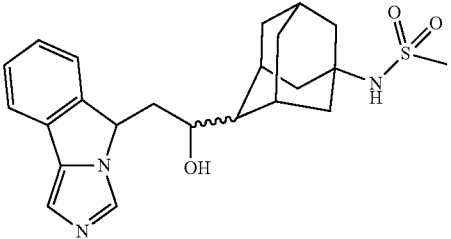

168A/168B m/z: [M+H]$^+$ 428

168A: $^1$H NMR (400 MHz, DMSO-d$_6$): δ 7.93 (s, 1H), 7.62 (t, J=7.2 Hz, 2H), 7.40 (t, J=7.6 Hz, 1H), 7.26-7.30 (m, 1H), 7.13 (s, 1H), 6.82 (s, 1H), 5.43-5.50 (two m, 1H), 5.07, 5.16 (two d, J=6.8 Hz, 1H), 4.03-4.06 (m, 1H), 2.92 (s, 3H), 2.40 (br s, 1H), 2.16-2.19 (m, 1H), 1.99-2.01 (m, 2H), 1.71-1.85 (m, 7H), 1.51-1.62 (m, 3H).

168B: $^1$H NMR (400 MHz, DMSO-d$_6$): δ 7.93, 7.96 (two s, 1H), 7.61 (d, J=8.8 Hz, 2H), 7.39 (t, J=7.2 Hz, 1H), 7.28-7.32 (m, 1H), 7.12 (s, 1H), 6.82 (s, 1H), 5.43-5.46 (m, 1H), 5.00, 5.08 (two d, J=7.2 Hz, 1H), 4.05-4.07 (m, 1H), 2.93 (s, 3H), 2.36 (br s, 1H), 1.97-1.99 (m, 3H), 1.82-1.88 (m, 7H), 1.36-1.46 (m, 3H).

169A/169B m/z: [M+H]$^+$ 454

169A: $^1$H NMR (400 MHz, DMSO-d$_6$): δ 7.96, 7.99 (two s, 1H), 7.61-7.64 (m, 2H), 7.40 (t, J=7.2 Hz, 1H), 7.26-7.28 (m, 1H), 7.14, 7.17 (two s, 1H), 6.81, 6.84 (two s, 1H), 5.44-5.47 (m, 1H), 5.08 (d, J=7.2 Hz, 1H), 4.04-4.06 (m, 1H), 2.46-2.48 (m, 1H), 2.40 (br s, 1H), 2.17-2.20 (m, 1H), 2.01-2.03 (m, 2H), 1.71-1.85 (m, 6H), 1.52-1.67 (m, 5H), 1.39-1.41 (m, 1H), 0.90-0.92 (m, 4H).

169B: $^1$H NMR (400 MHz, DMSO-d$_6$): δ 7.95 (s, 1H), 7.60-7.62 (m, 2H), 7.39 (t, J=7.2 Hz, 1H), 7.28-7.32 (m, 1H), 7.13 (s, 1H), 6.81 (s, 1H), 5.43-5.47 (m, 1H), 5.01, 5.08 (two d, J=7.2 Hz, 1H), 4.03-4.07 (m, 1H), 2.50-2.51 (m, 1H), 2.36 (br s, 1H), 1.97-2.01 (m, 3H), 1.82-1.90 (m, 6H), 1.39-1.63 (m, 4H), 1.24-1.27 (m, 2H), 0.90-0.94 (m, 4H).

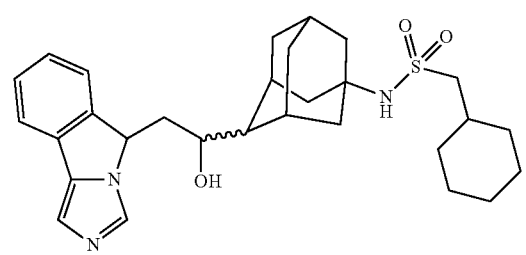

170A/170B

The HCl salts of 170A and 170B were prepared according to the preparation method of compound 1-A.

m/z: [M+H]⁺ 510

170A (HCl salt): $^1$H NMR (400 MHz, DMSO-d$_6$): δ 14.55 (br s, 1H), 9.27-9.37 (m, 1H), 7.93 (s, 1H), 7.87-7.89 (m, 1H), 7.78-7.80 (m, 1H), 7.45-7.59 (m, 2H), 6.82, 6.91 (two s, 1H), 5.83-5.86 (m, 1H), 4.09-4.12 (m, 1H), 2.84-2.87 (m, 1H), 2.33-2.38 (m, 1H), 2.07-2.17 (m, 2H), 1.97-2.01 (m, 2H), 1.74-1.87 (m, 8H), 1.50-1.67 (m, 6H), 1.37-1.45 (m, 2H), 1.14-1.29 (m, 4H), 1.02-1.08 (m, 2H).

Example 80: Synthesis of Compounds 191A-193A, 191B-193B

Compounds 191A-193A, 191B-193B were prepared according to example 78 compounds 161A and 161B, by replacing compound 1.1 and 1-(4-acetyladamantan-1-yl)-3-(4-cyanophenyl) urea to compound 2.1 and corresponding acetyladamantan derivative (compounds 24.1, 53.1 and 54.1).

191A/191B

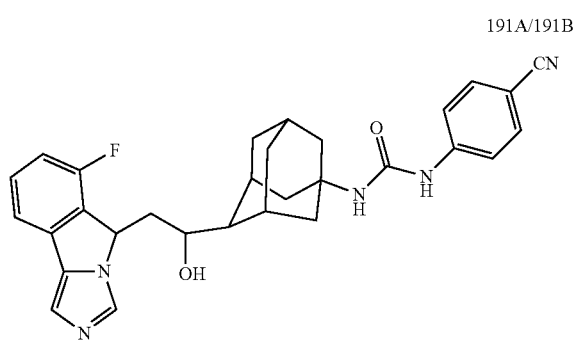 [SMILES: N#Cc1ccc(NC(=O)NC23CC4CC(C2)C(C(O)CC2c5c(F)cccc5-c5cncn52)C(C4)C3)cc1]

The HCl salts of 191A and 191B were prepared according to the preparation method of compound 1-A.

m/z: [M+H]⁺ 512

191A (HCl salt): $^1$H NMR (400 MHz, DMSO-d$_6$): δ 14.68 (s, 1H), 9.32-9.42 (m, 2H), 8.00 (s, 1H), 7.51-7.73 (m, 6H), 7.36-7.38 (m, 1H), 6.42, 6.34 (two s, 1H), 6.06-6.08 (m, 1H), 3.78-3.92 (m, 1H), 2.51-2.52 (m, 1H), 1.57-2.30 (m, 16H).

191B (HCl salt): $^1$H NMR (400 MHz, DMSO-d$_6$): δ 14.77 (s, 1H), 9.41-9.45 (m, 2H), 8.01 (s, 1H), 7.51-7.74 (m, 6H), 7.35-7.39 (m, 1H), 6.51, 6.49 (two s, 1H), 6.07-6.08 (m, 1H), 3.90-3.91 (m, 1H), 2.51-2.52 (m, 1H), 1.23-2.28 (m, 16H).

192A/192B

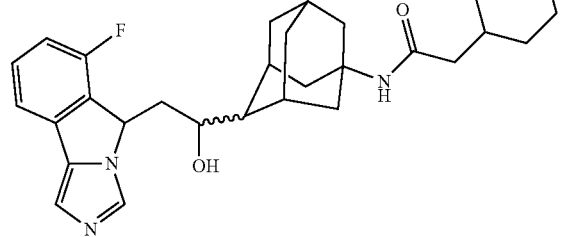

m/z: [M+H]⁺ 492

192A: $^1$H NMR (400 MHz, DMSO-d$_6$): δ 7.98 (s, 1H), 7.42-7.47 (m, 2H), 7.17-7.21 (m, 2H), 7.06-7.11 (m, 1H), 5.59-5.72 (two m, 1H), 4.80, 5.18 (two d, J=6.8 Hz, 1H), 3.86-3.88 (m, 1H), 2.38-2.44 (m, 1H), 2.30 (br s, 1H), 1.97-2.04 (m, 2H), 1.87-1.89 (m, 4H), 1.52-1.81 (m, 13H), 1.33-1.36 (m, 1H), 1.10-1.24 (m, 4H), 0.85-0.93 (m, 2H).

193A/193B

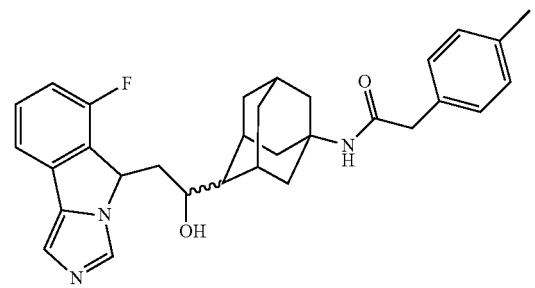

m/z: [M+H]⁺ 500

193A: $^1$H NMR (400 MHz, DMSO-d$_6$): δ 7.96 (s, 1H), 7.42-7.49 (m, 3H), 7.17 (s, 1H), 7.06-7.12 (m, 5H), 5.58-5.72 (two m, 1H), 4.79, 5.18 (two d, J=7.2 Hz, 1H), 3.89-3.83, 4.03-4.05 (two m, 1H), 3.27-3.29 (m, 2H), 2.38-2.43 (m, 1H), 2.30 (br s, 1H), 2.28 (s, 3H), 1.97-2.03 (m, 2H), 1.52-1.89 (m, 11H), 1.33-1.36 (m, 1H).

Example 81: Synthesis of Compounds 200A and 200B

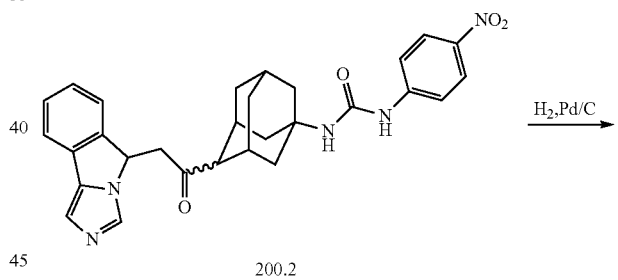

200.2

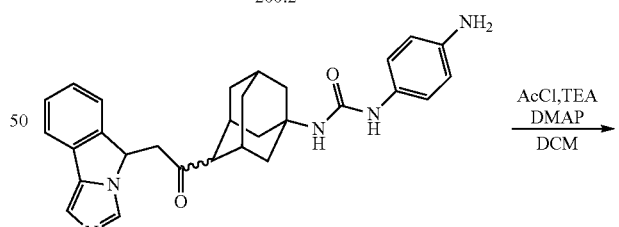

200.3A/200.3B

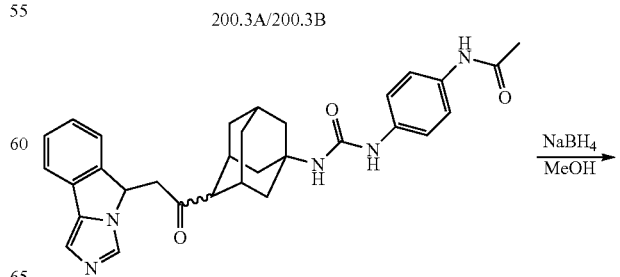

200.4A/200.4B

-continued

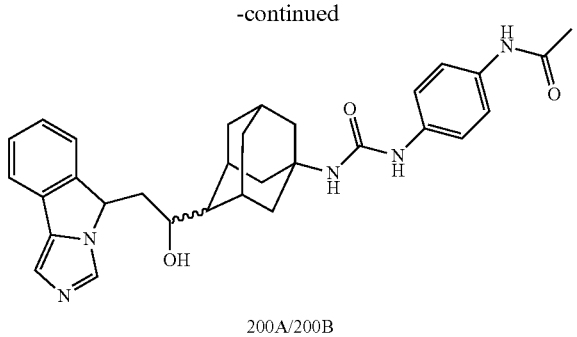

200A/200B

Step 1: Synthesis of Compounds 200.3A and 200.3B

Compound 200.2 was prepared according to the preparation method of compound 161.3 in example 78, which was used compound 1.1 and compound 26.1 as starting materials.

A mixture of compound 200.2 (113 mg, 0.22 mmol) and Pd/C (56 mg) in methanol (15 mL) was stirred at room temperature for overnight under $H_2$ atmosphere. Then the reaction mixture was filtered through a celite pad, and the filtrate was concentrated to afford the crude compound 200.3 (a mixture of stereoisomers), which was purified by flash column chromatography on silica gel (0-3% solution of methanol in dichloromethane) to afford 200.3A (55 mg, less polar, yield: 51%) and 200.3B (42 mg, more polar, yield: 39%) as pale yellow solids.

m/z: [M+H]$^+$ 513

Step 2: Synthesis of Compound 200.4A

A mixture of compound 200.3A (55 mg, 0.11 mmol), acetyl chloride (10 mg, 0.13 mmol), TEA (17 mg, 0.17 mmol) and DMAP (1.4 mg, 0.01 mmol) in dichloromethane (30 mL) was stirred at room temperature for 3 h, and then the mixture was concentrated to afford the crude compound, which was purified by flash column chromatography on silica gel (0-60% solution of ethyl acetate in petroleum ether) to afford compound 200.4A (45 mg, yield 75%) as a pale yellow solid.

m/z: [M+H]$^+$ 524

Step 3: Synthesis of Compound 200A/200B

To an ice-cooling solution of compound 200.4 (45 mg, 0.08 mmol) in methanol (3.0 mL) was added NaBH$_4$ (6.5 mg, 0.16 mmol). The resulted mixture was stirred at room temperature for 30 min, and then the mixture was diluted with cold water (20 mL). The resulted precipitate was filtered, and washed with cold water, dried under vacuum to afford compound 200A (40 mg, yield 88%) as a white solid. Compound 200B was prepared according to compound 200A, by using compound 200.3B as a starting material.

The HCl salts of 200A and 200B were prepared according to the preparation method of compound 1-A.

m/z: [M+H]$^+$ 526

200A (HCl salt): $^1$H NMR (400 MHz, DMSO-d$_6$): δ 14.55 (br s, 1H), 9.77 (s, 1H), 9.35 (s, 1H), 8.33 (s, 1H), 7.92 (s, 1H), 7.83-7.88 (m, 2H), 7.51-7.58 (m, 2H), 7.42 (d, J=8.8 Hz, 2H), 7.27 (d, J=9.2 Hz, 2H), 5.94 (s, 1H), 5.85 (t, J=12.8 Hz, 1H), 5.31-5.34 (m, 1H), 4.16-4.21 (m, 1H), 2.14-2.38 (m, 4H), 2.00 (s, 3H), 1.39-1.88 (m, 10H).

Example 82: Synthesis of Compounds 201A and 201B

Compounds 201A, 201B were prepared according to example 81 compounds 200A and 200B, by using compound 17 as a starting material.

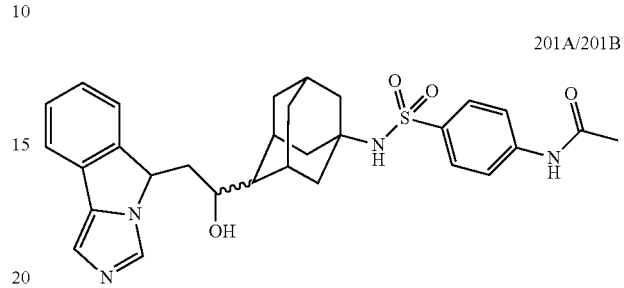

201A/201B

The HCl salts of 201A and 201B were prepared according to the preparation method of compound 1-A.

m/z: [M+H]$^+$ 547

201A (HCl salt): $^1$H NMR (400 MHz, DMSO-d$_6$): δ 10.27 (s, 1H), 7.91 (s, 1H), 7.71-7.31 (m, 3H), 7.62-7.67 (m, 1H), 7.54 (t, J=8.0 Hz, 1H), 7.39-7.43 (m, 2H), 7.33 (t, J=7.6 Hz, 1H), 7.13 (s, 1H), 5.38-5.41 (m, 1H), 5.06 (d, J=6.8 Hz, 1H), 3.93-3.97 (m, 1H), 2.30 (br s, 1H), 2.07 (s, 3H), 2.06 (br s, 1H), 1.89-1.92 (m, 2H), 1.73-1.77 (m, 2H), 1.58-1.63 (m, 4H), 1.45-1.51 (m, 5H), 1.31-1.34 (m, 2H).

Example 83: Synthesis of Compound 202A/202B

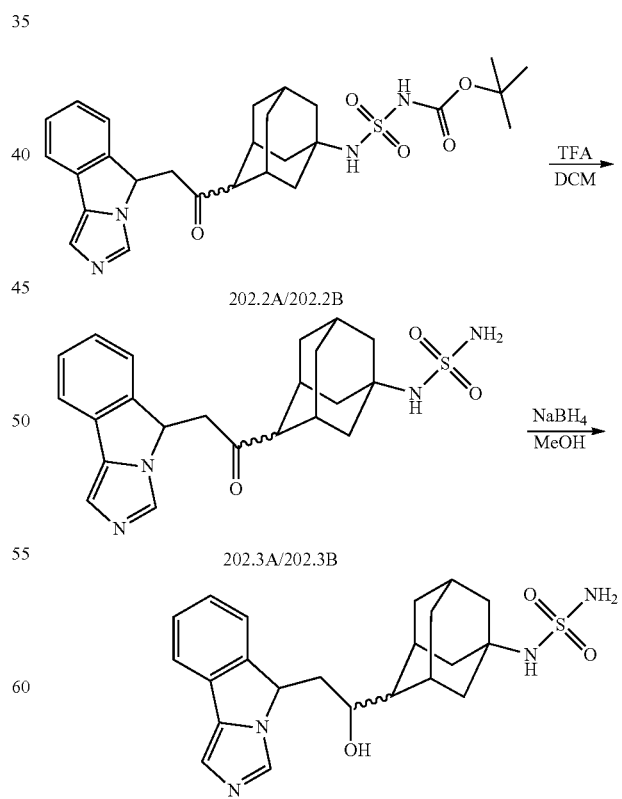

202A/202B

Step 1: Synthesis of Compound 202.3A

Compounds 202.2A and 202.2B was prepared according to the preparation method of compound 161.3A/161.3B in example 78, which was used compound 1.1 and compound 39.1 as starting materials.

A mixture of compound 202.2A (140 mg, 0.27 mmol), TFA (2 mL) in dichloromethane (8 mL) was stirred at room temperature for 3 h, and then the mixture was concentrated to afford the crude compound, which was purified by flash column chromatography on silica gel (1~10% solution of methanol in dichloromethane) to afford compound 202.3A (110 mg, yield: 97%) as a white solid.

m/z: [M+H]$^+$ 427

Step 2: Synthesis of Compound 202A/202B

To an ice-cooling solution of compound 202.3A (110 mg, mmol) in methanol (5 mL) was added NaBH$_4$ (50 mg, 1.3 mmol). The resulted mixture was stirred at room temperature for 30 min, and then the mixture was diluted with cold water (10 mL). The resulted precipitate was filtered, and washed with cold water, dried under vacuum to afford compound 202A (18 mg, yield: 16%) as a white solid. Compound 202B was prepared according to compound 202A, by using compound 202.2B as a starting material.

The HCl salts of 202A and 202B were prepared according to the preparation method of compound 1-A.

m/z: [M+H]$^+$ 429

202A (HCl salt): $^1$H NMR (400 MHz, DMSO-d$_6$): δ 7.93, 7.95 (s, 1H), 7.60-7.63 (m, 2H), 7.27-7.48 (m, 2H), 7.13, 7.16 (two s, 1H), 6.33-6.55 (m, 3H), 5.41-5.50 (m, 1H), 5.14, 5.04 (two d, J=7.2 Hz, 1H), 4.04-4.11 (m, 1H), 2.40 (s, 1H), 1.24-2.12 (m, 14H).

202B (HCl salt): $^1$H NMR (400 MHz, DMSO-d$_6$): δ 7.93 (s, 1H), 7.61 (d, J=8.4 Hz, 2H), 7.39 (t, J=7.6 Hz, 1H), 7.30 (t, J=7.6 Hz, 1H), 7.12 (s, 1H), 6.43 (s, 2H), 6.31 (s, 1H), 5.43-5.46 (m, 1H), 4.98 (m, J=7.8 Hz, 1H), 4.02-4.11 (m, 1H), 2.34 (s, 1H), 1.80-2.03 (m, 9H), 1.22-1.45 (m, 5H).

Example 84: Synthesis of Compound 203

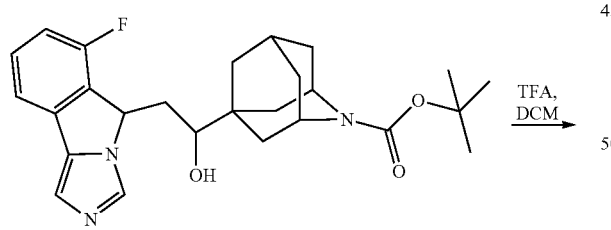

31

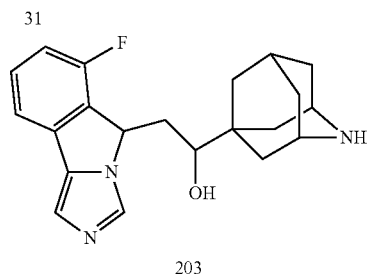

203

To an ice-cooling solution of compound 31 (15 mg, 0.033 mmol) in DCM (5 mL) was added TFA (1 mL). The resulted mixture was stirred at room temperature for 2 h, and then concentrated under vacuum. The residue was purified by pre-HPLC to afford compound 203 (TFA salt, 4 mg, yield: 26%) as a white solid.

$^1$H NMR (400 MHz, MeOD-d$_4$): δ 9.19 (s, 1H), 7.84 (s, 1H), 7.67-7.74 (m, 1H), 7.59-7.64 (m, 1H), 7.29-7.34 (m, 1H), 5.96, 6.14 (two brs, 1H), 3.77 (brs, 1H), 3.57-3.59 (m, 1H), 2.59-2.63 (m, 1H), 2.25 (s, 1H), 1.71-2.11 (m, 11H).

m/z: [M+H]$^+$ 452

Example 85: Synthesis of Compound 204

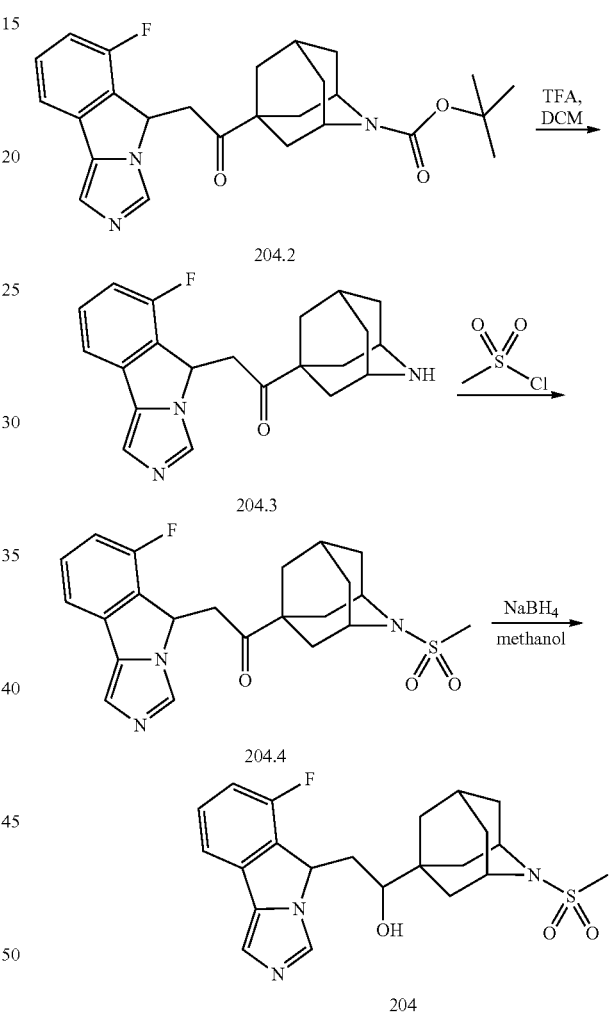

Compound 204.2 was prepared according to example 1 compound 1.3, by using compound 2.1 and 60.1 as starting materials.

Step 1: Synthesis of Compound 204.3

To a solution of compound 204.2 (100 mg, 0.221 mmol) in DCM (3 mL) was added TFA (1 mL). The mixture was stirred at room temperature for 30 min, and then concentrated under vacuum. Then the residue was added toluene (1 mL) and concentrated again under vacuum to afford compound 204.3 (120 mg, yield: 94%) as a white solid.

m/z: [M+H]$^+$ 352

Step 2: Synthesis of Compound 204.4

To a solution of compound 204.3 (120 mg, 0.207 mmol) and TEA (105 mg, 1.04 mmol) in dichloromethane (3 mL) was added methanesulfonyl chloride (47 mg, 0.41 mmol). The resulted mixture was stirred at room temperature for 1 h, and then the reaction was quenched by addition of water (3 mL). The organic phase was separated. The aqueous phase was extracted with dichloromethane (5 mL×2). The combined organic phase was washed with brine, dried over sodium sulfate and concentrated under vacuum. The residue was purified by pre-TLC (5% solution of methanol in dichloromethane) to afford compound 204.4 (85 mg, yield: 96%) as a white solid.

Step 3: Synthesis of Compound 204

To an ice-cooling solution of compound 204.4 (85 mg, 0.198 mmol) in methanol (5 mL) was added NaBH$_4$ (16 mg, 0.423 mmol). The resulted mixture was stirred at room temperature for 15 min, and then the reaction was quenched by addition of water (0.5 mL). The mixture was concentrated under vacuum. The residue was purified by prep-TLC (7% solution of methanol in dichloromethane, contained 0.1% NH$_3$.H$_2$O) to afford compound 204 (65 mg, yield: 76%) as a white solid.

$^1$H NMR (400 MHz, CDCl$_3$-d): δ 8.09, 8.42 (two s, 1H), 7.33-7.41 (m, 2H), 7.19 (brs, 1H), 6.96-7.02 (m, 1H), 5.71-5.73 (m, 0.15H), 5.48 (t, J=4.9 Hz, 0.85H), 4.18 (br s, 2H), 3.46 (d, J=9.2 Hz, 1H), 2.91 (s, 3H), 2.38-2.43 (m, 1H), 2.25 (brs, 1H), 1.93-2.06 (m, 3H), 1.81 (t, J=14.0 Hz, 2H), 1.56-1.72 (m, 7H).

m/z: [M+H]$^+$ 432

Example 86: Synthesis of Compound 205 and 206

Compounds 205 and 206 were prepared according to example 21 compound 45, by using compound 203 and corresponding sulfonyl chloride as starting materials.

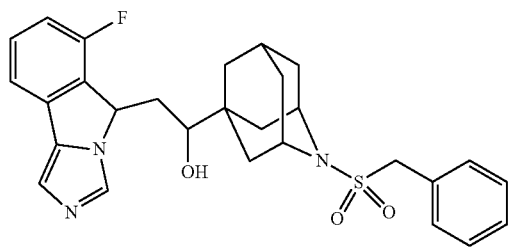

205

$^1$H NMR (400 MHz, MeOD-d$_4$): δ 9.17, 9.12 (two s, 1H), 7.82 (s, 1H), 7.67-7.72 (m, 1H), 7.58-7.63 (m, 1H), 7.43 (brs, 2H), 7.33 (brs, 4H), 5.91, 6.09 (two br s, 1H), 4.29 (s, 2H), 3.87 (br s, 2H), 3.39-3.41 (m, 1H), 2.50-2.54 (m, 2H), 1.30-2.11 (m, 11H).

m/z: [M+H]$^+$ 508

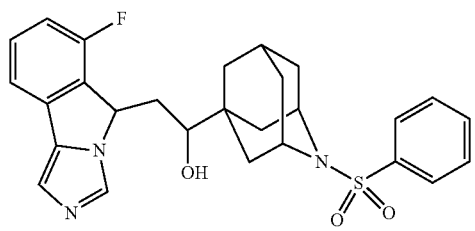

206

$^1$H NMR (400 MHz, MeOD-d$_4$): δ 9.09, 9.14 (two s, 1H), 7.81-7.88 (m, 3H), 7.55-7.72 (m, 5H), 7.29-7.35 (m, 1H), 5.89, 6.05 (two br s, 1H), 4.19, 4.22 (two br s, 2H), 3.37 (br s, 1H), 2.86 (d, J=12.0 Hz, 0.5H), 2.40-2.46 (m, 1.5H), 1.32-2.21 (m, 11H).

m/z: [M+H]$^+$ 494

Example 87: Synthesis of Compound 207

Compounds 207 was prepared according to example 31 compounds 49, by using compound 203 and corresponding acid as starting materials.

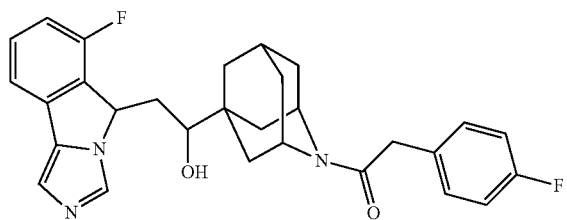

207

$^1$H NMR (400 MHz, MeOD-d$_4$): δ 9.14, 9.18 (two s, 1H), 7.83 (s, 1H), 7.59-7.72 (m, 2H), 7.28-7.33 (m, 3H), 7.04-7.08 (m, 2H), 5.92, 6.09 (two br s, 1H), 4.30 (br s, 1H), 3.75 (br s, 2H), 3.43-3.46 (m, 1H), 2.52-2.55 (m, 1H), 1.95-2.35 (m, 3H), 1.32-1.73 (m, 10H).

m/z: [M+H]$^+$ 490

Example 88: Synthesis of Compound 208

Compounds 208 were prepared according to example 36 compounds 54, by using compound 203 and corresponding isocyanate as starting materials.

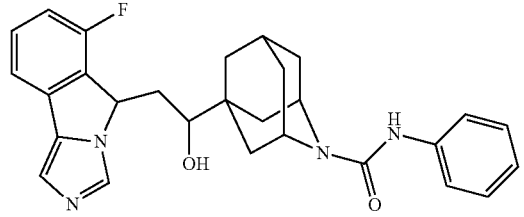

208

$^1$H NMR (400 MHz, MeOD-d$_4$): δ 9.25, 9.14 (two s, 1H), 7.84 (s, 1H), 7.76-7.57 (m, 2H), 7.41-7.22 (m, 5H), 7.08-6.98 (m, 1H), 6.17-5.92 (m, 1H), 4.53-4.35 (m, 2H), 3.52-3.42 (m, 1H), 2.68-2.53 (m, 1H), 2.23 (br s, 1H), 2.14-2.02 (m, 1H), 1.96-1.85 (m, 2H), 1.82-1.48 (m, 8H).

m/z: [M+H]$^+$ 473

Example 89: Synthesis of Compound 209

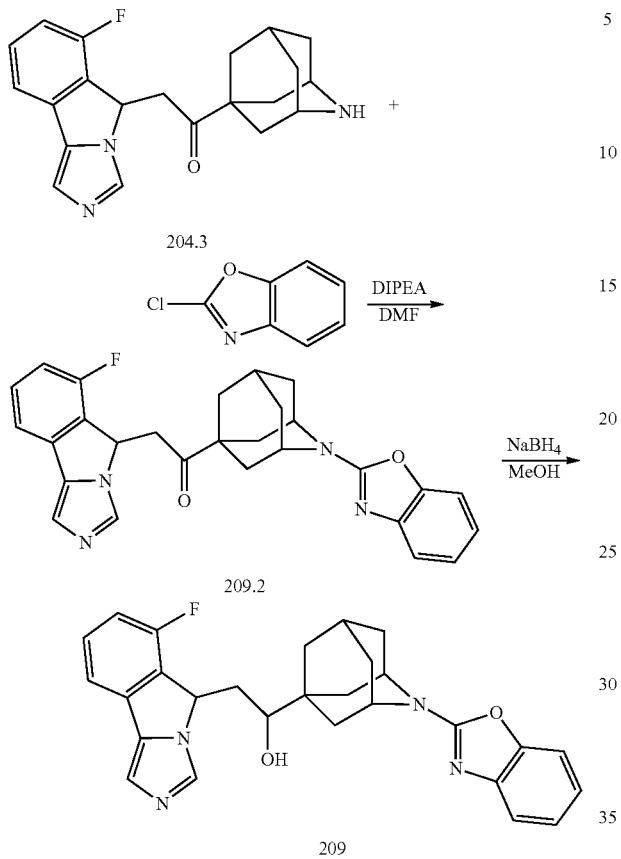

Step 1: Synthesis of Compound 209.2

A solution of compound 204.3 (100 mg, 0.221 mmol), 2-chlorobenzo[d]oxazole (102 mg, 0.664 mmol) and DIPEA (143 mg, 1.11 mmol) in DMF (3 mL) was stirred at 80° C. for 30 min, and then the reaction was quenched by addition of water (5 mL). The mixture was extracted with ethyl acetate (5 mL×3). The combined organic phase was washed with brine, dried over sodium sulfate and concentrated under vacuum. The residue was purified by prep-TLC (5% solution of methanol in dichloromethane) to afford compound 209.2 (75 mg, yield: 73%) as a yellow solid.

m/z: [M+H]$^+$ 469

Step 2: Synthesis of Compound 209

To an ice-cooling solution of compound 209.2 (75 mg, 0.16 mmol) in methanol (5 mL) was added NaBH$_4$ (10 mg, 0.264 mmol). The resulted mixture was stirred at room temperature for 5 min, and then the reaction was quenched by addition of water (0.5 mL). The mixture was concentrated under vacuum. The residue was purified by prep-TLC (7% solution of methanol in dichloromethane) to afford compound 209 (60 mg, yield: 80%) as a white solid.

$^1$H NMR (400 MHz, CDCl$_3$-d): δ 7.93 (br s, 1H), 7.32-7.40 (m, 3H), 7.15-7.26 (m, 3H), 6.93-7.04 (m, 2H), 5.68 (d, J=9.4 Hz, 0.2H), 5.48 (t, J=4.6 Hz, 0.8H), 5.32 (s, 1H), 4.61 (s, 2H), 3.37-3.49 (m, 1H), 1.63-2.49 (m, 14H).

m/z: [M+H]$^+$ 471

Example 90: Synthesis of Compound 210

Compound 210 was prepared according to example 89 compound 209, by using compound 204.3 and 2-chloro-5-phenyloxazole as starting materials.

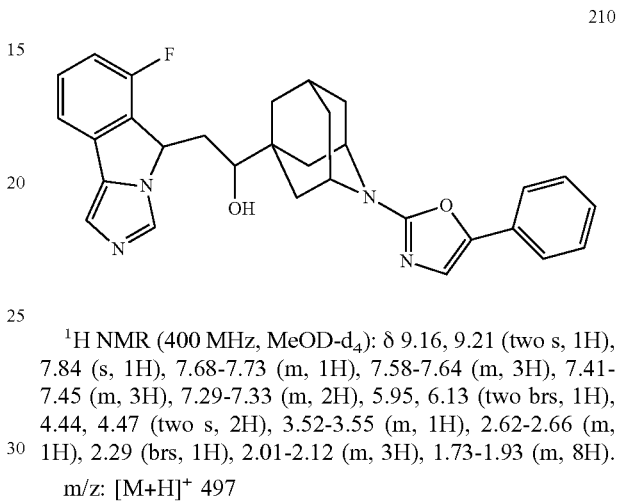

$^1$H NMR (400 MHz, MeOD-d$_4$): δ 9.16, 9.21 (two s, 1H), 7.84 (s, 1H), 7.68-7.73 (m, 1H), 7.58-7.64 (m, 3H), 7.41-7.45 (m, 3H), 7.29-7.33 (m, 2H), 5.95, 6.13 (two brs, 1H), 4.44, 4.47 (two s, 2H), 3.52-3.55 (m, 1H), 2.62-2.66 (m, 1H), 2.29 (brs, 1H), 2.01-2.12 (m, 3H), 1.73-1.93 (m, 8H).

m/z: [M+H]$^+$ 497

Example 91: Synthesis of Prodrug (Compound 300)

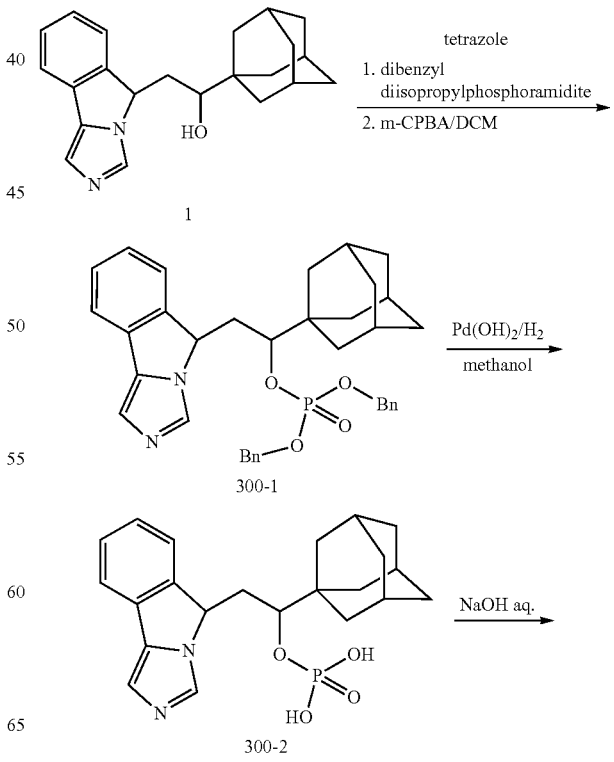

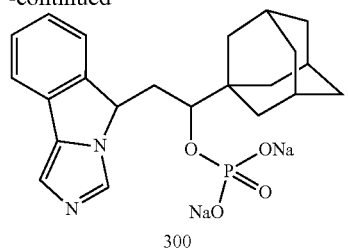

300

Step 1: Synthesis of Compound 300-1

To a solution of compound 1 (250 mg, 0.75 mmol) and tetrazole (115 mg, 1.65 mmol) in dichloromethane (10 mL) was added dibenzyl diisopropylphosphoramidite (285 mg, 0.83 mmol) at 0~10° C. The resulted mixture was stirred at room temperature for 2 h, then added water, extracted with dichloromethane (25 mL×3). The combined organic phase was washed with brine, dried over sodium sulfate, filtered and concentrated. The residue was dissolved in dichloromethane (20 mL), added 3-chloroperoxybenzoic acid (324 mg, 1.88 mmol). The resulted mixture was stirred at room temperature for 3 h, then diluted with saturated sodium bisulfate solution (30 mL), extracted with dichloromethane (30 mL×3). The combined organic phase was washed with brine, dried over sodium sulfate, filtered and concentrated, the residue was purified by column chromatography on silica gel (petroleum ether:ethyl acetate=1:2) to afford compound 300-1 (300 mg, yield: 66%) as a white solid.

m/z: [M+H]$^+$ 595

Step 2: Synthesis of Compound 300-2

To a solution of compound 300-1 (240 mg, 0.40 mmol) in methanol (20 mL) was added palladium hydroxide (20 mg, 10%). The resulted mixture was stirred under hydrogen (1 atm) at room temperature for overnight, then filtered, the filtrate was concentrated, the residue was purified by column chromatography on silica gel (dichloromethane:methane=10:1) to afford compound 300-2 (100 mg, yield: 100%) as a off-white solid.

m/z: [M+H]$^+$ 415

Step 3: Synthesis of Compound 300

To a solution of compound 300-2 (100 mg, 0.24 mmol) in methanol (5 mL) was added sodium hydroxide solution (4.8 mL, 0.1 M). The resulted mixture was stirred at room temperature for 30 min, then concentrated to afford compound 300 (110 mg, yield: 99%) as an off-white solid.

m/z: [M+2H-2Na]$^+$ 415

$^1$H NMR (400 MHz, DMSO-d$_6$): δ 8.00 (s, 1H), 7.93-7.98 (m, 2H), 7.54 (d, J=7.6 Hz, 1H), 7.30-7.34 (m, 1H), 7.20-7.22 (m, 1H), 7.08 (s, 1H), 6.02 (br s, 1H), 4.17-4.22 (m, 1H), 2.04-2.07 (m, 1H), 1.86 (br s, 3H), 1.65-1.70 (m, 1H), 1.44-1.58 (m, 11H).

Example 92: Synthesis of Prodrug (Compound 301)

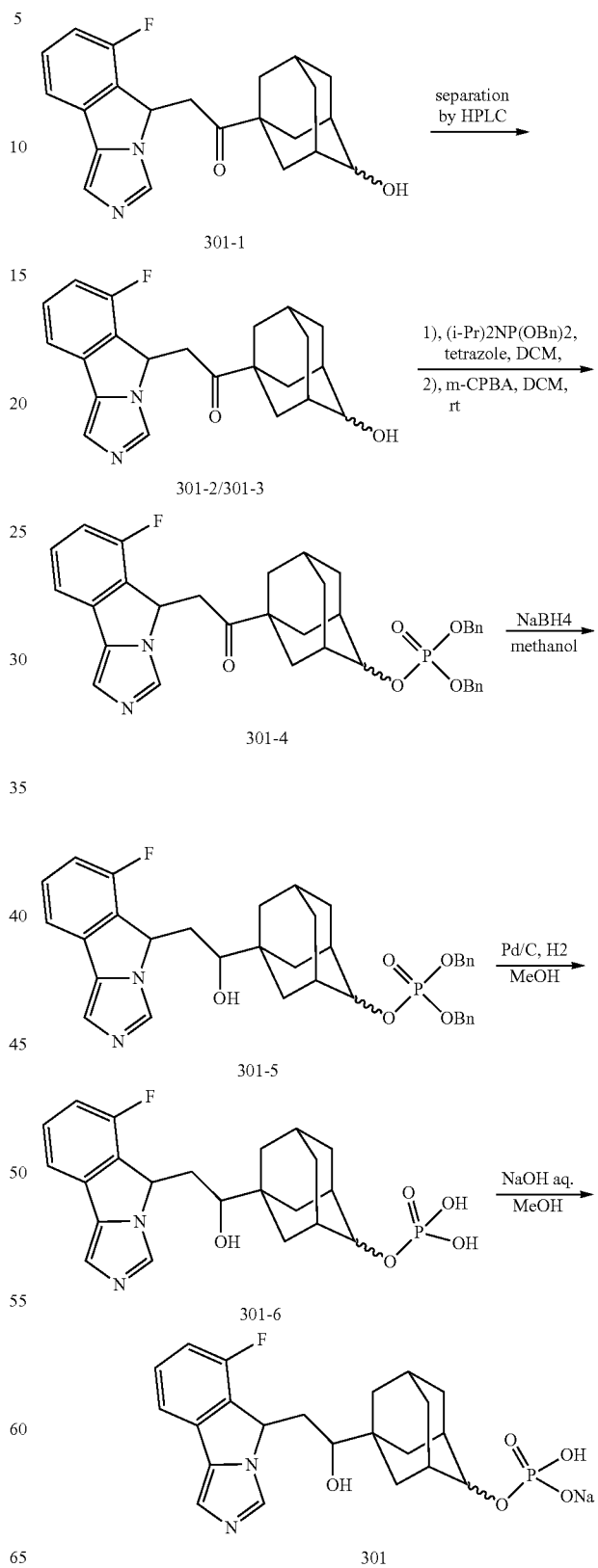

Step 1: Synthesis of Compounds 301-2 and 301-3

Compound 301-1 was prepared according example 1 compound 1.3 in step 2, by using compound 2.1 and 15.1 as starting materials.

Compound 301-1 (1.8 g, a mixture of stereoisomers) was separated by pre-HPLC (Separation method: K) to afford 301-2 (750 mg, the peak time: 6.1~6.9 min) and 301-3 (690 mg, the peak time: 7.5~8.4 min) as white solids.

Step 2: Synthesis of Compound 301-4

To a solution of compound 301-2 (500 mg, 1.37 mmol) and tetrazole (210 mg, 3.01 mmol) in DCM (20 mL) was added dibenzyl diisopropylphosphoramidite (565 mg, 1.64 mmol) at 0-10° C. The resulted mixture was stirred at room temperature for 2 h, then added water, extracted with dichloromethane (50 mL×3). The combined organic phase was washed with brine, dried over sodium sulfate, filtered and concentrated. The residue was dissolved in dichloromethane (50 mL), added 3-chloroperoxybenzoic acid (324 mg, 1.88 mmol). The resulted mixture was stirred at room temperature for 3 h, then diluted with saturated sodium bisulfate solution (30 mL), extracted with dichloromethane (30 mL×3). The combined organic phase was washed with brine, dried over sodium sulfate, filtered and concentrated, the residue was purified by column chromatography on silica gel (petroleum ether:ethyl acetate=1:2) to afford compound 301-4 (490 mg, yield: 57%) as a white solid.

m/z: [M+H]$^+$ 627

Step 3: Synthesis of Compound 301-5

To a solution of compound 301-4 (490 mg, 0.78 mmol) in a mixed solvent of methanol (10 mL) and ethanol (20 mL) was added NaBH$_4$ (40 mg, 1.56 mmol). The resulted mixture was stirred at room temperature for 0.5 h, and then the reaction was quenched by addition of H$_2$O (5 mL), the organic phase was extracted with DCM (20 mL×3), the combined organic phase was washed with brine, dried over sodium sulfate, filtered and concentrated. The residue was purified by column chromatography on silica gel (DCM:methanol=15:1) to afford compound 301-5 (480 mg, yield: 98%) as a off-white solid.

m/z: [M+H]$^+$ 601

Step 4: Synthesis of Compound 301-6

To a solution of compound 301-5 (200 mg, 0.32 mmol) in methanol (20 mL) was added wet Pd/C (20 mg, 10%). The resulted mixture was stirred under hydrogen (1 atm) at room temperature for overnight, then filtered, the filtrate was concentrated, the residue was purified by column chromatography on silica gel (dichloromethane:methane=10:1) to afford compound 301-6 (100 mg, yield: 70%) as an off-white solid.

m/z: [M+H]$^+$ 449

Step 5: Synthesis of Compound 301

To a solution of compound 301-6 (100 mg, 0.22 mmol) in methanol (5 mL) was added sodium hydroxide solution (2.2 mL, 0.1 M). The resulted mixture was stirred at room temperature for 30 min, then concentrated to afford compound 301 (100 mg, yield: 97%) as an off-white solid.

m/z: [M+H-Na]$^+$ 449

$^1$H NMR (400 MHz, DMSO-d$_6$): δ 9.18 (s, 1H), 7.89 (s, 1H), 7.67-7.70 (m, 1H), 7.56-7.61 (m, 1H), 7.27-7.35 (m, 1H), 5.93-5.94 (m, 1H), 4.84-4.86 (m, 1H), 4.18-4.19 (m, 1H), 3.13-3.15 (m, 1H), 2.42-2.44 (m, 1H), 1.92-2.04 (m, 5H), 1.41-1.53 (m, 6H), 1.31-1.36 (m, 2H).

Example 93: Synthesis of Prodrug (Compound 302)

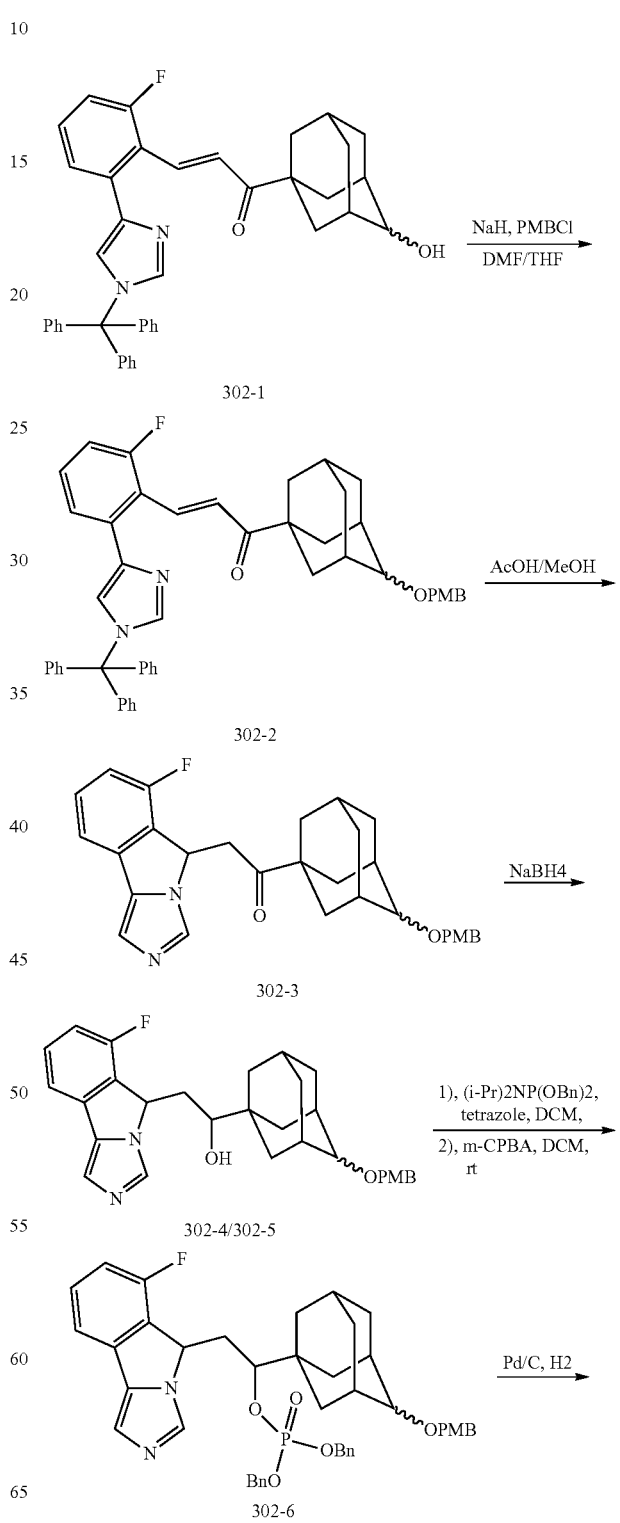

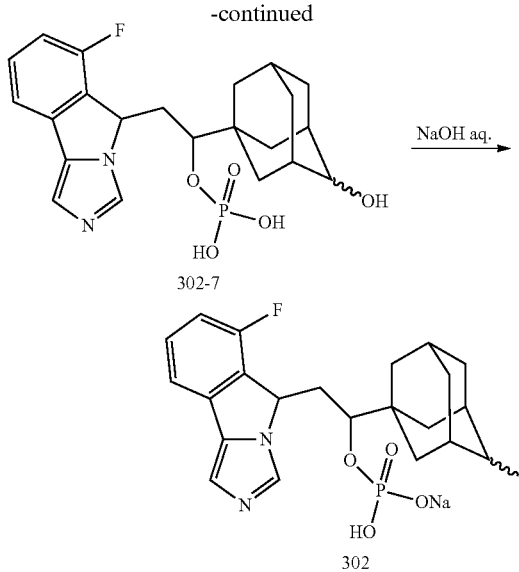

Step 1: Synthesis of Compound 302-2

Compound 302-1 was prepared according example 1 compound 1.2 in step 1, by using compound 2.1 and 15.1 as starting materials.

To a solution of compound 302-1 (2.5 g, 4.11 mmol) in a mixed solvent of DMF (35 mL) and THF (35 mL) was added NaH (60% w/w, 411 mg, 10.3 mmol) in small portions, the mixture was stirred at room temperature for 30 min, and then the mixture was added 4-methoxybenzylchloride (PMBCl) (962 mg, 6.17 mmol). The resulted mixture was stirred at room temperature for overnight, then the reaction was quenched by addition of $H_2O$ (100 mL), the organic phase was extracted with DCM (200 mL×3), the combined organic phase was washed with brine, dried over sodium sulfate, filtered and concentrated. The residue was purified by column chromatography on silica gel (petroleum ether:ethyl acetate=2:1) to afford compound 302-2 (2.1 g, yield: 70%) as a white solid.

m/z: $[M+H]^+$ 729

Step 2: Synthesis of Compound 302-3

To a solution of compound 302-2 (2.0 g, 2.74 mmol) in methanol (25 mL) was added acetic acid (3.5 mL). The resulted mixture was stirred at reflux for 3 h, then diluted with water (100 mL), the mixture was extracted with ethyl acetate (100 mL×3). The combined organic phase was washed with saturated sodium bicarbonate solution (100 mL) and brine, dried over sodium sulfate, filtered and concentrated. The residue was purified by column chromatography on silica gel (petroleum ether:ethyl acetate=1:1) to afford compound 302-3 (980 mg, yield: 74%) as a white solid.

m/z: $[M+H]^+$ 333

Step 3: Synthesis of Compounds 302-4 and 302-5

To a solution of compound 302-3 (980 mg, 2.02 mmol) in a mixed solvent of methanol (20 mL) and ethanol (30 mL) was added $NaBH_4$ (91 mg, 4.04 mmol). The resulted mixture was stirred at room temperature for 0.5 h, and then the reaction was quenched by addition of $H_2O$ (30 mL), the organic phase was extracted with DCM (100 mL), the combined organic phase was washed with brine, dried over sodium sulfate, filtered and concentrated. The residue was purified by column chromatography on silica gel (DCM: methanol=15:1) to afford a crude compound (a mixture of stereoisomers) (960 mg, yield: 97%), which was then separated by pre-HPLC (Separation method: L) to afford 302-4 (360 mg, the peak time: 6.8-7.6 min) and 302-5 (390 mg, the peak time: 8.6-9.4 min) as white solids.

m/z: $[M+H]^+$ 601

Step 4: Synthesis of Compound 302-6

To a solution of compound 302-4 (320 mg, 0.53 mmol) and tetrazole (93.3 mg, 1.33 mmol) in DCM (22 mL) was added dibenzyl diisopropylphosphoramidite (200 mg, 0.58 mmol) at 0~10° C. The resulted mixture was stirred at room temperature for 2 h, then added water, extracted with dichloromethane (50 mL×3). The combined organic phase was washed with brine, dried over sodium sulfate, filtered and concentrated. The residue was dissolved in dichloromethane (20 mL), added 3-chloroperoxybenzoic acid (136 mg, 0.78 mmol). The resulted mixture was stirred at room temperature for 2 h, then diluted with saturated sodium bisulfate solution (20 mL), extracted with dichloromethane (30 mL×3). The combined organic phase was washed with brine, dried over sodium sulfate, filtered and concentrated, the residue was purified by column chromatography on silica gel (petroleum ether:ethyl acetate=1:1) to afford compound 302-6 (270 mg, yield: 68%) as a white solid.

m/z: $[M+H]^+$ 749

Step 5: Synthesis of Compound 302-7

To a solution of compound 302-6 (240 mg, 0.32 mmol) in methanol (25 mL) was added wet Pd/C (24 mg, 10%). The resulted mixture was stirred under hydrogen (1 atm) at room temperature for overnight, then filtered, the filtrate was concentrated, the residue was purified by column chromatography on silica gel (dichloromethane:methane=10:1) to afford compound 302-7 (130 mg, yield: 90%) as an off-white solid.

m/z: $[M+H]^+$ 449

Step 6: Synthesis of Compound 302

To a solution of compound 302-7 (130 mg, 0.29 mmol) in methanol (5 mL) was added sodium hydroxide solution (2.9 mL, 0.1 M). The resulted mixture was stirred at room temperature for 30 min, then concentrated to afford compound 302 (132 mg, yield: 97%) as an off-white solid.

m/z: $[M+H-Na]^+$ 449

$^1$H NMR (400 MHz, $CD_3OD$-d): δ 9.24 (s, 1H), 7.68 (s, 1H), 7.63-7.65 (m, 1H), 7.54-7.60 (m, 1H), 7.24-7.28 (m, 1H), 6.41-6.44 (m, 1H), 4.38-4.41 (m, 1H), 3.76-3.82 (m, 1H), 2.64-2.67 (m, 1H), 2.11-2.14 (m, 1H), 1.93-2.01 (m, 3H), 1.78-1.85 (m, 3H), 1.62-1.73 (m, 4H), 1.42-1.51 (m, 3H).

Biology Assays

Example 1: IDO1 Enzymatic Assay

In this disclosure, the bioactivity of compounds was assayed using the method reported in the literature (Sono, M. et al *J. Biol. Chem.* 1980, 255, 1339-45), The assay principle is based on UV absorption using a recombinant IDO1 and L-tryptophan substrate. The UV absorption signal at 321 nm is correlated with the amount of N-formylkynurenine reaction product of IDO1. The detailed experimental method is as follow:

The compounds described in this disclosure were dissolved in 10% DMSO to predefined concentration. All of the reactions were conducted at room temperature in this disclosure. Human recombinant IDO1 (BPS Bioscience) was added so that its concentration was 200 nm in the reaction buffer solution (200 μL). The solution also contained 500 nM tryptophan, ascorbic acid (20 mM), methylene blue (10 μM), 126ydroxyl peroxidase (10 g/mL) and sodium phosphate buffer solution Ph 6.5 (100 mM). 10 μL test compound solution was added into the above reaction solution (200 μL), so that the final concentration of DMSO in all reaction wells was 0.5%. % concentration was volume %. After 80 min incubation of the reaction solution, the UV absorbance was measured using TECAN Infinite M1000 plate reader. For the negative control (blank), 10 μl of the assay buffer was added instead of the IDO1

All reagents (excluding human recombinant IDO1) were purchased from Sigma Aldrich, MO, USA.

The percent activity in the presence of each compound was calculated according to the following equation: % activity=$[(A-A_b)/(A_f-A_b)] \times 100$, where A=the absorption signal in the presence of the compound, $A_b$=the absorption signal of blank, $A_f$=the absorption signal in the absence of the compound. The percent inhibition was calculated according to the following equation: % inhibition=100−% activity. The $IC_{50}$ was calculated using non-linear regression in Graph Pad Prism® 4.

The assay result of the test compounds in this disclosure, the $IC_{50}$ range is as follow: + represents 10-100 μM, ++ represents 1-10 μM, +++ represents 0.5-1 μM, ++++ represents 0.1-0.5 μM, +++++ represents <0.1 μM.

| Compound No. | hIDO1 $IC_{50}$ | Compound No. | hIDO1 $IC_{50}$ |
|---|---|---|---|
| 1 | +++++ | 1-1 | ++ |
| 1-2 | +++++ | 1-3 | +++++ |
| 1-4 | ++ | 2 | ++ |
| 3 | ++++ | 4 | ++++ |
| 7 | ++++ | 8 | ++++ |
| 9 | +++++ | 10A | +++++ |
| 10A-2 | +++++ | 10A-3 | ++ |
| 10B | ++++ | 11A | +++++ |
| 11A-2 | +++++ | 14A | +++++ |
| 13 | +++++ | 14A-4 | +++++ |
| 14A-1 | ++ | 21 | +++++ |
| 22 | +++++ | 23A | +++++ |
| 23A-1 | +++++ | 23A-2 | ++ |
| 23A-3 | +++++ | 23A-4 | ++ |
| 23B | ++++ | 25 | +++++ |
| 26A | +++++ | 26A-2 | ++ |
| 26A-3 | +++++ | 26B | ++++ |
| 40 | ++ | 45A | +++++ |
| 45A-1 | +++++ | 45A-4 | ++++ |
| 46 | +++++ | 49 | +++++ |
| 52A | +++++ | 52B | ++++ |
| 53A | +++++ | 55 | +++++ |
| 58 | ++++ | 61A | +++++ |
| 62A | +++++ | | |

Example 2: HeLa Cell Based IDO1 Inhibition Assay

HeLa cell line was purchased from ATCC, cultured in MEM/EBSS medium supplemented with 10% FBS, penn-step (100,000 U/L), non-essential amino acid (0.1 Mm), sodium pyruvate (1.0 Mm). Cells were cultured at 37° C., 95% humidity and 5% $CO_2$. IFN-γ was used to induce IDO1 which resulted in the production of N-formylkynurenine from tryptophan. The detailed experimental method is as follow:

25,000 HeLa cells were placed on 96-well plates. Each well contained 100 μl culture medium, subsequently IFN-γ and test compounds at specific concentrations (concentration range between 10 μM and 1 Nm, so that the final volume of culture medium was 200 μL) were added and IFN-γ was used to induce IDO1 expression. After incubation, 140 μL supernatant was transferred to 96-well plates. After adding 6.1 N TCA (10 μL), the plates were continuously incubated at 50° C. for 30 min, to hydrolyze N-formylkynurenine produced by IDO to kynurenine. The reaction solution was then centrifuged at 2500 rpm for 10 min to remove precipitate. 100 μL/well supernatant was then transferred to another 96-well plate. 100 μL of 2% (w/v) 4-N,N-dimethyl aminobenzaldehyde acetic acid solution was added and incubated at room temperature for 10 min. The yellow color derived from kynurenine was recorded by measuring absorbance at 480 nm using a microplate reader (TECAN Infinite M1000 Pro).

The % inhibition of test compounds at a series of concentrations was in reference to the reduction of kynurenine in test samples relative to 0.5% DMSO (% volume) blank solution, the $IC_{50}$ was calculated using non-linear regression in Graph Pad Prism® 4.

The assay result of the test compounds in this disclosure, the $IC_{50}$ range is as follow: + represents 10-100 μM, ++ represents 1-10 μM, +++ represents 0.5-1 μM, ++++ represents 0.1-0.5 μM, +++++ represents <0.1 μM.

| Compound No. | HeLa cell IDO1 $IC_{50}$ | Compound No. | HeLa cell IDO1 $IC_{50}$ |
|---|---|---|---|
| 1 | ++++ | 1-2 | ++++ |
| 1-3 | +++++ | 4 | +++ |
| 9 | ++++ | 10A | +++++ |
| 11A | +++++ | 11A-2 | +++++ |
| 11A-3 | ++ | 13 | ++++ |
| 14A | +++++ | 14A-4 | +++++ |
| 15A | +++++ | 16 | ++++ |
| 21 | +++++ | 22 | ++++ |
| 23A | +++++ | 23A-1 | ++++ |
| 23A-3 | +++++ | 24A | +++++ |
| 24B | ++++ | 25 | ++++ |
| 26A | +++++ | 26A-3 | +++++ |
| 45A | +++++ | 45A-1 | +++++ |
| 45A-4 | ++++ | 46 | +++++ |
| 47A | +++++ | 47B | +++++ |
| 49 | +++++ | 52A | +++++ |
| 52B | +++++ | 55 | +++++ |
| 55A | +++++ | 55B | ++++ |
| 58 | +++++ | 61A | +++++ |
| 66 | +++++ | 67B | +++++ |
| 69A | +++++ | 69B | +++ |
| 71 | +++++ | 81A | +++++ |
| 87 | +++ | 88 | ++++ |
| 93A | +++++ | 97 | +++++ |
| 100 | +++++ | 101 | ++++ |
| 102 | ++ | 108A | +++++ |
| 123 | +++++ | 124A | +++++ |
| 125A | +++++ | 125B | +++++ |
| 132A | ++++ | 132B | ++ |
| 161A | ++++ | 161B | +++ |
| 162A | ++++ | 162B | ++++ |
| 165A | +++++ | 165B | +++ |
| 167A | ++++ | 167B | ++++ |
| 168A | +++++ | 168B | ++ |
| 208 | +++++ | Ref. A | ++++ |

Example 3: Three-Point IDO1 Cellular Assay

To perform the 3-point HeLa cell based IDO1 assay, HeLa cells were seeded at 25,000 cells per well into 96-well microplate in 100 μL of growth medium. Cells were incubated at 37° C. and 5% $CO_2$ overnight. The next day 100 μL per well of diluted inhibitor in growth medium at 10, 100 and 1000 nM, respectively, was added at a final concentration of 100 ng/ML human IFN-γ. Cells were incubated at 37° C. in a $CO_2$ incubator for 18 hours. The next day 140 μL of medium was removed into a new 96-well plate and 10 μL of 6.1 N TCA was added. The plate was incubated at 50° C. for 30 min to hydrolyze N-formylkynurenine produced by IDO1 to kynurenine. The plate was then centrifuged at 2500 rpm for 10 min to remove sediments. 100 μl of supernatant per well was transferred to another 96-well plate and mixed with 100 μL of 2% (w/v) 4-(Dimethylamino) benzaldehyde in acetic acid. The plate was incubated at room temperature for 10 minutes, the yellow color derived from kynurenine was recorded by measuring absorbance at 480 nm using a microplate reader (TECAN Infinite M1000 Pro). Cell based assays were performed in triplicate at each concentration. The absorbance data were analyzed using the computer software, Graphpad Prism. In the absence of the compound and presence of 100 ng/ML IFN-γ, the absorbance $(A_t)$ in each data set was defined as 100%. The absorbance of medium blank $(A_b)$ in each data set was defined as 0%. The percent absorbance in the presence of each compound was calculated according to the following equation: % Absorbance=$(A-A_b)/(A_t-A_b)$, where A=the absorbance in the presence of the compound and IFN-γ, $A_b$=the absorbance of medium blank, and $A_t$=the absorbance in the absence of the compounds and presence of IFN-γ. The values of % absorbance versus the compound concentrations were then determined.

The following compounds inhibition values of % were greater than 50% at 1000 nM: compounds 5, 6, 12A, 23B, 18, 27, 31, 35, 45B, 48A, 50A, 50B, 51A, 51B, 54, 56A, 56B, 61B, 62A, 62B, 63, 67A, 75B, 76, 80, 91A, 98A, 104, 106A, 109A, 112A, 114A, 133, 135B, 137, 142, 143A, 144B, 145, 146, 147A, 149, 152, 163B, 164B, 169B, 170A-A, 191A, 191B, 200A, 201A, 202A, 204, 205, 206, 207 and 210.

The following compounds inhibition values of % were greater than 50% at 100 nM: 11B, 19, 29A, 30, 46A, 46B, 53A, 53B, 64, 68, 84A, 89, 93B, 94A, 95A, 96A, 105A, 107A, 110A, 111A, 122, 127, 131A, 135A, 136, 151, 153, 163A, 164A, 166B, 169A, 192A, 193A, and 209.

The following compounds inhibition values of % were greater than 50% at 10 nM: 65, 70A, 75A, 82A, 83A, 85A and 126.

Example 4: TDO2 Enzymatic Assay

The TDO2 enzymatic assay was performed by UV absorption using a recombinant TDO2 and L-Tryptophan substrate. The UV absorption signal at 321 nm is correlated with the amount of N-formylkynurenine reaction product of TDO2. The compounds were diluted in 10% DMSO and 5 μL of the dilution was added to a 100 μL reaction so that the final concentration of DMSO is 0.5% in all of reactions. All of the reactions were conducted at room temperature. The 100 μL reaction mixture in TDO2 Assay Buffer contains 50 nM TDO2, the indicated amount of the inhibitor, 200 μM tryptophan, and the coupled reaction components. The reaction mixture incubated for 75 min prior to reading the UV absorption signal. For the negative control (blank), 5 μl of the assay buffer was added instead of the TDO2.

Absorption signals were measured using a Tecan Infinite M1000 plate reader. Binding experiments were performed in duplicate at each concentration. The percent activity in the presence of each compound was calculated according to the following equation: % activity=$[(A-A_b)/(A_t-A_b)]\times 100$, where A=the absorption signal in the presence of the compound, $A_b$=the absorption signal of blank, $A_t$=the absorption signal in the absence of the compound. The percent inhibition was calculated according to the following equation: % inhibition=100-% activity. The $IC_{50}$ was calculated using non-linear regression in Graph Pad Prism® 4.

The assay result of the test compounds in this disclosure, the $IC_{50}$ range is as follow: + represents 10-100 μM, ++ represents 1-10 μM, +++ represents 0.5-1 μM, ++++ represents <0.5 μM.

| Compound No. | TDO2 $IC_{50}$ | Compound No. | TDO2 $IC_{50}$ |
|---|---|---|---|
| 11A-2 | ++++ | 23A-3 | ++++ |
| 26A-3 | ++++ | 45A-1 | ++++ |
| 45A-4 | ++ | Ref. B | + |

Ref.A and Ref.B are used in Biology examples 2 and 4 as positive control compounds, the chemical names are as bellow:

Ref.A: (1R,4r)-4-((R)-2-((S)-6-fluoro-5H-imidazo[5,1-a]isoindol-5-yl)-1-hydroxyethyl) cyclohexanol Ref.B: 4-amino-N-(3-chloro-4-fluorophenyl)-N'-hydroxy-1,2,5-oxadiazole-3-carboximidamide

Example 5: Animal Model Assays

Female mice (C57BL/6, 6-8 week old) were purchased from Shanghai Laboratory Animal Center, Chinese Academy of Sciences, Shanghai, China. Mice were housed under pathogen-free conditions with autoclaved rodent chow and water available ad libitum. Each mouse was inoculated s.c. with colon cancer MC38 cells in 0.1 mL PBS over the right lower flank. When the tumor volume reached 40 $mm^3$, mice were randomized based on initial tumor volume measurements and treated with either vehicle or compound 23A-3. Tumor volumes were measured with electronic digital caliper and calculated using the formula length (mm)×width $(mm)^2/2$ and expressed in $mm^3$. Student's t-test was used to evaluate the statistical significance of observed differences.

Results are shown in FIG. 1. FIG. 1 shows the result of compounds in present disclosure as a single agent in the Treatment of Subcutaneous MC38 Mouse Colon cancer Syngeneic Model in C57BL/6 Mice, wherein the mean tumor volume of the mice treated with either vehicle or compound 23A-3 is measured and plotted versus the dosing days. It can be seen that compound 23A-3 of the present disclosure has significant tumor growth inhibition effect.

What is claimed is:

1. A compound of formula (I), an isomer, or a pharmaceutically acceptable salt thereof;

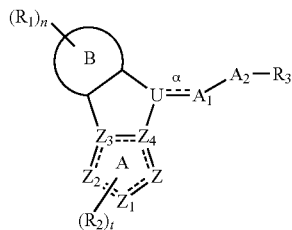

wherein, n is 1, 2 or 3; t is 1 or 2; U is $CR_4$, bond α is a single bond;

A ring is 5-membered diaza-aryl;

Z, $Z_1$, $Z_2$, $Z_3$ and $Z_4$ in A ring are selected from 1) $Z_1$ an $Z_4$ are N; Z, $Z_2$ and $Z_3$ are C; and 2) $Z_1$ and $Z_3$ are N; Z, $Z_2$ and $Z_4$ are C;

B ring is benzene or a 5- or 6-membered heteroaromatic ring;

$A_1$ is —$(CR_9R_{9a})_m$—;

$R_9$ is independently hydrogen, halogen, substituted or unsubstituted alkyl, substituted or unsubstituted cycloalkyl, substituted or unsubstituted heterocyclolalkyl, substituted or unsubstituted alkoxy, wherein the substituted alkyl, substituted cycloalkyl, substituted heterocycloalkyl, or substituted alkoxy is alkyl, cycloalkyl, heterocycloalkyl, or alkoxy substituted by one or more substituent(s) at any position independently selected from halogen, hydroxyl, alkyl, heterocycloalkyl, cycloalkyl, alkoxy, amino, aryl, heteroaryl, —$SR_6$, —$NR_6R_{6a}$, —$S(O)_2NR_6R_{6a}$, —$NR_8C(O)NR_6R_{6a}$, —$NR_6C(O)R_{6a}$, —$NR_6S(O)_2R_{6a}$, —$C(O)R_6$, —$S(O)_{0-2}R_6$, —$C(O)OR_6$, —$C(O)NR_6R_{6a}$, —$(CH_2)_rOH$, and —$(CH_2)_rNR_6R_{6a}$;

$R_{9a}$ is independently hydrogen, deuterium, halogen, substituted or unsubstituted alkyl; or $R_9$ and $R_{9a}$ together with the carbon atom to which they are attached form a 3- to 8-membered mono-cycloalkyl ring, wherein the substituted alkyl is alkyl substituted by one or more substituent(s) at any position independently selected from hydroxyl, halogen, and $C_{3-6}$ cycloalkyl;

$A_2$ is —$C(=R_7)(CR_5R_{5a})_m$—, or —$(CR_5R_{5a})_m$—;

$R_5$ and $R_{5a}$ are independently hydrogen, hydroxyl, halogen, alkyl, amino, —$SR_6$, —$OR_6$, —$NR_6R_{6a}$, —$NR_6S(O)_2R_{6a}$, —$S(O)_2NR_6R_{6a}$, —$(CH_2)_rS(O)_{0-2}CH_3$, —$OS(O)_3H$, —$OP(O)(O-R_6)_2$, —$OC(O)R_6$, —$OC(O)NR_6R_{6a}$, —$C(O)NR_6R_{6a}$, —$(CH_2)_rC(O)OH$, —$(CH_2)_rOH$, —$(CH_2)_rC(O)NR_6R_{6a}$, or —$(CH_2)_rNR_6R_{6a}$;

$R_1$ is hydrogen, halogen, hydroxyl, alkyl, alkoxy, alkylthiol, haloalkyl, haloalkoxy, amino, $C_{2-6}$alkynyl, $C_{2-6}$alkenyl, aryl, cycloalkyl, heterocycloalkyl, heteroaryl, —SH, —CN, —$NO_2$, —$OC(O)R_6$, —$OC(O)OR_6$, —$OC(O)NR_6R_{6a}$, —$C(O)OR_6$, —$C(O)R_6$, —$C(O)NR_6R_{6a}$, —$NR_6R_{6a}$, —$NR_6C(O)R_{6a}$, —$NR_6C(O)OR_{6a}$, —$NR_6C(O)NR_6R_{6a}$, —$(CH_2)_rNR_6R_{6a}$, —$NR_6S(O)_2R_{6a}$, —$S(O)_{0-2}R_6$, or —$S(O)_2NR_6R_{6a}$;

$R_2$ is hydrogen, halogen, hydroxyl, alkyl, alkoxy, alklthiol, haloalkyl, haloalkoxy, amino, $C_{2-6}$ alkynyl, $C_{2-6}$ alkenyl, aryl, cycloalkyl, heterocycloalkyl, heteroaryl, —SH, —CN, —$NO_2$, or —$NR_6R_{6a}$;

$R_3$ is substituted or unsubstituted bridged tricycloalkyl, or substituted or unsubstituted bridged heterocycloalkyl; wherein the substituted bridged tricycloalkyl, or substituted bridged heterocycloaklyl is substituted by one or more $R_{10}$;

$R_4$ is hydrogen, deuterium, halogen, —CN, —C(O)OH, tetrazole, substituted or unsubstituted alkyl, substituted or unsubstituted alkoxy, wherein the substituted alkyl, substituted alkoxy is substituted at any position by one or more $R_{12}$ which is independently selected from halogen, hydroxyl, alkyl, bridged tricycloalkyl, alkoxy, aryl, heteroaryl, amino, substituted or unsubstituted cycloalkyl, substituted or unsubstituted heterocycloalkyl, —$SR_6$, —$NR_6R_{6a}$, —$S(O)_2NR_6R_{6a}$, —$NR_6C(O)NR_6R_{6a}$, —$C(O)R_6$, —$S(O)_{0-2}R_6$, —$C(O)OR_6$, —$(CH_2)_rOH$, and —$(CH_2)_rNR_6R_{6a}$, further wherein the substituted cycloalkyl, or substituted heterocycloalkyl is substituted by one or more of substituent(s) independently selected from hydroxyl, amino, and halogen;

$R_{10}$ is independently -L-$C(R_8)=R_{10a}$, —$NO_2$, —CN, —OH, —$NH_2$, —SH, halogen, substituted or unsubstituted alkyl, substituted or unsubstituted alkoxy, substituted or unsubstituted aryl, substituted or unsubstituted heteroaryl, substituted or unsubstituted cycloalkyl, substituted or unsubstituted heterocycloalkyl, substituted or unsubstituted arylalkyl, substituted or unsubstituted heteroarylalkyl, substituted or unsubstituted cycloalkylalkyl, substituted or unsubstituted heterocycloalkylalkyl, substituted or unsubstituted bridged tricycloalkyl, substituted or unsubstituted $C_{2-6}$ alkynyl, substituted or unsubstituted $C_{2-6}$ alkenyl, —$C_{2-6}$ alkynyl-$R_{8b}$, -L-$R_8$, —O-L-$R_8$, —$S(O)_{0-2}$-L-$R_8$, —$N(R_8)$-L-$R_{8b}$, -L-$OR_{8b}$, -L-$OC(O)R_{8b}$, -L-$OC(O)NR_8R_{8b}$, -L-$OC(O)OR_{8b}$, -L-$OP(O)(O-R_8)_2$, -L-B$(O-R_8)_2$, -L-$OS(O)_2(OH)$, -L-$OS(O)_{1-2}R_{8b}$, -L-$S(O)_{1-2}OR_{8b}$, -L-$S(O)_2NR_8R_{8b}$, -L-$S(O)_{0-2}R_{8b}$, -L-$S(O)_2N(R_8)C(O)NR_8R_{8b}$, -L-$C(O)OR_{8b}$, -L-$C(O)R_{8b}$, -L-$C(O)N(OH)R_{8b}$, -L-$C(=R_7)NR_8R_{8b}$, -L-$NR_8R_{8b}$, -L-$N(R_8)C(O)OR_{8b}$, -L-$N(R_8)C(=R_7)R_{8b}$, -L-$N(R_8)C(O)N(R_8)S(O)_2R_{8b}$, -L-$N(R_8)OR_{8b}$, -L-$N(R_8)C(=R_7)NR_8R_{8b}$, -L-$N(R_8)S(O)_{1-2}R_{8b}$, -L-$N(R_8)S(O)_{1-2}NR_8R_{8b}$, or $R_8$ and $R_{8b}$ together with the nitrogen atom to which they are attached, form a 3- to 8-membered mono-heterocycloalkyl ring; wherein the substituted alkyl, substituted alkoxy, substituted cycloalkyl, substituted heterocycloalkyl, substituted aryl, substituted heteroaryl, substituted cycloalkylalkyl, substituted heterocycloalkylalkyl, substituted arylalkyl, substituted heteroarylalkyl, substituted bridged tricycloalkyl, substituted $C_{2-6}$ alkenyl, or substituted $C_{2-6}$ alkynyl, is substituted by 1 to 3 $R_{13}$ at any position;

$R_{13}$ is —OH, —SH, —CN, —$NO_2$, —$NH_2$, halogen, alkylthiol, —$C(=R_7)NR_6R_{6a}$, —$OC(O)R_6$, —$OC(O)OR_6$, —$OC(O)NR_6R_{6a}$, —$C(O)OR_6$, —$C(O)R_6$, —$C(O)NR_6R_{6a}$, —$NR_6R_{6a}$, —$NR_6C(O)R_{6a}$, —$NR_6C(=R_7)R_{6a}$, —$NR_6C(O)OR_{6a}$, —$NR_6C(O)NR_6R_{6a}$, —$NR_6C(=R_7)NR_6R_{6a}$, —$(CH_2)_rNR_6R_{6a}$, —$NR_6S(O)_2R_{6a}$, —$NR_6S(O)_2NR_6R_{6a}$, —$S(O)_{0-2}R_6$, —$S(O)_2NR_6R_{6a}$, substituted or unsubstituted alkyl, substituted or unsubstituted alkoxy, substituted or unsubstituted $C_{2-6}$ alkenyl, substituted or unsubstituted $C_{2-6}$ alkynyl, substituted or unsubstituted aryl, substituted or unsubstituted cycloalkyl, substituted or unsubstituted heterocycloalkyl, or substituted or unsubstituted heteroaryl; wherein the substituted alkyl, substituted alkoxy, substituted $C_{2-6}$ alkenyl, substituted $C_{2-6}$ alkynyl, substituted aryl, substituted heteroaryl, substituted cycloalkyl, or substituted heterocycloalkyl is substituted at any position by 1 to 3 substituent(s) independently selected from $C_{1-3}$ alkyl, halogen, $C_{1-3}$ alkoxy, halo-$C_{1-3}$ alkoxy, hydroxyl, and amino;

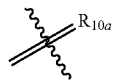

is selected from =O, =S, =N($R_{8b}$), =N(O$R_{8b}$), =C($R_{8b}$)$_2$, =C($R_{8b}$)(O$R_{8b}$), and =C($R_{8b}$)(NH$R_{8b}$);

L is a bond or $L_1$, wherein $L_1$ is —(C$R_8R_{8a}$)$_r$—; or $R_8$ and $R_{8a}$ together with the carbon atom to which they are attached, form a 3- to 8-membered mono-cycloalkyl ring;

$R_8$ is independently hydrogen, substituted or unsubstituted alkyl, substituted or unsubstituted alkoxy, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, or

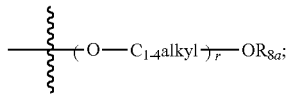

$R_{8a}$ is selected from hydrogen, halogen, hydroxyl, amino, substituted or unsubstituted alkyl, substituted or unsubstituted alkoxy, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, and substituted or unsubstituted heteroarylalkyl;

$R_{8b}$ is selected from hydrogen, substituted or unsubstituted alkyl, substituted or unsubstituted alkoxy, substituted or unsubstituted cycloalkyl, substituted or unsubstituted heterocycloalkyl, substituted or unsubstituted aryl, substituted or unsubstituted heteroaryl, substituted or unsubstituted cycloalkylalkyl, substituted or unsubstituted heterocycloalkylalkyl, substituted or unsubstituted arylalkyl, substituted or unsubstituted heteroarylalkyl, -$L_1$-$R_8$, -$L_1$-O$R_8$, -$L_1$-N($R_8$)$_2$, -$L_1$-C(O)O$R_8$, -$L_1$-OC(O)$R_8$, -$L_1$-C(O)N($R_8$)$_2$, -$L_1$-N($R_8$)C(O)$R_8$, -$L_1$-N($R_8$)C(O)N($R_8$)$_2$, -$L_1$-N($R_8$)C(S)N($R_8$)$_2$, -$L_1$-OS(O)$_{1-2}R_8$, -$L_1$-S(O)$_{1-2}$O$R_8$, -$L_1$-S(O)$_{0-2}R_8$, -$L_1$-N($R_8$)S(O)$_2$N($R_8$)$_2$, -$L_1$-S(O)$_2$N($R_8$)$_2$, -$L_1$-N($R_8$)S(O)$_2R_8$, -$L_1$-N($R_8$)C(O)N($R_8$)S(O)$_2R_8$, and -$L_1$-OP(O)(O—$R_8$)$_2$;

further wherein the substituted alkyl, substituted alkoxy, substituted cycloalkyl, substituted heterocycloalkyl, substituted aryl, substituted heteroaryl, substituted cycloalkylalkyl, substituted heterocycloalkylalkyl, substituted arylalkyl, or substituted heteroarylalkyl in $R_8$, $R_{8a}$ or $R_{8b}$ is substituted at any position by 1 to 3 $R_{14}$ group independently selected from —OH, —SH, —CN, —NO$_2$, —NH$_2$, halogen, alkylthiol, —C(=$R_7$)NR$_6R_{6a}$, —OC(O)$R_6$, —OC(O)O$R_6$, —OC(O)NR$_6R_{6a}$, —C(O)O$R_6$, —C(O)$R_6$, —C(O)NR$_6R_{6a}$, —NR$_6R_{6a}$, —NR$_6$C(O)$R_{6a}$, —NR$_6$C(=$R_7$)$R_{6a}$, —NR$_6$C(O)O$R_{6a}$, —NR$_6$C(O)NR$_6R_{6a}$, —NR$_6$C(=$R_7$)NR$_6R_{6a}$, —(CH$_2$)$_r$NR$_6R_{6a}$, —NR$_6$S(O)$_2R_{6a}$, —NR$_6$S(O)$_2$NR$_6R_{6a}$, —S(O)$_{0-2}R_6$, —S(O)$_2$NR$_6R_{6a}$, substituted or unsubstituted alkyl, substituted or unsubstituted alkoxy, substituted or unsubstituted $C_{2-6}$ alkenyl, substituted or unsubstituted $C_{2-6}$ alkynyl, substituted or unsubstituted aryl, substituted or unsubstituted cycloalkyl, substituted or unsubstituted heterocycloalkyl, and substituted or unsubstituted heteroaryl, wherein the substituted alkyl, substituted alkoxy, substituted $C_{2-6}$ alkenyl, substituted $C_{2-6}$ alkynyl, or substituted aryl, substituted heteroaryl, substituted cycloalkyl, or substituted heterocycloalkyl in $R_{14}$ group is substituted at any position by 1 to 3 substituent(s) independently selected from $C_{1-3}$ alkyl, halogen, $C_{1-3}$ alkoxy, halo-$C_{1-3}$ alkoxy, hydroxyl, and amino;

is independently =O, =S, =N($R_6$), or =N(O$R_6$);

$R_6$ and $R_{6a}$ is independently hydrogen, alkyl, haloalkyl, cycloalkyl, heterocycloalkyl, aryl, heteroaryl, heterocycloalkylalkyl, cycloalkylalkyl, arylalkyl, or heteroarylalkyl, or $R_6$ and $R_{6a}$ together with the nitrogen atom to which they are attached, form a 3- to 8-membered mono-heterocycloalkyl ring;

r is an integer ranging from 1 to 8; and m is 0, 1, 2, or 3.

2. The compound or the pharmaceutically acceptable salt thereof of claim 1, wherein $R_{8b}$ is hydrogen, substituted or unsubstituted $C_{1-4}$ alkyl, substituted or unsubstituted $C_{1-4}$ alkoxy, substituted or unsubstituted $C_{3-8}$ cycloalkyl, substituted or unsubstituted 5- to 8-membered heterocycloalkyl, substituted or unsubstituted $C_{6-10}$ aryl, substituted or unsubstituted 5- to 10-membered heteroaryl, substituted or unsubstituted $C_{3-8}$ cycloalkyl-$C_{1-4}$ alkyl, substituted or unsubstituted 5- to 8-membered heterocycloalkyl-$C_{1-4}$ alkyl, substituted or unsubstituted $C_{6-10}$ aryl-$C_{1-4}$alkyl, substituted or unsubstituted 5- to 6-membered heteroaryl-$C_{1-4}$ alkyl, -$L_1$-$R_8$, -$L_1$-O$R_8$, -$L_1$-N($R_8$)$_2$, -$L_1$-C(O)O$R_8$, -$L_1$-OC(O)$R_8$, -$L_1$-C(O)N($R_8$)$_2$, -$L_1$-N($R_8$)C(O)$R_8$, -$L_1$-N($R_8$)C(O)N($R_8$)$_2$, -$L_1$-N($R_8$)C(S)N($R_8$)$_2$, -$L_1$-OS(O)$_{1-2}R_8$, -$L_1$-S(O)$_{1-2}$O$R_8$, -$L_1$-S(O)$_{0-2}R_8$, -$L_1$-N($R_8$)S(O)$_2$N($R_8$)$_2$, -$L_1$-S(O)$_2$N($R_8$)$_2$, -$L_1$-N($R_8$)S(O)$_2R_8$, -$L_1$-N($R_8$)C(O)N($R_8$)S(O)$_2R_8$, or -$L_1$-OP(O)(O—$R_8$)$_2$; and further wherein substituted $C_{1-4}$ alkyl, substituted $C_{1-4}$ alkoxy, substituted $C_{3-8}$ cycloalkyl, substituted 5- to 8-membered heterocycloalkyl, substituted $C_{6-10}$ aryl, substituted 5- to 10-membered heteroaryl, substituted $C_{3-8}$ cycloalkyl-$C_{1-4}$ alkyl, substituted 5- to 8-membered heterocycloalkyl-$C_{1-4}$ alkyl, substituted $C_{6-10}$ aryl-$C_{1-4}$ alkyl, or substituted 5- to 6-membered heteroaryl-$C_{1-4}$ alkyl for $R_{8b}$ is substituted at any position by 1 to 3 $R_{14}$.

3. The compound or the pharmaceutically acceptable salt thereof of claim 1, wherein $R_8$ is hydrogen, substituted or unsubstituted $C_{1-4}$ alkyl, substituted or unsubstituted $C_{1-4}$ alkoxy, substituted or unsubstituted $C_{3-8}$ cycloalkyl, substituted or unsubstituted 5- to 8-membered heterocycloalkyl, substituted or unsubstituted $C_{6-10}$ aryl, substituted or unsubstituted 5- to 10-membered heteroaryl, substituted or unsubstituted $C_{3-8}$ cycloalkyl-$C_{1-4}$ alkyl, substituted or unsubstituted 5- to 8-membered heterocycloalkyl-$C_{1-4}$ alkyl, substituted or unsubstituted $C_{6-10}$ aryl $C_{1-4}$ alkyl, substituted or unsubstituted 5- to 6-membered heteroaryl-$C_{1-4}$ alkyl, or

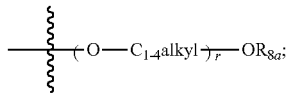

and further wherein the substituted $C_{1-4}$ alkyl, substituted $C_{1-4}$ alkoxy, substituted $C_{3-8}$ cycloalkyl, substituted 5- to 8-membered heterocycloalkyl, substituted $C_{6-10}$ aryl, substituted 5- to 10-membered heteroaryl, substituted $C_{3-8}$ cycloalkyl-$C_{1-4}$ alkyl, substituted 5- to 8-membered heterocycloalkyl-$C_{1-4}$ alkyl, substituted $C_{6-10}$ aryl $C_{1-4}$alkyl, or substituted 5- to 6-membered heteroaryl-$C_{1-4}$ alkyl for $R_8$ is substituted at any position by 1 to 3 $R_{14}$.

4. The compound or the pharmaceutically acceptable salt thereof of claim 1, wherein $R_{8a}$ is hydrogen, halogen, hydroxyl, amino, substituted or unsubstituted $C_{1-4}$ alkyl, substituted or unsubstituted $C_{1-4}$ alkoxy, substituted or unsubstituted $C_{3-8}$ cycloalkyl, substituted or unsubstituted 5- to 8-membered heterocycloalkyl, substituted or unsubstituted $C_{6-10}$ aryl, substituted or unsubstituted 5- to 10-membered heteroaryl, substituted or unsubstituted $C_{3-8}$ cycloalkyl-$C_{1-4}$ alkyl, substituted or unsubstituted 5- to 8-membered heterocycloalkyl-$C_{1-4}$ alkyl, substituted or unsubstituted $C_{6-10}$ aryl $C_{1-4}$ alkyl, substituted or unsubstituted 5- to 6-membered heteroaryl-$C_{1-4}$ alkyl, and wherein the substituted $C_{1-4}$ alkyl, substituted $C_{1-4}$ alkoxy, substituted $C_{3-8}$ cycloalkyl, substituted 5- to 8-membered heterocycloalkyl, substituted $C_{6-10}$ aryl, substituted 5- to 6-membered heteroaryl, substituted $C_{3-8}$ cycloalkyl-$C_{1-4}$ alkyl, substituted 5- to 8-membered heterocycloalkyl-$C_{1-4}$ alkyl, substituted $C_{6-10}$ aryl $C_{1-4}$ alkyl, substituted 5- to 6-membered heteroaryl-$C_{1-4}$ alkyl for $R_{8a}$ is substituted at any position by 1 to 3 $R_{14}$.

5. The compound or the pharmaceutically acceptable salt thereof of claim 1, wherein $R_4$ is hydrogen, fluorine, hydroxyl, $C_{1-4}$alkyl, or $C_{1-4}$alkoxy,
or U is CH, bond α is a single bond,
or B ring is benzene, thiophene, pyridine, or pyrimidine,
or $R_9$ is hydrogen, halogen, substituted or unsubstituted $C_{1-4}$ alkyl, or substituted or unsubstituted $C_{1-4}$ alkoxy, and wherein the substituted $C_{1-4}$ alkyl or substituted $C_{1-4}$ alkoxy is a $C_{1-4}$ alkyl or $C_{1-4}$ alkoxy substituted by one or more substituent(s) at any position independently selected from halogen, hydroxyl, alkyl, heterocycloalkyl, cycloalkyl, alkoxy, amino, aryl, heteroaryl, —$SR_6$, —$NR_6R_{6a}$, —$S(O)_2NR_6R_{6a}$, —$NR_6C(O)NR_6R_{6a}$, —$NR_6C(O)R_{6a}$, —$NR_6S(O)_2R_{6a}$, —$C(O)R_6$, —$S(O)_{0-2}R_6$, —$C(O)OR_6$, —$C(O)NR_6R_{6a}$, —$(CH_2)_rOH$, and —$(CH_2)_rNR_6R_{6a}$; further wherein $R_6$, $R_{6a}$, and r are as defined in claim 1; $R_{9a}$ is hydrogen, deuterium, halogen, or substituted or unsubstituted $C_{1-4}$ alkyl, wherein the substituted $C_{1-4}$ alkyl is alkyl substituted by one or more substituent(s) at any position independently selected from hydroxyl, halogen, and $C_{3-6}$cycloalkyl,
or $R_5$ or $R_{5a}$ in $A_2$ is hydrogen, —$SR_6$, —$OR_6$, —$NR_6R_{6a}$, —$NHSO_2R_6$, —$NR_6SO_2R_{6a}$, —$OP(O)(O-R_6)_2$, —$OC(O)R_6$.

6. The compound or the pharmaceutically acceptable salt thereof of claim 1, wherein $A_1$ is —$CH_2$—, —CHF—, —$CF_2$—, —$CHCH_3$— or —$C(CH_3)_2$—,
or $A_2$ is —CHF—, —CH(CN)—, —CH(COOH)—, —CH(OH)—, —CH(OPO_3H)—, —$C(CH_3)(OH)$—,

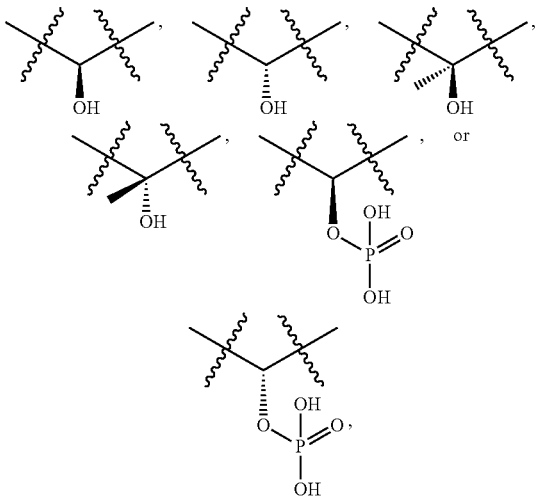

or $R_1$ is —OH, —SH, —CN, hydrogen, halogen, amino, $C_{1-3}$ alkoxy, $C_{1-3}$ alkylthiol, $C_{1-3}$ alkyl, halo-$C_{1-3}$ alkyl or halo-$C_{1-3}$ alkoxy,
or $R_2$ is —OH, —SH, —$NH_2$, hydrogen, halogen, $C_{1-3}$ alkoxy, $C_{1-3}$ alkylthiol, $C_{1-3}$ alkyl, or halo-$C_{1-3}$ alkyl.

7. The compound or the pharmaceutically acceptable salt thereof of claim 1, wherein $R_3$ is substituted or unsubstituted bridged $C_{7-10}$ tricycloalkyl, or substituted or unsubstituted bridged 7- to 10-membered heterocycloalkyl, and further wherein the substituted bridged $C_{7-10}$ tricycloalkyl, or substituted bridged 7- to 10-membered heterocycloalkyl is substituted by one or more $R_{10}$ which is as defined in claim 1,
or $R_3$ is substituted or unsubstituted 2-azabicyclo[2.2.1]heptyl, substituted or unsubstituted 2-oxabicyclo[2.2.1]heptyl, substituted or unsubstituted 2,5-diazabicyclo[2.2.1] heptyl, substituted or unsubstituted (1S, 5S)-9-oxabicyclo[3.3.1]nonyl, substituted or unsubstituted (1R, 5S)-8-oxabicyclo[3.2.1]octyl, substituted or unsubstituted (1R, 5S)-3-oxabicyclo[3.2.1]octyl, substituted or unsubstituted (1R, 5S)-3-azabicyclo[3.2.1]octyl, substituted or unsubstituted (1R, 5S)-8-azabicyclo[3.2.1]octyl, substituted or unsubstituted quinuclidinyl, substituted or unsubstituted 2-aza-bicyclo[2.2.2]octyl, or substituted or unsubstituted 2-azaadamantanyl, and wherein the substituted 2-azabicyclo[2.2.1]heptyl, substituted 2-oxabicyclo[2.2.1]heptyl, substituted 2,5-diazabicyclo[2.2.1]heptyl, substituted (1 S, 5S)-9-oxabicyclo[3.3.1]nonyl, substituted (1R, 5S)-8-oxabicyclo[3.2.1]octyl, substituted (1R, 5S)-3-oxabicyclo[3.2.1]octyl, substituted (1R, 5S)-3-azabicyclo[3.2.1]octyl, substituted (1R, 5S)-8-azabicyclo[3.2.1]octyl, substituted quinuclidinyl, substituted 2-aza-bicyclo[2.2.2] octyl, or substituted 2-azaadamantanyl is substituted by one or more $R_{10}$ which is as defined in claim 1,
or $R_3$ is substituted or unsubstituted adamantanyl, and wherein the substituted adamantanyl is substituted by one or more $R_{10}$ which is as defined in claim 1,
or $R_{10}$ is independently —$NO_2$, —CN, —OH, —$NH_2$, —SH, halogen, substituted or unsubstituted alkyl, substituted or unsubstituted alkoxy, substituted or unsubstituted aryl, substituted or unsubstituted heteroaryl, —$N(R_8)$-L-$R_{8b}$, -L-$R_8$, —O-L-$R_8$, -L-C(O)$R_{8b}$, -L-C(=$R_7$)$NR_8R_{8b}$, -L-S(O)$_2R_{8b}$, -L-$NR_8R_{8b}$, -L-N($R_8$)C (=R₇)R₈ᵦ, -L-N(R₈)C(=R₇)NR₈R₈ᵦ, and -L-N(R₈)S(O)₂R₈ᵦ, wherein the substituted alkyl, substituted alkoxy, substituted aryl, substituted heteroaryl is substituted by 1 to 3 R₁₃, and further wherein R₇, L, and R₁₃ are the same as defined in claim 1, and R₈, R₈ᵦ are as defined in claims 1, 2, or 3.

8. The compound or the pharmaceutically acceptable salt thereof of claim 1, wherein the substituted or unsubstituted alkyl for R₁₀ is substituted or unsubstituted C₁₋₄ alkyl, the substituted or unsubstituted alkoxy for R₁₀ is substituted or unsubstituted C₁₋₄ alkoxy, the substituted or unsubstituted aryl for R₁₀ is substituted or unsubstituted C₆₋₁₀ aryl, the substituted or unsubstituted heteroaryl for R₁₀ is substituted or unsubstituted 5- to 10-membered heteroaryl, the substituted or unsubstituted cycloalkyl for R₁₀ is substituted or unsubstituted C₃₋₈ cycloalkyl, the substituted or unsubstituted heterocycloalkyl for R₁₀ is substituted or unsubstituted 5- to 8-membered heterocycloalkyl, the substituted or unsubstituted cycloalkylalkyl for R₁₀ is substituted or unsubstituted C₃₋₈ cycloalkyl-C₁₋₄ alkyl, the substituted or unsubstituted heterocycloalkylalkyl for R₁₀ is substituted or unsubstituted 5- to 8-membered heterocycloalkyl-C₁₋₄ alkyl, the substituted or unsubstituted arylalkyl for R₁₀ is substituted or unsubstituted C₆₋₁₀ aryl-C₁₋₄alkyl, the substituted or unsubstituted heteroarylalkyl for R₁₀ is substituted or unsubstituted 5- to 10-membered heteroaryl-C₁₋₄ alkyl, or the substituted or unsubstituted bridged tricycloalkyl for R₁₀ is substituted or unsubstituted adamantanyl, and wherein the substituted C₁₋₄ alkyl, substituted C₁₋₄ alkoxy, substituted C₆₋₁₀ aryl, substituted 5- to 10-membered heteroaryl, substituted C₃₋₈ cycloalkyl, substituted 5- to 8-membered heterocycloalkyl, substituted C₃₋₈ cycloalkyl-C₁₋₄ alkyl, substituted 5- to 8-membered heterocycloalkyl-C₁₋₄ alkyl, substituted C₆₋₁₀ aryl-C₁₋₄alkyl, substituted 5- to 10-membered heteroaryl-C₁₋₄ alkyl, or substituted adamantanyl is substituted by 1 to 3 R₁₃.

9. The compound or the pharmaceutically acceptable salt thereof of claim 1, wherein R₁₃ is independently F, Cl, Br, —OH, —SH, —CN, —NO₂, —NH₂, C₁₋₄alkylthiol, C₃₋₈cycloalkyl, —C(O)NR₆R₆ₐ, —OC(O)R₆, —OC(O)OR₆, —OC(O)NR₆R₆ₐ, —C(O)OR₆, —C(O)R₆, —C(O)NR₆R₆ₐ, —NR₆R₆ₐ, —NR₆C(O)R₆ₐ, —NR₆C(O)R₆ₐ, —NR₆C(O)OR₆ₐ, —NR₆C(O)NR₆R₆ₐ, —NR₆C(O)NR₆R₆ₐ, —NR₆S(O)₂R₆ₐ, —NR₆S(O)₂NR₆R₆ₐ, —S(O)₀₋₂R₆, —S(O)₂NR₆R₆ₐ, —(CH₂)ᵣNR₆R₆ₐ, substituted or unsubstituted C₁₋₄ alkyl, substituted or unsubstituted C₁₋₄ alkoxy, substituted or unsubstituted C₂₋₆ alkenyl, substituted or unsubstituted C₂₋₆ alkynyl, substituted or unsubstituted phenyl, substituted or unsubstituted 5- to 6-membered heteroaryl, substituted or unsubstituted C₃₋₈ cycloalkyl, or substituted or unsubstituted 5- to 8-membered heterocycloalkyl;
further wherein the substituted C₁₋₄ alkyl, substituted C₁₋₄ alkoxy, substituted C₂₋₆ alkenyl, substituted C₂₋₆ alkynyl, substituted phenyl, substituted 5- to 6-membered heteroaryl, substituted C₃₋₈ cycolalkyl, or substituted 5- to 8-membered heterocycloalkyl is substituted at any position by 1 to 3 substituent(s) independently selected from C₁₋₃ alkyl, halogen, C₁₋₃ alkoxy, halo-C₁₋₃ alkoxy hydroxyl, and amino.

10. The compound or the pharmaceutically acceptable salt thereof of claim 1, wherein R₁₄ is independently F, Cl, Br, —OH, —SH, —CN, —NO₂, —NH₂, C₁₋₄ alkylthiol, C₃₋₈ cycloalkyl, —C(O)NR₆R₆ₐ, —OC(O)R₆, —OC(O)OR₆, —OC(O)NR₆R₆ₐ, —C(O)OR₆, —C(O)R₆, —C(O)NR₆R₆ₐ, —NR₆R₆ₐ, —NR₆C(O)R₆ₐ, —NR₆C(O)R₆ₐ, —NR₆C(O)OR₆ₐ, —NR₆C(O)NR₆R₆ₐ, —NR₆C(O)NR₆R₆ₐ, —(CH₂)ᵣNR₆R₆ₐ, —NR₆S(O)₂R₆ₐ, —NR₆S(O)₂NR₆R₆ₐ, —S(O)₀₋₂R₆, —S(O)₂NR₆R₆ₐ, substituted or unsubstituted C₁₋₄ alkyl, substituted or unsubstituted C₁₋₄ alkoxy, substituted or unsubstituted C₂₋₆ alkenyl, substituted or unsubstituted C₂₋₆ alkynyl, substituted or unsubstituted phenyl, substituted or unsubstituted 5- to 6-membered heteroaryl, substituted or unsubstituted C₃₋₈ cycloalkyl, or substituted or unsubstituted 5- to 8-membered heterocycloalkyl;
and wherein the substituted C₁₋₄ alkyl, substituted C₁₋₄ alkoxy, substituted C₂₋₆ alkenyl, substituted C₂₋₆ alkynyl, substituted phenyl, substituted 5- to 6-membered heteroaryl, substituted C₃₋₈ cycolalkyl, or substituted 5- to 8-membered heterocycloalkyl is substituted at any position by 1 to 3 substituent(s) independently selected from C₁₋₃ alkyl, halogen, C₁₋₃ alkoxy, halo-C₁₋₃ alkoxy hydroxyl, and amino.

11. The compound or the pharmaceutically acceptable salt thereof of claim 1, wherein R₆ and R₆ₐ are independently hydrogen, C₁₋₄ alkyl, halo-C₁₋₄ alkyl, C₃₋₈ cycloalkyl, 5- to 8-membered heterocycloalkyl, C₆₋₁₀ aryl, 5- to 6-membered heteroaryl, 5- to 8-membered heterocycloalkyl-C₁₋₄ alkyl, C₃₋₈ cycloalkyl-C₁₋₄ alkyl, C₆₋₁₀ aryl-C₁₋₄ alkyl, or 5- to 6-membered heteroaryl-C₁₋₄ alkyl, or R₆ and R₆ₐ together with the nitrogen atom to which they are attached, form a 3- to 8-membered mono-heterocycloalkyl ring.

12. The compound or the pharmaceutically acceptable salt thereof of claim 1, wherein

is =O, =S, =N—OH, or =NH,
or L₁ is —CH₂—, —CH₂CH₂—, —CH₂CH₂CH₂— or —C(CH₃)₂—,
or R₁₀ is hydrogen, F, Cl, Br, methyl, ethyl, methoxy, ethoxy, isopropoxy, cyclohexyloxy, phenoxy, benzyloxy, phenyl, pyridinyl, pyrimidinyl, tetrazole, carboxyl, —OH, —NO₂, —NH₂, —NHC(O)CH₃, —C(O)NH₂, —CN, —OCF₃, —CF₃, —CH₂OH, —CH₂NH₂, —OP(O)(OH)₂,

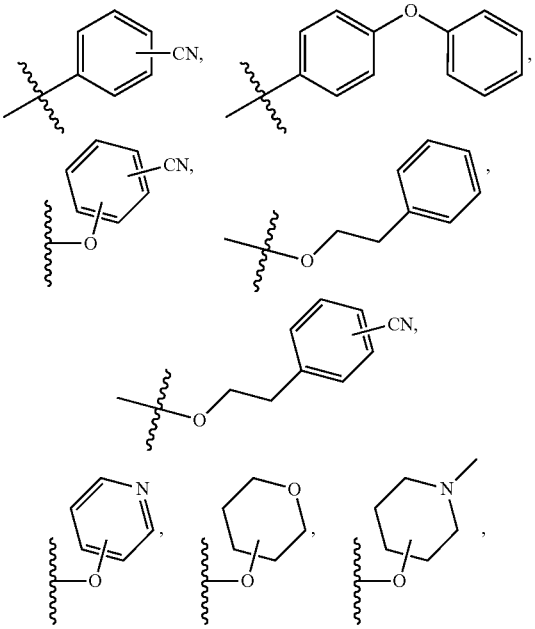

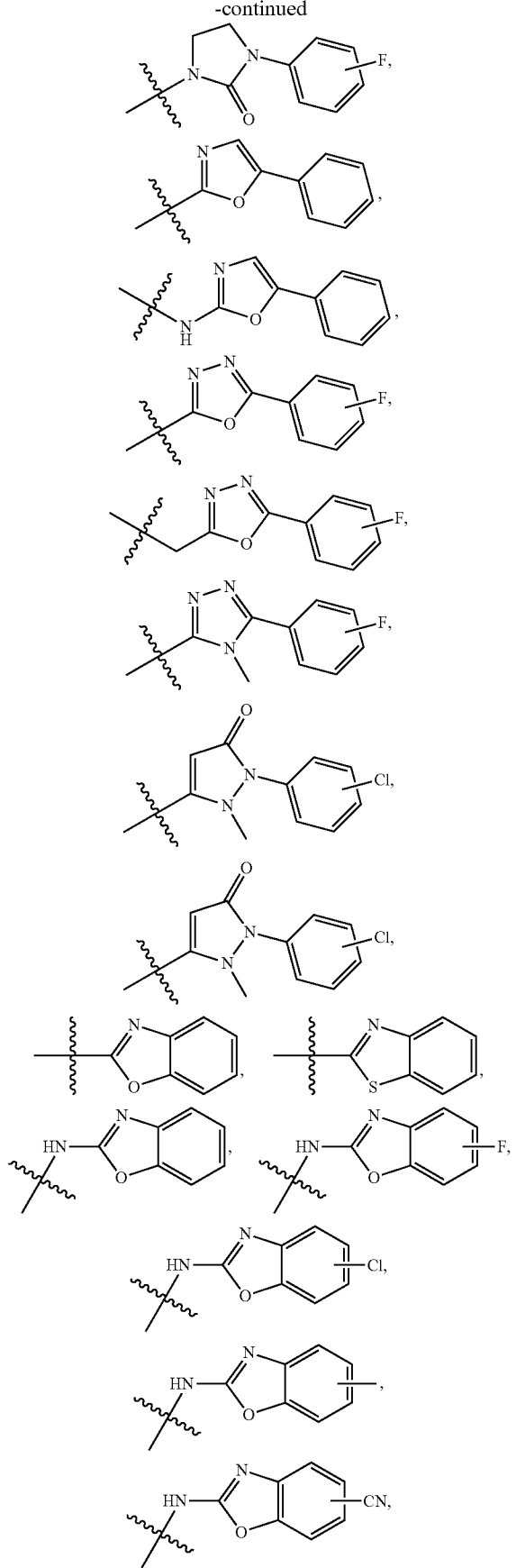
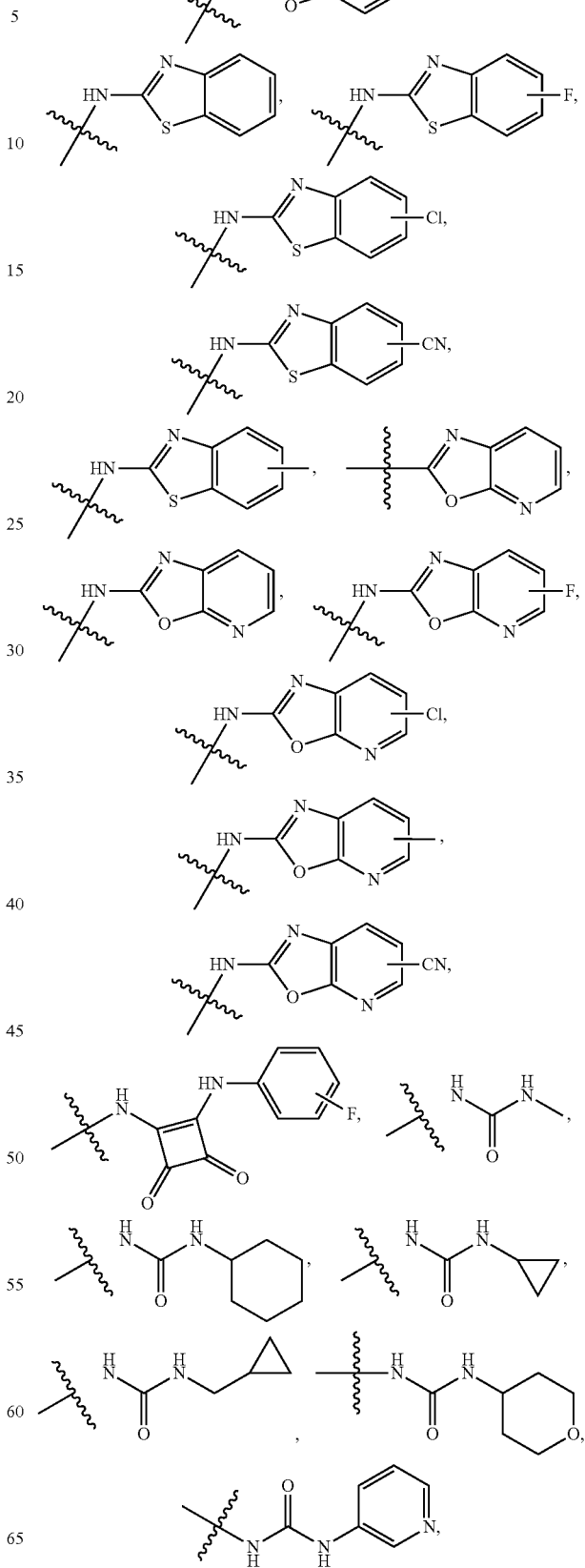

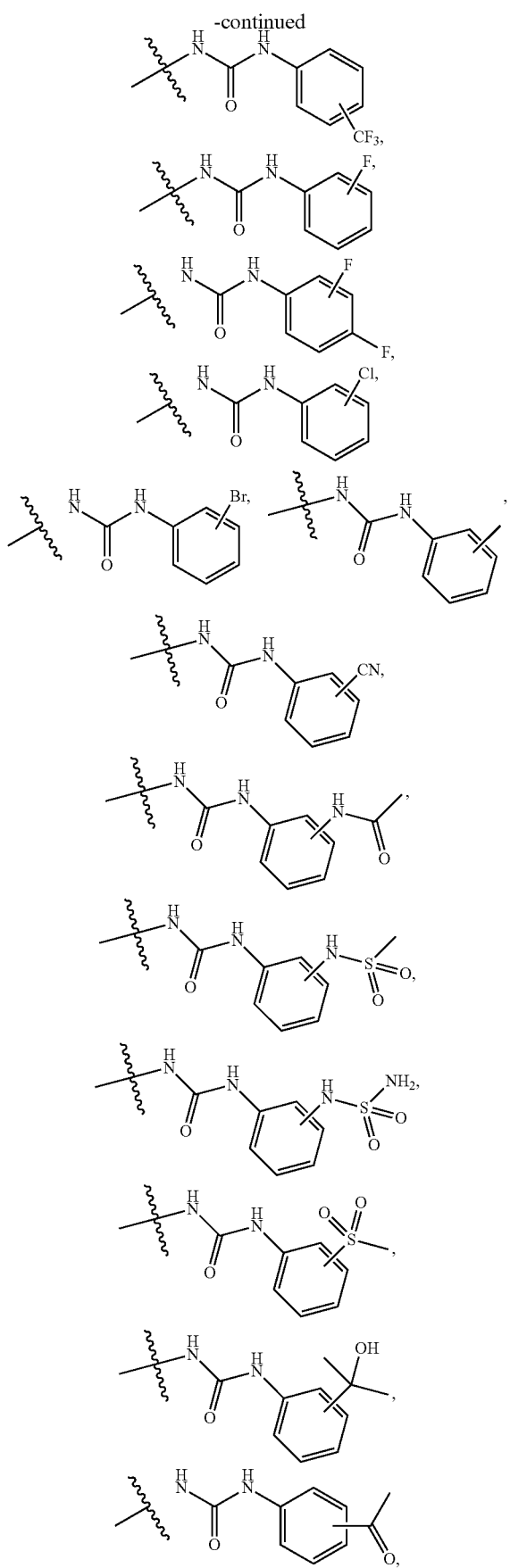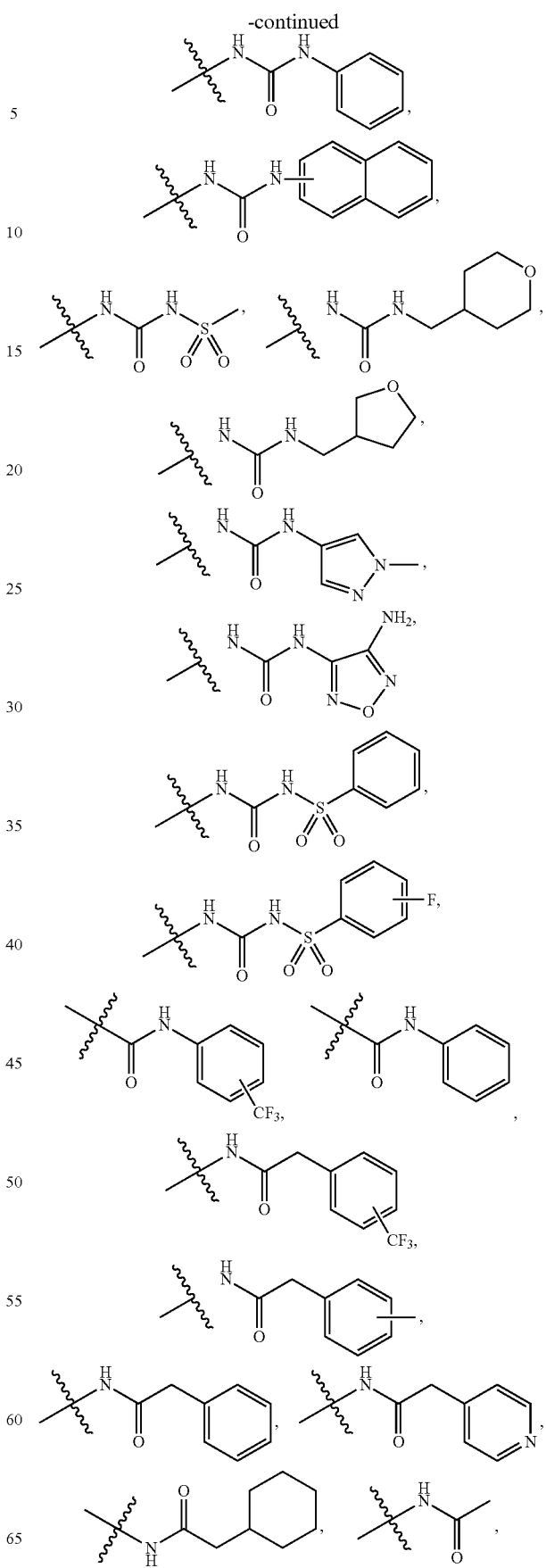

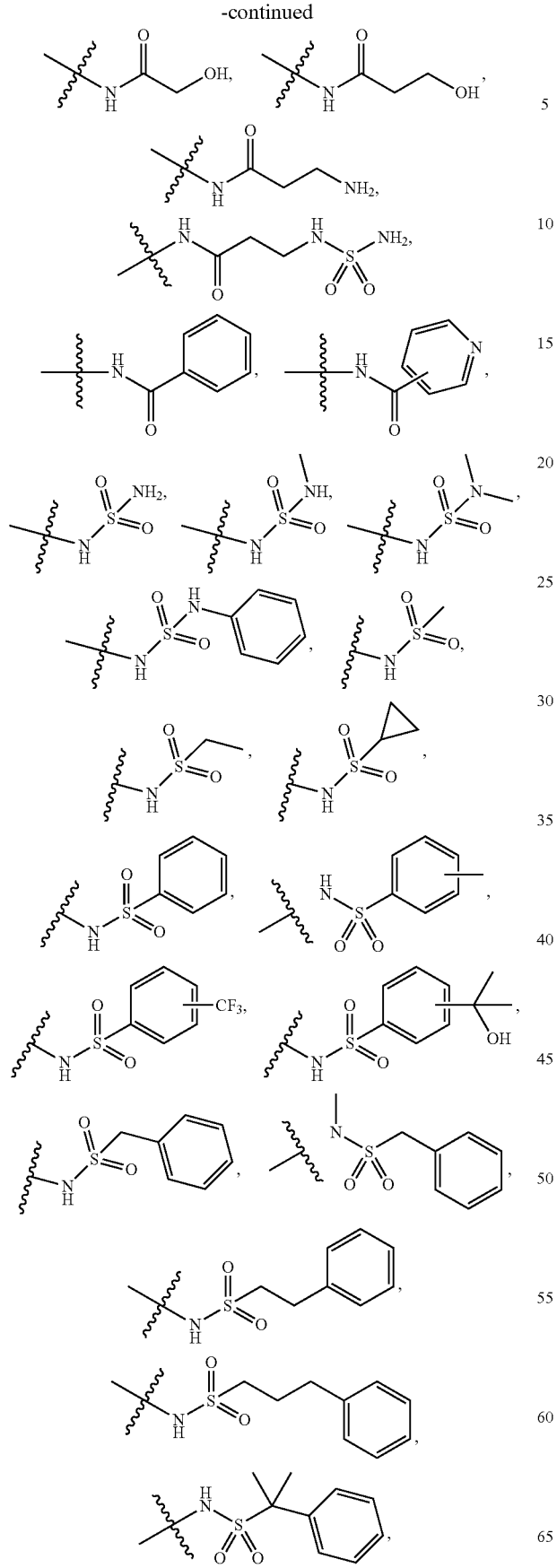
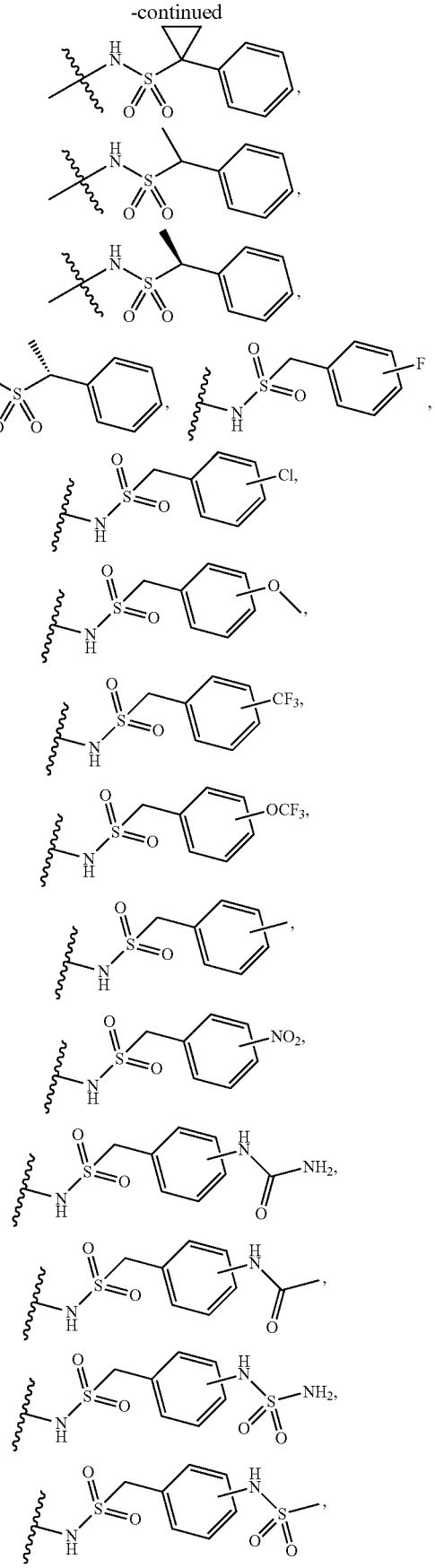

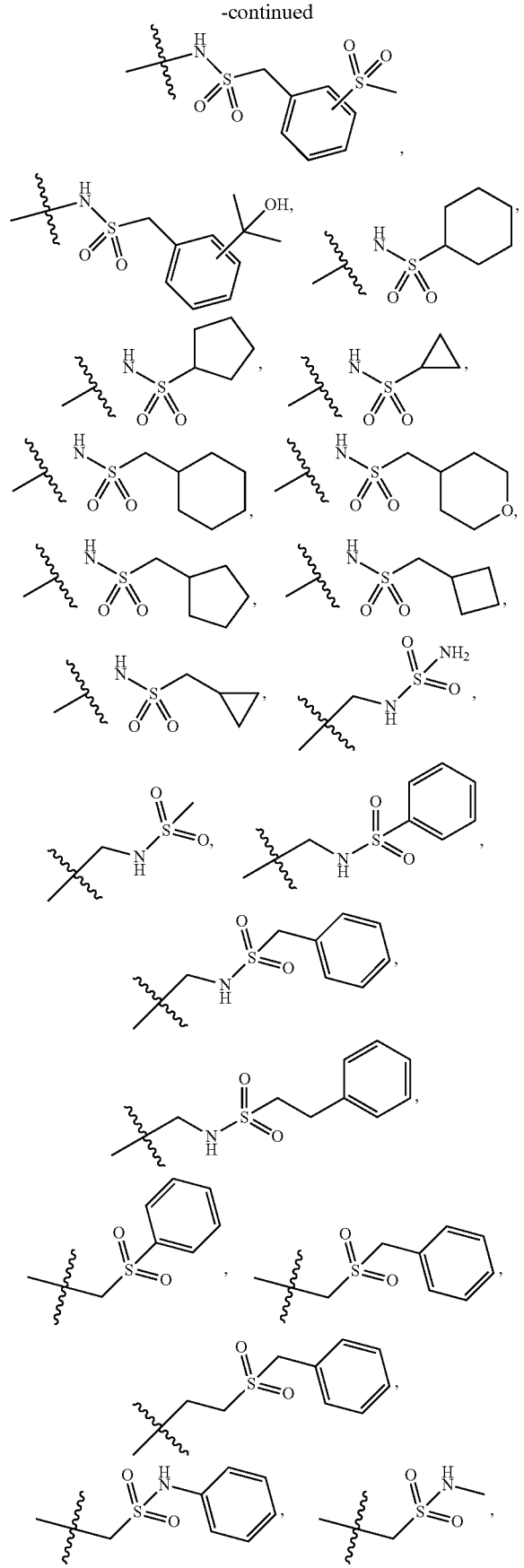
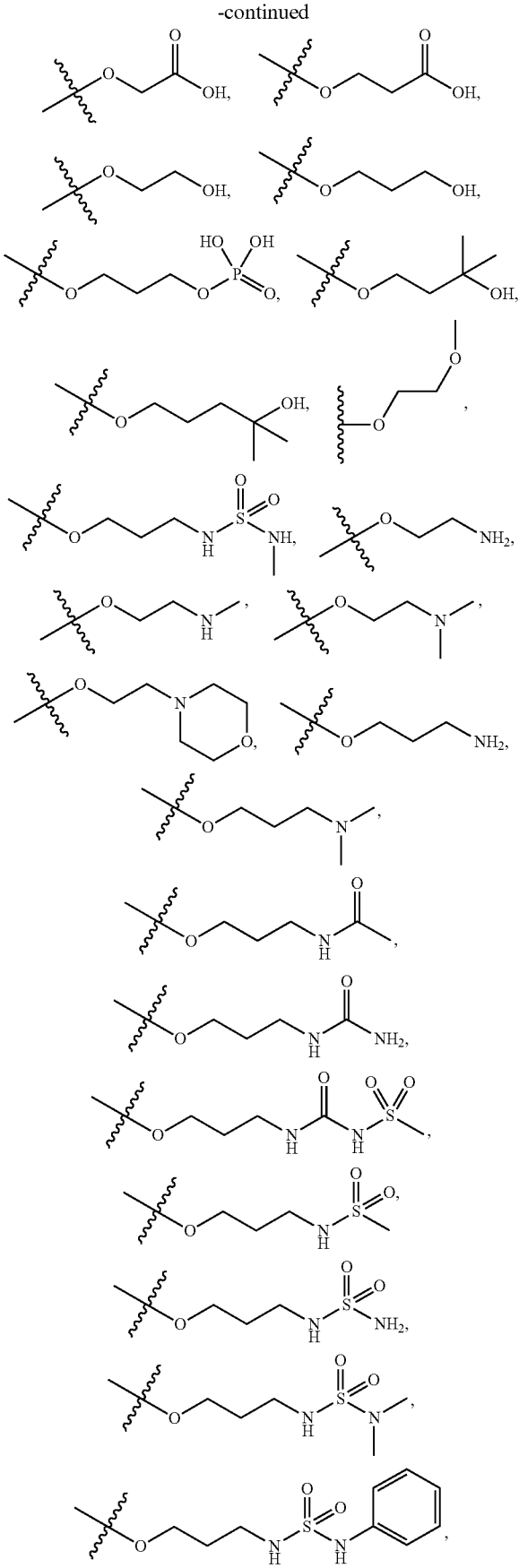

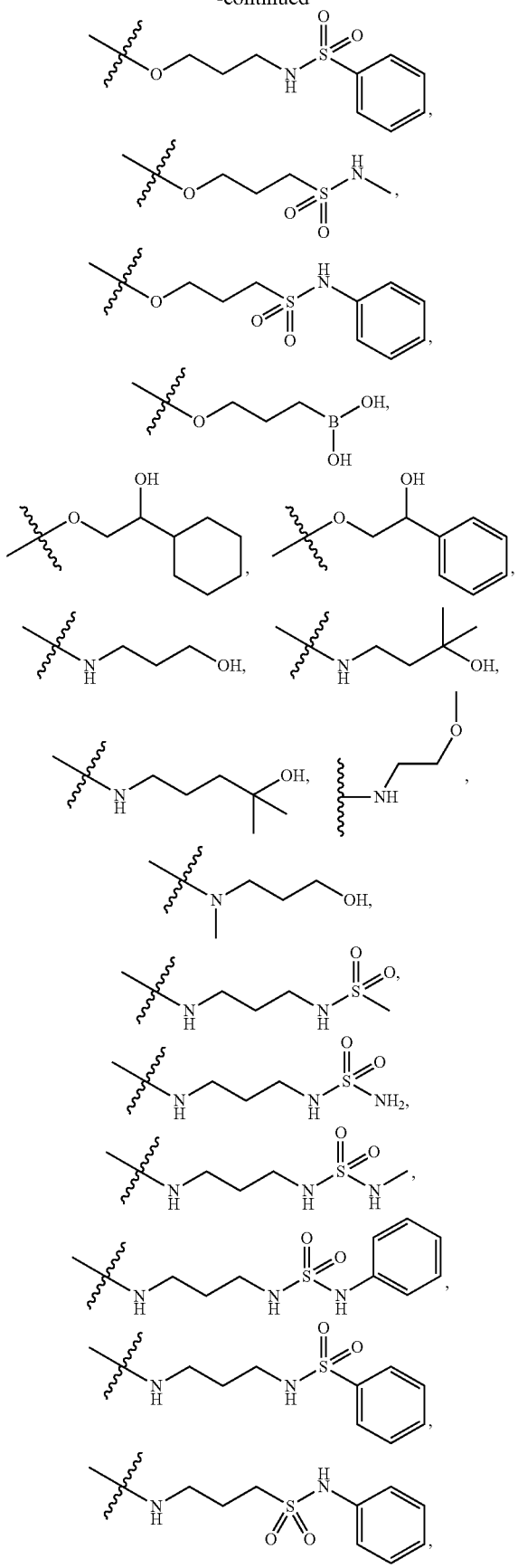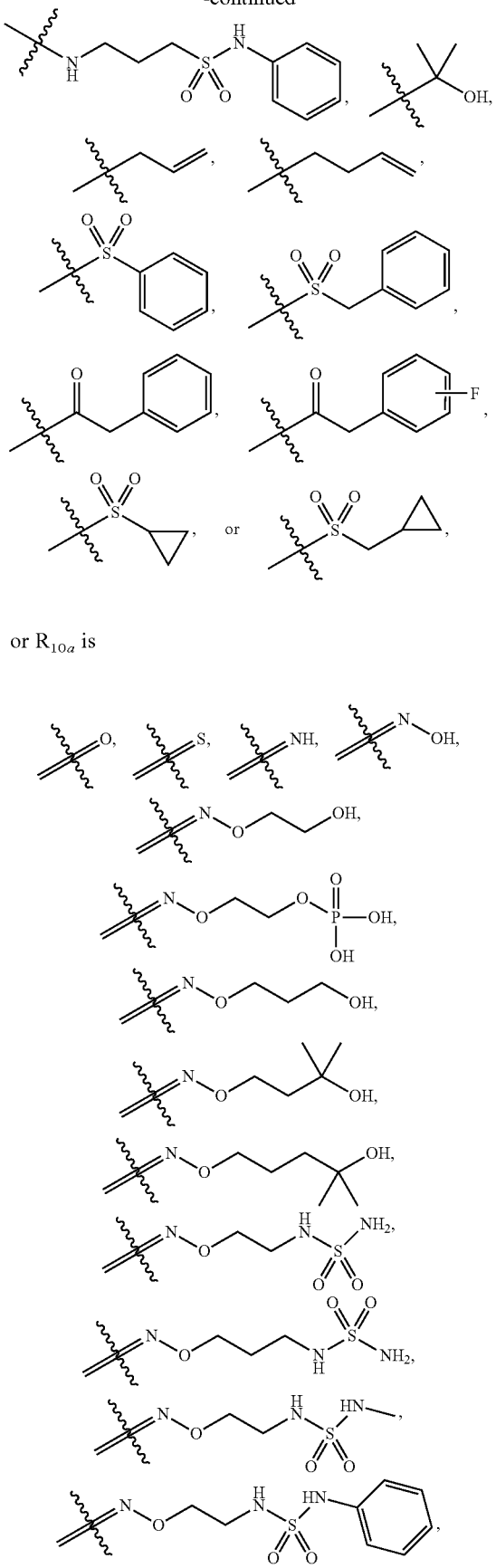
or $R_{10a}$ is

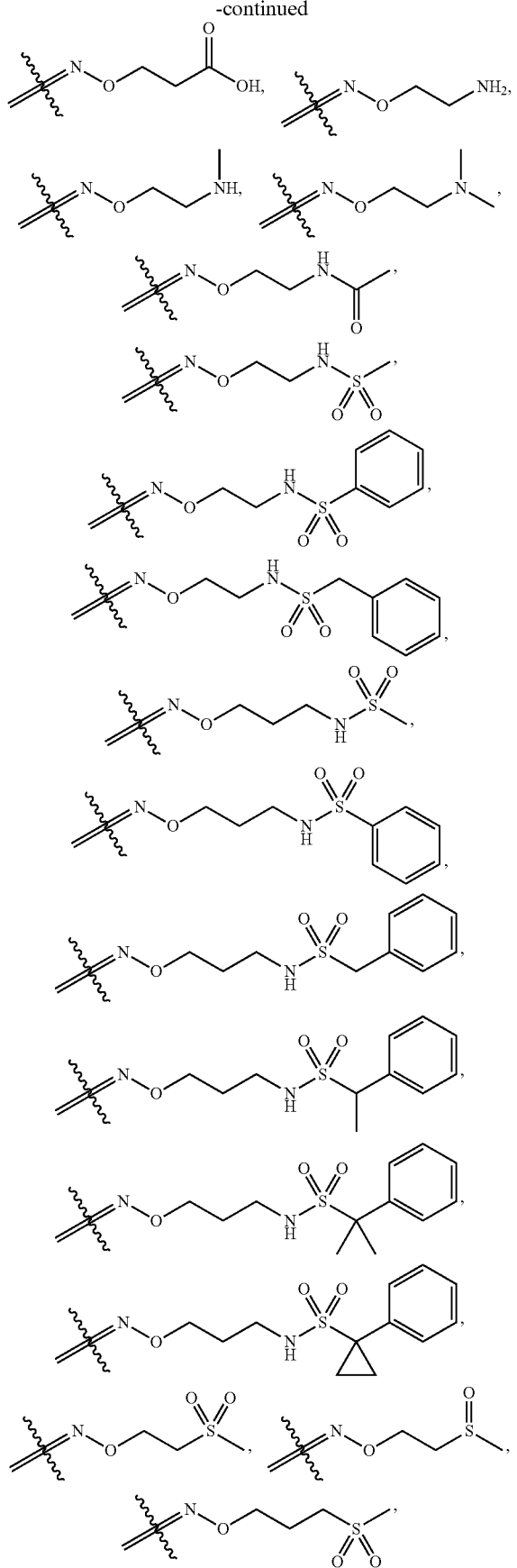
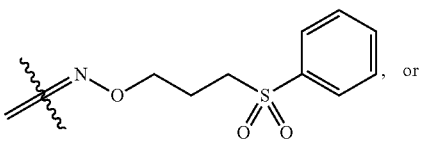, or
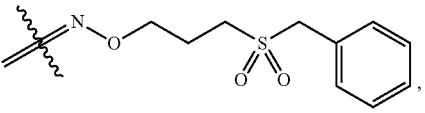,
or R₃ is
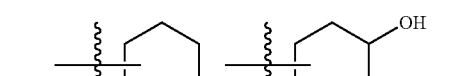
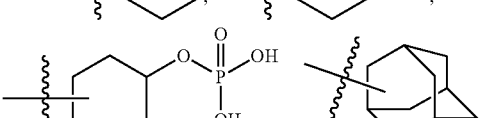
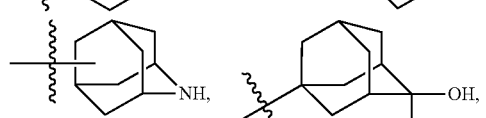
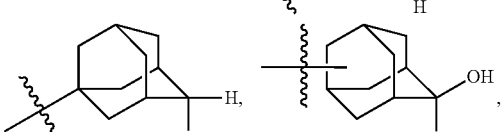
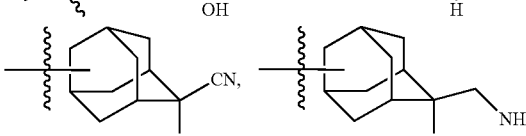
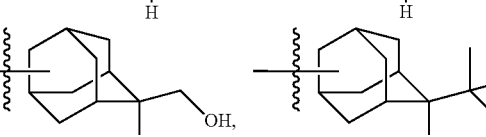
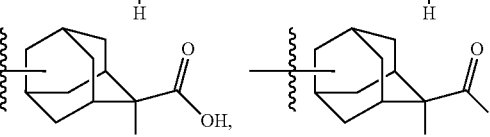
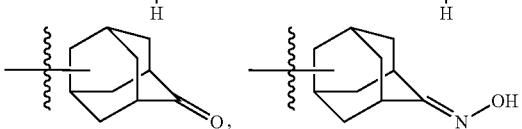
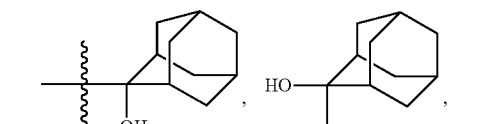
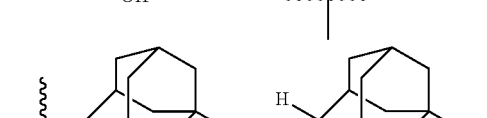
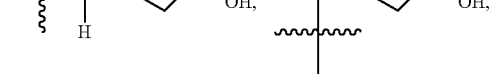

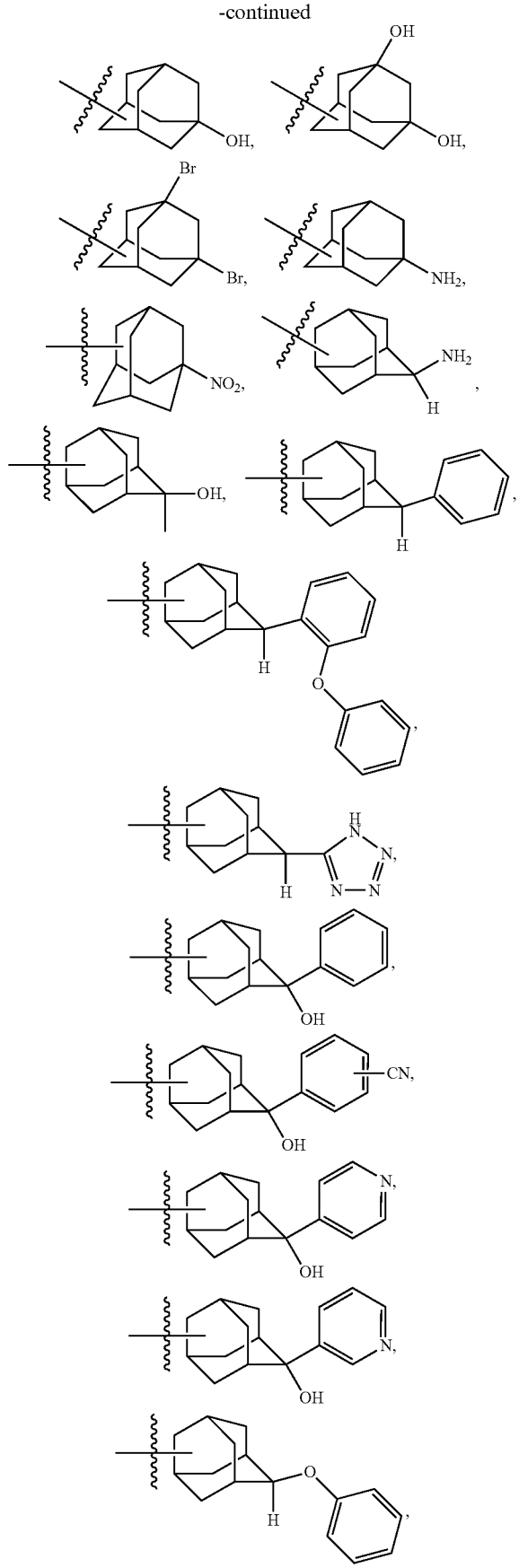
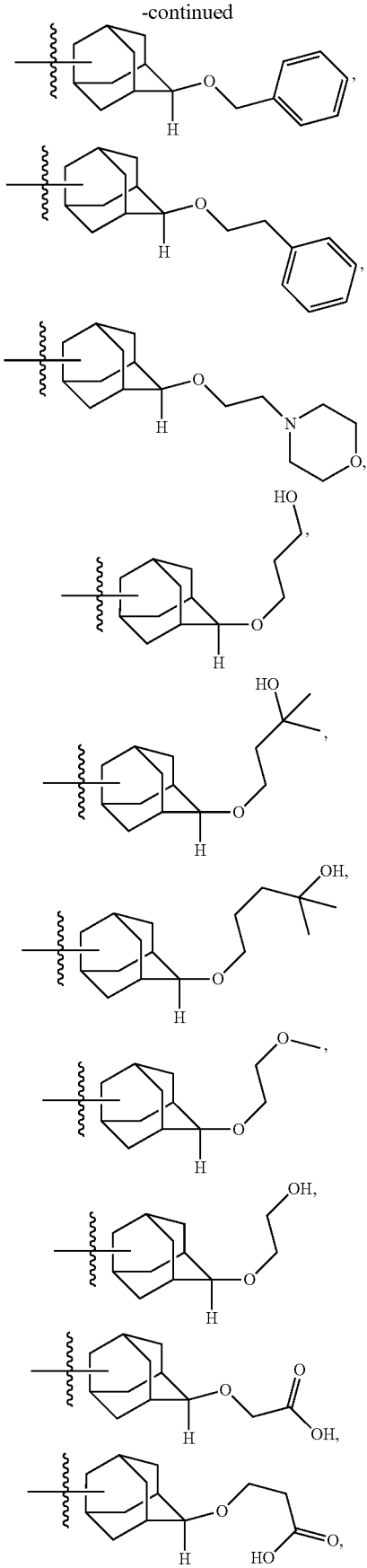

299
-continued
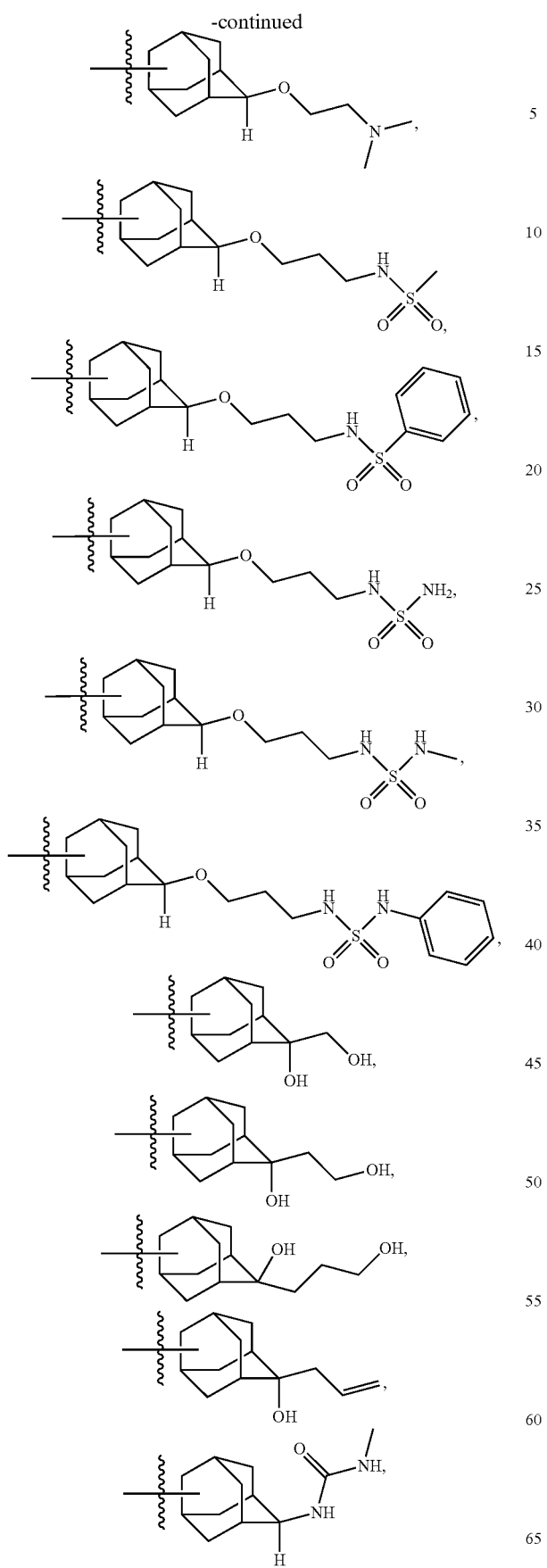
300
-continued
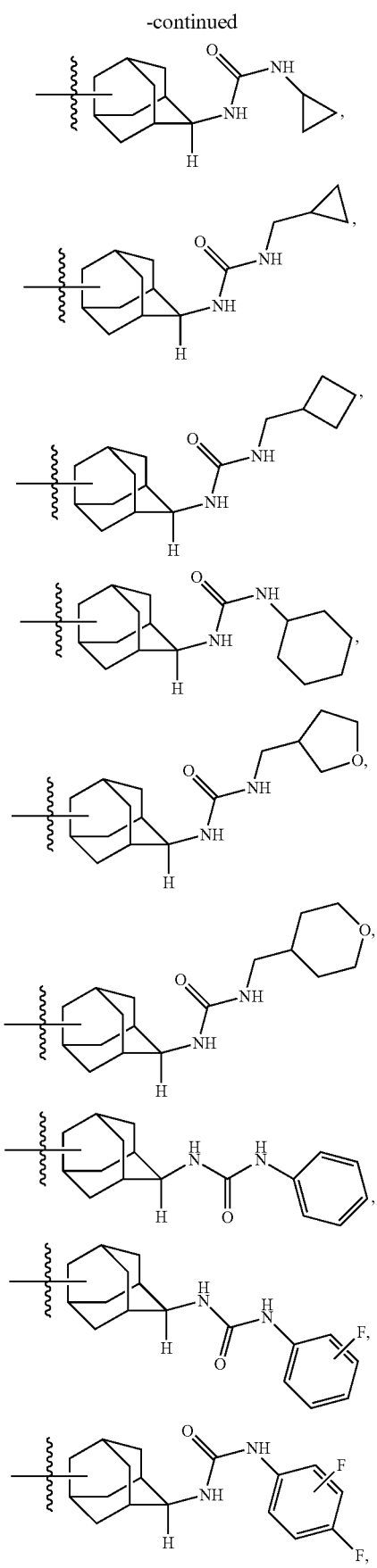

301
-continued
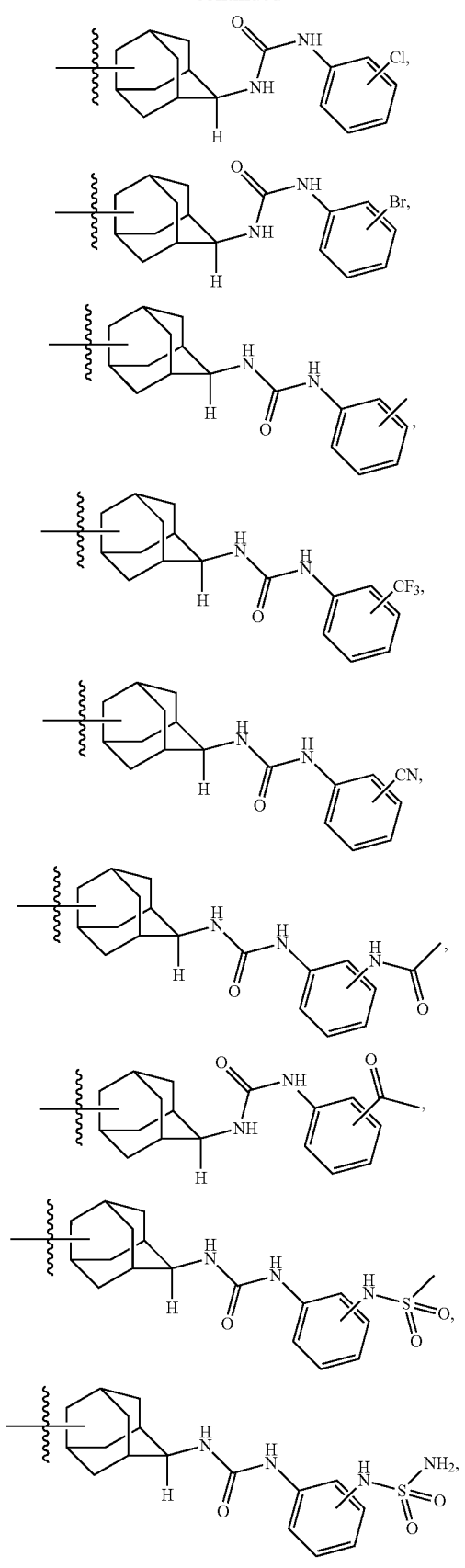
302
-continued
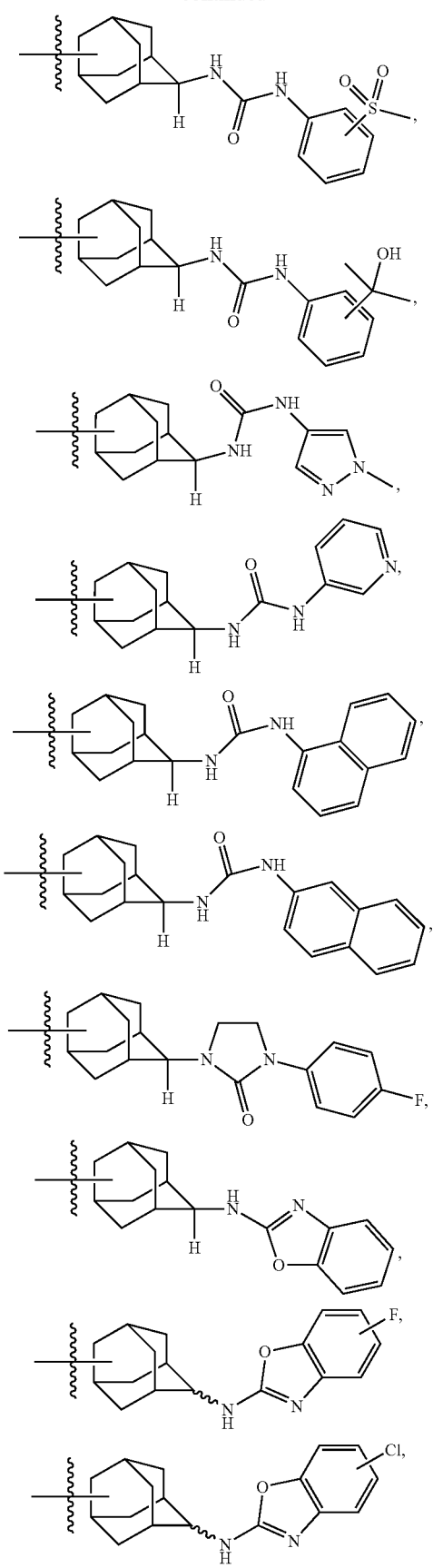

303
-continued
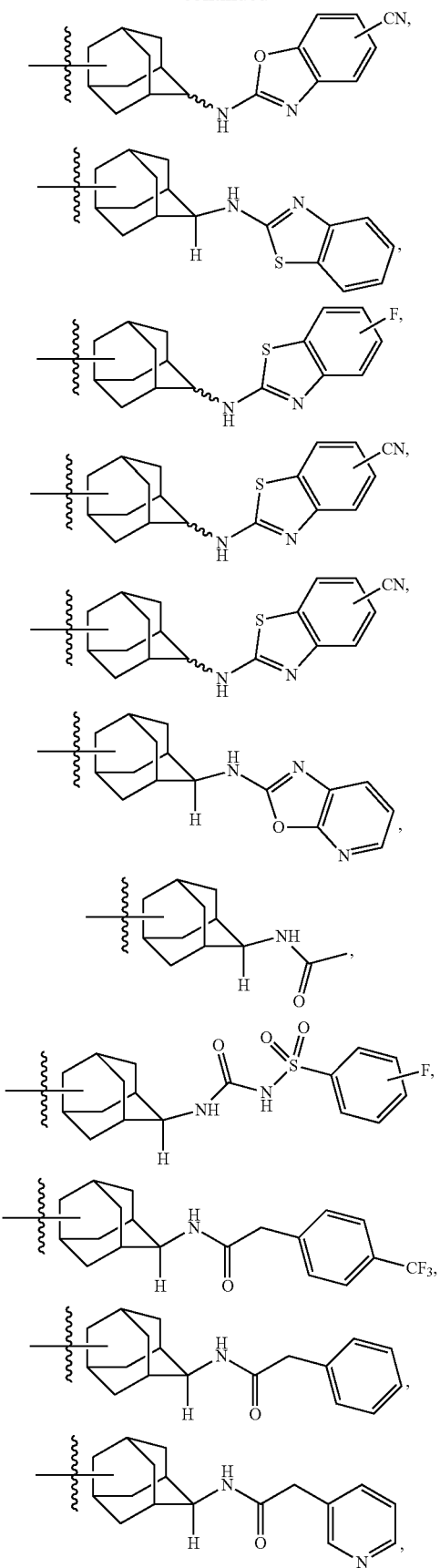
304
-continued
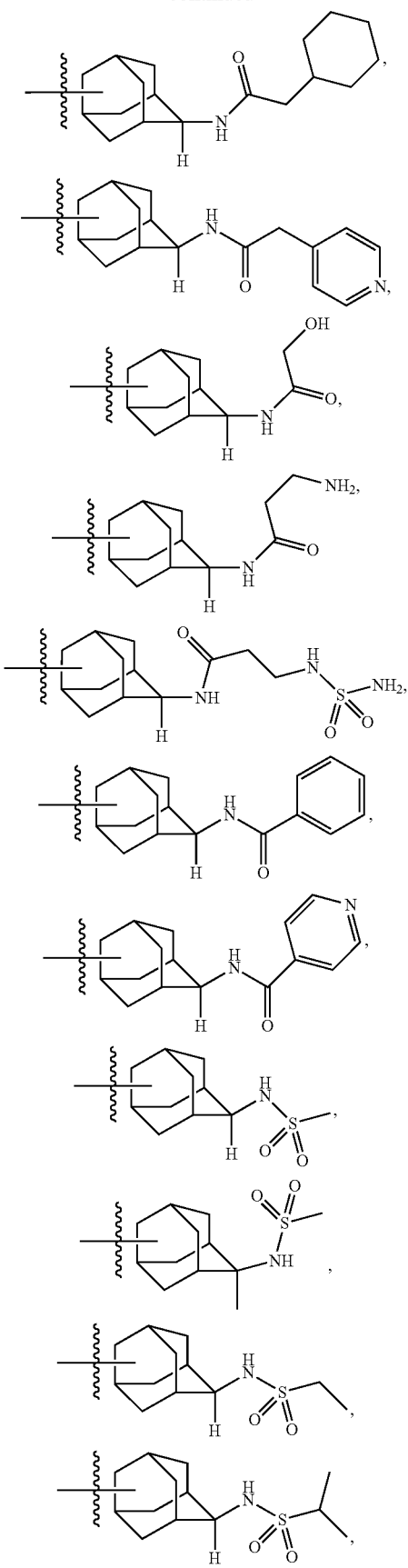

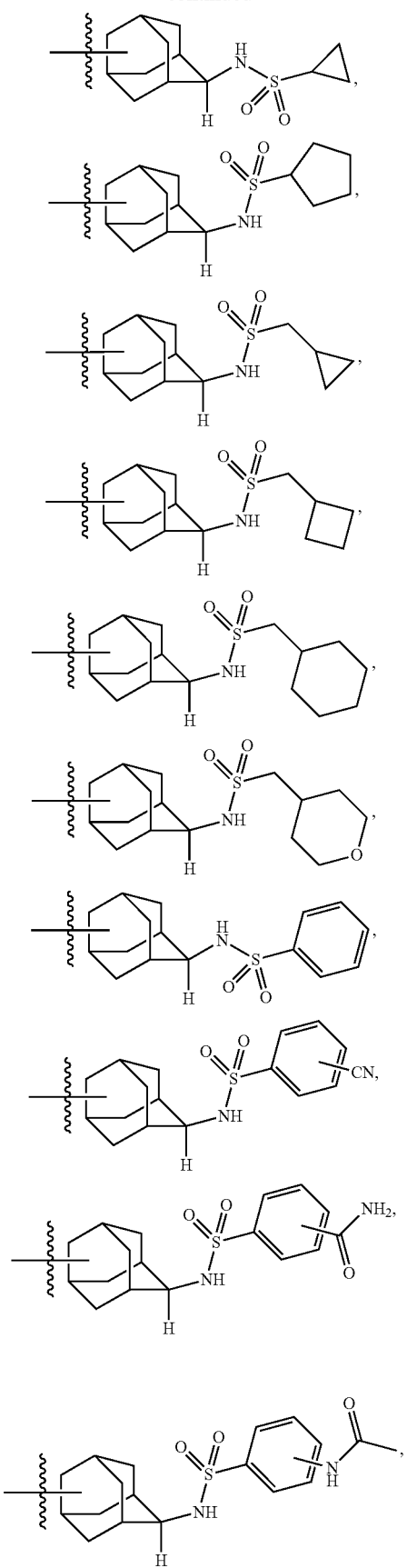
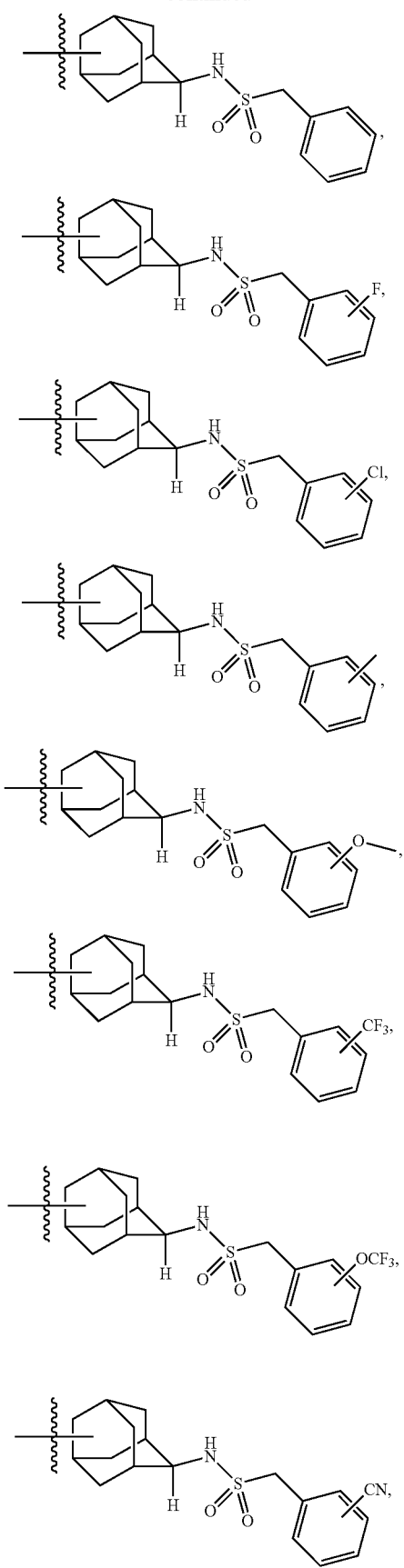

307
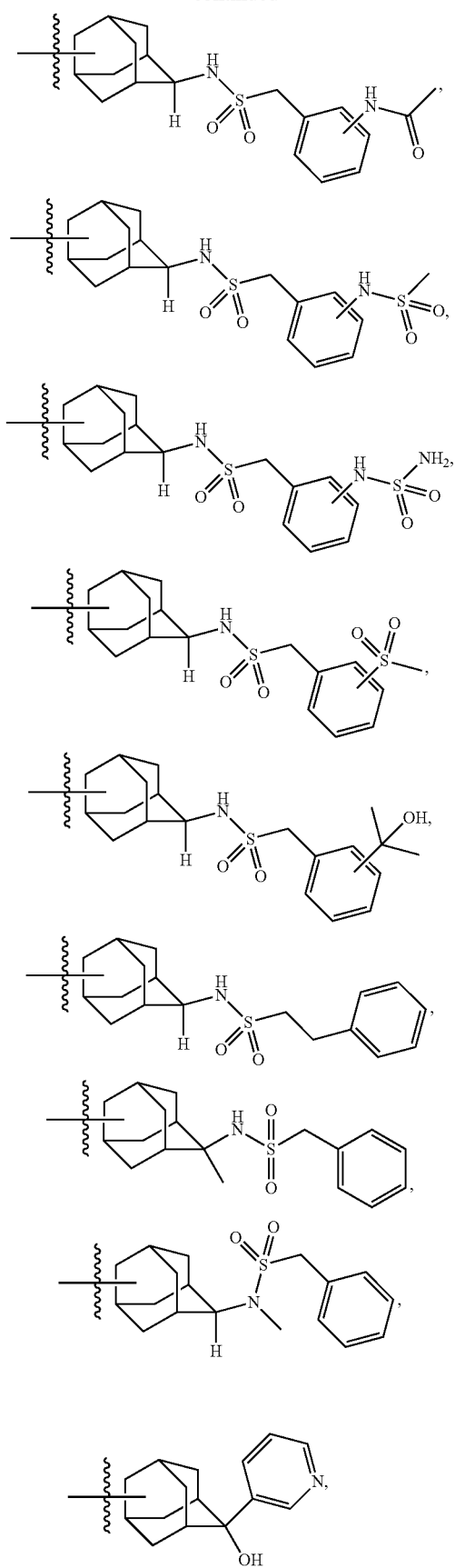
308
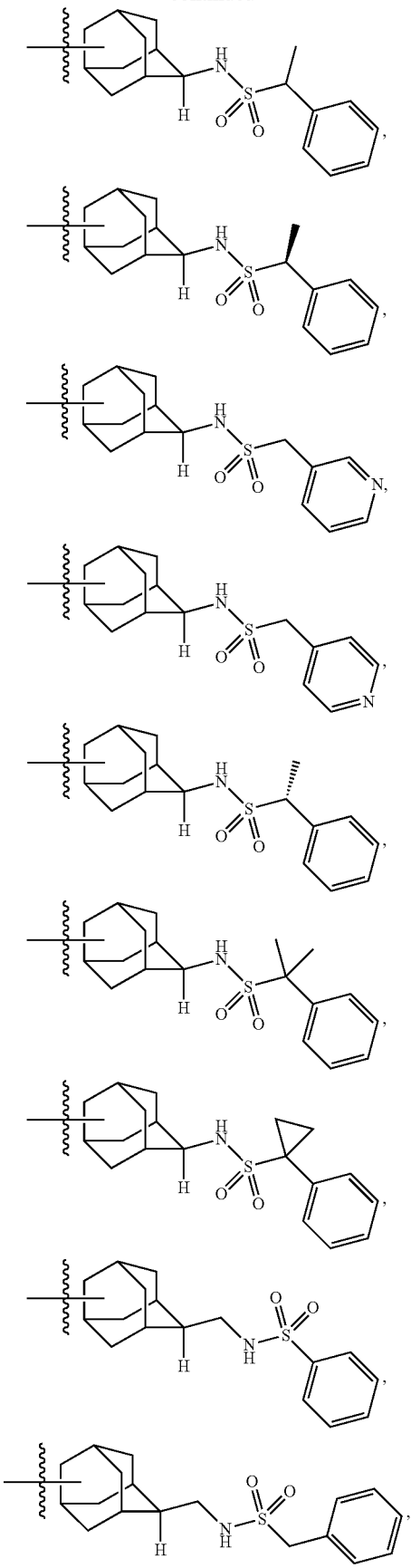

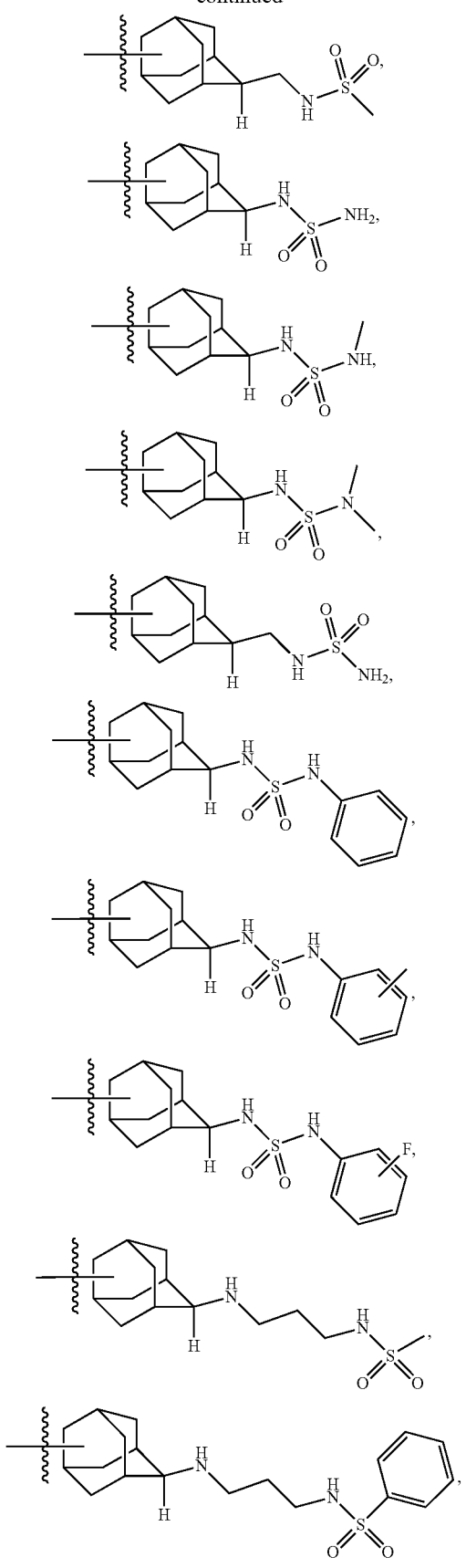
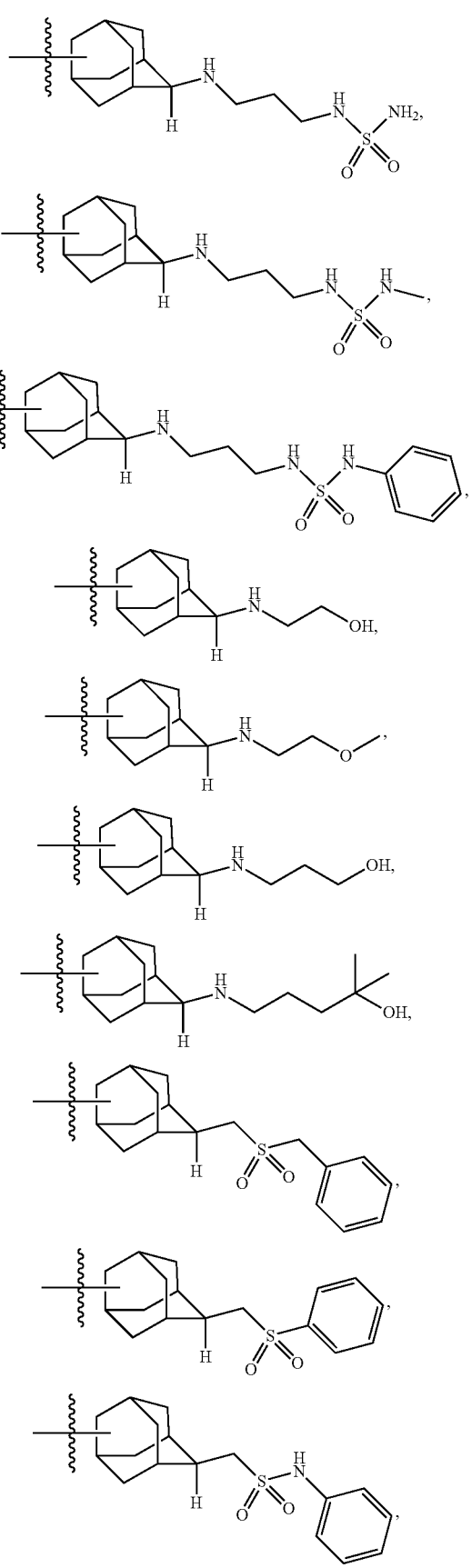

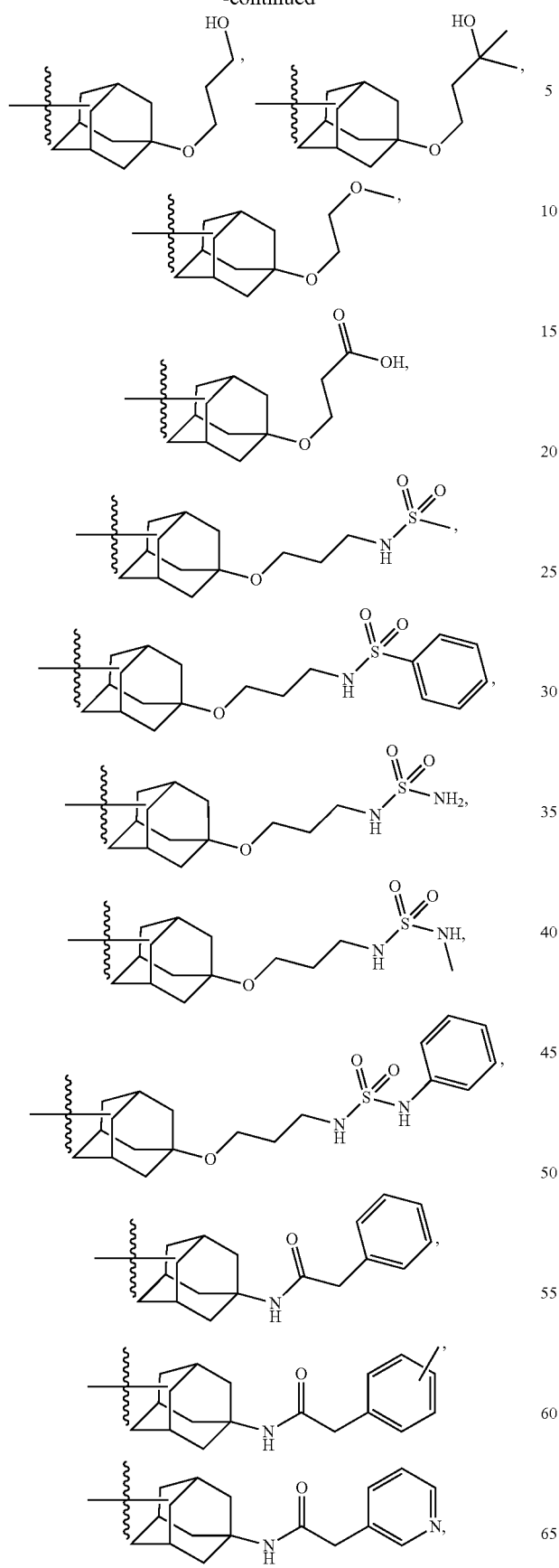
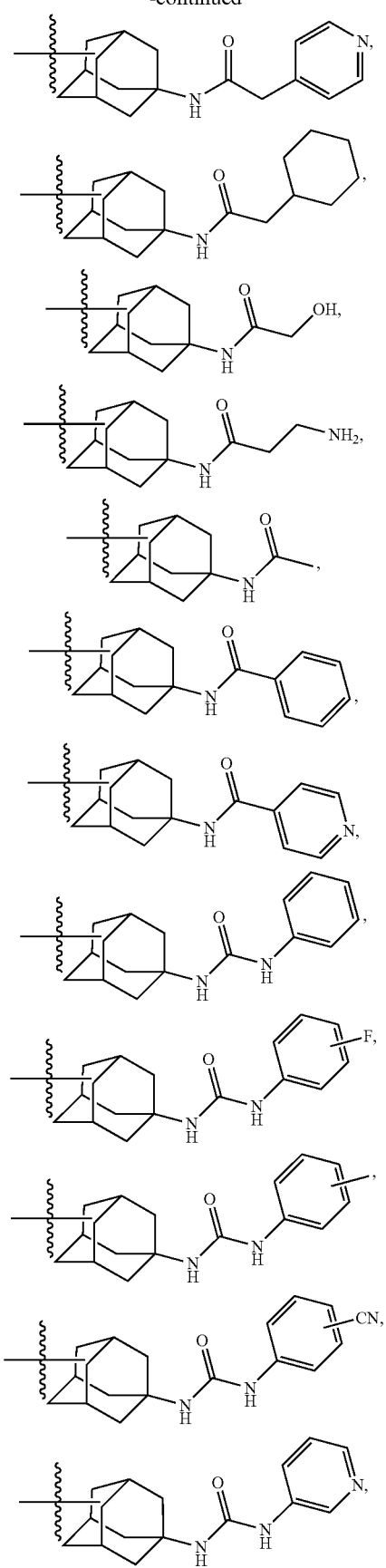

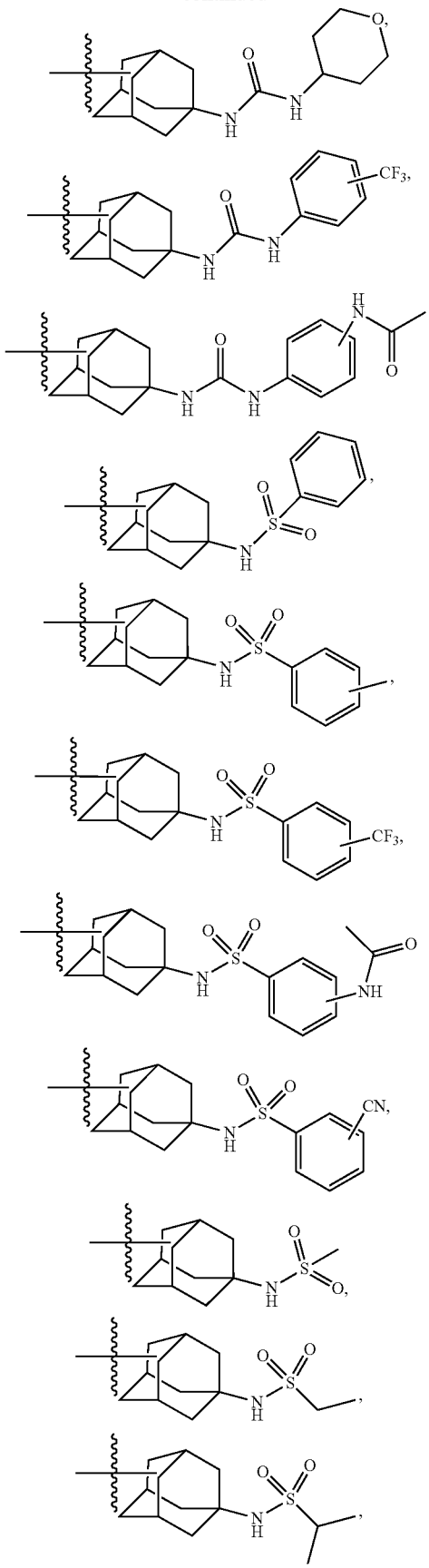
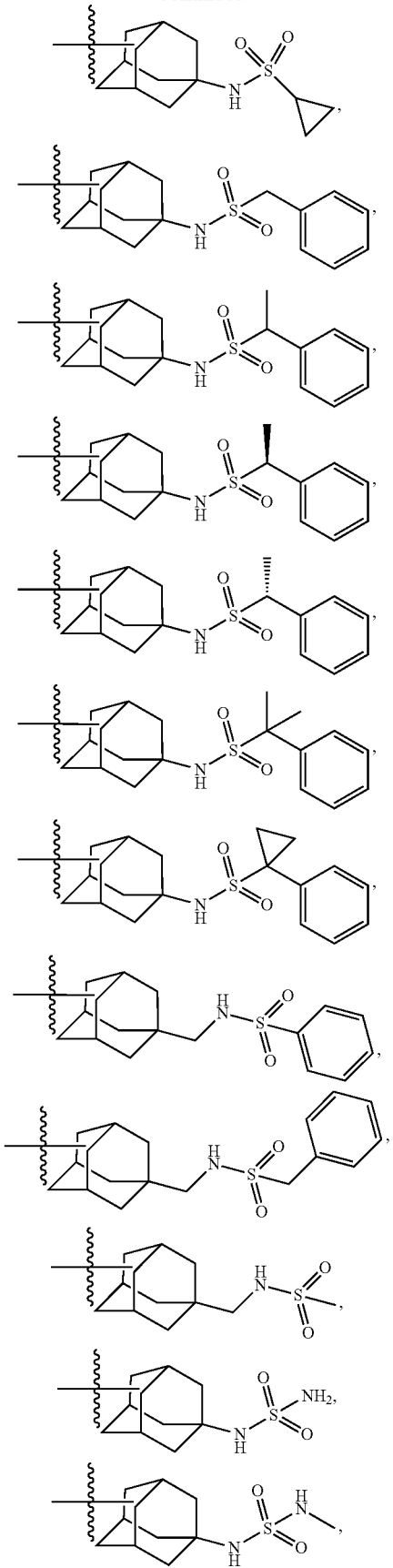

315
-continued
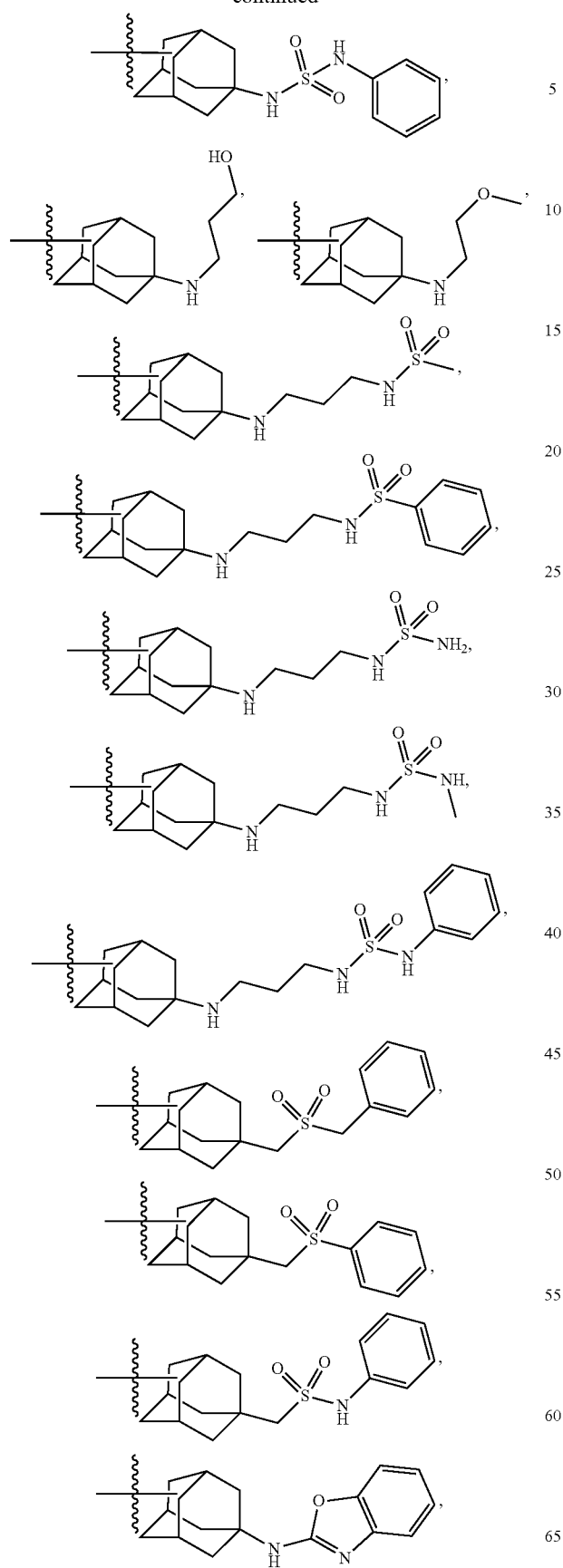
316
-continued
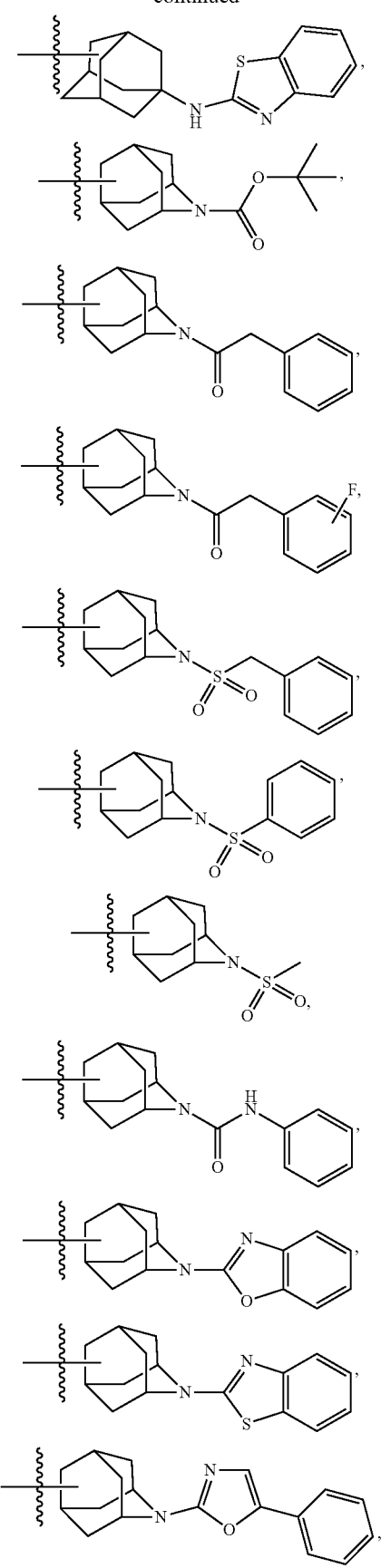

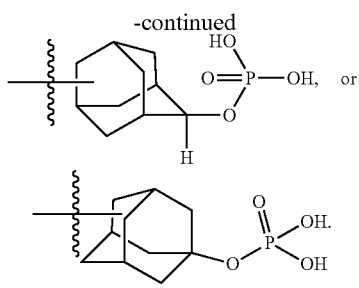

13. The compound or the pharmaceutically acceptable salt thereof of claim 1, wherein the compound of formula (I) or the pharmaceutically acceptable salt thereof is
1) a compound of formula (IA) or a pharmaceutically acceptable salt thereof,
2) a compound of formula (IB) or a pharmaceutically acceptable salt thereof,
3) a compound of formula (IC) or a pharmaceutically acceptable salt thereof,
4) a compound of formula (ID) or a pharmaceutically acceptable salt thereof,
5) a compound of formula (IA-1) or a pharmaceutically acceptable salt thereof,
6) a compound of formula (IB-1) or a pharmaceutically acceptable salt thereof,
7) a compound of formula (IE) or a pharmaceutically acceptable salt thereof,
8) a compound of formula (IF) or a pharmaceutically acceptable salt thereof,
9) a compound of formula (IF-1) or a pharmaceutically acceptable salt thereof,
10) a compound of formula (IG) or a pharmaceutically acceptable salt thereof,
11) a compound of formula (IH) or a pharmaceutically acceptable salt thereof,
12) a compound of formula (IJ) or a pharmaceutically acceptable salt thereof, or
13) a compound of formula (IK) or a pharmaceutically acceptable salt thereof, (IA)

(IB)

(IC) 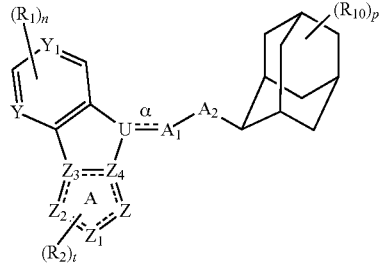

(ID) 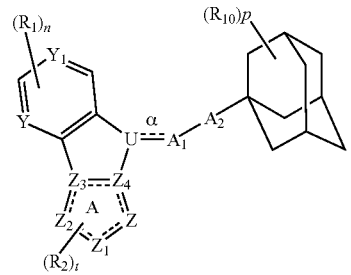

(IA-1) 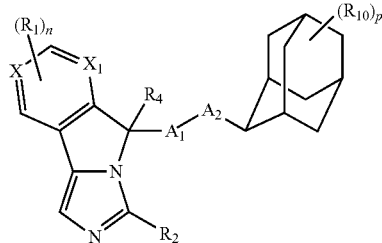

(IB-1) 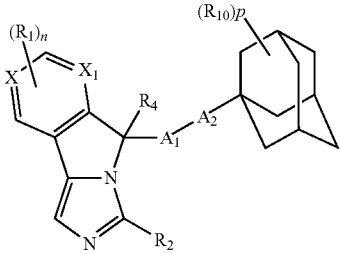

(IE) 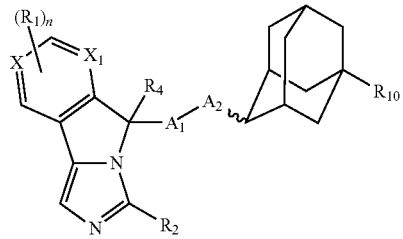

(IF) 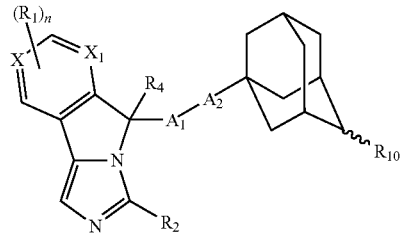

(IF-1)

(IG)

(IH)

(IJ)

(IK)

wherein,
in formula (IA), (IB), (IC) and (ID), Y, $Y_1$, X, and $X_1$ are independently C or N; p is 1 or 2; Z, $Z_1$, $Z_2$, $Z_3$, $Z_4$, $R_1$, $R_2$, U, bond α, $A_1$, $A_2$, $R_{10}$, n and t are the same as described in claim 1,
in formula (IA-1) and (IB-1), X and $X_1$ are independently C or N; p is 1 or 2, $R_1$, $R_2$, $R_4$, $R_{10}$, $A_1$, $A_2$, and n are the same as defined in claim 1,
in formula (IE) and (IF), X and $X_1$ are independently C or N; $R_1$, $R_2$, $R_4$, $R_{10}$, n, $A_1$, and $A_2$ are the same as defined in claim 1, the stereoisomeric configurations of the single bond labeled with ⁓ are cis, trans, or a mixture of cis/trans,
in formula (IF-1), $R_1$ is hydrogen or halogen; $R_{10}$ is independently hydrogen, substituted or unsubstituted alkyl, substituted or unsubstituted aryl, substituted or unsubstituted heteroaryl, or -L-$R_8$, wherein substituted alkyl, aryl, and heteroaryl are substituted by 1, 2, or 3 $R_{13}$, further wherein $R_8$, and $R_{13}$ are the same as defined in claim 1; $A_1$ and $A_2$ are the same as defined in claim 1; the stereoisomeric configurations of the single bond labeled with ⁓ are cis, trans, or a mixture of cis/trans,
in formula (IG) and (IH), X, $X_1$, Y, and $Y_1$ are independently C or N; $R_1$, $R_4$, $R_{10}$, n, $A_1$, and $A_2$ are the same as defined in claim 1,
in formula (IJ) and (IK), Y, $Y_1$, X, and $X_1$ are independently C or N; Z, $Z_1$, $Z_2$, $Z_3$, $Z_4$, $R_1$, $R_2$, $R_3$, $R_5$, t, and n are the same as defined in claim 1; the stereoisomeric configurations of carbon atoms labeled with * are respectively (S, S), (S, R), (R, S), (R, R).

14. The compound or the pharmaceutically acceptable salt thereof of claim 13, wherein Z and $Z_2$ are C, $Z_1$ is N, and one of $Z_3$ and $Z_4$ is N and the other is C in formula (IA), (IB), (IC) and (ID),
or bond α is a single bond, U is $CR_4$ in formulae (IA), (IB), (IC) and (ID), or $R_4$ in formulae (IA-1), (IB-1), (IE), (IF), (IG), and (IH) is hydrogen, hydroxyl, fluorine, or methyl,
or X and $X_1$ in formulae (IA), (IA-1), (IB), (IB-1), (IE), and (IF) are C; or Y and $Y_1$ in formulae (IC) and (ID) are C,
or one of X and $X_1$ in formulae (IA), (IA-1), (IB), (IB-1), (IE), and (IF) is N and the other is C,
or $R_1$ in formulae (IA), (IA-1), (IB), (IB-1), (IC), (ID), (IE), (IF), (IG), (IH), (IJ), and (IK) is —OH, —SH, —CN, hydrogen, halogen, amino, $C_{1-3}$ alkoxy, $C_{1-3}$ alkylthiol, $C_{1-3}$ alkyl, halo-$C_{1-3}$ alkyl, or halo-$C_{1-3}$ alkoxy, and n is 2 in in formulae (IG), (IH), (IJ), and (IK), or $R_2$ in formulae (IA), (IA-1), (IB), (IB-1), (IC), (ID), (IE), (IF), (IG), (IH), (IJ), and (IK) is —OH, —SH, —NH$_2$, hydrogen, halogen, $C_{1-3}$ alkoxy, $C_{1-3}$ alkylthiol, $C_{1-3}$ alkyl, or halo-$C_{1-3}$ alkyl, and t is 2 in in formulae (IG), (IH), (IJ), and (IK), or $A_1$ in formulae (IA), (IA-1), (IB), (IB-1), (IC), (ID), (IE), (IF), (IF-1) (IG), and (IH) is —CH$_2$—, —CHF—, —CF$_2$—, —CHCH$_3$— or —C(CH$_3$)$_2$—,
or $A_2$ in formulae (IA), (IA-1), (IB), (IB-1), (IC), (ID), (IE), (IF), (IF-1), (IG), and (IH) is —CHF—, —CH(CN)—, —CH(COOH)—, or Y, Y₁, X, and X₁ are C in formulae (IG), (IH), (IJ), and (IK), or Z and Z₂ are C, Z₁ is N, and one of Z₃ and Z₄ is N and the other is C in formulae (IJ), and (IK), or R₅ in formulae (IJ), and (IK) is independently H, OH, alkyl, —OR₆, and —OP(O)(O—R₆)₂, wherein R₆ is H or alkyl, or R₃ in formulae (IJ), and (IK) is unsubstituted adamantanyl or adamantanyl substituted with 1 or 2 R₁₀, or R₃ in formulae (IJ), and (IK) is unsubstituted 2-azaadamantanyl or 2-azaadamantanyl substituted with 1 or 2 R₁₀, or R₁₀ in formulae (IA), (IA-1), (IB), (IB-1), (IC), (ID), (IE), (IF), (IF-1), (IG), and (IH) is independently —NO₂, —CN, —OH, —NH₂, —SH, halogen, substituted or unsubstituted alkyl, substituted or unsubstituted alkoxy, substituted or unsubstituted aryl, substituted or unsubstituted heteroaryl, —N(R₈)-L-R₈ᵦ, -L-R₈, —O-L-R₈, -L-C(O)R₈ᵦ, -L-C(=R₇)NR₈R₈ᵦ, -L-S(O)₂R₈ᵦ, -L-NR₈R₈ᵦ, -L-N(R₈)C(=R₇)R₈ᵦ, -L-N(R₈)C(=R₇)NR₈R₈ᵦ, and -L-N(R₈)S(O)₂R₈ᵦ, wherein substituted alkyl, substituted alkoxy, substituted aryl, and substituted heteroaryl are substituted by 1, 2, or 3 R₁₃.

15. The compound or the pharmaceutically acceptable salt thereof of claim 1, wherein the compound is

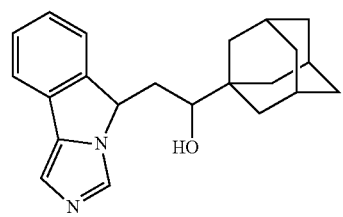

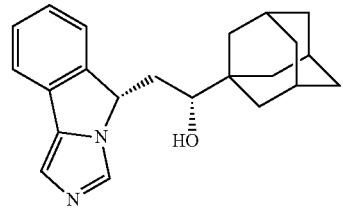

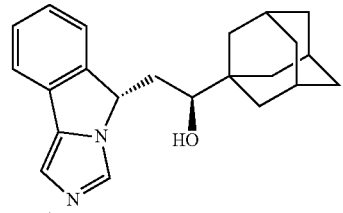

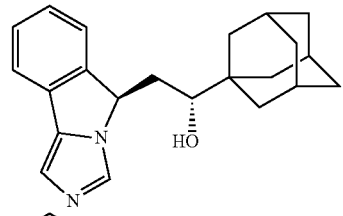

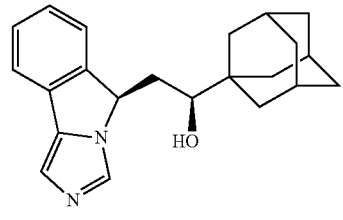

-continued

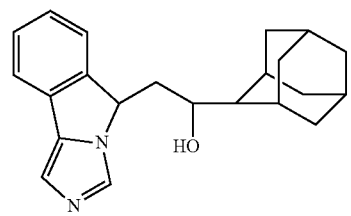

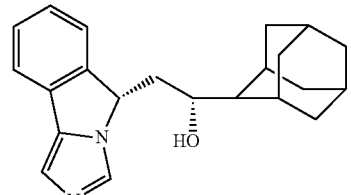

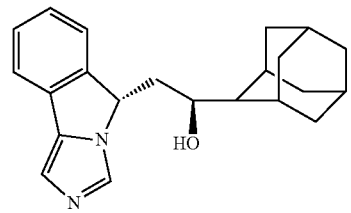

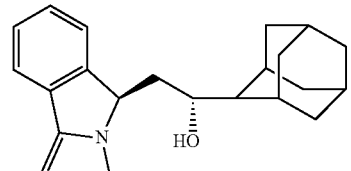

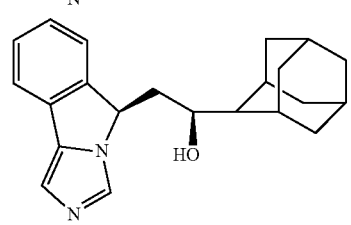

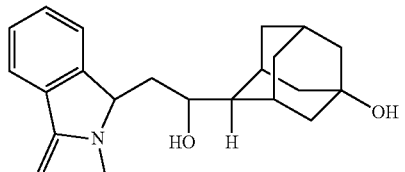

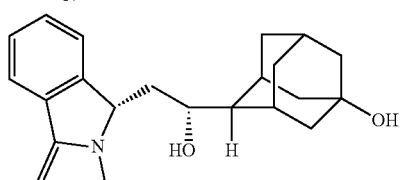

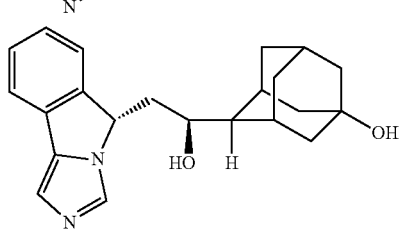

323
-continued
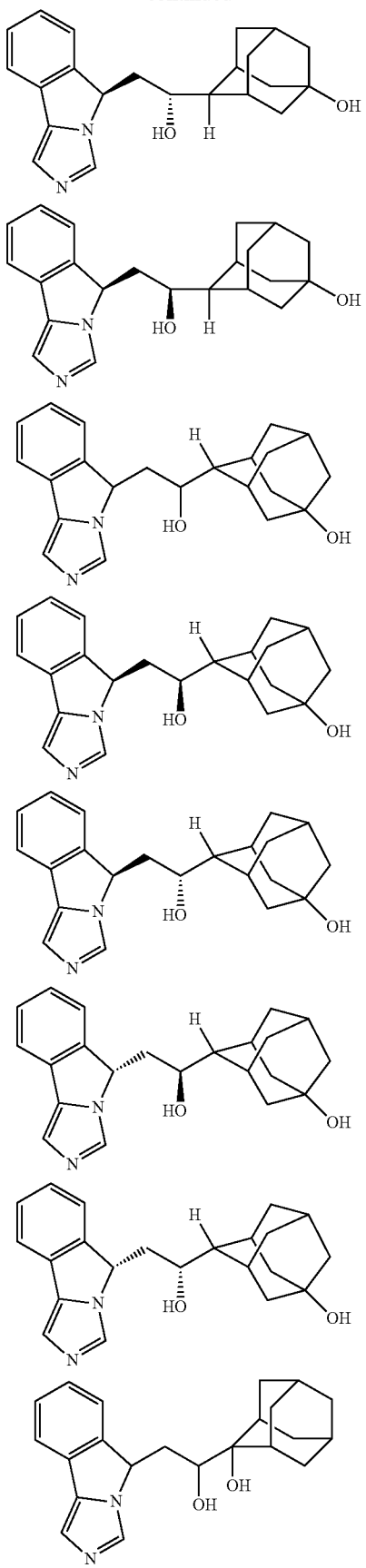
324
-continued
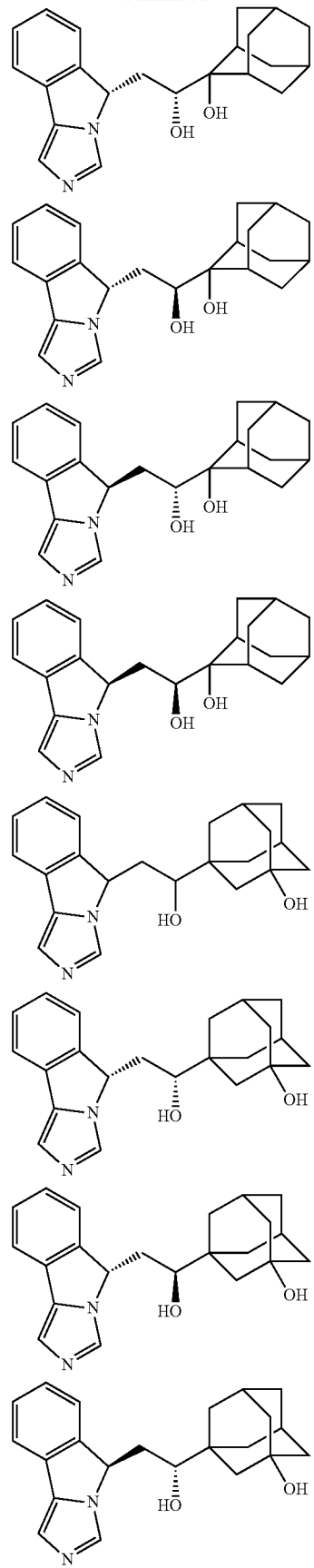

325
-continued
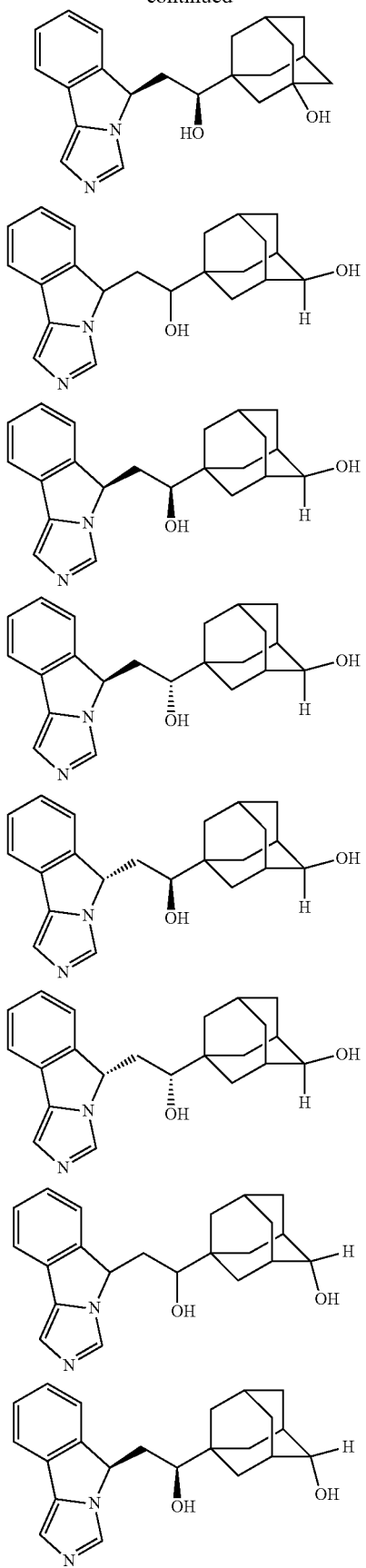
326
-continued
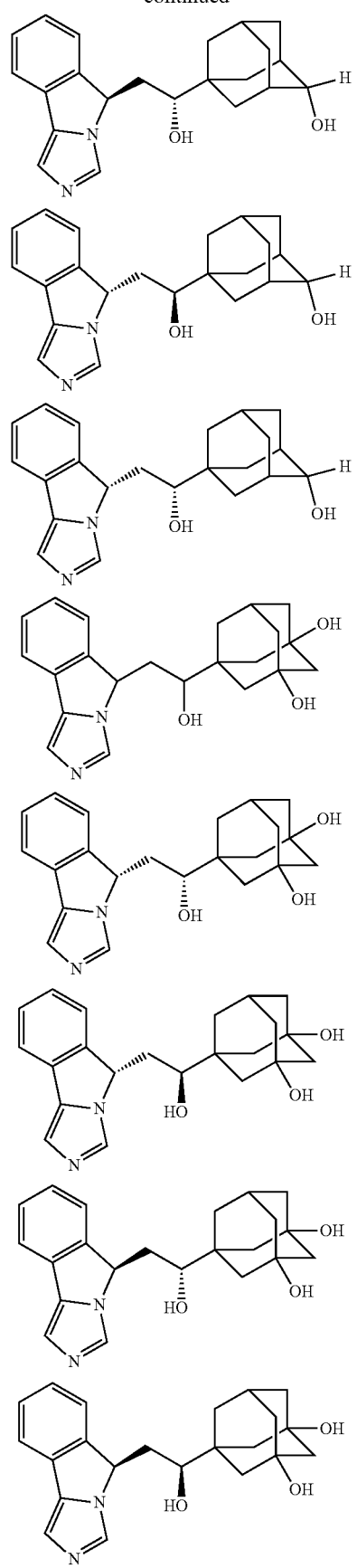

327
-continued
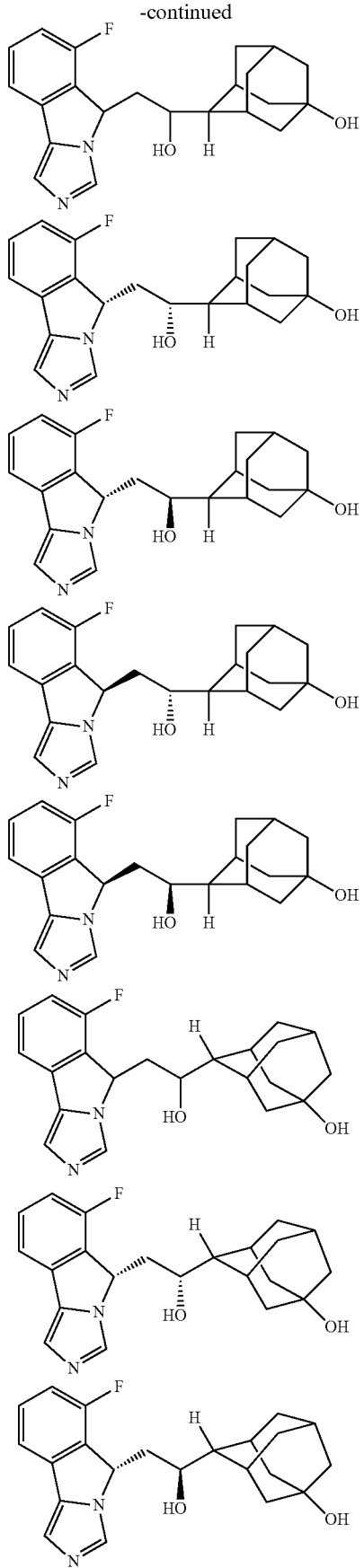
328
-continued
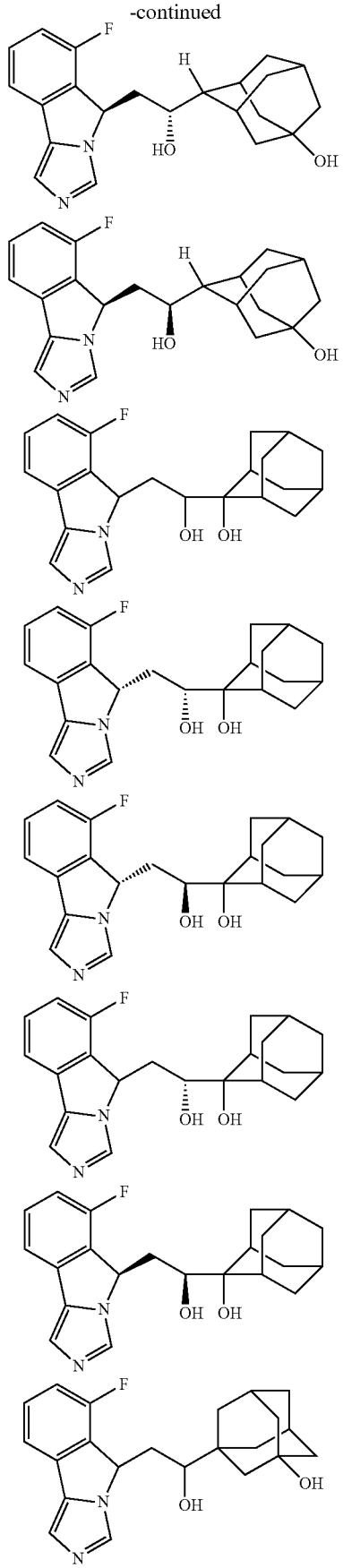

329
-continued
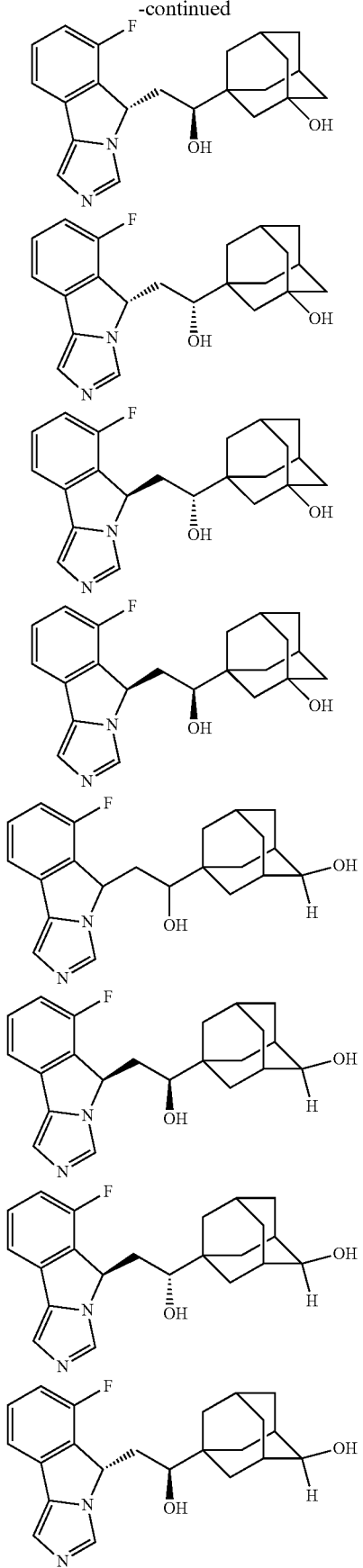
330
-continued
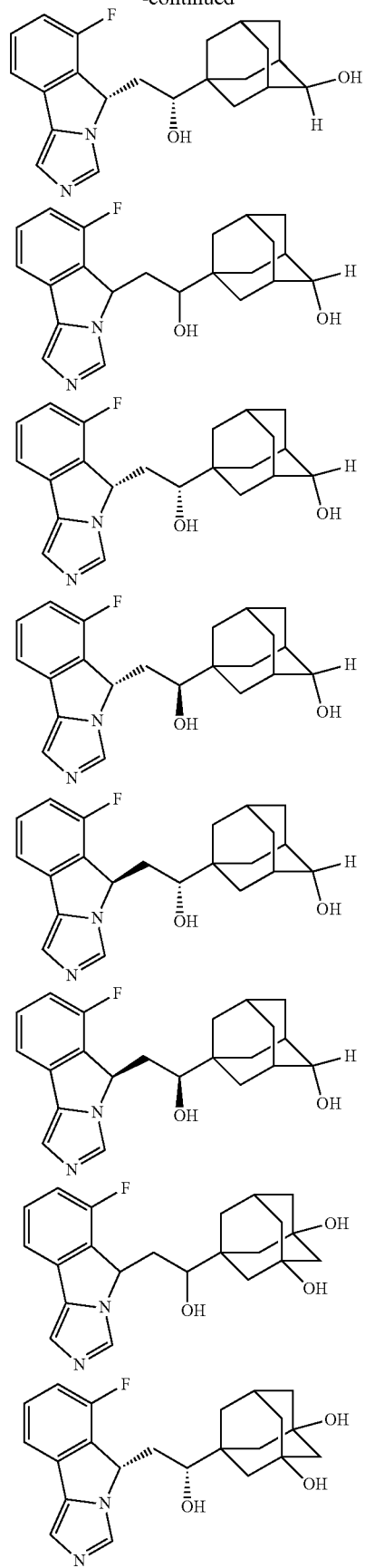

331
-continued
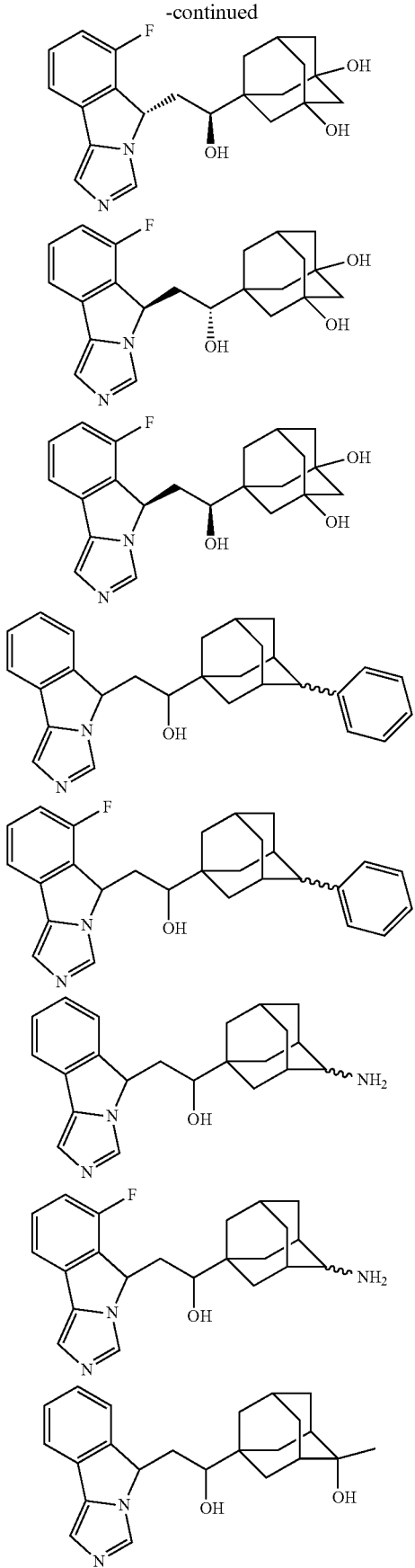
332
-continued
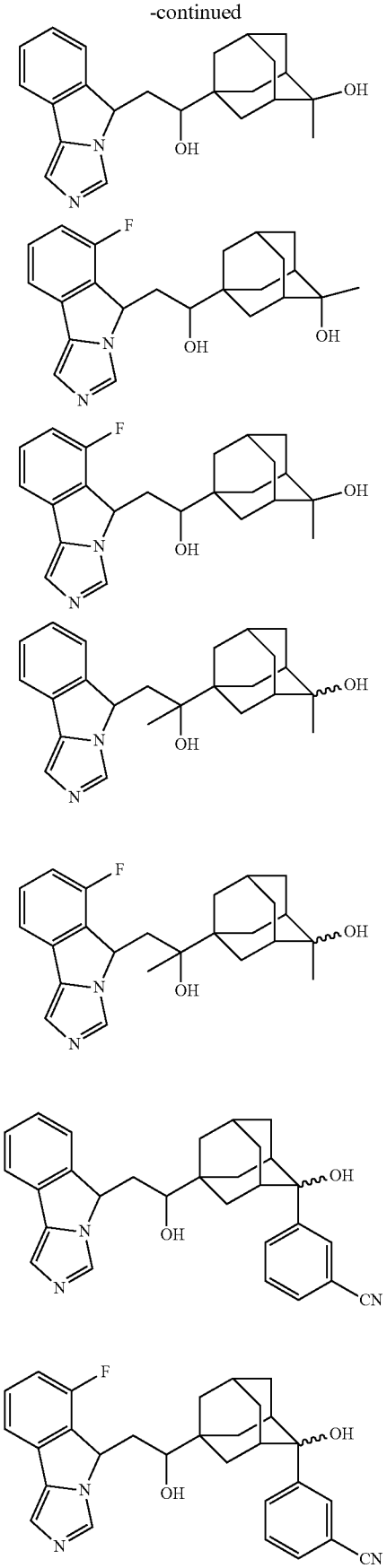

333
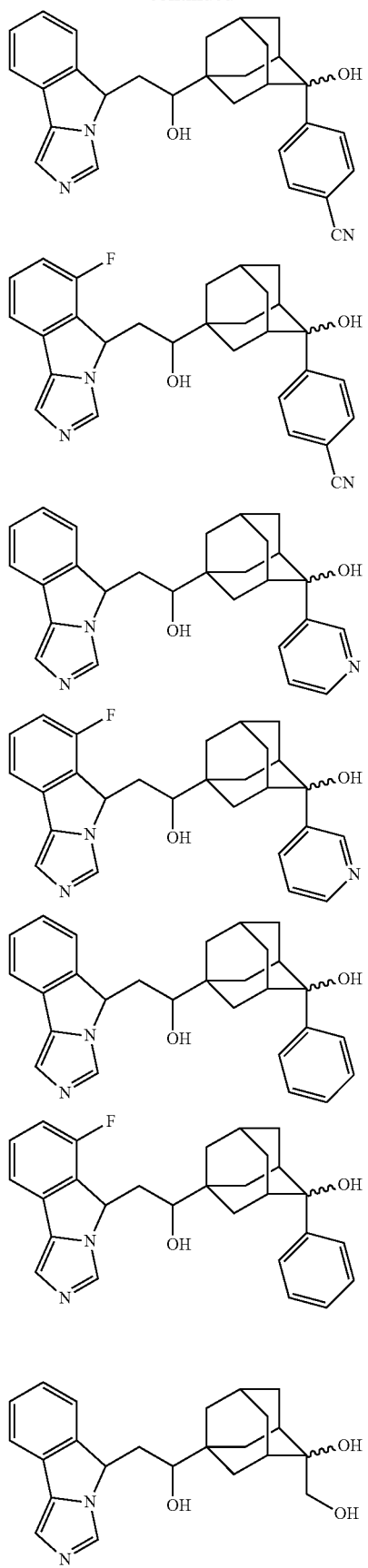
334
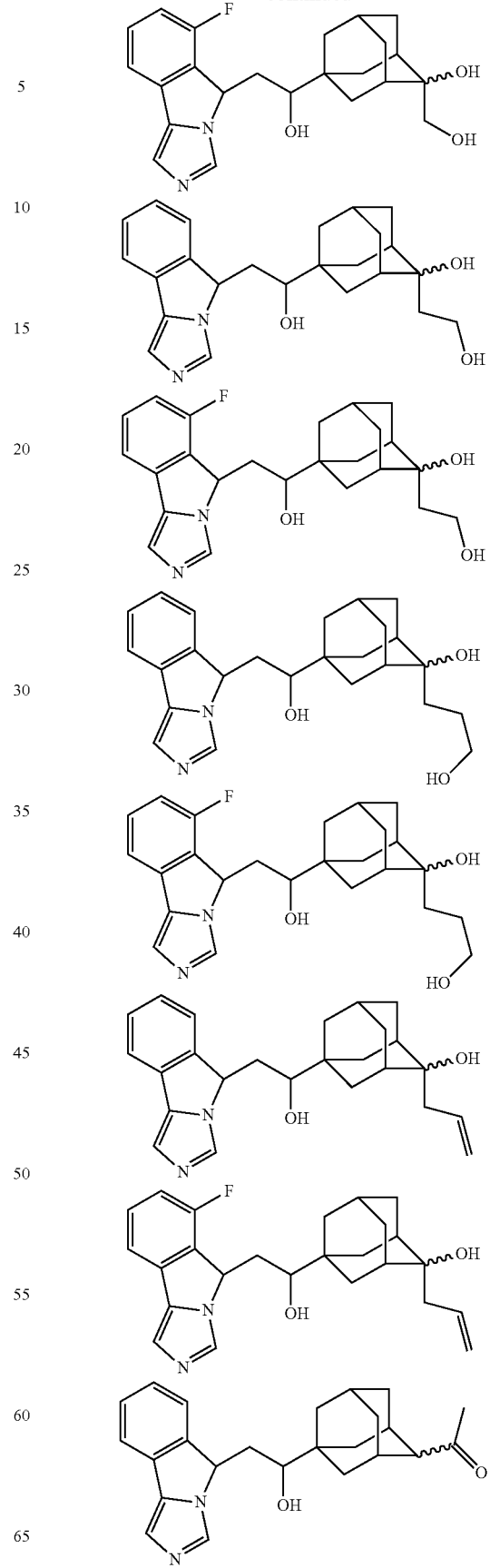

335
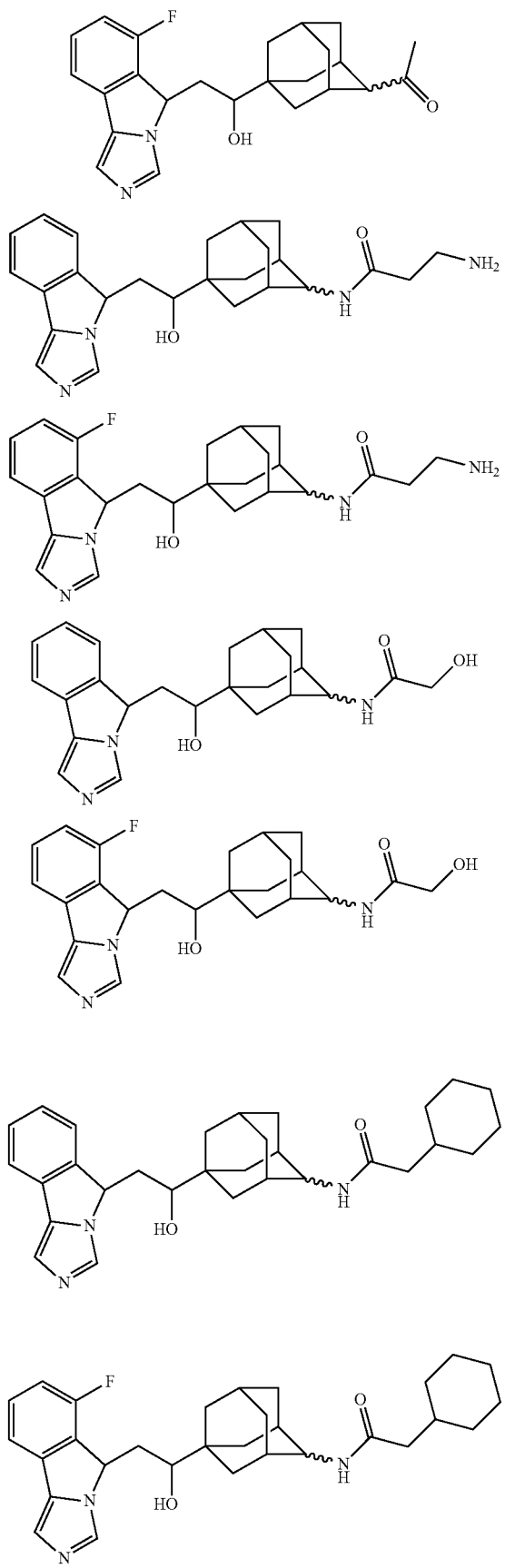
336
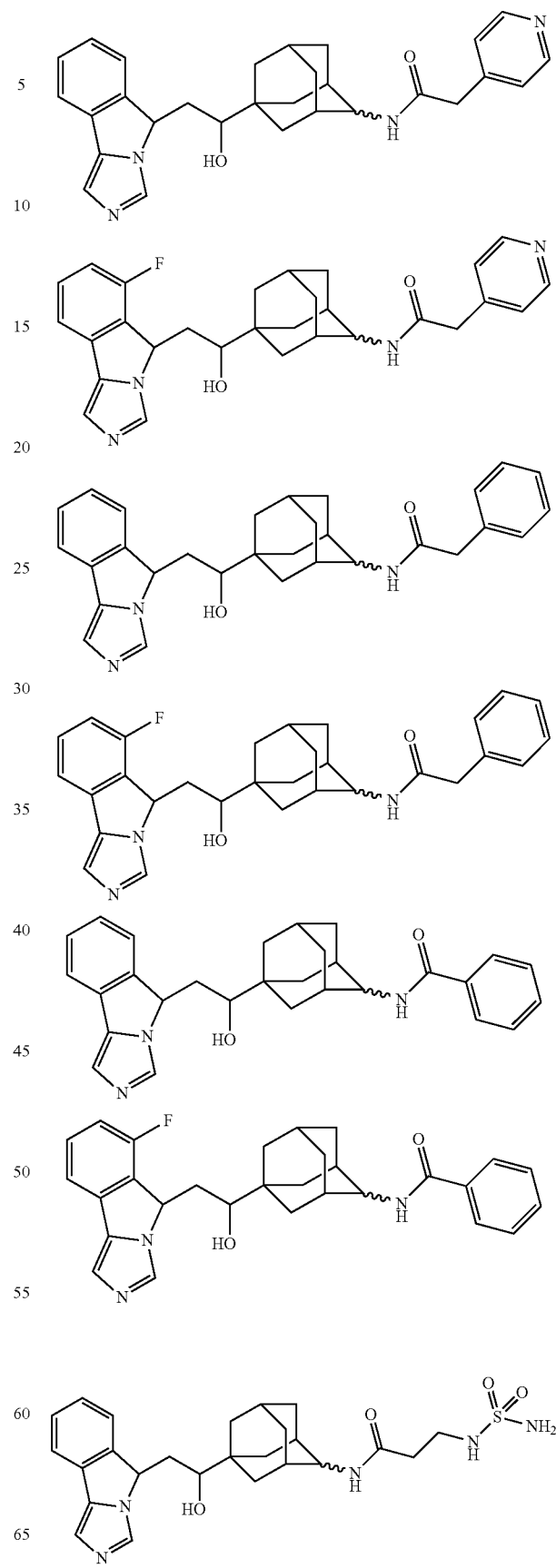

337
-continued
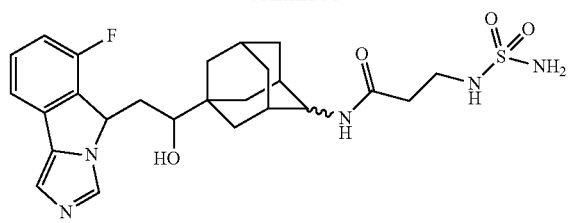
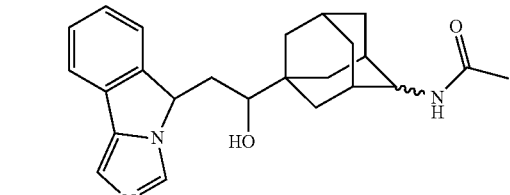
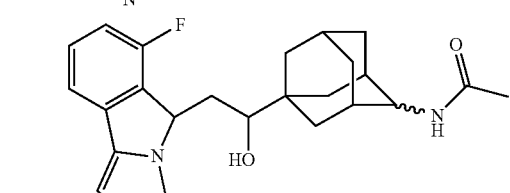
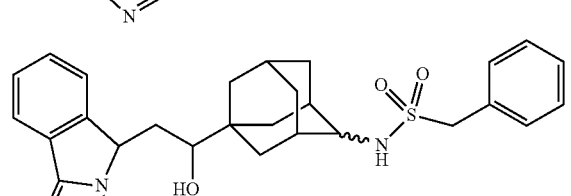
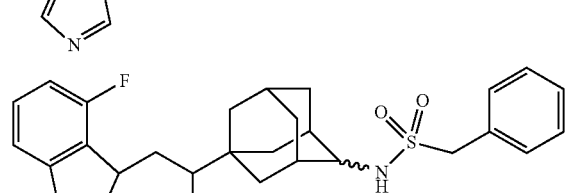
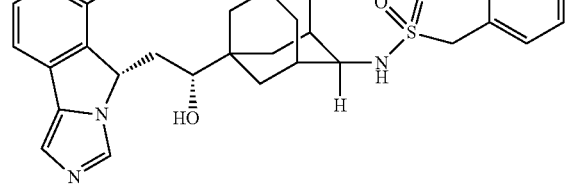
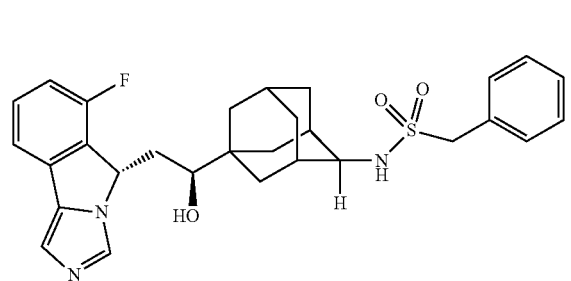
338
-continued
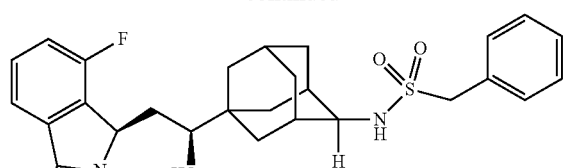
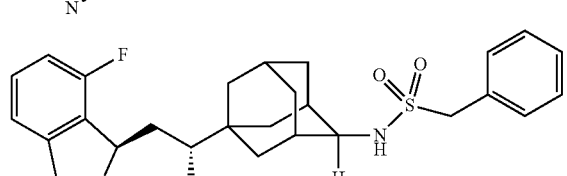
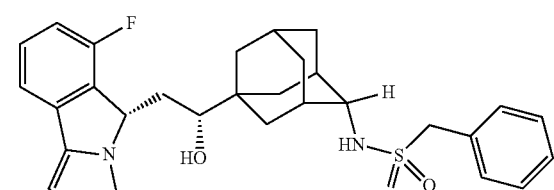
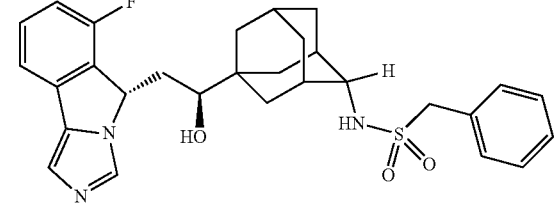
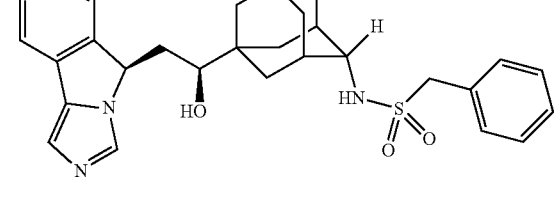
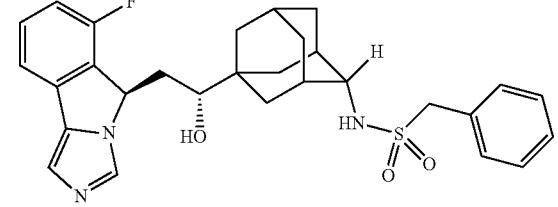

339
-continued
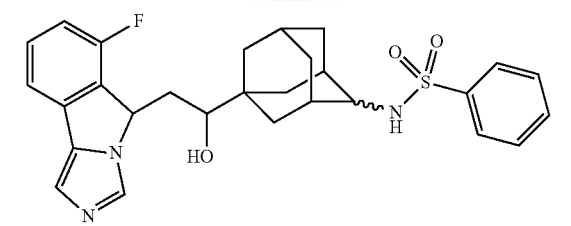
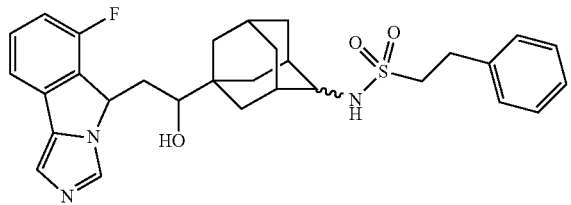
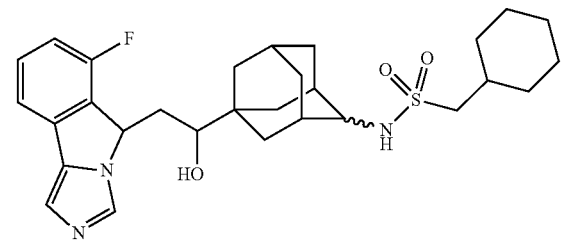
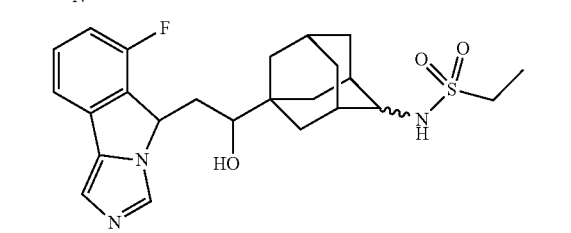
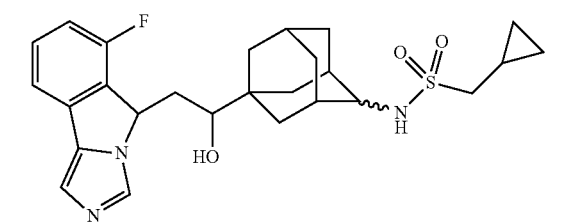
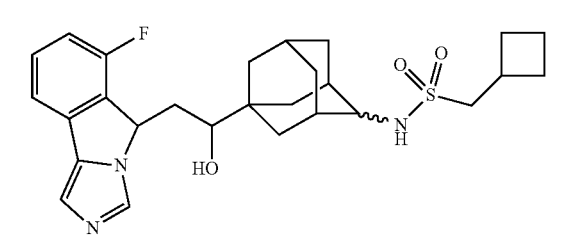
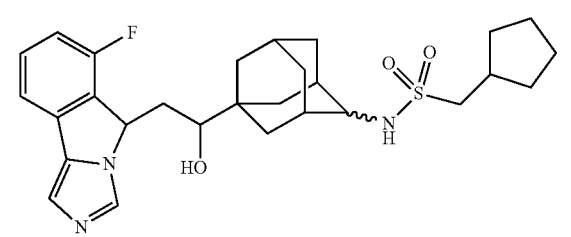
340
-continued
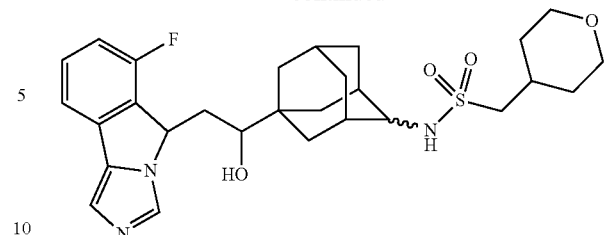
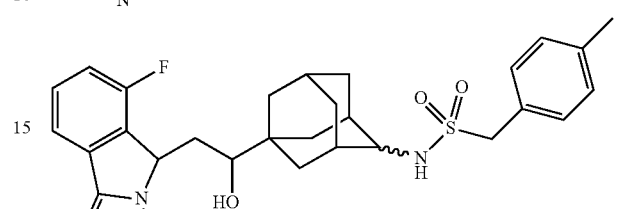
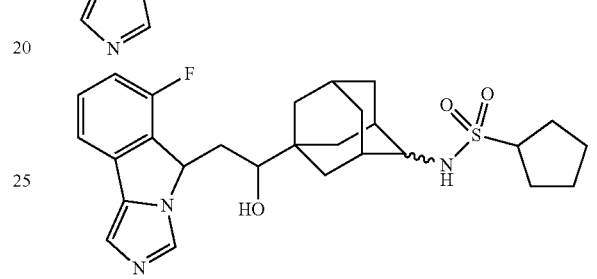
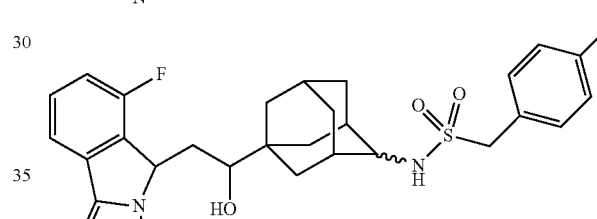
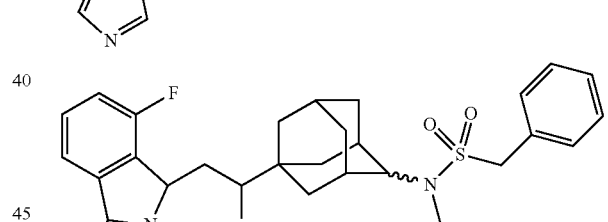
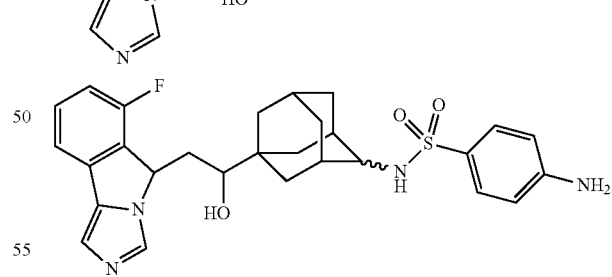
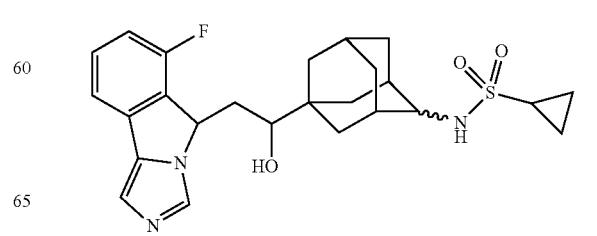

341
-continued
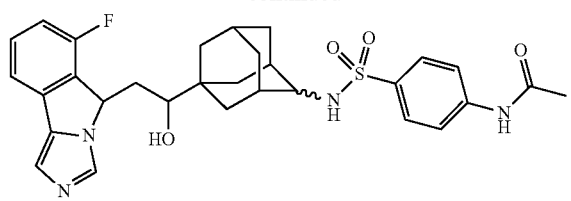
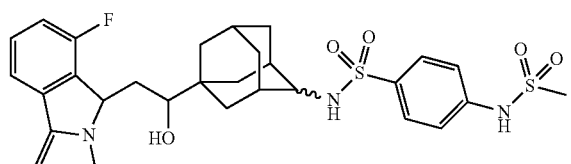
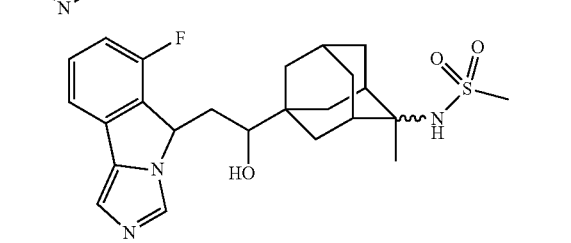
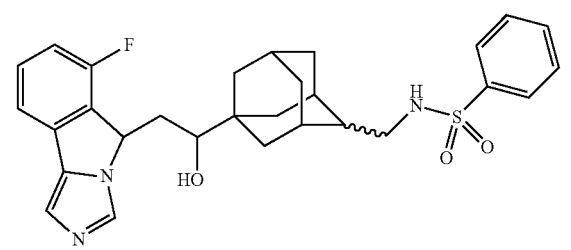
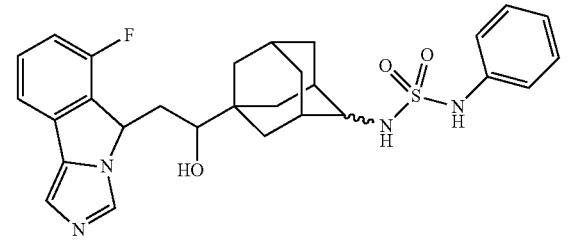
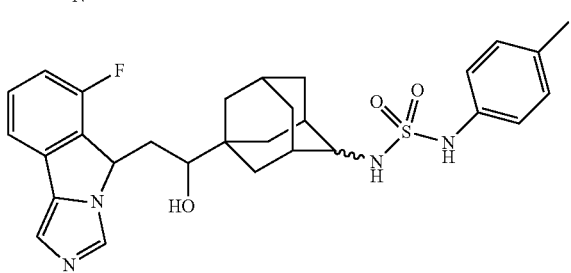
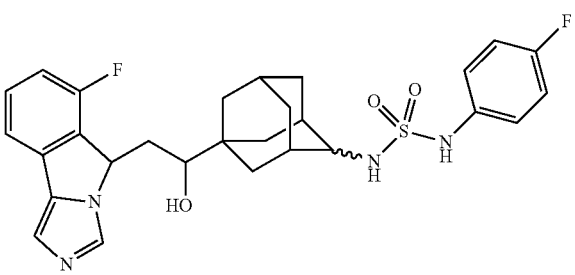
342
-continued
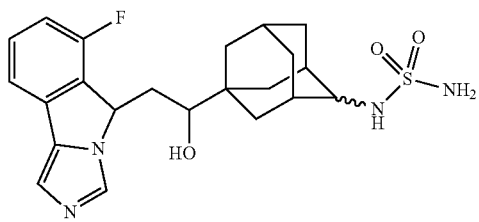
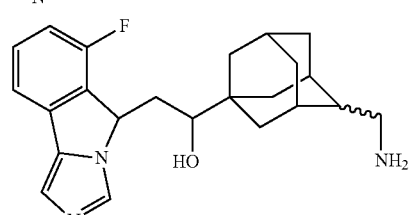
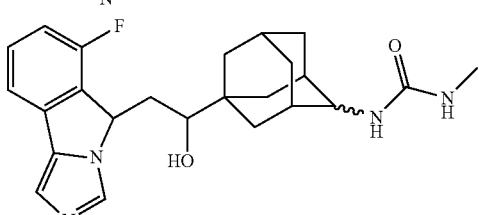
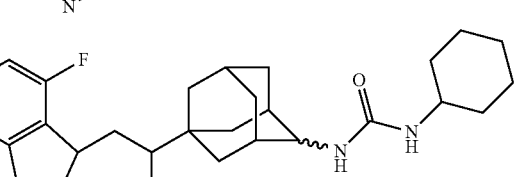
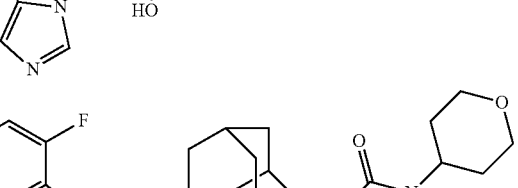
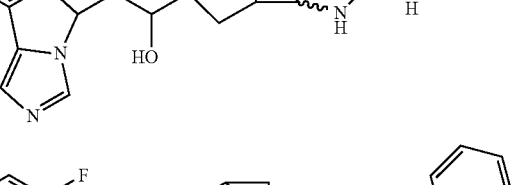
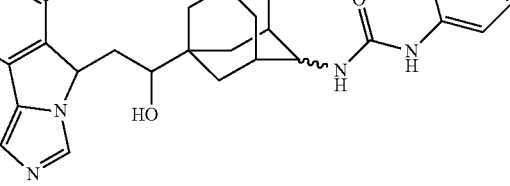
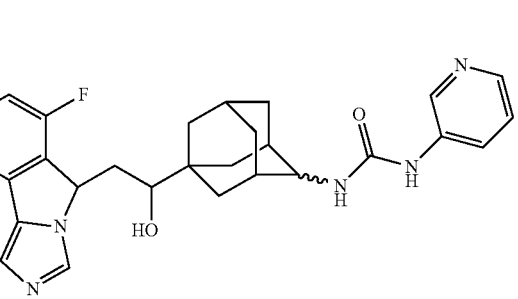

343
-continued
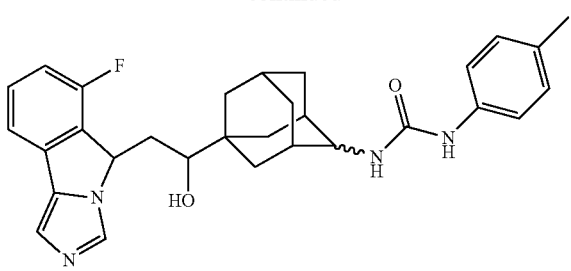
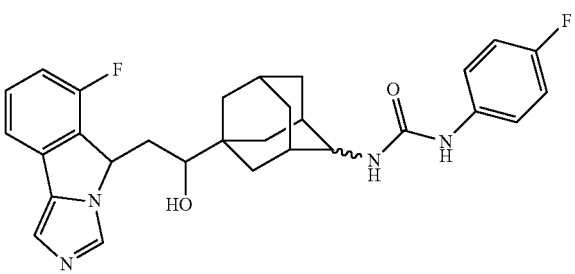
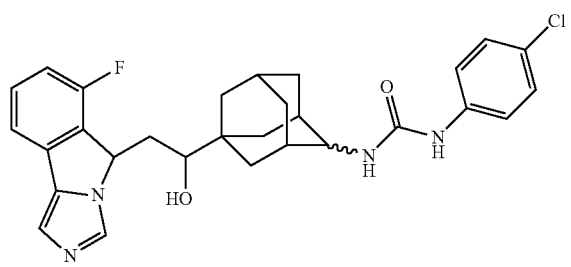
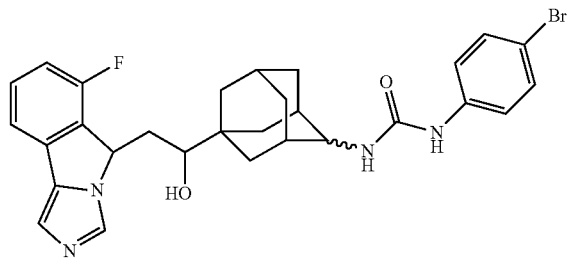
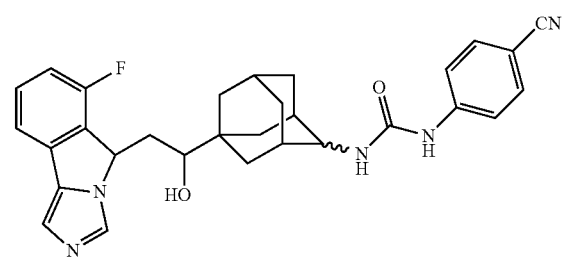
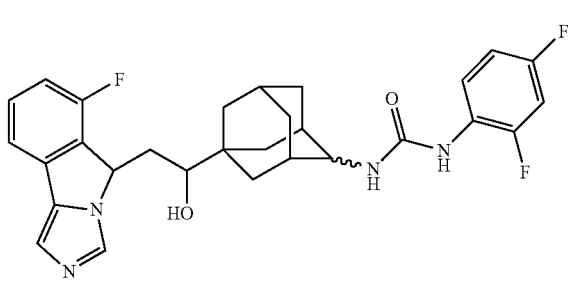
344
-continued
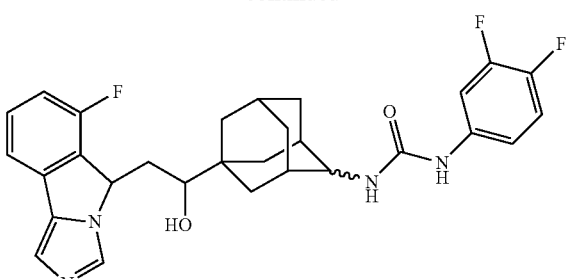
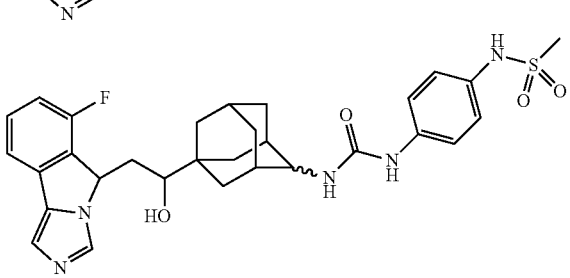
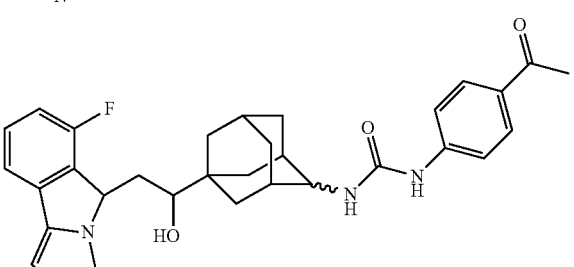
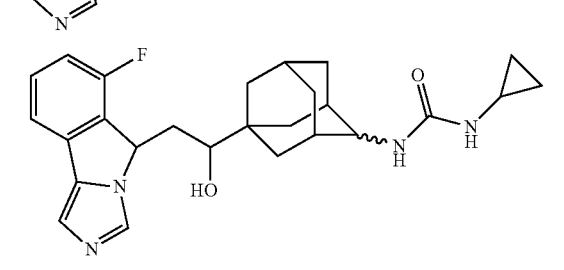
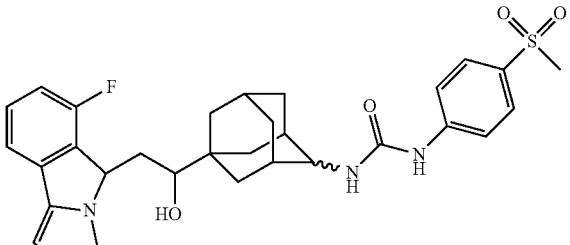
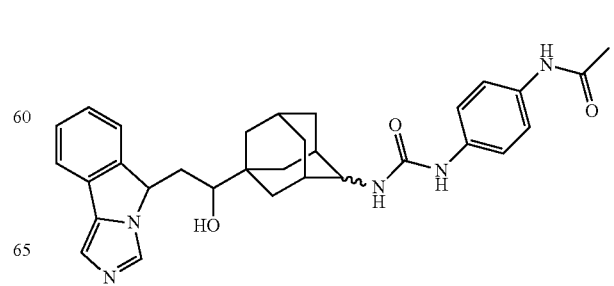

345
-continued
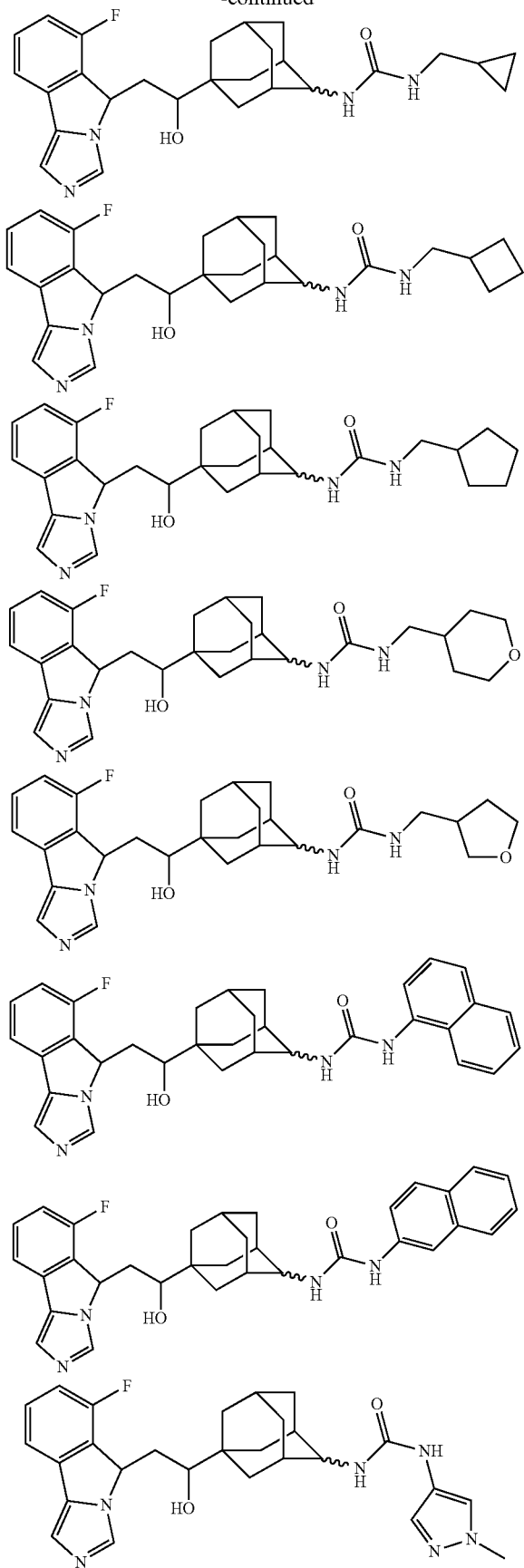
346
-continued
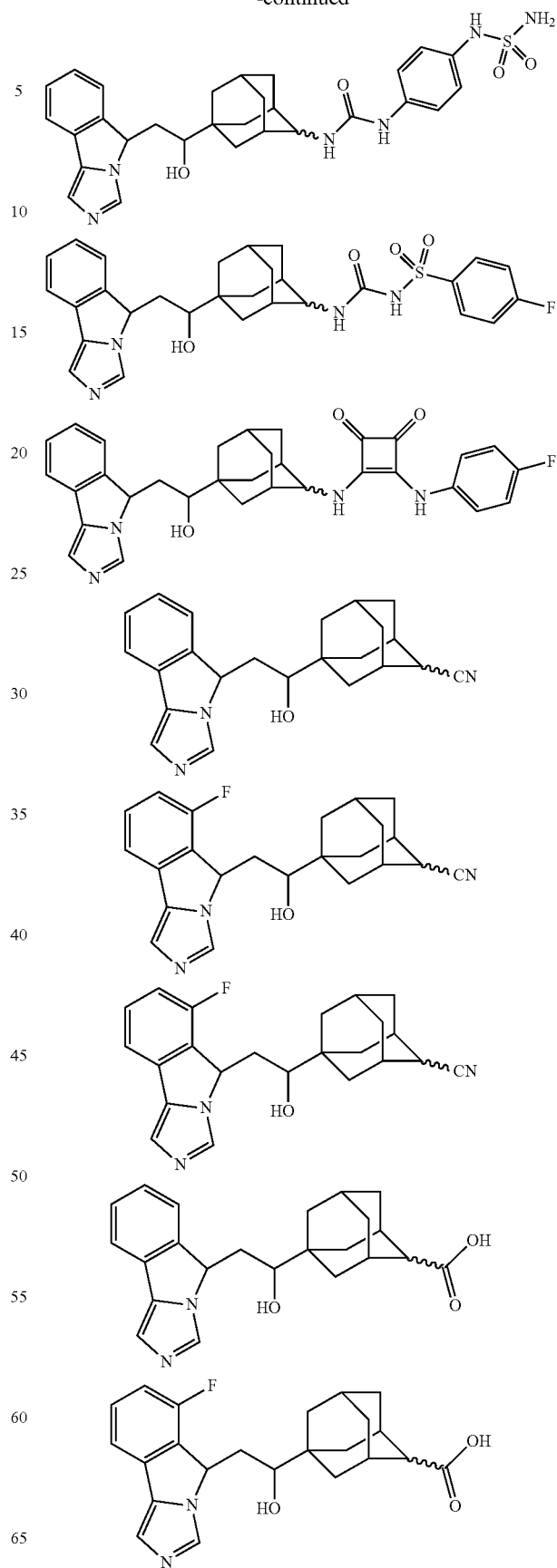

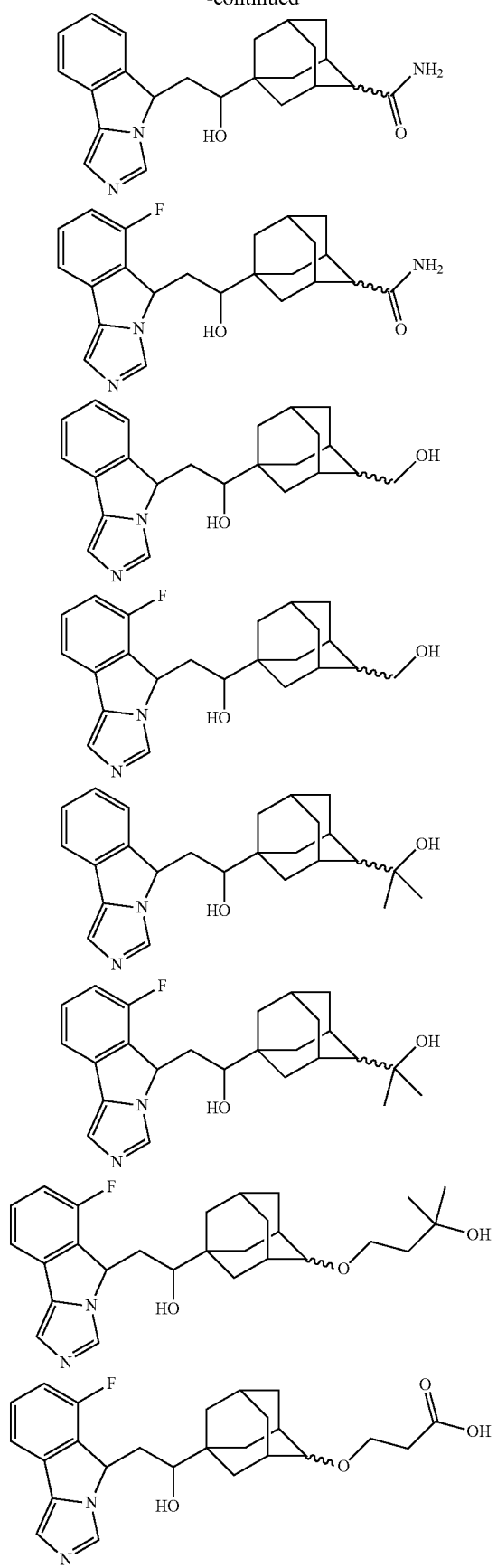
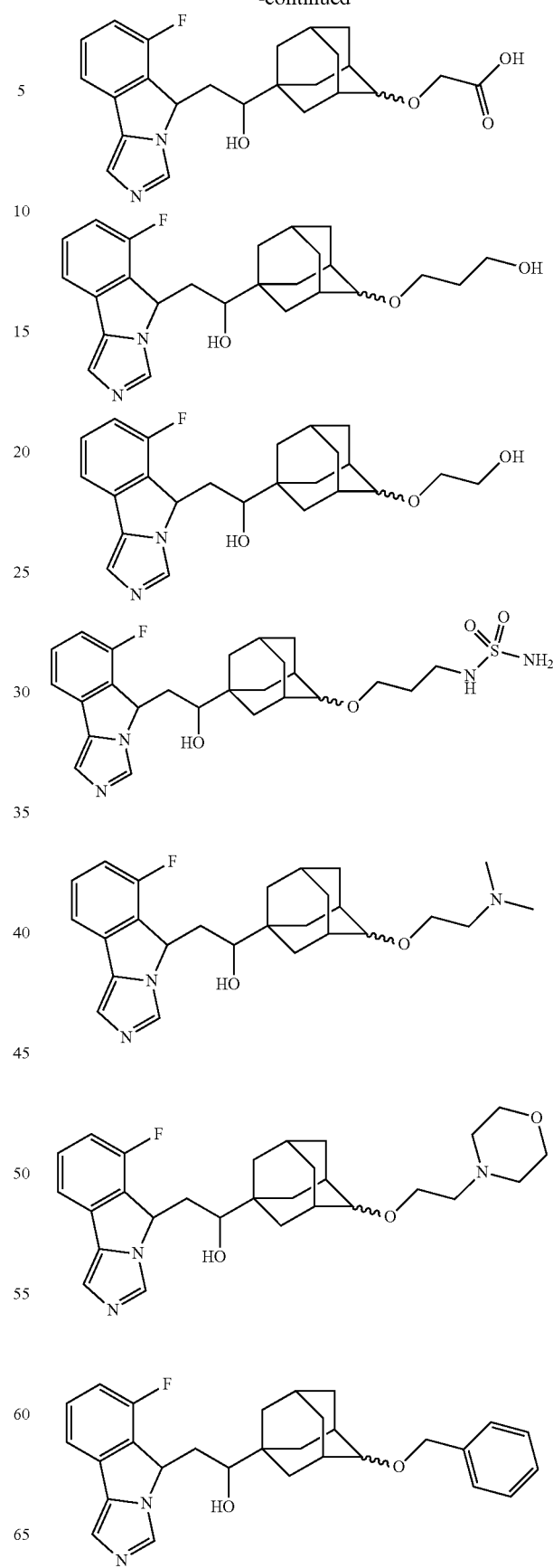

349
-continued
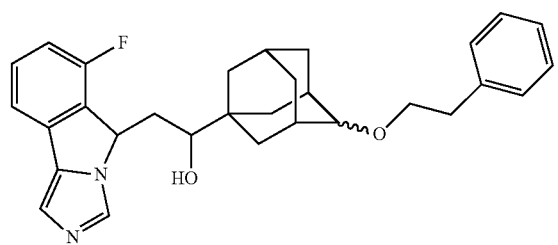
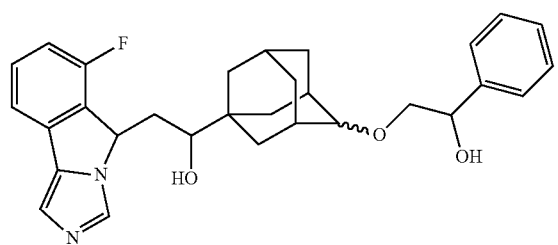
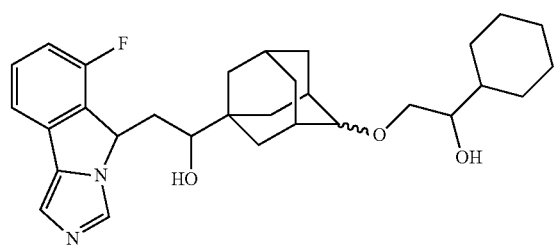
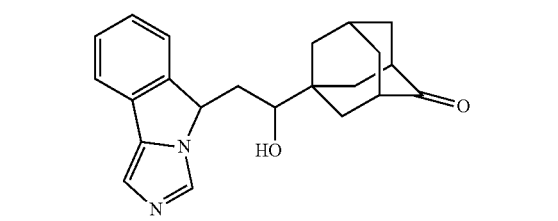
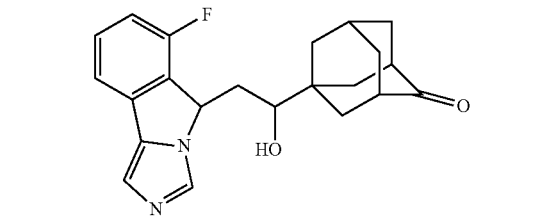
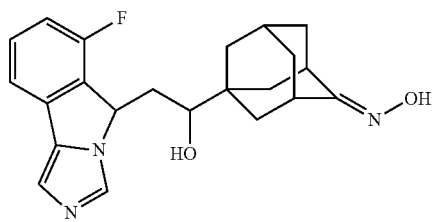
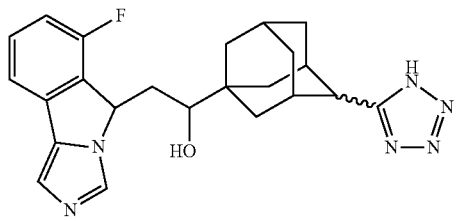
350
-continued
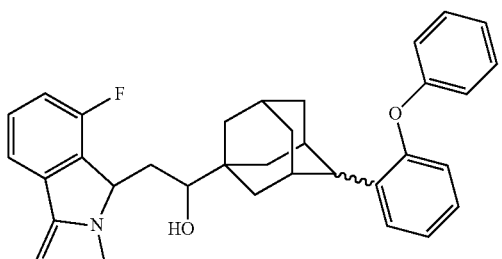
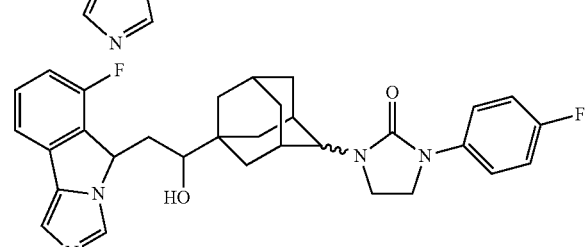
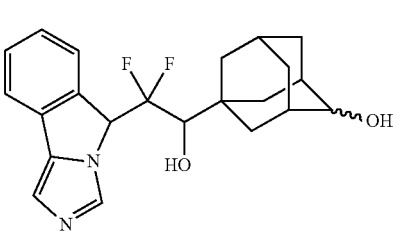
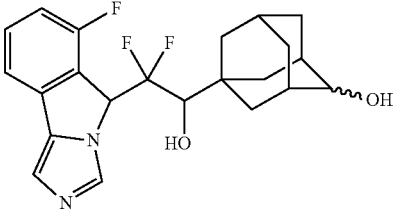
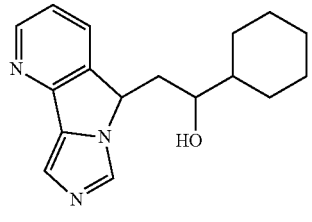
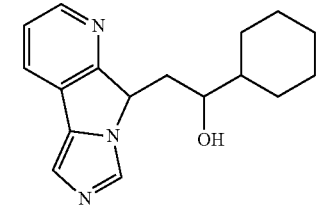
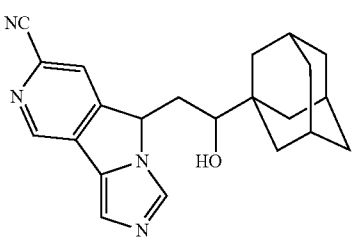

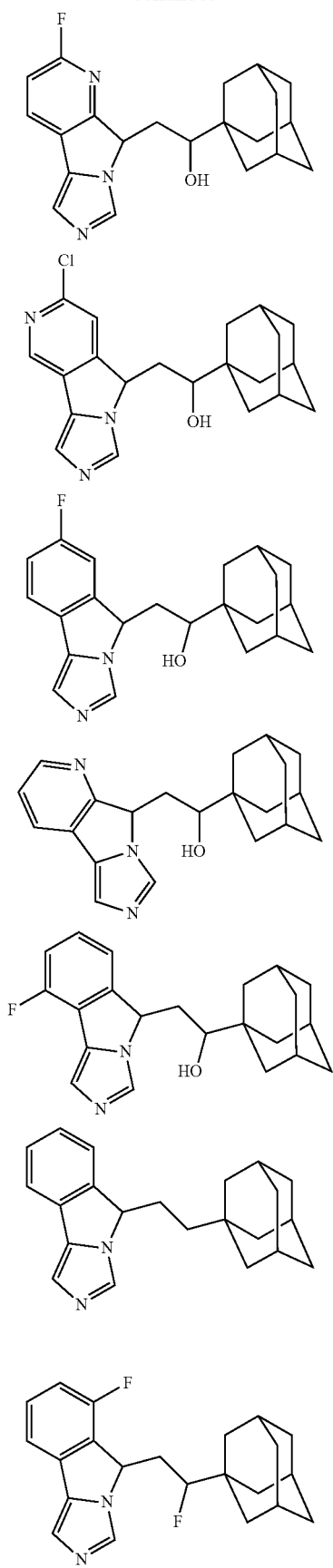
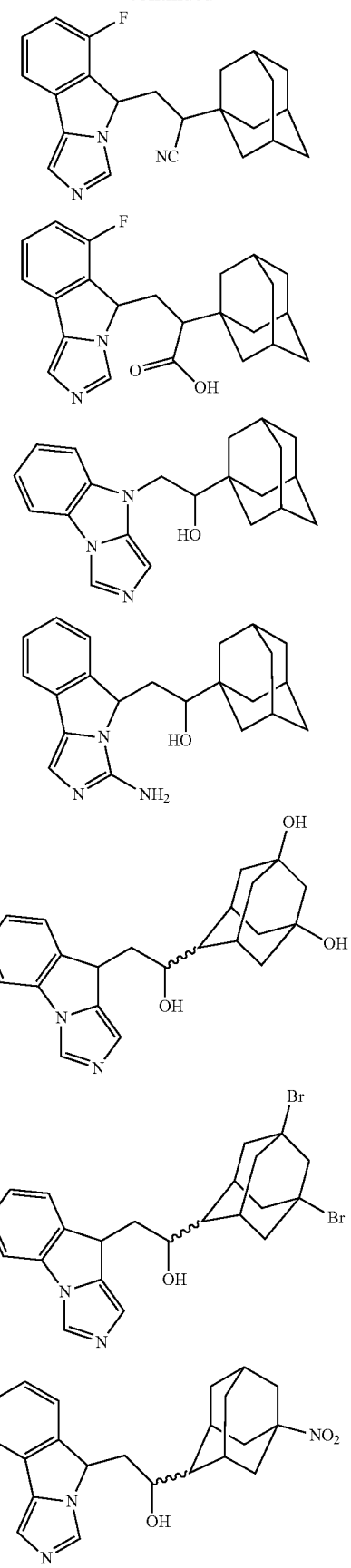

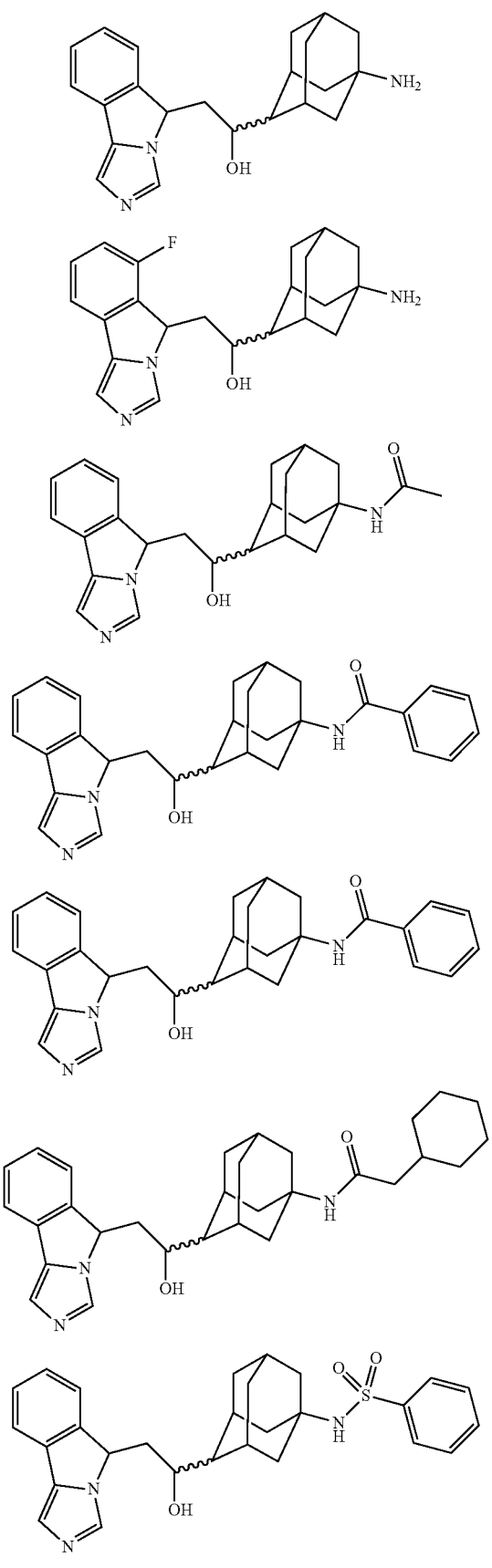
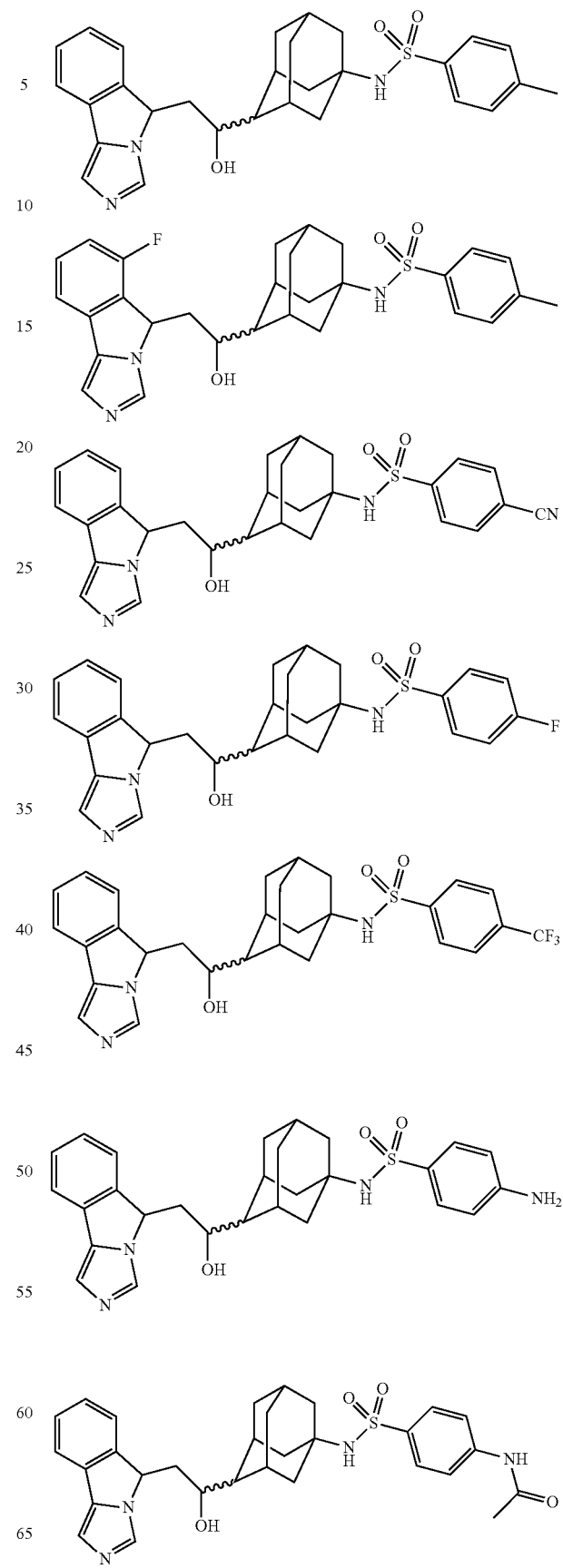

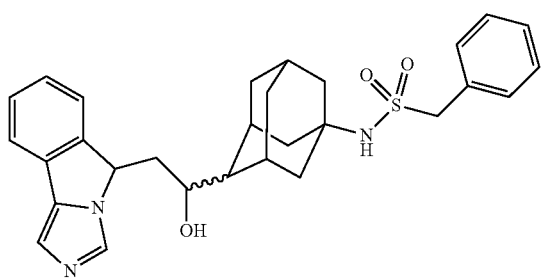
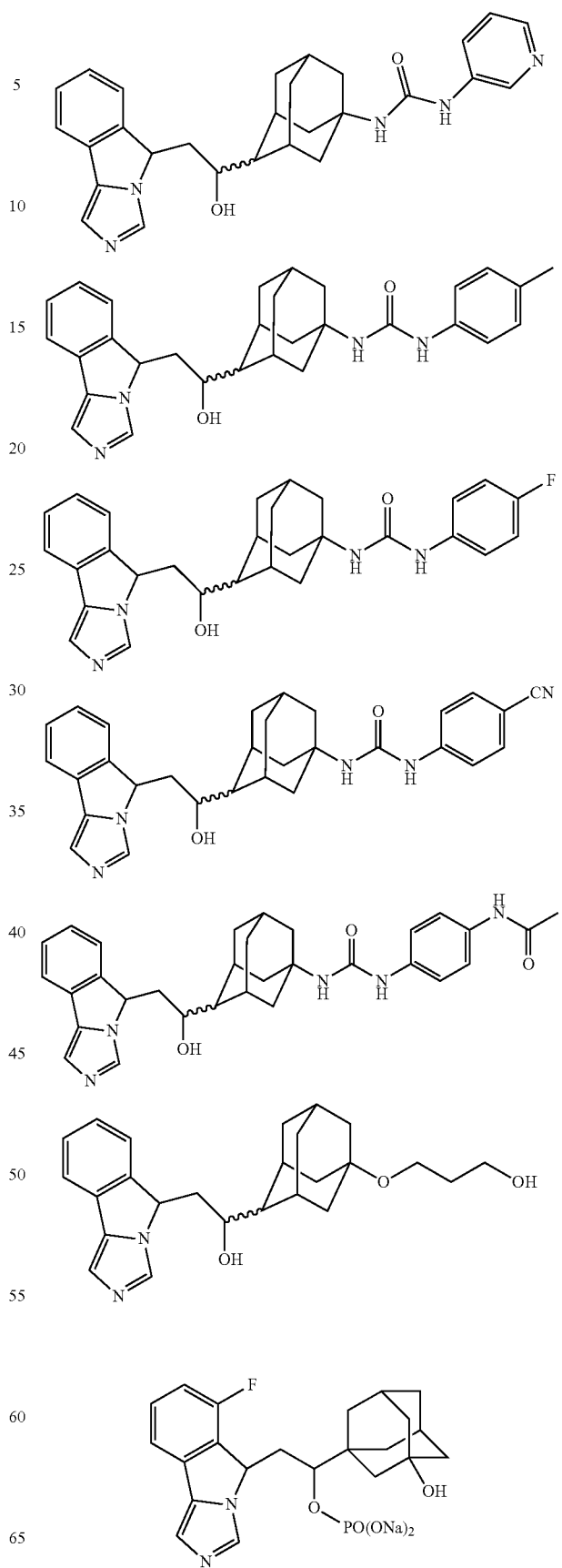

357
-continued
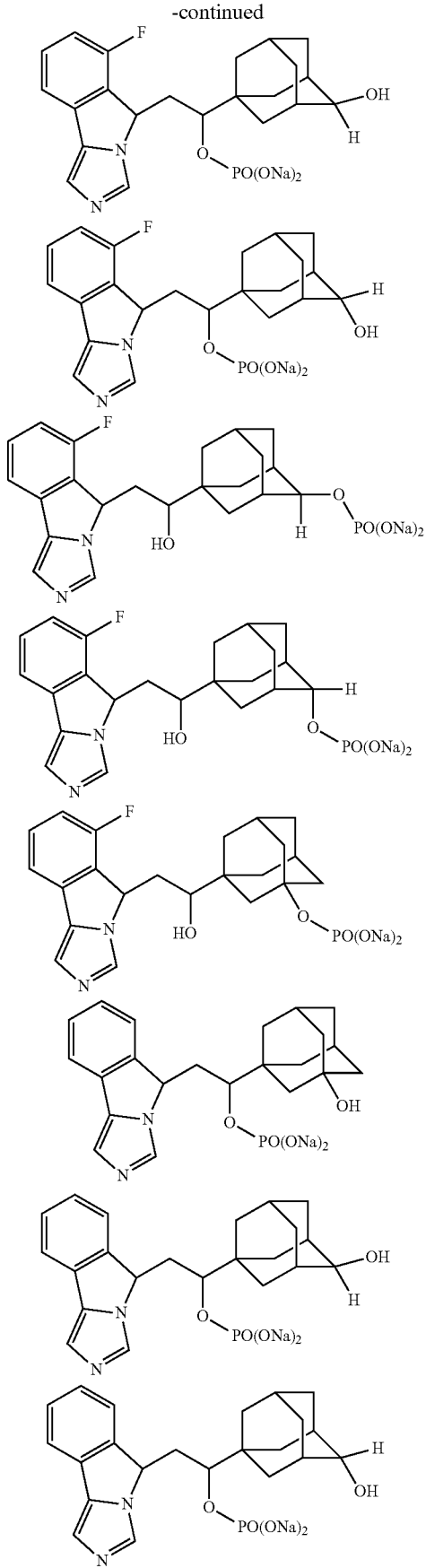
358
-continued
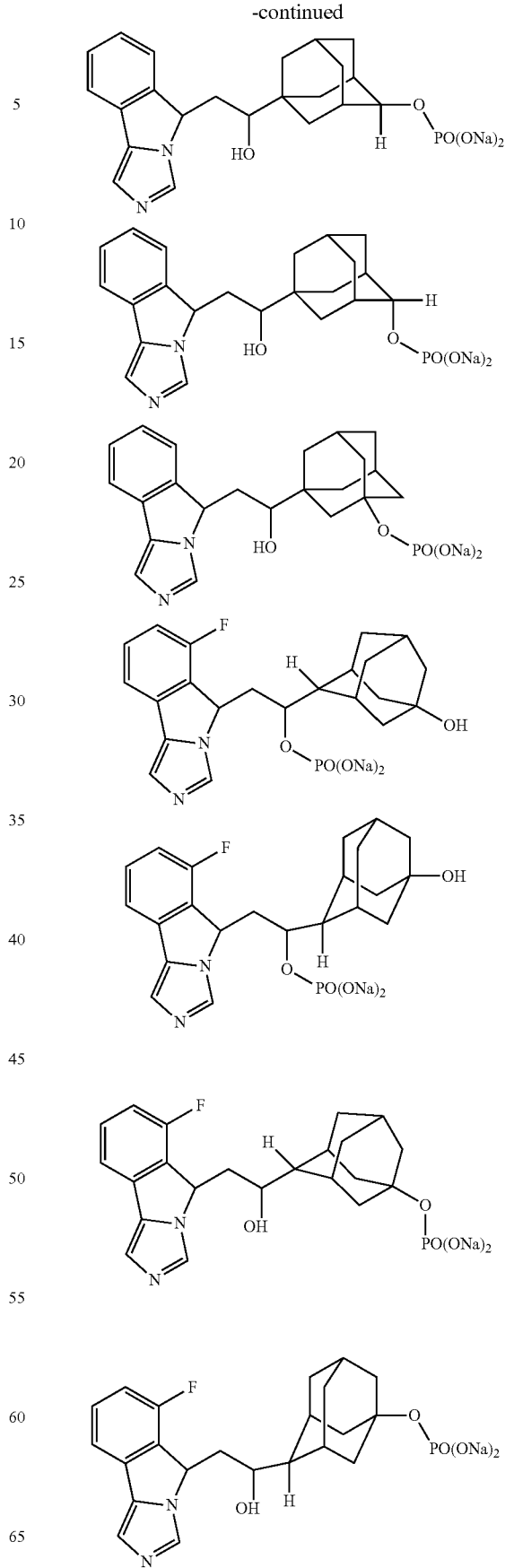

-continued
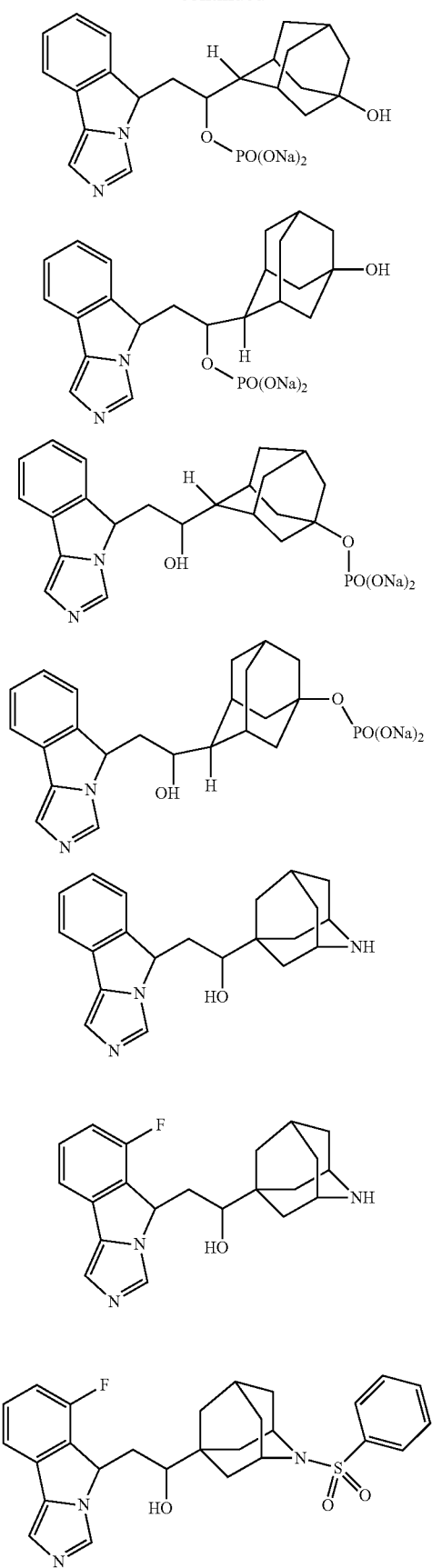 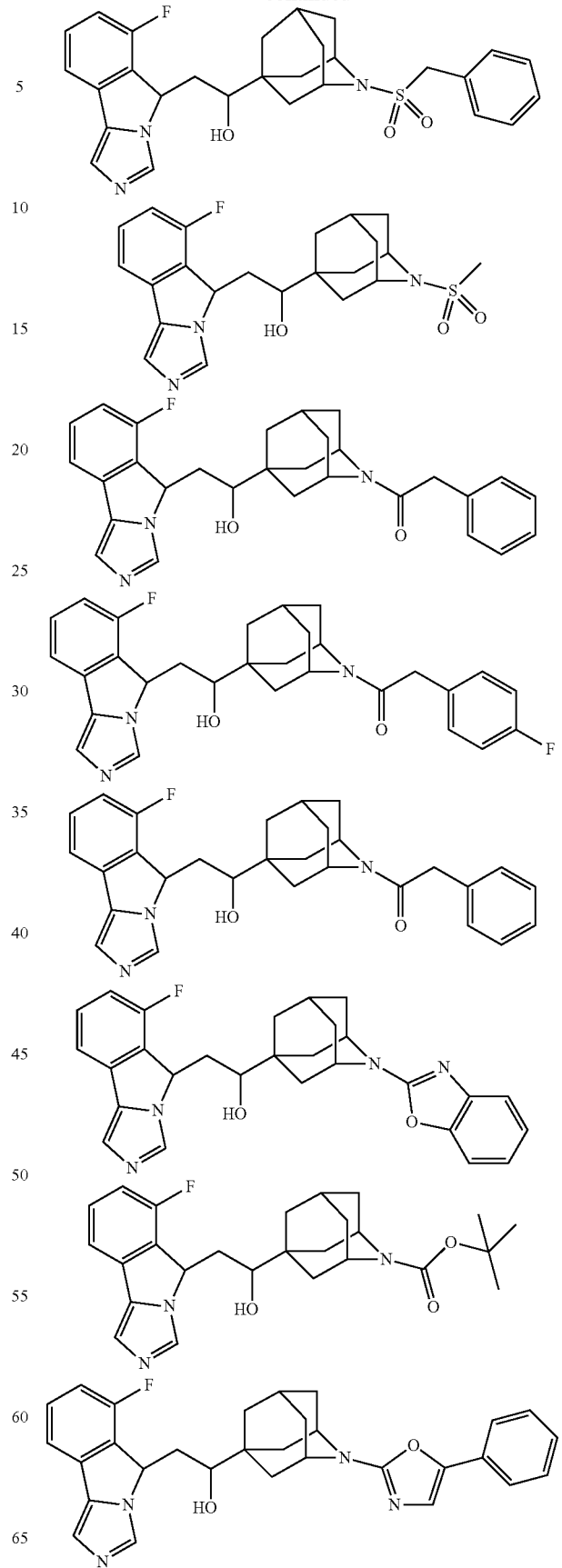

361
-continued
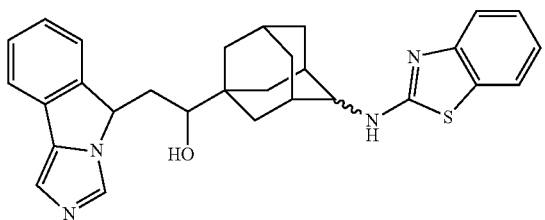
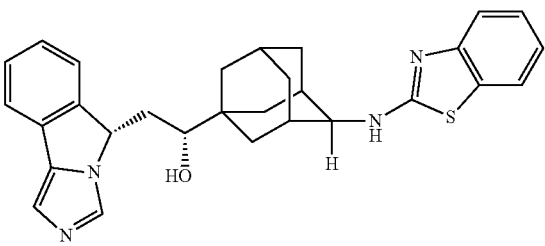
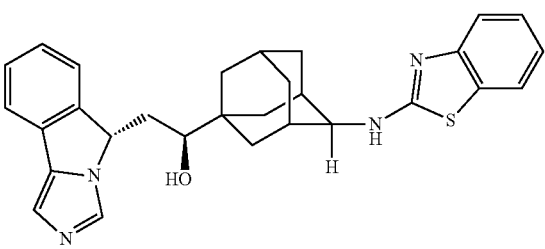
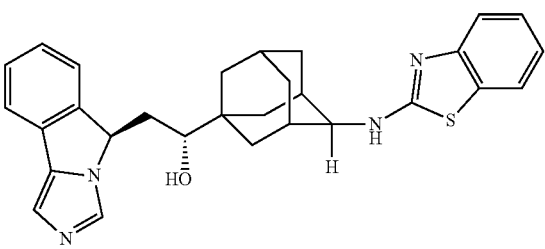
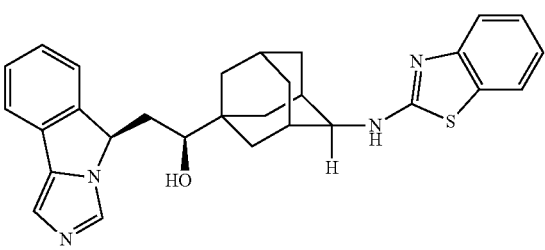
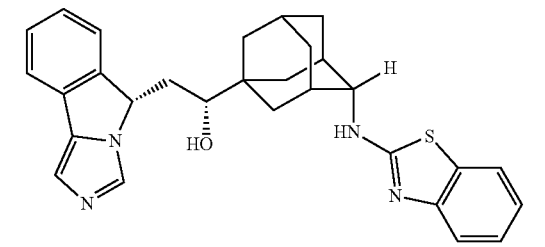
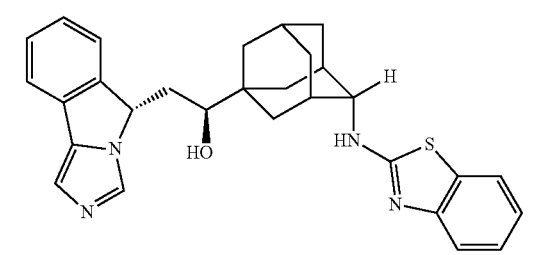
362
-continued
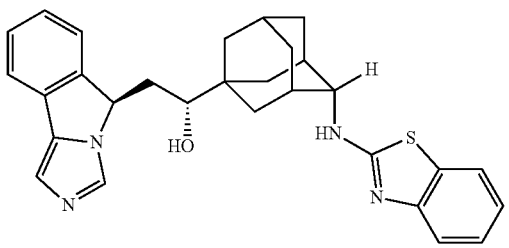
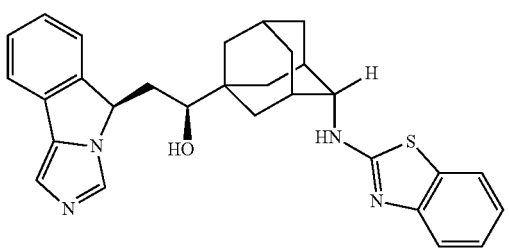
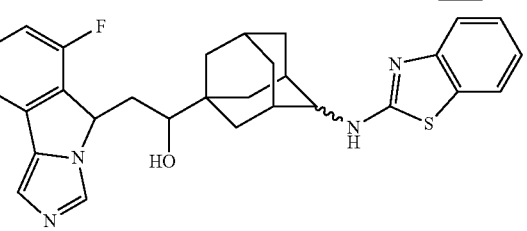
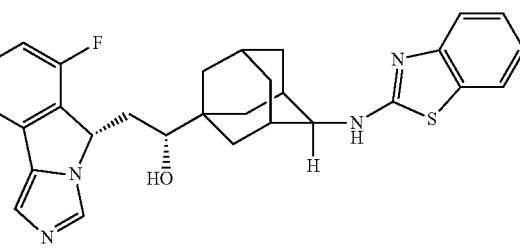
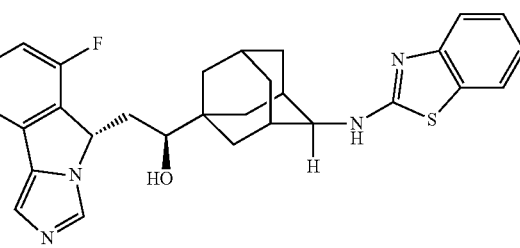
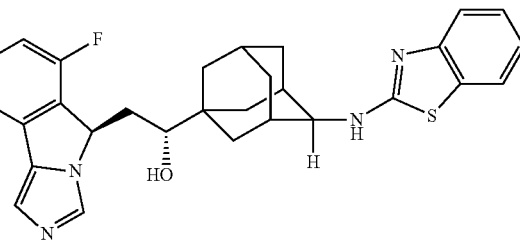
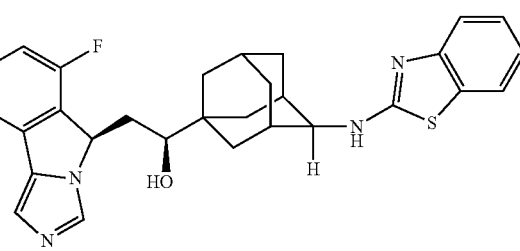

363 -continued
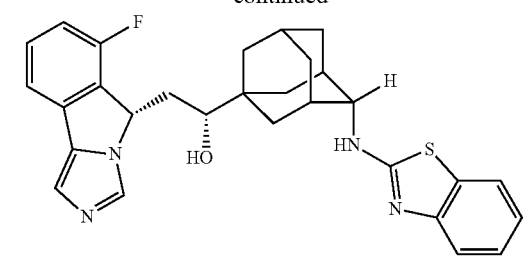
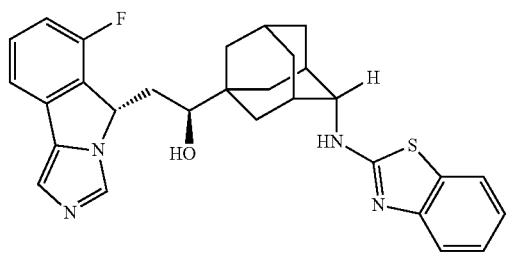
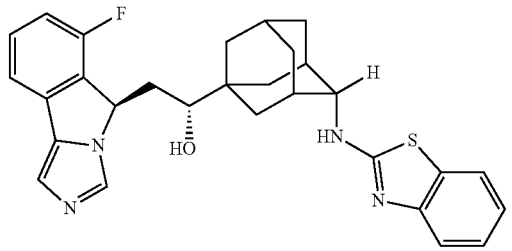
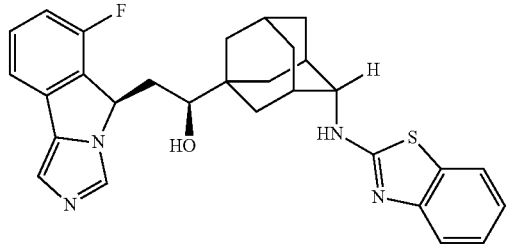
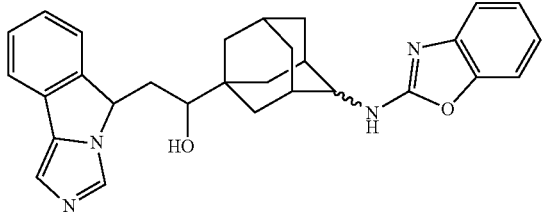
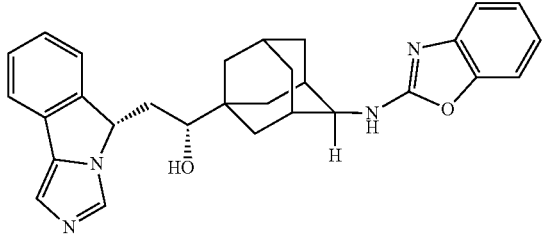
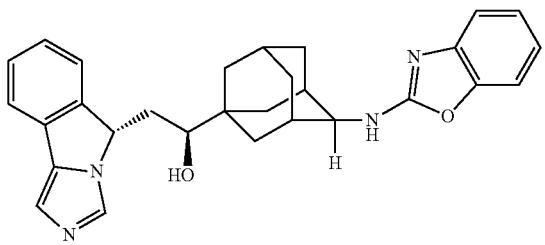
364 -continued
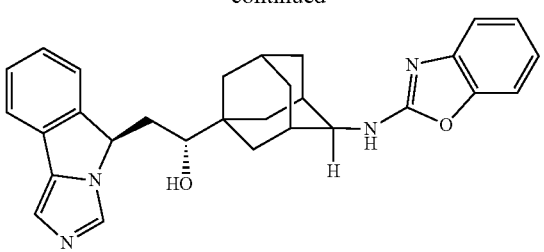
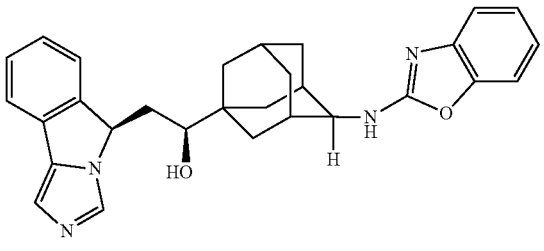
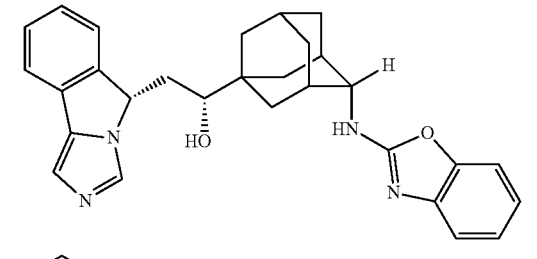
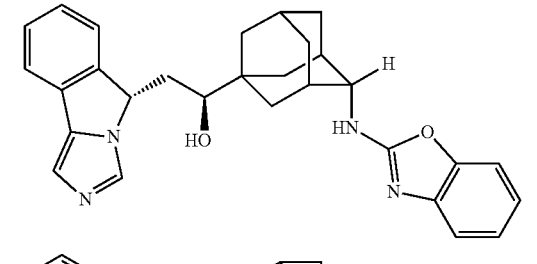
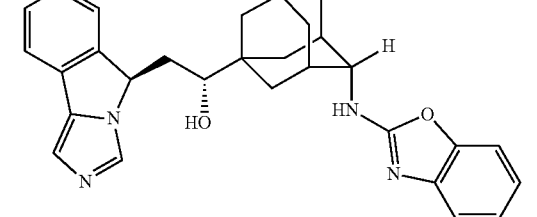
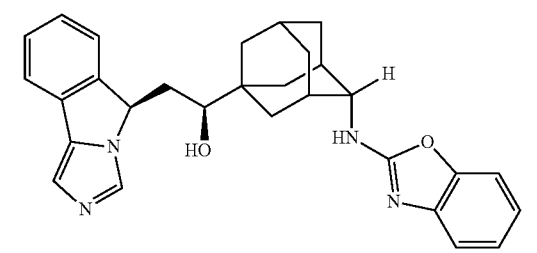
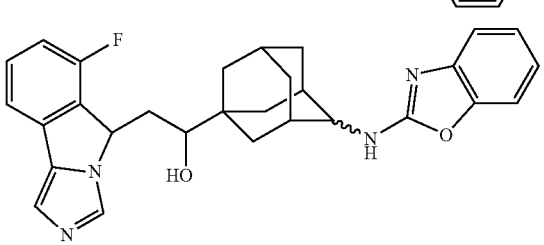

365
-continued
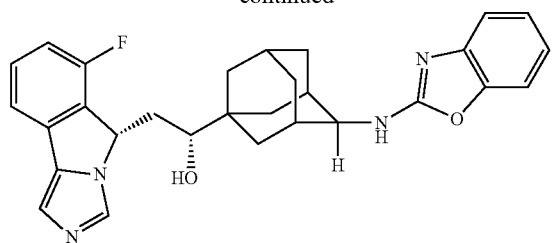
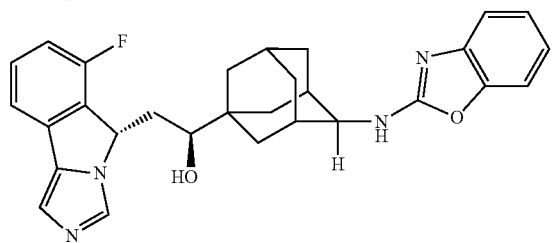
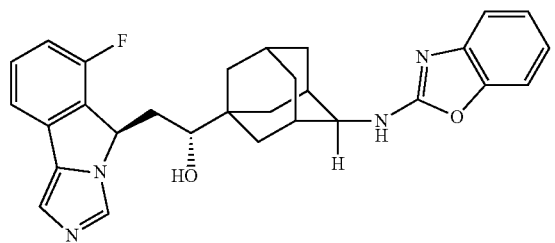
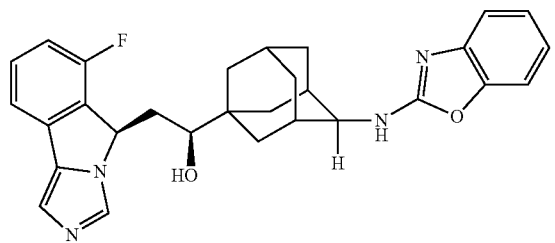
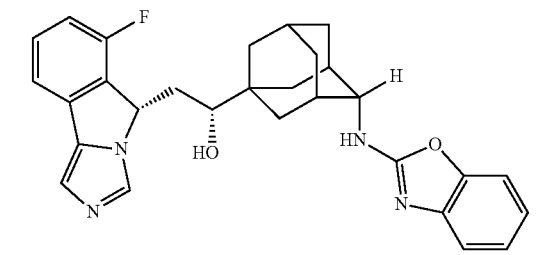
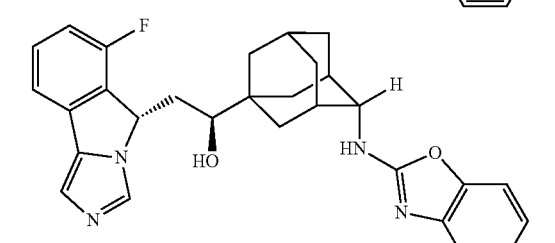
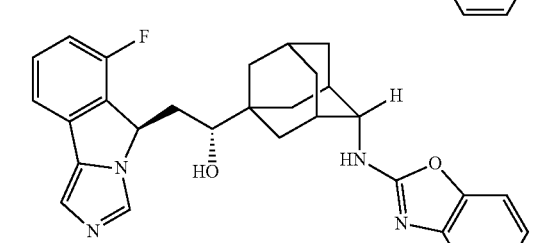
366
-continued
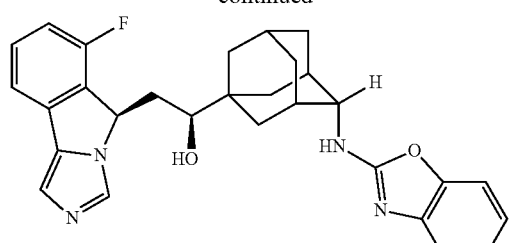
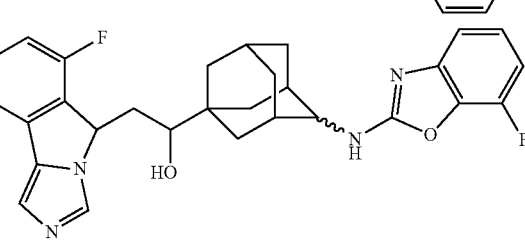
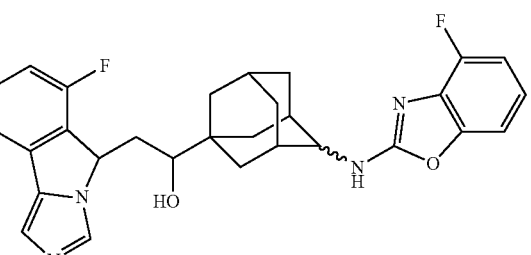
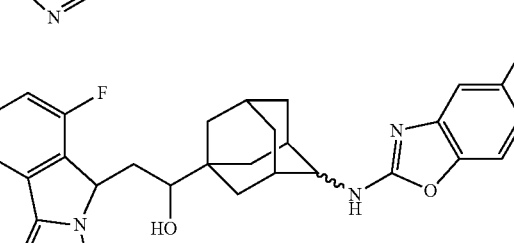
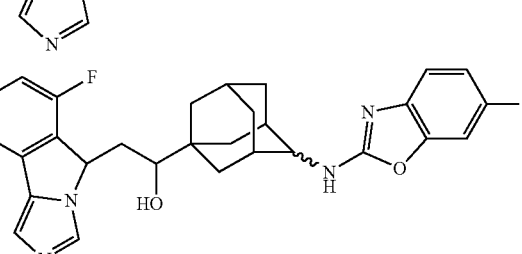
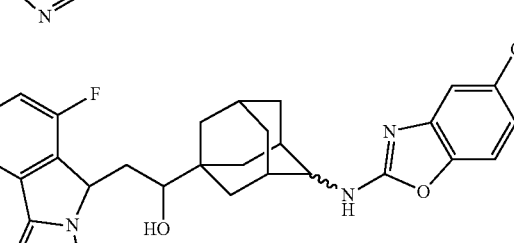
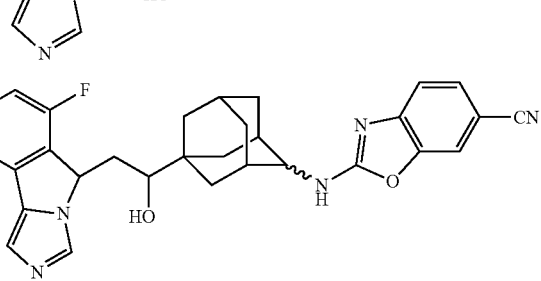

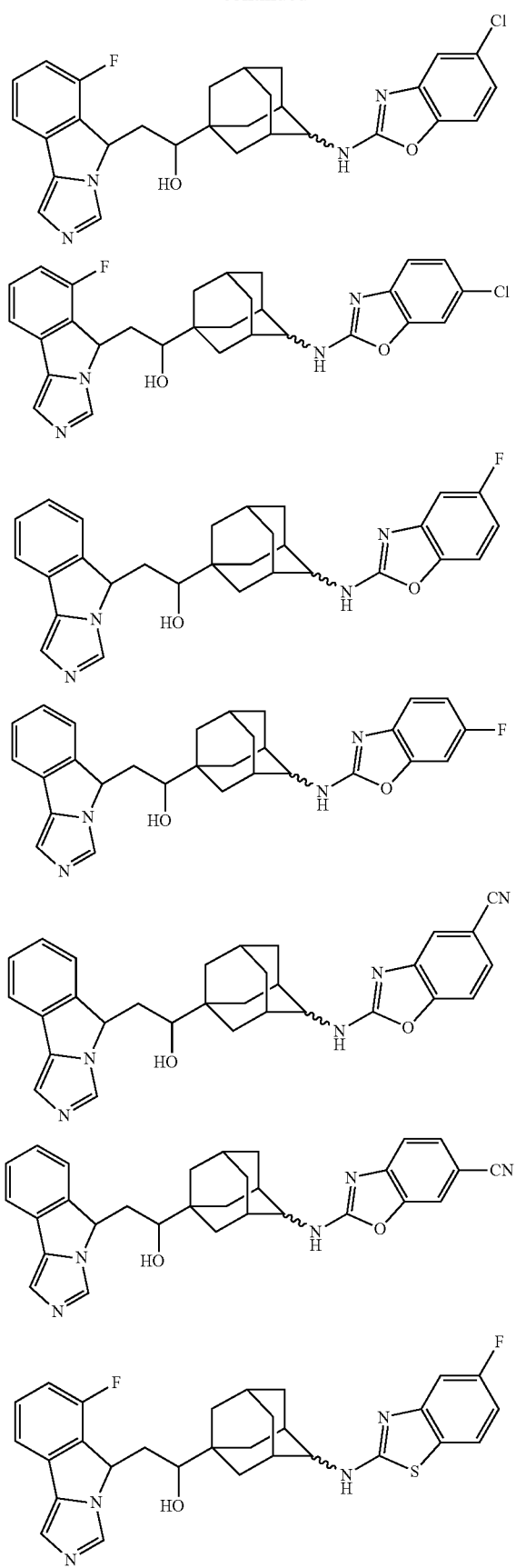
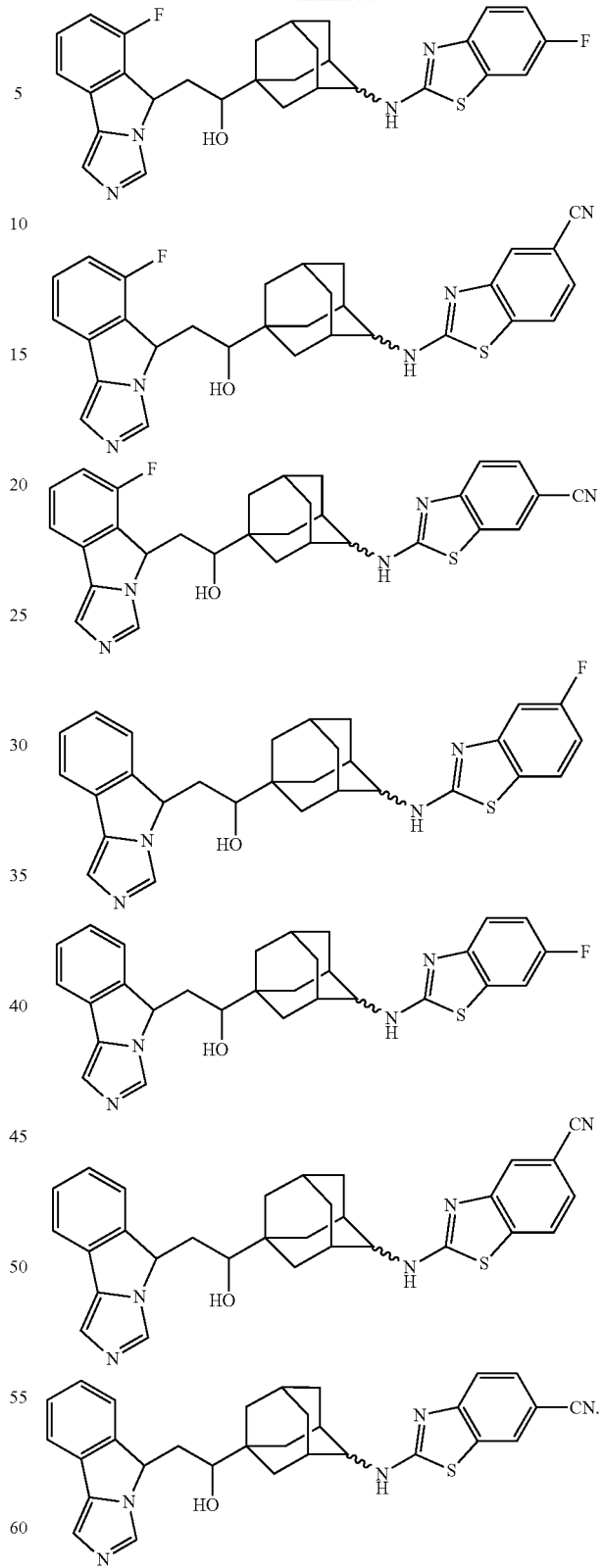
16. A pharmaceutical composition comprising 1) the compound and/or the pharmaceutically acceptable salt thereof of claim 1, and 2) a pharmaceutically acceptable excipient.

17. A method for treating a disease treatable by inhibition of IDO1 and/or TDO2 in a mammal comprising administering to the mammal in recognized need of such treatment, a therapeutically effective amount of the compound and/or the pharmaceutically acceptable salt thereof of claim 1.

18. A method for treating a disease treatable by inhibition of IDO1 and/or TDO2 in a mammal comprising administering to the mammal in recognized need of such treatment, a therapeutically effective amount of the pharmaceutical composition of claim 16.

19. The method of claim 17, further comprising administering to the mammal in recognized need of such treatment an additional agent prior to, concurrent with, or subsequent to the compound of claim 1, the additional agent is selected from anti-microtubule agents, alkylating agents, topoisomerase I/II inhibitors, platinum coordination complexes, antimetabolites, immunotherapeutic agents, signal transduction pathway inhibitors, and angiogenesis inhibitors, or the disease treatable by inhibition of IDO1 and/or TDO2 is cancer, viral infection, or autoimmune disease, or the mammal is human.

20. The method of claim 18, further comprising administering to the mammal in recognized need of such treatment an additional agent prior to, concurrent with, or subsequent to the pharmaceutical composition of claim 16, the additional agent is selected from anti-microtubule agents, alkylating agents, topoisomerase I/II inhibitors, platinum coordination complexes, antimetabolites, immunotherapeutic agents, signal transduction pathway inhibitors, and angiogenesis inhibitors, or the disease treatable by inhibition of IDO1 and/or TDO2 is cancer, viral infection, or autoimmune disease, or the mammal is human.

* * * * *